(12) United States Patent
Shi et al.

(10) Patent No.: US 12,031,148 B2
(45) Date of Patent: Jul. 9, 2024

(54) RNA ADENO-ASSOCIATED VIRUS (RAAV) VECTOR AND USES THEREOF

(71) Applicant: Huidagene Therapeutics Pte., Ltd., Singapore (SG)

(72) Inventors: Linyu Shi, Singapore (SG); Weiya Bai, Singapore (SG)

(73) Assignee: HUIDAGENE THERAPEUTICS (SINGAPORE) PTE. LTD., Singapore (SG)

( * ) Notice: Subject to any disclaimer, the term of this patent is extended or adjusted under 35 U.S.C. 154(b) by 0 days.

(21) Appl. No.: 17/836,222

(22) Filed: Jun. 9, 2022

(65) Prior Publication Data
US 2023/0062529 A1 Mar. 2, 2023

Related U.S. Application Data

(63) Continuation of application No. PCT/CN2022/075366, filed on Feb. 7, 2022.

(30) Foreign Application Priority Data

Feb. 7, 2021 (WO) ................ PCT/CN2021/075874

(51) Int. Cl.
*C12N 15/90* (2006.01)
*C12N 15/10* (2006.01)
*C12N 15/86* (2006.01)

(52) U.S. Cl.
CPC ......... *C12N 15/902* (2013.01); *C12N 15/102* (2013.01); *C12N 15/86* (2013.01); *C12N 2310/20* (2017.05); *C12N 2750/14143* (2013.01)

(58) Field of Classification Search
None
See application file for complete search history.

(56) References Cited

FOREIGN PATENT DOCUMENTS

| | | |
|---|---|---|
| CN | 109055375 A | 12/2018 |
| CN | 109207477 A | 1/2019 |
| CN | 110114461 A | 8/2019 |
| CN | 110312799 A | 10/2019 |
| CN | 111349148 A | 6/2020 |
| WO | 2018/131551 A1 | 7/2018 |

OTHER PUBLICATIONS

Gee et al., Extracellular nanovesicles for packaging of CRISPR-Cas9 protein and sgRNA to induce therapeutic exon skipping. Nat Commun. Mar. 13, 2020;11(1):1334.
Tran et al., AAV-Genome Population Sequencing of Vectors Packaging CRISPR Components Reveals Design-Influenced Heterogeneity. Mol Ther Methods Clin Dev. Jul. 9, 2020;18:639-651.
International Search Report and Written Opinion for Application No. PCT/CN2022/075366, dated May 12, 2022, 11 pages.

*Primary Examiner* — Nancy J Leith
(74) *Attorney, Agent, or Firm* — McCarter & English, LLP; Yu Lu

(57) ABSTRACT

The invention described herein provides a recombinant DNA viral particle comprising a protein shell encapsulating an RNA vector genome, as well as related compositions and uses thereof.

45 Claims, 33 Drawing Sheets
Specification includes a Sequence Listing.

FIG. 1C

1. ITR1-3
2. ITR2-3
3. ITR3-3
4. ITR4-3
5. ITR5-3
6. ITR6-3
7. ITR7-3

```
                    D sequence              TRS                    RBE
       ----NNTACCCCTAG--TGATGGAGTTGGCCACTCCCTCTATGCGCGCTCGCTCGCTCGG
1      -----TTACCCCTAG--TGATGGAGTTGCCCACTCCCTCTCTGCGCGCTCGCTCGCTCGG  53
2      ---AGGAACCCTAG--TGATGGAGTTGGCCACTCCCTCTCTGCGCGCTCGCTCGCTCAC    55
3      -----ATACCTCTAG--TGATGGAGTTGGCCACTCCCTCTATGCGCACTCGCTCGCTCGG   53
4      ----GGCAAACCAGA--TGATGGAGTTGGCCACATTAGCTATGCGCGCTCGCTCACTCAC   54
5      TACAAAACCTCCTTGCTTGAGAGTGTGGCACTCTCCCCCTGTCGCGTTCGCTCGCTCGC    60
6      -----ATACCCCTAG--TGATGGAGTTGCCCACTCCCTCTATGCGCGCTCGCTCGCTCGG   53
7      ---CGGTACCCCTAG--TGATGGAGTTGGCCACTCCCTCTATGCGCGCTCGCTCGCTCGG   55

T----------GGGGCCTGCNGACCAAAG-GTCNCCAGACGGCNGNGCTCTGCNCGGCC
1      T----------GGGGCCTGCGGACCAAAG-GTCCGCAGACGGCAGAGCTCTGCTCTGCC   101
2      T----------GAGGCCGGCGACCAAAG-GTCGCCCGACGCCCGGGCTTTGCCCGGGC    103
3      T----------GGGGCCTGGCGACCAAAG-GTCGCCAGACGGACGTGCTTTGCACGTCC  101
4      T----------CGGCCCTGGAGACCAAAG-GTCTCCAGACTGCCGGCCTCTGGCCGGCA  102
5      TGGCTCGTTTGGGGGGTGGCAGCTCAAAGAGCTGCCAGACGACGGCCCTCTGGCCGTCG  120
6      T----------GGGGCCGGCAGAGCAGAG-CTCTGCCGTCTGCGGACCTTTGGTCCGCA  101
7      T----------GGGGCCTGCGGACCAAAG-GTCCGCAGACGGCAGAGCTCTGCTCTGCC  103

RBE
       GGCC-----------CCACCGAGCGAGCGAGCGCGCATAGAGGGAGTGGCCAA
1      GGCC-----------CCACCGAGCGAGCGAGCGCGCAGAGAGGGAGTGGGCAA  143
2      GGCC-----------TCAGTGAGCGAGCGAGCGCGCAGAGAGGGAGTGGCCAA  145
3      GGCC-----------CCACCGAGCGAGCGAGTGCGCATAGAGGGAGTGGCCAA  143
4      GGGC-----------CGAGTGAGTGAGCGAGCGCGCATAGAGGGAGTGGCCAA  144
5      CCCCCCCAAACGAGCCAGCGAGCGAGCGAACGCGACAGGGGGAGAG------  167
6      GGCC-----------CCACCGAGCGAGCGAGCGCGCATAGAGGGAGTGGCCAA  143
7      GGCC-----------CCACCGAGCGAGCGAGCGCGCATAGAGGGAGTGGCCAA  145
```

Flowchart of RAAV titration

Primers and probes for Q-PCR

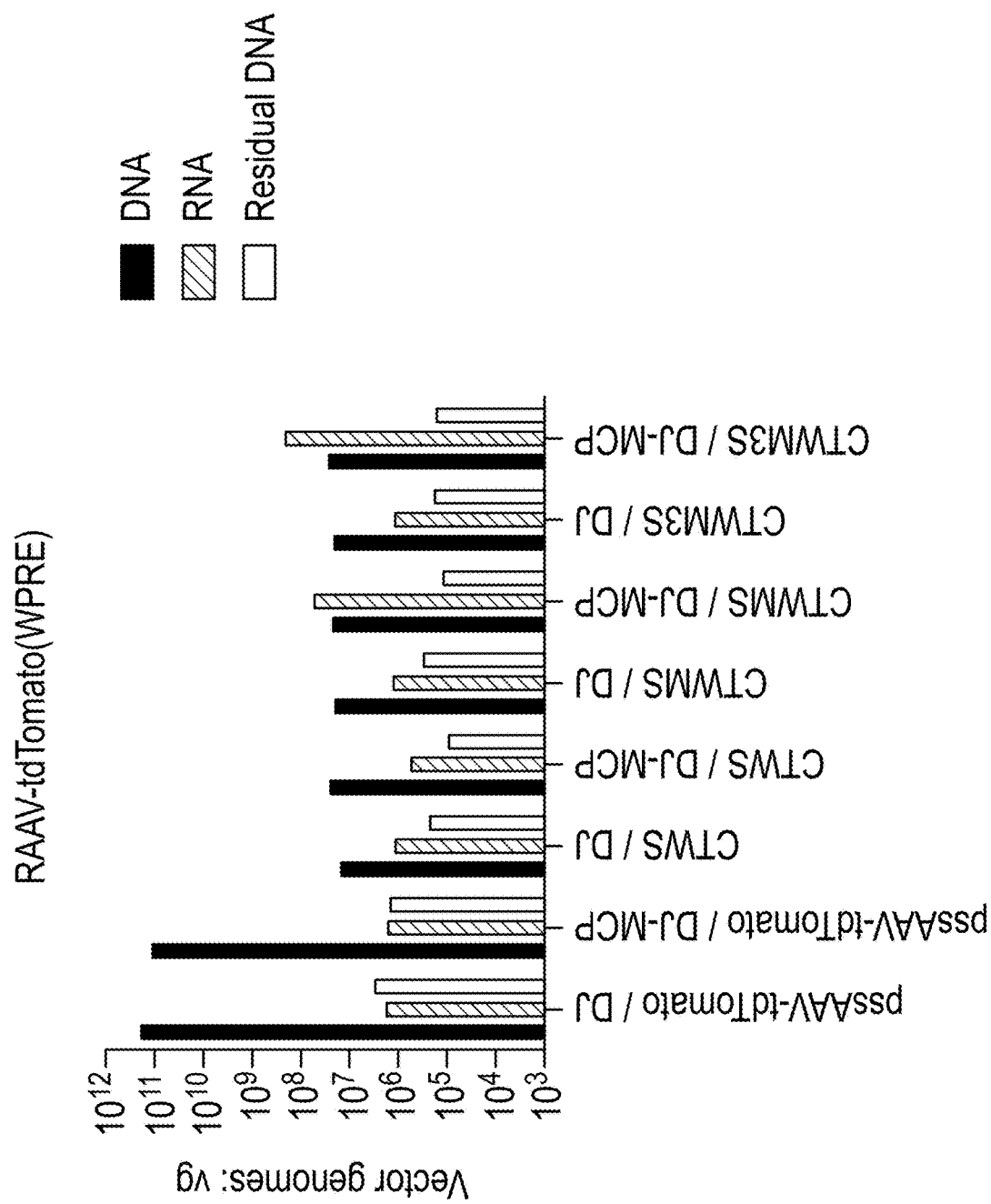

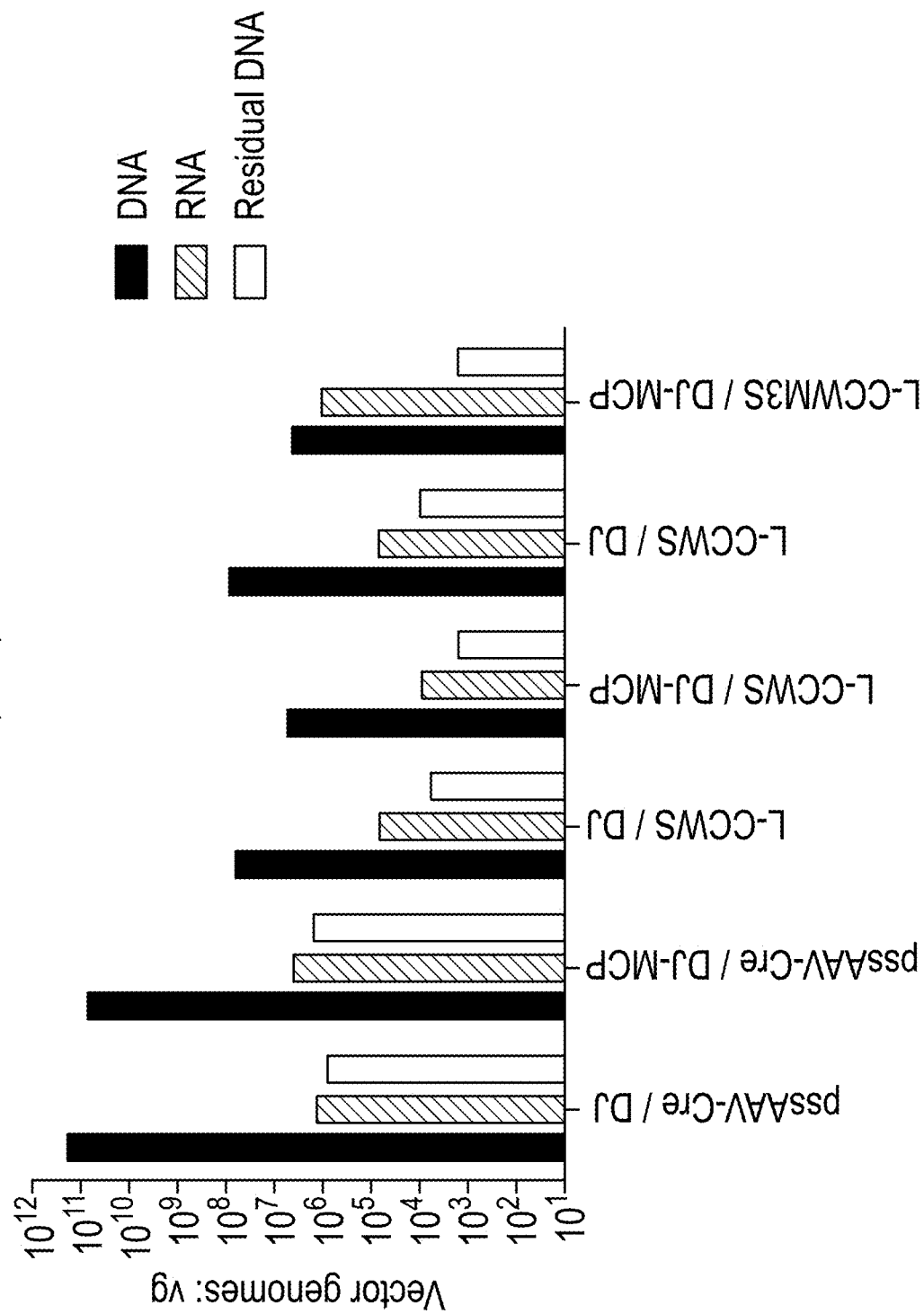

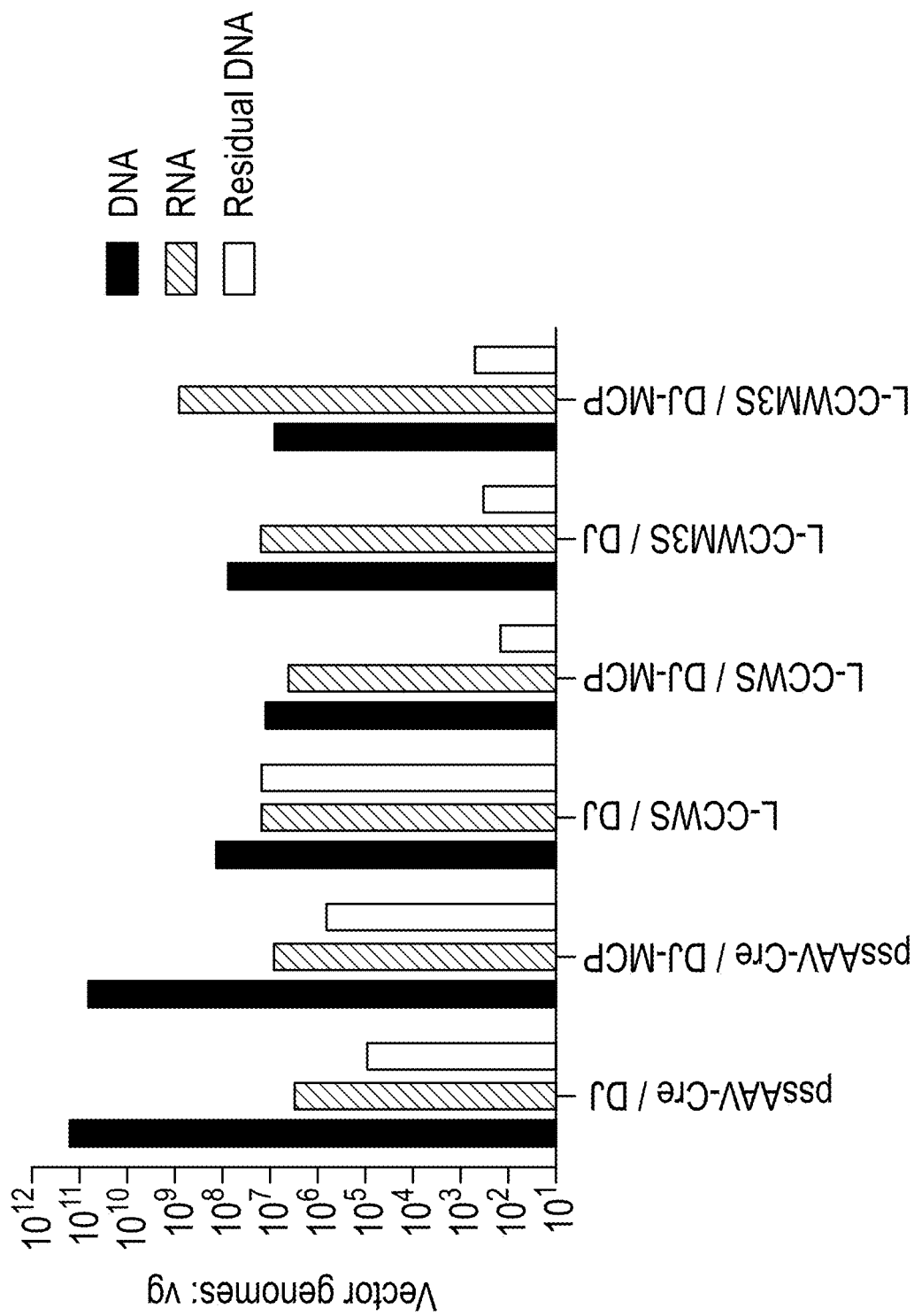

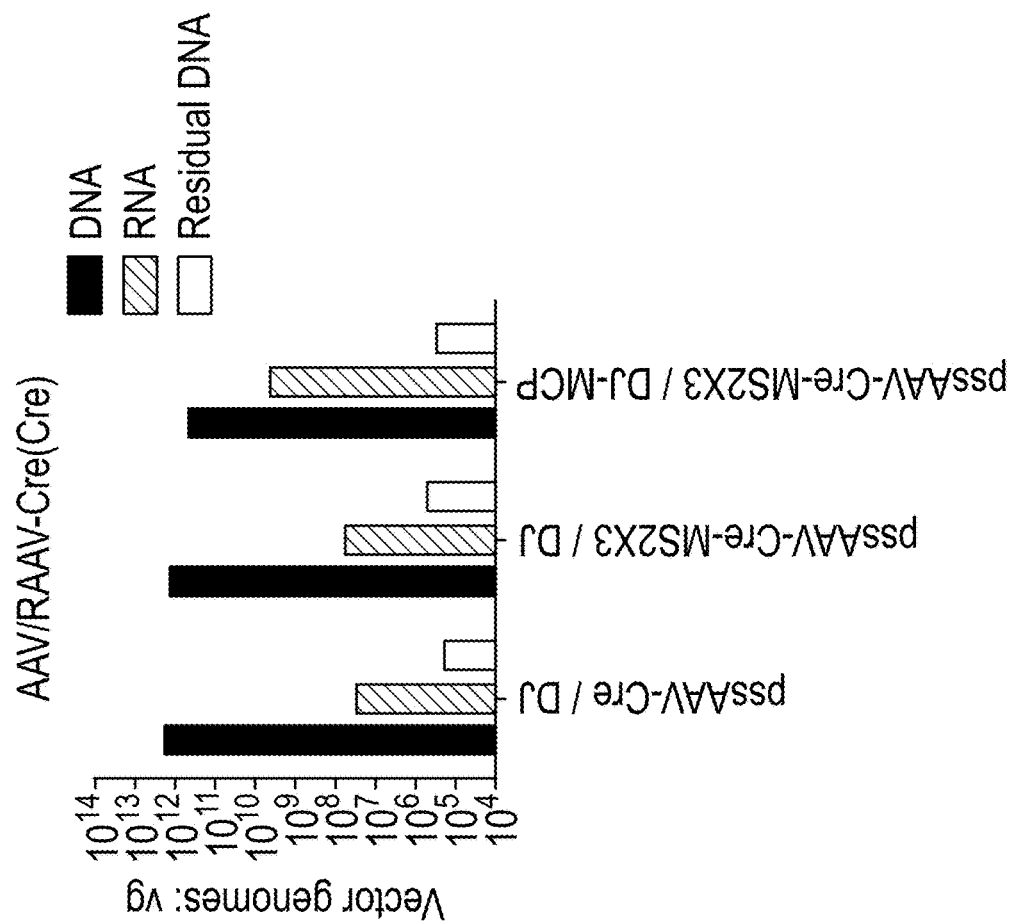
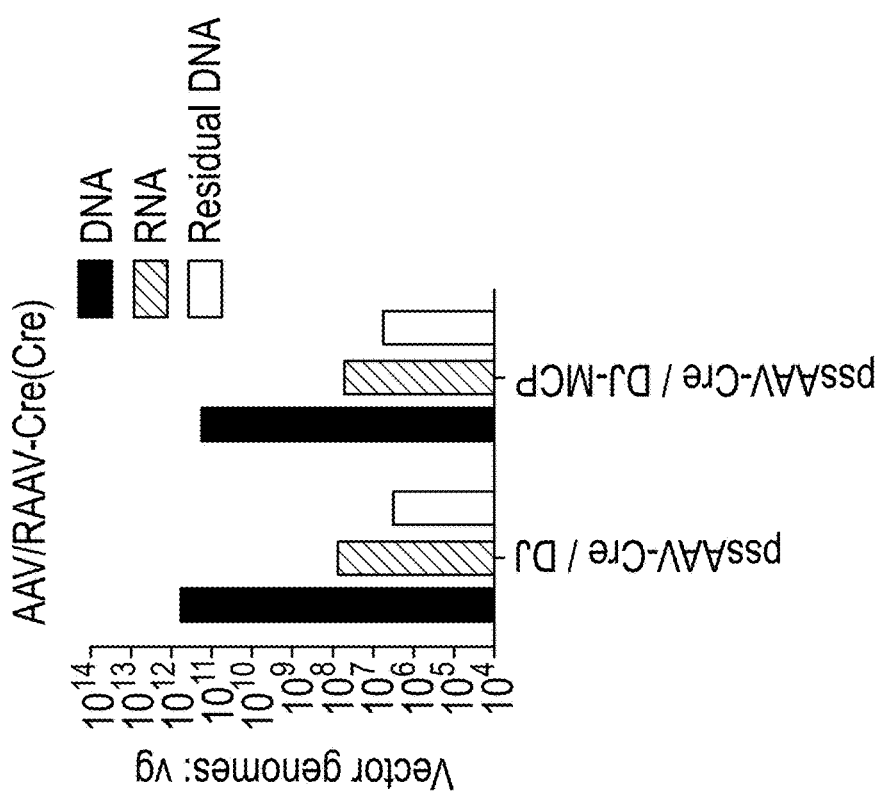
FIG. 11A
FIG. 11B

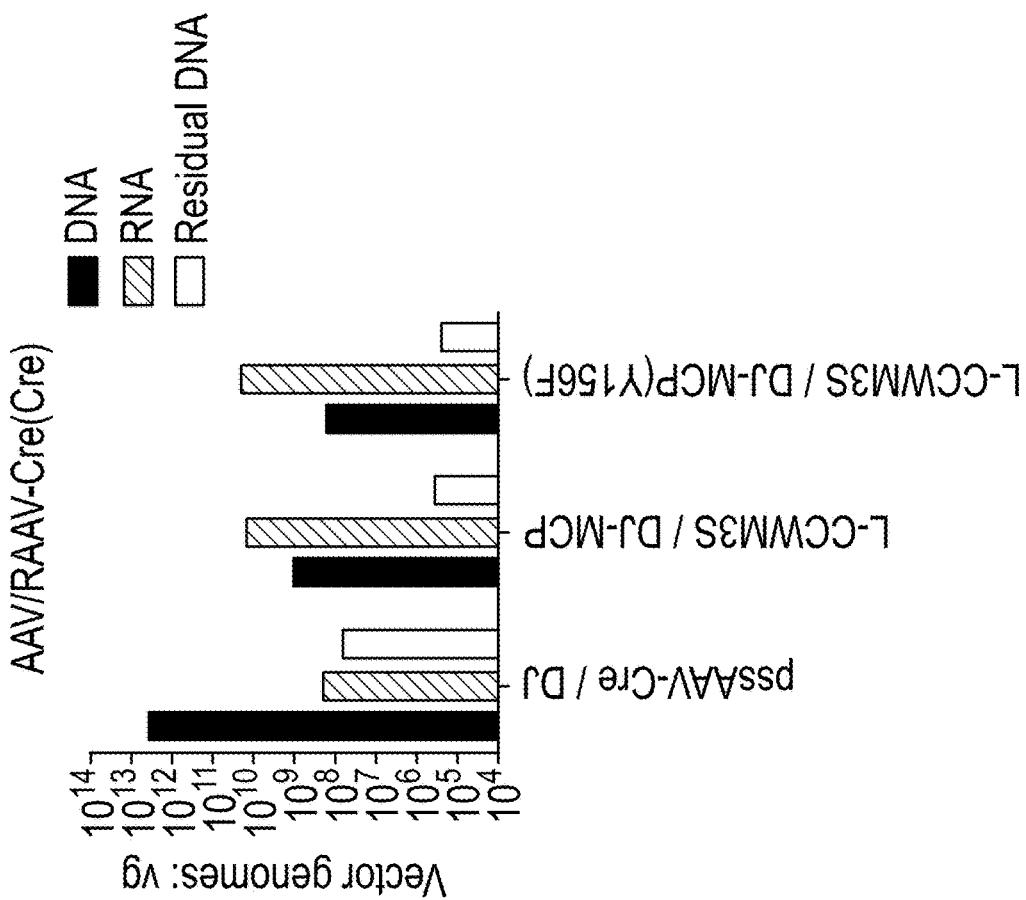
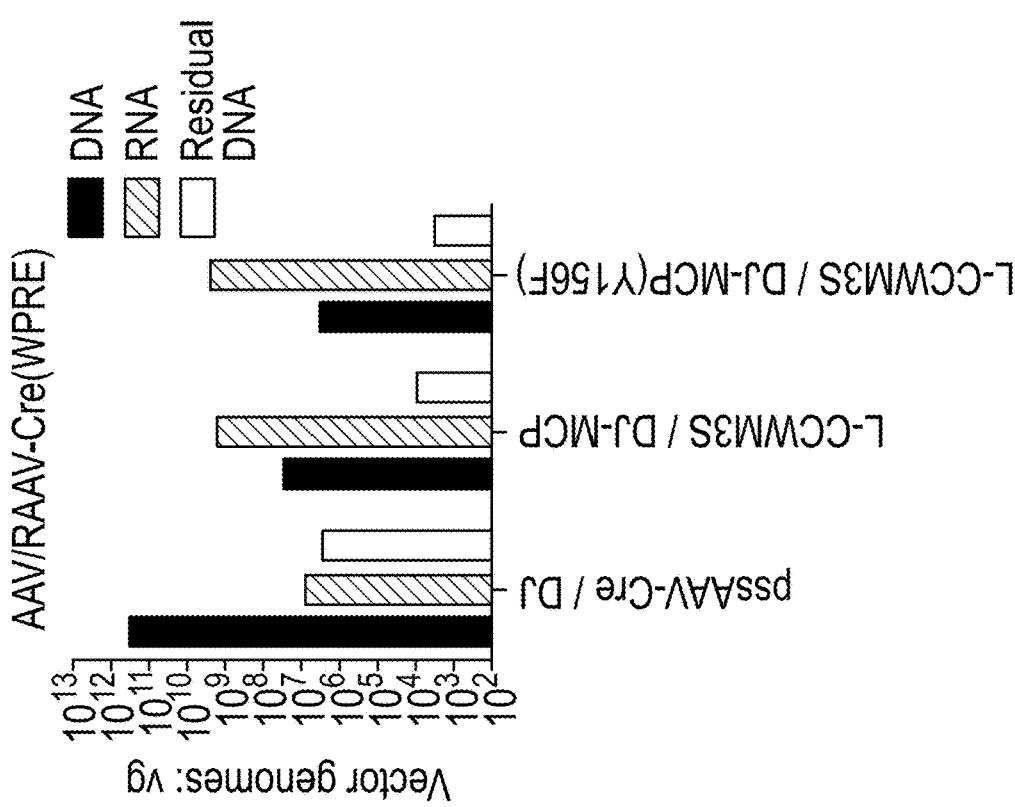

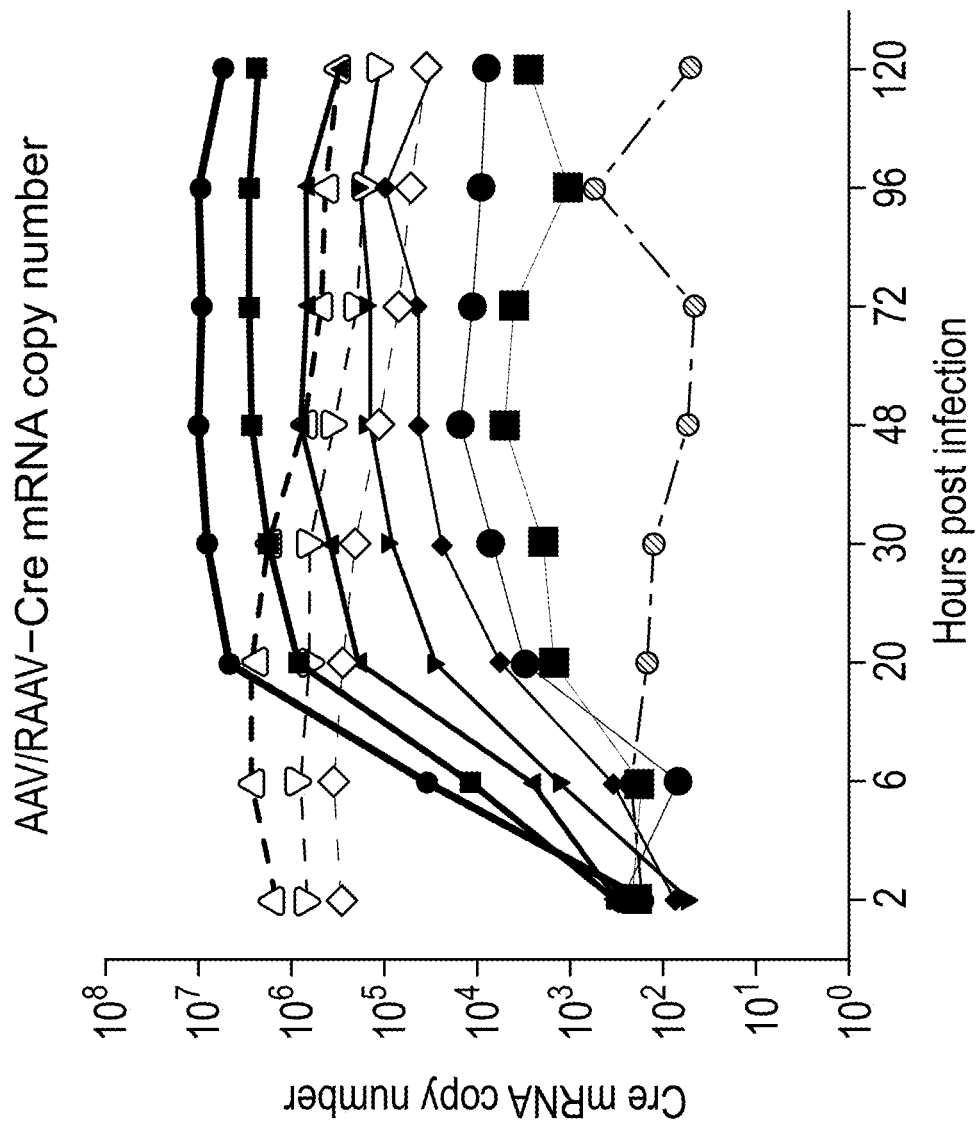

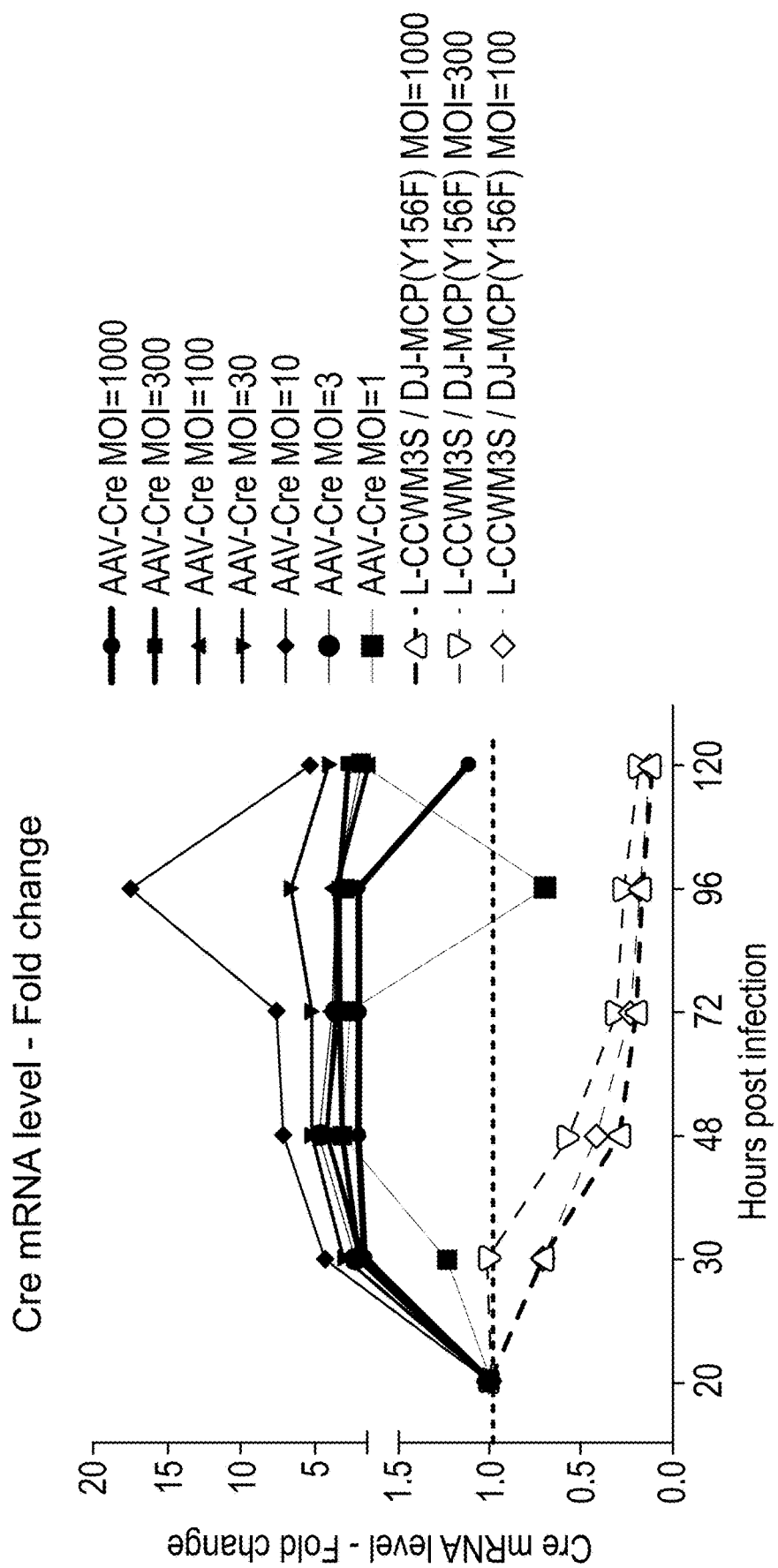

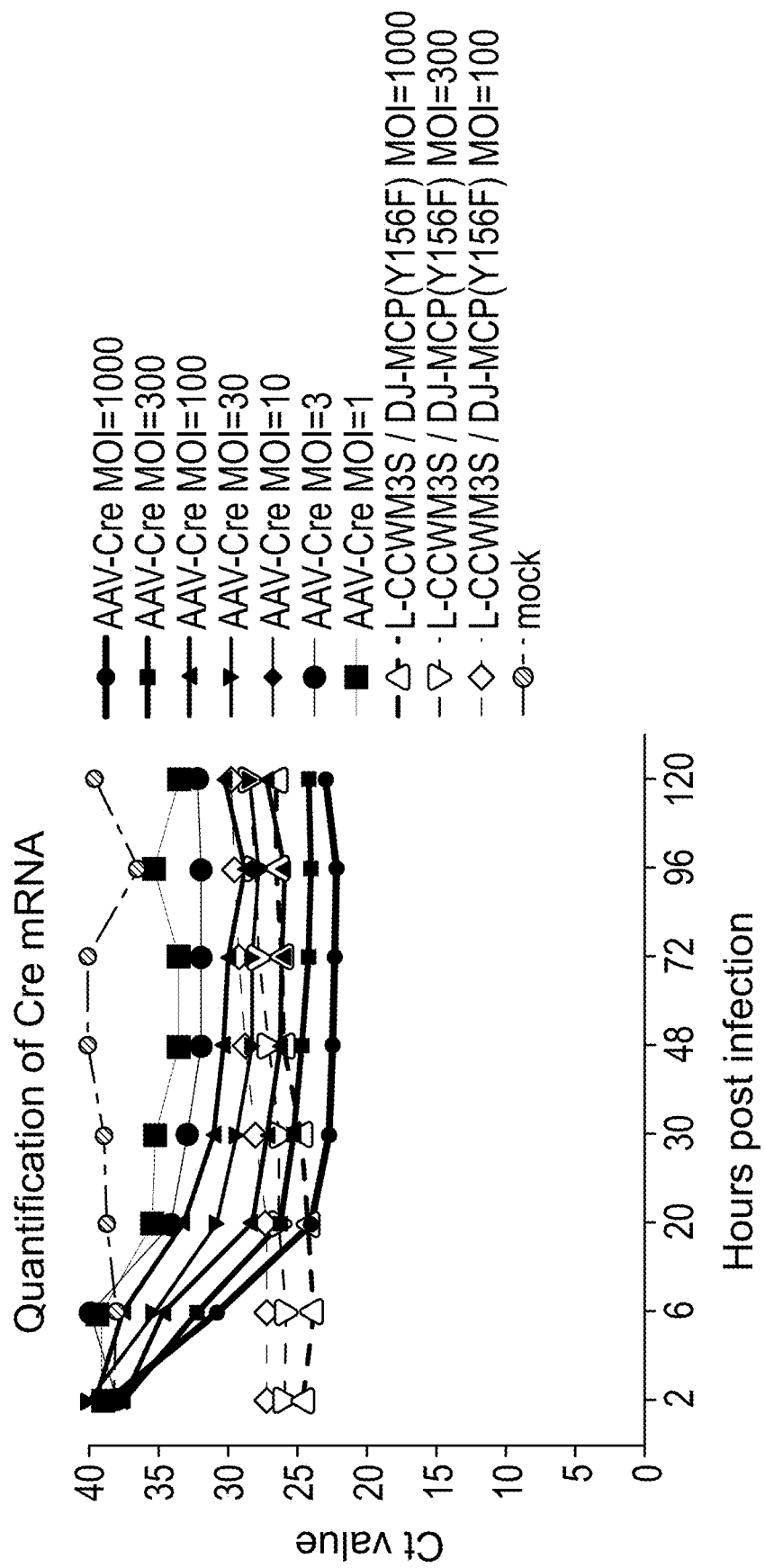

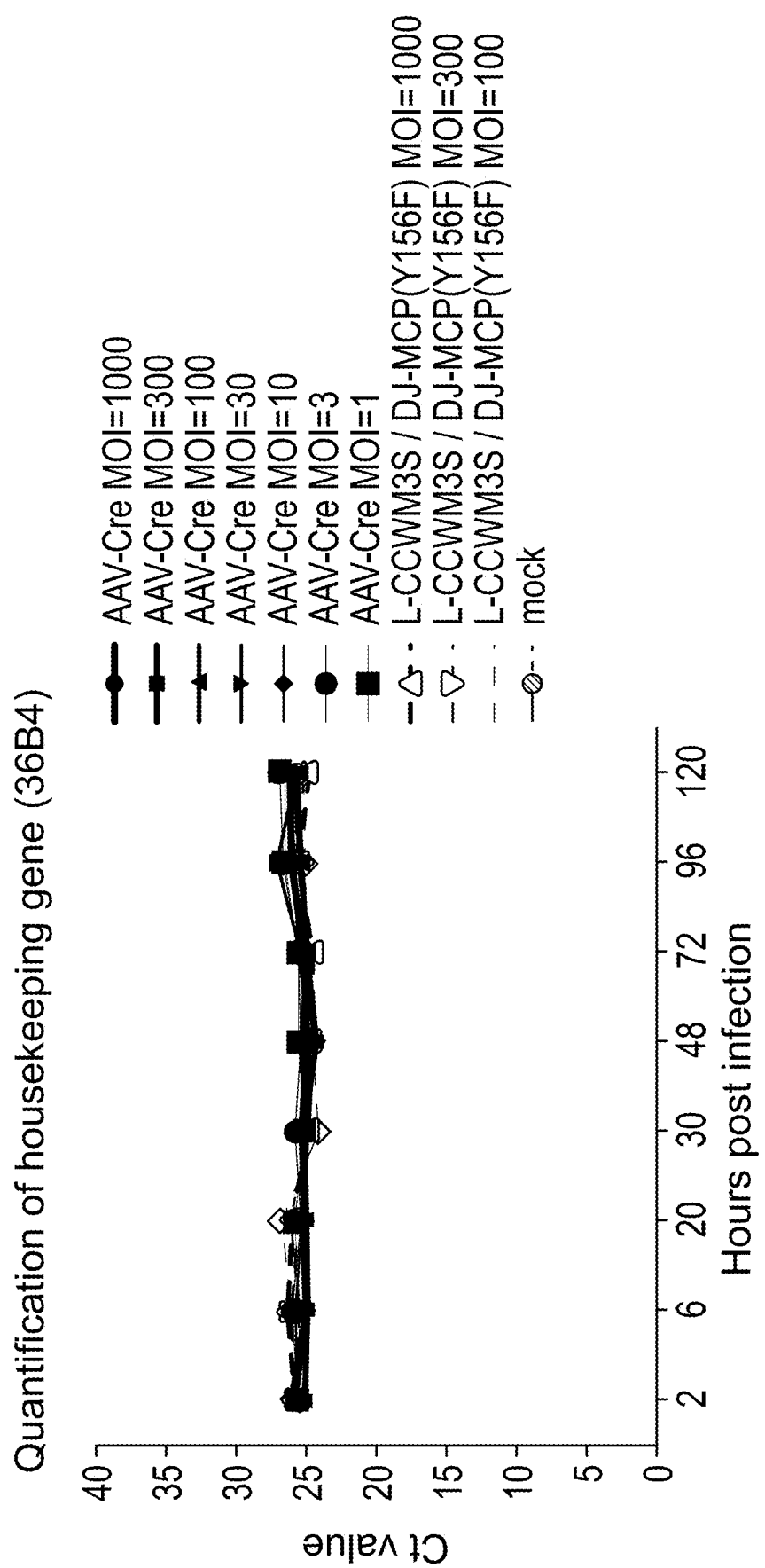

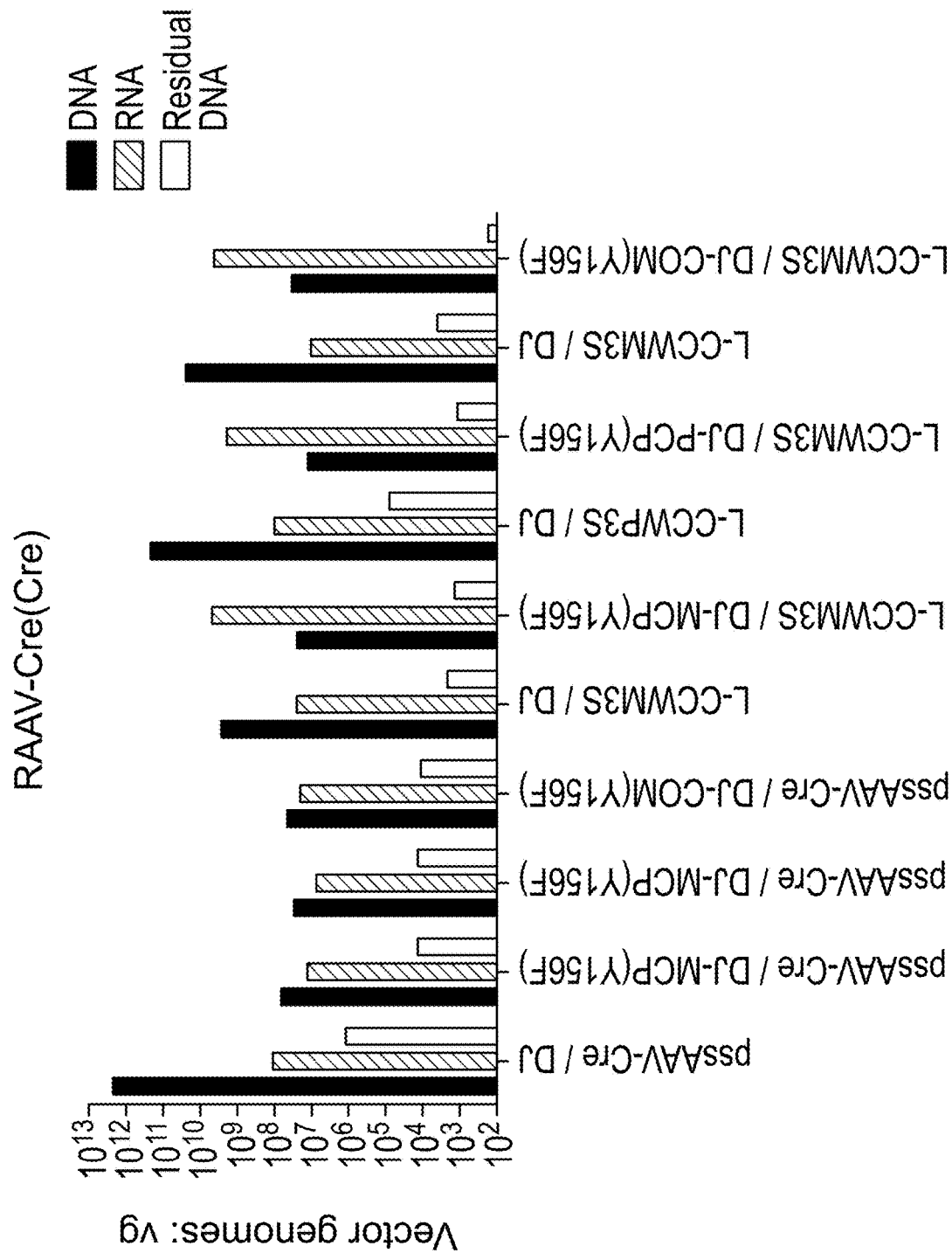

RNA ADENO-ASSOCIATED VIRUS (RAAV) VECTOR AND USES THEREOF

REFERENCE TO RELATED APPLICATION

The instant application is a continuation application, filed under 35 U.S.C. 111(a), of International Patent Application No. PCT/CN2022/075366, filed on Feb. 7, 2022, which claims foreign priority under 35 U.S.C. 365 (b), to International Patent Application No. PCT/CN2021/075874, filed on Feb. 7, 2021, the entire contents of each of the above-referenced applications, including any sequence listing and drawings, are incorporated herein by reference.

SEQUENCE LISTING

The instant application contains a Sequence Listing which has been submitted electronically in ASCII format and is hereby incorporated by reference in its entirety. Said ASCII copy, created on Jul. 19, 2023, is named 132045-00601_SL.txt and is 302,369 bytes in size.

BACKGROUND OF THE INVENTION

Adeno-associated virus (AAV) is a small (about 20 nm in diameter) replication-defective, nonenveloped virus that infects human and other primate species. It belongs to the genus Dependoparvovirus within the family Parvoviridae. Wild type AAV can infect both dividing and non-dividing cells and may incorporate its genome into that of the host cell. Its life cycle is dependent on the presence of a helper virus, such as adenovirus (AdV), hence its name and taxonomy classification.

AAV is found in multiple vertebrate species, including human and non-human primates (NHPs). The current consensus is that AAV does not cause any human diseases, and only causes a very mild immune response. It is composed of an icosahedral protein capsid of about 20-25 nm in diameter, and a single-stranded DNA (ssDNA) genome of about 4.7 kb that can either be the plus (sense) or minus (anti-sense) strand.

The AAV capsid comprises three types of subunit, VP1, VP2 and VP3, totaling 60 copies in a ratio of 1:1:10 (VP1:VP2:VP3). The genome is flanked by two T-shaped inverted terminal repeats (ITRs) at the ends that largely serve as the viral origins of replication and the packaging signal. The rep gene encodes four proteins required for viral replication. The Rep proteins are named after their molecular masses: Rep78, Rep68, Rep52 and Rep40. The cap gene encodes the translation from different start codons. In addition, a third gene, which encodes assembly activating protein (AAP), is encoded within the cap coding sequence in a different reading frame, and has been shown to promote virion assembly.

Currently, thirteen AAV serotypes and numerous variants have been identified, they recognize distinct cell receptors, and thereby display different tissue-type and cell-type tropism profiles. The in vivo tissue tropisms of AAV1-13 have also been well studied in many animal models.

The AAV ITR sequences comprise 145 nucleotides each. The ITR sequences can each form a hairpin for self-priming, which allows primase-independent synthesis of the second DNA strand. The ITRs were also shown to be required for both integration of the AAV DNA into the host cell genome (19th chromosome in humans) and rescue from it as well as for efficient encapsidation of the AAV DNA combined with generation of a fully assembled, DNase-resistant AAV particles.

The AAV2 ITR serves as origin of replication and is composed of two arm palindromes (namely B-B' and C-C') embedded in a larger stem palindrome (A-A'). The ITR can acquire two configurations (i.e., flip and flop). See FIG. 1. The flip and flop configurations have the B-B' and the C-C' palindrome closest to the 3' end, respectively. The 20-nucleotide D sequence or D region is present only once at each end of the AAV genome and thus remains single-stranded.

The ITR also contains a ~22-bp sequence—Rep-binding element (RBE)—that binds the AAV Rep78 and Rep68 proteins in a specific orientation. If the ITR is in the palindromic (hairpinned) configuration, the Rep protein also contacts a 5-base sequence at the tip of one of the short palindromes (RBE'), which activates the Rep DNA helicase and strand-specific endonuclease activities to help AAV replication and packaging (see FIG. 1).

The RBE comprises a tetranucleotide repeat (e.g., 4 repeats) with the consensus sequence of 5'-GNGC-3'. The ATP-dependent DNA helicase activities of Rep78 and Rep68 remodel the A-A' region, generating a stem-loop that locates at the summit the terminal resolution site (trs or TRS) in a single-stranded form. In this configuration, the strand- and site-specific endonuclease catalytic domain of Rep78 and Rep68 introduces a nick at the trs. The nucleotides at the apex of the T-shaped structure correspond to an additional RBE (RBE') that stabilizes the association between the two largest Rep proteins and the ITR.

In AAV life cycle, when AAV DNA is uncoated in the nucleus, the ITR of the incoming single-stranded genome snaps into a hairpin that provides a natural 3'-OH primer for the synthesis of the second strand. This produces a duplex molecule that has a covalently closed (hairpinned) end. The large Rep proteins then bind RBE and RBE' within the hairpin, and the activated endonuclease cleaves one strand at a specific site within a recognition sequence called the terminal resolution site (trs). This creates a new 3'-OH primer that is used to repair the ITR to form a normal blunt-ended duplex molecule. During cleavage, a molecule of Rep78 or Rep68 is covalently attached to the 5'-end phosphate via a tyrosine-phosphate linkage. The ITR is then reconfigured into a double hairpin to produce a 3'-OH primer that directs strand displacement synthesis down the length of the genome using the cellular complexes. This displaces a single strand, which is packaged, and reforms a duplex molecule that is covalently closed at one end, beginning a new cycle of nicking, repair, and strand displacement synthesis. Each time this cycle is repeated, a new single strand is generated for packaging. Because the two ends are identical, the process occurs equally well from both ends, generating both positive and negative strands for packaging.

Since AAV is capable of transducing a wide range of species and tissues in vivo with no evidence of toxicity, and generates relatively mild innate and adaptive immune responses, it has been widely used in gene therapy.

AAV vectors are composed of the same capsid sequence and structure as found in wild-type AAVs (wtAAVs). However, AAV vectors encapsidate genomes that are devoid of all AAV protein-coding sequences and have transgene expression cassettes designed in their place. The only sequences of viral origin are the ITRs, which are needed to guide genome replication and packaging during vector production. The complete removal of viral coding sequences maximizes the packaging capacity of AAV vectors, and contributes to their low immunogenicity and cytotoxicity when delivered in vivo.

Because AAV vectors optimally accommodate genomes that are under 4.7 kb, the payload must be carefully designed to consider not only the transgene sequence but also the inclusion of regulatory elements necessary for gene expression (for example, promoter, enhancer, intron and polyadenylation signal).

A popular AAV vector production method is triple transfection of HEK293T cells, which harbor constitutively expressed AdV E1a and E1b genes, with a packaging plasmid expressing rep and cap genes, a transgene plasmid to be packaged into AAV capsids, and a helper plasmid containing other AdV genes that serve helper function, such as the E2A, E4 and VA RNA genes that are essential for replication, message RNA (mRNA) processing and translation, respectively. Fortunately, the transgene expression cassette that is built with AAV2 ITRs can be packaged into any serotype capsids by merely exchanging the capsid-coding region in the packaging plasmid or helper virus.

AAV vectors recognize and bind distinct cell receptors, and get into the cells by internalization. Intact AAV vector particles in endosomes undergo a series of pH-dependent structural changes necessary for transduction and traffic through the cytosol via the cytoskeletal network. After endosomal escape, AAV vector enters the nucleus through the nuclear pore complex, where it undergoes capsid uncoating to release the genome.

The single-stranded AAV vectors genome that is released in the nucleus is not immediately ready for gene expression until it is converted to a double-stranded form—a requirement of transcription and a rate-limiting step for transduction.

Second strand synthesis is initiated from the self-primed ITR at the 3"-end of the genome. Additionally, double-stranded genomes can be achieved by strand annealing, whereby plus-stranded and minus-stranded genomes that are packaged into separate virions anneal by Watson-Crick base pairing once in the nucleus. The double-stranded genome then undergoes circularization via intra-molecular or inter-molecular genome recombination at the ITRs. This circularization and concatemerization process stabilizes the AAV vectors genome as episomal DNA, leading to gene expression that persists in post mitotic cells (FIG. 2).

CRISPR has brought new momentum to gene therapy. CRISPR is a powerful genome editing tool, and it has shown potential in curing genetic, acquired and infectious diseases. However, delivery of the cellular components for CRISPR is still a major hurdle for its clinical translation. So far, the most successful in vivo gene editing with CRISPR uses AAV as a delivery vector.

However, conventional AAV delivery has suffered from multiple practical difficulties, including 1) off-targeting effects increased by prolonged Cas9 expression, 2) stimulation of Cas9-specific immune responses, 3) high frequency of virus integrations in the CRISPR induced double-stranded breaks. Recent studies confirm the wide spread pre-existing immunity against Cas9 in human population, which might bring an extra challenge to the edited cells if Cas9 is consistently expressing.

Thus, there is a need to improve existing gene editing tools, such as the Cas9-mediated gene editing tools.

SUMMARY OF THE INVENTION

One aspect of the invention provides a ribonucleotide (RNA) sequence capable of being packaged into a DNA virus viral particle, the RNA sequence comprises: (1) an RNA sequence of interest (RSI), e.g., a RNA coding sequence for a gene of interest (GOI), a protein (e.g., a therapeutic protein, an antigen protein, or a gene-editing protein such as a CRISPR/Cas effector enzyme ("a Cas protein" for short), a ZFN protein, a TALEN protein)-encoding RNA, such as, a mRNA, or a non-coding, functional RNA (such as, a transfer RNA (tRNA), a ribosomal RNA (rRNA), a small interfering RNA (siRNA), a short hairpin RNA (shRNA), an antisense RNA, an antisense oligonucleotide, a micro RNA (miRNA), or an RNA component of a CRISPR-Cas (e.g., Cas9, Cas12, Cas13) system, including a guide RNA (or a gRNA), such as, a single guide RNA (or a sgRNA, a chimeric RNA, an RNA chimera), a CRISPR RNA (crRNA), and a tracr RNA), or a precursor thereof; and, (2) an RNA-packaging signal (RPS) capable of interacting, e.g., binding, directly or indirectly, to an RPS-interacting molecule that facilitates packaging of the RNA sequence into the DNA virus viral particle; optionally, a DNA sequence encoding or corresponding to the RNA sequence, or a reverse complement of the DNA sequence, has reduced, diminished, or substantially no capacity of being packaged into the DNA virus viral particle (e.g., the DNA sequence or the reverse complement thereof lacks a DNA packaging signal such as a functional AAV ITR for AAV packaging).

In certain embodiments, the DNA virus viral particle is an AAV viral particle or an oncolytic viral particle.

In certain embodiments, the RPS is located at or near the 5' end of the RSI, at or near the 3' end of the RSI, or internal to the RSI (e.g., inside an intron of an mRNA).

In certain embodiments, the RNA sequence comprises more than one (e.g., 1, 2, 3, or more) RPS that are identical or different.

In certain embodiments, two or more (e.g., 3) of the more than one RPS are adjacent to each other, or are in tandem, via the same or different linkers.

In certain embodiments, the RNA sequence comprises two or more RPS that are not adjacent to each other (e.g., one each located at or near one end of the RNA sequence of interest (RSI)).

In certain embodiments, the RPS comprises a transcribed modified AAV inverted terminal repeat (ITR), wherein the transcribed modified AAV ITR: (a) comprises a transcribed functional Rep-Binding Element (RBE), optionally further comprising a transcribed functional RBE'; and, (b) lacks either a transcribed terminal resolution site (TRS), or a transcribed reverse complement TRS (rcTRS), or both; optionally, the transcribed modified AAV ITR further comprises a transcribed D region sequence (D sequence or D' sequence); and/or optionally, the RPS-interacting molecule is Rep78, Rep68, Rep52, and/or Rep40.

In certain embodiments, the transcribed modified AAV ITR is within the 3' end 1000 nucleotides, 800 nucleotides, 500 nucleotides, 300 nucleotides, or 200 nucleotides of the RNA; optionally, the transcribed modified AAV ITR is 5' to a polyA sequence, a polyA signal sequence (e.g., AAUAAA), or a sequence for RNA transcription termination (e.g., a histone downstream element).

In certain embodiments, the transcribed modified AAV ITR is modified based on a transcribed wild-type flip or flop ITR; optionally, the wild-type flip or flop ITR is from AAV1, AAV2, AAV3A, AAV3B, AAV4, AAV5, AAV6, AAV7, AAVrh74, AAV8, AAV9, AAV10, AAV11, AAV12, or AAV13 (optionally, the wild-type flop ITR has the nucleotide sequence of SEQ ID NO: 1).

In certain embodiments, the transcribed modified AAV ITR lacks both the transcribed TRS and the transcribed rcTRS.

In certain embodiments, the transcribed modified AAV ITR comprises the transcribed D region sequence (optionally, the modified AAV ITR has the nucleotide sequence of SEQ ID NO: 3).

In certain embodiments, the transcribed modified AAV ITR lacks the transcribed D region sequence (optionally, the modified AAV ITR has the nucleotide sequence of SEQ ID NO: 2).

In certain embodiments, the RNA sequence further comprises a second transcribed modified AAV ITR having a second transcribed functional RBE sequence but lacking either a second transcribed TRS or a second transcribed rcTRS or both; optionally, the second transcribed modified AAV ITR further comprises a second transcribed D region sequence.

In certain embodiments, the transcribed modified AAV ITR and the second transcribed modified AAV ITR are identical (or different).

In certain embodiments, the transcribed modified AAV ITR, and the second transcribed modified AAV ITR (if present), comprise a deletion from, a mutation in, or an insertion into a corresponding transcribed wild-type AAV ITR D region sequence or a corresponding transcribed wild-type TRS/rcTRS.

In certain embodiments, the second transcribed modified AAV ITR is within 5' end 1000 nucleotides, 800 nucleotides, 500 nucleotides, 250 nucleotides, or 150 nucleotides of the RNA sequence.

In certain embodiments, the RPS comprises an MS2 sequence, an PP7 binding site, or a com binding site, and the RPS-interacting molecule comprises an RPS-interacting protein (RPSIP) capably of interacting, e.g., binding, directly or indirectly, to the RPS, such as a bacteriophage-derived MS2 coat protein (MCP) for an MS2 sequence, a PP7 bacteriophage coat protein (PCP) for an PP7 binding site, or a phage COM protein (COM) for a com binding site.

In certain embodiments, the RPSIP is associated directly or indirectly with (e.g., fused to) a protein component of the viral packaging system for the DNA virus viral particle (such as Rep78 and/or Rep68 of adeno-associated virus 2 (AAV2), or assembly-activating protein (AAP)).

In certain embodiments, the RNA sequence comprises or preferably does not comprise a transcribed DNA packaging signal, for example, a transcribed wild-type AAV ITR sequence (e.g., the RNA sequence comprises a transcribed modified AAV ITR sequence having an addition, a deletion, and/or a substitution of a nucleotide of a corresponding transcribed wild-type AAV ITR sequence to reduce the DNA packaging capability of the DNA virus viral particle).

In certain embodiments, the RNA sequence further comprises: (1) a transcribed transcription enhancer; (2) a transcribed intron sequence or exon sequence (such as one for enhancing protein expression); (3) a 5' UTR sequence; (4) a 3' UTR sequence; (5) a polyA sequence, or a polyadenylation (polyA) signal sequence and optionally a GU-rich region downstream of the polyA signal sequence; (6) a posttranscriptional regulatory element or sequence, such as a transcribed Woodchuck Hepatitis Virus (WHP) Posttranscriptional Regulatory Element (WPRE) sequence; and/or, (7) a transcription termination sequence (such as a histone downstream element), optionally, the RNA sequence comprises an RPS located 3' to the posttranscriptional regulatory element or sequence, and 5' to the polyA sequence or the polyA signal sequence.

In certain embodiments, the RNA sequence comprises, in 5' to 3' orientation, the RSI, the optional transcribed WPRE sequence; the RPS (such as the transcribed modified AAV ITR, the MS2 sequence, the PP7 binding site, or the com binding site); and the polyA sequence or the polyA signal sequence.

In certain embodiments, the GOI comprises a protein (e.g., a fluorescent protein, a therapeutic protein, an antigen protein, or a gene-editing protein such as a Cas protein, a ZFN protein, a TALEN protein), an enzyme (such as a Cre protein, or a CRISPR/Cas effector enzyme, e.g., Cas9, Cas12, Cas13, or a variant thereof), a structural protein, an mRNA, a non-coding RNA (ncRNA), an siRNA, a piRNA, a short hairpin RNA or shRNA, a microRNA (miRNA) or a precursor thereof (including pre-miRNA and pri-miRNA), a ribosomal RNA (rRNA), an antisense sequence or oligonucleotide (ASO), an RNA component of a CRISPR-Cas system, including a guide RNA (or a gRNA), such as, a single guide RNA (or a sgRNA, a chimeric RNA, an RNA chimera), a CRISPR RNA (crRNA), and a tracr RNA, a guide RNA or gRNA for a CRISPR/Cas effector enzyme, an rRNA, a tRNA, a snoRNA, a snRNA, an exRNA, a scaRNA, a lncRNA, a Xist, and a HOTAIR.

In certain embodiments, the RNA sequence is a single-stranded RNA less than about 8,900 nucleotides in length, less than about 8,000 nucleotides in length, less than about 7,000 nucleotides in length, less than about 6,000 nucleotides in length, less than about 5,200 nucleotides in length, less than about 4,000 nucleotides in length, less than about 3,000 nucleotides in length, less than about 2,000 nucleotides in length, about 4,700-5,200 nucleotides in length, about 4,700-5,000 nucleotide in length, about 4,700-4,800 nucleotides in length, or about 4,700 nucleotides in length.

Another aspect of the invention provides a polynucleotide comprising a cassette encoding the RNA sequence of the invention; optionally, the polynucleotide is a DNA sequence (e.g., a DNA plasmid), optionally comprising a stuffer sequence in the backbone of the DNA plasmid, and/or optionally comprising no functional DNA packaging signal such as AAV ITR.

In certain embodiments, the polynucleotide further comprises a promoter operably linked to and driving the transcription of the RNA sequence encoded by the cassette.

In certain embodiments, the promoter is a ubiquitous promoter.

In certain embodiments, the promoter is a tissue-specific promoter.

In certain embodiments, the promoter is a constitutive promoter.

In certain embodiments, the promoter is an inducible promoter.

In certain embodiments, the polynucleotide further comprises an enhancer that enhances the transcription of the RNA sequence driven by the promoter.

Another aspect of the invention provides a recombinant DNA virus viral particle comprising an RNA genome (such as the RNA sequence of the invention or the RNA sequence transcribed from the polynucleotide of the invention) packaged within the protein shell (such as capsid) of a DNA virus (such as an AAV virus, or an oncolytic virus).

In certain embodiments, the DNA virus is AAV, and the recombinant DNA virus viral particle is a recombinant RNA adeno-associated virus (rRAAV) particle, comprising: (1) an AAV capsid; and, (2) the RNA sequence of the invention or the RNA sequence transcribed from the polynucleotide of the invention packaged within the AAV capsid.

In certain embodiments, the AAV capsid comprises a capsid from an AAV of the serotype AAV1, AAV2, AAV3A, AAV3B, AAV4, AAV5, AAV6, AAV7, AAV8, AAV9, AAV10, AAV11, AAV12, AAV13, AAV-DJ, AAV PHP.eB, Anc80L65, Anc80L65AAP, AAVrh74, or 7m8.

Another aspect of the invention provides a population of recombinant DNA virus viral particles (e.g., rRAAV particles) comprising a plurality of recombinant DNA virus viral particle (e.g., rRAAV particle) of the invention, wherein at least about 10%, 20%, 30%, 40%, 50%, 60%, 70%, 80%, 90%, 95%, 96%, 97%, 98%, 99% or more of the recombinant DNA virus viral particles (e.g., rRAAV particles) within the population have the RNA sequence of the invention or the RNA sequence transcribed from the polynucleotide of the invention packaged therein.

Another aspect of the invention provides a host cell comprising the RNA sequence of the invention, the polynucleotide of the invention, the RNA sequence transcribed from the polynucleotide of the invention, the recombinant DNA virus viral particle (e.g., rRAAV particle) of the invention, and/or the population of recombinant DNA virus viral particles (e.g., rRAAV particles) of the invention.

In certain embodiments, the host cell further comprises a viral packaging system that facilitates packaging of the RNA sequence of the invention or the RNA sequence transcribed from the polynucleotide of the invention into the DNA virus viral particle.

In certain embodiments, the viral packaging system comprises: (1) an AAV rep gene (e.g., coding sequence for Rep78, Rep68, Rep52, and/or Rep40) and an AAV cap gene (e.g., coding sequence for VP1, VP2, VP3, AAP, and/or MAAP), under the transcriptional control of one or more promoters that drive the transcription of the rep gene and cap gene, or the expression products thereof; (2) one or more coding sequences for one or more proteins required for AAV packaging, such as adenoviral E2A, E4, and VA genes, or the one or more proteins; and (3) the RPS-interacting molecule or a coding sequence thereof; optionally, the capacity of the viral packaging system of packaging a DNA sequence into the DNA virus viral particle is reduced, diminished, or substantially eliminated by, for example, (1) removing a part or all of the DNA packaging signals such as AAV ITR on the polynucleotide encoding the RNA sequence of the invention or on the polynucleotide of the invention, (2) modifying, e.g., mutating, the AAV rep gene, the AAV cap gene, and/or the one or more coding sequences for one or more proteins required for AAV packaging to reduce, diminish, or substantially eliminate the capacity of the respective translated protein to facilitate the packaging of the DNA sequence into the DNA virus viral particle (e.g., a Y156F mutation in the common sequence of Rep78 and Rep68 proteins, KDE-mu, or EKE-mu); and/or (3) enlarging the size of the polynucleotide encoding the RNA sequence of the invention or the polynucleotide of the invention.

In certain embodiments, the host cell is a mammalian cell (such as HEK293 cells) or an insect cell (such as Sf9 or Sf21 cells).

Another aspect of the invention provides a method of generating the recombinant DNA virus viral particle (e.g., rRAAV particle) of the invention or the population of recombinant DNA virus viral particles (e.g., rRAAV particles) of the invention, the method comprising: a) culturing the host cell of the invention for a sufficient time, and b) harvesting the recombinant DNA virus viral particle or the population of recombinant DNA virus viral particles.

In certain embodiments, the method further comprises isolating or purifying the recombinant DNA virus viral particle or the population of recombinant DNA virus viral particles.

Another aspect of the invention provides a method of generating a recombinant DNA virus viral particle (e.g., rRAAV particle) or a population of recombinant DNA virus viral particles, the method comprising: a) contacting a viral packaging system (e.g., a AAV packaging system) with the RNA sequence of the invention or the RNA sequence transcribed from the polynucleotide of the invention for a period of time sufficient to produce the recombinant DNA virus viral particle or the population of recombinant DNA virus viral particles, and b) harvesting the recombinant DNA virus viral particle or the population of recombinant DNA virus viral particles; and, optionally, c) isolating or purifying the harvested recombinant DNA virus viral particle or population of recombinant DNA virus viral particles.

In certain embodiments, the viral packaging system (e.g., a AAV packaging system) comprises: (1) one or more proteins for assemblying the protein shell (e.g., VP1, VP2, and/or VP3 for assembling AAV capsid) of the DNA virus viral particle for packaging the RNA sequence, or one or more coding sequences thereof; (2) one or more proteins (e.g., Rep78, Rep68, Rep52, and/or Rep40 for AAV packaging) for facilitating the assemblying of the protein shell and/or the packaging of the RNA sequence into the protein shell of the DNA virus viral particle, or one or more coding sequences thereof (e.g., adenoviral E2a, E4, and VA genes); and (3) the RPS-interacting molecule or a coding sequence thereof; optionally, the capacity of the viral packaging system of packaging a DNA sequence into the DNA virus viral particle is reduced, diminished, or substantially eliminated by, for example, (1) removing a part or all of the DNA packaging signals such as AAV ITR on the polynucleotide encoding the RNA sequence of the invention or on the polynucleotide of the invention, (2) modifying, e.g., mutating, the AAV rep gene, the AAV cap gene, and/or the one or more coding sequences for one or more proteins required for AAV packaging to reduce, diminish, or substantially eliminate the capacity of the respective translated protein to facilitate the packaging of the DNA sequence into the DNA virus viral particle (e.g., a Y156F mutation in the common sequence of Rep78 and Rep68 proteins, KDE-mu, or EKE-mu); and/or (3) enlarging the size of the polynucleotide encoding the RNA sequence of the invention or the polynucleotide of the invention.

Another aspect of the invention provides a system of packaging the RNA sequence of the invention or the RNA sequence transcribed from the polynucleotide of the invention into a DNA virus viral particle, comprising: (1) one or more proteins for assemblying the protein shell (e.g., VP1, VP2, and/or VP3 for assembling AAV capsid) of the DNA virus viral particle for packaging the RNA sequence, or one or more coding sequences thereof; (2) one or more proteins (e.g., Rep78, Rep68, Rep52, and/or Rep40 for AAV packaging) for facilitating the assemblying of the protein shell and/or the packaging of the RNA sequence into the protein shell of the DNA virus viral particle, or one or more coding sequences thereof (e.g., adenoviral E2a, E4, and VA genes); and (3) the RPS-interacting molecule or a coding sequence thereof; optionally, the capacity of the viral packaging system of packaging a DNA sequence into the DNA virus viral particle is reduced, diminished, or substantially eliminated by, for example, (1) removing a part or all of the DNA packaging signals such as AAV ITR on the polynucleotide encoding the RNA sequence of the invention or on the polynucleotide of the invention, (2) modifying, e.g., mutating, the AAV rep gene, the AAV cap gene, and/or the one or more coding sequences for one or more proteins required for AAV packaging to reduce, diminish, or substantially eliminate the capacity of the respective translated protein to facilitate the packaging of the DNA sequence into the DNA virus viral particle (e.g., a Y156F mutation in the common sequence of Rep78 and Rep68 proteins, KDE-mu, or EKE-mu); and/or (3) enlarging the size of the polynucleotide encoding the RNA sequence of the invention or the polynucleotide of the invention.

Another aspect of the invention provides a method of delivering a gene of interest (GOI) into a cell, a plant, or an animal, the method comprising contacting the cell, the plant, or the animal with the recombinant DNA virus viral particle (e.g., rRAAV particle) of the invention, the population of the recombinant DNA virus viral particles (e.g., rRAAV particles) of the invention, or the recombinant DNA virus viral particle (e.g., rRAAV particle) or the population of the recombinant DNA virus viral particles (e.g., rRAAV particles) produced by the method of the invention, wherein the GOI is encoded by the RNA sequence of the invention.

Another aspect of the invention provides a method of delivering an RNA sequence of interest (RSI) into a cell, a plant, or an animal, the method comprising contacting the cell, the plant, or the animal with the recombinant DNA virus viral particle (e.g., rRAAV particle) of the invention, the population of the recombinant DNA virus viral particles (e.g., rRAAV particles) of the invention, or the recombinant DNA virus viral particle (e.g., rRAAV particle) or the population of the recombinant DNA virus viral particles (e.g., rRAAV particles) produced by the method of the invention.

Another aspect of the invention provides a method of diagnosing, preventing, or treating a disease or disorder in a subject in need thereof, comprising administrating to the subject a therapeutically effective amount or dose of the population of the recombinant DNA virus viral particles (e.g., rRAAV particles) of the invention or produced by the method of the invention.

Another aspect of the invention provides a use of the recombinant DNA virus viral particle (e.g., rRAAV particle) of the invention, the population of the recombinant DNA virus viral particles (e.g., rRAAV particles) of the invention, or the recombinant DNA virus viral particle (e.g., rRAAV particle) or the population of the recombinant DNA virus viral particles (e.g., rRAAV particles) produced by the method of the invention in the manufacture of a medicament for diagnosing, preventing, or treating a disease or disorder in a subject in need thereof.

It should be understood that any one embodiment of the invention described herein, including those described only in the examples or claims, or only in one aspects/sections below, can be combined with any other one or more embodiments of the invention, unless explicitly disclaimed or improper.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1B and 1C show multi-sequence alignments of 5' (SEQ ID NOS 101, 25, 27, 29, 31, 33, 35, and 37, respectively, in order of appearance) (FIG. 1B) and 3' (SEQ ID NOS 102, 26, 28, 30, 32, 34, 36, and 38, respectively, in order of appearance) (FIG. 1C) ITR sequences from AAV1-7.

FIG. 5A is a flowchart for RAAV titration. FIG. 5B shows primers and probes for Q-PCR.

FIG. 6A shows titration of CITWS group. FIG. 6B shows titration of CTWIS group. FIG. 6C shows titration of CITWIS group.

FIG. 7A shows titration of RAAV-dITR-D vectors. FIG. 7B shows in vitro infection of RAAV-dITR-D vectors. The same volume (5 μL) of purified RAAV-dITR-D vectors had been used to infect $2\times10^5$ HEK293T cells in vitro. Fluorescence photos were taken 3 and 5 days post infection.

FIG. 8B shows the results of specific DNA and RNA packaging of the AAV-tdTomato and RAAV-tdTomato constructs by detecting the WPRE sequence in the packaged DNA or RNA. Efficient RNA packaging occurred when both the heterologous RNA Packaging Signal (RPS) and its cognate RPS binding protein (RBP, e.g., MCP for MS2) are both present.

FIG. 9A is a schematic diagram (not to scale) of the various plasmids, including the plasmid with the longer backbone sequence due to the inserted stuffer region (L-CTWM3S), used to generate the results in FIGS. 9B and 9C. FIG. 9B shows specific DNA packaging of AAV-tdTomato and RAAV-tdTomato by detecting the presence of CAG promoter sequence using CAG-specific primer pairs. FIG. 9C shows specific DNA and RNA packaging of AAV-tdTomato and RAAV-tdTomato by detecting the presence of WPRE sequence using WPRE-specific primer pairs. The results showed a surprising ~2-fold reduction of undesired DNA packaging by using enlarged/longer plasmid backbone sequence with stuffer sequences.

FIGS. 10A and 10B show efficient packaging of the Cre transgene into RAAV using the MS2/MCP packaging system. FIG. 10A shows specific DNA packaging of AAV-Cre and RAAV-Cre by detecting the presence of CAG promoter sequence using CAG-specific primer pairs. Note that the CAG sequence is not present in the RAAV RNA sequence, and the detected RNA signal was background. FIG. 10B shows specific DNA and RNA packaging of AAV-Cre and RAAV-Cre by detecting the presence of WPRE sequence using WPRE-specific primer pairs.

FIGS. 11A-11B show that RPS/RBP improved RNA packaging of conventional AAVs. FIG. 11A shows the results of AAV genome packaging in the presence of only DNA packaging signals (i.e., ITRs). FIG. 11B shows the AAV genome packaging in presence of both DNA packaging signals (ITRs) and RNA packaging signals (MS2X3).

FIGS. 12A-12D show the results of optimizing the RAAV system and identification of the properties of optimized RAAVs. FIG. 12A represents the specific genome packaging of AAV-Cre and RAAV-Cre by detecting WPRE sequence. FIG. 12B represents the specific genome packaging of AAV-Cre and RAAV-Cre by detecting Cre sequence. FIG. 12C shows silver staining analysis of the composition of the AAV and RAAV particles. FIG. 12D shows the morphology analysis of the AAV and RAAV particles by TEM, scale bar 100 nm.

FIG. 13A shows that engineered Rep reduced DNA packaging of the conventional AAV. FIG. 13B shows reduction of DNA packaging in RAAV by using various mutant MCP fusion proteins, including double mutant MCP fusion protein DJ-MCPX2.

FIGS. 14A-14D show that the RAAV viral particles express functional transgene-encoded proteins. Samples are designated the same way in FIGS. 14A-14C. FIG. 14A shows a time course of Cre mRNA levels in infected cells. FIG. 14B shows fold change of Cre mRNA levels in infected cells from 20 hrs post infection. FIG. 14C shows a time course of Cre DNA levels in infected cells. FIG. 14D shows percentage of infected cells quantified by flow cytometry 5 days after infection, n=2 replicates.

FIGS. 15A-15D show results of DNA and mRNA analysis for the AAV or RAAV infected Ai9-MEF cells. FIG. 15A shows Ct value of the Cre mRNA. FIG. 15B shows Ct value of the Cre DNA. FIG. 15C shows Ct value of the GAPDH mRNA. FIG. 15D shows Ct value of the 36B4 DNA.

FIG. 17A shows Western blot analysis of the lifespan of Cre protein in infected cells after conventional AAV delivery.

FIG. 17B shows Western blot analysis of the lifespan of Cre protein in infected cells after RAAV delivery.

FIG. 18 shows additional functional RPS/RBP pairs—the PP7/PCP pair, and the com/COM pair—tested in the RAAV system.

FIG. 19 shows that the RAAV system is applicable for various AAV serotypes, including AAV-DJ, AAV5, AAV8, and AAV9.

FIG. 20A represents the specific genome packaging of RAAV-Cre by detecting Cre sequence. FIG. 20B shows comparison of the RNA packaging efficiency of RAAVs with AAP N- or C-terminal fusions (AM or MA fusion constructs).

FIG. 21A shows transfer of high dose of AAV-Cre into the hippocampus of Ai9-Mice. FIG. 21B shows transfer of low dose of AAV-Cre into the hippocampus of Ai9-Mice. FIG. 21C shows transfer of high dose of RAAV-Cre into the hippocampus of Ai9-Mice.

DETAILED DESCRIPTION OF THE INVENTION

1. Overview

Figure 1A:
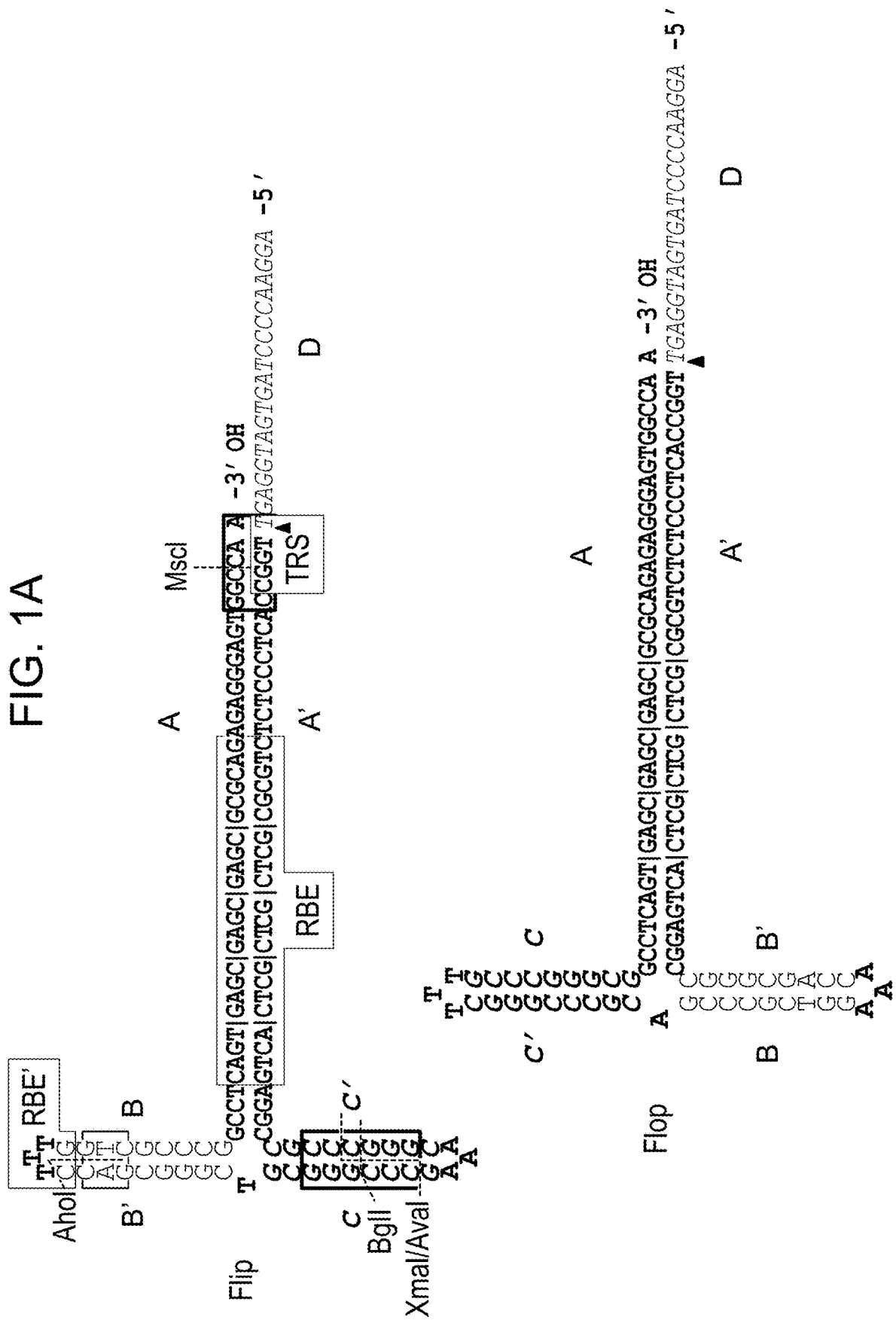
FIG. 1A shows the structure and sequence of the wild type ITR of AAV2, including the A:A' stem region sequences, the B:B' and C:C' T region sequences, and the unpaired D region sequence, in both the flip (SEQ ID NO: 5) and flop (SEQ ID NO: 28) configuration of 3' ITR. The RBE, RBE' and the TRS are also shown.

The invention described herein provides a recombinant viral particle comprising a DNA virus protein shell, and a "vector genome" comprising RNA, such as single-stranded RNA (rather than DNA). The "vector genome" may not be a typical viral RNA, in that it may have very little, if any, virus-originated sequences, other than the RNA Packaging Signal (RPS) described herein below. That is, the DNA virus normally or naturally encapsidates a DNA viral vector genome inside the protein shell, while the recombinant version of the DNA virus viral particle as described herein encapsidates instead an RNA. By "RNA" or "ribonucleic acid" it means a stretch of ribonucleotides each composed of a phosphate, a ribose, and a base (A (adenine), U (uracil), G (guanine), or C (cytosine)), each of which ribonucleotides may be modified (for example, base-modified, glycosyl-modified, phosphate-modified, e.g., oxygen-modified, fluorine-modified, sulphur-modified, pseudo-modified (e.g., pseudo-uridine-modified), methylated, capped (e.g., 5-capped)) or unmodified, and, optionally, fused directly or indirectly with a stretch of deoxyribonucleotides each composed of a phosphate, a deoxyribose, and a base (A (adenine), T (thymine), G (guanine), or C (cytosine)), each of which deoxyribonucleotides may be modified (for example, base-modified, glycosyl-modified, phosphate-modified, e.g., oxygen-modified, fluorine-modified, sulphur-modified, pseudo-modified, methylated, capped (e.g., 5-capped)) or unmodified, e.g., a RNA-DNA chimera, a DNA-RNA-DNA chimera, a RNA-DNA-RNA chimera.

A typical (non-limiting) example of such a recombinant DNA virus viral particle is adeno-associated virus (AAV), which normally/naturally encapsidates a single-stranded DNA (ssDNA) vector genome. Another non-limiting example of such DNA virus is an oncolytic DNA virus, such as an oncolytic herpes virus (e.g., herpes simplex virus or HSV), an oncolytic adenovirus, a vaccinia virus (VACV), vesicular stomatitis virus (VSV), etc.

The invention is partly based on the surprising discovery that, transcribed AAV ITR, in RNA form, can facilitate high efficiency direct packaging of transcribed RNA encompassing such transcribed AAV ITR into conventional AAV viral particles.

The invention described herein is also partly based on the surprising discovery that, other than the transcribed AAV ITR (RNA), certain artificial or heterologous RNA sequences and their cognate/corresponding/native RNA binding proteins can also serve as pairs of RNA Packaging Signals (RPS) and RPS-Interacting Proteins (RPSIPs) to replace the function of wild-type packaging signal sequences and interacting proteins useful for DNA virus packaging, thus packaging an RNA into a DNA virus protein shell that normally/naturally encapsidates a DNA vector genome.

For example, in wild-type AAV, the ITR sequences at the 5' and 3' ends of the DNA vector genome comprise sequence elements such as Rep-Binding Element (RBE) and RBE' that can interact with the Rep proteins (such as Rep68 and Rep78). The Rep proteins bind the ITR and facilitate the packaging of AAV ssDNA vector genome comprising such ITR sequence elements into the AAV viral particle.

The inventors have discovered that, by providing, as an RPS, a transcribed ITR sequence, and/or an artificial or heterologous RNA sequence, such as the MS2 sequence, to an RNA sequence of interest (RSI), the resulting RNA sequence comprised of the RPS and the RSI can be efficiently packaged into an AAV viral protein shell in the presence of MCP—the bacteriophage-derived MS2 coat protein (MCP) that naturally binds MS2. The ability of the artificial RPS/RPSIP pair—e.g., MS2/MCP—to facilitate RNA packaging into a DNA virus protein shell, does not depend on the presence of, but can function independently of, the native ITR packaging signal for DNA packaging. In a sense, the heterologous MS2-MCP pair constitutes an artificial system of RPS and RPSIP pair that can effectively replace the natural ITR-Rep DNA packaging system, with the former efficiently facilitates RNA packaging. Such RNA-containing DNA virus, such as AAV, maybe referred herein as R-DNA viral particle (or RAAV in the case of AAV), or recombinant R-DNA viral particle (or rRAAV in the case of AAV).

The R-DNA viral particle and RAAV viral particles of the invention can be used to deliver the RNA transcript of any transgene or gene of interest (GOI) of suitable length (e.g., within the packaging limit of the various DNA virus or AAVs) or any guide RNA to a host cell compatible with the tropism of the DNA viral protein shell or AAV viral capsid shell. As used herein, the recombinant DNA viral particles such as recombinant AAV vectors, vector genomes, and recombinant AAV viral particles or recombinant AAV particles, are referred to herein as rRAAV vectors (recombinant RNA adeno-associated virus vectors), vector genomes, and recombinant RAAV (rRAAV) viral particles or rRAAV particles, respectively (the "rRAAV vectors" and "rRAAV particles" are used exchangeably herein).

Specifically, on the one hand, just like any normal or conventional AAV vectors, the subject RAAV vectors can also be composed of any of the same capsid shells found in any wild-type AAVs carrying DNA as the viral genetic material. Thus, the subject RAAV vectors possess all the usual advantages derived from the AAV shell, such as specific/broad tropism and low immunogenicity.

However, on the other hand, the genome of the subject RAAV vectors are comprised of RNAs (e.g., mRNAs), which have short lifespans, and thereby leading to a transient expression of any encoded gene product on such RNA genetic material.

Such transient expression is desired in at least some cases. For example, the RAAV vectors of the invention are advantageous for in vivo DNA gene editing, since time-restricted exposure to RAAV-encoded DNA gene editors (such as the mRNA coding sequence for a CRISPR/Cas system effector enzyme Cas9 and variants thereof fused to a base editor) may enable efficient gene editing. Such transiently expressed DNA editors also improves the safety profile of the gene therapy, by reducing off-target gene targeting, and reducing immunogenicity compared to the persistent expression of the same DNA gene editors expressed from conventional DNA-based AAV vectors.

In addition, compared to traditional DNA-based AAV vectors, the subject RAAV vectors can carry longer transgenes, because of the exclusion of at least the promoter (and also any non-transcribed enhancer sequences that may be) required for expression of the GOI encoded by a DNA-based AAV vector.

Although the subject rRAAV vectors have different sequence elements and organization compared to traditional DNA-based AAV vectors, the rRAAV viral particles have the same entry and intracellular-trafficking processes as the conventional DNA-based AAV vectors. However, they have quite different fates after entering into the host cell nucleus. After entering into the nucleus, the mRNA genome of the subject RAAV vector is released and subsequently transported to the cytoplasm, leading to translation. As is understood, mRNAs generally have short lifespans, ranging from several minutes to days, and are eventually degraded via many cellular mechanisms. However, the limited mRNA lifespan still enables the host cell to complete the protein synthesis, often without the delay due to the 2' strand cDNA synthesis in DNA-based AAV vectors, and allowing the encoded proteins to function rapidly.

Numerous such RPS/RPSIP pairs can be used for RNA packaging into DNA virus. The inventors have demonstrated at least two additional such pairs, including the PP7 sequence and the PP7 bacteriophage coat protein (PCP), and the com sequence and the phage COM protein (COM), that efficiently package RNA comprising the heterologous RPS (i.e., PP7 and com sequences, respectively). The three pairs of RPS/RPSIP as demonstrated encompass at least two categories. Unlike MS2/MCP and PP7/PCP that are natural viral packaging systems, com/COM is not a natural viral packaging system but known to be transcription regulators that play roles in the transcription initiation of the bacteriophage Mu mom gene. Numerous transcribed modified AAV ITR sequences can also be used as RPS of the invention.

The invention described herein is also not limited to a specific serotype of DNA virus (e.g., a specific AAV serotype). The inventors have demonstrated efficient packaging of RNA sequences with suitable RPS into representative AAV viruses including AAV5, AAV8, AAV9, and AAV-DJ, using in conjunction with compatible RPSIP in each case.

The invention described herein is also based on the discovery that the efficiency of packaging undesired DNA into natural DNA virus viral particles can be decreased by several independent approaches.

In certain embodiments, the undesired DNA packaging efficiency can be reduced by increasing the overall size of the DNA vector from which the RNA of interest is transcribed. For example, in the often used triple transfection method for AAV production, the gene of interest (GOI) can be carried by a first plasmid, the required Rep and Cap proteins are encoded by the rep and cap genes on a second plasmid, while the other AAV packaging required components are provided by a third plasmid. According to this embodiment of the invention, the RNA sequence to be packaged into the DNA virus can be transcribed from the first plasmid, and the overall size of the first plasmid can be artificially increased by including a random stuffer sequence (e.g., an intron), such as a stuffer sequence that is at least about 1 kb, 2 kb, 3 kb, 4 kb, 5 kb or more in length, or a stuffer sequence that increases the overall size of the first plasmid by 1 kb, 2 kb, 3 kb, 4 kb, 5 kb or more, e.g., to about 6 kb, 7 kb, 8 kb, 9 kb, 10 kb or more, etc.

In certain other embodiments, the undesired DNA packaging efficiency can be reduced by inhibiting the function of a canonical element that facilitates DNA packaging. Such a canonical element for DNA packaging may include a DNA sequence (such as an element of the AAV ITR sequence that facilitates DNA packaging, including the trs sequence, the RBE or RBE' sequence, or the entire ITR sequence of an AAV); and/or a protein element participating in the DNA packaging, such as, a protein that interacts with the DNA sequence (such as a mutant Rep68 or Rep 78 protein that lacks or has diminished trs-endonuclease activity).

Thus, one aspect of the invention provides a ribonucleotide (RNA) sequence capable of being packaged into a DNA virus viral particle, such as a DNA virus that naturally packages DNA, wherein the RNA sequence comprises: (1) an RNA sequence of interest (RSI); and, (2) an RNA-packaging signal (RPS) capable of interacting, e.g., binding, directly or indirectly to an RPS-interacting molecule (e.g., an RPS-interacting protein or RPSIP) that facilitates packaging of the RNA sequence into the DNA virus viral particle.

Such an RNA sequence can comprise any RSI (RNA), which may be encoded by "a gene of interest" or "GOI" (DNA).

As used herein, "a gene of interest" or "GOI" includes any coding sequence for a protein or polypeptide, including intron and exon sequences, and/or coding sequence for any non-translated RNA or non-coding RNA (ncRNA, such as siRNA, piRNA, short hairpin RNA or shRNA, microRNA or miRNA or precursors thereof including pre-miRNA and pri-miRNA, antisense sequence or oligonucleotide (ASO), guide RNA or gRNA for CRISPR/Cas, rRNA, tRNA, snoRNA, snRNA, exRNA, scaRNA, lncRNA, Xist, and HOTAIR, etc.).

Similarly, representative (non-limiting) RSI includes, for example, a protein (e.g., a therapeutic protein, an antigen protein, or a gene-editing protein such as a CRISPR/Cas effector enzyme ("a Cas protein" for short), a ZFN protein, a TALEN protein)-encoding RNA, such as an mRNA, or a non-coding, functional RNA (such as a transfer RNA (tRNA), a ribosomal RNA (rRNA), a transfer-messenger RNA (tmRNA), a small interfering RNA (siRNA), a short hairpin RNA (shRNA), an antisense RNA or oligonucleotide (ASO), a micro RNA (miRNA), an RNA aptamer, or an RNA component of a CRISPR-Cas (e.g., Cas9, Cas12, Cas13) system, such as, a single guide RNA (or an sgRNA, a chimeric RNA, an RNA chimera), a CRISPR RNA (crRNA) and a tracr RNA), or a precursor thereof, or an RNA component of a RISC complex or RNAi pathway (such as shRNA, miRNA, or siRNA), a regulatory RNA, Piwi-interacting RNAs (piRNAs), small nucleolar RNAs (snoRNAs), a long non-coding RNA (lncRNA) (including intergenic lincRNA, intronic ncRNA, and sense/antisense lncRNA), a long intervening/intergenic noncoding RNA (lincRNA), an enhancer RNA, a bacterial small RNA (sRNA), snRNA, exRNA, scaRNA, Xist, and HOTAIR, and a precursor thereof.

The RNA sequence of the invention or GOI can comprise one coding sequence, or more than one (e.g., 2, 3, 4, 5, 6, 7, 8, 9, 10 or more) coding sequences. The length of the coding sequence, or the combined length of all coding sequences, may be no more than the maximum length of RNA that can be packaged into a particular or chosen DNA virus viral particle (e.g., AAV viral particle), which can differ from one specific DNA virus (e.g., AAV) viral particle from another.

In certain embodiments, a DNA sequence encoding or corresponding to the RNA sequence of the invention, or a reverse complement of the DNA sequence, has reduced, diminished, or substantially no capacity of being packaged into the DNA virus viral particle. For example, the DNA sequence may encode the RNA sequence of the invention (e.g., the DNA sequence has the reverse complement sequence of the RNA sequence of the invention). The DNA sequence may also correspond to the RNA sequence of the invention, in that the DNA sequence has otherwise identical nucleotide sequence as the RNA sequence of the invention, except that the DNA sequence has T's, instead of the U's in the RNA sequence of the invention. Regardless, the DNA sequence or the reverse complement thereof may lack a functional DNA packaging signal for packaging into the DNA virus viral particle, such as an AAV ITR for AAV packaging, such that the DNA sequence or the reverse complement thereof (DNA) has reduced, diminished, or substantially no capacity of being packaged into the DNA virus viral particle.

In certain embodiments, the RNA sequence of the invention is transcribed from a DNA construct, such as transcribed from a DNA plasmid encoding the RNA sequence, wherein the DNA construct/plasmid comprises a stuffer sequence (e.g., an intron sequence) in its backbone sequence to enhance packaging of the RNA sequence of the invention, and/or to reduce undesired packaging of DNA into the DNA virus viral particle. For example, the RNA sequence of the invention can be transcribed from a DNA construct/plasmid, and the overall size of the DNA construct/plasmid can be artificially increased by including a random DNA stuffer sequence, such as a stuffer sequence that is at least about 1 kb, 2 kb, 3 kb, 4 kb, 5 kb or more in length, or a stuffer sequence that increases the overall size of the DNA construct/plasmid by 1 kb, 2 kb, 3 kb, 4 kb, 5 kb or more, e.g., to about 6 kb, 7 kb, 8 kb, 9 kb, 10 kb or more, etc. The stuffer sequence can be located upstream (e.g., immediately upstream) of the transcription unit comprising the coding sequence for the RNA sequence of the invention (see FIG. 9A, in which a long stuffer sequence of >3 kb is inserted immediately upstream of a CAG promoter that drives the transcription of an exemplary RNA sequence of the invention). In certain embodiments, the stuffer sequence is inserted immediately upstream of a promoter operably linked to the codon sequence for the RNA sequence of the invention. Optionally, in some embodiment, the coding sequence for the RNA sequence of the invention is devoid of a functional natural DNA packaging signals for the DNA virus viral particle, such as devoid of a functional ITR sequence that supports packaging into an AAV viral particle.

In certain embodiments, the RNA sequence of the invention is capable of being packaged into a DNA virus viral particle that is an AAV viral particle. Any AAV virus can be used to package the RNA sequence of the invention, including, but not limited to, AAV1, AAV2, AAV3A, AAV3B, AAV4, AAV5, AAV6, AAV7, AAV8, AAV9, AAV10, AAV 11, AAV 12, AAV 13, AAVrh10, AAVrh74, AAVhu32, AAVhu37, AAV-DJ, AAV PHP.eB, Anc80L65, Anc80L65AAP, AAVrh74, or 7m8.

In certain embodiments, the RNA sequence of the invention is capable of being packaged into a DNA virus viral particle that is an oncolytic viral particle. Exemplary (non-limiting) oncolytic viral particles include: oncolytic herpes virus (e.g., herpes simplex virus or HSV), an oncolytic adenovirus, a vaccinia virus (VACV), vesicular stomatitis virus (VSV), etc.

The location of the RPS in the RNA sequence of the invention can be flexible. In certain embodiments, the RPS is located at or near the 5' end of the RNA sequence of the invention, at or near the 3' end of the RNA sequence of the invention, or internal to the RNA sequence of the invention. In certain embodiments, the RPS is located at or near the 5' end of the RNA sequence of interest (RSI), at or near the 3' end of the RNA sequence of interest (RSI), or internal to the RNA sequence of interest (e.g., inside an intron of an mRNA).

There can be one or more RPS in the RNA sequence of the invention. In certain embodiments, the RNA sequence of the invention comprises more than one (e.g., 1, 2, 3, or more) RPS that are identical or substantially identical. In certain embodiments, the RNA sequence of the invention comprises more than one (e.g., 1, 2, 3, or more) RPS, and at least two of which are different from each other.

In cases where more than one RPS are present on the RNA sequence of the invention, at least two of the more than one RPS are adjacent to each other, such as in tandem, with an optional linker sequence in between. The linker between any two adjacent RPS sequences may be the same or different. The linker sequence may be a randomized RNA sequence with no substantial secondary structure, no known functional sequences or elements, and/or may be less than 50% in GC content. The length of the linker may be any where between 1-1 kb, 1-500 bases, 1-200 bases, 1 to about 100 bases, 1 to about 60 bases, about 5 to about 55 bases, about 10 to about 30 bases, or about 15-25 bases.

In certain embodiments, the RNA sequence of the invention comprises 3 RPS sequences adjacent to one another, separated by two linker sequences, each independently about 20 or about 50 bases. For example, the first two of three identical RPS sequences may be separated by a linker of 20 bases, and/or the last two of the RPS sequences may be separated by a linker of 51 bases.

In certain embodiments, the RNA sequence of the invention comprises more than one RPS (e.g., 1, 2, 3, 4, or 5 RPS), wherein at least two of the more than one RPS are not adjacent to each other. For example, one of the RPS may be located at the 5' end of the RNA sequence of the invention, while another RPS may be located at the 3' end of the RNA sequence of the invention, and an optional $3^{rd}$ RPS may be located inside an intron of an mRNA as the RSI within the RNA sequence of the invention. A $4^{th}$ and/or a $5^{th}$ RPS may be located close or adjacent to any one the first, second, or third RPS.

In certain embodiments, the RNA sequence of the invention comprises at least two (e.g., two or more) RPS sequences that are not adjacent to each other, e.g., one each located at or near one end of the RNA sequence of interest (RSI).

In certain embodiments, the RPS comprises a transcribed modified AAV inverted terminal repeat (ITR), wherein the transcribed modified AAV ITR (a) comprises a transcribed functional Rep-Binding Element (RBE), optionally further comprising a transcribed functional RBE'; and, (b) lacks either a transcribed terminal resolution site (TRS), or a transcribed reverse complement TRS (rcTRS), or both. In certain embodiments, the transcribed modified AAV ITR further comprises a transcribed D region sequence (D sequence or D' sequence). In certain embodiments, the RPS-interacting molecule is Rep78, Rep68, Rep52, and/or Rep40.

As used herein, "AAV viral particle" includes viral particles comprising any wild-type capsids of adeno-associated virus (AAV) (belonging to the genus Dependoparvovirus, which in turn belongs to the family Parvoviridae), as well as engineered or variants thereof having modified sequence and/or tissue or host tropism.

As used herein, "intron" refers to a non-coding segment of a DNA or an RNA, which are normally removed a transcribed RNA through splicing. However, the RNA sequence of the invention may comprise an intron sequence, such as an intron sequence from a heterologous gene ("heterologous" with respect to the gene of interest or GOI, which is to be expressed as a transgene delivered to a host cell by the rRAAV viral particle of the invention), in order to enhance the expression of the GOI. Such intron sequence in the RNA sequence of the invention may or may not be removed by splicing. In addition, such intron sequence may further comprise a transcribed enhancer or a part thereof, since certain enhancers can be located within an intron of a coding DNA.

As used herein, "exon" refers to a coding segment of a DNA or an RNA, which exon is to be translated into a protein sequence. However, in certain embodiments, an exon sequence within the RNA sequence of the invention may encode part of or the entirety of the GOI to be expressed as a transgene delivered to a host cell by the rRAAV viral particle of the invention. In other embodiments, an exon sequence within the RNA sequence of the invention may belong to a heterologous gene (with respect to the GOI), and the presence of such exon may enhance the expression of the GOI.

As used herein, "coding sequence" includes a polynucleotide sequence of a DNA or an RNA which encodes a product that can be (a) a protein or a polypeptide, or (2) other than a protein or a polypeptide (e.g., ncRNA, such as siRNA, piRNA, short hairpin RNA or shRNA, microRNA or miRNA or precursors thereof including pre-miRNA and pri-miRNA, antisense sequence or oligonucleotide (ASO), guide RNA or gRNA for CRISPR/Cas, rRNA, tRNA, snoRNA, snRNA, exRNA, scaRNA, lncRNA, Xist, and HOTAIR, etc.).

The ribonucleotide coding sequence for the gene of interest may be further processed inside the cell, once the RNA content of the RAAV viral particle is separated from the AAV capsid and released into the cell. Processing of the coding sequence can produce one or more RNA products, such as siRNA, miRNA, and/or mRNA, which may be further translated into protein product(s), or be incorporated into other cellular machinery such as the RISC complex or a CRISPR/Cas effector enzyme (such as a Class 2, type II, V, or VI effector enzyme).

As used herein, the term "transcribed," and grammatical variations thereof, refers to a nucleotide sequence comprising ribonucleic acid (RNA) nucleotides that have been transcribed from a DNA template (e.g., double-stranded DNA and/or single-stranded DNA). The transcribed RNA molecule can corresponds to either a plus strand or a minus strand of an AAV ssDNA, wherein the transcribed plus strand RNA was transcribed from the minus strand of the DNA template and the transcribed minus strand RNA was transcribed from the plus strand of the DNA template. In certain embodiments, the transcribed RNA molecule can either be transcribed from the sense or antisense strand of a double stranded DNA template. For example, when the dsDNA sequence is represented by the sequence of only one strand (such as SEQ ID NO: 1), a transcribed RNA using the dsDNA as template may have the same sequence as the sense strand or the antisense strand, as the case may be. That is, RNA transcribed from double-stranded DNA shown as SEQ ID NO: 1 may have the same sequence as SEQ ID NO: 1 or its reverse complement, except that the T's in DNA are replaced by U's in the transcribed RNA.

The transcribed modified AAV inverted terminal repeat (ITR) sequence of the invention is an RNA sequence (as opposed to the single-stranded DNA sequence in the conventional AAV viral genome encapsidated within the AAV viral particle). As the wild-type AAV ITR DNA sequence, the transcribed modified AAV ITR sequence (RNA) also supports binding of the RNA sequence of the invention to the AAV Rep protein, and is thus capable of supporting the direct packaging of the RNA sequence of the invention into the AAV viral particle. In certain embodiments, the transcribed modified ITR sequence comprises a transcribed Rep-binding element (RBE) (e.g., a transcribed functional RBE), and optionally a transcribed RBE' (e.g., a transcribed functional RBE'), for Rep binding. In certain embodiments, the transcribed modified ITR sequence supports or facilitates packaging or encapsidation of the RNA sequence into an AAV viral particle.

In certain embodiments, the modified ITR comprises a wild-type RBE.

In certain embodiments, the modified ITR comprises a functional RBE that retains at least about 60%, 70%, 80%, 90%, 95%, 100% or more of the ability of wild-type RBE for supporting AAV packaging, such as Rep binding. In certain embodiments, the functional RBE comprises up to about 30%, 25%, 20%, 15%, 10%, or 5% of sequence variation compared to the wild-type RBE, due to, for example, insertion, deletion, substitution, and/or other mutation of one or more nucleotides of the RBE.

In certain embodiments, the modified AAV ITR DNA template, from which the transcribed modified AAV ITR is transcribed, is defective as an ITR, in that it lacks one or more functions of the corresponding wild-type AAV ITR, such as being able to be cleaved at the TRS (transcribed terminal resolution site, see below). This can be due to, for example, the lack of a functional TRS. In one embodiment, the wild-type TRS is completely deleted such that the modified ITR has no TRS. In one embodiment, the wild-type TRS is mutated by deleting, inserting, substituting, and/or mutating one or more nucleotides such that it can no longer to recognized and cleaved by Rep during AAV replication.

In certain embodiments, the modified AAV ITR DNA template retains the RBE or a functional variant thereof as described herein, and optionally the RBE' or a functional variant thereof. In certain embodiments, the RBE and/or RBE' is/are functional with respect to binding to AAV Rep78/68.

The transcribed modified AAV inverted terminal repeat (ITR) of the invention further lacks either a transcribed terminal resolution site (TRS), or a transcribed reverse complement TRS (rcTRS), or both. In certain embodiments, the TRS is at the 5' end of the modified AAV ITR. In certain embodiments, the TRS is between the D region sequence and the RBE.

In certain embodiments, the transcribed modified AAV ITR lacks both the transcribed TRS and the transcribed rcTRS.

As used herein, "terminal resolution site" or "TRS" refers to the single-stranded DNA sequence in the single-stranded AAV vector genome (plus or minus strand) that is recognized and nicked by the AAV Rep proteins during AAV replication. As used herein, "reverse complement TRS (rcTRS)" refers to the single-stranded DNA sequence in the single-stranded AAV vector genome (plus or minus strand) that is reverse complement sequence of the TRS. The rcTRS pairs with the TRS to form a double stranded DNA region at one end of the A region stem. See FIGS. 1A-1C.

In AAV2 ITR, the TRS comprises the sequence of TTGGC, with the Rep cleavage site in between the two T's; while the rcTRS comprises the sequence of GCCAA. One TRS is located at the juncture of the D and A region sequences, and is at the most 5' end of the A region sequence (e.g., between the D region sequence and the RBE). See FIGS. 1B and 1C for the TRS and rcTRS in 5' and 3' ITR multi-sequence alignment of representative AAV's.

As used herein, a "transcribed TRS" is a single-stranded RNA sequence resulting from transcribing the TRS DNA template. For AAV2 TRS comprising TTGGC, the transcribed TRS comprises GCCAA.

As used herein, a "transcribed rcTRS" is a single-stranded RNA sequence resulting from transcribing the rcTRS DNA template. For AAV2 rcTRS comprising GCCAA, the transcribed rcTRS comprises UUGGC.

Thus, a transcribed modified AAV ITR "lacks a transcribed AAV2 TRS," if it does not have the GCCAA sequence at the location the GCCAA sequence normally appears in a corresponding transcribed wild-type AAV2 ITR, e.g., due to complete deletion of the GCCAA sequence, or due to insertion, deletion, substitution, and/or other mutation of one or more nucleotides within the GCCAA sequence. This can result from transcribing a modified AAV ITR having a complete deletion of the TRS (TTGGC), or due to insertion, deletion, substitution, and/or other mutation of one or more nucleotides within the wild-type TRS.

Thus, in certain embodiments, the RNA sequence of the invention or the transcribed modified AAV ITR lacks a transcribed functional TRS.

Similarly, a transcribed modified AAV ITR "lacks a transcribed AAV2 rcTRS," if it does not have the UUGGC sequence at the location the UUGGC sequence normally appears in a corresponding transcribed wild-type AAV2 ITR, e.g., due to complete deletion of the GCCAA sequence, or due to insertion, deletion, substitution, and/or other mutation of one or more nucleotides within the GCCAA sequence. This can result from transcribing a modified AAV ITR having a complete deletion of the rcTRS, or due to insertion, deletion, substitution, and/or other mutation of one or more nucleotides within the wild-type rcTRS.

In certain embodiments, the transcribed modified AAV ITR further comprises a transcribed D region sequence (D or D' sequence in a wild-type AAV ITR) or a mutant D region sequence (e.g., one with one or more nucleotide insertion, deletion, substitution, and/or other mutation) that substantially retains the function of a wild-type D region sequence. In other embodiment, the transcribed modified AAV ITR does not comprises a transcribed D region sequence, or does not comprise a mutant D region sequence (e.g., one with one or more nucleotide insertion, deletion, substitution, and/or other mutation) that substantially retains the function of a wild-type D region sequence.

In certain embodiments, the transcribed modified AAV ITR comprises the transcribed (functional) D region sequence. Optionally, the modified AAV ITR DNA template has the nucleotide sequence of SEQ ID NO: 3. Optionally, the transcribed modified AAV ITR comprises an RNA equivalent of SEQ ID NO: 3 (i.e., the RNA equivalent has the same base sequence as the DNA sequence of SEQ ID NO: 3). Optionally, the transcribed modified AAV ITR comprises an RNA equivalent of the reverse complement of SEQ ID NO: 3 (i.e., the RNA equivalent has the same base sequence as the DNA sequence of the reverse complement of SEQ ID NO: 3).

In certain embodiments, the transcribed modified AAV ITR lacks the transcribed (functional) D region sequence. Optionally, the modified AAV ITR DNA template has the nucleotide sequence of SEQ ID NO: 2. Optionally, the transcribed modified AAV ITR comprises an RNA equivalent of SEQ ID NO: 2 (i.e., the RNA equivalent has the same base sequence as the DNA sequence of SEQ ID NO: 2). Optionally, the transcribed modified AAV ITR comprises an RNA equivalent of the reverse complement of SEQ ID NO:

2 (i.e., the RNA equivalent has the same base sequence as the DNA sequence of the reverse complement of SEQ ID NO: 2).

As used herein, "D region sequence" refers to either the D sequence or its reverse complement D' sequence. Location of the D region sequence depends on whether the ITR takes the "flip" or the "flop" configuration. See FIGS. 1A-1C. For example, in wild-type AAV2 ITR (see FIG. 2 of Srivastava et al., J. Viol. 45(2):555-564, 1983, incorporated herein by reference), the plus strand ssDNA sequence comprises, from 5' to 3', palindromic sequence segments named A, B, B', C, C', A', D, . . . , D', A, C, C, B, B', and A', in which A:A', B:B', C:C' and D:D' are reverse complement sequences of each other and can form base-paired stem sequences (though the D and D' sequences may not actually base-pair with each other in the ssDNA AAV vector genome). The 5' ITR of the plus strand has the B:B' stem closer to one end (5' end) of the sequence than the C:C' stem, and is known as the flip ITR. The 3' ITR of the plus strand has the C:C' stem closer to one end (3' end) of the sequence than the B:B' stem, and is known as the flop ITR.

The transcribed modified AAV ITR sequence of the invention may lack a functional transcribed D region sequence (D or D' sequence) by, for example, deletion, insertion, substitution, and/or other mutation of one or more nucleotides of the transcribed wild-type D region sequence.

In certain embodiments, the RNA or transcribed modified AAV ITR sequence of the invention comprises a mutated transcribed D region sequence and/or a mutated transcribed TRS sequence. In certain embodiments, the RNA or transcribed modified AAV ITR sequence of the invention comprises no transcribed D region sequence and/or no transcribed TRS/rcTRS sequence.

In certain embodiments, the transcribed modified AAV ITR is modified based on a transcribed wild-type flip ITR or a wild-type flop ITR.

In certain embodiments, the wild-type flip ITR or the wild-type flop ITR is from AAV1, AAV2, AAV3A, AAV3B, AAV4, AAV5, AAV6, AAV7, AAV8, AAV9, AAV10, AAV 11, AAV 12, AAV 13, AAVrh10, AAVrh74, AAVhu32, AAVhu37, AAV PHP.eB, Anc80L65, Anc80L65AAP, AAVrh74, or 7m8. Optionally, the wild-type flop ITR has the nucleotide sequence of SEQ ID NO: 1.

In certain embodiments, the transcribed D region sequence is present, and is not within the 3' end 50 nucleotides (e.g., 40 nt, 30 nt, 25 nt, or 20 nt) of the RNA.

In certain embodiments, the transcribed D region sequence is present, and is within the 3' end 50 nucleotides (e.g., 40 nt, 30 nt, 25 nt, or 20 nt) of the RNA.

In certain embodiments, the transcribed modified AAV ITR is within the 3' end 1000 nucleotides of the RNA. In certain embodiments, the transcribed modified AAV ITR is within the 3' end 800 nucleotides of the RNA. In certain embodiments, the transcribed modified AAV ITR is within the 3' end 500 nucleotides of the RNA. In certain embodiments, the transcribed modified AAV ITR is within the 3' end 300 nucleotides of the RNA. In certain embodiments, the transcribed modified AAV ITR is within the 3' end 200 nucleotides of the RNA.

In certain embodiments, the transcribed modified AAV ITR is 5' to a polyA sequence, a polyA signal sequence (e.g., AAUAAA), or a sequence for RNA transcription termination (e.g., a histone downstream element).

As used herein, "polyA sequence" or "polyA tail" refers to a string of adenine ribonucleotides or adenosine monophosphates (e.g., a string of RNA with each base therewithin an adenine). Such a polyA tail is important for the nuclear export, translation and stability of mRNA. The length of the polyA sequence can vary in different mRNA or the RNA sequence of the invention, and can be about 250 nucleotides of polyA, about 230 nucleotides of polyA, about 200 nucleotides of polyA, about 180 nucleotides of polyA, about 160 nucleotides of polyA, about 140 nucleotides of polyA, about 120 nucleotides of polyA, about 100 nucleotides of polyA, or less.

As used herein, "polyA signal sequence" refers to an RNA sequence (such as AAUAAA) that is located downstream of the most 3' exon, and is recognized by an RNA cleavage complex that cleaves off the 3' terminal sequence of a newly transcribed RNA by RNA polymerase (such as Pol II) such that polyadenylation can occur. Polyadenylate polymerase then adds and extends the poly(A) tail by adding adenosine monophosphate units from ATP to the nascent cleaved 3' end of the RNA. The initial RNA cleavage is typically catalyzed by the enzyme CPSF (cleavage/polyadenylation specificity factor), and occurs about 10-30 nucleotides downstream of its binding site—the polyA signal sequence, which is often AAUAAA on the transcribed RNA. The sequence at/or immediately 5' to the site of RNA cleavage is frequently (but not always) CA. The polyA signal sequence recognized by the RNA cleavage complex varies between different groups of eukaryotes, with most human polyadenylation sites containing the AAUAAA sequence, though this sequence is less common in plants and fungi mRNA. In addition, other variants that bind more weakly to CPSF exist. All such sequence motifs recognized by the RNA cleavage complex to enable RNA cleavage and the subsequent polyadenylation are within the scope of the polyA signal sequence.

Also as used herein, "a transcribed GU-rich region downstream of the polyA site" refers to a sequence that may be used by other proteins (such as the cleavage stimulation factor or CstF) to enhance binding specificity of CPSF to the polyA signal sequence (e.g., AAUAAA).

In certain embodiments, the RNA sequence of the invention further comprises a recognition sequence for CFI (cleavage factor I), such as a set of UGUAA sequences in mammals, that can recruit CPSF even if the AAUAAA polyA signal sequence is missing.

As used herein, "a sequence for RNA transcription termination" includes an RNA sequence motif present at or near the 3' end of a transcribed RNA (such as a transcribed RNA without a polyA tail) that terminates transcription. Almost all eukaryotic mRNAs are polyadenylated, with the exception of metazoan replication-dependent histone mRNAs, in which mRNA processing occurs at a site of highly conserved stem-loop structure and a purine rich region around 20 nucleotides downstream. These are the few (if not the only) eukaryotic mRNAs that lack a poly(A) tail, ending instead in a stem-loop structure followed by a purine-rich sequence, termed histone downstream element (HDE) or histone 3' UTR stem-loop. HDE directs where the RNA is cleaved during/after transcription, so that the 3' end of the histone mRNA is formed. HDE is involved in nucleocytoplasmic transport of the histone mRNAs, and in the regulation of stability and of translation efficiency in the cytoplasm.

In certain embodiments, the RNA sequence of the invention further comprises a second transcribed modified AAV ITR of the invention. In certain embodiments, the second transcribed modified AAV ITR has a transcribed functional RBE sequence but lacks either a second transcribed TRS or a second transcribed rcTRS or both; optionally, the second transcribed modified AAV ITR further comprises or lacks a second transcribed D region sequence. In certain embodiments, the second transcribed modified AAV ITR comprises a second transcribed mutated D region sequence and/or a second transcribed mutated TRS sequence.

In certain embodiments, for the RNA sequence of the invention having two transcribed modified AAV ITR, the transcribed modified AAV ITR and the second transcribed modified AAV ITR are identical.

In certain embodiments, for the RNA sequence of the invention having two transcribed modified AAV ITR, the transcribed modified AAV ITR and the second transcribed modified AAV ITR are different.

In certain embodiments, the transcribed modified AAV ITR, the second transcribed modified AAV ITR (if present), comprise a deletion from, a mutation in, or an insertion into a corresponding transcribed wild-type AAV ITR D region sequence or a corresponding transcribed wild-type TRS/rcTRS.

In certain embodiments, for the RNA sequence of the invention having two transcribed modified AAV ITR, the second transcribed modified AAV ITR is within 5' end 1000 nucleotides, 800 nucleotides, 500 nucleotides, 250 nucleotides, or 150 nucleotides of the RNA sequence.

In certain embodiments, the RPS comprises an MS2 sequence, an PP7 binding site, or a com binding site, and the RPS-interacting molecule comprises an RPS-interacting protein (RPSIP) capably of interacting, e.g., recognizing and binding, directly or indirectly, to the RPS, such as a bacteriophage-derived MS2 coat protein (MCP) for an MS2 sequence, a PP7 bacteriophage coat protein (PCP) for an PP7 binding site, or a phage COM protein (COM) for a com binding site. Sequences of these RPS/RPSIP pair are described in the sequence section of the specification.

Any of the one or more RPS sequences described herein above, including any of the transcribed modified ITR sequences, and any of the MS2 sequence, PP7 binding site, and/or com binding site, alone or in combination, can facilitate the packaging of the RNA sequence of the invention into the DNA virus viral particle, in the presence of a suitable/compatible cognate RPSIP.

In certain embodiments, the RPSIP is, or is associated directly or indirectly with, a protein component of the viral packaging system for the DNA virus viral particle. For example, in some embodiments, the RPSIP is a protein component of the viral packaging system for the DNA virus, such as, Rep78, Rep68, Rep52, and/or Rep40 for AAV. For example, in some embodiments, the RPSIP may be directly fused to a protein component of the viral packaging system for the DNA virus. Exemplary protein components of the viral packaging system for AAV include any of the Rep proteins (such as Rep78 and/or Rep68 of adeno-associated virus 2 (AAV2)), and/or any of the assembly-activating protein (AAP).

In certain embodiments, the fusion is an N-terminal fusion wherein the RPSIP (such as MCP, PCP, or COM) is fused N-terminal to a Rep68/78 protein, and/or to an AAP.

In certain embodiments, the fusion is an N-terminal fusion wherein the RPSIP (such as MCP, PCP, or COM) is fused C-terminal to a Rep68/78 protein, and/or to an AAP.

In certain embodiments, the fusion is a direct fusion with no linker sequences in-between.

In certain embodiments, the fusion is through one or more linker sequence, such as a flexible peptide linker that may include a Gly and Ser rich linker or GS linker. Representative GS linkers include 1, 2, 3, 4, 5 or more repeats of Gly or Ser, such as GS, GSS, GSSS (SEQ ID NO: 105), GSSSS (SEQ ID NO: 106), and repeats thereof (e.g., $(GS_p)_n$ (SEQ ID NO: 148), wherein p is an integer between 1-5, and n is an integer between 1-20. One typical such GS linker is $GS_3$ (SEQ ID NO: 105) linker or $GS_4$ (SEQ ID NO: 106) linker. In certain embodiments, p is 3 or 4, and n is 1.

In certain embodiments, the RNA sequence of the invention can comprise, but preferably does not comprise, a transcribed DNA packaging signal, for example, a transcribed wild-type AAV ITR sequence. For example, the RNA sequence of the invention may comprise a transcribed modified AAV ITR sequence having an addition, a deletion, and/or a substitution of a nucleotide of a corresponding transcribed wild-type AAV ITR sequence to reduce the DNA packaging capability of the DNA virus viral particle.

In certain embodiments, the RNA sequence of the invention further comprises one or more of: (1) a coding sequence for a protein (such as an mRNA encoding a therapeutic protein or a CRISPR/Cas effector enzyme including any of the Cas effectors described herein below, e.g., Cas9, or a variant thereof, optionally fused to a base editor), a non-coding RNA (ncRNA), or a functional RNA (such as a tRNA, a ribosomal RNA (rRNA), an RNAi reagent or precursor thereof, siRNA, shRNA, miRNA or precursors thereof including pre-miRNA and pri-miRNA, antisense RNA (ASO), piRNA, an RNA component of CRISPR-Cas system such as a guide RNA (or gRNA), a single guide RNA (or sgRNA, chimeric RNA, RNA chimera), a CRISPR RNA (crRNA), or a tracr RNA), snoRNA, snRNA, exRNA, scaRNA, lncRNA, Xist, and HOTAIR, etc.); (2) a transcribed transcription enhancer; (3) a transcribed intron sequence or exon sequence (such as one for enhancing protein expression); (4) a 5' UTR sequence; (5) a 3' UTR sequence; (6) a polyA sequence, or a (transcribed) polyadenylation (polyA) signal sequence, and optionally a transcribed polyA site and a transcribed GU-rich region downstream of the polyA site; (7) a posttranscriptional regulatory element or sequence, such as a transcribed Woodchuck Hepatitis Virus (WHP) Posttranscriptional Regulatory Element (WPRE) sequence; and/or, (8) a transcription termination sequence (such as a histone downstream element).

In certain embodiments, the RNA sequence of the invention comprises an RPS located 3' to the posttranscriptional regulatory element or sequence, and 5' to the polyA sequence or the polyA signal sequence.

For example, in certain embodiments, the RNA sequence of the invention comprises, in 5' to 3' orientation, the RSI; the optional transcribed WPRE sequence (that may or may not be present); the RPS (such as the transcribed modified AAV ITR, the MS2 sequence, the PP7 binding site, or the com binding site); and the polyA sequence or the polyA signal sequence.

In certain embodiments, the RNA sequence of the invention encodes, or the GOI comprises, a protein (e.g., a fluorescent protein, a therapeutic protein, an antigen protein, or a gene-editing protein such as a Cas protein, a ZFN protein, a TALEN protein), an enzyme (such as a Cre protein, or a CRISPR/Cas effector enzyme, e.g., Cas9, Cas12, Cas13, or a variant thereof), a structural protein, an mRNA, a non-coding RNA (ncRNA), an siRNA, a piRNA, a short hairpin RNA or shRNA, a microRNA (miRNA) or a precursor thereof (including pre-miRNA and pri-miRNA), a ribosomal RNA (rRNA), an antisense sequence or oligonucleotide (ASO), an RNA component of a CRISPR-Cas system, including a guide RNA (or a gRNA), such as a single guide RNA (or an sgRNA, a chimeric RNA, an RNA chimera), a CRISPR RNA (crRNA), and a tracr RNA, a guide RNA or gRNA for a CRISPR/Cas effector enzyme, an rRNA, a tRNA, a snoRNA, a snRNA, an exRNA, a scaRNA, a lncRNA, a Xist, and a HOTAIR.

The overall length of the RNA sequence of the invention depends on the packaging capacity of the AAV viral particle. Most AAV viral particles have a packaging capacity of about 4,700-5,200 nucleotides, but certain AAV viral particles such as AAV5 particles can package up to 8,900 nucleotides.

Thus, in certain embodiments, the RNA sequence of the invention to be packaged into an AAV viral particle is a single-stranded RNA (ssRNA) less than about 8,900 nucleotides in length.

In certain embodiments, the RNA sequence is a ssRNA less than about 8,000 nucleotides in length. In certain embodiments, the RNA sequence is a ssRNA less than about 7,000 nucleotides in length. In certain embodiments, the RNA sequence is a ssRNA less than about 6,000 nucleotides in length. In certain embodiments, the RNA sequence is a ssRNA less than about 5,200 nucleotides in length. In certain embodiments, the RNA sequence is a ssRNA less than about 4,000 nucleotides in length. In certain embodiments, the RNA sequence is a ssRNA less than about 3,000 nucleotides in length. In certain embodiments, the RNA sequence is a ssRNA less than about 2,000 nucleotides in length.

In certain embodiments, the RNA sequence is a ssRNA about 4,700-5,200 nucleotides in length. In certain embodiments, the RNA sequence is a ssRNA about 4,700-5,000 nucleotide in length. In certain embodiments, the RNA sequence is a ssRNA about 4,700-4,800 nucleotides in length. In certain embodiments, the RNA sequence is a ssRNA about 4,700 nucleotides in length.

Another aspect of the invention provides a polynucleotide comprising a (transcription) cassette encoding the RNA sequence of the invention; optionally, the polynucleotide is a DNA sequence (e.g., a DNA plasmid), optionally comprising a stuffer sequence in the backbone of the DNA plasmid, and/or optionally comprising no functional DNA packaging signal such as AAV ITR.

In certain embodiments, the polynucleotide comprising the cassette is a DNA vector encoding the RNA sequence of the invention. Such DNA vector and/or the cassette thereof can be used to transcribe and produce the RNA sequence of the invention for further packaging into, e.g., an AAV viral particle.

In certain embodiments, the polynucleotide further comprises a promoter operably linked to and driving the transcription of the RNA sequence of the invention encoded by the cassette to produce the RNA sequence of the invention.

In certain embodiments, the promoter is a ubiquitous promoter.

In certain embodiments, the promoter is a tissue-specific promoter.

In certain embodiments, the promoter is a constitutive promoter.

In certain embodiments, the promoter is an inducible promoter.

In certain embodiments, the polynucleotide further comprises an enhancer that enhances the transcription of the RNA sequence driven by the promoter.

Another aspect of the invention provides a recombinant DNA virus viral particle comprising an RNA genome (such as the RNA sequence of the invention, or the RNA sequence transcribed from the polynucleotide of the invention) packaged within the protein shell (such as capsid) of a DNA virus (such as an AAV virus, or an oncolytic virus).

In certain embodiments, the DNA virus is AAV, and the recombinant DNA virus viral particle is a recombinant RNA adeno-associated virus (rRAAV) particle, comprising: (1) an AAV capsid; and, (2) the RNA sequence of the invention, or the RNA sequence transcribed from the polynucleotide of the invention, packaged within the AAV capsid.

In certain embodiments, the AAV capsid comprises a capsid from an AAV of the serotype AAV1, AAV2, AAV3A, AAV3B, AAV4, AAV5, AAV6, AAV7, AAVrh74, AAV8, AAV9, AAV10, AAV11, AAV12, AAV13, AAV-DJ, AAV PHP.eB, Anc80L65, Anc80L65AAP, or 7m8.

A related aspect of the invention provides a population of recombinant DNA virus viral particles (e.g., rRAAV particles) comprising a plurality of recombinant DNA virus viral particle (e.g., rRAAV particle) of the invention, wherein at least about 10%, 20%, 30%, 40%, 50%, 60%, 70%, 80%, 90%, 95%, 96%, 97%, 98%, 99% or more of the recombinant DNA virus viral particles (e.g., rRAAV particles) within the population have encapsidated RNA sequence of the invention, or the RNA sequence transcribed from the polynucleotide of the invention packaged therein.

In certain embodiments, the population of recombinant viral particles (e.g., rRAAV particles) comprises at least $1 \times 10^4$ viral particles, at least $2 \times 10^4$ viral particles, at least $5 \times 10^4$ viral particles, at least $1 \times 10^5$ viral particles, at least $2 \times 10^5$ viral particles, at least $5 \times 10^5$ viral particles, at least $1 \times 10^6$ viral particles, at least $2 \times 10^6$ viral particles, at least $5 \times 10^6$ viral particles, at least $1 \times 10^7$ viral particles, at least $2 \times 10^7$ viral particles, at least $5 \times 10^7$ viral particles, at least $1 \times 10^8$ viral particles, at least $2 \times 10^8$ viral particles, at least $5 \times 10^8$ viral particles, at least $1 \times 10^9$ viral particles, at least $2 \times 10^9$ viral particles, at least $5 \times 10^9$ viral particles, at least $1 \times 10^{10}$ viral particles, at least $2 \times 10^{10}$ viral particles, at least $5 \times 10^{10}$ viral particles, at least $1 \times 10^{11}$ viral particles, at least $2 \times 10^{11}$ viral particles, at least $5 \times 10^{11}$ viral particles, at least $1 \times 10^{12}$ viral particles, at least $2 \times 10^{12}$ viral particles, at least $5 \times 10^{12}$ viral particles, at least $1 \times 10^{13}$ viral particles, at least $2 \times 10^{13}$ viral particles, at least $5 \times 10^{13}$ viral particles, at least $1 \times 10^{14}$ viral particles, at least $2 \times 10^{14}$ viral particles, at least $5 \times 10^{14}$ viral particles, at least $1 \times 10^{15}$ viral particles, at least $2 \times 10^{15}$ viral particles, at least $5 \times 10^{15}$ viral particles, at least $1 \times 10^{16}$ viral particles, at least $2 \times 10^{16}$ viral particles, or at least $5 \times 10^{16}$ viral particles.

In certain embodiments, at most 50%, 45%, 40%, 35%, 30%, 25%, 20%, 15%, 10%, 5%, 3%, 2%, 1%, 0.1%, 0.01% or less of the population of recombinant viral particles encapsidate non-RNA (e.g., DNA) within the viral particles.

Another aspect of the invention provides a host cell comprising the RNA sequence of the invention, the polynucleotide of the invention, the RNA sequence transcribed from the polynucleotide of the invention, the recombinant DNA virus viral particle (e.g., rRAAV particle) of the invention, and/or the population of recombinant DNA virus viral particle (e.g., rAAV particle) of the invention.

In certain embodiments, the host cell further comprises a viral packaging system that facilitates packaging of the RNA sequence of the invention, or the RNA sequence transcribed from the polynucleotide of the invention into the DNA virus viral particle.

In certain embodiments, the viral packaging system comprises: (1) an AAV rep gene (e.g., coding sequence for Rep78, Rep68, Rep52, and/or Rep40) and an AAV cap gene (e.g., coding sequence for VP1, VP2, and/or VP3, AAP, and/or MAAP), under the transcriptional control of one or more promoters that drive the transcription of the rep gene and cap gene, or the expression products thereof; (2) one or more coding sequences for one or more proteins required for AAV packaging, such as adenoviral E2A, E4, and VA genes, or the one or more proteins; and (3) the RPS-interacting molecule or a coding sequence thereof.

In certain embodiments, the capacity of the viral packaging system of packaging a DNA sequence into the DNA virus viral particle is reduced, diminished, or substantially eliminated by, for example, (1) removing a part or all of the DNA packaging signals such as AAV ITR on the polynucleotide encoding the RNA sequence of the invention or on the polynucleotide of the invention, (2) modifying, e.g., mutating, the AAV rep gene, the AAV cap gene, and/or the one or more coding sequences for one or more proteins required for AAV packaging to reduce, diminish, or substantially eliminate the capacity of the respective translated protein in order to facilitate the packaging of the DNA sequence into the DNA virus viral particle (e.g., a Y156F mutation in the common sequence of Rep78 and Rep68 proteins, KDE-mu, or EKE-mu); and/or (3) enlarging the size of the polynucleotide encoding the RNA sequence of the invention or the polynucleotide of the invention. In an embodiment, enlarging the size of the polynucleotide encoding the RNA sequence of the invention or the polynucleotide of the invention is made by inserting a stuffer sequence (e.g., an intron) into (e.g., the backbone of) the polynucleotide (e.g., a DNA plasmid).

In certain embodiments, the AAV rep gene, the AAV cap gene, and/or the proteins required for AAV packaging comprises a mutation that diminishes or reduces capacity to facilitate packaging of DNA into the DNA virus viral particle.

In certain embodiments, the Rep68/Rep 78 protein required for DNA packaging comprises a mutation that compromises or diminishes its trs-endonuclease activity. The trs-endonuclease activity is believed to be required to resolve AAV replication (DNA) intermediates at the trs sequence or site, such that individual units of AAV ssDNA can be resolved before packaging into the AAV capsid.

In certain embodiments, the trs-endonuclease mutation comprise a Y156F mutation in the common sequence of Rep78 and Rep68 proteins.

In certain embodiments, the Rep78/Rep68 proteins comprise a KDE-mu mutation (see sequence below in the sequence section).

In certain embodiments, Rep78/Rep68 proteins comprise a EKE-mu mutation (see sequence below in the sequence section).

In certain embodiments, Rep78/Rep68 proteins comprise two or more mutations selected form the Y156F mutation, the KDE-mu mutation, and the EKE-mu mutation.

In certain embodiments, the Rep68/Rep78 are from any one of the AAVs with serotype of AAV1, AAV2, AAV3A, AAV3B, AAV4, AAV5, AAV6, AAV7, AAV8, AAV9, AAV10, AAV11, AAV12, AAV13, AAV-DJ, AAV PHP.eB, Anc80L65, Anc80L65AAP, AAVrh74, or 7m8, and has a corresponding trs-endonuclease mutation of the Y156F mutation, the KDE-mu mutation, and/or the EKE-mu mutation.

In certain embodiments, the host cell further comprises: (1) a coding sequence for an AAV rep gene and an AAV cap gene, under the transcriptional control of one or more promoters that drive the transcription of the rep gene and cap gene; and, (2) coding sequences for proteins required for AAV packaging, such as adenoviral E2A, E4, and VA genes.

In certain embodiments, the host cell is a mammalian cell, such as a HEK293 cell or a variant thereof (e.g., HEK293T cell), or an insect cell, such as Sf9 or Sf21 cells.

Another aspect of the invention provides a method of generating the recombinant DNA virus viral particle (e.g., rRAAV particle) or the population of recombinant DNA virus viral particles (e.g., rRAAV particles) of the invention, the method comprising: a) culturing the host cell of the invention for a sufficient time, and b) harvesting the recombinant DNA virus viral particle or the population of recombinant DNA virus viral particles.

In certain embodiments, the method further comprises isolating or purifying the recombinant DNA virus viral particle or the population of recombinant DNA virus viral particles.

Another aspect of the invention provides a method of generating a recombinant DNA virus viral particle (e.g., rRAAV particle) or a population of recombinant DNA virus viral particles, the method comprising: a) contacting a viral packaging system (e.g., an AAV packaging system) with the RNA sequence of the invention or the RNA sequence transcribed from the polynucleotide of the invention, for a period of time sufficient to produce the recombinant DNA virus viral particle of the invention, or the population of recombinant DNA virus viral particles of the invention, and b) harvesting the recombinant DNA virus viral particle of the invention, or the population of recombinant DNA virus viral particles of the invention; and, optionally, c) isolating or purifying the harvested recombinant DNA virus viral particle of the invention, or the population of recombinant DNA virus viral particles of the invention.

In certain embodiments, the viral packaging system (e.g., a AAV packaging system) comprises: (1) one or more proteins for assemblying the protein shell (e.g., VP1, VP2, and/or VP3 for assembling AAV capsid) of the DNA virus viral particle for packaging the RNA sequence, or one or more coding sequences thereof; (2) one or more proteins (e.g., Rep78, Rep68, Rep52, and/or Rep40 for AAV packaging) for facilitating the assemblying of the protein shell and/or the packaging of the RNA sequence into the protein shell of the DNA virus viral particle, or one or more coding sequences thereof (e.g., adenoviral E2a, E4, and VA genes); and (3) the RPS-interacting molecule or a coding sequence thereof. Optionally, the capacity of the viral packaging system of packaging a DNA sequence into the DNA virus viral particle is reduced, diminished, or substantially eliminated by, for example, (1) removing a part or all of the DNA packaging signals such as AAV ITR on the polynucleotide encoding the RNA sequence of the invention, or on the polynucleotide of the invention, (2) modifying, e.g., mutating, the AAV rep gene, the AAV cap gene, and/or the one or more coding sequences for one or more proteins required for AAV packaging to reduce, diminish, or substantially eliminate the capacity of the respective translated protein to facilitate the packaging of the DNA sequence into the DNA virus viral particle (e.g., a Y156F mutation in the common sequence of Rep78 and Rep68 proteins, KDE-mu, or EKE-mu); and/or (3) enlarging the size of the polynucleotide encoding the RNA sequence of the invention or the polynucleotide of the invention.

Another aspect of the invention provides a system of packaging the RNA sequence of the invention or the RNA sequence transcribed from the polynucleotide of the invention into a DNA virus viral particle, the system comprising: (1) one or more proteins for assemblying the protein shell (e.g., VP1, VP2, and/or VP3 for assembling AAV capsid) of the DNA virus viral particle for packaging the RNA sequence, or one or more coding sequences thereof; (2) one or more proteins (e.g., Rep78, Rep68, Rep52, and/or Rep40 for AAV packaging) for facilitating the assemblying of the protein shell and/or the packaging of the RNA sequence of the invention into the protein shell of the DNA virus viral particle, or one or more coding sequences thereof (e.g., adenoviral E2a, E4, and VA genes); and (3) the RPS-interacting molecule or a coding sequence thereof. Optionally, the capacity of the viral packaging system of packaging a DNA sequence into the DNA virus viral particle is reduced, diminished, or substantially eliminated by, for example, (1) removing a part or all of the DNA packaging signals such as AAV ITR on the polynucleotide encoding the RNA sequence of the invention or on the polynucleotide of the invention, (2) modifying, e.g., mutating, the AAV rep gene, the AAV cap gene, and/or the one or more coding sequences for one or more proteins required for AAV packaging to reduce, diminish, or substantially eliminate the capacity of the respective translated protein to facilitate the packaging of the DNA sequence into the DNA virus viral particle (e.g., a Y156F mutation in the common sequence of Rep78 and Rep68 proteins, KDE-mu, or EKE-mu); and/or (3) enlarging the size of the polynucleotide encoding the RNA sequence of the invention or the polynucleotide of the invention.

Another aspect of the invention provides a method of delivering an RNA sequence of interest (RSI) into a cell, a plant, or an animal, the method comprising contacting the cell, the plant, or the animal with the recombinant DNA virus viral particle (e.g., rRAAV particle) of the invention, the population of recombinant DNA virus viral particles (e.g., rRAAV particles) of the invention, or the recombinant DNA virus viral particle (e.g., rRAAV particle) or the population of recombinant DNA virus viral particles (e.g., rRAAV particles) produced by the method of the invention, wherein the GOI is optionally encoded by the RNA sequence of the invention.

Another aspect of the invention provides a method of diagnosing, preventing, or treating a disease or disorder in a subject in need thereof, comprising administrating to the subject a therapeutically effective amount or dose of the population of the recombinant DNA virus viral particles (e.g., rRAAV particles) of the invention, or produced by the method of the invention.

Another aspect of the invention provides a use of the recombinant DNA virus viral particle (e.g., rRAAV particle) of the invention, the population of the recombinant DNA virus viral particles (e.g., rRAAV particles) of the invention, or the recombinant DNA virus viral particle (e.g., rRAAV particle) or the population of the recombinant DNA virus viral particles (e.g., rRAAV particles) produced by the method of the invention, in the manufacture of a medicament for diagnosing, preventing, or treating a disease or disorder in a subject in need thereof.

Another aspect of the invention provides a fusion protein or a conjugate, comprising an RPSIP of the invention fused or conjugated to a protein component of the viral packaging system for the DNA virus, wherein the RPSIP interacts with/binds to an RPS on the RNA sequence of the invention to facilitate the packaging of the RNA sequence into the DNA virus.

In certain embodiments, the RPS is MS2, and the RPSIP is MCP.

In certain embodiments, the RPS is PP7 binding site, and the RPSIP is PCP.

In certain embodiments, the RPS is com, and the RPSIP is phage COM protein.

In certain embodiments, the fusion or conjugate comprises more than one RPSIP, each independently binds to one or more RPS on the RNA sequence of the invention. In certain embodiments, at least two of the more than one RPSIP are identical. In certain embodiments, at least two of the more than one RPSIP are different.

In certain embodiments, the fusion or conjugate comprises two MCP in tandem.

In certain embodiments, the protein component of the viral packaging system for the DNA virus comprises a Rep protein of an AAV, such as a Rep68 or a Rep78 of the AAV.

In certain embodiments, the Rep protein comprises one or more mutations that compromises or diminishes trs-endonuclease activity. In certain embodiments, the mutations comprise the Y156F mutation, the KDE-mu mutation, and/or the EKE-mu mutation.

In certain embodiments, the protein component of the viral packaging system for the DNA virus comprises an assembly-activating protein (AAP).

In certain embodiments, the RPSIP is fused to the protein component of the viral packaging system for the DNA virus (e.g., a Rep protein or an AAP) directly.

In certain embodiments, the RPSIP is fused to the protein component of the viral packaging system for the DNA virus (e.g., a Rep protein or an AAP) through a peptide linker.

In certain embodiments, the peptide linker is a flexible linker, such as a Gly and Ser containing linker. In certain embodiments, the Gly and Ser containing linker comprises 1-20 repeats (e.g., 1-5 or 1-3 repeats) of $GS_n$, wherein n is 1, 2, 3, 4, or 5. In certain embodiments, the $GS_n$ linker is $GS_2$, $GS_3$ (SEQ ID NO: 105), or $GS_4$ (SEQ ID NO: 106), with 1-4 (e.g., 2) repeats. In certain embodiments, the linker is GSSGSS (SEQ ID NO: 107).

In certain embodiments, the fusion protein comprises MCP and Rep, wherein the Rep optionally comprises a Y156F mutation, a KDE-mu mutation, and/or a EKE-mu mutation. In certain embodiments, MCP is fused N-terminal to Rep (MCP-Rep). In certain embodiments, the Rep fused to MCP comprises a Y156F mutation, a KDE-mu mutation, and/or a EKE-mu mutation. In certain embodiments, the MCP-Rep fusion is linked by a $GS_n$ linker, such as GSSGSS (SEQ ID NO: 107). In certain embodiments, the MCP-Rep comprises two MCP in tandem (e.g., without any linker between the two MCP moieties). In certain embodiments, the MCP is C-terminal to another $GS_n$ linker, such as GSSGSS (SEQ ID NO: 107).

In certain embodiments, the fusion protein comprises PCP and Rep, wherein the Rep optionally comprises a Y156F mutation, a KDE-mu mutation, and/or a EKE-mu mutation. In certain embodiments, PCP is fused N-terminal to Rep (PCP-Rep). In certain embodiments, the Rep fused to PCP comprises a Y156F mutation, a KDE-mu mutation, and/or a EKE-mu mutation. In certain embodiments, the PCP-Rep fusion is linked by a $GS_n$ linker, such as GSSGSS (SEQ ID NO: 107). In certain embodiments, the PCP-Rep comprises two PCP in tandem (e.g., without any linker between the two PCP moieties). In certain embodiments, the PCP is C-terminal to another $GS_n$ linker, such as GSSGSS (SEQ ID NO: 107).

In certain embodiments, the fusion protein comprises COM and Rep, wherein the Rep optionally comprises a Y156F mutation, a KDE-mu mutation, and/or a EKE-mu mutation. In certain embodiments, COM is fused N-terminal to Rep (COM-Rep). In certain embodiments, the Rep fused to COM comprises a Y156F mutation, a KDE-mu mutation, and/or a EKE-mu mutation. In certain embodiments, the COM-Rep fusion is linked by a $GS_n$ linker, such as GSSGSS (SEQ ID NO: 107). In certain embodiments, the COM-Rep comprises two COM in tandem (e.g., without any linker between the two COM moieties). In certain embodiments, the COM is C-terminal to another $GS_n$ linker, such as GSSGSS (SEQ ID NO: 107).

In certain embodiments, the fusion protein comprises MCP and AAP. In certain embodiments, MCP is fused N-terminal to AAP (MCP-AAP, or MA). In certain embodiments, MCP is fused C-terminal to AAP (AAP-MCP, or AM). In certain embodiments, the MCP-AAP or AAP-MCP fusion is linked by a $GS_n$ linker, such as GSSGSS (SEQ ID NO: 107). In certain embodiments, the MCP-AAP fusion is C-terminal to another $GS_n$ linker, such as GSSGSS (SEQ ID NO: 107). In certain embodiments, the AAP-MCP fusion is N-terminal to another $GS_n$ linker, such as GSSGSS (SEQ ID NO: 107).

Another aspect of the invention provides a polynucleotide encoding any one of the fusions between the RPSIP of the invention and the protein component of the viral packaging system for the DNA virus (e.g., AAP or a Rep protein).

With the general aspects of the invention described herein above, the following sections provides additional details for specific elements of the invention described herein. Each specific element is contemplated to be able to combined with any one or more additional elements of the invention, even though all possible combinations or permutations of the elements are not explicitly recited.

2. AAV Serotypes

AAV particles packaging ribopolynucleotides of the invention may comprise or be derived from any natural or recombinant AAV serotypes.

According to the present disclosure, the AAV particles may utilize or be based on a serotype selected from any of the following serotypes, and variants thereof, including but not limited to: AAV1, AAV10, AAV106.1/hu.37, AAV11, AAV114.3/hu.40, AAV 12, AAV127.2/hu.41, AAV127.5/hu.42, AAV128.1/hu.43, AAV128.3/hu.44, AAV130.4/hu.48, AAV145.1/hu.53, AAV145.5/hu.54, AAV145.6/hu.55, AAV16.12/hu.11, AAV16.3, AAV16.8/hu.10, AAV161.10/hu.60, AAV161.6/hu.61, AAV1-7/rh.48, AAV1-8/rh.49, AAV2, AAV2.5T, AAV2-15/rh.62, AAV223.1, AAV223.2, AAV223.4, AAV 223.5, AAV223.6, AAV223.7, AAV2-3/rh.61, AAV24.1, AAV2-4/rh.50, AAV2-5/rh.51, AAV27.3, AAV29.3/bb.1, AAV29.5/bb.2, AAV2G9, AAV-2-pre-miRNA-101, AAV3, AAV3.1/hu.6, AAV3.1/hu.9, AAV3-11/rh.53, AAV3-3, AAV33.12/hu. 17, AAV33.4/hu. 15, AAV33.8/hu.16, AAV3-9/rh.52, AAV3a, AAV3b, AAV4, AAV4-19/rh.55, AAV42.12, AAV42-10, AAV42-11, AAV42-12, AAV42-13, AAV42-15, AAV42-1b, AAV42-2, AAV42-3a, AAV42-3b, AAV42-4, AAV42-5a, AAV42-5b, AAV42-6b, AAV42-8, AAV42-aa, AAV43-1, AAV43-12, AAV43-20, AAV43-21, AAV43-23, AAV43-25, AAV43-5, AAV4-4, AAV44.1, AAV44.2, AAV44.5, AAV46.2/hu.28, AAV46.6/hu.29, AAV4-8/r 11.64, AAV4-8/rh.64, AAV4-9/rh.54, AAV5, AAV52.1/hu.20, AAV52/hu.19, AAV5-22/rh.58, AAV5-3/rh.57, AAV54.1/hu.21, AAV54.2/hu.22, AAV54.4R/hu.27, AAV54.5/hu.23, AAV54.7/hu.24, AAV58.2/hu.25, AAV6, AAV6.1, AAV6.1.2, AAV6.2, AAV7, AAV7.2, AAV7.3/hu.7, AAV8, AAV-8b, AAV-8h, AAV9, AAV9.11, AAV9.13, AAV9.16, AAV9.24, AAV9.45, AAV9.47, AAV9.61, AAV9.68, AAV9.84, AAV9.9, AAV A3.3, AAV A3.4, AAV A3.5, AAV A3.7, AAV-b, AAVC1, AAVC2, AAVC5, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAV-DJ, AAV-DJ8, AAVF3, AAVF5, AAV-h, AAVH-1/hu.1, AAVH2, AAVH-5/hu.3, AAVH6, AAVhE1.1, AAVhER1.14, AAVhEr1.16, AAVhEr1.18, AAVhER1.23, AAVhEr1.35, AAVhEr1.36, AAVhEr1.5, AAVhEr1.7, AAVhEr1.8, AAVhEr2.16, AAVhEr2.29, AAVhEr2.30, AAVhEr2.31, AAVhEr2.36, AAVhEr2.4, AAVhEr3.1, AAVhu. 1, AAVhu.10, AAVhu.11, AAVhu. 1, AAVhu.12, AAVhu.13, AAVhu.14/9, AAVhu.15, AAVhu.16, AAVhu.17, AAVhu.18, AAVhu.19, AAVhu.2, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.3, AAVhu.31, AAVhu.32, AAVhu.34, AAVhu.35, AAVhu.37, AAVhu.39, AAVhu.4, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.5, AAVhu.51, AAVhu.52, AAVhu.53, AAVhu.54, AAVhu.55, AAVhu.56, AAVhu.57, AAVhu.58, AAVhu.6, AAVhu.60, AAVhu.61, AAVhu.63, AAVhu.64, AAVhu.66, AAVhu.67, AAVhu.7, AAVhu.8, AAVhu.9, AAVhu.t 19, AAVLG-10/rh.40, AAVLG-4/rh.38, AAVLG-9/hu.39, AAVLG-9/hu.39, AAV-LK01, AAV-LK02, AAVLK03, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK17, AAV-LK18, AAV-LK19, AAVN721-8/rh.43, AAV-PAEC, AAV-PAEC11, AAV-PAEC12, AAV-PAEC2, AAV-PAEC4, AAV-PAEC6, AAV-PAEC7, AAV-PAEC8, AAVpi. 1, AAVpi.2, AAVpi.3, AAVrh.10, AAVrh.12, AAVrh.13, AAVrh. 13R, AAVrh.14, AAVrh.17, AAVrh.18, AAVrh.19, AAVrh.2, AAVrh.20, AAVrh.21, AAVrh.22, AAVrh.23, AAVrh.24, AAVrh.25, AAVrh.2R, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.43, AAVrh.44, AAVrh.45, AAVrh.46, AAVrh.47, AAVrh.48, AAVrh.48, AAVrh.48.1, AAVrh.48.1.2, AAVrh.48.2, AAVrh.49, AAVrh.50, AAVrh.51, AAVrh.52, AAVrh.53, AAVrh.54, AAVrh.55, AAVrh.56, AAVrh.57, AAVrh.58, AAVrh.59, AAVrh.60, AAVrh.61, AAVrh.62, AAVrh.64, AAVrh.64R1, AAVrh.64R2, AAVrh.65, AAVrh.67, AAVrh.68, AAVrh.69, AAVrh.70, AAVrh.72, AAVrh.73, AAVrh.74, AAVrh.8, AAVrh.8R, AAVrh8R, AAVrh8R A586R mutant, AAVrh8R R533A mutant, BAAV, BNP61 AAV, BNP62 AAV, BNP63 AAV, bovine AAV, caprine AAV, Japanese AAV 10, true type AAV (ttAAV), UPENN AAV 10, AAV-LK16, AAAV, AAV Shuffle 100-1, AAV Shuffle 100-2, AAV Shuffle 100-3, AAV Shuffle 100-7, AAV Shuffle 10-2, AAV Shuffle 10-6, AAV Shuffle 10-8, AAV SM 100-10, AAV SM 100-3, AAV SM 10-1, AAV SM 10-2, and/or AAV SM 10-8.

In certain embodiments, the AAV serotype may comprise a mutation in the AAV9 sequence, such as the sequence described by Pulicherla et al. (*Molecular Therapy* 19(6): 1070-1078, 2011), such as AAV9.9, AAV9.11, AAV9.13, AAV9.16, AAV9.24, AAV9.45, AAV9.47, AAV9.61, AAV9.68, AAV9.84.

In certain embodiments, the AAV serotype may comprise a sequence described in U.S. Pat. No. 6,156,303, such as AAV3B (SEQ ID NOs: 1 and 10 of U.S. Pat. No. 6,156,303), AAV6 (SEQ ID NOs: 2, 7 and 11 of U.S. Pat. No. 6,156,303), AAV2 (SEQ ID NOs: 3 and 8 of U.S. Pat. No. 6,156,303), AAV3A (SEQ ID NOs: 4 and 9, of U.S. Pat. No. 6,156,303), or derivatives thereof.

In certain embodiments, the serotype may be AAV-DJ or a variant thereof, such as AAVDJ8 (or AAV-DJ8), as described by Grimm et al. (*Journal of Virology* 82(12): 5887-5911, 2008). The amino acid sequence of AAV-DJ8 may comprise two or more mutations in order to remove the heparin binding domain (HBD). As a non-limiting example, the AAV-DJ sequence described as SEQ ID NO: 1 in U.S. Pat. No. 7,588,772 may comprise two mutations: (1) R587Q (Arg at amino acid 587 is changed to glutamine Gln), and (2)

R590T. As another non-limiting example, the AAV-DJ sequence may comprise three mutations: (1) K406R, (2) R587Q, and (3) R590T.

In certain embodiments, the AAV serotype may comprise a sequence as described in WO2015/121501, such as true type AAV (ttAAV) (SEQ ID NO: 2 of WO2015/121501), the so-called UPenn AAV10 (SEQ ID NO: 8 of WO2015/121501), or the so-called Japanese AAV10 (SEQ ID NO: 9 of WO2015/121501), or variants thereof.

AAV capsid serotype selection or use may be from a variety of species. In certain embodiments, the AAV may be an avian AAV (aAAV). The aAAV serotype may comprise a sequence described in U.S. Pat. No. 9,238,800, such as aAAV (SEQ ID NOs: 1, 2, 4, 6, 8, 10, 12, and 14 of U.S. Pat. No. 9,238,800), or variants thereof.

In certain embodiments, the AAV may be a bovine AAV (bAAV). The bAAV serotype may comprise a sequence described in U.S. Pat. No. 9,193,769, such as bAAV (SEQ ID NOs: 1 and 6 of U.S. Pat. No. 9,193,769), or variants thereof. The bAAV serotype may comprise a sequence as described in U.S. Pat. No. 7,427,396, such as bAAV (SEQ ID NOs: 5 and 6 of U.S. Pat. No. 7,427,396), or variants thereof.

In certain embodiments, the AAV may be a caprine AAV. The caprine AAV serotype may comprise a sequence described in U.S. Pat. No. 7,427,396, such as caprine AAV (SEQ ID NO: 3 of U.S. Pat. No. 7,427,396), or variants thereof.

In certain embodiments, the AAV may be engineered as a hybrid AAV from two or more parental serotypes.

In certain embodiments, the AAV may be AAV2G9, which comprises sequences from AAV2 and AAV9. The AAV2G9 AAV serotype may comprise a sequence described in US 2016-0017005 A1. (incorporated herein by reference).

In certain embodiments, the AAV may be a serotype generated by the AAV9 capsid library with mutations in amino acids 390-627 (VP1 numbering) as described by Pulicherla et al. (*Molecular Therapy* 19(6): 1070-1078, 2011, incorporated herein by reference). The serotype and corresponding nucleotide and amino acid substitutions may be, but is not limited to: AAV9.1 (G1594C; D532H), AAV6.2 (T1418A and T1436X; V473D and I479K), AAV9.3 (T1238A; F413Y), AAV9.4 (T1250C and A1617T; F417S), AAV9.5 (A1235G, A1314T, A1642G, C1760T; Q412R, T548A, A587V), AAV9.6 (T1231A; F411I), AAV9.9 (G1203A, G1785T, W595C), AAV9.10 (A1500G, T1676C; M559T), AAV9.11 (A1425T, A1702C, A1769T; T568P, Q590L), AAV9.13 (A1369C, A1720T; N457H, T574S), AAV9.14 (T1340A, T1362C, T1560C, G1713A; L447H), AAV9.16 (A1775T; Q592L), AAV9.24 (T1507C, T1521G; W503R), AAV9.26 (A1337G, A1769C; Y446C, Q590P), AAV9.33 (A1667C; D556A), AAV9.34 (A1534G, C1794T; N512D), AAV9.35 (A1289T, T1450A, C1494T, A1515T, C1794A, G1816A; Q430L, Y484N, N98K, V6061), AAV9.40 (A1694T, E565V), AAV9.41 (A1348T, T1362C; T450S), AAV9.44 (A1684C, A1701T, A1737G; N562H, K567N), AAV9.45 (A1492T, C1804T; N498Y, L602F), AAV9.46 (G1441C, T1525C, T1549G; G481R, W509R, L517V), 9.47 (G1241A, G1358A, A1669G, C1745T; S414N, G453D, K557E, T582I), AAV9.48 (C1445T, A1736T; P482L, Q579L), AAV9.50 (A1638T, C1683T, T1805A; Q546H, L602H), AAV9.53 (G1301A, A1405C, C1664T, G1811T; R134Q, S469R, A555V, G604V), AAV9.54 (C1531A, T1609A; L511I, L537M), AAV9.55 (T1605A; F535L), AAV9.58 (C1475T, C1579A; T492I, H527N), AAV.59 (T1336C; Y446H), AAV9.61 (A1493T; N4981), AAV9.64 (C1531A, A1617T; L511I), AAV9.65 (C1335T, T1530C, C1568A; A523D), AAV9.68 (C1510A; P504T), AAV9.80 (G1441A; G481R), AAV9.83 (C1402A, A1500T; P468T, E500D), AAV9.87 (T1464C, T1468C; S490P), AAV9.90 (A1196T; Y399F), AAV9.91 (T1316G, A1583T, C1782G, T1806C; L439R, K528I), AAV9.93 (A1273G, A1421G, A1638C, C1712T, G1732A, A1744T, A1832T; S425G, Q474R, Q546H, P571L, G578R, T582S, D611V), AAV9.94 (A1675T; M559L) and AAV9.95 (T1605A; F535L).

In certain embodiments, the AAV may be a serotype comprising at least one AAV capsid CD8$^+$ T-cell epitope. As a non-limiting example, the serotype may be AAV1, AAV2 or AAV 8.

In certain embodiments, the AAV may be a variant, such as PHP.A or PHP.B as described in Deverman (*Nature Biotechnology*. 34(2): 204-209, 2016, incorporated herein by reference).

In certain embodiments, the AAV may be a serotype generated by Cre-recombination-based AAV targeted evolution (CREATE) described by Deverman et al., (*Nature Biotechnology* 34(2):204-209, 2016, incorporated herein by reference). In certain embodiments, the AAV serotypes generated in this manner have improved CNS transduction and/or neuronal and astrocytic tropism, as compared to other AAV serotypes.

In some embodiments, the AAV serotypes may be an AAV9 derivative with a 7-amino acid insertion between amino acids 588-589. Non-limiting examples of these 7-amino acid insertions include PHP.A, PHP.B, PHP.B2, PHP.B3, PHP.N, PHP.S, G2A12, G2A15, G2A3, G2B4, and G2B5.

In certain embodiments, the AAV may be a serotype selected from any of those found in SEQ ID NOs: 4,734-5,302 and in Table 2 of WO2018/002719A1 (incorporated herein by reference). In certain embodiments, the AAV may be encoded by a sequence, fragment or variant as described in SEQ ID NOs: 4,734-5,302 of WO2018/002719A1 (incorporated herein by reference).

In certain embodiments, the AAV VP1 capsid sequence is one of the following: AAV1, AAV2, AAV3A, AAV3B, AAV4, AAV5, AAV6, AAV7, AAV8, AAV9, AAV10, AAV11, AAV12, AAV13, AAV-DJ, AAV PHP.eB, Anc80L65, Anc80L65AAP, or 7m8.

Protein sequences of the above representative VP1 capsids are provided below.

```
MAADGYLPDWLEDNLSEGIREWWDLKPGAPKPKANQQKQDDGRGLVLPGYKYLGPFNGLDKGEPVNAA

DAAALEHDKAYDQQLKAGDNPYLRYNHADAEFQERLQEDTSFGGNLGRAVFQAKKRVLEPLGLVEEGA

KTAPGKKRPVEQSPQEPDSSSGIGKTGQQPAKKRLNFGQTGDSESVPDPQPLGEPPATPAAVGPTTMA

SGGGAPMADNNEGADGVGNASGNWHCDSTWLGDRVITTSTRTWALPTYNNHLYKQISSASTGASNDNH

YFGYSTPWGYFDFNRFHCHFSPRDWQRLINNNWGFRPKRLNFKLFNIQVKEVTTNDGVTTIANNLTST
```

VQVFSDSEYQLPYVLGSAHQGCLPPFPADVFMIPQYGYLTLNNGSQAVGRSSFYCLEYFPSQMLRTGN

NFTFSYTFEEVPFHSSYAHSQSLDRLMNPLIDQYLYYLNRTQNQSGSAQNKDLLFSRGSPAGMSVQPK

NWLPGPCYRQQRVSKTKTDNNNSNFTWTGASKYNLNGRESIINPGTAMASHKDDEDKFFPMSGVMIFG

KESAGASNTALDNVMITDEEEIKATNPVATERFGTVAVNFQSSSTDPATGDVHAMGALPGMVWQDRDV

YLQGPIWAKIPHTDGHFHPSPLMGGFGLKNPPPQILIKNTPVPANPPAEFSATKFASFITQYSTGQVS

VEIEWELQKENSKRWNPEVQYTSNYAKSANVDFTVDNNGLYTEPRPIGTRYLTRPL (AAV1; SEQ ID NO: 6)

MAADGYLPDWLEDTLSEGIRQWWKLKPGPPPPKPAERHKDDSRGLVLPGYKYLGPFNGLDKGEPVNEA

DAAALEHDKAYDRQLDSGDNPYLKYNHADAEFQERLKEDTSFGGNLGRAVFQAKKRVLEPLGLVEEPV

KTAPGKKRPVEHSPVEPDSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNHLYKQISSQSGASNDNHY

FGYSTPWGYFDFNRFHCHESPRDWQRLINNNWGFRPKRLNFKLENIQVKEVTQNDGTTTIANNLTSTV

QVFTDSEYQLPYVLGSAHQGCLPPFPADVFMVPQYGYLTLNNGSQAVGRSSFYCLEYFPSQMLRTGNN

FTFSYTFEDVPFHSSYAHSQSLDRLMNPLIDQYLYYLSRTNTPSGTTTQSRLQFSQAGASDIRDQSRN

WLPGPCYRQQRVSKTSADNNNSEYSWTGATKYHLNGRDSLVNPGPAMASHKDDEEKFFPQSGVLIFGK

QGSEKTNVDIEKVMITDEEEIRTTNPVATEQYGSVSTNLQRGNRQAATADVNTQGVLPGMVWQDRDVY

LQGPIWAKIPHTDGHFHPSPLMGGFGLKHPPPQILIKNTPVPANPSTTFSAAKFASFITQYSTGQVSV

EIEWELQKENSKRWNPEIQYTSNYNKSVNVDFTVDTNGVYSEPRPIGTRYLTRNL (AAV2; SEQ ID NO: 7)

MAADGYLPDWLEDNLSEGIREWWALKPGVPQPKANQQHQDNRRGLVLPGYKYLGPGNGLDKGEPVNEA

DAAALEHDKAYDQQLKAGDNPYLKYNHADAEFQERLQEDTSFGGNLGRAVFQAKKRILEPLGLVEEAA

KTAPGKKGAVDQSPQEPDSSSGVGKSGKQPARKRLNFGQTGDSESVPDPQPLGEPPAAPTSLGSNTMA

SGGGAPMADNNEGADGVGNSSGNWHCDSQWLGDRVITTSTRTWALPTYNNHLYKQISSQSGASNDNHY

FGYSTPWGYFDFNRFHCHFSPRDWQRLINNNWGFRPKKLSFKLFNIQVRGVTQNDGTTTIANNLTSTV

QVFTDSEYQLPYVLGSAHQGCLPPFPADVFMVPQYGYLTLNNGSQAVGRSSFYCLEYFPSQMLRTGNN

FQFSYTFEDVPFHSSYAHSQSLDRLMNPLIDQYLYYLNRTQGTTSGTTNQSRLLFSQAGPQSMSLQAR

NWLPGPCYRQQRLSKTANDNNNSNFPWTAASKYHLNGRDSLVNPGPAMASHKDDEEKFFPMHGNLIFG

KEGTTASNAELDNVMITDEEEIRTTNPVATEQYGTVANNLQSSNTAPTTGTVNHQGALPGMVWQDRDV

YLQGPIWAKIPHTDGHFHPSPLMGGFGLKHPPPQIMIKNTPVPANPPTTFSPAKFASFITQYSTGQVS

VEIEWELQKENSKRWNPEIQYTSNYNKSVNVDFTVDTNGVYSEPRPIGTRYLTRNL (AAV3A; SEQ ID NO: 8)

MAADGYLPDWLEDNLSEGIREWWALKPGVPQPKANQQHQDNRRGLVLPGYKYLGPGNGLDKGEPVNEA

DAAALEHDKAYDQQLKAGDNPYLKYNHADAEFQERLQEDTSFGGNLGRAVFQAKKRILEPLGLVEEAA

KTAPGKKRPVDQSPQEPDSSSGVGKSGKQPARKRLNFGQTGDSESVPDPQPLGEPPAAPTSLGSNTMA

SGGGAPMADNNEGADGVGNSSGNWHCDSQWLGDRVITTSTRTWALPTYNNHLYKQISSQSGASNDNHY

FGYSTPWGYFDFNRFHCHFSPRDWQRLINNNWGFRPKKLSFKLFNIQVKEVTQNDGTTTIANNLTSTV

QVFTDSEYQLPYVLGSAHQGCLPPFPADVFMVPQYGYLTLNNGSQAVGRSSFYCLEYFPSQMLRTGNN

FQFSYTFEDVPFHSSYAHSQSLDRLMNPLIDQYLYYLNRTQGTTSGTTNQSRLLFSQAGPQSMSLQAR

NWLPGPCYRQQRLSKTANDNNNSNFPWTAASKYHLNGRDSLVNPGPAMASHKDDEEKFFPMHGNLIFG

KEGTTASNAELDNVMITDEEEIRTTNPVATEQYGTVANNLQSSNTAPTTRTVNDQGALPGMVWQDRDV

YLQGPIWAKIPHTDGHFHPSPLMGGFGLKHPPPQIMIKNTPVPANPPTTFSPAKFASFITQYSTGQVS

-continued

VEIEWELQKENSKRWNPEIQYTSNYNKSVNVDFTVDTNGVYSEPRPIGTRYLTRNL (AAV3B; SEQ
ID NO: 9)

MTDGYLPDWLEDNLSEGVREWWALQPGAPKPKANQQHQDNARGLVLPGYKYLGPGNGLDKGEPVNAAD
AAALEHDKAYDQQLKAGDNPYLKYNHADAEFQQRLQGDTSFGGNLGRAVFQAKKRVLEPLGLVEQAGE
TAPGKKRPLIESPQQPDSSTGIGKKGKQPAKKKLVFEDETGAGDGPPEGSTSGAMSDDSEMRAAAGGA
AVEGGQGADGVGNASGDWHCDSTWSEGHVTTTSTRTWVLPTYNNHLYKRLGESLQSNTYNGFSTPWGY
FDFNRFHCHFSPRDWQRLINNNWGMRPKAMRVKIFNIQVKEVTTSNGETTVANNLTSTVQIFADSSYE
LPYVMDAGQEGSLPPFPNDVFMVPQYGYCGLVTGNTSQQQTDRNAFYCLEYFPSQMLRTGNNFEITYS
FEKVPFHSMYAHSQSLDRLMNPLIDQYLWGLQSTTTGTTLNAGTATTNFTKLRPTNFSNFKKNWLPGP
SIKQQGFSKTANQNYKIPATGSDSLIKYETHSTLDGRWSALTPGPPMATAGPADSKFSNSQLIFAGPK
QNGNTATVPGTLIFTSEEELAATNATDTDMWGNLPGGDQSNSNLPTVDRLTALGAVPGMVWQNRDIYY
QGPIWAKIPHTDGHFHPSPLIGGFGLKHPPPQIFIKNTPVPANPATTFSSTPVNSFITQYSTGQVSVQ
IDWEIQKERSKRWNPEVQFTSNYGQQNSLLWAPDAAGKYTEPRAIGTRYLTHHL (AAV4; SEQ ID
NO: 10)

MSFVDHPPDWLEEVGEGLREFLGLEAGPPKPKPNQQHQDQARGLVLPGYNYLGPGNGLDRGEPVNRAD
EVAREHDISYNEQLEAGDNPYLKYNHADAEFQEKLADDTSFGGNLGKAVFQAKKRVLEPFGLVEEGAK
TAPTGKRIDDHFPKRKKARTEEDSKPSTSSDAEAGPSGSQQLQIPAQPASSLGADTMSAGGGGPLGDN
NQGADGVGNASGDWHCDSTWMGDRVVTKSTRTWVLPSYNNHQYREIKSGSVDGSNANAYFGYSTPWGY
FDFNRFHSHWSPRDWQRLINNYWGFRPRSLRVKIFNIQVKEVTVQDSTTTIANNLTSTVQVFTDDDYQ
LPYVVGNGTEGCLPAFPPQVFTLPQYGYATLNRDNTENPTERSSFFCLEYFPSKMLRTGNNFEFTYNF
EEVPFHSSFAPSQNLFKLANPLVDQYLYRFVSTNNTGGVQFNKNLAGRYANTYKNWFPGPMGRTQGWN
LGSGVNRASVSAFATTNRMELEGASYQVPPQPNGMTNNLQGSNTYALENTMIFNSQPANPGTTATYLE
GNMLITSESETQPVNRVAYNVGGQMATNNQSSTTAPATGTYNLQEIVPGSVWMERDVYLQGPIWAKIP
ETGAHFHPSPAMGGFGLKHPPPMMLIKNTPVPGNITSFSDVPVSSFITQYSTGQVTVEMEWELKKENS
KRWNPEIQYTNNYNDPQFVDFAPDSTGEYRTTRPIGTRYLTRPL (AAV5; SEQ ID NO: 11)

MAADGYLPDWLEDNLSEGIREWWDLKPGAPKPKANQQKQDDGRGLVLPGYKYLGPFNGLDKGEPVNAA
DAAALEHDKAYDQQLKAGDNPYLRYNHADAEFQERLQEDTSFGGNLGRAVFQAKKRVLEPFGLVEEGA
KTAPGKKRPVEQSPQEPDSSSGIGKTGQQPAKKRLNFGQTGDSESVPDPQPLGEPPATPAAVGPTTMA
SGGGAPMADNNEGADGVGNASGNWHCDSTWLGDRVITTSTRTWALPTYNNHLYKQISSASTGASNDNH
YFGYSTPWGYFDFNRFHCHFSPRDWQRLINNNWGFRPKRLNFKLFNIQVKEVTTNDGVTTIANNLTST
VQVFSDSEYQLPYVLGSAHQGCLPPFPADVFMIPQYGYLTLNNGSQAVGRSSFYCLEYFPSQMLRTGN
NFTFSYTFEDVPFHSSYAHSQSLDRLMNPLIDQYLYYLNRTQNQSGSAQNKDLLFSRGSPAGMSVQPK
NWLPGPCYRQQRVSKTKTDNNNSNFTWTGASKYNLNGRESIINPGTAMASHKDDKDKFFPMSGVMIFG
KESAGASNTALDNVMITDEEEIKATNPVATERFGTVAVNLQSSSTDPATGDVHVMGALPGMVWQDRDV
YLQGPIWAKIPHTDGHFHPSPLMGGFGLKHPPPQILIKNTPVPANPPAEFSATKFASFITQYSTGQVS
VEIEWELQKENSKRWNPEVQYTSNYAKSANVDFTVDNNGLYTEPRPIGTRYLTRPL (AAV6; SEQ
ID NO: 12)

MAADGYLPDWLEDNLSEGIREWWDLKPGAPKPKANQQKQDNGRGLVLPGYKYLGPFNGLDKGEPVNAA
DAAALEHDKAYDQQLKAGDNPYLRYNHADAEFQERLQEDTSFGGNLGRAVFQAKKRVLEPLGLVEEGA
KTAPAKKRPVEPSPQRSPDSSTGIGKKGQQPARKRLNFGQTGDSESVPDPQPLGEPPAAPSSVGSGTV

-continued

AAGGGAPMADNNEGADGVGNASGNWHCDSTWLGDRVITTSTRTWALPTYNNHLYKQISSETAGSTNDN

TYFGYSTPWGYFDFNRFHCHFSPRDWQRLINNNWGFRPKKLRFKLFNIQVKEVTTNDGVTTIANNLTS

TIQVFSDSEYQLPYVLGSAHQGCLPPFPADVFMIPQYGYLTLNNGSQSVGRSSFYCLEYFPSQMLRTG

NNFEFSYSFEDVPFHSSYAHSQSLDRLMNPLIDQYLYYLARTQSNPGGTAGNRELQFYQGGPSTMAEQ

AKNWLPGPCFRQQRVSKTLDQNNNSNFAWTGATKYHLNGRNSLVNPGVAMATHKDDEDRFFPSSGVLI

FGKTGATNKTTLENVLMTNEEEIRPTNPVATEEYGIVSSNLQAANTAAQTQVVNNQGALPGMVWQNRD

VYLQGPIWAKIPHTDGNFHPSPLMGGFGLKHPPPQILIKNTPVPANPPEVFTPAKFASFITQYSTGQV

SVEIEWELQKENSKRWNPEIQYTSNFEKQTGVDFAVDSQGVYSEPRPIGTRYLTRNL (AAV7; SEQ

ID NO: 13)

MAADGYLPDWLEDNLSEGIREWWALKPGAPKPKANQQKQDDGRGLVLPGYKYLGPFNGLDKGEPVNAA

DAAALEHDKAYDQQLQAGDNPYLRYNHADAEFQERLQEDTSFGGNLGRAVFQAKKRVLEPLGLVEEGA

KTAPGKKRPVEPSPQRSPDSSTGIGKKGQQPARKRLNFGQTGDSESVPDPQPLGEPPAAPSGVGPNTM

AAGGGAPMADNNEGADGVGSSSGNWHCDSTWLGDRVITTSTRTWALPTYNNHLYKQISNGTSGGATND

NTYFGYSTPWGYFDFNRFHCHFSPRDWQRLINNNWGFRPKRLSFKLFNIQVKEVTQNEGTKTIANNLT

STIQVFTDSEYQLPYVLGSAHQGCLPPFPADVFMIPQYGYLTLNNGSQAVGRSSFYCLEYFPSQMLRT

GNNFQFTYTFEDVPFHSSYAHSQSLDRLMNPLIDQYLYYLSRTQTTGGTANTQTLGFSQGGPNTMANQ

AKNWLPGPCYRQQRVSTTTGQNNNSNFAWTAGTKYHLNGRNSLANPGIAMATHKDDEERFFPSNGILI

FGKQNAARDNADYSDVMLTSEEEIKTTNPVATEEYGIVADNLQQQNTAPQIGTVNSQGALPGMVWQNR

DVYLQGPIWAKIPHTDGNFHPSPLMGGFGLKHPPPQILIKNTPVPADPPTTFNQSKLNSFITQYSTGQ

VSVEIEWELQKENSKRWNPEIQYTSNYYKSTSVDFAVNTEGVYSEPRPIGTRYLTRNL (AAV8;

SEQ ID NO: 14)

MAADGYLPDWLEDNLSEGIREWWALKPGAPQPKANQQHQDNARGLVLPGYKYLGPGNGLDKGEPVNAA

DAAALEHDKAYDQQLKAGDNPYLKYNHADAEFQERLKEDTSFGGNLGRAVFQAKKRLLEPLGLVEEAA

KTAPGKKRPVEQSPQEPDSSAGIGKSGAQPAKKRLNFGQTGDTESVPDPQPIGEPPAAPSGVGSLTMA

SGGGAPVADNNEGADGVGSSSGNWHCDSQWLGDRVITTSTRTWALPTYNNHLYKQISNSTSGGSSNDN

AYFGYSTPWGYFDFNRFHCHFSPRDWQRLINNNWGFRPKRLNFKLFNIQVKEVTDNNGVKTIANNLTS

TVQVFTDSDYQLPYVLGSAHEGCLPPFPADVFMIPQYGYLTLNDGSQAVGRSSFYCLEYFPSQMLRTG

NNFQFSYEFENVPFHSSYAHSQSLDRLMNPLIDQYLYYLSKTINGSGQNQQTLKFSVAGPSNMAVQGR

NYIPGPSYRQQRVSTTVTQNNNSEFAWPGASSWALNGRNSLMNPGPAMASHKEGEDRFFPLSGSLIFG

KQGTGRDNVDADKVMITNEEEIKTTNPVATESYGQVATNHQSAQAQAQTGWVQNQGILPGMVWQDRDV

YLQGPIWAKIPHTDGNEHPSPLMGGFGMKHPPPQILIKNTPVPADPPTAFNKDKLNSFITQYSTGQVS

VEIEWELQKENSKRWNPEIQYTSNYYKSNNVEFAVNTEGVYSEPRPIGTRYLTRNL (AAV9; SEQ

ID NO: 15)

MAADGYLPDWLEDNLSEGIREWWDLKPGAPKPKANQQKQDDGRGLVLPGYKYLGPFNGLDKGEPVNAA

DAAALEHDKAYDQQLKAGDNPYLRYNHADAEFQERLQEDTSFGGNLGRAVFQAKKRVLEPLGLVEEAA

KTAPGKKRPVEPSPQRSPDSSTGIGKKGQQPAKKRLNFGQTGESESVPDPQPIGEPPAGPSGLGSGTM

AAGGGAPMADNNEGADGVGSSSGNWHCDSTWLGDRVITTSTRTWALPTYNNHLYKQISNGTSGGSTND

NTYFGYSTPWGYFDFNRFHCHFSPRDWQRLINNNWGFRPKRLSFKLFNIQVKEVTQNEGTKTIANNLT

STIQVFTDSEYQLPYVLGSAHQGCLPPFPADVFMIPQYGYLTLNNGSQAVGRSSFYCLEYFPSQMLRT

GNNFEFSYTFEDVPFHSSYAHSQSLDRLMNPLIDQYLYYLSRTQSTGGTQGTQQLLFSQAGPANMSAQ

AKNWLPGPCYRQQRVSTTLSQNNNSNFAWTGATKYHLNGRDSLVNPGVAMATHKDDEERFFPSSGVLM

-continued

FGKQGAGRDNVDYSSVMLTSEEEIKTTNPVATEQYGVVADNLQQANTGPIVGVNSQGALPGMVWQNR

DVYLQGPIWAKIPHTDGNFHPSPLMGGFGLKHPPPQILIKNTPVPADPPTTFSQAKLASFITQYSTGQ

VSVEIEWELQKENSKRWNPEIQYTSNYYKSTNVDFAVNTEGTYSEPRPIGTRYLTRNL (AAV10;

SEQ ID NO: 16)

MAADGYLPDWLEDNLSEGIREWWDLKPGAPKPKANQQKQDDGRGLVLPGYKYLGPFNGLDKGEPVNAA

DAAALEHDKAYDQQLKAGDNPYLRYNHADAEFQERLQEDTSFGGNLGRAVFQAKKRVLEPLGLVEEGA

KTAPGKKRPLESPQEPDSSSGIGKKGKQPARKRLNFEEDTGAGDGPPEGSDTSAMSSDIEMRAAPGGN

AVDAGQGSDGVGNASGDWHCDSTWSEGKVTTTSTRTWVLPTYNNHLYLRLGTTSSSNTYNGFSTPWGY

FDFNRFHCHFSPRDWQRLINNNWGLRPKAMRVKIFNIQVKEVTTSNGETTVANNLTSTVQIFADSSYE

LPYVMDAGQEGSLPPFPNDVFMVPQYGYCGIVTGENQNQTDRNAFYCLEYFPSQMLRTGNNFEMAYNF

EKVPFHSMYAHSQSLDRLMNPLLDQYLWHLQSTTSGETLNQGNAATTFGKIRSGDFAFYRKNWLPGPC

VKQQRFSKTASQNYKIPASGGNALLKYDTHYTLNNRWSNIAPGPPMATAGPSDGDFSNAQLIFPGPSV

TGNTTTSANNLLFTSEEEIAATNPRDTDMFGQIADNNQNATTAPITGNVTAMGVLPGMVWQNRDIYYQ

GPIWAKIPHADGHFHPSPLIGGFGLKHPPPQIFIKNTPVPANPATTFTAARVDSFITQYSTGQVAVQI

EWEIEKERSKRWNPEVQFTSNYGNQSSMLWAPDTTGKYTEPRVIGSRYLTNHL (AAV11; SEQ ID

NO: 17)

MAADGYLPDWLEDNLSEGIREWWALKPGAPQPKANQQHQDNGRGLVLPGYKYLGPFNGLDKGEPVNEA

DAAALEHDKAYDKQLEQGDNPYLKYNHADAEFQQRLATDTSFGGNLGRAVFQAKKRILEPLGLVEEGV

KTAPGKKRPLEKTPNRPTNPDSGKAPAKKKQKDGEPADSARRTLDFEDSGAGDGPPEGSSSGEMSHDA

EMRAAPGGNAVEAGQGADGVGNASGDWHCDSTWSEGRVTTTSTRTWVLPTYNNHLYRIGTTANSNTY

NGFSTPWGYFDFNRFHCHFSPRDWQRLINNNWGLRPKSMRVKIFNIQVKEVTTSNGETTVANNLTSTV

QIFADSTYELPYVMDAGQEGSFPPFPNDVFMVPQYGYCGWTGKNQNQTDRNAFYCLEYFPSQMLRTG

NNFEVSYQFEKVPFHSMYAHSQSLDRMMNPLLDQYLWHLQSTTTGNSLNQGTATTTYGKITTGDFAYY

RKNWLPGACIKQQKFSKNANQNYKIPASGGDALLKYDTHTTLNGRWSNMAPGPPMATAGAGDSDFSNS

QLIFAGPNPSGNTTTSSNNLLFTSEEEIATTNPRDTDMFGQIADNNQNATTAPHIANLDAMGIVPGMV

WQNRDIYYQGPIWAKVPHTDGHFHPSPLMGGFGLKHPPPQIFIKNTPVPANPNTTFSAARINSFLTQY

STGQVAVQIDWEIQKEHSKRWNPEVQFTSNYGTQNSMLWAPDNAGNYHELRAIGSRFLTHHL (AAV12; SEQ ID NO: 18)

MTDGYLPDWLEDNLSEGVREWWALQPGAPKPKANQQHQDNARGLVLPGYKYLGPGNGLDKGEPVNAAD

AAALEHDKAYDQQLKAGDNPYLKYNHADAEFQERLQEDTSFGGNLGRAVFQAKKRILEPLGLVEEAAK

TAPGKKRPVEQSPAEPDSSSGIGKSGQQPARKRLNFGQTGDTESVPDPQPLGQPPAAPSGVGSTTMAS

GGGAPMADNNEGADGVGNSSGNWHCDSQWLGDRVITTSTRTWALPTYNNHLYKQISSQSGATNDNHYF

GYSTPWGYFDFNRFHCHFSPRDWQRLINNNWGFRPKRLNFKLFNIQVKEVTQNDGTTTIANNLTSTVQ

VFTDSEYQLPYVLGSAHQGCLPPFPADVFMVPQYGYLTLNNGSQAVGRSSFYCLEYFPSQMLRTGNNF

QFSYTFEDVPFHSSYAHSQSLDRLMNPLIDQYLYYLNRTQTASGTQQSRLLFSQAGPTSMSLQAKNWL

PGPCYRQQRLSKQANDNNSNFPWTGATKYHLNGRDSLVNPGPAMASHKDDKEKFFPMHGTLIFGKEG

TNANNADLENVMITDEEEIRTTNPVATEQYGTVSNNLQNSNAGPTTGTVNHQGALPGMVWQDRDVYLQ

GPIWAKIPHTDGHFHPSPLMGGFGLKHPPPQIMIKNTPVPANPPTNFSAAKFASFITQYSTGQVSVEI

EWELQKENSKRWNPEIQYTSNYNKSVNVDFTVDTNGVYSEPRPIGTRYLTRNL (AAV13; SEQ ID

NO: 19)

-continued

MAADGYLPDWLEDTLSEGIRQWWKLKPGPPPPKPAERHKDDSRGLVLPGYKYLGPFNGLDKGEPVNEA

DAAALEHDKAYDRQLDSGDNPYLKYNHADAEFQERLKEDTSFGGNLGRAVFQAKKRLLEPLGLVEEAA

KTAPGKKRPVEHSPVEPDSSSGTGKAGQQPARKRLNFGQTGDADSVPDPQPIGEPPAAPSGVGSLTMA

AGGGAPMADNNEGADGVGNSSGNWHCDSTWMGDRVITTSTRTWALPTYNNHLYKQISNSTSGGSSNDN

AYFGYSTPWGYFDFNRFHCHFSPRDWQRLINNNWGFRPKRLSFKLFNIQVKEVTQNEGTKTIANNLTS

TIQVFTDSEYQLPYVLGSAHQGCLPPFPADVFMIPQYGYLTLNNGSQAVGRSSFYCLEYFPSQMLRTG

NNFQFTYTFEDVPFHSSYAHSQSLDRLMNPLIDQYLYYLSRTQTTGGTTNTQTLGFSQGGPNTMANQA

KNWLPGPCYRQQRVSKTSADNNNSEYSWTGATKYHLNGRDSLVNPGPAMASHKDDEEKFFPQSGVLIF

GKQGSEKTNVDIEKVMITDEEEIRTTNPVATEQYGSVSTNLQRGNRQAATADVNTQGVLPGMVWQDRD

VYLQGPIWAKIPHTDGHFHPSPLMGGFGLKHPPPQILIKNTPVPADPPTTFNQSKLNSFITQYSTGQV

SVEIEWELQKENSKRWNPEIQYTSNYYKSTSVDFAVNTEGVYSEPRPIGTRYLTRNL (AAV-DJ;

SEQ ID NO: 20)

MAADGYLPDWLEDNLSEGIREWWALKPGAPQPKANQQHQDNARGLVLPGYKYLGPGNGLDKGEPVNAA

DAAALEHDKAYDQQLKAGDNPYLKYNHADAEFQERLKEDTSFGGNLGRAVFQAKKRLLEPLGLVEEAA

KTAPGKKRPVEQSPQEPDSSAGIGKSGAQPAKKRLNFGQTGDTESVPDPQPIGEPPAAPSGVGSLTMA

SGGGAPVADNNEGADGVGSSSGNWHCDSQWLGDRVITTSTRTWALPTYNNHLYKQISNSTSGGSSNDN

AYFGYSTPWGYFDFNRFHCHFSPRDWQRLINNNWGFRPKRLNFKLFNIQVKEVTDNNGVKTIANNLTS

TVQVFTDSDYQLPYVLGSAHEGCLPPFPADVFMIPQYGYLTLNDGSQAVGRSSFYCLEYFPSQMLRTG

NNFQFSYEFENVPFHSSYAHSQSLDRLMNPLIDQYLYYLSRTINGSGQNQQTLKFSVAGPSNMAVQGR

NYIPGPSYRQQRVSTTVTQNNNSEFAWPGASSWALNGRNSLMNPGPAMASHKEGEDRFFPLSGSLIFG

KQGTGRDNVDADKVMITNEEEIKTTNPVATESYGQVATNHQSDGTLAVPFKAQAQTGWVQNQGILPGM

VWQDRDVYLQGPIWAKIPHTDGNFHPSPLMGGFGMKHPPPQILIKNTPVPADPPTAFNKDKLNSFITQ

YSTGQVSVEIEWELQKENSKRWNPEIQYTSNYYKSNNVEFAVNTEGVYSEPRPIGTRYLTRNL (AAV

PHP.eB; SEQ ID NO: 21)

MAADGYLPDWLEDNLSEGIREWWDLKPGAPKPKANQQKQDDGRGLVLPGYKYLGPFNGLDKGEPVNAA

DAAALEHDKAYDQQLKAGDNPYLRYNHADAEFQERLQEDTSFGGNLGRAVFQAKKRVLEPLGLVEEGA

KTAPGKKRPVEQSPQEPDSSSGIGKKGQQPARKRLNFGQTGDSESVPDPQPLGEPPAAPSGVGSNTMA

AGGGAPMADNNEGADGVGNASGNWHCDSTWLGDRVITTSTRTWALPTYNNHLYKQISSQSGGSTNDNT

YFGYSTPWGYFDFNRFHCHFSPRDWQRLINNNWGFRPKKLNFKLFNIQVKEVTTNDGTTTIANNLTST

VQVFTDSEYQLPYVLGSAHQGCLPPFPADVFMIPQYGYLTLNNGSQAVGRSSFYCLEYFPSQMLRTGN

NFQFSYTFEDVPFHSSYAHSQSLDRLMNPLIDQYLYYLSRTQTTSGTAGNRTLQFSQAGPSSMANQAK

NWLPGPCYRQQRVSKTTNQNNNSNFAWTGATKYHLNGRDSLVNPGPAMATHKDDEDKFFPMSGVLIFG

KQGAGNSNVDLDNVMITNEEEIKTTNPVATEEYGTVATNLQSANTAPATGTVNSQGALPGMVWQDRDV

YLQGPIWAKIPHTDGHFHPSPLMGGFGLKHPPPQILIKNTPVPANPPTTFSPAKFASFITQYSTGQVS

VEIEWELQKENSKRWNPEIQYTSNYNKSTNVDFAVDTNGVYSEPRPIGTRYLTRNL (Anc80L65;

SEQ ID NO: 22)

MAADGYLPDWLEDNLSEGIREWWDLKPGAPKPKANQQKQDDGRGLVLPGYKYLGPFNGLDKGEPVNAA

DAAALEHDKAYDQQLKAGDNPYLRYNHADAEFQERLQEDTSFGGNLGRAVFQAKKRVLEPLGLVEEGA

KTAPGKKRPVEQSPQEPDSSSGIGKKGQQPARKRLNFGQTGDSESVPDPQPLGEPPAAPSGVGSNTMA

AGGGAPMADNNEGADGVGNASGNWHCDSTWLGDRVITTSTRTWALPTYNNHLYKQISSQSGGSTNDNT

YFGYSTPWGYFDFNRFHCHFSPRDWQRLINNNWGFRPKKLNFKLFNIQVKEVTTNDGTTTIANNLTST

-continued

```
VQVFTDSEYQLPYVLGSAHQGCLPPFPADVFMIPQYGYLTLNNGSQAVGRSSFYCLEYFPSQMLRTGN

NFQFSYTFEDVPFHSSYAHSQSLDRLMNPLIDQYLYYLSRTQTTSGTAGNRTLQFSQAGPSSMANQAK

NWLPGPCYRQQRVSKTTNQNNNSNFAWTGATKYHLNGRDSLVNPGPAMATHKDDEDKFFPMSGVLIFG

KQGAGNSNVDLDNVMITNEEEIKTTNPVATEEYGTVATNLQSANTAPATGTVNSQGALPGMVWQDRDV

YLQGPIWAKIPHTDGHFHPSPLMGGFGLKHPPPQILIKNTPVPANPPTTFSPAKFASFITQYSTGQVS

VEIEWELQKENSKRWNPEIQYTSNYNKSTNVDFAVDTNGVYSEPRPIGTRYLTRNL (Anc80L65AAP; SEQ ID NO: 23)

MAADGYLPDWLEDTLSEGIRQWWKLKPGPPPPKPAERHKDDSRGLVLPGYKYLGPFNGLDKGEPVNEA

DAAALEHDKAYDRQLDSGDNPYLKYNHADAEFQERLKEDTSFGGNLGRAVFQAKKRVLEPLGLVEEPV

KTAPGKKRPVEHSPVEPDSSSGTGKAGQQPARKRLNFGQTGDADSVPDPQPLGQPPAAPSGLGTNTMA

TGSGAPMADNNEGADGVGNSSGNWHCDSTWMGDRVTTTSTRTWALPTYNNHLYKQISSQSGASNDNHY

FGYSTPWGYFDFNRFHCHFSPRDWQRLINNNWGFRPKRLNFKLFNIQVKEVTQNDGTTTIANNLTSTV

QVFTDSEYQLPYVLGSAHQGCLPPFPADVFMVPQYGYLTLNNGSQAVGRSSFYCLEYFPSQMLRTGNN

FTFSYTFEDVPFHSSYAHSQSLDRLMNPLIDQYLYYLSRTNTPSGTTTQSRLQFSQAGASDIRDQSRN

WLPGPCYRQQRVSKTSADNNNSEYSWTGATKYHLNGRDSLVNPGPAMASHKDDEEKFFPQSGVLIFGK

QGSEKTNVDIEKVMITDEEEIRTTNPVATEQYGSVSTNLQRGNLALGETTRPARQAATADVNTQGVLP

GMVWQDRDVYLQGPIWAKIPHTDGHFHPSPLMGGFGLKHPPPQILIKNTPVPANPSTTFSAAKFASFI

TQYSTGQVSVEIEWELQKENSKRWNPEIQYTSNYNKSINVDFTVDTNGVYSEPRPIGTRYLTRNL (7m8; SEQ ID NO: 24)
```

3. Modified AAV ITR

Any transcribed AAV ITR sequences (RNA) can be modified according to the disclosure herein, by engineering the encoding modified AAV ITR DNA template to, e.g., eliminate or inactivate the TRS or equivalent thereof, and/or to eliminate the D region sequence thereof. The transcribed modified AAV ITR, resulting from transcribing such modified AAV ITR DNA template, retains the ability to facilitate the packaging of the RNA sequence of the invention into an AAV viral particle.

During AAV DNA replication, the ITRs are nicked by the virus-encoded Rep proteins at the terminal resolution site (TRS). This origin function requires three DNA sequence elements, namely the Rep binding element (RBE), a small palindrome that comprises a single tip of an internal hairpin within the terminal repeat (RBE'), and the TRS. Rep is tethered to the RBE (DNA) in a specific orientation during TRS nicking. This orientation appears to align Rep on the AAV ITR, allowing specific nucleotide contacts with the RBE' and directing nicking to the TRS. Alterations in the polarity or position of the RBE relative to the TRS greatly inhibit Rep nicking. Substitutions within the RBE' also reduce Rep specific activity, but only to a lesser extent. Rep interactions with the RBE and RBE' during TRS nicking are functionally distinct, in that the Rep contact with the RBE is necessary for both the DNA helicase activity and the TRS cleavage. Meanwhile, Rep interaction with RBE' is required primarily for ITR unwinding and formation of the TRS stem-loop structure, but is not required for TRS cleavage.

At least one transcribed modified ITR sequence (RNA) of the invention is present on the RNA sequence of the invention. The transcribed modified ITR sequence of the invention is preferably located closer to the 3' end of the RNA sequence of the invention.

In certain embodiments, the RNA sequence of the invention comprises two transcribed modified ITR sequences.

In certain embodiments, the two transcribed modified ITR sequences may be derived from the same AAV serotype.

In another embodiment, the two transcribed modified ITR sequences may be derived from two different AAVs of different serotypes.

In certain embodiments, the transcribed modified ITR sequence(s) include(s) an insertion, deletion, and/or a mutation.

In some embodiments, the rRAAV RNA sequence of the invention comprises one transcribed modified/mutated ITR sequence and one transcribed wild-type ITR sequence.

In some embodiments, the transcribed modified ITR sequence(s) is/are based on a wild-type ITR in either the flip orientation or the flop orientation.

The subject transcribed modified ITR sequences, or their coding DNA sequences, can be readily prepared based on wild-type ITR sequences known in the art.

Figure 1B:
Figure 2:
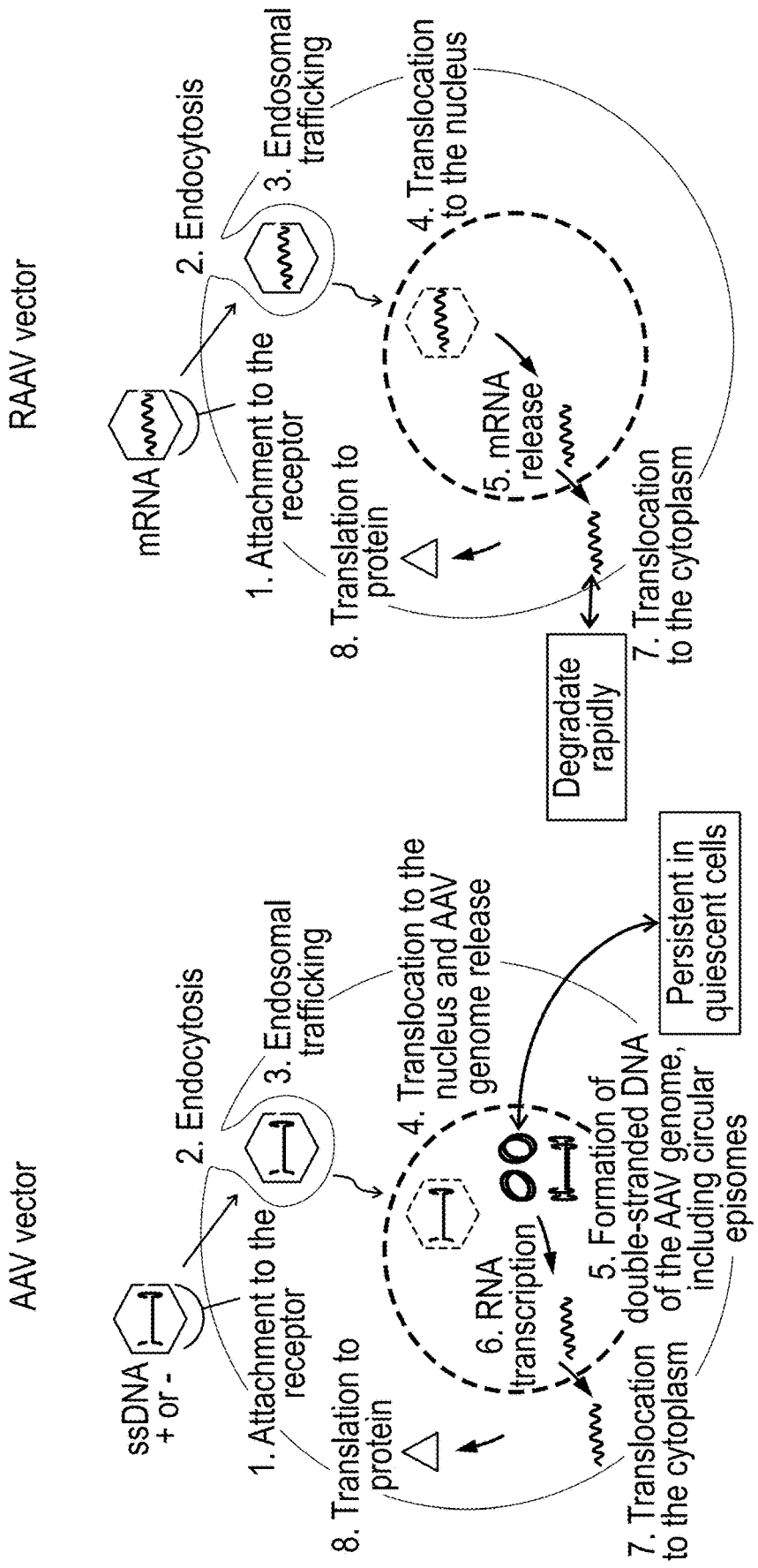
FIG. 2 shows the life cycle of an AAV vector/viral particle, and the subject RAAV vector/viral particle.

Representative (non-limiting) wild-type ITR sequences (DNA) including at least the following sequences listed in Table 1. A multi-sequence alignment for the 5' ITR sequences, and a multi-sequence alignment for the 3' ITR sequences of AAV1-AAV7 are shown in FIGS. 1B and 1C, respectively, including the consensus sequences, the TRS, the RBE, and the D region sequences.

TABLE 1

Representative Wild-type AAV Inverted Terminal Repeat (ITR) Sequences

| AAV ITR | DNA Sequences |
|---|---|
| AAV1 5' ITR | TTGCCCACTCCCTCTCTGCGCGCTCGCTCGCTCGGTGGGGCCTGCGGAC CAAAGGTCCGCAGACGGCAGAGCTCTGCTCTGCCGGCCCCACCGAGCGA GCGAGCGCGCAGAGAGGGAGTGGGCAACTCCATCACTAGGGGTAA (SEQ ID NO: 25) |
| AAV1 3' ITR | TTACCCCTAGTGATGGAGTTGCCCACTCCCTCTCTGCGCGCTCGCTCGC TCGGTGGGGCCTGCGGACCAAAGGTCCGCAGACGGCAGAGCTCTGCTCT GCCGGCCCCACCGAGCGAGCGAGCGCGCAGAGAGGGAGTGGGCAA (SEQ ID NO: 26) |
| AAV2 5' ITR | TTGGCCACTCCCTCTCTGCGCGCTCGCTCGCTCACTGAGGCCGGGCGAC CAAAGGTCGCCCGACGCCCGGGCTTTGCCCGGGCGGCCTCAGTGAGCGA GCGAGCGCGCAGAGAGGGAGTGGCCAACTCCATCACTAGGGGTTCCT (SEQ ID NO: 27) |
| AAV2 3' ITR | AGGAACCCCTAGTGATGGAGTTGGCCACTCCCTCTCTGCGCGCTCGCTC GCTCACTGAGGCCGGGCGACCAAAGGTCGCCCGACGCCCGGGCTTTGCC CGGGCGGCCTCAGTGAGCGAGCGAGCGCGCAGAGAGGGAGTGGCCAA (SEQ ID NO: 28) |
| AAV3 5' ITR | TTGGCCACTCCCTCTATGCGCACTCGCTCGCTCGGTGGGGCCTGGCGAC CAAAGGTCGCCAGACGGACGTGCTTTGCACGTCCGGCCCCACCGAGCGA GCGAGTGCGCATAGAGGGAGTGGCCAACTCCATCACTAGAGGTAT (SEQ ID NO: 29) |
| AAV3 3' ITR | ATACCTCTAGTGATGGAGTTGGCCACTCCCTCTATGCGCACTCGCTCGC TCGGTGGGGCCTGGCGACCAAAGGTCGCCAGACGGACGTGCTTTGCACG TCCGGCCCCACCGAGCGAGCGAGTGCGCATAGAGGGAGTGGCCAA (SEQ ID NO: 30) |
| AAV4 5' ITR | TTGGCCACTCCCTCTATGCGCGCTCGCTCACTCACTCGGCCCTGGAGAC CAAAGGTCTCCAGACTGCCGGCCTCTGGCCGGCAGGGCCGAGTGAGTGA GCGAGCGCGCATAGAGGGAGTGGCCAACTCCATCATCTAGGTTTGCCC (SEQ ID NO: 31) |
| AAV4 3' ITR | GGCAAACCAGATGATGGAGTTGGCCACATTAGCTATGCGCGCTCGCTCA CTCACTCGGCCCTGGAGACCAAAGGTCTCCAGACTGCCGGCCTCTGGCC GGCAGGGCCGAGTGAGTGAGCGAGCGCGCATAGAGGGAGTGGCCAA (SEQ ID NO: 32) |
| AAV5 5' ITR | CTCTCCCCCCTGTCGCGTTCGCTCGCTCGCTGGCTCGTTTGGGGGGTG GCAGCTCAAAGAGCTGCCAGACGACGGCCCTCTGGCCGTCGCCCCCCCA AACGAGCCAGCGAGCGAGCGAACGCGACAGGGGGGAGAGTGCCACACTC TCAAGCAAGGGGGTTTTGTA (Seq ID NO: 33) |
| AAV5 3' ITR | TACAAAACCTCCTTGCTTGAGAGTGTGGCACTCTCCCCCCTGTCGCGTT CGCTCGCTCGCTGGCTCGTTTGGGGGGGTGGCAGCTCAAAGAGCTGCCA GACGACGGCCCTCTGGCCGTCGCCCCCCCAAACGAGCCAGCGAGCGAGC GAACGCGACAGGGGGAGAG (Seq ID NO: 34) |
| AAV6 5' ITR | TTGGCCACTCCCTCTCTGCGCGCTCGCTCGCTCACTGAGGCCGGGCGAC CAAAGGTCGCCCGACGCCCGGGCTTTGCCCGGGCGGCCTCAGTGAGCGA GCGAGCGCGCAGAGAGGGAGTGGCCAACTCCATCACTAGGGGTTCCT (SEQ ID NO: 35) |
| AAV6 3' ITR | ATACCCCTAGTGATGGAGTTGCCCACTCCCTCTATGCGCGCTCGCTCGC TCGGTGGGGCCGGCAGAGCAGAGCTCTGCCGTCTGCGGACCTTTGGTCC GCAGGCCCCACCGAGCGAGCGAGCGCGCATAGAGGGAGTGGGCAA (SEQ ID NO: 36) |
| AAV7 5' ITR | TTGGCCACTCCCTCTATGCGCGCTCGCTCGCTCGGTGGGGCCTGCGGAC CAAAGGTCCGCAGACGGCAGAGCTCTGCTCTGCCGGCCCCACCGAGCGA GCGAGCGCGCATAGAGGGAGTGGCCAACTCCATCACTAGGGGTACCG (SEQ ID NO: 37) |
| AAV7 3' ITR | CGGTACCCCTAGTGATGGAGTTGGCCACTCCCTCTATGCGCGCTCGCTC GCTCGGTGGGGCCTGCGGACCAAAGGTCCGCAGACGGCAGAGCTCTGCT CTGCCGGCCCCACCGAGCGAGCGAGCGCGCATAGAGGGAGTGGCCAA (SEQ ID NO: 38) |

As used herein, "RBE sequence" or "RBE" refers to the AAV ITR sequences within the A:A' palindromic stem sequences that, when base-paired, form a stem (usually a double stranded region of about 21-23, or about 22 bp) and facilitate ITR binding to AAV Rep proteins (Rep78 and Rep68). A representative RBE sequence is shown in FIG. 1A, in both the flip and flop configurations of the wild-type AAV2 ITR.

Wild-type ITR sequences of the numerous AAV serotypes known in the art are readily available, each can be aligned with the other AAV ITRs as in FIGS. 1B and 1C. The results of the alignment can be used to identify the RBE sequences for any AAV ITR.

A "transcribed (functional) RBE" refers to a transcribed RNA corresponding to the RBE DNA template, which is either wild-type RBE, or a functional variant thereof with one or more nucleotide insertions, deletions, substitutions, and/or other mutations, so long as the functional variant RBE substantially retains the ability to bind to Rep (e.g., retains at least about 60%, 70%, 80%, 90%, 95%, or enhanced binding to Rep of the same serotype). In certain embodiments, the RBE DNA template or the transcribed RBE RNA differs from the wild-type sequence by no more than 10, 9, 8, 7, 6, 5, 4, 3, 2, 1 nucleotide(s). In certain embodiments, the functional RBE comprises up to about 30%, 25%, 20%, 15%, 10%, or 5% of sequence variation compared to the wild-type RBE, due to, for example, insertion, deletion, substitution, and/or other mutation of one or more nucleotides of the RBE.

In certain embodiments, the nucleotide sequence difference does not result in loss of paired base pair (e.g., a GC pair in the wild-type RBE can be changed to CG, AT/AU or TA/UA in the variant RBE without losing the original paired base pair).

In certain embodiments, the transcribed modified ITR sequence (RNA) retains a transcribed Rep-binding element (transcribed RBE) or a functional variant thereof, to facilitate Rep-mediated packaging. For example, the RBE DNA sequence for wild-type AAV2 ITR is SEQ ID NO: 5.

In certain embodiments, the transcribed modified ITR sequence (RNA) further retains a transcribed Rep-binding element' (transcribed RBE') sequence. For example, in FIG. 1A, the CTTTG DNA sequence forming the hairpin or loop structure in the B:B' segment of the flip ITR is the RBE' sequence.

In certain embodiments, the transcribed modified ITR sequence lacks a transcribed TRS, and/or a transcribed rcTRS, or both.

In certain embodiments, the RNA sequence of the invention lacks a transcribed (functional) TRS sequence, due to the fact that its corresponding DNA sequence lacks certain sequence elements of the wild-type TRS, such that wild-type TRS function is lost in the DNA (e.g., the sequence or internal strand normally occupied by the wild-type TRS sequence between the A:A' segment and D region sequence, which is normally recognized and cleaved by endonuclease during AAV replication, is not cleaved if present in the ssDNA vector genome of AAV ITR).

For example, in some embodiments, the reverse complement of the TRS may be deleted or mutated, as in the dITR and dITR-D sequence used in the examples.

Alternatively or in addition, the TRS normally between the A:A' segment and D region sequence may lack one or more nucleotides, or have one or more nucleotide substitutions or mutations (such as lacking or substituting/mutating 4 nucleotides in the dITR sequence used in the examples).

In certain embodiments, the entire or nearly the entire TRS/rcTRS in the wild-type sequence is deleted such that the resulting RNA transcript lacks a functional TRS sequence.

In certain embodiments, a part of the wild-type TRS/rcTRS sequence is altered/mutated by, for example, having an insertion, deletion, substitution, and/or other mutation in the wild-type sequence, such that the mutated TRS/rcTRS produces a corresponding RNA transcript that lacks a transcribed functional TRS. For example, in certain embodiments, 1 2, 3, 4, or 5 consecutive or non-consecutive TRS nucleotides and/or rcTRS nucleotides can be deleted or substituted in a mutated sequence.

In certain embodiments, the transcribed modified ITR sequence is transcribed from a modified ITR lacking a D region sequence, or at least a functional D region sequence (D sequence or D' sequence, depending on the flip or flop configuration). For example, in some embodiments, the entire D region sequence is deleted such that the resulting RNA transcript lacks a transcribed functional D region sequence. In other embodiments, at least a portion of the D region sequence is mutated (e.g., having deletion, insertion, substitution, and/or other mutation) such that the resulting RNA transcript lacks a transcribed functional D region sequence. In certain embodiments, the mutated D region sequence has no more than 10, 9, 8, 7, 6, 5, 4, 3, 2, or 1 nucleotide of the wild-type sequence.

In certain embodiments, the modified ITR sequence (DNA template) lacks 1, 2, 3, 4, 5, 6, 7, 8, 9, or 10 most 5' end nucleotides of the wild-type ITR sequence. For example, the dITR sequence (SEQ ID NO: 2) and the dITR-D sequence (SEQ ID NO: 3) both lack the most 5' end 8 nucleotides compared to the wild-type ITR sequence (SEQ ID NO: 1).

Corresponding DNA sequences encoding any of the above described transcribed RNA coding sequence (DNA coding sequence for the GOI), transcribed modified AAV ITR (modified AAV ITR), transcribed functional RBE (functional RBE), transcribed functional D region sequence (functional D region sequence), and transcribed functional TRS sequence (functional TRS sequence) are expressly contemplated as within the scope of the invention.

4. Introns, Exons, UTRs, Enhancers, and Other Elements

The RNA sequence of the invention to be encapsidated in the rRAAV viral particles of the invention may further comprise additional optional sequence elements (such as expression control elements) that may enhance or regulate the expression of the GOI.

Expression control elements present within the RNA sequence of the invention facilitate proper heterologous polynucleotide (e.g., GOI) transcription and/or translation, including, e.g., splicing signal for introns, maintenance of the correct reading frame of the gene to permit in-frame translation of mRNA and, stop codons etc.

Typically, expression control elements, some within the RNA sequence of the invention, and others present on the DNA encoding the RNA sequence of the invention, are nucleic acid sequence(s), such as promoters and enhancers that influence expression of an operably linked heterologous polynucleotide (e.g., GOI). Such elements typically act in cis but may also act in trans. Expression control can be effected at the level of transcription, translation, splicing, message stability, etc. Typically, an expression control element that modulates transcription is juxtaposed near the 5' end (i.e., "upstream") of the transcribed polynucleotide. Expression control elements can also be located at the 3' end (i.e., "downstream") of the transcribed sequence or within the transcript (e.g., in an intron). Expression control elements can be located at a distance away from the transcribed gene of interest sequence (e.g., 100 to 500, 500 to 1000, 2,000 to 5,000, or more nucleotides from the gene of interest polynucleotide). Nevertheless, owing to the polynucleotide length limitations for viral vectors, such as AAV vectors, such expression control elements will typically be within 1-1,000, 1-500, 1-250, or 1-100 nucleotides from the transcribed gene of interest sequence.

Some non-limiting expression control elements that may be present on the RNA sequence of the invention, or DNA encoding the RNA sequence of the invention, are described in further details herein below.

Introns

Introns are known to possess a posttranscriptional regulatory element that efficiently induces transport of mRNA out of the nucleus and enhances mRNA stability.

In certain embodiments, the rRAAV can include one or more introns or a fragment thereof. In some embodiments, the one or more introns are fragments of the gene of interest. In some embodiments, the one or more introns are heterologous to the gene of interest.

Introns have been reported to affect the levels of gene expression. This effect is known as Intron Mediated Enhancement (IME) of gene expression (Lu et al., *Mol Genet Genomics* 279:563-572, 2008). In some embodiments, the levels of gene expression are increases by about 1.5-fold, about 2-fold, about 2.5-fold, about 3-fold, about 3.5 fold, about 4-fold, about 4.5-fold, about 5-fold, about 5.5-fold, about 6-fold, about 6.5-fold, about 7-fold, about 7.5-fold, about 8-fold, about 8.5-fold, about 9-fold, about 9.5-fold, or about 10-fold when compared to gene expression from a sequence without the one or more introns.

Non-limiting introns include SV40 intron, beta globin intron, and short chimeric intron (CIB). Other introns include the ColE2-RNA-OUT, OIPR, and R6K-RNA-OUT introns described in Lu et al., Hum Gene Ther. 2017; 28(1):125-134 (incorporated by reference); the human hemoglobin subunit beta (HBB2) synthetic intron (Snyder et al., Hum Gene Ther, 8 (1997), pp. 1891-1900, incorporated by reference).

In some embodiments, the one or more introns may be less than 25 nucleotides, less than 50 nucleotides, less than 100 nucleotides, less than 150 nucleotides, less than 200 nucleotides, less than 250 nucleotides, less than 300 nucleotides, less than 350 nucleotides, less than 400 nucleotides, less than 450 nucleotides, or less than 500 nucleotides.

In some embodiments, the one or more introns may be more than 25 nucleotides, more than 50 nucleotides, more than 100 nucleotides, more than 150 nucleotides, more than 200 nucleotides, more than 250 nucleotides, more than 300 nucleotides, more than 350 nucleotides, more than 400 nucleotides, more than 450 nucleotides, or more than 500 nucleotides.

In some embodiments, the one or more introns may be about 50 to about 100 nucleotides, about 50 to about 200 nucleotides, about 50 to about 300 nucleotides, about 50 to about 400 nucleotides, about 50 to about 500 nucleotides, about 100 to about 200 nucleotides, about 100 to about 300 nucleotides, about 100 to about 400 nucleotides, about 100 to about 500 nucleotides, about 200 to about 300 nucleotides, about 200 to about 400 nucleotides, about 200 to about 500 nucleotides, about 300 to about 400 nucleotides, about 300 to about 500 nucleotides, or about 400 to about 500 nucleotides.

Enhancers

The term "enhancer" as used herein can refer to a sequence that is located adjacent to the gene of interest Enhancer elements are typically located upstream of a promoter element in the DNA encoding the RNA sequence of the invention, but can also be located downstream of or within an intron sequence (e.g., a gene of interest) and remain functional. Thus the enhancer or part thereof may be present in the transcribed RNA sequence of the invention.

Non-limiting examples of suitable enhancers include a CMV enhancer.

In certain embodiments, an enhancer element can be located 100 base pairs, 200 base pairs, or 300 or more base pairs upstream or downstream of a gene of interest (e.g., in the RNA sequence of the invention or a DNA coding sequence therefor). Enhancer elements typically increase expressed of a gene of interest above increased expression afforded by a promoter element.

Untranslated Regions (UTRs)

As used herein, "Untranslated Regions" ("UTRs") refer to RNA that are not translated after transcription. For example, the 5' UTR is upstream of the start code of the gene of interest and the 3' UTR is downstream of the stop codon of the gene of interest. In some embodiments, the 5' and/or 3' UTRs may have an insertion, deletion, or modification to enhance stability of the transcribed gene of interest. For Example, the 5' UTR may comprise a translation initiation sequence such as, but not limited to, a Kozak sequence and an internal ribosome entry site (IRES). Kozak sequences have the consensus CCR(A/G)CCAUGG (SEQ ID NO: 108), where R is a purine (adenine or guanine) three bases upstream of the start codon (AUG), which is followed by another 'G'.

3' UTRs are known to have stretches of Adenosines and Uridines embedded in them. These AU rich signatures are particularly prevalent in genes with high rates of turnover. Based on their sequence features and functional properties, the AU rich elements (AREs) can be separated into three classes (Chen et al, 1995): Class I AREs contain several dispersed copies of an AUUUA motif within U-rich regions. C-Myc and MyoD contain class I AREs. Class II AREs possess two or more overlapping UUAUUUA(U/A)(U/A) nonamers. Molecules containing this type of AREs include GM-CSF and TNF-α. Class III ARES are less well defined. These U rich regions do not contain an AUUUA motif. c-Jun and Myogenin are two well-studied examples of this class. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo. Any of these 5' and/or 3' UTR sequences can be present in the RNA sequence of the invention.

In some embodiments, the 5' UTR and/or 3'UTR may comprise heterologous sequence to the gene of interest. In some embodiments, the 5' UTR and/or 3' UTR are native to the gene of interest.

In certain embodiments, a 5' UTR and/or a 3' UTR from an mRNA normally expressed in a specific tissue or organ, such as lung, liver, pancreas, endothelial cells, CNS, neurons, astrocytes, skeletal muscle, cardiac muscle, smooth muscle, blood, hematopoietic cells may be used in the RNA sequence of the invention comprising a GOI targeted to one or more of these tissues.

Polyadenylation Sequence

In certain embodiments, the RNA sequence of the invention comprise a transcribed modified AAV ITR that is 5' to a polyA sequence, a polyA signal sequence (e.g., AAUAAA), or a sequence for RNA transcription termination (e.g., a histone downstream element).

The "polyA sequence," "polyA tail," "polyA signal sequence," and "a sequence for RNA transcription termination" are defined herein above.

In certain embodiments, the RNA sequence of the invention comprises a polyA tail. Such RNA sequence can be packaged into the rRAAV viral particles of the invention and be delivered directly into a target cell, and the GOI encoded by the RNA sequence of the invention can be directly translated.

In certain embodiments, the RNA sequence of the invention comprises a polyA signal sequence and optionally a transcribed GU-rich region downstream of the polyA site. Such RNA sequence can be packaged into the rRAAV viral particles of the invention and be delivered directly into a target cell. Once inside the target cell, the polyA signal sequence may be recognized and further processed by the cytosolic polyA addition enzymes to produce a polyA tail, before the GOI encoded by the RNA sequence of the invention is translated.

Representative polyA signal sequence and surrounding sequences include human growth hormone (hGH) polyA sequence (see Liu et al., Gene Ther 20:308-317, 2013, incorporated by reference), bovine growth hormone polyadenylation signal (bGHpA) (Goodwin and Rottman, J Biol Chem. 1992 Aug. 15; 267(23):16330-4, incorporated by reference), SV40 early or late polyadenylation signal, and the synthetic polyA signal used in Choi et al. (Mol Brain. 2014; 7:17, incorporated herein by reference).

Transcription Enhancer

As used herein, a "transcription enhancer" refer to cis-acting nucleotide sequences that can increase the transcription of the gene of interest. In some embodiments, the transcription enhancer can be located in the intron or partially in an exon region of the transcribed RAAV RNA sequence of the invention.

WPRE

In certain embodiments, the RNA sequence of the invention comprises a transcribed WPRE sequence, encoded by the WPRE sequence on the encoding DNA.

Woodchuck Hepatitis Virus (WHP) Posttranscriptional Regulatory Element (WPRE) is a 600-bp or so DNA sequence that, when transcribed, creates a tertiary structure enhancing expression.

WPRE is commonly used in molecular biology to increase expression of genes delivered by viral vectors. It is a tripartite regulatory element with gamma, alpha, and beta components. The alpha component is 80 bp long: GCCACGGCGGAACTCATCGCCGCCTGCCTTGCCC-GCTGCTGGACAGGGGCTCGGCTGTTGGGCACTG-ACAATTCCGTGG T (SEQ ID NO: 39). When used alone, the alpha component is only 9% as active as the full tripartite WPRE sequence, which is 100% identical to base pairs 1093-1684 of the Woodchuck hepatitis B virus (WHV8) genome.

In certain embodiments, the transcribed WPRE sequence or part thereof (such as the gamma, alpha, and beta elements, preferably in the given order) is present in a 3' UTR region of a GOI on the subject RNA sequence encapsidated in the rRAAV viral particle of the invention, to substantially increase stability and protein yield of the RNA sequence of the invention.

In certain embodiments, the WPRE sequence is a shorted WPRE (WPRE2) containing a minimal gamma element and a partial alpha-beta element (see Kalev-Zylinska, J Neurosci. 2007, 27: 10456-10467, incorporated by reference).

In certain embodiments, the WPRE sequence is a shorted WPRE (WPRE3) containing minimal gamma and alpha elements (see Choi et al., Mol Brain 7, 17 (2014), incorporated by reference).

In certain embodiments, the RNA sequence of the invention comprises a WPRE sequence and a GOI lacking introns.

Promoters

The term "promoter" as used herein is defined as a DNA sequence recognized by the synthetic machinery of the cell, or introduced synthetic machinery, required to initiate the specific transcription of a polynucleotide sequence.

Thus the RNA sequence of the invention does not comprise a promoter. On the other hand, a DNA encoding the RNA sequence of the invention (such as an expression cassette or expression vector encoding the RNA sequence of the invention) comprises a promoter for transcribing the RNA sequence of the invention.

As used herein, the term "promoter/regulatory sequence" means a nucleic acid sequence which is required for expression of a gene product operably linked to the promoter/regulatory sequence. In some instances, this sequence may be the core promoter sequence. In other instances, this sequence may also include an enhancer sequence and other regulatory elements which are required for expression of the gene product. The promoter/regulatory sequence may, for example, be one which expresses the gene product (e.g., the RNA sequence of the invention) in a tissue or cell type specific manner.

As used herein, the term "operable linkage" or "operably linked" refers to a physical or functional juxtaposition of the components so described as to permit them to function in their intended manner. In the example of an expression control element in operable linkage with a heterologous polynucleotide, the relationship is such that the control element modulates expression of the heterologous polynucleotide. More specifically, for example, two DNA sequences operably linked means that the two DNAs are arranged (cis or trans) in such a relationship that at least one of the DNA sequences is able to exert a physiological effect upon the other sequence.

In certain embodiments, the promoter is a constitutive promoter.

As used herein, a "constitutive" promoter is a nucleotide sequence which, when operably linked with a polynucleotide which encodes or specifies a gene product, causes the gene product to be produced in a cell under most or all physiological conditions of the cell.

In certain embodiments, a promoter that can be used to constitutively drive the expression of the RNA sequence of the invention from a DNA encoding the same can include: a 13 glucuronidase (GUSB) promoter, a cytomegalovirus (CMV) immediate-early (Ie) enhancer and/or promoter, a chicken β-actin (CBA) promoter or derivative thereof such as a CAG promoter, CB promoter, a (human) elongation factor 1α-subunit (EF1α) promoter, and a ubiquitin C (UBC) promoter.

In certain embodiments, the promoter is an inducible promoter.

As used herein, an "inducible" promoter is a nucleotide sequence which, when operably linked with a polynucleotide which encodes or specifies a gene product, causes the gene product to be produced in a cell substantially only when an inducer which corresponds to the promoter is present in the cell.

In certain embodiments, the promoter is a tissue-specific promoter, a species specific promoter, or a cell cycle-specific promoter. See Parr et al., Nat. Med. 3:1145-9, 1997 (entire contents incorporated herein by reference).

As used herein, a "tissue- or cell-type-specific" promoter is a nucleotide sequence which, when operably linked with a polynucleotide encodes or specified by a gene, causes the gene product to be produced in a specific cell type or a specific tissue preferentially, due to, for example, the cell/tissue is a cell type or tissue type in which the promoter is normally active.

Tissue- or cell type-specific promoters may include neuronal tissue specific promoter; CNS- or PNS-specific promoter such as astrocyte, oligodendrocyte, or neuronal promotor; hematopietic lineage specific promoter such as B cell promoter, T cell promoter, NK cell promoter, monocyte promoter, leukocyte promoter, macrophage promoter; endothelial cell promoter; pancreatic promoter; liver/hepatic cell promoter; lung tissue promoter, etc.

Representative tissue-specific promoters include prion promoter, neuron-specific enolase (NSE), neurofilament light (NFL) promoter, neurofilament heavy (NFH) promoter, platelet-derived growth factor (PDGF), platelet-derived growth factor B-chain (PDGF-β), synapsin (Syn), synapsin 1 (Syn 1), methyl-CpG binding protein 2 (MeCP2), Ca2+/calmodulin-dependent protein kinase II (CaMKII), metabotropic glutamate receptor 2 (mGluR2), neurofilament light (NFL) or heavy (NFH), β-globin minigene nβ2, preproenkephalin (PPE), enkephalin (Enk) and excitatory amino acid transporter 2 (EAAT2) promoters.

Astrocyte-specific promoters include glial fibrillary acidic protein (GFAP) and EAAT2 promoters.

Oligodendrocyte-specific promoters include the myelin basic protein (MBP) promoter.

In some embodiments, the promoter is heterologous to the gene of interest. In some embodiments, the promoter is the natural promoter of the gene of interest. In some embodiments, the heterologous promoter includes an insertion, deletion, substitution, and/or other mutation. In some embodiments, the natural promoter includes an insertion, deletion, substitution, and/or other mutation.

In certain embodiments, the promoter is a Pol II promoter. In certain embodiments, the promoter is a Pol III promoter, such as U6 promoter.

5. Vectors (Plasmids or Bacmids

As used herein, a "vector" generally refers to a composition of matter which comprises an isolated nucleic acid (DNA or RNA) and which can be used to deliver the isolated nucleic acid to the interior of a cell.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids, bacmids (e.g., naked or contained in liposomes) and viruses (e.g., lentiviruses, retroviruses, adenoviruses, and adeno-associated viruses) that incorporate the recombinant polynucleotide.

An rRAAV RNA sequence of the invention comprising a GOI is a vector for delivering the GOI into a target/host cell through a rRAAV viral particle encapsidating the vector.

In certain embodiments, the rRAAV RNA sequence of the invention is encoded by a DNA expression vector, such as a plasmid or bacmid (e.g., one that can be maintained or replicated like a baculovirus inside an insect cell). Such DNA expression vector can transcribe the RNA sequence of the invention within a suitable host cell, such as a mammalian packaging cell (e.g., HEK293T cells) or an insect packaging cell (e.g., Sf9 cells), such that the subject rRAAV viral particles can be produced in the presence of other elements necessary for rRAAV packaging (such as rep and cap coding sequences).

Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

In some embodiments, the RAAV is transcribed from a plasmid or bacmid. The plasmid or bacmid can include the gene of interest sequence. In some embodiments, the promoter is operably linked to the gene of interest and is located upstream of the gene of interest. In some embodiments, promoter is not in the transcribed RAAV.

6. AAV Particles and Populations of AAV Particles

In certain embodiments, the invention provides an isolated rRAAV viral particle comprising any one of the RNA sequence of the invention encapsidated within any one of the AAV capsid or viral particle described herein.

In some embodiments, the AAV capsid or viral particle is of a serotype or a combination of one or more serotypes described herein.

In the rRAAV vectors or RNA sequence of the present invention, the rRAAV genome (RNA) may be either a single stranded (ss) nucleic acid or a double stranded (ds), self-complementary (sc) nucleic acid.

A related aspect of the invention provides a population of recombinant viral particles (e.g., rRAAV particles) comprising a plurality of recombinant viral particle (e.g., rRAAV particle) of the invention, wherein at least about 10%, 20%, 30%, 40%, 50%, 60%, 70%, 80%, 90%, 95%, 96%, 97%, 98%, 99% or more of the recombinant viral particles (e.g., rRAAV particles) within the population have encapsidated RNA sequence of the invention.

In some embodiments, the population of rRAAV particles contain a plurality of rRAAV viral particle of the invention, wherein about 40%, 50%, 60%, 70%, 80%, 90%, 95%, 96%, 97%, 98%, 99% or more of the rRAAV particles within the population have encapsidated RNA sequence of the invention.

In certain embodiments, the population of recombinant viral particles (e.g., rRAAV particles) comprises at least $1 \times 10^4$ viral particles, at least $2 \times 10^4$ viral particles, at least $5 \times 10^4$ viral particles, at least $1 \times 10^5$ viral particles, at least $2 \times 10^5$ viral particles, at least $5 \times 10^5$ viral particles, at least $1 \times 10^6$ viral particles, at least $2 \times 10^6$ viral particles, at least $5 \times 10^6$ viral particles, at least $1 \times 10^7$ viral particles, at least $2 \times 10^7$ viral particles, at least $5 \times 10^7$ viral particles, at least $1 \times 10^8$ viral particles, at least $2 \times 10^8$ viral particles, at least $5 \times 10^8$ viral particles, at least $1 \times 10^9$ viral particles, at least $2 \times 10^9$ viral particles, at least $5 \times 10^9$ viral particles, at least $1 \times 10^{10}$ viral particles, at least $2 \times 10^{10}$ viral particles, at least $5 \times 10^{10}$ viral particles, at least $1 \times 10^{11}$ viral particles, at least $2 \times 10^{11}$ viral particles, at least $5 \times 10^{11}$ viral particles, at least $1 \times 10^{12}$ viral particles, at least $2 \times 10^{12}$ viral particles, at least $5 \times 10^{12}$ viral particles, at least $1 \times 10^{13}$ viral particles, at least $2 \times 10^{13}$ viral particles, at least $5 \times 10^{13}$ viral particles, at least $1 \times 10^{14}$ viral particles, at least $2 \times 10^{14}$ viral particles, at least $5 \times 10^{14}$ viral particles, at least $1 \times 10^{15}$ viral particles, at least $2 \times 10^{15}$ viral particles, at least $5 \times 10^{15}$ viral particles, at least $1 \times 10^{16}$ viral particles, at least $2 \times 10^{16}$ viral particles, or at least $5 \times 10^{16}$ viral particles.

In certain embodiments, at most 50%, 45%, 40%, 35%, 30%, 25%, 20%, 15%, 10%, 5%, 3%, 2%, 1%, 0.1%, 0.01% or less of the population of recombinant viral particles encapsidate non-RNA (e.g., DNA) within the viral particles.

7. Host Cells and AAV Production

General principles of rAAV production are known in the art. See review in, for example, Carter (*Current Opinions in Biotechnology*, 1533-539, 1992); and Muzyczka, Curr. Topics in Microbial, and *Immunol* 158:97-129, 1992, both incorporated herein by reference). Various approaches are described in Ratschin et al (*Mol. Cell. Biol.* 4:2072, 1984; Hermonat et al. (*Proc. Natl. Acad. Sci. USA* 81:6466, 1984); Tratschin et al. (*Mol. Cell. Biol.* 5:3251, 1985); McLaughlin et al. (*J. Virol* 62:1963, 1988); and Lebkowski et al. (*Mol. Cell. Biol* 7:349, 1988), Samulski et al. (*J. Virol* 63:3822-3828, 1989); U.S. Pat. No. 5,173,414; WO 95/13365 and U.S. Pat. No. 5,658,776; WO 95/13392; WO 96/17947; PCT/US98/18600; WO 97/09441; WO 97/08298; WO 97/21825; WO 97/06243; WO 99/11764; Perrin et al. (*Vaccine* 13:1244-1250, 1995; Paul et al. (*Human Gene Therapy* 4:609-615, 1993); Clark et al. (*Gene Therapy* 3:1124-1132, 1996; U.S. Pat. Nos. 5,786,211; 5,871,982; and 6,258,595.

AAV vector serotypes can be matched to target cell types. For example, Table 2 of WO2018002719A1 lists exemplary cell types that can be transduced by the indicated AAV serotypes (incorporated herein by reference).

Packaging cells are used to form virus particles that are capable of infecting a host cell. Such cells include HEK293 and Sf9 cells, which can be used to package AAV and adenovirus.

Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions can be supplied in trans by the packaging cell line, usually as a result of expression of these viral functions/proteins (such as the rep and cap genes for AAV) either as transgenes integrated into the packaging cell, or as transgenes on a second viral vector or expression vector introduced into the packaging cell.

For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a gene of interest) to be packaged into AAV particles, an AAV helper function vector, and an accessory function vector. An AAV helper function vector encodes the "AAV helper function" sequences (e.g., rep and cap), which function in trans for productive AAV replication and encapsidation. Preferably, the AAV helper function vector supports efficient AAV vector production without generating any detectable wild-type AAV virions (e.g., AAV virions containing functional rep and cap genes). The accessory function vector encodes nucleotide sequences for non-AAV derived viral and/or cellular functions upon which AAV is dependent for replication (e.g., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some embodiments, the subject rRAAV is produced using a baculovirus expression system packaged in insect cells such as Sf9 cells. See, for example, WO2007046703, WO2007148971, WO2009014445, WO2009104964, WO2013036118, WO2011112089, WO2016083560, WO2015137802, and WO2019016349, all incorporated herein by reference.

The vector titers are usually expressed as viral genomes per ml (vg/ml). In certain embodiments, viral titers is above $1 \times 10^9$, above $5 \times 10^{10}$, above $1 \times 10^{11}$, above $5 \times 10^{11}$, above $1 \times 10^{12}$, above $5 \times 10^{12}$, or above $1 \times 10^{13}$ vg/ml.

8. Gene of Interest (GOI) or RNA Sequence of Interest (RSI)

The rRAAV viral particles of the invention can be used to deliver any gene of interest (GOI) or RNA sequence of Interest (RSI) to a host cell, for any purpose, so long as the GOI is an RNA within the packaging limit of the chosen AAV viral capsid or AAV viral particle shell, such as about 4,700 nucleotides overall length for most AAV viral particles, up to about 8,900 nucleotides for certain large capacity AAV viral particles such as AAV5.

In certain embodiments, representative (non-limiting) RNA sequence of interest (RSI) includes, for example, a protein-encoding RNA, an mRNA, a non-coding RNA (ncRNA), a tRNA, a ribosomal RNA (rRNA), a transfer-messenger RNA (tmRNA), an antisense oligonucleotide (ASO), an RNA aptamer, an RNA component of CRISPR-Cas system such as a single guide RNA (or sgRNA, chimeric RNA, RNA chimera), CRISPR RNA (crRNA), tracr RNA, or an RNA component of a RISC complex or RNAi pathway (such as shRNA, miRNA, or siRNA), a regulatory RNA, Piwi-interacting RNAs (piRNAs), small nucleolar RNAs (snoRNAs), a long non-coding RNA (lncRNA) (including intergenic lincRNA, intronic ncRNA, and sense/antisense lncRNA), a long intervening/intergenic noncoding RNA (lincRNA), an enhancer RNA, a bacterial small RNA (sRNA), snRNA, exRNA, scaRNA, Xist, and HOTAIR, and a precursor thereof.

In certain embodiments, the RNA sequence of the invention comprises a coding sequence for a protein or polypeptide.

In certain embodiments, protein or polypeptide is a wild-type protein or functional equivalent or variant thereof (such as an enzyme or a structural protein) that can be used to replace a defective protein in a target cell, tissue, or organism.

In certain embodiments, protein or polypeptide is a wild-type protein or functional equivalent or variant thereof (such as an enzyme or a structural protein) that can be used to antagonize the detrimental effect of a compound (small molecule compound, or macromolecules such as lipids, fatty acids, protein, nucleic acid, etc) in a target cell, tissue, or organism.

For example, in certain embodiments, the RNA sequence of the invention comprises a coding sequence for an effector enzyme of CRISPR/Cas system.

In certain embodiments, the CRISPR-Cas system is a Class 1 system, and the effector enzyme is a type I, III, or IV effector enzyme.

In certain embodiments, the CRISPR-Cas system is a Class 2 system, and the effector enzyme is a type II, V, or VI effector enzyme.

For example, in some embodiments, the effector enzyme is a Class 2, type II enzyme such as Cas9, including *Streptococcus pyogenes* (SpCas9) or SaCas9 (see WO 2014/093622 (PCT/US2013/074667), incorporated by reference).

In certain embodiments, the Cas effector enzyme is a Class 2, type V Cas protein, including Cas12a (formerly known as Cpf1, such as *Francisella novicida* Cas12a), C2c1, and C2c3.

In certain embodiments, the Cas effector enzyme is a Class 2, type VI Cas protein, including Cas13a (also known as C2c2), Cas13b, Cas13c, Cas13d, Cas13e, and Cas13f. These Cas proteins use their crRNA to recognize target RNA sequences, rather than target DNA sequences in Cas9 and Cas12a.

In certain embodiments, the Cas effector enzyme is any one of the Cas effector enzymes described in WO2020/028555 (entire content incorporated herein by reference), including any of Cas9, Cas12 (e.g., Cas12a, Cas12b, Cas12c, Cas12d, etc.), Cas13 (e.g., Cas13a, Cas13b (such as Cas13b-t1, Cas13b-t2, Cas13b-t3), Cas13c, Cas13d, etc.), Cas14, CasX, and CasY.

In certain embodiments, the Cas effector enzyme is fused to a DNA and/or RNA base editor, such as Cytosine or Adenine base editors (CBEs or ABEs). In certain embodiments, the base editor preferentially edits DNA bases and optionally have reduced or substantially no off-target RNA base editing capability. In certain embodiments, the base editor preferentially edits RNA bases and optionally have reduced or substantially no off-target DNA base editing capability. In certain embodiments, the base editor edits both DNA and RNA bases.

In certain embodiments, the base editor is a first, second (BE2), third (BE3), or fourth generation (BE4) base editor. In certain embodiments, the base editor is a dual base editor.

In certain embodiments, the base editor is an RNA adenosine deaminase (ADAR), such as ADAR1, ADAR2, or ADARDD including ADAR2DD (E488Q).

In any of the above embodiments, the RNA sequence of the invention can further comprise a guide RNA sequence designed to be loaded into the encoded CRISPR/Cas effector enzyme for binding to a target polynucleotide sequence complementary to the guide RNA. Such gRNA sequence can be processed by cellular nucleases and be released/separated from the RNA sequence of the invention after the RNA sequence of the invention has been delivered by the rRAAV viral particles of the invention to a target host cell. For example, the gRNA can be present in an unpaired 5' or 3' flanking region sequence of a pri-miRNA hairpin structure that is part of the RNA sequence of the invention, and, upon processing of the pri-miRNA by cellular enzymes such as Drosha, is released/separated from the primary pri-miRNA transcript.

In certain embodiments, the RNA sequence of the invention comprises a coding sequence for an effector enzyme of CRISPR/Cas system, and further comprising a coding sequence for the DNA or RNA base-editing enzyme or domain, such that a fusion of a Cas effector enzyme and the DNA/RNA base-editing enzyme/domain is encoded by the RNA sequence. In certain embodiments, the Cas effector enzyme is defective in nuclease activity, such that it is able to bind to a target polynucleotide sequence through the guide RNA it binds, but is unable to cleave the DNA/RNA target polynucleotide.

In certain embodiments, the RNA sequence of the invention comprises a coding sequence for a variant or derivative of the effector enzyme of CRISPR/Cas system, wherein the variant comprises deletions (such as N and/or C terminal deletions, e.g., N-terminal deletion of no more than 210 residues, and/or a C-terminal deletion of no more than 180 residues for Cas13e or Cas13f), insertions, or substitutions of a wild-type CRISPR/Cas system effector enzyme but substantially retains the ability of the wild-type effector enzyme to bind to the gRNA, and/or to cleave the target polynucleotide. In certain embodiments, the variant lacks activity to cleave a target polynucleotide.

In certain embodiments, the RNA base-editing domain encoded by the RNA sequence of the invention is an adenosine deaminase, such as a double-stranded RNA-specific adenosine deaminase (e.g., ADAR1 or ADAR2); apolipoprotein B mRNA editing enzyme; catalytic polypeptide-like (APOBEC); or activation-induced cytidine deaminase (AID).

In certain embodiments, the RNA base-editing domain encoded by the RNA sequence of the invention comprises an adenosine deaminase and/or a cytidine deaminase, such as a cytidine deaminase acting on RNA (CDAR), such as a double-stranded RNA-specific adenosine deaminase (ADAR) (e.g., ADAR1 or ADAR2), apolipoprotein B mRNA editing enzyme, catalytic polypeptide-like (APOBEC, such as APOBEC1, APOBEC2, APOBEC3A, APOBEC3B, APOBEC3C, APOBEC3D, APOBEC3E, APOBEC3F, APOBEC3G, APOBEC3H, and APOBEC4), activation-induced cytidine deaminase (AID), a cytidine deaminase 1 (CDA1), or a mutant thereof.

In certain embodiments, the ADAR has E488Q/T375G double mutation or is ADAR2DD.

In certain embodiments, the base-editing domain is further fused to an RNA-binding domain, such as MS2.

In certain embodiments, the variant or derivative of the encoded CRISPR/Cas effector enzyme further comprises an RNA methyltransferase, a RNA demethylase, an RNA splicing modifier, a localization factor, or a translation modification factor.

In certain embodiments, the Cas effector enzyme, the variant/derivative, or a functional fragment thereof comprises a nuclear localization signal (NLS) sequence or a nuclear export signal (NES).

In certain embodiments, the Cas effector enzyme, the variant/derivative thereof, or the functional fragment thereof, is fused to a heterologous functional domain. In certain embodiments, the heterologous functional domain comprises: a nuclear localization signal (NLS), a reporter protein or a detection label (e.g., GST, HRP, CAT, GFP, HcRed, DsRed, CFP, YFP, BFP), a localization signal, a protein targeting moiety, a DNA binding domain (e.g., MBP, Lex A DBD, Gal4 DBD), an epitope tag (e.g., His, myc, V5, FLAG, HA, VSV-G, Trx, etc), a transcription activation domain (e.g., VP64 or VPR), a transcription inhibition domain (e.g., KRAB moiety or SID moiety), a nuclease (e.g., FokI), a deamination domain (e.g., ADAR1, ADAR2, APOBEC, AID, or TAD), a methylase, a demethylase, a transcription release factor, an HDAC, a polypeptide having ssRNA cleavage activity, a polypeptide having dsRNA cleavage activity, a polypeptide having ssDNA cleavage activity, a polypeptide having dsDNA cleavage activity, a DNA or RNA ligase, or any combination thereof. In certain embodiments, the heterologous functional domain is fused N-terminally, C-terminally, or internally in the fusion protein.

In certain embodiments, the RNA sequence of the invention comprises a coding sequence for a CasPR (CRISPR-associated Protein for Class 1 pre-crRNA processing) fusion protein, comprising a CasPR (or a homolog, an ortholog, a paralog, a variant, a derivative, or a functional fragment thereof) fused to a heterologous functional domain; or a functional variant thereof.

In certain embodiments, the CasPR is Cas5d, Cash, or Csf5.

In certain embodiments, the CasPR is MtCas6 (I-A) (Sequence 1), MmCas6 (I-B) (Sequence 2), SpCas5d (I-C1) (Sequence 3), BhCas5d (I-C2) (Sequence 4), SaCas6 (I-D) (Sequence 5), EcCas6e (I-E) (Sequence 6), PaCas6f (I-F) (Sequence 7), MtCas6 (III-A) (Sequence 8), PfCas6 (III-B) (Sequence 9), PaCsf5 (IV-A1) (Sequence 10), or MtCsf5 (IV-A2) (Sequence 11). All sequences incorporated herein by reference.

| Sequence No. | Description |
|---|---|
| 1 | MtCas6 Amino Acid Sequence |
| 2 | MmCas6 Amino Acid Sequence |
| 3 | SpCas5d Amino Acid Sequence |
| 4 | BhCas5d Amino Acid Sequence |
| 5 | SaCas6 Amino Acid Sequence |
| 6 | EcCas6e Amino Acid Sequence |
| 7 | PaCas6f Amino Acid Sequence |
| 8 | MtCas6 Amino Acid Sequence |
| 9 | PfCas6 Amino Acid Sequence |
| 10 | PaCsf5 Amino Acid Sequence |
| 11 | MtCsf5 Amino Acid Sequence |
| 12 | MtCas6 Direct Repeat (DR) Sequence |
| 13 | MmCas6 Direct Repeat (DR) Sequence |
| 14 | SpCas5d Direct Repeat (DR) Sequence |
| 15 | BhCas5d Direct Repeat (DR) Sequence |
| 16 | SaCas6 Direct Repeat (DR) Sequence |
| 17 | EcCas6e Direct Repeat (DR) Sequence |
| 18 | PaCas6f Direct Repeat (DR) Sequence |
| 19 | MtCas6 Direct Repeat (DR) Sequence |
| 20 | PfCas6 Direct Repeat (DR) Sequence |
| 21 | PaCsf5 Direct Repeat (DR) Sequence |
| 22 | MtCsf5 Direct Repeat (DR) Sequence |
| 23 | MtCas6 Direct Repeat (DR) Transcript Sequence |
| 24 | MmCas6 Direct Repeat (DR) Transcript Sequence |
| 25 | SpCas5d Direct Repeat (DR) Transcript Sequence |
| 26 | BhCas5d Direct Repeat (DR) Transcript Sequence |
| 27 | SaCas6 Direct Repeat (DR) Transcript Sequence |
| 28 | EcCas6e Direct Repeat (DR) Transcript Sequence |
| 29 | PaCas6f Direct Repeat (DR) Transcript Sequence |
| 30 | MtCas6 Direct Repeat (DR) Transcript Sequence |
| 31 | PfCas6 Direct Repeat (DR) Transcript Sequence |
| 32 | PaCsf5 Direct Repeat (DR) Transcript Sequence |
| 33 | MtCsf5 Direct Repeat (DR) Transcript Sequence |

(Seq Id No: 1)
MPLIFKIGYNVIPLQDVILPTPSSKVLKYLIQSGKLIPSLKDLITSRDKY
KPIFISHLGFNQRRIFQTNGNLKTITKGSRLSSIIAFSTQANVLSEVADE
GIFETVYGKFHIMIESIEIVEVEKLKEEVEKHMNDNIRVRFVSPTLLSSK
VLLPPSLSERYKKIHAGYSTLPSVGLIVAYAYNVYCNLIGKKEVEVRAFK
FGILSNALSRIIGYDLHPVTVAIGEDSKGNLRKARGVMGWIEFDIPDERL
KRRALNYLLTSSYLGIGRSRGIGFGEIRLEFRKIEEKEG (Seq Id No: 2)
MDLEYMHISYPNILLNMRDGSKLRGYFAKKYIDEEIVHNHRDNAFVYKYP
QIQFKIIDRSPLIIGIGSLGINFLESKRIFFEKELIISNDTNDITEVNVH
KDMDHFGTTDKILKYQFKTPWMALNAKNSEIYKNSDEIDREEFLKRVLIG
NILSMSKSLGYTIEEKLKVKINLKEVPVKFKNQNMVGFRGEFYINFDIPQ
YLGIGRNVSRGFGTVVKV (Seq Id No: 3)
MYRSRDFYVRVSGQRALFTNPATKGGSERSSYSVPTRQALNGIVDAIYYK
PTFTNIVTEVKVINQIQTELQGVRALLHDYSADLSYVSYLSDVVYLIKFH
FVWNEDRKDLNSDRLPAKHEAIMERSIRKGGRRDVFLGTRECLGLLDDIS
QEEYETTVSYYNGVNIDLGIMFHSFAYPKDKKTPLKSYFTKTVMKNGVIT
FKAQSECDIVNTLSSYAFKAPEEIKSVNDECMEYDAMEKGEN (Seq Id No: 4)
MRNEVQFELFGDYALFTDPLTKIGGEKLSYSVPTYQALKGIAESIYWKPT
IVFVIDELRVMKPIQMESKGVRPIEYGGGNTLAHYTYLKDVHYQVKAHFE
FNLHRPDLAFDRNEGKHYSILQRSLKAGGRRDIFLGARECQGYVAPCEFG
SGDGFYDGQGKYHLGTMVHGFNYPDETGQHQLDVRLWSAVMENGYIQFPR
PEDCPIVRPVKEMEPKIFNPDNVQSAEQLLHDLGGE (Seq Id No: 5)
MPNDPYSLYSIVIELGAAEKGFPTGILGRSLHSQVLQWFKQDNPFLATEL
HQSQISPFSISPLMGKRHAKLTKAGDRLFFRICLLRGDLLQPLLNGIEQT
VNQSVCLDKFRFRLCQTHILPGSHPLAGASHYSLISQTPVSSKITLDFKS
STSFKVDRKIIQVFPLGEHVFNSLLRRWNNFAPEDLHFSQVDWSIPIAAF
DVKTIPIHLKKVEIGAQGWVTYIFPNTEQAKIASVLSEFAFFSGVGRKTT
MGMGQVQVRS (Seq Id No: 6)
MYLSKVI1ARAWSRDLYQLHQGLWHLFPNRPDAARDFLFHVEKRNTPEGC
HVLLQSAQMPVSTAVATVIKTKQVEFQLQVGVPLYFRLRANPIKTILDNQ
KRLDSKGNIKRCRVPLIKEAEQIAWLQRKLGNAARVEDVHPISERPQYFS
GDGKSGKIQTVCFEGVLTINDAPALIDLVQQGIGPAKSMGCGLLSLAPL (Seq Id No: 7)
MDHYLDIRLRPDPEFPPAQLMSVLFGKLHQALVAQGGDRIGVSFPDLDES

RSRLGERLRIHASADDLRALLARPWLEGLRDHLQFGEPAVVPHPTPYRQV

SRVQAKSNPERLRRRLMRRHDLSEEEARKRIPDTVARALDLPFVTLRSQS

TGQHFRLFIRHGPLQVTAEEGGFTCYGLSKGGFVPWE (Seq Id No: 8)
MAARRGGIRRTDLLRRSGQPRGRHRASAAESGLTWISPTLILVGFSHRGD

RRMTEHLSRLTLTLEVDAPLERARVATLGPHLHGVLMESIPADYVQTLHT

VPVNPYSQYALARSTTSLEWKISTLTNEARQQIVGPINDAAFAGFRLRAS

GIATQVTSRSLEQNPLSQFARIFYARPETRKFRVEFLTPTAFKQSGEYVF

WPDPRLVFQSLAQKYGAIVDGEEPDPGLIAEFGQSVRLSAFRVASAPFAV

GAARVPGFTGSATFTVRGVDTFASYIAALLWFGEFSGCGIKASMGMGAIR

VQPLAPREKCVPKP (Seq Id No: 9)
MRFLIRLVPEDKDRAFKVPYNHQYYLQGLIYNAIKSSNPKLATYLHEVKG

PKLFTYSLFMAEKREHPKGLPYFLGYKKGFFYFSTCVPEIAEALVNGLLM

NPEVRLWDERFYLHEIKVLREPKKFNGSTFVTLSPIAVTVVRKGKSYDVP

PMEKEFYSIIKDDLQDKYVMAYGDKPPSEFEMEVLIAKPKRFRIKPGIYQ

TAWHLVFRAYGNDDLLKVGYEVGFGEKNSLGFGMVKVEGNKTTKEAEEQE

KITFNSREELKTGV (Seq Id No: 10)
MFVTQVIFNIGERTYPDRARAMVAELMDGVQPGLVATLMNYIPGTSTSRT

EFPTVQFGGASDGFCLLGFGDGGGAIVRDAVPLIHAALARRMPDRIIQVE

HKEHSLSAEARPYVLSYTVPRMVVQKKQRHAERLLHEAEGKAHLEGLFLR

SLQRQAAAVGLPLPENLEVEFKGAVGDFAAKHNPNSKVAYRGLRGAVFDV

NARLGGIWTAGFMLSKGYGQFNATHQLSGAVNALSE (Seq Id No: 11)
MHQTLIRINWPKGFKCPPAEFREKLAKSEMFPPEFFHYGTELAVWDKQTA

EVEGKIKTVSKEKIIKTFDKPIPLNGRAPVRVIGGQAWAGVIADPEMEGM

LIPHLGSILKVASSAAGCAVKIELEQRKFGISYTEYPVKYNLRELVLKRR

CEDARSTDIESLIADRIWGGVSGESYYGIDGTCAKFGFEPPSREQLELRI

FPMKNIGLHMKSSDGLSKEYMSLIDAEVWMNAKLEGVWQVGNLISRGYGR

FIKSIGAQS

Seq Id No: 12:
GATAATCTCTTATAGAATTGAAAG

Seq Id No: 13:
CTAAAAGAATAACTTGCAAAATAACAAGCATTGAAAC

Seq Id No: 14:
GTCTCACCCTTCATGGGTGAGTGGATTGAAAT

Seq Id No: 15:
GTCGCACTCTTCATGGGTGCGTGGATTGAAAT

Seq Id No: 16:
GTTTCAGTCCCGTAGTCGGGATTTAGTGGTTGGAAAG

Seq Id No: 17:
GAGTTCCCCGCGCCAGCGGGGATAAACCG

Seq Id No: 18:
GTTCACTGCCGTATAGGCAGCTAAGAAA

Seq Id No: 19:
GTCGTCAGACCCAAAACCCCGAGAGGGGACGGAAAC

Seq Id No: 20:
GTTACAATAAGACTAAAATAGAATTGAAAG

Seq Id No: 21:
GTATTTCCCGCGTGCGCGGGGGTGAGCGG

Seq Id No: 22:
TATTGGATACACCCACTCATTGGTGGGTGGTTAGAAC

Seq Id No: 23:
GAUAAUCUCUUAUAGAAUUGAAAG

Seq Id No: 24:
CUAAAAGAAUAACUUGCAAAAUAACAAGCAUUGAAAC

Seq Id No: 25:
GUCUCACCCUUCAUGGGUGAGUGGAUUGAAAU

Seq Id No: 26:
GUCGCACUCUUCAUGGGUGCGUGGAUUGAAAU

Seq Id No: 27:
GUUUCAGUCCCGUAGUCGGGAUUUAGUGGUUGGAAAG

Seq Id No: 28:
GAGUUCCCCGCGCCAGCGGGGAUAAACCG

Seq Id No: 29:
GUUCACUGCCGUAUAGGCAGCUAAGAAA

Seq Id No: 30:
GUCGUCAGACCCAAAACCCCGAGAGGGGACGGAAAC

Seq Id No: 31:
GUUACAAUAAGACUAAAAUAGAAUUGAAAG

Seq Id No: 32:
GUAUUUCCCGCGUGCGCGGGGUGAGCGG

Seq Id No: 33:
UAUUGGAUACACCCACUCAUUGGUGGGUGGUUAGAAC

In certain embodiments, the heterologous functional domain fused to the CasPR comprises: a nuclear localization signal (NLS), a reporter protein or a detection label (e.g., GST, HRP, CAT, GFP, HcRed, DsRed, CFP, YFP, BFP), a localization signal, a protein targeting moiety, a DNA binding domain (e.g., MBP, Lex A DBD, Gal4 DBD), an epitope tag (e.g., His, myc, V5, FLAG, HA, VSV-G, Trx, etc), a transcription activation domain (e.g., VP64 or VPR), a transcription inhibition domain (e.g., KRAB moiety or SID moiety), a nuclease (e.g., FokI), a deamination domain (e.g., ADAR1, ADAR2, APOBEC, AID, or TAD), a methylase, a demethylase, a transcription release factor, an HDAC, a polypeptide having ssRNA cleavage activity, a polypeptide having dsRNA cleavage activity, a polypeptide having ssDNA cleavage activity, a polypeptide having dsDNA cleavage activity, a DNA or RNA ligase, or any combination thereof. In certain embodiments, the heterologous functional domain comprises an RNA base editor. In certain embodiments, the RNA base editor edits A→G single base change. In certain embodiments, the RNA base editor edits C→U single base change. In certain embodiments, the RNA base editor comprises ADAR2DD or a derivative thereof. In certain embodiments, the ADAR2DD derivative comprises the E488Q/T375A double mutations.

In certain embodiments, the fusion protein has the amino acid sequence of any one of Sequences 45-55.

```
MtCas6 (I-A):
                                                    (SEQ ID NO: 45)
ATGCCCAAGAAGAAGCGGAAGGTGATGCCTCTGATCTTCAAGATCGGCTATAACGTGATCCC

CCTGCAGGACGTGATCCTGCCCACCCCTTCCAGCAAGGTGCTGAAGTACCTGATCCAGAGCG

GCAAGCTGATCCCCAGCCTGAAGGACCTGATCACCAGCCGGGACAAGTACAAGCCAATCTTC

ATCTCCCACCTGGGCTTCAACCAGCGGAGGATTTTCCAGACCAACGGCAATCTGAAAACCAT

CACCAAGGGCAGTAGACTGAGCTCCATCATCGCCTTCAGCACCCAGGCCAACGTGCTGTCCG

AGGTGGCCGATGAAGGGATCTTCGAAACCGTGTACGGAAAGTTCCACATCATGATCGAAAGC

ATCGAGATCGTGGAGGTGGAAAAGCTGAAGGAGGAGGTGGAGAAGCACATGAACGACAACAT

CAGAGTGAGATTCGTGTCTCCCACACTGCTGAGCTCCAAGGTGCTGCTGCCCCCCAGCCTGT

CCGAAAGATACAAGAAGATCCACGCCGGGTACAGCACCCTGCCCAGCGTGGGCCTGATCGTG

GCCTACGCCTACAACGTGTACTGCAATCTGATCGGCAAGAAGGAAGTGGAAGTGCGGGCCTT

CAAGTTTGGAATCCTGAGCAACGCCCTGTCCAGAATCATCGGCTACGACCTGCACCCTGTGA

CCGTGGCCATCGGCGAGGACAGCAAGGGGAATCTGAGAAAGGCTCGGGGCGTGATGGGCTGG

ATCGAGTTCGACATCCCCGACGAAAGACTGAAGCGGCGGGCCCTGAACTATCTGCTGACCAG

CAGCTACCTGGGCATCGGGAGATCTCGGGGCATCGGCTTCGGCGAGATCCGGCTGGAGTTCC

GGAAGATTGAAGAGAAGGAGGGACCCAAGAAGAAGCGGAAGGTGGGTGGAGGCGGAGGTTCT

GGGGGAGGAGGTAGTGGCGGTGGTGGTTCAGGAGGCGGCGGAAGCCAGCTGCATTTACCGCA

GGTTTTAGCTGACGCTGTCTCACGCCTGGTCATAGGTAAGTTTGGTGACCTGACCGACAACT

TCTCCTCCCCTCACGCTCGCAGAATAGGTCTGGCTGGAGTCGTCATGACAACAGGCACAGAT

GTTAAAGATGCCAAGGTGATATGTGTTTCTACAGGAGCAAAATGTATTAATGGTGAATACCT

AAGTGATCGTGGCCTTGCATTAAATGACTGCCATGCAGAAATAGTATCTCGGAGATCCTTGC

TCAGATTTCTTTATACACAACTTGAGCTTTACTTAAATAACGAGGATGATCAAAAAGATCC

ATCTTTCAGAAATCAGAGCGAGGGGGGTTTAGGCTGAAGGAGAATATACAGTTTCATCTGTA

CATCAGCACCTCTCCCTGTGGAGATGCCAGAATCTTCTCACCACATGAGGCAATCCTGGAAG

AACCAGCAGATAGACACCCAAATCGTAAAGCAAGAGGACAGCTACGGACCAAAATAGAGGCT

GGTCAGGGGACGATTCCAGTGCGCAACAATGCGAGCATCCAAACGTGGGACGGGGTGCTGCA

AGGGGAGCGGCTGCTCACCATGTCCTGCAGTGACAAGATTGCACGCTGGAACGTGGTGGGCA

TCCAGGGATCACTGCTCAGCATTTTCGTGGAGCCCATTTACTTCTCGAGCATCATCCTGGGC

AGCCTTTACCACGGGGACCACCTTTCCAGGGCCATGTACCAGCGGATCTCCAACATAGAGGA

CCTGCCACCTCTCTACACCCTCAACAAGCCTTTGCTCACAGGCATCAGCAATGCAGAAGCAC

GGCAGCCAGGGAAGGCCCCCATATTCAGTGTCAACTGGACGGTAGGCGACTCCGCTATTGAG

GTCATCAACGCCACGACTGGGAAGGGAGAGCTGGCCGCGCGTCCCGCCTGTGTAAGCACGC

GTTGTACTGTCGCTGGATGCGTGTGCACGGCAAGGTTCCCTCCCACTTACTACGCTCCAAGA

TTACCAAGCCCAACGTGTACCATGAGACAAAGCTGGCGGCAAAGGAGTACCAGGCCGCCAAG

GCGCGTCTGTTCACAGCCTTCATCAAGGCGGGGCTGGGGGCCTGGGTGGAGAAGCCCACCGA

GCAGGACCAGTTCTCACTCACGTAA

MmCas6 (I-B):
                                                    (SEQ ID NO: 46)
ATGCCCAAGAAGAAGCGGAAGGTGATGGACCTGGAGTACATGCACATCTCCTACCCTAACAT

CCTGCTGAACATGCGGGACGGCAGCAAGCTGCGGGGCTACTTCGCCAAGAAGTACATCGACG
```

-continued

```
AAGAGATTGTGCACAACCACAGAGACAACGCCTTTGTGTACAAGTACCCCCAGATCCAGTTT

AAGATCATCGATAGAAGCCCCCTGATCATCGGCATTGGCTCTCTGGGCATCAATTTCCTGGA

GAGCAAGCGGATCTTCTTCGAGAAGGAACTGATTATCAGCAACGACACCAACGACATCACCG

AGGTGAACGTGCACAAGGACATGGATCACTTCGGCACGACCGACAAGATCCTGAAGTACCAG

TTCAAGACCCCTTGGATGGCACTGAACGCCAAGAATAGCGAGATCTACAAGAACTCTGACGA

GATCGACCGGGAGGAGTTCCTGAAGAGAGTGCTGATTGGGAATATCCTGAGCATGTCTAAGA

GCCTGGGCTATACCATCGAAGAAAAGCTGAAGGTGAAGATTAACCTGAAGGAAGTGCCCGTG

AAGTTCAAGAACCAGAACATGGTGGGCTTTCGGGGCGAGTTCTACATCAACTTCGACATCCC

TCAGTATCTGGGCATCGGCCGGAATGTGTCCCGGGGATTCGGCACAGTGGTGAAGGTGCCCA

AGAAGAAGCGGAAGGTGGGTGGAGGCGGAGGTTCTGGGGGAGGAGGTAGTGGCGGTGGTGGT

TCAGGAGGCGGCGGAAGCCAGCTGCATTTACCGCAGGTTTTAGCTGACGCTGTCTCACGCCT

GGTCATAGGTAAGTTTGGTGACCTGACCGACAACTTCTCCTCCCCTCACGCTCGCAGAATAG

GTCTGGCTGGAGTCGTCATGACAACAGGCACAGATGTTAAAGATGCCAAGGTGATATGTGTT

TCTACAGGAGCAAAATGTATTAATGGTGAATACCTAAGTGATCGTGGCCTTGCATTAAATGA

CTGCCATGCAGAAATAGTATCTCGGAGATCCTTGCTCAGATTTCTTTATACACAACTTGAGC

TTTACTTAAATAACGAGGATGATCAAAAAAGATCCATCTTTCAGAAATCAGAGCGAGGGGGG

TTTAGGCTGAAGGAGAATATACAGTTTCATCTGTACATCAGCACCTCTCCCTGTGGAGATGC

CAGAATCTTCTCACCACATGAGGCAATCCTGGAAGAACCAGCAGATAGACACCCAAATCGTA

AAGCAAGAGGACAGCTACGGACCAAAATAGAGGCTGGTCAGGGGACGATTCCAGTGCGCAAC

AATGCGAGCATCCAAACGTGGGACGGGGTGCTGCAAGGGGAGCGGCTGCTCACCATGTCCTG

CAGTGACAAGATTGCACGCTGGAACGTGGTGGGCATCCAGGGATCACTGCTCAGCATTTTCG

TGGAGCCCATTTACTTCTCGAGCATCATCCTGGGCAGCCTTTACCACGGGGACCACCTTTCC

AGGGCCATGTACCAGCGGATCTCCAACATAGAGGACCTGCCACCTCTCTACACCCTCAACAA

GCCTTTGCTCACAGGCATCAGCAATGCAGAAGCACGGCAGCCAGGGAAGGCCCCCATATTCA

GTGTCAACTGGACGGTAGGCGACTCCGCTATTGAGGTCATCAACGCCACGACTGGGAAGGGA

GAGCTGGGCCGCGCGTCCCGCCTGTGTAAGCACGCGTTGTACTGTCGCTGGATGCGTGTGCA

CGGCAAGGTTCCCTCCCACTTACTACGCTCCAAGATTACCAAGCCCAACGTGTACCATGAGA

CAAAGCTGGCGGCAAAGGAGTACCAGGCCGCCAAGGCGCGTCTGTTCACAGCCTTCATCAAG

GCGGGGCTGGGGGCCTGGGTGGAGAAGCCCACCGAGCAGGACCAGTTCTCACTCACGTAA
```

SpCas5d (I-C1):

(SEQ ID NO: 47)
```
ATGCCCAAGAAGAAGCGGAAGGTGATGAGAAATGAAGTGCAGTTCGAGCTGTTCGGCGACTA

CGCCCTGTTCACCGACCCCCTGACCAAGATCGGCGGCGAAAAGCTGAGCTACAGCGTGCCTA

CCTACCAGGCCCTGAAGGGCATCGCCGAGAGCATCTACTGGAAGCCCACCATCGTGTTCGTG

ATCGACGAACTGCGGGTCATGAAGCCCATTCAGATGGAGTCTAAGGGCGTGAGGCCCATCGA

GTACGGCGGCGGCAACACCCTGGCCCACTACACCTACCTGAAGGATGTGCACTACCAGGTGA

AGGCCCACTTCGAGTTCAACCTGCACCGGCCCGACCTGGCCTTCGATAGAAACGAGGGCAAG

CACTACTCCATCCTGCAGAGAAGCCTGAAGGCCGGCGGCAGAAGAGATATTTTCCTGGGCGC

CCGGGAGTGCCAGGGCTACGTGGCCCCCTGCGAGTTCGGCAGCGGCGACGGCTTCTACGACG

GCCAGGGCAAGTACCACCTGGGAACCATGGTGCACGGTTTCAACTACCCCGACGAAACCGGA

CAGCACCAGCTGGATGTGAGACTGTGGTCTGCCGTCATGGAAAACGGCTACATCCAGTTCCC

CCGCCCTGAGGACTGCCCCATCGTGCGGCCTGTGAAGGAGATGGAACCCAAGATCTTCAACC
```

-continued

```
CCGACAACGTGCAGTCCGCCGAACAGCTGCTGCACGACCTGGGCGGCGAACCCAAGAAGAAG

CGGAAGGTGGGTGGAGGCGGAGGTTCTGGGGGAGGAGGTAGTGGCGGTGGTGGTTCAGGAGG

CGGCGGAAGCCAGCTGCATTTACCGCAGGTTTTAGCTGACGCTGTCTCACGCCTGGTCATAG

GTAAGTTTGGTGACCTGACCGACAACTTCTCCTCCCCTCACGCTCGCAGAATAGGTCTGGCT

GGAGTCGTCATGACAACAGGCACAGATGTTAAAGATGCCAAGGTGATATGTGTTTCTACAGG

AGCAAAATGTATTAATGGTGAATACCTAAGTGATCGTGGCCTTGCATTAAATGACTGCCATG

CAGAAATAGTATCTCGGAGATCCTTGCTCAGATTTCTTTATACACAACTTGAGCTTTACTTA

AATAACGAGGATGATCAAAAAAGATCCATCTTTCAGAAATCAGAGCGAGGGGGGTTTAGGCT

GAAGGAGAATATACAGTTTCATCTGTACATCAGCACCTCTCCCTGTGGAGATGCCAGAATCT

TCTCACCACATGAGGCAATCCTGGAAGAACCAGCAGATAGACACCCAAATCGTAAAGCAAGA

GGACAGCTACGGACCAAAATAGAGGCTGGTCAGGGACGATTCCAGTGCGCAACAATGCGAG

CATCCAAACGTGGGACGGGGTGCTGCAAGGGGAGCGGCTGCTCACCATGTCCTGCAGTGACA

AGATTGCACGCTGGAACGTGGTGGGCATCCAGGGATCACTGCTCAGCATTTTCGTGGAGCCC

ATTTACTTCTCGAGCATCATCCTGGGCAGCCTTTACCACGGGGACCACCTTTCCAGGGCCAT

GTACCAGCGGATCTCCAACATAGAGGACCTGCCACCTCTCTACACCCTCAACAAGCCTTTGC

TCACAGGCATCAGCAATGCAGAAGCACGGCAGCCAGGGAAGGCCCCCATATTCAGTGTCAAC

TGGACGGTAGGCGACTCCGCTATTGAGGTCATCAACGCCACGACTGGGAAGGGAGAGCTGGG

CCGCGCGTCCCGCCTGTGTAAGCACGCGTTGTACTGTCGCTGGATGCGTGTGCACGGCAAGG

TTCCCTCCCACTTACTACGCTCCAAGATTACCAAGCCCAACGTGTACCATGAGACAAAGCTG

GCGGCAAAGGAGTACCAGGCCGCCAAGGCGCGTCTGTTCACAGCCTTCATCAAGGCGGGGCT

GGGGGCCTGGGTGGAGAAGCCCACCGAGCAGGACCAGTTCTCACTCACGTAA
```

BhCas5d (I-C2):
(SEQ ID NO: 48)

```
ATGCCCAAGAAGAAGCGGAAGGTGATGTACAGAAGCCGGGACTTCTACGTGAGAGTGTCCGG

CCAGCGGGCCCTGTTCACCAACCCCGCCACCAAGGGCGGCTCCGAACGGAGCTCCTACTCCG

TGCCTACCCGGCAGGCCCTGAACGGGATTGTGGACGCCATCTACTACAAGCCCACGTTCACC

AACATCGTGACCGAGGTGAAGGTGATTAACCAGATCCAGACCGAACTGCAGGGCGTGCGGGC

CCTGCTGCATGACTACAGCGCCGACCTGAGCTACGTGTCCTACCTGAGCGACGTGGTGTACC

TGATTAAGTTTCATTTCGTGTGGAACGAGGATAGAAAGGACCTGAATAGCGACCGGCTGCCA

GCCAAGCATGAGGCCATCATGGAGCGGTCTATCCGGAAGGGCGGCAGACGGGACGTGTTCCT

GGGCACCAGAGAATGCCTGGGCCTGCTGGACGACATCAGCCAGGAAGAATACGAAACCACAG

TGAGCTATTACAATGGGGTGAACATCGACCTGGGCATCATGTTCCACAGCTTCGCTTACCCC

AAGGACAAGAAAACCCCCCTGAAGTCCTACTTCACAAAGACCGTGATGAAGAACGGCGTGAT

CACCTTCAAGGCCCAGTCCGAATGCGATATTGTGAACACCCTGAGCTCCTACGCCTTCAAGG

CCCCCGAGGAGATCAAGAGCGTGAACGACGAGTGCATGGAGTACGACGCCATGGAGAAGGGC

GAAAACCCCAAGAAGAAGCGGAAGGTGGGTGGAGGCGGAGGTTCTGGGGGAGGAGGTAGTGG

CGGTGGTGGTTCAGGAGGCGGCGGAAGCCAGCTGCATTTACCGCAGGTTTTAGCTGACGCTG

TCTCACGCCTGGTCATAGGTAAGTTTGGTGACCTGACCGACAACTTCTCCTCCCCTCACGCT

CGCAGAATAGGTCTGGCTGGAGTCGTCATGACAACAGGCACAGATGTTAAAGATGCCAAGGT

GATATGTGTTTCTACAGGAGCAAAATGTATTAATGGTGAATACCTAAGTGATCGTGGCCTTG

CATTAAATGACTGCCATGCAGAAATAGTATCTCGGAGATCCTTGCTCAGATTTCTTTATACA
```

-continued

```
CAACTTGAGCTTTACTTAAATAACGAGGATGATCAAAAAAGATCCATCTTTCAGAAATCAGA

GCGAGGGGGTTTAGGCTGAAGGAGAATATACAGTTTCATCTGTACATCAGCACCTCTCCCT

GTGGAGATGCCAGAATCTTCTCACCACATGAGGCAATCCTGGAAGAACCAGCAGATAGACAC

CCAAATCGTAAAGCAAGAGGACAGCTACGGACCAAAATAGAGGCTGGTCAGGGGACGATTCC

AGTGCGCAACAATGCGAGCATCCAAACGTGGGACGGGGTGCTGCAAGGGGAGCGGCTGCTCA

CCATGTCCTGCAGTGACAAGATTGCACGCTGGAACGTGGTGGGCATCCAGGGATCACTGCTC

AGCATTTTCGTGGAGCCCATTTACTTCTCGAGCATCATCCTGGGCAGCCTTTACCACGGGGA

CCACCTTTCCAGGGCCATGTACCAGCGGATCTCCAACATAGAGGACCTGCCACCTCTCTACA

CCCTCAACAAGCCTTTGCTCACAGGCATCAGCAATGCAGAAGCACGGCAGCCAGGGAAGGCC

CCCATATTCAGTGTCAACTGGACGGTAGGCGACTCCGCTATTGAGGTCATCAACGCCACGAC

TGGGAAGGGAGAGCTGGGCCGCGCGTCCCGCCTGTGTAAGCACGCGTTGTACTGTCGCTGGA

TGCGTGTGCACGGCAAGGTTCCCTCCCACTTACTACGCTCCAAGATTACCAAGCCCAACGTG

TACCATGAGACAAAGCTGGCGGCAAAGGAGTACCAGGCCGCCAAGGCGCGTCTGTTCACAGC

CTTCATCAAGGCGGGGCTGGGGGCCTGGGTGGAGAAGCCCACCGAGCAGGACCAGTTCTCAC

TCACGTAA
```

SaCas6 (I-D):

(SEQ ID NO: 49)
```
ATGCCCAAGAAGAAGCGGAAGGTGATGCCCAACGATCCCTACAGCCTGTACTCCATCGTGAT

CGAACTGGGCGCCGCCGAAAAGGGATTCCCCACAGGCATCCTGGGCAGAAGCCTGCATAGCC

AGGTGCTGCAGTGGTTCAAGCAGGATAACCCCTTCCTGGCCACCGAGCTGCACCAGAGCCAG

ATCTCCCCCTTCTCCATCTCTCCACTGATGGGCAAGCGGCACGCCAAGCTGACCAAGGCCGG

CGACCGGCTGTTCTTTCGGATCTGCCTGCTGAGAGGAGATCTGCTGCAGCCCCTGCTGAACG

GCATTGAGCAGACCGTGAACCAGAGCGTGTGCCTGGACAAGTTCCGGTTCCGGCTGTGCCAG

ACCCACATCCTGCCCGGCAGCCACCCTCTGGCTGGCGCCTCCCACTATAGCCTGATCAGCCA

GACCCCAGTGAGCTCCAAGATTACCCTGGACTTCAAGAGTTCTACCTCCTTCAAGGTGGACC

GGAAGATCATCCAAGTGTTCCCTCTGGGCGAACACGTGTTCAACAGCCTGCTCAGACGCTGG

AATAACTTCGCCCCCGAGGACCTGCACTTCTCTCAGGTGGACTGGAGCATCCCCATCGCCGC

ATTCGACGTGAAAACCATCCCCATCCACCTGAAGAAGGTCGAGATCGGCGCACAGGGCTGGG

TGACCTACATCTTCCCCAACACAGAACAGGCCAAGATCGCCTCCGTGCTGAGCGAATTCGCC

TTCTTCAGCGGAGTGGGACGGAAAACCACCATGGGCATGGGCCAGGTGCAGGTGCGGTCCCC

CAAGAAGAAGCGGAAGGTGGGTGGAGGCGGAGGTTCTGGGGGAGGAGGTAGTGGCGGTGGTG

GTTCAGGAGGCGGCGGAAGCCAGCTGCATTTACCGCAGGTTTTAGCTGACGCTGTCTCACGC

CTGGTCATAGGTAAGTTTGGTGACCTGACCGACAACTTCTCCTCCCCTCACGCTCGCAGAAT

AGGTCTGGCTGGAGTCGTCATGACAACAGGCACAGATGTTAAAGATGCCAAGGTGATATGTG

TTTCTACAGGAGCAAAATGTATTAATGGTGAATACCTAAGTGATCGTGGCCTTGCATTAAAT

GACTGCCATGCAGAAATAGTATCTCGGAGATCCTTGCTCAGATTTCTTTATACACAACTTGA

GCTTTACTTAAATAACGAGGATGATCAAAAAGATCCATCTTTCAGAAATCAGAGCGAGGGG

GGTTTAGGCTGAAGGAGAATATACAGTTTCATCTGTACATCAGCACCTCTCCCTGTGGAGAT

GCCAGAATCTTCTCACCACATGAGGCAATCCTGGAAGAACCAGCAGATAGACACCCAAATCG

TAAAGCAAGAGGACAGCTACGGACCAAAATAGAGGCTGGTCAGGGGACGATTCCAGTGCGCA

ACAATGCGAGCATCCAAACGTGGGACGGGGTGCTGCAAGGGGAGCGGCTGCTCACCATGTCC

TGCAGTGACAAGATTGCACGCTGGAACGTGGTGGGCATCCAGGGATCACTGCTCAGCATTTT
```

-continued

CGTGGAGCCCATTTACTTCTCGAGCATCATCCTGGGCAGCCTTTACCACGGGGACCACCTTT

CCAGGGCCATGTACCAGCGGATCTCCAACATAGAGGACCTGCCACCTCTCTACACCCTCAAC

AAGCCTTTGCTCACAGGCATCAGCAATGCAGAAGCACGGCAGCCAGGGAAGGCCCCCATATT

CAGTGTCAACTGGACGGTAGGCGACTCCGCTATTGAGGTCATCAACGCCACGACTGGGAAGG

GAGAGCTGGGCCGCGCGTCCCGCCTGTGTAAGCACGCGTTGTACTGTCGCTGGATGCGTGTG

CACGGCAAGGTTCCCTCCCACTTACTACGCTCCAAGATTACCAAGCCCAACGTGTACCATGA

GACAAAGCTGGCGGCAAAGGAGTACCAGGCCGCCAAGGCGCGTCTGTTCACAGCCTTCATCA

AGGCGGGGCTGGGGGCCTGGGTGGAGAAGCCCACCGAGCAGGACCAGTTCTCACTCACGTAA

EcCas6e (I-E):

(SEQ ID NO: 50)

ATGCCTAAGAAGAAGCGGAAGGTGTACCTGAGCAAGGTGATCATCGCCAGAGCCTGGAGCAG

AGACCTGTACCAGCTGCACCAGGGCCTGTGGCACCTGTTCCCCAACCGGCCCGACGCCGCCC

GGGATTTCCTGTTCCACGTGGAGAAGAGAAACACCCCGGAAGGCTGCCACGTGCTGCTGCAG

AGCGCACAGATGCCTGTGAGCACCGCCGTGGCCACCGTGATCAAGACCAAGCAGGTGGAGTT

CCAGCTGCAGGTGGGCGTGCCCCTGTATTTCAGGCTGCGGGCGAATCCCATCAAGACCATCC

TGGACAACCAGAAGCGGCTGGACAGCAAGGGCAACATCAAGAGGTGCAGAGTGCCTCTGATC

AAGGAGGCCGAACAGATCGCCTGGCTGCAGCGGAAGCTGGGCAATGCCGCCAGAGTGGAGGA

CGTGCACCCCATCAGCGAGCGGCCCCAGTACTTCTCCGGCGACGGAAAGAGCGGAAAGATCC

AGACCGTGTGCTTCGAGGGCGTGCTGACCATCAACGACGCACCCGCCCTGATCGACCTCGTG

CAGCAGGGGATCGGCCCTGCCAAGTCCATGGGCTGCGGACTGCTGTCCCTGGCCCCCCTGCC

CAAGAAGAAGCGGAAGGTGGGTGGAGGCGGAGGTTCTGGGGGAGGAGGTAGTGGCGGTGGTG

GTTCAGGAGGCGGCGGAAGCCAGCTGCATTTACCGCAGGTTTTAGCTGACGCTGTCTCACGC

CTGGTCATAGGTAAGTTTGGTGACCTGACCGACAACTTCTCCTCCCCTCACGCTCGCAGAAT

AGGTCTGGCTGGAGTCGTCATGACAACAGGCACAGATGTTAAAGATGCCAAGGTGATATGTG

TTTCTACAGGAGCAAAATGTATTAATGGTGAATACCTAAGTGATCGTGGCCTTGCATTAAAT

GACTGCCATGCAGAAATAGTATCTCGGAGATCCTTGCTCAGATTTCTTTATACACAACTTGA

GCTTTACTTAAATAACGAGGATGATCAAAAAAGATCCATCTTTCAGAAATCAGAGCGAGGGG

GGTTTAGGCTGAAGGAGAATATACAGTTTCATCTGTACATCAGCACCTCTCCCTGTGGAGAT

GCCAGAATCTTCTCACCACATGAGGCAATCCTGGAAGAACCAGCAGATAGACACCCAAATCG

TAAAGCAAGAGGACAGCTACGGACCAAAATAGAGGCTGGTCAGGGGACGATTCCAGTGCGCA

ACAATGCGAGCATCCAAACGTGGGACGGGGTGCTGCAAGGGGAGCGGCTGCTCACCATGTCC

TGCAGTGACAAGATTGCACGCTGGAACGTGGTGGGCATCCAGGGATCACTGCTCAGCATTTT

CGTGGAGCCCATTTACTTCTCGAGCATCATCCTGGGCAGCCTTTACCACGGGGACCACCTTT

CCAGGGCCATGTACCAGCGGATCTCCAACATAGAGGACCTGCCACCTCTCTACACCCTCAAC

AAGCCTTTGCTCACAGGCATCAGCAATGCAGAAGCACGGCAGCCAGGGAAGGCCCCCATATT

CAGTGTCAACTGGACGGTAGGCGACTCCGCTATTGAGGTCATCAACGCCACGACTGGGAAGG

GAGAGCTGGGCCGCGCGTCCCGCCTGTGTAAGCACGCGTTGTACTGTCGCTGGATGCGTGTG

CACGGCAAGGTTCCCTCCCACTTACTACGCTCCAAGATTACCAAGCCCAACGTGTACCATGA

GACAAAGCTGGCGGCAAAGGAGTACCAGGCCGCCAAGGCGCGTCTGTTCACAGCCTTCATCA

AGGCGGGGCTGGGGGCCTGGGTGGAGAAGCCCACCGAGCAGGACCAGTTCTCACTCACGTAA

-continued

PaCas6f (I-F):

(SEQ ID NO: 51)
ATGCCTAAGAAGAAGAGAAAGGTGGACCACTACCTGGACATTAGACTGCGCCCTGACCCAGA

GTTCCCTCCTGCCCAGCTGATGTCTGTGCTGTTTGGCAAGCTGCACCAGGCCCTGGTGGCCC

AGGGCGGTGACAGAATCGGAGTGTCTTTCCCTGATCTGGACGAATCTAGATCTAGACTGGGA

GAGAGACTGAGAATCCACGCGTCTGCCGACGACCTGAGAGCTCTGCTGGCCAGACCATGGCT

GGAAGGACTGCGCGACCACCTGCAGTTCGGTGAACCTGCCGTGGTGCCTCACCCAACTCCAT

ACAGACAGGTGAGTAGAGTGCAGGCAAAGTCTAATCCAGAGAGACTGAGACGCAGACTGATG

AGAAGGCATGACCTGTCCGAAGAAGAAGCCAGAAAGAGAATCCCAGACACAGTGGCCAGAGC

CCTGGATCTGCCTTTTGTGACCCTGAGAAGCCAGTCTACCGGCCAGCACTTCAGACTGTTTA

TTCGCCACGGACCACTGCAGGTGACCGCCGAAGAGGGAGGTTTTACCTGCTACGGACTGAGC

AAGGGAGGTTTCGTGCCTTGGTTCCCCAAGAAGAAGCGGAAGGTGGGTGGAGGCGGAGGTTC

TGGGGGAGGAGGTAGTGGCGGTGGTGGTTCAGGAGGCGGCGGAAGCCAGCTGCATTTACCGC

AGGTTTTAGCTGACGCTGTCTCACGCCTGGTCATAGGTAAGTTTGGTGACCTGACCGACAAC

TTCTCCTCCCCTCACGCTCGCAGAATAGGTCTGGCTGGAGTCGTCATGACAACAGGCACAGA

TGTTAAAGATGCCAAGGTGATATGTGTTTCTACAGGAGCAAAATGTATTAATGGTGAATACC

TAAGTGATCGTGGCCTTGCATTAAATGACTGCCATGCAGAAATAGTATCTCGGAGATCCTTG

CTCAGATTTCTTTATACACAACTTGAGCTTTACTTAAATAACGAGGATGATCAAAAAAGATC

CATCTTTCAGAAATCAGAGCGAGGGGGGTTTAGGCTGAAGGAGAATATACAGTTTCATCTGT

ACATCAGCACCTCTCCCTGTGGAGATGCCAGAATCTTCTCACCACATGAGGCAATCCTGGAA

GAACCAGCAGATAGACACCCAAATCGTAAAGCAAGAGGACAGCTACGGACCAAAATAGAGGC

TGGTCAGGGGACGATTCCAGTGCGCAACAATGCGAGCATCCAAACGTGGGACGGGGTGCTGC

AAGGGGAGCGGCTGCTCACCATGTCCTGCAGTGACAAGATTGCACGCTGGAACGTGGTGGGC

ATCCAGGGATCACTGCTCAGCATTTTCGTGGAGCCCATTTACTTCTCGAGCATCATCCTGGG

CAGCCTTTACCACGGGGACCACCTTTCCAGGGCCATGTACCAGCGGATCTCCAACATAGAGG

ACCTGCCACCTCTCTACACCCTCAACAAGCCTTTGCTCACAGGCATCAGCAATGCAGAAGCA

CGGCAGCCAGGGAAGGCCCCCATATTCAGTGTCAACTGGACGGTAGGCGACTCCGCTATTGA

GGTCATCAACGCCACGACTGGGAAGGGAGAGCTGGGCCGCGCGTCCCGCCTGTGTAAGCACG

CGTTGTACTGTCGCTGGATGCGTGTGCACGGCAAGGTTCCCTCCCACTTACTACGCTCCAAG

ATTACCAAGCCCAACGTGTACCATGAGACAAAGCTGGCGGCAAAGGAGTACCAGGCCGCCAA

GGCGCGTCTGTTCACAGCCTTCATCAAGGCGGGGCTGGGGGCCTGGGTGGAGAAGCCCACCG

AGCAGGACCAGTTCTCACTCACGTAA

MtCas6 (III-A):

(SEQ ID NO: 52)
ATGCCCAAGAAGAAGCGGAAGGTGATGGCCGCCAGAAGAGGCGGAATCCGGAGAACCGACCT

GCTGCGGAGGTCTGGCCAGCCTCGGGGCAGACACCGGGCCTCCGCCGCCGAGAGCGGCCTGA

CATGGATCTCCCCTACCCTGATCCTGGTGGGCTTCAGCCACAGGGGCGATAGGAGAATGACC

GAGCACCTGTCCAGACTGACCCTGACCCTGGAAGTGGATGCCCCCCTGGAGAGAGCCCGGGT

GGCCACCCTGGGCCCCCACCTGCATGGCGTGCTGATGGAGTCTATCCCCGCCGACTACGTGC

AGACACTGCACACAGTGCCGGTGAACCCTTACAGCCAGTACGCTCTGGCCCGGAGCACCACC

AGCCTGGAGTGGAAGATCTCCACCCTGACAAATGAGGCCCGGCAGCAGATCGTCGGCCCCAT

CAACGACGCCGCCTTCGCCGGCTTCCGGCTGCGGGCCAGCGGCATCGCCACCCAGGTGACAA

GCAGAAGCCTGGAGCAGAACCCCCTGTCCCAGTTTGCCAGAATCTTCTACGCCAGGCCCGAA

-continued

```
ACCCGCAAGTTCAGAGTGGAGTTCCTGACCCCCACCGCCTTCAAGCAGAGCGGCGAGTACGT
GTTTTGGCCCGATCCCAGACTGGTGTTCCAGTCCCTGGCCCAGAAGTACGGCGCCATCGTGG
ACGGAGAAGAGCCCGACCCCGGCCTGATCGCCGAGTTTGGCCAGTCCGTGAGACTGAGCGCC
TTCAGAGTGGCCAGCGCCCCTTTTGCCGTGGGCGCCGCCAGGGTGCCCGGATTCACCGGCAG
CGCCACCTTCACCGTGCGGGGAGTGGACACCTTCGCCAGCTACATCGCCGCTCTGCTGTGGT
TCGGCGAGTTCAGCGGATGCGGCATCAAGGCCTCCATGGGAATGGGCGCCATCCGGGTGCAG
CCTCTGGCCCCCCGGGAGAAGTGCGTGCCCAAGCCCCCCAAGAAGAAGCGGAAGGTGGGTGG
AGGCGGAGGTTCTGGGGGAGGAGGTAGTGGCGGTGGTGGTTCAGGAGGCGGCGGAAGCCAGC
TGCATTTACCGCAGGTTTTAGCTGACGCTGTCTCACGCCTGGTCATAGGTAAGTTTGGTGAC
CTGACCGACAACTTCTCCTCCCCTCACGCTCGCAGAATAGGTCTGGCTGGAGTCGTCATGAC
AACAGGCACAGATGTTAAAGATGCCAAGGTGATATGTGTTTCTACAGGAGCAAAATGTATTA
ATGGTGAATACCTAAGTGATCGTGGCCTTGCATTAAATGACTGCCATGCAGAAATAGTATCT
CGGAGATCCTTGCTCAGATTTCTTTATACACAACTTGAGCTTTACTTAAATAACGAGGATGA
TCAAAAAGATCCATCTTTCAGAAATCAGAGCGAGGGGGGTTTAGGCTGAAGGAGAATATAC
AGTTTCATCTGTACATCAGCACCTCTCCCTGTGGAGATGCCAGAATCTTCTCACCACATGAG
GCAATCCTGGAAGAACCAGCAGATAGACACCCAAATCGTAAAGCAAGAGGACAGCTACGGAC
CAAAATAGAGGCTGGTCAGGGGACGATTCCAGTGCGCAACAATGCGAGCATCCAAACGTGGG
ACGGGGTGCTGCAAGGGGAGCGGCTGCTCACCATGTCCTGCAGTGACAAGATTGCACGCTGG
AACGTGGTGGGCATCCAGGGATCACTGCTCAGCATTTTCGTGGAGCCCATTTACTTCTCGAG
CATCATCCTGGGCAGCCTTTACCACGGGACCACCTTTCCAGGGCCATGTACCAGCGGATCT
CCAACATAGAGGACCTGCCACCTCTCTACACCCTCAACAAGCCTTTGCTCACAGGCATCAGC
AATGCAGAAGCACGGCAGCCAGGGAAGGCCCCCATATTCAGTGTCAACTGGACGGTAGGCGA
CTCCGCTATTGAGGTCATCAACGCCACGACTGGGAAGGGAGAGCTGGGCCGCGCGTCCCGCC
TGTGTAAGCACGCGTTGTACTGTCGCTGGATGCGTGTGCACGGCAAGGTTCCCTCCCACTTA
CTACGCTCCAAGATTACCAAGCCCAACGTGTACCATGAGACAAAGCTGGCGGCAAAGGAGTA
CCAGGCCGCCAAGGCGCGTCTGTTCACAGCCTTCATCAAGGCGGGGCTGGGGGCCTGGGTGG
AGAAGCCCACCGAGCAGGACCAGTTCTCACTCACGTAA
```

PfCas6 (III-B):

(SEQ ID NO: 53)
```
ATGCCCAAGAAGAAGCGGAAGGTGATGAGATTCCTGATCAGACTGGTGCCCGAGGACAAGGA
CAGAGCCTTCAAGGTGCCTTACAACCACCAGTACTATCTGCAGGGCCTGATCTACAACGCCA
TCAAGTCCTCCAACCCCAAGCTGGCCACCTACCTGCACGAGGTGAAGGGCCCCAAGCTGTTC
ACCTACAGCCTGTTCATGGCCGAAAAGCGGGAGCACCCTAAGGGCCTGCCCTACTTTCTGGG
CTACAAGAAGGGCTTCTTCTACTTCAGCACCTGCGTGCCCGAGATCGCCGAGGCCCTGGTGA
ACGGCCTGCTGATGAATCCCGAGGTGCGGCTGTGGGACGAGAGATTCTACCTGCACGAAATC
AAGGTCCTGCGGGAGCCCAAGAAGTTCAACGGCAGCACCTTCGTGACCCTGAGCCCCATCGC
CGTGACCGTGGTGAGAAAGGGCAAGTCCTACGACGTGCCCCCCATGGAAAAGGAGTTCTACA
GCATTATCAAGGATGACCTGCAGGACAAGTACGTGATGGCCTACGGCGACAAGCCCCCCAGT
GAGTTCGAGATGGAAGTGCTGATCGCCAAGCCCAAGCGGTTCCGGATCAAGCCCGGCATCTA
TCAGACCGCCTGGCACCTGGTGTTTCGGGCCTACGGCAATGACGACCTGCTGAAGGTGGGCT
ACGAAGTGGGATTCGGGGAGAAGAACTCCCTGGGATTCGGAATGGTCAAGGTGGAGGGCAAC
```

-continued

```
AAGACCACCAAGGAAGCCGAAGAACAGGAGAAGATCACCTTCAACTCCCGGGAAGAGCTGAA

AACAGGCGTGCCCAAGAAGAAGCGGAAGGTGGGTGGAGGCGGAGGTTCTGGGGGAGGAGGTA

GTGGCGGTGGTGGTTCAGGAGGCGGCGGAAGCCAGCTGCATTTACCGCAGGTTTTAGCTGAC

GCTGTCTCACGCCTGGTCATAGGTAAGTTTGGTGACCTGACCGACAACTTCTCCTCCCCTCA

CGCTCGCAGAATAGGTCTGGCTGGAGTCGTCATGACAACAGGCACAGATGTTAAAGATGCCA

AGGTGATATGTGTTTCTACAGGAGCAAAATGTATTAATGGTGAATACCTAAGTGATCGTGGC

CTTGCATTAAATGACTGCCATGCAGAAATAGTATCTCGGAGATCCTTGCTCAGATTTCTTTA

TACACAACTTGAGCTTTACTTAAATAACGAGGATGATCAAAAAAGATCCATCTTTCAGAAAT

CAGAGCGAGGGGGGTTTAGGCTGAAGGAGAATATACAGTTTCATCTGTACATCAGCACCTCT

CCCTGTGGAGATGCCAGAATCTTCTCACCACATGAGGCAATCCTGGAAGAACCAGCAGATAG

ACACCCAAATCGTAAAGCAAGAGGACAGCTACGGACCAAAATAGAGGCTGGTCAGGGGACGA

TTCCAGTGCGCAACAATGCGAGCATCCAAACGTGGGACGGGGTGCTGCAAGGGGAGCGGCTG

CTCACCATGTCCTGCAGTGACAAGATTGCACGCTGGAACGTGGTGGGCATCCAGGGATCACT

GCTCAGCATTTTCGTGGAGCCCATTTACTTCTCGAGCATCATCCTGGGCAGCCTTTACCACG

GGGACCACCTTTCCAGGGCCATGTACCAGCGGATCTCCAACATAGAGGACCTGCCACCTCTC

TACACCCTCAACAAGCCTTTGCTCACAGGCATCAGCAATGCAGAAGCACGGCAGCCAGGGAA

GGCCCCCATATTCAGTGTCAACTGGACGGTAGGCGACTCCGCTATTGAGGTCATCAACGCCA

CGACTGGGAAGGGAGAGCTGGGCCGCGCGTCCCGCCTGTGTAAGCACGCGTTGTACTGTCGC

TGGATGCGTGTGCACGGCAAGGTTCCCTCCCACTTACTACGCTCCAAGATTACCAAGCCCAA

CGTGTACCATGAGACAAAGCTGGCGGCAAAGGAGTACCAGGCCGCCAAGGCGCGTCTGTTCA

CAGCCTTCATCAAGGCGGGGCTGGGGGCCTGGGTGGAGAAGCCCACCGAGCAGGACCAGTTC

TCACTCACGTAA
```

PaCsf5 (IV-A1):

(SEQ ID NO: 54)
```
ATGCCTAAGAAGAAGCGGAAGGTGTTCGTGACCCAGGTGATCTTCAACATCGGCGAACGGAC

GTACCCCGACAGGGCTCGGGCTATGGTGGCCGAGCTGATGGATGCGTCCAGCCTGGCCTGG

TGGCCACCCTGATGAACTACATCCCCGGCACCAGCACGAGCCGGACAGAGTTCCCCACCGTG

CAGTTCGGCGGCGCCAGCGACGGCTTTTGCCTGCTGGGCTTCGGCGACGGCGGCGGCGCCAT

CGTGAGAGATGCCGTGCCCCTGATCCACGCCGCCCTGGCAAGGCGGATGCCTGATCGGATCA

TCCAGGTGGAACACAAGGAGCACAGCCTGTCCGCCGAGGCCCGGCCCTACGTGCTGAGCTAC

ACCGTGCCTCGGATGGTGGTGCAGAAGAAGCAGCGGCACGCCGAGAGACTGCTGCACGAAGC

CGAGGGAAAGGCTCACCTGGAGGGCCTGTTCCTGCGGAGCCTGCAGAGGCAGGCCGCCGCCG

TGGGCCTGCCCCTGCCCGAGAACCTGGAGGTGGAGTTCAAGGGAGCCGTGGGCGACTTCGCC

GCAAAGCACAATCCAAATAGCAAGGTGGCCTACCGGGGACTGAGAGGCGCCGTGTTCGATGT

GAACGCCAGACTGGGCGGCATCTGGACCGCCGGATTCATGCTGAGCAAGGGCTACGGCCAGT

TTAACGCCACCCACCAGCTGAGCGGCGCCGTGAACGCTCTGTCCGAACCCAAGAAGAAGCGG

AAGGTGGGTGGAGGCGGAGGTTCTGGGGGAGGAGGTAGTGGCGGTGGTGGTTCAGGAGGCGG

CGGAAGCCAGCTGCATTTACCGCAGGTTTTAGCTGACGCTGTCTCACGCCTGGTCATAGGTA

AGTTTGGTGACCTGACCGACAACTTCTCCTCCCCTCACGCTCGCAGAATAGGTCTGGCTGGA

GTCGTCATGACAACAGGCACAGATGTTAAAGATGCCAAGGTGATATGTGTTTCTACAGGAGC

AAAATGTATTAATGGTGAATACCTAAGTGATCGTGGCCTTGCATTAAATGACTGCCATGCAG

AAATAGTATCTCGGAGATCCTTGCTCAGATTTCTTTATACACAACTTGAGCTTTACTTAAAT
```

-continued

```
AACGAGGATGATCAAAAAAGATCCATCTTTCAGAAATCAGAGCGAGGGGGGTTTAGGCTGAA

GGAGAATATACAGTTTCATCTGTACATCAGCACCTCTCCCTGTGGAGATGCCAGAATCTTCT

CACCACATGAGGCAATCCTGGAAGAACCAGCAGATAGACACCCAAATCGTAAAGCAAGAGGA

CAGCTACGGACCAAAATAGAGGCTGGTCAGGGGACGATTCCAGTGCGCAACAATGCGAGCAT

CCAAACGTGGGACGGGGTGCTGCAAGGGGAGCGGCTGCTCACCATGTCCTGCAGTGACAAGA

TTGCACGCTGGAACGTGGTGGGCATCCAGGGATCACTGCTCAGCATTTTCGTGGAGCCCATT

TACTTCTCGAGCATCATCCTGGGCAGCCTTTACCACGGGGACCACCTTTCCAGGGCCATGTA

CCAGCGGATCTCCAACATAGAGGACCTGCCACCTCTCTACACCCTCAACAAGCCTTTGCTCA

CAGGCATCAGCAATGCAGAAGCACGGCAGCCAGGGAAGGCCCCCATATTCAGTGTCAACTGG

ACGGTAGGCGACTCCGCTATTGAGGTCATCAACGCCACGACTGGGAAGGGAGAGCTGGGCCG

CGCGTCCCGCCTGTGTAAGCACGCGTTGTACTGTCGCTGGATGCGTGTGCACGGCAAGGTTC

CCTCCCACTTACTACGCTCCAAGATTACCAAGCCCAACGTGTACCATGAGACAAAGCTGGCG

GCAAAGGAGTACCAGGCCGCCAAGGCGCGTCTGTTCACAGCCTTCATCAAGGCGGGGCTGGG

GGCCTGGGTGGAGAAGCCCACCGAGCAGGACCAGTTCTCACTCACGTAA
```

MtCsf5 (IV-A2):

(SEQ ID NO: 55)
```
ATGCCCAAGAAGAAGAGAAAGGTGCACCAGACCCTGATCCGGATCAACTGGCCCAAGGGATT

CAAGTGCCCCCCTGCCGAGTTCCGGGAAAAGCTGGCCAAGAGCGAGATGTTCCCCCCCGAGT

TCTTCCACTACGGCACGGAACTGGCCGTGTGGGACAAGCAGACCGCCGAGGTGGAGGGCAAG

ATCAAGACCGTGTCCAAGGAGAAGATCATCAAGACCTTTGACAAGCCCATCCCCCTGAATGG

CCCGGGCCCCGGTCAGAGTGATCGGCGGCCAGGCCTGGGCCGGCGTGATCGCCGACCCCGAGA

TGGAGGGCATGCTGATCCCACACCTGGGGAGCATCCTGAAGGTGGCCAGCAGCGCGGCCGGA

TGCGCAGTGAAGATCGAACTGGAACAGAGAAAGTTCGGCATCAGCTACACCGAGTACCCCGT

GAAGTACAACCTGCGGGAGCTGGTGCTGAAGAGAAGATGCGAGGACGCCCGGTCTACCGATA

TCGAGAGCCTGATTGCCGATAGAATCTGGGGCGGCGTGTCCGGCGAGAGCTACTATGGCATC

GACGGCACATGCGCCAAGTTTGGCTTCGAACCCCCCAGCAGAGAGCAGCTGGAGCTGCGGAT

CTTCCCCATGAAGAACATCGGACTGCACATGAAGTCCAGCGACGGACTGTCCAAGGAGTACA

TGAGCCTGATTGACGCCGAGGTGTGGATGAACGCTAAGCTGGAAGGAGTGTGGCAGGTGGGC

AACCTGATCAGCAGGGGCTACGGCCGGTTCATCAAGTCTATCGGCGCCCAGTCCCCCAAGAA

GAAGCGGAAGGTGGGTGGAGGCGGAGGTTCTGGGGGAGGAGGTAGTGGCGGTGGTGGTTCAG

GAGGCGGCGGAAGCCAGCTGCATTTACCGCAGGTTTTAGCTGACGCTGTCTCACGCCTGGTC

ATAGGTAAGTTTGGTGACCTGACCGACAACTTCTCCTCCCCTCACGCTCGCAGAATAGGTCT

GGCTGGAGTCGTCATGACAACAGGCACAGATGTTAAAGATGCCAAGGTGATATGTGTTTCTA

CAGGAGCAAAATGTATTAATGGTGAATACCTAAGTGATCGTGGCCTTGCATTAAATGACTGC

CATGCAGAAATAGTATCTCGGAGATCCTTGCTCAGATTTCTTTATACACAACTTGAGCTTTA

CTTAAATAACGAGGATGATCAAAAAAGATCCATCTTTCAGAAATCAGAGCGAGGGGGGTTTA

GGCTGAAGGAGAATATACAGTTTCATCTGTACATCAGCACCTCTCCCTGTGGAGATGCCAGA

ATCTTCTCACCACATGAGGCAATCCTGGAAGAACCAGCAGATAGACACCCAAATCGTAAAGC

AAGAGGACAGCTACGGACCAAAATAGAGGCTGGTCAGGGGACGATTCCAGTGCGCAACAATG

CGAGCATCCAAACGTGGGACGGGGTGCTGCAAGGGGAGCGGCTGCTCACCATGTCCTGCAGT

GACAAGATTGCACGCTGGAACGTGGTGGGCATCCAGGGATCACTGCTCAGCATTTTCGTGGA
```

```
                                    -continued
GCCCATTTACTTCTCGAGCATCATCCTGGGCAGCCTTTACCACGGGGACCACCTTTCCAGGG

CCATGTACCAGCGGATCTCCAACATAGAGGACCTGCCACCTCTCTACACCCTCAACAAGCCT

TTGCTCACAGGCATCAGCAATGCAGAAGCACGGCAGCCAGGGAAGGCCCCCATATTCAGTGT

CAACTGGACGGTAGGCGACTCCGCTATTGAGGTCATCAACGCCACGACTGGGAAGGGAGAGC

TGGGCCGCGCGTCCCGCCTGTGTAAGCACGCGTTGTACTGTCGCTGGATGCGTGTGCACGGC

AAGGTTCCCTCCCACTTACTACGCTCCAAGATTACCAAGCCCAACGTGTACCATGAGACAAA

GCTGGCGGCAAAGGAGTACCAGGCCGCCAAGGCGCGTCTGTTCACAGCCTTCATCAAGGCGG

GGCTGGGGGCCTGGGTGGAGAAGCCCACCGAGCAGGACCAGTTCTCACTCACGTAA
```

In certain embodiments, the heterologous functional domain is fused N-terminally, C-terminally, or internally in the fusion protein.

In certain embodiments, the functional variant of the CasPR fusion comprises a protein having the amino acid sequence of: (1) any one of Sequences 1-11, except for 1, 2, 3, 4, 5, 6, 7, 8, 9, or 10 amino acid substitutions, additions, or deletions, wherein the protein maintains the ability of one of Sequences 1-11 for binding to a direct repeat sequence of a Class 1, type I, III, or IV CRISPR system (e.g., any one of Sequences 12-33); or, (2) at least 80%, 85%, 90%, 91%, 92%, 93%, 94%, 95%, 96%, 97%, 98%, 99% or more sequence identity with any one of Sequences 1-11, wherein the protein maintains the ability of one of the CasPRs of Sequences 1-11 for binding to a direct repeat sequence of a Class 1, type I, III, or IV CRISPR system (e.g., any one of Sequences 12-33); optionally, with the proviso that the protein is not any one of Sequences 1-11. All sequences incorporated herein by reference.

In certain embodiments, the RNA sequence of the invention further encodes a CasPR guide RNA comprising a guide sequence capable of hybridizing to a target RNA, and a direct repeat (DR) sequence 3' (or 5') to the guide sequence. In certain embodiments, the DR sequence has substantially the same secondary structure as the secondary structure of any one of Sequences 12-33. In certain embodiments, the DR sequence is encoded by any one of Sequences 12-33, or a functional portion thereof that binds to a cognate wild-type CasPR. In certain embodiments, the target RNA is encoded by a eukaryotic DNA. In certain embodiments, the eukaryotic DNA is a non-human mammalian DNA, a non-human primate DNA, a human DNA, a plant DNA, an insect DNA, a bird DNA, a reptile DNA, a rodent DNA, a fish DNA, a worm/nematode DNA, a yeast DNA. In certain embodiments, the target RNA is an mRNA.

In certain embodiments, the CasPR guide sequence is between 15-120 nucleotides, between 20-100 nucleotides, between 25-80 nucleotides, between 15-55 nucleotides, between 25-35 nucleotides, or about 30 nucleotides.

In certain embodiments, the CasPR guide sequence is 90-100% complementary to the target RNA. In certain embodiments, the CasPR guide RNA results from processing of a pre-crRNA transcript by the CasPR, and wherein the pre-crRNA comprises two or more guide RNAs having different guide sequences for different target RNAs.

In certain embodiments, the variant or derivative of the CasPR fusion comprises conserved amino acid substitutions of one or more residues of any one of Sequences 1-11; optionally, the variant or derivative of the CasPR fusion comprises only conserved amino acid substitutions. In certain embodiments, the derivative of the CasPR fusion is capable of binding to the CasPR guide sequence hybridized to the target RNA, but has no RNase catalytic activity due to a mutation in the RNase catalytic site of the CasPR. In certain embodiments, the derivative of the CasPR fusion has an N-terminal deletion of no more than 5, 10, 15, 20, 25, 30, 35, 40, 45, or 50 residues, and/or a C-terminal deletion of no more than 5, 10, 15, 20, 25, 30, 35, 40, 45, or 50 residues.

In certain embodiments, the CasPR is a Cas5d, a Cas6, or a Csf5, such as MtCas6 (I-A), MmCas6 (I-B), SpCas5d (I-C1), BhCas5d (I-C2), SaCas6 (I-D), EcCas6e (I-E), PaCas6f (I-F), MtCas6 (III-A), PfCas6 (III-B), PaCsf5 (IV-A1), or MtCsf5 (IV-A2).

In certain embodiments, the heterologous functional domain of the CasPR fusion comprises an RNA base-editing domain. In certain embodiments, the RNA base-editing domain comprises an adenosine deaminase and/or a cytidine deaminase, such as a cytidine deaminase acting on RNA (CDAR), such as a double-stranded RNA-specific adenosine deaminase (ADAR) (e.g., ADAR1 or ADAR2), apolipoprotein B mRNA editing enzyme, catalytic polypeptide-like (APOBEC, such as APOBEC1, APOBEC2, APOBEC3A, APOBEC3B, APOBEC3C, APOBEC3D, APOBEC3E, APOBEC3F, APOBEC3G, APOBEC3H, and APOBEC4), activation-induced cytidine deaminase (AID), a cytidine deaminase 1 (CDA1), or a mutant thereof. In certain embodiments, the ADAR comprises E488Q/T375G double mutation or comprises ADAR2DD. In certain embodiments, the base-editing domain is further fused to an RNA-binding domain, such as MS2.

In certain embodiments, the derivative of the CasPR fusion further comprises an RNA methyltransferase, a RNA demethylase, an RNA splicing modifier, a localization factor, or a translation modification factor.

In certain embodiments, the CasPR, the homolog, the ortholog, the paralog, the variant, the derivative, or the functional fragment comprises a nuclear localization signal (NLS) sequence or a nuclear export signal (NES).

In certain embodiments, targeting of the target RNA results in a modification of the target RNA. In certain embodiments, the modification of the target RNA is a cleavage of the target RNA. In certain embodiments, the modification of the target RNA is deamination of an adenosine (A) to an inosine (I), and/or deamination of a cytidine (C) to a uracil (U).

In certain embodiments, the RNA sequence of the invention encodes a codon-optimized polynucleotide encoding a wild-type CasPR (e.g., Cas5d, Cas6, or Csf5), a homolog thereof, an ortholog thereof, a paralog thereof, a variant or derivative thereof, or a functional fragment thereof, wherein the polynucleotide is codon-optimized for mammalian (e.g., human) expression, optionally, the wild-type CasPR has the amino acid sequence of any one of Sequences 1-11. In certain embodiments, the codon-optimized polynucleotide has the amino acid sequence of any one of Sequences 34-44. In certain embodiments, the codon-optimized polynucleotide further comprises sequence encoding a heterologous functional domain. In certain embodiments, the heterologous functional domain comprises an RNA base editor.

MtCas6 (I-A):
(SEQ ID NO: 34)
ATGCCTCTGATCTTCAAGATCGGCTATAACGTGATCCCCCTGCAGGACGTGATCCTGCCCAC

CCCTTCCAGCAAGGTGCTGAAGTACCTGATCCAGAGCGGCAAGCTGATCCCCAGCCTGAAGG

ACCTGATCACCAGCCGGGACAAGTACAAGCCAATCTTCATCTCCCACCTGGGCTTCAACCAG

CGGAGGATTTTCCAGACCAACGGCAATCTGAAAACCATCACCAAGGGCAGTAGACTGAGCTC

CATCATCGCCTTCAGCACCCAGGCCAACGTGCTGTCCGAGGTGGCCGATGAAGGGATCTTCG

AAACCGTGTACGGAAAGTTCCACATCATGATCGAAAGCATCGAGATCGTGGAGGTGGAAAAG

CTGAAGGAGGAGGTGGAGAAGCACATGAACGACAACATCAGAGTGAGATTCGTGTCTCCCAC

ACTGCTGAGCTCCAAGGTGCTGCTGCCCCCCAGCCTGTCCGAAAGATACAAGAAGATCCACG

CCGGGTACAGCACCCTGCCCAGCGTGGGCCTGATCGTGGCCTACGCCTACAACGTGTACTGC

AATCTGATCGGCAAGAAGGAAGTGGAAGTGCGGGCCTTCAAGTTTGGAATCCTGAGCAACGC

CCTGTCCAGAATCATCGGCTACGACCTGCACCCTGTGACCGTGGCCATCGGCGAGGACAGCA

AGGGGAATCTGAGAAAGGCTCGGGCGTGATGGGCTGGATCGAGTTCGACATCCCCGACGAA

AGACTGAAGCGGCGGGCCCTGAACTATCTGCTGACCAGCAGCTACCTGGGCATCGGGAGATC

TCGGGGCATCGGCTTCGGCGAGATCCGGCTGGAGTTCCGGAAGATTGAAGAGAAGGAGGGA

MmCas6 (I-B):
(SEQ ID NO: 35)
ATGGACCTGGAGTACATGCACATCTCCTACCCTAACATCCTGCTGAACATGCGGGACGGCAG

CAAGCTGCGGGGCTACTTCGCCAAGAAGTACATCGACGAAGAGATTGTGCACAACCACAGAG

ACAACGCCTTTGTGTACAAGTACCCCCAGATCCAGTTTAAGATCATCGATAGAAGCCCCCTG

ATCATCGGCATTGGCTCTCTGGGCATCAATTTCCTGGAGAGCAAGCGGATCTTCTTCGAGAA

GGAACTGATTATCAGCAACGACACCAACGACATCACCGAGGTGAACGTGCACAAGGACATGG

ATCACTTCGGCACGACCGACAAGATCCTGAAGTACCAGTTCAAGACCCCTTGGATGGCACTG

AACGCCAAGAATAGCGAGATCTACAAGAACTCTGACGAGATCGACCGGGAGGAGTTCCTGAA

GAGAGTGCTGATTGGGAATATCCTGAGCATGTCTAAGAGCCTGGGCTATACCATCGAAGAAA

AGCTGAAGGTGAAGATTAACCTGAAGGAAGTGCCCGTGAAGTTCAAGAACCAGAACATGGTG

GGCTTTCGGGGCGAGTTCTACATCAACTTCGACATCCCTCAGTATCTGGGCATCGGCCGGAA

TGTGTCCCGGGGATTCGGCACAGTGGTGAAGGTG

SpCas5d (I-C1):
(SEQ ID NO: 36)
ATGAGAAATGAAGTGCAGTTCGAGCTGTTCGGCGACTACGCCCTGTTCACCGACCCCCTGAC

CAAGATCGGCGGCGAAAAGCTGAGCTACAGCGTGCCTACCTACCAGGCCCTGAAGGGCATCG

CCGAGAGCATCTACTGGAAGCCCACCATCGTGTTCGTGATCGACGAACTGCGGGTCATGAAG

CCCATTCAGATGGAGTCTAAGGGCGTGAGGCCCATCGAGTACGGCGGCGGCAACACCCTGGC

CCACTACACCTACCTGAAGGATGTGCACTACCAGGTGAAGGCCCACTTCGAGTTCAACCTGC

ACCGGCCCGACCTGGCCTTCGATAGAAACGAGGGCAAGCACTACTCCATCCTGCAGAGAAGC

CTGAAGGCCGGCGGCAGAAGAGATATTTTCCTGGGCGCCCGGGAGTGCCAGGGCTACGTGGC

CCCCTGCGAGTTCGGCAGCGGCGACGGCTTCTACGACGGCCAGGGCAAGTACCACCTGGGAA

CCATGGTGCACGGTTTCAACTACCCCGACGAAACCGGACAGCACCAGCTGGATGTGAGACTG

TGGTCTGCCGTCATGGAAAACGGCTACATCCAGTTCCCCCGCCCTGAGGACTGCCCCATCGT

GCGGCCTGTGAAGGAGATGGAACCCAAGATCTTCAACCCCGACAACGTGCAGTCCGCCGAAC

AGCTGCTGCACGACCTGGGCGGCGAA

BhCas5d (I-C2):

(SEQ ID NO: 37)
ATGTACAGAAGCCGGGACTTCTACGTGAGAGTGTCCGGCCAGCGGGCCCTGTTCACCAACCC

CGCCACCAAGGGCGGCTCCGAACGGAGCTCCTACTCCGTGCCTACCCGGCAGGCCCTGAACG

GGATTGTGGACGCCATCTACTACAAGCCCACGTTCACCAACATCGTGACCGAGGTGAAGGTG

ATTAACCAGATCCAGACCGAACTGCAGGGCGTGCGGGCCCTGCTGCATGACTACAGCGCCGA

CCTGAGCTACGTGTCCTACCTGAGCGACGTGGTGTACCTGATTAAGTTTCATTTCGTGTGGA

ACGAGGATAGAAAGGACCTGAATAGCGACCGGCTGCCAGCCAAGCATGAGGCCATCATGGAG

CGGTCTATCCGGAAGGGCGGCAGACGGGACGTGTTCCTGGGCACCAGAGAATGCCTGGGCCT

GCTGGACGACATCAGCCAGGAAGAATACGAAACCACAGTGAGCTATTACAATGGGGTGAACA

TCGACCTGGGCATCATGTTCCACAGCTTCGCTTACCCCAAGGACAAGAAAACCCCCCTGAAG

TCCTACTTCACAAAGACCGTGATGAAGAACGGCGTGATCACCTTCAAGGCCCAGTCCGAATG

CGATATTGTGAACACCCTGAGCTCCTACGCCTTCAAGGCCCCCGAGGAGATCAAGAGCGTGA

ACGACGAGTGCATGGAGTACGACGCCATGGAGAAGGGCGAAAAC

SaCas6 (I-D):

(SEQ ID NO: 38)
ATGCCCAACGATCCCTACAGCCTGTACTCCATCGTGATCGAACTGGGCGCCGCCGAAAAGGG

ATTCCCCACAGGCATCCTGGGCAGAAGCCTGCATAGCCAGGTGCTGCAGTGGTTCAAGCAGG

ATAACCCCTTCCTGGCCACCGAGCTGCACCAGAGCCAGATCTCCCCCTTCTCCATCTCTCCA

CTGATGGGCAAGCGGCACGCCAAGCTGACCAAGGCCGGCGACCGGCTGTTCTTTCGGATCTG

CCTGCTGAGAGGAGATCTGCTGCAGCCCCTGCTGAACGGCATTGAGCAGACCGTGAACCAGA

GCGTGTGCCTGGACAAGTTCCGGTTCCGGCTGTGCCAGACCCACATCCTGCCCGGCAGCCAC

CCTCTGGCTGGCGCCTCCCACTATAGCCTGATCAGCCAGACCCCAGTGAGCTCCAAGATTAC

CCTGGACTTCAAGAGTTCTACCTCCTTCAAGGTGGACCGGAAGATCATCCAAGTGTTCCCTC

TGGGCGAACACGTGTTCAACAGCCTGCTCAGACGCTGGAATAACTTCGCCCCCGAGGACCTG

CACTTCTCTCAGGTGGACTGGAGCATCCCCATCGCCGCATTCGACGTGAAAACCATCCCCAT

CCACCTGAAGAAGGTCGAGATCGGCGCACAGGGCTGGGTGACCTACATCTTCCCCAACACAG

AACAGGCCAAGATCGCCTCCGTGCTGAGCGAATTCGCCTTCTTCAGCGGAGTGGGACGGAAA

ACCACCATGGGCATGGGCCAGGTGCAGGTGCGGTCC

EcCas6e (I-E):

(SEQ ID NO: 39)
ATGTACCTGAGCAAGGTGATCATCGCCAGAGCCTGGAGCAGAGACCTGTACCAGCTGCACCA

GGGCCTGTGGCACCTGTTCCCCAACCGGCCCGACGCCGCCCGGGATTTCCTGTTCCACGTGG

AGAAGAGAAACACCCCGGAAGGCTGCCACGTGCTGCTGCAGAGCGCACAGATGCCTGTGAGC

ACCGCCGTGGCCACCGTGATCAAGACCAAGCAGGTGGAGTTCCAGCTGCAGGTGGGCGTGCC

CCTGTATTTCAGGCTGCGGGCGAATCCCATCAAGACCATCCTGGACAACCAGAAGCGGCTGG

ACAGCAAGGGCAACATCAAGAGGTGCAGAGTGCCTCTGATCAAGGAGGCCGAACAGATCGCC

TGGCTGCAGCGGAAGCTGGGCAATGCCGCCAGAGTGGAGGACGTGCACCCCATCAGCGAGCG

GCCCCAGTACTTCTCCGGCGACGGAAAGAGCGGAAAGATCCAGACCGTGTGCTTCGAGGGCG

TGCTGACCATCAACGACGCACCCGCCCTGATCGACCTCGTGCAGCAGGGGATCGGCCCTGCC

AAGTCCATGGGCTGCGGACTGCTGTCCCTGGCCCCCCTG

-continued

PaCas6f (I-F):

(SEQ ID NO: 40)
ATGGACCACTACCTGGACATTAGACTGCGCCCTGACCCAGAGTTCCCTCCTGCCCAGCTGAT

GTCTGTGCTGTTTGGCAAGCTGCACCAGGCCCTGGTGGCCCAGGGCGGTGACAGAATCGGAG

TGTCTTTCCCTGATCTGGACGAATCTAGATCTAGACTGGGAGAGAGACTGAGAATCCACGCG

TCTGCCGACGACCTGAGAGCTCTGCTGGCCAGACCATGGCTGGAAGGACTGCGCGACCACCT

GCAGTTCGGTGAACCTGCCGTGGTGCCTCACCCAACTCCATACAGACAGGTGAGTAGAGTGC

AGGCAAAGTCTAATCCAGAGAGACTGAGACGCAGACTGATGAGAAGGCATGACCTGTCCGAA

GAAGAAGCCAGAAAGAGAATCCCAGACACAGTGGCCAGAGCCCTGGATCTGCCTTTTGTGAC

CCTGAGAAGCCAGTCTACCGGCCAGCACTTCAGACTGTTTATTCGCCACGGACCACTGCAGG

TGACCGCCGAAGAGGGAGGTTTTACCTGCTACGGACTGAGCAAGGGAGGTTTCGTGCCTTGG

TTC

MtCas6 (III-A):

(SEQ ID NO: 41)
ATGGCCGCCAGAAGAGGCGGAATCCGGAGAACCGACCTGCTGCGGAGGTCTGGCCAGCCTCG

GGGCAGACACCGGGCCTCCGCCGCCGAGAGCGGCCTGACATGGATCTCCCCTACCCTGATCC

TGGTGGGCTTCAGCCACAGGGGCGATAGGAGAATGACCGAGCACCTGTCCAGACTGACCCTG

ACCCTGGAAGTGGATGCCCCCCTGGAGAGAGCCCGGGTGGCCACCCTGGGCCCCCACCTGCA

TGGCGTGCTGATGGAGTCTATCCCCGCCGACTACGTGCAGACACTGCACACAGTGCCGGTGA

ACCCTTACAGCCAGTACGCTCTGGCCCGGAGCACCACCAGCCTGGAGTGGAAGATCTCCACC

CTGACAAATGAGGCCCGGCAGCAGATCGTCGGCCCCATCAACGACGCCGCCTTCGCCGGCTT

CCGGCTGCGGGCCAGCGGCATCGCCACCCAGGTGACAAGCAGAAGCCTGGAGCAGAACCCCC

TGTCCCAGTTTGCCAGAATCTTCTACGCCAGGCCCGAAACCCGCAAGTTCAGAGTGGAGTTC

CTGACCCCCACCGCCTTCAAGCAGAGCGGCGAGTACGTGTTTTGGCCCGATCCCAGACTGGT

GTTCCAGTCCCTGGCCCAGAAGTACGGCGCCATCGTGGACGGAGAAGAGCCCGACCCCGGCC

TGATCGCCGAGTTTGGCCAGTCCGTGAGACTGAGCGCCTTCAGAGTGGCCAGCGCCCCTTTT

GCCGTGGGCGCCGCCAGGGTGCCCGGATTCACCGGCAGCGCCACCTTCACCGTGCGGGGAGT

GGACACCTTCGCCAGCTACATCGCCGCTCTGCTGTGGTTCGGCGAGTTCAGCGGATGCGGCA

TCAAGGCCTCCATGGGAATGGGCGCCATCCGGGTGCAGCCTCTGGCCCCCCGGGAGAAGTGC

GTGCCCAAGCCC

PfCas6 (III-B):

(SEQ ID NO: 42)
ATGAGATTCCTGATCAGACTGGTGCCCGAGGACAAGGACAGAGCCTTCAAGGTGCCTTACAA

CCACCAGTACTATCTGCAGGGCCTGATCTACAACGCCATCAAGTCCTCCAACCCCAAGCTGG

CCACCTACCTGCACGAGGTGAAGGGCCCCAAGCTGTTCACCTACAGCCTGTTCATGGCCGAA

AAGCGGGAGCACCCTAAGGGCCTGCCCTACTTTCTGGGCTACAAGAAGGGCTTCTTCTACTT

CAGCACCTGCGTGCCCGAGATCGCCGAGGCCCTGGTGAACGGCCTGCTGATGAATCCCGAGG

TGCGGCTGTGGGACGAGAGATTCTACCTGCACGAAATCAAGGTCCTGCGGGAGCCCAAGAAG

TTCAACGGCAGCACCTTCGTGACCCTGAGCCCCATCGCCGTGACCGTGGTGAGAAAGGGCAA

GTCCTACGACGTGCCCCCCATGGAAAAGGAGTTCTACAGCATTATCAAGGATGACCTGCAGG

ACAAGTACGTGATGGCCTACGGCGACAAGCCCCCAGTGAGTTCGAGATGGAAGTGCTGATC

GCCAAGCCCAAGCGGTTCCGGATCAAGCCCGGCATCTATCAGACCGCCTGGCACCTGGTGTT

-continued

```
TCGGGCCTACGGCAATGACGACCTGCTGAAGGTGGGCTACGAAGTGGGATTCGGGGAGAAGA

ACTCCCTGGGATTCGGAATGGTCAAGGTGGAGGGCAACAAGACCACCAAGGAAGCCGAAGAA

CAGGAGAAGATCACCTTCAACTCCCGGGAAGAGCTGAAAACAGGCGTG
```

PaCsf5 (IV-A1):
(SEQ ID NO: 43)
```
ATGTTCGTGACCCAGGTGATCTTCAACATCGGCGAACGGACGTACCCCGACAGGGCTCGGGC

TATGGTGGCCGAGCTGATGGATGGCGTCCAGCCTGGCCTGGTGGCCACCCTGATGAACTACA

TCCCCGGCACCAGCACGAGCCGGACAGAGTTCCCCACCGTGCAGTTCGGCGGCGCCAGCGAC

GGCTTTTGCCTGCTGGGCTTCGGCGACGGCGGCGGCGCCATCGTGAGAGATGCCGTGCCCCT

GATCCACGCCGCCCTGGCAAGGCGGATGCCTGATCGGATCATCCAGGTGGAACACAAGGAGC

ACAGCCTGTCCGCCGAGGCCCGGCCCTACGTGCTGAGCTACACCGTGCCTCGGATGGTGGTG

CAGAAGAAGCAGCGGCACGCCGAGAGACTGCTGCACGAAGCCGAGGGAAAGGCTCACCTGGA

GGGCCTGTTCCTGCGGAGCCTGCAGAGGCAGGCCGCCGCCGTGGGCCTGCCCCTGCCCGAGA

ACCTGGAGGTGGAGTTCAAGGGAGCCGTGGGCGACTTCGCCGCAAAGCACAATCCAAATAGC

AAGGTGGCCTACCGGGGACTGAGAGGCGCCGTGTTCGATGTGAACGCCAGACTGGGCGGCAT

CTGGACCGCCGGATTCATGCTGAGCAAGGGCTACGGCCAGTTTAACGCCACCCACCAGCTGA

GCGGCGCCGTGAACGCTCTGTCCGAA
```

MtCsf5 (IV-A2):
(SEQ ID NO: 44)
```
ATGCACCAGACCCTGATCCGGATCAACTGGCCCAAGGGATTCAAGTGCCCCCCTGCCGAGTT

CCGGGAAAAGCTGGCCAAGAGCGAGATGTTCCCCCCCGAGTTCTTCCACTACGGCACGGAAC

TGGCCGTGTGGGACAAGCAGACCGCCGAGGTGGAGGGCAAGATCAAGACCGTGTCCAAGGAG

AAGATCATCAAGACCTTTGACAAGCCCATCCCCCTGAATGGCCGGGCCCCGGTCAGAGTGAT

CGGCGGCCAGGCCTGGGCCGGCGTGATCGCCGACCCCGAGATGGAGGGCATGCTGATCCCAC

ACCTGGGGAGCATCCTGAAGGTGGCCAGCAGCGCGGCCGGATGCGCAGTGAAGATCGAACTG

GAACAGAGAAAGTTCGGCATCAGCTACACCGAGTACCCCGTGAAGTACAACCTGCGGGAGCT

GGTGCTGAAGAGAAGATGCGAGGACGCCCGGTCTACCGATATCGAGAGCCTGATTGCCGATA

GAATCTGGGCGGCGTGTCCGGCGAGAGCTACTATGGCATCGACGGCACATGCGCCAAGTTT

GGCTTCGAACCCCCAGCAGAGAGCAGCTGGAGCTGCGGATCTTCCCCATGAAGAACATCGG

ACTGCACATGAAGTCCAGCGACGGACTGTCCAAGGAGTACATGAGCCTGATTGACGCCGAGG

TGTGGATGAACGCTAAGCTGGAAGGAGTGTGGCAGGTGGGCAACCTGATCAGCAGGGGCTAC

GGCCGGTTCATCAAGTCTATCGGCGCCCAGTCC
```

In certain embodiments, the RNA sequence of the invention encodes a non-naturally occurring polynucleotide comprising a derivative of any one of Sequences 12-33, wherein the derivative (i) has one or more (e.g., 1, 2, 3, 4, 5, 6, 7, 8, 9 or 10) nucleotides additions, deletions, substitutions, and/or other mutations compared to any one of Sequences 12-33; (ii) has at least 20%, 30%, 40%, 50%, 60%, 70%, 80%, 90%, 95%, or 97% sequence identity to any one of Sequences 12-33; (iii) hybridize under stringent conditions with any one of Sequences 12-33, or any of (i) and (ii); or (iv) is a complement of any of (i)-(iii), provided that the derivative is not any one of Sequences 12-33, and that the derivative encodes an RNA (or is an RNA) that has maintained substantially the same secondary structure (e.g., stems, loops, bulges, single-stranded regions) as any of the RNA encoded by Sequences 12-33. In certain embodiments, the derivative functions as a DR sequence for any one of the CasPR, the ortholog thereof, the paralog thereof, the variant thereof, the derivative thereof, or the functional fragment thereof, of the invention.

In certain embodiments, the RNA sequence of the invention comprises a coding sequence for an engineered Clustered Regularly Interspaced Short Palindromic Repeat (CRISPR)-Cas13 effector enzyme, wherein the engineered Cas13: (1) comprises a mutation in a region spacially close to an endonuclease catalytic domain of the corresponding wild-type Cas13 effector enzyme; (2) substantially preserves guide sequence-specific endonuclease cleavage activity of the wild-type Cas13 towards a target RNA complementary to the guide sequence; and, (3) substantially lacks guide sequence-independent collateral endonuclease cleavage activity of the wild-type Cas13 towards a non-target RNA that does not bind to the guide sequence.

In certain embodiments, the Cas13 is a Cas13a, a Cas13b, a Cas13c, a Cas13d (including CasRx), a Cas13e, or a Cas13f.

In certain embodiments, the Cas13e has the amino acid sequence of SEQ ID NO: 4 of PCT/CN2020/119559 (incorporated herein by reference).

In certain embodiments, the region includes residues within 120, 110, 100, 90, or 80 amino acids from any residues of the endonuclease catalytic domain (e.g., an RXXXXH domain) in the primary sequence of the Cas13.

In certain embodiments, the region includes residues more than 100, 110, 120, or 130 residues away from any residues of the endonuclease catalytic domain in the primary sequence of the Cas13, but are spacially within 1-10 or 5 angstrom of a residue of the endonuclease catalytic domain.

In certain embodiments, the endonuclease catalytic domain is a HEPN domain, optionally a HEPN domain comprising an RXXXXH motif. In certain embodiments, the RXXXXH motif comprises a R{N/H/K}X1X2X3H sequence. In certain embodiments, in the R{N/H/K}X1X2X3H sequence, X1 is R, S, D, E, Q, N, G, or Y; X2 is I, S, T, V, or L; and X3 is L, F, N, Y, V, I, S, D, E, or A. In certain embodiments, the RXXXXH motif is an N-terminal RXXXXH motif comprising an RNXXXH sequence, such as an RNIY/FI {F/Y}SH sequence (SEQ ID NO: 95). In certain embodiments, the N-terminal RXXXXH motif has a RNYFSH sequence (SEQ ID NO: 96). In certain embodiments, the N-terminal RXXXXH motif has a RNFYSH sequence (SEQ ID NO: 97). In certain embodiments, the RXXXXH motif is a C-terminal RXXXXH motif comprising an R{N/A/R} {A/K/S/F} {A/L/F} {F/H/L}H sequence. In certain embodiments, the C-terminal RXXXXH motif has a RN(A/K)ALH sequence (SEQ ID NO: 98). In certain embodiments, the C-terminal RXXXXH motif has a RAFFHH (SEQ ID NO: 99) or RRAFFH sequence (SEQ ID NO: 100).

In certain embodiments, the region comprises, consists essentially of, or consists of residues corresponding to residues between residues 2-187, 227-242, or 634-755 of SEQ ID NO: 4 of PCT/CN2020/119559 (incorporated by reference). In certain embodiments, the region comprises, consists essentially of, or consists of residues corresponding to residues between residues 35-51, 52-67, 156-171, 666-682, or 712-727 of SEQ ID NO: 4 of PCT/CN2020/119559 (incorporated by reference).

In certain embodiments, the mutation comprises, consists essentially of, or consists of substitutions, within a stretch of 15-20 consecutive amino acids within the region, one or more charged or polar residues to a charge-neutral short chain aliphatic residue (such as A). In certain embodiments, the stretch is about 16 or 17 residues. In certain embodiments, substantially all, except for up to 1, 2, or 3, charged and polar residues within the stretch are substituted. In certain embodiments, a total of about 7, 8, 9, or 10 charged and polar residues within the stretch are substituted. In certain embodiments, the N- and C-terminal 2 residues of the stretch are substituted to amino acids the coding sequences of which contain a restriction enzyme recognition sequence. In certain embodiments, the N-terminal two residues are VF, and the C-terminal 2 residues are ED, and the restriction enzyme is BpiI. In certain embodiments, the one or more charged or polar residues comprise N, Q, R, K, H, D, E, Y, S, and T residues. In certain embodiments, the one or more charged or polar residues comprise R, K, H, N, Y, and/or Q residues. In certain embodiments, one or more Y residue(s) within the stretch is substituted. In certain embodiments, the one or more Y residues(s) correspond to Y672, Y676, and/or Y751 of wild-type Cas13e.1 (SEQ ID NO: 4 of PCT/CN2020/119559 (incorporated by reference)). In certain embodiments, the stretch is residues 35-51, 52-67, 156-171, 666-682, or 712-727 of SEQ ID NO: 4 of PCT/CN2020/119559 (incorporated by reference). In certain embodiments, the mutation comprises Ala substitution(s) corresponding to any one or more of SEQ ID NOs: 37-39, 45, and 48 of PCT/CN2020/119559 (incorporated by reference). In certain embodiments, the charge-neutral short chain aliphatic residue is Ala (A). In certain embodiments, the mutation comprises, consists essentially of, or consists of substitutions within 2, 3, 4, or 5 the stretches of 15-20 consecutive amino acids within the region.

In certain embodiments, the engineered Cas13 preserves at least about 50%, 60%, 70%, 80%, 85%, 90%, 95%, 96%, 97%, 98%, or 99% of the guide sequence-specific endonuclease cleavage activity of the wild-type Cas13 towards the target RNA.

In certain embodiments, the engineered Cas13 lacks at least about 80%, 85%, 90%, 95%, 96%, 97%, 98%, 99%, or 100% of the guide sequence-independent collateral endonuclease cleavage activity of the wild-type Cas13 towards the non-target RNA.

In certain embodiments, the engineered Cas13 preserves at least about 80-90% of the guide sequence-specific endonuclease cleavage activity of the wild-type Cas13 towards the target RNA, and lacks at least about 95-100% of the guide sequence-independent collateral endonuclease cleavage activity of the wild-type Cas13 towards the non-target RNA.

In certain embodiments, the engineered Cas13 of the invention has an amino acid sequence at least 80%, 85%, 90%, 95%, 96%, 97%, 98%, 99%, 99.1%, 99.2%, 99.3%, 99.4%, 99.5%, 99.6%, 99.7%, 99.8%, or 99.86% identical to any one of SEQ ID NOs: 6-10 of PCT/CN2020/119559 (incorporated by reference), excluding any one or more of the regions defined by SEQ ID NOs: 16, 20, 24, 28, and 32 of PCT/CN2020/119559 (incorporated by reference).

In certain embodiments, the amino acid sequence contains up to 1, 2, 3, 4, or 5 differences in each of one or more regions defined by SEQ ID NO: 16, 20, 24, 28, and 32 of PCT/CN2020/119559 (incorporated by reference), as compared to SEQ ID NOs: 17, 21, 25, 29, and 33 of PCT/CN2020/119559 (incorporated by reference), respectively.

In certain embodiments, he engineered Cas13 of the invention has the amino acid sequence of any one of SEQ ID NOs: 6-10 of PCT/CN2020/119559 (incorporated by reference). In certain embodiments, the engineered Cas13 of the invention has the amino acid sequence of SEQ ID NO: 9 or 10 of PCT/CN2020/119559 (incorporated by reference).

In certain embodiments, the engineered Cas13 of the invention further comprises a nuclear localization signal (NLS) sequence or a nuclear export signal (NES). In certain embodiments, the engineered Cas13 comprises an N- and/or a C-terminal NLS.

In certain embodiments, the RNA sequence of the invention encoding the engineered CRISPR/Cas13 effector enzyme of the invention is codon-optimized for expression in a eukaryote, a mammal, such as a human or a non-human mammal, a plant, an insect, a bird, a reptile, a rodent (e.g., mouse, rat), a fish, a worm/nematode, or a yeast.

In certain embodiments, the RNA sequence of the invention comprises a coding sequence for the engineered Clustered Regularly Interspaced Short Palindromic Repeat (CRISPR)-Cas13 effector enzyme, the coding sequence having (i) one or more (e.g., 1, 2, 3, 4, 5, 6, 7, 8, 9 or 10) nucleotides additions, deletions, substitutions, and/or other mutations compared to the wild-type sequence; (ii) at least 50%, 60%, 70%, 80%, 90%, 95%, or 97% sequence identity to the wild-type sequence; (iii) hybridize under stringent conditions with the wild-type sequence, or any of (i) and (ii); or (iv) is a complement of any of (i)-(iii).

In certain embodiments, the RNA sequence of the invention comprises a coding sequence for a non-coding RNA (ncRNA), such as siRNA, piRNA, short hairpin RNA or shRNA, microRNA or miRNA or precursors thereof including pre-miRNA and pri-miRNA, antisense sequence or oligonucleotide (ASO), guide RNA or gRNA for CRISPR/Cas, rRNA, tRNA, snoRNA, snRNA, exRNA, scaRNA, lncRNA, Xist, and HOTAIR, etc.

9. Method of Use

The rRAAV viral particles and RNA sequences of the invention can be used to deliver any GOI/RSI to any suitable target cell, tissue, or organism for any use for gene therapy.

In certain embodiments, the rRAAV viral particles and RNA sequences of the invention can be used in a method of treatment, in which a defective or loss of function disease gene can be replaced by a functional version of the gene to restore the lost function. For example, in certain embodiments, a wild-type coding sequence, or a variant coding sequence encoding a variant protein of the wild-type protein and having preserved at least one desired functions of the wild-type protein can be delivered to the target cell/tissue/organ, to express the encoded wild-type of variant thereof, in order to compensate for the loss of function of the disease gene.

In certain other embodiments, the rRAAV viral particles and RNA sequences of the invention can be used in a method of treatment, in which a defective or gain of function disease gene can be knocked out, knocked down, or otherwise down-regulated by a gene targeting agent to alleviate the detrimental effect of the disease gene. The gene targeting agent can be a CRISPR/Cas effector enzyme (such as an engineered Cas9 or Cas13 effector enzyme as described herein), optionally with a guide RNA that is provided simultaneously (or separately), that together target the disease gene. In certain embodiments, the gene targeting agent can be a Cas effector enzyme linked to a DNA or RNA base editor for DNA-RNA base editing. In certain embodiments, the gene targeting agent is an siRNA, shRNA, microRNA, or antisense RNA.

In certain embodiments, the invention provides a method of modifying a target RNA in a target cell, the method comprising contacting the target cell with an rRAAV viral particle or RNA sequence of the invention encoding a CasPR or engineered CRISPR/Cas effector enzyme described herein (or ortholog, paralog, variant, derivative, or functional fragment thereof), wherein a guide sequence for the CasPR/Cas effector enzyme is complementary to at least 15 nucleotides of the target RNA, and wherein the CasPR/engineered Cas effector enzyme associates with the guide sequence to form a complex that binds to and modified the target RNA.

In certain embodiments, the invention provides a method of treating a condition or disease in a subject in need thereof, the method comprising administering to the subject a composition comprising the an rRAAV viral particle or RNA sequence of the invention encoding a CasPR or engineered CRISPR/Cas effector enzyme described herein (or ortholog, paralog, variant, derivative, or functional fragment thereof), wherein a guide sequence for the CasPR/Cas effector enzyme is complementary to at least 15 nucleotides of the target RNA, and wherein the CasPR/engineered Cas effector enzyme associates with the guide sequence to form a complex that binds to and modified the target RNA, thereby treating the condition or disease in the subject.

In certain embodiments, the target RNA is modified by cleavage by the CasPR or engineered Cas effector enzyme complex. In certain embodiments, the target RNA is modified by deamination by a derivative comprising a double-stranded RNA-specific adenosine and/or cytidine deaminase. In certain embodiments, the target RNA is an mRNA, a tRNA, an rRNA, a non-coding RNA, an lncRNA, or a nuclear RNA. In certain embodiments, the target RNA is within a cell. In certain embodiments, the cell is a cancer cell. In certain embodiments, the cell is infected with an infectious agent. In certain embodiments, the infectious agent is a virus, a prion, a protozoan, a fungus, or a parasite. In certain embodiments, the cell is a neuronal cell (e.g., astrocyte, glial cell (e.g., Muller glia cell, oligodendrocyte, ependymal cell, Schwan cell, NG2 cell, or satellite cell)).

In certain embodiments, the condition or disease is a cancer or an infectious disease. In certain embodiments, the cancer is Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, or urinary bladder cancer. In certain embodiments, the method is an in vitro method, an in vivo method, or an ex vivo method. In certain embodiments, upon binding of the complex to the target RNA, the engineered Cas13 does not exhibit substantial (or detectable) collateral RNase activity.

In certain embodiments, the condition or disease is a neurological condition such as glaucoma, age-related RGC loss, optic nerve injury, retinal ischemia, Leber's hereditary optic neuropathy, a neurological condition associated with degeneration of RGC neurons, a neurological condition associated with degeneration of functional neurons in the striatum of a subject in need thereof, Parkinson's disease, Alzheimer's disease, Huntington's disease, Schizophrenia, depression, drug addiction, movement disorder such as chorea, choreoathetosis, and dyskinesias, bipolar disorder, Autism spectrum disorder (ASD), or dysfunction.

In certain embodiments, the method of the invention causes one or more of: (i) in vitro or in vivo induction of cellular senescence; (ii) in vitro or in vivo cell cycle arrest; (iii) in vitro or in vivo cell growth inhibition and/or cell growth inhibition; (iv) in vitro or in vitro induction of anergy; (v) in vitro or in vitro induction of apoptosis; and (vi) in vitro or in vitro induction of necrosis.

Further Embodiments of the Invention

1. A polynucleotide sequence, including, but not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof, capable of being packaged into a DNA virus viral particle, said polynucleotide sequence comprises:
  (1) a polynucleotide sequence of interest (PSI), e.g., a RNA coding sequence for a gene of interest (GOI), a protein (e.g., a therapeutic protein, an antigen protein, or a gene-editing protein such as a CRISPR/Cas effector enzyme ("a Cas protein" for short), a ZFN protein, a TALEN protein)-encoding RNA, such as, a mRNA, or a non-coding, functional RNA (such as, a transfer RNA (tRNA), a ribosomal RNA (rRNA), a small interfering RNA (siRNA), a short hairpin RNA (shRNA), an antisense RNA, an antisense oligonucleotide, a micro RNA (miRNA), or an RNA component of a CRISPR-Cas (e.g., Cas9, Cas12, Cas13) system, including a guide RNA (or a gRNA), such as, a single guide RNA (or a sgRNA, a chimeric RNA, an RNA chimera), a CRISPR RNA (crRNA), and a tracr RNA), or a precursor thereof; and,
  (2) a polynucleotide-packaging signal (PPS) capable of interacting, e.g., binding, directly or indirectly, to an PPS-interacting molecule that facilitates packaging of the polynucleotide sequence into the DNA virus viral particle;
  optionally, a DNA sequence encoding or corresponding to said polynucleotide sequence, or a reverse complement of said DNA sequence, has reduced, diminished, or substantially no capacity of being packaged into the DNA virus viral particle (e.g., the DNA sequence or the reverse complement thereof lacks a DNA packaging signal such as a functional AAV ITR for AAV packaging).
2. The polynucleotide sequence of any preceding embodiment, wherein the DNA virus viral particle is an AAV viral particle or an oncolytic viral particle.
3. The polynucleotide sequence of any preceding embodiment, wherein the PPS is located at or near the 5' end of the PSI, at or near the 3' end of the PSI, or internal to the PSI (e.g., inside an intron of an mRNA).
4. The polynucleotide sequence of any preceding embodiment, comprising more than one (e.g., 1, 2, 3, or more) PPS that are identical or different.
5. The polynucleotide sequence of any preceding embodiment, wherein two or more (e.g., 3) of said more than one PPS are adjacent to each other, or are in tandem, via the same or different linkers.
6. The polynucleotide sequence of any preceding embodiment, comprising two or more PPS that are not adjacent to each other (e.g., one each located at or near one end of the polynucleotide sequence of interest (PSI)).
7. The polynucleotide sequence of any preceding embodiment, wherein the PPS comprises a transcribed modified AAV inverted terminal repeat (ITR), wherein said transcribed modified AAV ITR:
  (a) comprises a transcribed functional Rep-Binding Element (RBE), optionally further comprising a transcribed functional RBE'; and,
  (b) lacks either a transcribed terminal resolution site (TRS), or a transcribed reverse complement TRS (rcTRS), or both;
  optionally, said transcribed modified AAV ITR further comprises a transcribed D region sequence (D sequence or D' sequence); and/or optionally, the PPS-interacting molecule is Rep78, Rep68, Rep52, and/or Rep40.
8. The polynucleotide sequence of any preceding embodiment, wherein the transcribed modified AAV ITR is within the 3' end 1000 nucleotides, 800 nucleotides, 500 nucleotides, 300 nucleotides, or 200 nucleotides of the RNA; optionally, the transcribed modified AAV ITR is 5' to a polyA sequence, a polyA signal sequence (e.g., AAUAAA), or a sequence for RNA transcription termination (e.g., a histone downstream element).
9. The polynucleotide sequence of any preceding embodiment, wherein the transcribed modified AAV ITR is modified based on a transcribed wild-type flip or flop ITR; optionally, said wild-type flip or flop ITR is from AAV1, AAV2, AAV3A, AAV3B, AAV4, AAV5, AAV6, AAV7, AAVrh74, AAV8, AAV9, AAV10, AAV11, AAV12, or AAV13 (optionally, said wild-type flop ITR has the nucleotide sequence of SEQ ID NO: 1).
10. The polynucleotide sequence of any preceding embodiment, wherein the transcribed modified AAV ITR lacks both the transcribed TRS and the transcribed rcTRS.
11. The polynucleotide sequence of any preceding embodiment, wherein the transcribed modified AAV ITR comprises the transcribed D region sequence (optionally, said modified AAV ITR has the nucleotide sequence of SEQ ID NO: 3).
12. The polynucleotide sequence of any preceding embodiment, wherein the transcribed modified AAV ITR lacks the transcribed D region sequence (optionally, said modified AAV ITR has the nucleotide sequence of SEQ ID NO: 2).
13. The polynucleotide sequence of any preceding embodiment, further comprising a second transcribed modified AAV ITR having a second transcribed functional RBE sequence but lacking either a second transcribed TRS or a second transcribed rcTRS or both; optionally, said second transcribed modified AAV ITR further comprises a second transcribed D region sequence.
14. The polynucleotide sequence of any preceding embodiment, wherein the transcribed modified AAV ITR and the second transcribed modified AAV ITR are identical (or different).
15. The polynucleotide sequence of any preceding embodiment, wherein the transcribed modified AAV ITR, and the second transcribed modified AAV ITR (if present), comprise a deletion from, a mutation in, or an insertion into a corresponding transcribed wild-type AAV ITR D region sequence or a corresponding transcribed wild-type TRS/rcTRS.
16. The polynucleotide sequence of any preceding embodiment, wherein the second transcribed modified AAV ITR is within 5' end 1000 nucleotides, 800 nucleotides, 500 nucleotides, 250 nucleotides, or 150 nucleotides of the polynucleotide sequence.
17. The polynucleotide sequence of any preceding embodiment, wherein the PPS comprises an MS2 sequence, an PP7 binding site, or a com binding site, and the PPS-interacting molecule comprises an PPS-interacting protein (PPSIP) capably of interacting, e.g., binding, directly or indirectly, to the PPS, such as a bacteriophage-derived MS2 coat protein (MCP) for an MS2 sequence, a PP7 bacteriophage coat protein (PCP) for an PP7 binding site, or a phage COM protein (COM) for a com binding site.
18. The polynucleotide sequence of any preceding embodiment, wherein the PPSIP is associated directly or indirectly with (e.g., fused to) a protein component of the viral packaging system for the DNA virus viral particle (such as Rep78 and/or Rep68 of adeno-associated virus 2 (AAV2), or assembly-activating protein (AAP)).

19. The polynucleotide sequence of any preceding embodiment, wherein the polynucleotide sequence comprises or preferably does not comprise a transcribed DNA packaging signal, for example, a transcribed wild-type AAV ITR sequence (e.g., the polynucleotide sequence comprises a transcribed modified AAV ITR sequence having an addition, a deletion, and/or a substitution of a nucleotide of a corresponding transcribed wild-type AAV ITR sequence to reduce the DNA packaging capability of the DNA virus viral particle).

20. The polynucleotide sequence of any preceding embodiment, further comprising:
    (1) a transcribed transcription enhancer;
    (2) a transcribed intron sequence or exon sequence (such as one for enhancing protein expression);
    (3) a 5' UTR sequence;
    (4) a 3' UTR sequence;
    (5) a polyA sequence, or a polyadenylation (polyA) signal sequence and optionally a GU-rich region downstream of the polyA signal sequence;
    (6) a posttranscriptional regulatory element or sequence, such as a transcribed Woodchuck Hepatitis Virus (WHP) Posttranscriptional Regulatory Element (WPRE) sequence; and/or,
    (7) a transcription termination sequence (such as a histone downstream element), optionally, the polynucleotide sequence comprises an PPS located 3' to the posttranscriptional regulatory element or sequence, and 5' to the polyA sequence or the polyA signal sequence.

21. The polynucleotide sequence of any preceding embodiment, comprising, in 5' to 3' orientation, the PSI, the optional transcribed WPRE sequence; the PPS (such as the transcribed modified AAV ITR, the MS2 sequence, the PP7 binding site, or the com binding site); and the polyA sequence or the polyA signal sequence.

22. The polynucleotide sequence of any preceding embodiment, wherein the GOI comprises a protein (e.g., a fluorescent protein, a therapeutic protein, an antigen protein, or a gene-editing protein such as a Cas protein, a ZFN protein, a TALEN protein), an enzyme (such as a Cre protein, or a CRISPR/Cas effector enzyme, e.g., Cas9, Cas12, Cas13, or a variant thereof), a structural protein, an mRNA, a non-coding RNA (ncRNA), an siRNA, a piRNA, a short hairpin RNA or shRNA, a microRNA (miRNA) or a precursor thereof (including pre-miRNA and pri-miRNA), a ribosomal RNA (rRNA), an antisense sequence or oligonucleotide (ASO), an RNA component of a CRISPR-Cas system, including a guide RNA (or a gRNA), such as, a single guide RNA (or a sgRNA, a chimeric RNA, an RNA chimera), a CRISPR RNA (crRNA), and a tracr RNA, a guide RNA or gRNA for a CRISPR/Cas effector enzyme, an rRNA, a tRNA, a snoRNA, a snRNA, an exRNA, a scaRNA, a lncRNA, a Xist, and a HOTAIR.

23. The polynucleotide sequence of any preceding embodiment, which is a single-stranded RNA less than about 8,900 nucleotides in length, less than about 8,000 nucleotides in length, less than about 7,000 nucleotides in length, less than about 6,000 nucleotides in length, less than about 5,200 nucleotides in length, less than about 4,000 nucleotides in length, less than about 3,000 nucleotides in length, less than about 2,000 nucleotides in length, about 4,700-5,200 nucleotides in length, about 4,700-5,000 nucleotide in length, about 4,700-4,800 nucleotides in length, or about 4,700 nucleotides in length.

24. A polynucleotide comprising a cassette encoding the polynucleotide sequence of any preceding embodiment; optionally, the polynucleotide is a DNA sequence (e.g., a DNA plasmid), optionally comprising a stuffer sequence in the backbone of the DNA plasmid, and/or optionally comprising no functional DNA packaging signal such as AAV ITR.

25. The polynucleotide of any preceding embodiment, further comprising a promoter operably linked to and driving the transcription of the polynucleotide sequence encoded by the cassette.

26. The polynucleotide of any preceding embodiment, wherein the promoter is a ubiquitous promoter.

27. The polynucleotide of any preceding embodiment, wherein the promoter is a tissue-specific promoter.

28. The polynucleotide of any preceding embodiment, wherein the promoter is a constitutive promoter.

29. The polynucleotide of any preceding embodiment, wherein the promoter is an inducible promoter.

30. The polynucleotide of any preceding embodiment, further comprising an enhancer that enhances the transcription of the polynucleotide sequence driven by the promoter.

31. A recombinant DNA virus viral particle comprising an polynucleotide genome (such as the polynucleotide sequence of any preceding embodiment or the polynucleotide sequence transcribed from the polynucleotide of any preceding embodiment) packaged within the protein shell (such as capsid) of a DNA virus (such as an AAV virus, or an oncolytic virus).

32. The recombinant DNA virus viral particle of any preceding embodiment, wherein the DNA virus is AAV, and the recombinant DNA virus viral particle is a recombinant polynucleotide adeno-associated virus (rPAAV) particle, comprising:
    (1) an AAV capsid; and,
    (2) the polynucleotide sequence of any preceding embodiment or the polynucleotide sequence transcribed from the polynucleotide of any preceding embodiment packaged within said AAV capsid.

33. The recombinant DNA virus viral particle of any preceding embodiment, wherein the AAV capsid comprises a capsid from an AAV of the serotype AAV1, AAV2, AAV3A, AAV3B, AAV4, AAV5, AAV6, AAV7, AAV8, AAV9, AAV10, AAV11, AAV12, AAV13, AAV-DJ, AAV PHP.eB, Anc80L65, Anc80L65AAP, AAVrh74, or 7m8.

34. A population of recombinant DNA virus viral particles (e.g., rPAAV particles) comprising a plurality of recombinant DNA virus viral particle (e.g., rPAAV particle) of any preceding embodiment, wherein at least about 10%, 20%, 30%, 40%, 50%, 60%, 70%, 80%, 90%, 95%, 96%, 97%, 98%, 99% or more of the recombinant DNA virus viral particles (e.g., rPAAV particles) within said population have the polynucleotide sequence of any preceding embodiment or the polynucleotide sequence transcribed from the polynucleotide of any preceding embodiment packaged therein.

35. A host cell comprising the polynucleotide sequence of any preceding embodiment, the polynucleotide of any preceding embodiment, the polynucleotide sequence transcribed from the polynucleotide of any preceding embodiment, the recombinant DNA virus viral particle (e.g., rPAAV particle) of any preceding embodiment, and/or the population of recombinant DNA virus viral particles (e.g., rPAAV particles) of any preceding embodiment.

36. The host cell of any preceding embodiment, further comprising a viral packaging system that facilitates packaging of the polynucleotide sequence of any preceding embodiment or the polynucleotide sequence transcribed from the polynucleotide of any preceding embodiment into the DNA virus viral particle.

37. The host cell of any preceding embodiment, wherein the viral packaging system comprises:
   (1) an AAV rep gene (e.g., coding sequence for Rep78, Rep68, Rep52, and/or Rep40) and an AAV cap gene (e.g., coding sequence for VP1, VP2, VP3, AAP, and/or MAAP), under the transcriptional control of one or more promoters that drive the transcription of said rep gene and cap gene, or the expression products thereof;
   (2) one or more coding sequences for one or more proteins required for AAV packaging, such as adenoviral E2A, E4, and VA genes, or said one or more proteins; and
   (3) the PPS-interacting molecule or a coding sequence thereof;
   optionally, the capacity of the viral packaging system of packaging a DNA sequence into the DNA virus viral particle is reduced, diminished, or substantially eliminated by, for example, (1) removing a part or all of the DNA packaging signals such as AAV ITR on the polynucleotide encoding the polynucleotide sequence of any preceding embodiment or on the polynucleotide of any preceding embodiment, (2) modifying, e.g., mutating, said AAV rep gene, said AAV cap gene, and/or said one or more coding sequences for one or more proteins required for AAV packaging to reduce, diminish, or substantially eliminate the capacity of the respective translated protein to facilitate the packaging of the DNA sequence into the DNA virus viral particle (e.g., a Y156F mutation in the common sequence of Rep78 and Rep68 proteins, KDE-mu, or EKE-mu); and/or (3) enlarging the size of the polynucleotide encoding the polynucleotide sequence of any preceding embodiment or the polynucleotide of any preceding embodiment.

38. The host cell of any preceding embodiment, which is a mammalian cell (such as HEK293 cells) or an insect cell (such as Sf9 or Sf21 cells).

39. A method of generating the recombinant DNA virus viral particle (e.g., rPAAV particle) of any preceding embodiment or the population of recombinant DNA virus viral particles (e.g., rPAAV particles) of any preceding embodiment, the method comprising:
   a) culturing the host cell of any preceding embodiment for a sufficient time, and
   b) harvesting the recombinant DNA virus viral particle or the population of recombinant DNA virus viral particles.

40. The method of any preceding embodiment, further comprising isolating or purifying said recombinant DNA virus viral particle or said population of recombinant DNA virus viral particles.

41. A method of generating a recombinant DNA virus viral particle (e.g., rPAAV particle) or a population of recombinant DNA virus viral particles, the method comprising:
   a) contacting a viral packaging system (e.g., a AAV packaging system) with the polynucleotide sequence of any preceding embodiment or the polynucleotide sequence transcribed from the polynucleotide of any preceding embodiment for a period of time sufficient to produce the recombinant DNA virus viral particle or the population of recombinant DNA virus viral particles, and
   b) harvesting the recombinant DNA virus viral particle or the population of recombinant DNA virus viral particles; and, optionally,
   c) isolating or purifying the harvested recombinant DNA virus viral particle or population of recombinant DNA virus viral particles.

42. The method of any preceding embodiment, wherein the viral packaging system (e.g., a AAV packaging system) comprises:
   (1) one or more proteins for assemblying the protein shell (e.g., VP1, VP2, and/or VP3 for assembling AAV capsid) of the DNA virus viral particle for packaging the polynucleotide sequence, or one or more coding sequences thereof;
   (2) one or more proteins (e.g., Rep78, Rep68, Rep52, and/or Rep40 for AAV packaging) for facilitating the assemblying of the protein shell and/or the packaging of the polynucleotide sequence into the protein shell of the DNA virus viral particle, or one or more coding sequences thereof (e.g., adenoviral E2a, E4, and VA genes); and
   (3) the PPS-interacting molecule or a coding sequence thereof;
   optionally, the capacity of the viral packaging system of packaging a DNA sequence into the DNA virus viral particle is reduced, diminished, or substantially eliminated by, for example, (1) removing a part or all of the DNA packaging signals such as AAV ITR on the polynucleotide encoding the polynucleotide sequence of any preceding embodiment or on the polynucleotide of any preceding embodiment, (2) modifying, e.g., mutating, said AAV rep gene, said AAV cap gene, and/or said one or more coding sequences for one or more proteins required for AAV packaging to reduce, diminish, or substantially eliminate the capacity of the respective translated protein to facilitate the packaging of the DNA sequence into the DNA virus viral particle (e.g., a Y156F mutation in the common sequence of Rep78 and Rep68 proteins, KDE-mu, or EKE-mu); and/or (3) enlarging the size of the polynucleotide encoding the polynucleotide sequence of any preceding embodiment or the polynucleotide of any preceding embodiment.

43. A system of packaging the polynucleotide sequence of any preceding embodiment or the polynucleotide sequence transcribed from the polynucleotide of any preceding embodiment into a DNA virus viral particle, comprising:
   (1) one or more proteins for assemblying the protein shell (e.g., VP1, VP2, and/or VP3 for assembling AAV capsid) of the DNA virus viral particle for packaging the polynucleotide sequence, or one or more coding sequences thereof;

(2) one or more proteins (e.g., Rep78, Rep68, Rep52, and/or Rep40 for AAV packaging) for facilitating the assemblying of the protein shell and/or the packaging of the polynucleotide sequence into the protein shell of the DNA virus viral particle, or one or more coding sequences thereof (e.g., adenoviral E2a, E4, and VA genes); and (3) the PPS-interacting molecule or a coding sequence thereof;

optionally, the capacity of the viral packaging system of packaging a DNA sequence into the DNA virus viral particle is reduced, diminished, or substantially eliminated by, for example, (1) removing a part or all of the DNA packaging signals such as AAV ITR on the polynucleotide encoding the polynucleotide sequence of any preceding embodiment or on the polynucleotide of any preceding embodiment, (2) modifying, e.g., mutating, said AAV rep gene, said AAV cap gene, and/or said one or more coding sequences for one or more proteins required for AAV packaging to reduce, diminish, or substantially eliminate the capacity of the respective translated protein to facilitate the packaging of the DNA sequence into the DNA virus viral particle (e.g., a Y156F mutation in the common sequence of Rep78 and Rep68 proteins, KDE-mu, or EKE-mu); and/or (3) enlarging the size of the polynucleotide encoding the polynucleotide sequence of any preceding embodiment or the polynucleotide of any preceding embodiment.

44. A method of delivering a gene of interest (GOI) into a cell, a plant, or an animal, the method comprising contacting the cell, the plant, or the animal with the recombinant DNA virus viral particle (e.g., rPAAV particle) of any preceding embodiment, the population of the recombinant DNA virus viral particles (e.g., rPAAV particles) of any preceding embodiment, or the recombinant DNA virus viral particle (e.g., rPAAV particle) or the population of the recombinant DNA virus viral particles (e.g., rPAAV particles) produced by the method of any preceding embodiment, wherein said GOI is encoded by said polynucleotide sequence (of any preceding embodiment).

45. A method of delivering an polynucleotide sequence of interest (PSI) into a cell, a plant, or an animal, the method comprising contacting the cell, the plant, or the animal with the recombinant DNA virus viral particle (e.g., rPAAV particle) of any preceding embodiment, the population of the recombinant DNA virus viral particles (e.g., rPAAV particles) of any preceding embodiment, or the recombinant DNA virus viral particle (e.g., rPAAV particle) or the population of the recombinant DNA virus viral particles (e.g., rPAAV particles) produced by the method of any preceding embodiment.

46. A method of diagnosing, preventing, or treating a disease or disorder in a subject in need thereof, comprising administrating to the subject a therapeutically effective amount or dose of the population of the recombinant DNA virus viral particles (e.g., rPAAV particles) of any preceding embodiment or produced by the method of any preceding embodiment.

47. Use of the recombinant DNA virus viral particle (e.g., rPAAV particle) of any preceding embodiment, the population of the recombinant DNA virus viral particles (e.g., rPAAV particles) of any preceding embodiment, or the recombinant DNA virus viral particle (e.g., rPAAV particle) or the population of the recombinant DNA virus viral particles (e.g., rPAAV particles) produced by the method of any preceding embodiment in the manufacture of a medicament for diagnosing, preventing, or treating a disease or disorder in a subject in need thereof.

EXAMPLES

The examples herein below are provided to illustrate several exemplary embodiments of the invention, and are not limiting in any respect.

Example 1 Efficient Packaging of RNA into RAAV Viral Particles

This example demonstrates that RNA vector genome can be efficiently packaged into AAV viral capsids, especially with the modified/recombinant RNA designed for direct packaging into AAV capsids.

First, it was surprisingly shown that the AAV packaging signal-ITR (DNA), when transcribed (as RNA), was able to facilitate the packaging of the RNA sequence of the invention (e.g., the rRAAV vector genome RNA) into AAV particles, especially when it is presented in certain configurations (e.g., when the transcribed modified AAV ITR sequence is close to the 3' end of the transcribed RNA sequence of the invention).

Specifically, wild-type and modified AAV ITR sequences (DNA) from the ends of the AAV vector genome were moved into their respective transgene expression cassettes, to ensure that all the transgene transcripts (RNA's) contain a candidate packaging signal. In order to block the production of conventional AAV vectors with ssDNA genomes during RAAV production, optimized ITRs (dITR and dITR-D) were used instead of wild type ITR (Table 2).

TABLE 2

Nucleic Acid Sequences of Tested ITRs

| ITR Names | Nucleic Acid (DNA) Sequences |
|---|---|
| wild type ITR2 (Flop) | TTGGCCACTCCCTCTCTGCGCGCTCGCTCGCTCACTGAGGCCGCCCGGG CAAAGCCCGGGCGTCGGGCGACCTTTGGTCGCCCGGCCTCAGTGAGCGA GCGAGCGCGCAGAGAGGGAGTGGCCAA *CTCCATCACTAGGGGTTCCT* (SEQ ID NO: 1) |
| dITR | TCCCTCTCTGCGCGCTCGCTCGCTCACTGAGGCCGCCCGGGCAAAGCCC GGGCGTCGGGCGACCTTTGGTCGCCCGGCCTCAGTGAGCGAGCGAGCGC GCAGAGAGGGAGTGG (SEQ ID NO: 2) |
| dITR-D | TCCCTCTCTGCGCGCTCGCTCGCTCACTGAGGCCGCCCGGGCAAAGCCC GGGCGTCGGGCGACCTTTGGTCGCCCGGCCTCAGTGAGCGAGCGAGCGC GCAGAGAGGGAGTGGACTAG *CTCCATCACTAGGGGTTCCT* (SEQ ID NO: 3) |

Specifically, in the wild-type AAV2 ITR (ITR2) sequence in the Flop configuration, the TRS ("TTGGC") is at the 5' end of the ITR, and its reverse complement sequence GCCAA is double underlined. This sequence can be cloned into the coding plasmid in either direction (i.e., either the sequence shown as SEQ ID NO: 1, or its reverse complement sequence, can be used as template to transcribe the RNA sequence of the invention). In the experiments herein, the wild-type AAV2 ITR sequence was cloned in an orientation such that the transcribed RNA had the same sequence as SEQ ID NO: 1 (or SEQ ID NO: 2 or 3 below) except that T's were replaced by U's in the transcribed RNA. Regardless, upon transcription of either this sequence or its reverse transcript, the resulting transcribed RNA of the wild-type ITR2 comprises the palindromic transcribed RBE (shaded in grey). In the experiment herein, the transcribed RNA comprises a transcribed wild-type AAV2 ITR that is equivalent to SEQ ID NO: 1, except that all T's were replaced by U's. If the reverse complement sequence of SEQ ID NO: 1 were used as the DNA template, the transcribed RNA would comprise a transcribed TRS (UUGGC) encoded by GCCAA. The transcribed TRS is located between the transcribed RBE and the transcribed D sequence.

One of the modified ITR sequence is "delta ITR" (or "dITR" for short), which is defective because the dITR lacks both the D region sequence (bold italic), the TRS at the 5' end, and the reverse complement TRS sequence ("GC-CAA") except for the first G. Upon transcription of this sequence, the transcribed RNA of the dITR also comprises the palindromic transcribed RBE (shaded in grey), and a transcribed defective ITR that lacks a transcribed TRS (UUGGC) encoded by GCCAA. In this experiment, however, the reverse complement sequence of SEQ ID NO: 2 served as the DNA template, such that the transcribed RNA comprises a transcribed modified AAV2 ITR (transcribed dITR) having the same sequence as SEQ ID NO: 2, except that all T's were replaced by U's.

Another one of the modified ITR sequence is "dITR-D," which is also defective because it retains its D sequence ("CTCCATCACTAGGGGTTCCT," SEQ ID NO: 4) but lacks the 5' end TRS (TTGGC). In addition, only the first G in the reverse complement TRS (GCCAA) is retained in dITR-D, and the remaining CCAA sequence is replaced by an unrelated ACTAG sequence. In this experiment, the reverse complement sequence of SEQ ID NO: 3 served as the DNA template, such that the transcribed RNA comprises a transcribed modified AAV2 ITR (transcribed dITR-D) having the same sequence as SEQ ID NO: 3, except that all T's were replaced by U's.

Note that both the dITR and dITR-D sequences retain the shaded palindromic RBE sequence SEQ ID NOS 103-104, respectively (CTGCGCGCTCGCTCGCTCACTG . . . CAGTGAGCGAGCGAGCGCGCAG), and their respective transcribed modified ITR's also have the RBE sequence.

Such optimized ITR coding sequences (DNA) were inserted into two positions of the tdTomato expression cassette—one located in-between the promoter and the tdTomato coding sequence, and the other located in-between the Woodchuck Hepatitis Virus (WHP) Posttranscriptional Regulatory Element (WPRE) and the SV40 polyA signal.

Figure 3:
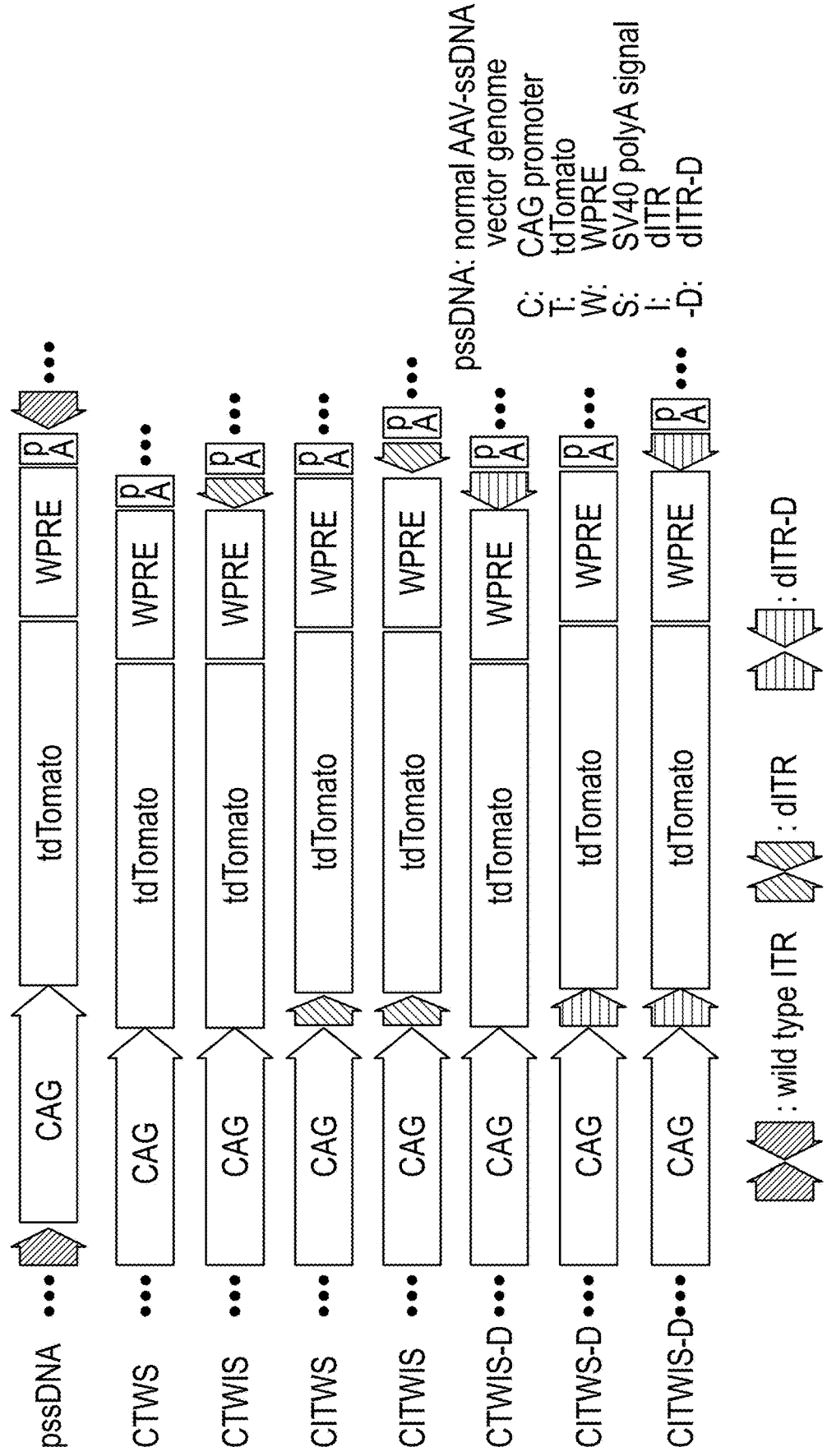
FIG. 3 is a schematic diagram of transgene plasmids of RAAV-ITR vectors and control vectors, showing the relative position and orientation of the promoter (such as the CAG promoter or "C"), the GOI coding sequence (such as the coding sequence for the reporter gene tdTomato or "T"), the WPRE sequence (or "W"), the SV40 polyA signal sequence (or "S"), and the wild-type ITR, mutated/optimized ITR (dITR or dITR-D).

Based on the sequences, numbers and positions of the optimized-ITRs used, a series of the various ITR-based RAAV vectors were constructed (see FIG. 3).

A conventional AAV vector with a ssDNA vector genome and no ITR sequences at either end ("CTWS," which stands for the sequence elements CAG promoter, tdTomato transgene, WPRE sequence, and SV40 polyA signal sequence) were used as a control. For this experiment, AAV serotype DJ was chosen because of its excellent transduction efficiency in cultured cells used. AAV-DJ is a synthetic serotype with a chimeric capsid of AAV-2, 8, and 9. It contains a heparin-binding domain in its capsid, which may efficiently transduce a broad range of cell types and escape from immune neutralization (Grimm et al., J. Virol. 82:5887-5911, 2008).

Figure 4:
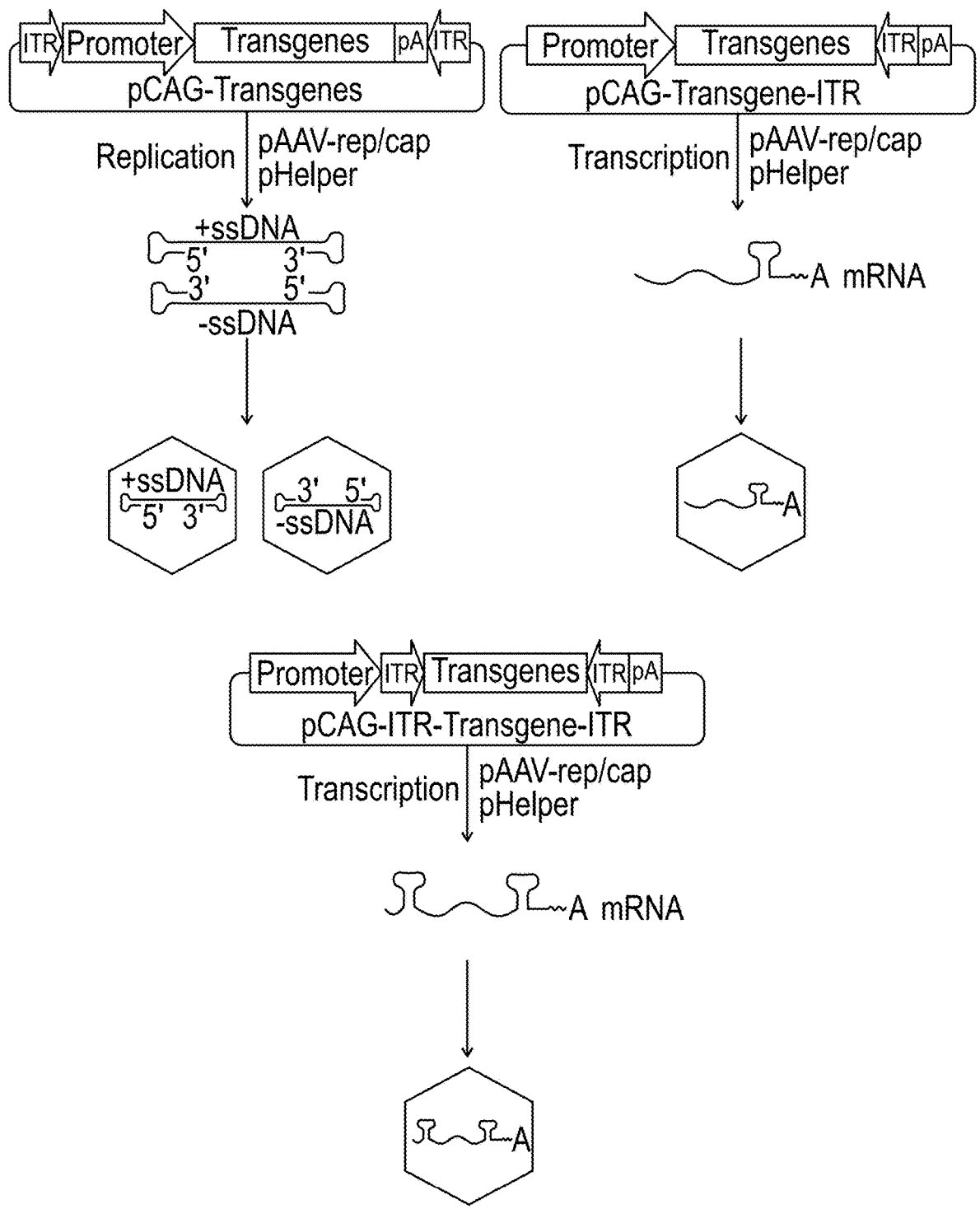
FIG. 4 is a schematic diagram showing the generation of AAV vectors and RAAV-ITR vectors with the triple-plasmid system. By co-transfecting three plasmids (e.g., a transgene plasmid, a packaging plasmid, and a helper plasmid) into a proper packaging cell like such as the HEK293 cells, recombinant AAV or RAAV viral vectors can be generated. Green ITR indicates wild type ITR, yellow ITR indicates optimized ITRs. pCAG-Transgene, pCAG-Transgene-ITR and pCAG-ITR-Transgene-ITR are transgene plasmids; pAAV-rep/cap is a packaging plasmid; and pHelper is the helper plasmid.

Both the various RAAV-ITR viral particles and the control viral particles were generated by using the triple-plasmid transfection system (FIG. 4).

In particular, the RAAV vectors were generated by co-transfecting tansgene plasmid, packaging plasmid and helper plasmid (weight ratio was 1:1:2) into HEK293T cells. The HEK293T cells were cultured in competent DMEM medium, and the cells were plated 24 hrs before transfection. Before transfection, the culture medium was replaced with fresh DMEM containing 2% PBS. PEI-MAX was used as the transfection reagent. The supernatant was then collected at Day 2 and Day 5 post transfection, and transfected cells were harvested on Day 5. RAAV vectors were purified by using iodixanol density gradient ultracentrifugation.

Figure 5A:
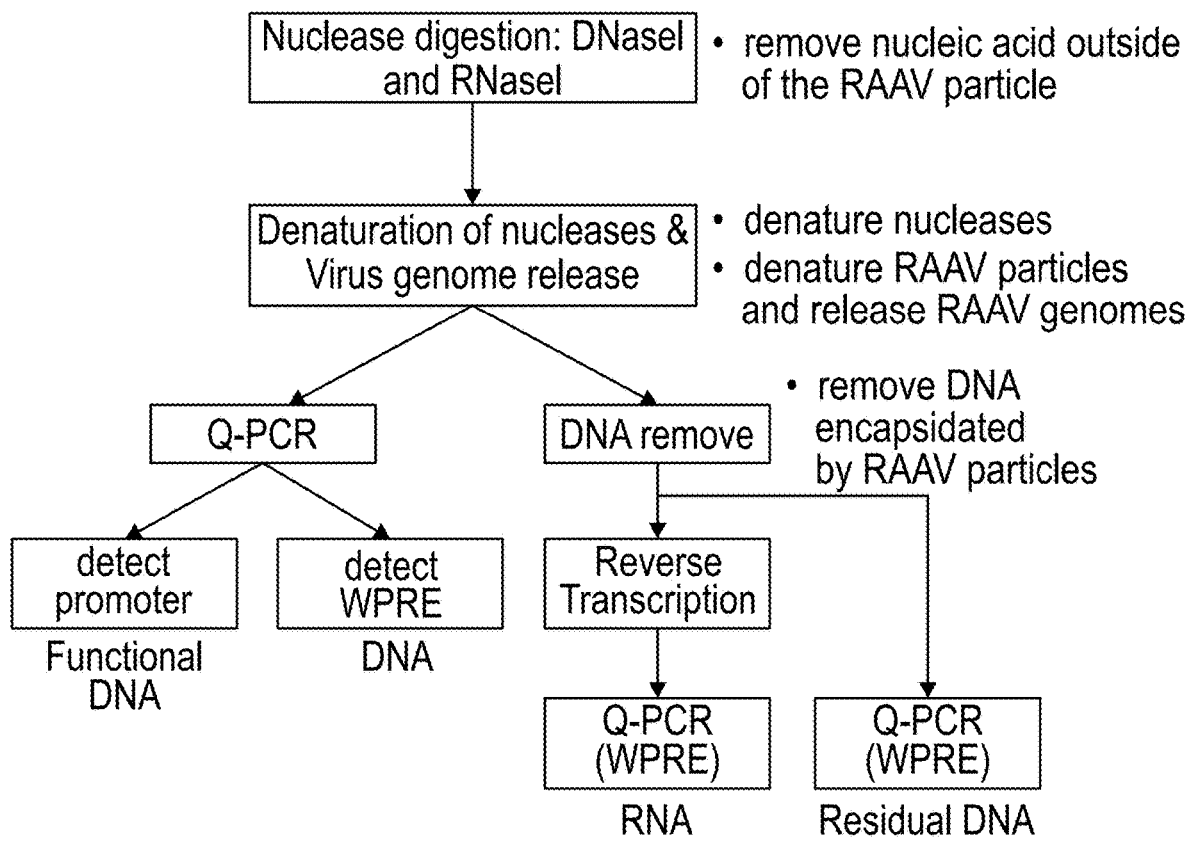
FIGS. 5A and 5B show representative viral vector titration process.

Viral titers (DNA titer and RNA titer) were determined by Q-PCR and Reverse transcription-PCR (RT-PCT), respectively, using the procedure in FIG. 5A.

Briefly, the harvested and purified RAAV viral particles were first subjected to DNase I and RNase I treatment at 37° C. for 2 hours to remove all nucleic acids outside the protein shells of the viral particles. Next, the nucleases were denatured at 100° C. for about 30 min, before the RAAV viral particles were denatured and ruptured to release the RAAV nucleic acid contents for further analysis.

Figure 5B:
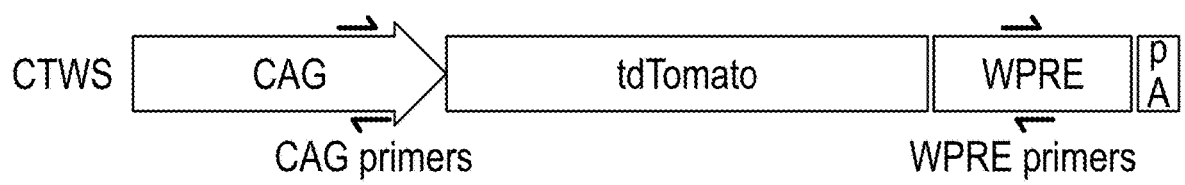

Q-PCR was used to analyze the nuclease-resistant products, in order to titrate the DNA vector genome encapsidated within the RAAV viral particles, Specifically, a primer pair specific for the promoter sequence was used in one set of Q-PCR to detect/quantitate any functional DNA, and a primer pair specific for the WPRE sequence was used in another set of Q-PCR to detect/quantitate any DNA vector genome encapsidated in the RAAV viral particles. See FIG. 5B.

Meanwhile, in another sample, any RAAV-encapsidated DNA was first removed by DNA removal through Dnase I digestion, before the remaining RNA was subjected to reverse-transcription, and the resulting cDNA was used as Q-PCR templates for detection/quantitation of WPRE sequences transcribed into RNA. To detect/quantitate any residue DNA that may be present after incomplete DNA removal, a sample after the DNA removal step was directly amplified using Q-PCR to detect any WPRE (DNA) sequences that might be present in that sample. See FIG. 5A.

To test the packaging efficiency of the CITWS construct (see FIG. 6A), when the conventional pssDNA construct (with wild-type ITR sequences on both ends) was used to generate viral particles, the vast majority of the viral particles contained functional DNA vector genome with promoter sequences and the WPRE sequences. Very occasionally (two orders of magnitude, or about 1% of the time), RNA vector genome was also packaged into viral particles (see the bar labelled as "RNA" which is about 2 orders of magnitude lower than the bar labelled as "DNA" and "Functional DNA"). Residual DNA is one order of magnitude less than the packaged RNA vector genome.

Figure 6A:
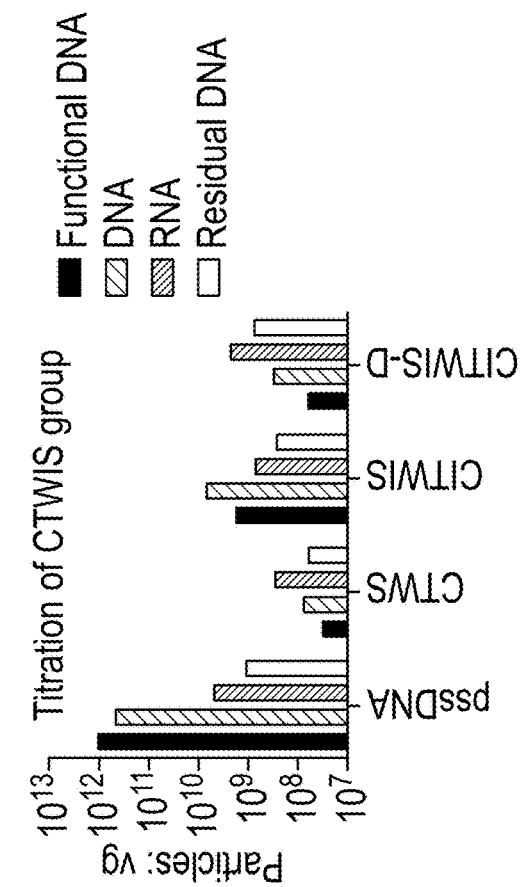
FIGS. 6A-6C show titration of RAAV-ITR vectors.

Meanwhile, removing the ITR sequences from both ends of the AAV vector genome essentially abolished packaging—the CTWS construct (ITR-free) in FIG. 6A produced 2-2.5 orders of magnitude less of packaged DNA, and even less RNA.

Adding back only one optimized ITR sequence (either the dITR or dITR-D sequence), between the 3' of the promoter and 5' to the GOI coding sequence, did not appear to enhance RNA packaging compared to the CTWS control, though DNA packaging seemed to have slightly improved. See FIG. 6A.

Figure 6B:
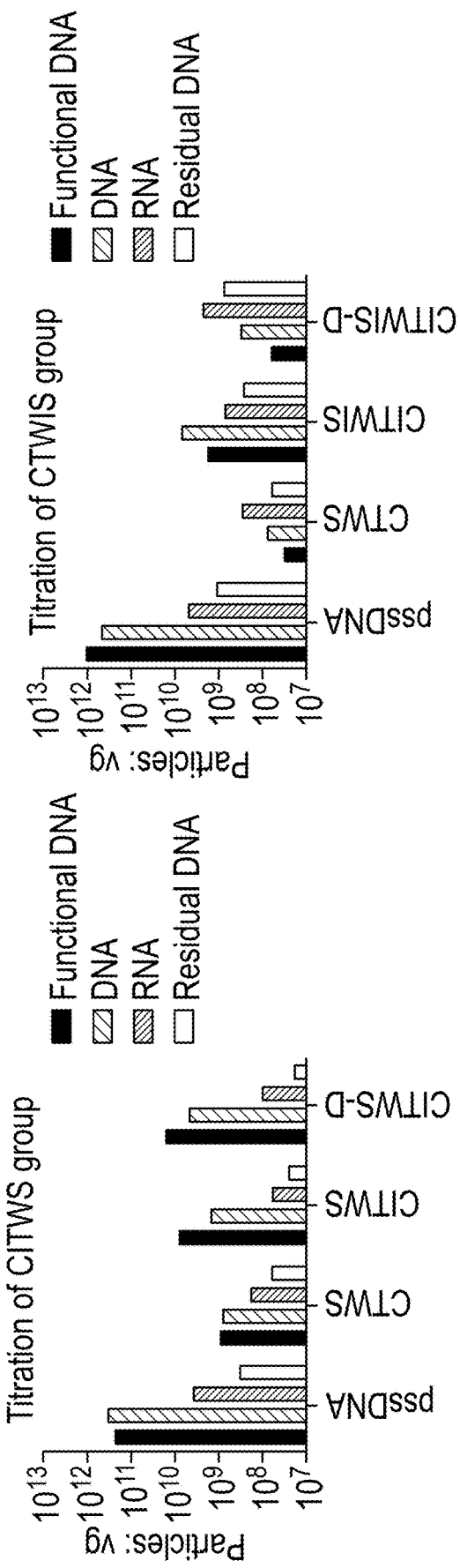

Interestingly, a very different result was achieved in FIG. 6B, in which the CTWIS constructs were tested. Specifically, essentially the same results were obtained regarding packaging the pssDNA constructs (compared FIGS. 6A and 6B)—most packaged viral particles contained DNA (99% or more) and negligible amount (1% or less) of RNA. However, including an optimized ITR sequence (dITR) between the 3' end of the WPRE sequence and the 5' end of the polyA sequence significantly reduced or even reversed the packaging efficiency difference between DNA and RNA. This effect is even more prominent when the dITR-D sequence was used, when the vast majority of the packaged nucleic acids are RNA (1-2 orders of magnitude over packaged DNA).

Essentially the same results were obtained if one additional (i.e., a second) optimized ITR sequence was inserted between the promoter and the GOI coding sequence in the CITWIS constructs. See FIG. 6C.

These results demonstrated that, optimized ITRs (dITR and dITR-D) impaired the replication of the conventional AAV vectors, thereby leading to a reduction of DNA packaging into the RAAV viral particle.

Figure 6C:
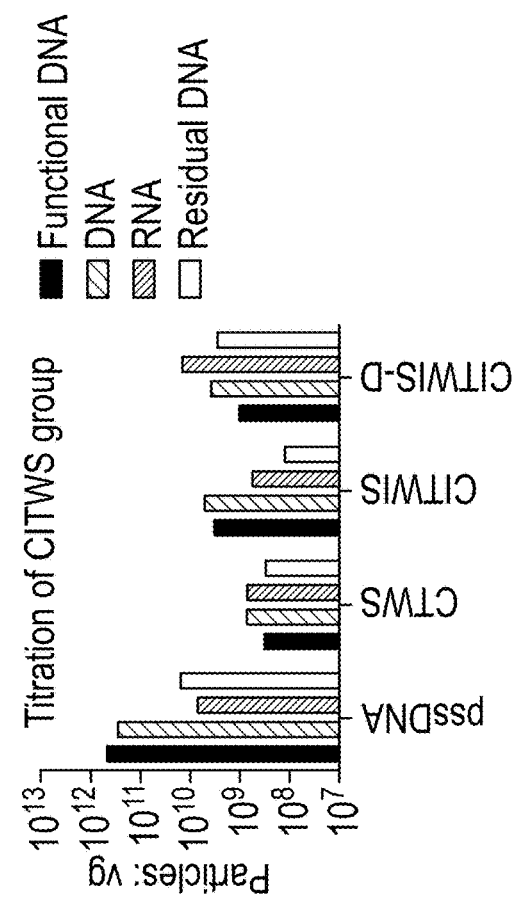

Compared to the control vector CTWS (ITR-free) and the RAAV-dITR vectors, RAAV vectors with the dITR-D optimized ITR seem to have a better ability to encapsidate the transcribed mRNAs directly into RAAV particles, especially when the dITR-D ITR is located downstream of the mRNA coding sequence and WPRE sequence (for example, just 5' to the polyA signal). See FIGS. 6A-6C. In contrast, a dITR-D sequence located upstream of the mRNA coding sequence (e.g., right after the promoter sequence in the expression construct) hardly facilitated direct mRNA packaging into the RAAV viral particles. Meanwhile, if another dITR-D sequence was inserted downstream of the mRNA coding sequence (e.g., right 5' to the polyA sequence), packaging of the resulting RAAV mRNAs was similarly highly increased (FIG. 6C).

In conclusion, CITWIS-D, which harbors dITR-D signals at both ends of its mRNA genome, has the best ability to encapsidate specific mRNAs, despite the fact that its yield (mRNA-harbouring particles) is 20-fold lower than the yield of conventional AAV vectors with ssDNA vector genomes (pssAAV group). Unlike the conventional AAV vectors, RAAV vector CITWIS-D have an impaired DNA packaging, with its DNA-carrying particles only taking up about 20% or less of the RAAV vector stock, and the percentage of the particles harbouring functional DNAs is even lower (e.g., less than 10%) (FIGS. 6A-6C).

Since the AAV packaging capacity is limited (<4700 nt), the undesired RAAV DNA packaging could be reduced by enlarging the size of the transgene plasmids, and functional DNA packaging could be further reduced by increasing the length of the transgene cassette, for example, by inserting cis-acting elements (such as, enhancer, intron, etc.) or non-functional stuffer sequence into the cassette.

Example 2 the RAAV Viral Particles are Functional

This example demonstrates that the subject RAAV-dITR-D vectors are infectious and can be used as gene delivery vectors.

The same volume of purified RAAV-dITR-D (CITWIS-D) vectors were used to infect $2 \times 10^5$ HEK293T cells in vitro, at the same MOI of about 50,000 (the MOI of the CITWIS-D vectors was calculated based on the sum of the number of DNA-particles and mRNA-particles).

Specifically, HEK293T cells were plated into 24-well plates about 24 hrs before infection. RAAV vectors were then mixed completely with 1 mL of DMEM (containing 2% FBS). The culture medium of the cells was then removed, and the cells were incubated with mixed RAAV vectors overnight. Fluorescence photos were taken 3 and 5 days post infection.

Figure 7A:
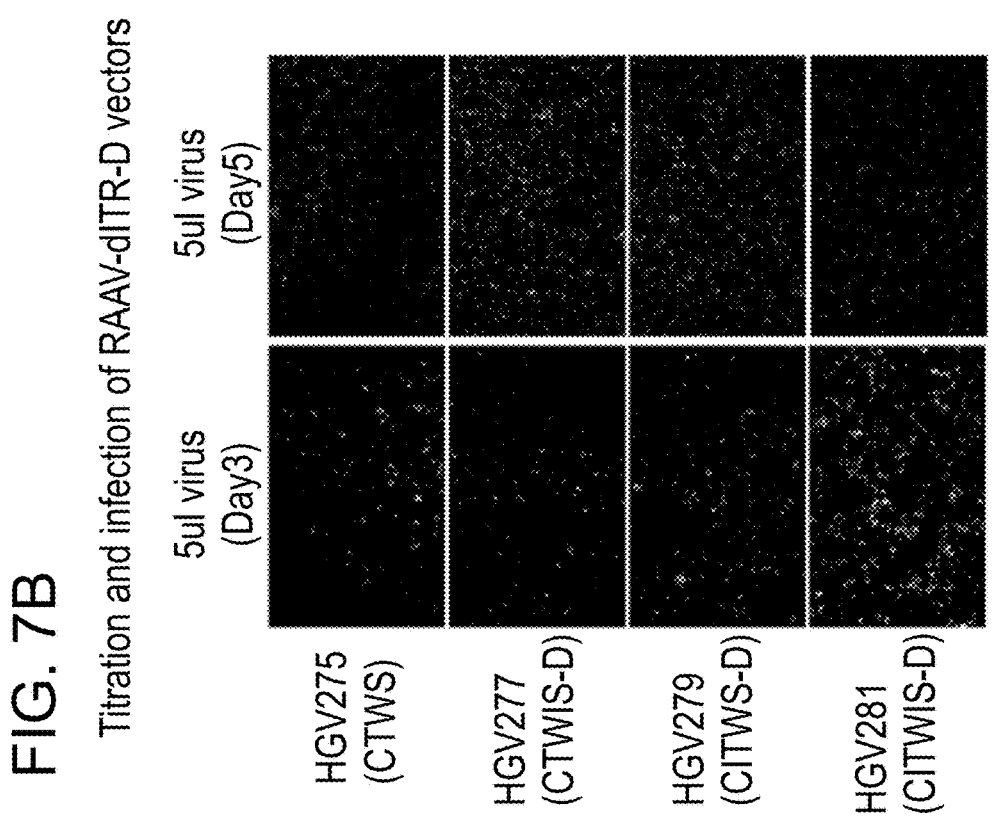
FIGS. 7A and 7B show titration and infection of RAAV-dITR-D vectors.
Figure 7B:
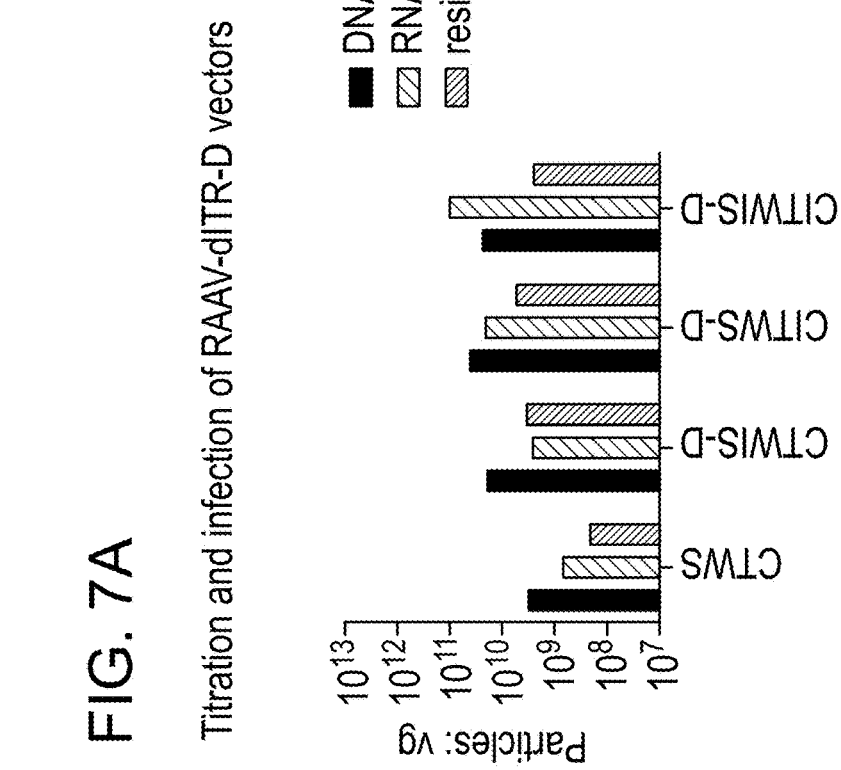

The results showed that, tdTomato expression by the CITWIS-D vector was quicker than that of the other vectors, but the expression was down-regulated rapidly too (see FIG. 7B). This quick expression and degradation phenomenon may be due to the short lifetime of its mRNA genome (FIG. 7B).

It is interesting to note that the CTWS construct without any ITR sequences were apparently packaged to some degree, though the precise mechanism underlying this packaging remains unclear. At least two possibilities can explain the packaging of mRNA vector genome when the CTWS vectors were used: overexpressed cellular mRNAs could be packaged into the RAAV vectors non-specifically, or CTWS mRNA might have some RNA structures that interact with Rep2 or Cap-DJ. Meanwhile, CTWS DNA packaging may be due to the small size of the plasmid CTWS, and DNA packaging may be reduced by increasing the size of the CTWS plasmid.

Example 3 Efficient Packaging of RNAs into RAAV Particles

This Example demonstrated that RNA genomes can be efficiently packaged into AAV capsids, especially with the modified/recombinant RNA constructs designed herein for direct packaging into AAV capsids to produce RAAV particles.

1. Design

The inventors have designed a strategy to utilize the strong interaction between bacteriophage-derived MS2 coat protein (MCP) and its recognizing stem loop MS2 as a novel packaging signal for packaging heterologous RNA into DNA virus viral particles.

First, in order to inhibit/reduce the production of conventional AAV particles with packaged ssDNA genomes during RAAV production, the conventional AAV packaging signals—ITRs—were removed. Instead, one copy or three copies of RNA packaging signals (RPS), MS2 stem loop (or "MS2" for short, its RNA sequence is set forth in the sequence tables below), were inserted into a tdTomato expression cassette, in-between the Woodchuck Hepatitis Virus (WHP) Posttranscriptional Regulatory Element (WPRE) and SV40 polyA signal, in order to ensure that all the transcribed mRNAs would have the RPS, so as to be recognized by the binding protein, bacteriophage-derived MS2 coat protein (or "MCP" for short, its amino acid sequence is set forth in the sequence tables below), corresponding to the MS2 (FIG. 8A).

Since AAV Rep proteins are non-structural proteins, and they conventionally serve as bridges between the ITRs of the ssDNA genomes and the AAV capsids during AAV packaging, MCP was fused to the N-terminus of Rep78 protein and Rep68 protein from AAV2 (Rep 68 is a C-terminal truncation of Rep 78, the amino acid sequences of the two fusions are set forth in the sequence tables below). The ability of these MCP-Rep78/68 fusions to interact with the MS2 sequence harbored inside the RNA genomes, and to facilitate the packaging of the RNA genomes into the AAV capsids was verified.

Figure 8A:
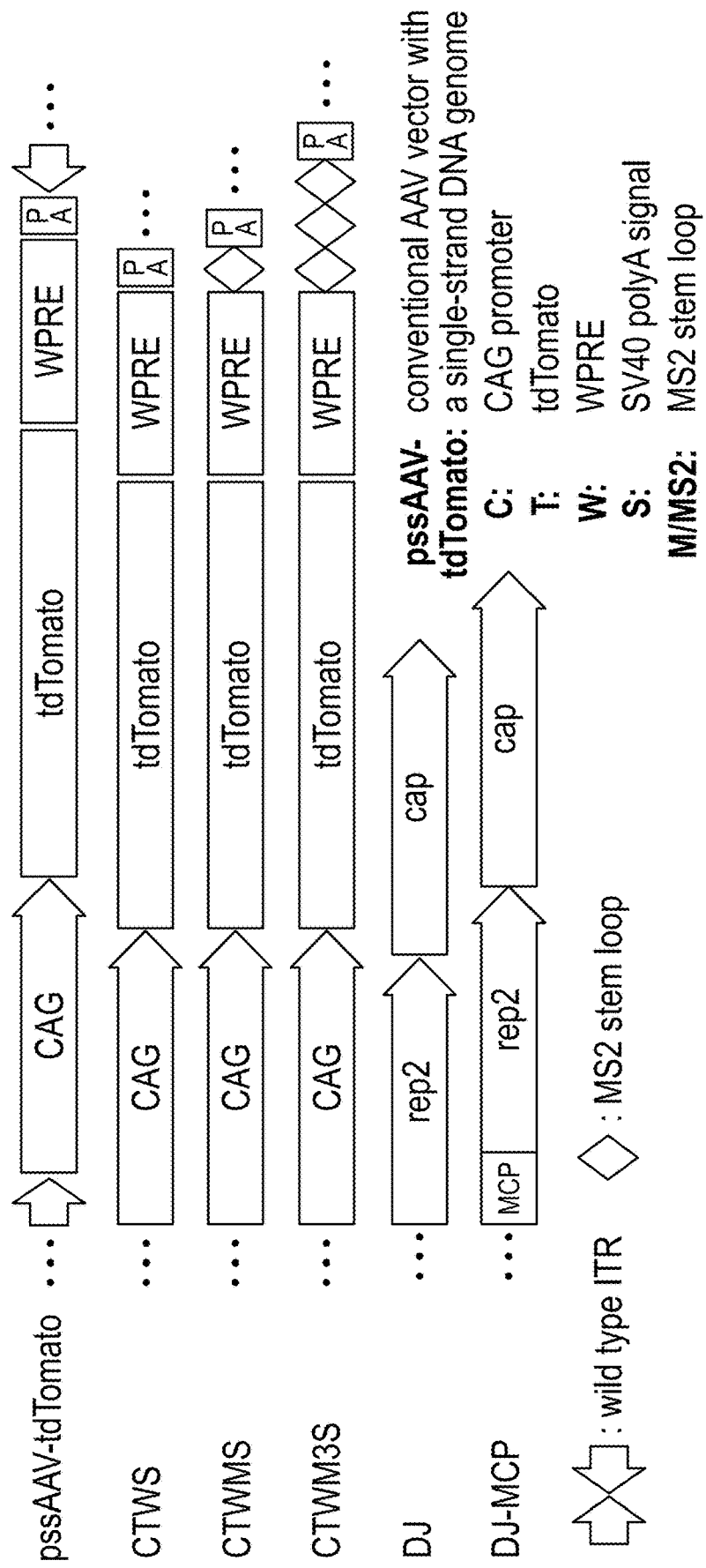
FIG. 8A is a schematic diagram (not to scale) showing the different plasmid constructs used to demonstrate efficient packaging of RNA into RAAV particles.

The conventional AAV vector pssAAV-tdTomato (with two wild type functional ITRs) and CTWS without functional wild-type ITRs ("CTWS," which stands for the sequence elements CAG promoter, tdTomato transgene, WPRE sequence, and SV40 polyA signal sequence) were used as controls (FIG. 8A). In this Example, AAV serotype DJ ("AAV-DJ" or "DJ") was selected for use because of its excellent transduction efficiency in the cultured cells, HEK293T cells, used in this Example. AAV-DJ is a synthetic serotype with a chimeric capsid of AAV-2, 8, and 9.

2. RAAV Packaging and Production

Both the RAAV and control AAV particles herein were produced by using conventional triple-plasmid transfection system mutatis mutandis, by co-transfecting the respective transgene plasmids, packaging plasmids, and helper plasmids in a weight ratio of 1:1:2 into HEK293T cells.

Specifically, the HEK293T cells were cultured in competent DMEM medium, and the cells were plated 24 hrs before transfection. Shortly before transfection, the culture medium was replaced with fresh DMEM containing 2% PBS. PEI-MAX was used as the transfection reagent. Transcription of the RPS-harboring transgene plasmids to generate the RNA genomes to be packaged occurred after the transfection into the infected cells. The supernatant was then collected at Day 2 and Day 5 post transfection, and the transfected cells were harvested on Day 5. The RAAV and control AAV particles were purified by using iodixanol density gradient ultracentrifugation.

3. Detection of Packaged Genomes

The purified RAAV and control AAV particles were first subjected to nuclease treatment, including DNase I and RNase I treatment, at 37° C. for 2 hours, in order to remove possibly existed nucleic acids outside the viral particles. Next, the nucleases and the RAAV or control AAV particles were denatured by proteinase K/SDS digestion at 65° C. for about 3 hrs to rupture the viral particles in order to release the genomes packaged therein. The nuclease-resistant polynucleotides containing the released viral genomes were then extracted and purified by phenol/chloroform extraction.

To detect the DNA genome titer of the control AAV and RAAV particles, Q-PCR was used to analyze the nuclease-resistant polynucleotides directly. A pair of WPRE primers (as set forth in the sequence tables below) specific for the WPRE sequence on the viral genomes was used in the Q-PCR to detect and quantitate any DNA genomes encapsidated in the control AAV or RAAV particles.

To detect the RNA genome titer of the control AAV and RAAV particles, any control AAV- or RAAV-encapsidated DNA genomes was removed by DNA removal through Dnase I digestion, before the encapsidated RNA genomes were subjected to reverse-transcription, and the resulting cDNA was used as Q-PCR templates for the detection and quantitation of WPRE sequences with the same pair of WPRE primers aforementioned. To detect and quantitate any potentially residual DNA that might be present due to the incomplete DNA removal, a sample after the DNA removal step was directly amplified (without reverse-transcription) using Q-PCR to detect the WPRE (DNA) sequence with the same pair of WPRE primers aforementioned, which was also used for all the other PCR reactions specific for WPRE sequence.

4. Comparison of Packaging Efficiency

When the conventional transgene plasmid containing the pssAAV-tdTomato construct (with wild-type ITRs on both ends) and the conventional packaging plasmid for AAV-DJ were used to produce the control AAV particles, the vast majority of the particles contained DNA genomes with the WPRE sequences. Very occasionally, RNA genomes were also packaged into the particles (see the bar labelled as "RNA," which was about 5 orders of magnitude lower than the bar labelled as "DNA"). The presence of residual DNA is comparable to that of RNA, which may be due to the inefficient digestion of packaged DNA genomes with DNase I before reverse-transcription.

Interestingly, when the recombinant packaging plasmid DJ-MCP (MCP fused to the N-terminus of Rep78 and 68 proteins) was used instead of DJ, the packaging of DNA genomes was slightly reduced (about 0.5 order of magnitude lower), but the pattern of viral genome distribution was almost the same, which DNA packaging was about 5 orders of magnitude higher than RNA packaging. This result indicated that fusing MCP to the N-terminus of Rep78/68 proteins did not significantly impair their natural functions (FIG. 8B).

Meanwhile, removing the ITRs from both ends of the pssAAV-tdTomato construct, leading to the CTWS construct, significantly abolished DNA packaging. The CTWS construct (ITR-free) produced about 4 orders of magnitude less of packaged DNA, and even less packaged RNA, no matter which packaging plasmid (DJ or DJ-MCP) was used.

Further, by adding one or three copies of the RPS (MS2) between the 3' of the WPRE and 5' of the SV40 polyA signal on the viral genomes without ITRs, the RAAV transgene plasmids, CTWMS and CTWM3S respectively, were obtained. In the absence of MCP, the CTWMS and CTWM3S constructs could barely be encapsidated as DNA or RNA genomes, just like the genome distribution pattern of CTWS. Surprisingly, the use of DJ-MCP as the packaging plasmid instead of DJ significantly reversed the packaging efficiency difference between DNA and RNA genomes, and the vast majority of the packaged genomes were RNA.

Compared to CTWS/DJ-MCP, the numbers of the packaged RNA genomes of CTWMS/DJ-MCP and CTWM3S/DJ-MCP were about 100- and 400-fold higher, respectively, whereas no significant difference was observed in the DNA-packaged number of the three. This result suggested that the MCP-Rep78/68 fusions could recognize the RPS, MS2, embedded in the RNA transcripts of the CTWMS and CTWM3S plasmids specifically and facilitate their RNA packaging into RAAV particles, and three copies of RPS in the CTWM3S construct provided an even better RNA packaging efficiency than one copy (FIG. 8B).

In conclusion, the introduction of the MS2/MCP pair into conventional AAV packaging system enabled the packaging of MS2-harboring RNA genomes into AAV particles in the presence of the MCP-Rep78/68 fusions, leading to the generation of RAAV particles. The undesired DNA packaging only constituted about 10% of the whole viral particle population produced by using CTWM3S/DJ-MCP.

In other words, the artificial/heterologous RNA packaging signal (RPS)—the MS2 sequence—can be used with its cognate binding protein MCP to replace the native DNA virus packaging signal pair (i.e., ITR and Rep), in order to dramatically boost the packaging efficiency of RNA into an otherwise DNA virus, while suppressing its inherent packaging of DNA into the same DNA virus.

Example 4 Enlarged Plasmid Backbone Reduced Undesired DNA Packaging of RAAV

This example demonstrates that increasing the backbone size of the AAV transgene plasmid by inserting a stuffer sequence into the backbone of the plasmid could reduce undesired DNA packaging into RAAV particles.

Although the CTWMS and CTWM3S constructs for RAAV particles in Example 3 did not have ITRs and no reverse packaging existed in the RAAV production, it was speculated that the relative small size (5-6 kb) of the RAAV transgene plasmids might still lead to undesired DNA packaging.

Figure 9A:
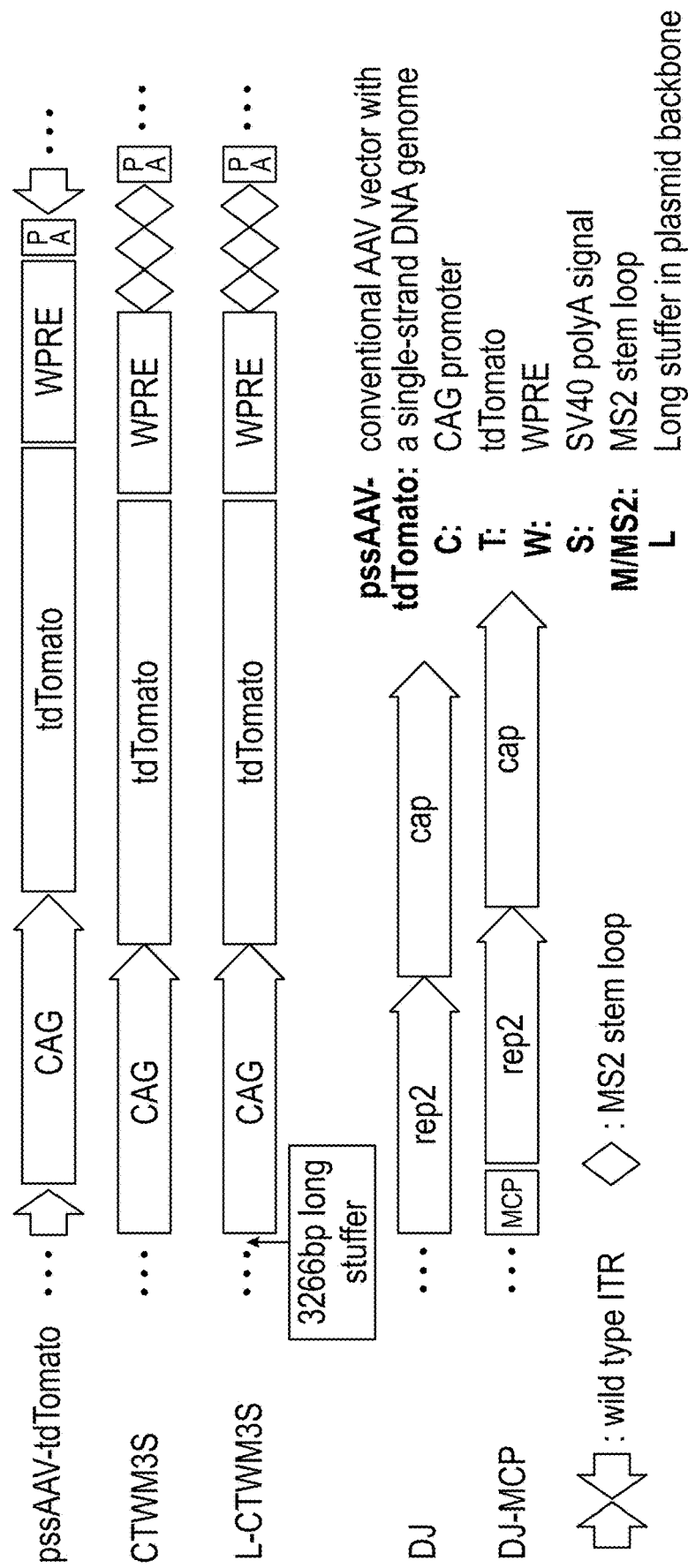
FIGS. 9A-9C show reduced DNA packaging using enlarged plasmid backbone.

Therefore, a 3266 bp non-coding sequence (stuffer sequence; see the sequence tables below) was inserted upstream of the tdTomato expression cassette of CTWM3S in order to increase the backbone length of the CTWM3S transgene plasmid, and the resulting construct was named L-CTWM3S. The schematic diagram of the plasmid is shown in FIG. 9A.

The conventional AAV genome construct, pssAAV-tdTomato, and the RAAV genome construct, CTWM3S, used in Example 3 were used as controls herein. In the same way as in Example 3, RAAV particles were produced by co-transfecting CTWM3S or L-CTWM3S transgene plasmid together with the packaging plasmid DJ-MCP and the helper plasmid into HEK293T cells, and the resulting RAAV particles were purified and the viral genomes were quantified. The same pair of WPRE primers were used to detect and quantitate any DNA and RNA genomes encapsidated in the AAV and RAAV particles, and an additional pair of CAG primers specific for the CAG promoter sequence in the viral genomes were used in Q-PCR to detect and quantitate any functional DNA (meaning DNA containing the CAG promoter sequence and able to express functional transgene proteins).

Figure 9B:
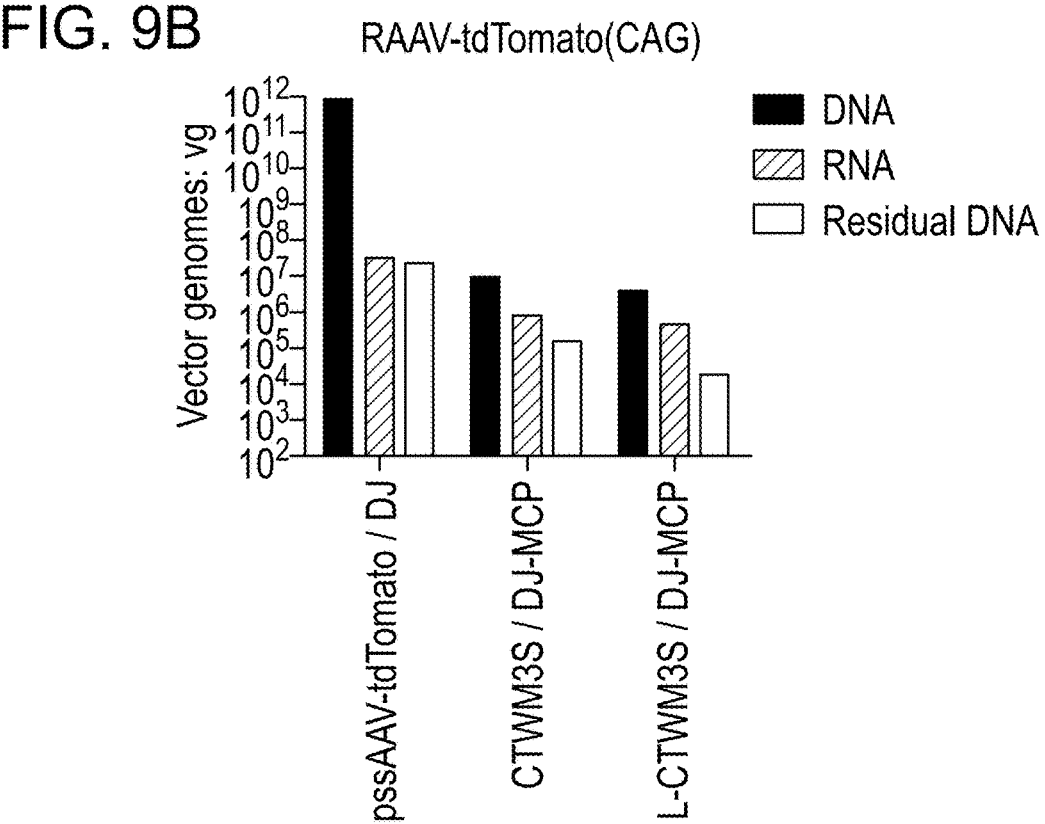

It was noted that the packaged RNA genomes cannot be detected with the CAG primers since they did not contain the CAG promoter, and the RNA columns on the drawings with CAG primers represented background RNA signals (see FIG. 9B).

Figure 9C:
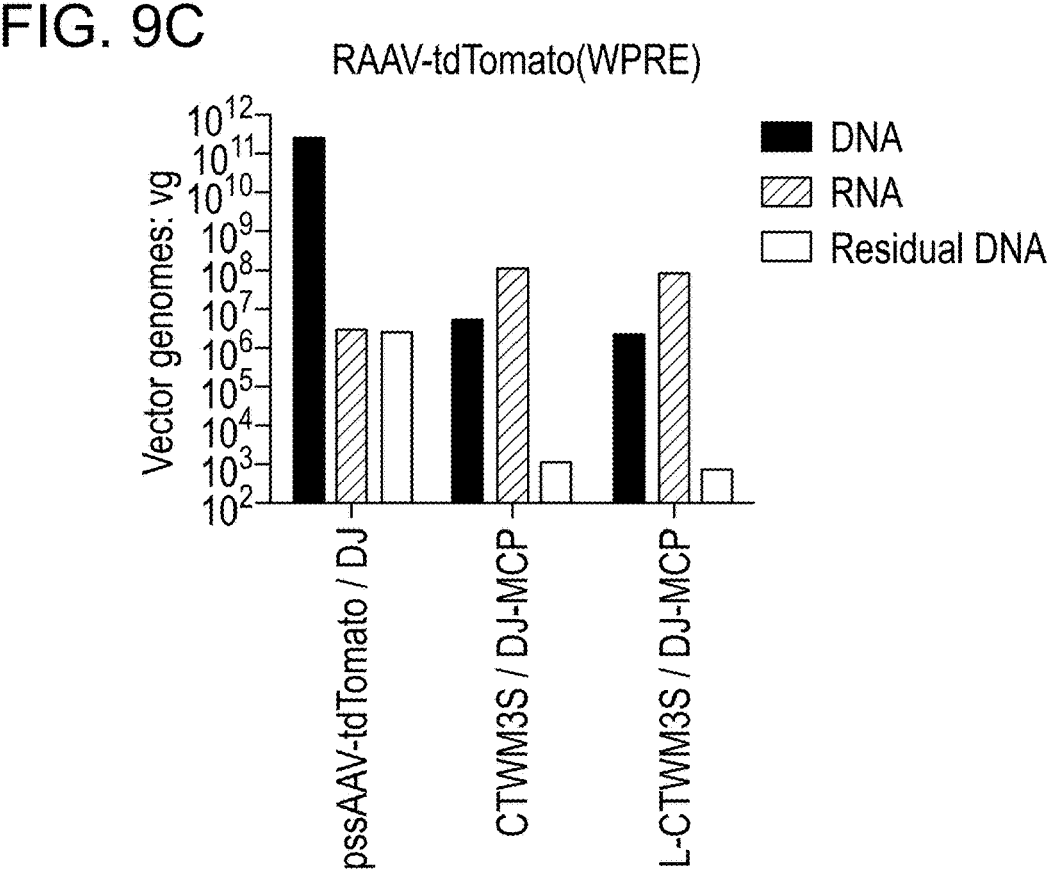

Surprisingly, the DNA genome titer of the L-CTWM3S group was about 2 times lower than that of the CTWM3S group, no matter which pair of primers was used in Q-PCR (see FIGS. 9B and 9C). The RNA genome titers of the CTWM3S and L-CTWM3S groups were substantially equivalent (see FIG. 9C). Since there is no CAG promoter sequence in the transcribed RNA from the CTWM3S and L-CTWM3S transgene plasmids, the packaged RNA genomes could only be detected with the pair of WPRE primers (FIG. 9C).

In conclusion, increasing the backbone length of the transgene plasmid could reduce undesired DNA packaging of the RAAV particles without interfering with their RNA packaging, showing that the deconstruction of the DNA packaging system and the establishment of the RNA packaging system in AAV particles are two separate lines, and this long-stuffer sequence was used to the RAAV transgene plasmids in the subsequent Examples.

Example 5 Using RAAV-MS2/MCP System for Additional Transgenes

In order to verify the general applicability of the RAAV-MS2/MCP system to additional transgenes, and to ensure that the observed RNA packaging is not a mere artifact associated with the reporter gene used, a series of AAV and RAAV transgene plasmids containing a Cre recombinase expression cassette were generated.

Conventional pssAAV-Cre (with the tdTomato coding sequence in the pssAAV-tdTomato construct in FIG. 8A replaced with a Cre coding sequence) and a corresponding L-CCWS construct (with the tdTomato coding sequence in CTWS in FIG. 8A replaced with the Cre coding sequence and inserted with the stuffer sequence in Example 4) were used as controls, with the second C standing for the Cre recombinase transgene. The L-CTWM3S construct in Example 4 was also redesigned as L-CCWM3S construct, after replacing the tdTomato coding sequence with the Cre coding sequence.

The Cre transgene plasmids were co-transfected with the packing plasmid DJ or DJ-MCP, and together with the helper plasmid in HEK293T cells, respectively, to produce AAV and RAAV particles. The resulting viral particles were purified, and the viral genomes were quantified as described in Example 3.

The same viral genome distribution results as AAV-tdTomato and RAAV-tdTomato were achieved for AAV-Cre and RAAV-Cre. For pssAAV-Cre, most viral particles contained DNA genomes, and the DNA genome titer was about 4-5 orders of magnitude higher than that of RNA genomes. For L-CCWS, DNA and RNA genomes were barely encapsidated, due to the lack of both DNA and RNA packaging signals. For L-CCWM3S, RNA packaging was significantly improved with DJ-MCP by about 200-fold compared to that of L-CCWS/DJ-MCP, and the undesired DNA-harboring viral particles only constituted about 1% of the whole viral particle population (FIGS. 10A and 10B).

Since the DJ-MCP fusion not only assisted the RNA packaging but also retained the DNA packaging ability, its performance was also assessed in a construct containing both DNA packaging signals (ITRs) and RNA packaging signals (3 copies of MS2) designated as pssAAV-Cre-MS2X3, which was constructed by inserting 3 copies of MS2 in-between WPRE and SV40 polyA of the pssAAV-Cre construct. The results showed that in the absence of MCP, most viral particles contained packaged DNA genomes, and only a negligible amount of RNA genomes was packaged with or without the RNA packaging signals. The RNA packaging was remarkably improved when DJ-MCP was used instead of DJ as the packaging plasmid in combination with the RNA binding signals, and surprisingly, the increased RNA packaging did not significantly interfere with the DNA packaging of the pssAAV-Cre-MS2X3 construct (FIG. 11B). In another view, it was also demonstrated that the introduction of the MS2/MCP pair could significantly increase RNA packaging even without removing the DNA packaging signal-ITRs, indicating that the deconstruction of the DNA packaging system and the establishment of the RNA packaging system in AAV particles are two separate lines and the removal of ITRs is not the essential basis for the increased RNA packaging by the introduction of RPS/RBP pair.

In conclusion, the subject RAAV-MS2/MCP system can be applied to any transgenes in general, such as the Cre recombinase as demonstrated above. Interestingly, the RAAV-Cre construct produced a better yield than that of the RAAV-tdTomato construct. While not wishing to be bound by any particular theory, this may be due to the simpler secondary structure of the Cre mRNA comparing to the tdTomato mRNA, based on online RNA secondary structure prediction such as that found at rna.tbi.univie.ac.at/cgi-bin/RNAWebSuite/RNAfold.cgi.

Example 6 Optimization of RAAV Production System and Identification of the Properties of Optimized RAAV Particles The endonuclease activity of the Rep68 and Rep78 proteins (Rep68/78) is essential for the DNA genome replication during the conventional DNA packaging of AAV particles. Without the functional trs-endonuclease, the newly-synthesized viral ssDNA cannot be released for packaging. It was investigated in this Example whether the undesired DNA packaging of RAAV particles could be further reduced by disrupting the activity of the trs-endonuclease.

To investigate this, three trs-endonuclease negative mutants were constructed, namely DJ-MCP (Y156F, wherein the Y156F mutation was in the common sequence of Rep68 and Rep78 proteins, i.e., Rep68-Y156F and Rep78-Y156F), DJ-MCP (KDE-mu) and DJ-MCP (EKE-mu) (see the sequence tables below).

The DNA and RNA packaging efficiencies for DJ-MCP (Y156F) were firstly assessed with the transgene plasmid, pssAAV-Cre-MS2X3 containing both the DNA and RNA packaging signals, as described in Example 5. DJ and DJ-MCP were set as packaging plasmid controls. Viral particles were produced, purified, and titrated as described in Example 3.

The results demonstrated that the Y156F mutation in DJ-MCP significantly reduced the ITR-mediated DNA packaging for pssAAV-Cre-MS2X3 without interfering with the RNA packaging.

Figure 13A:
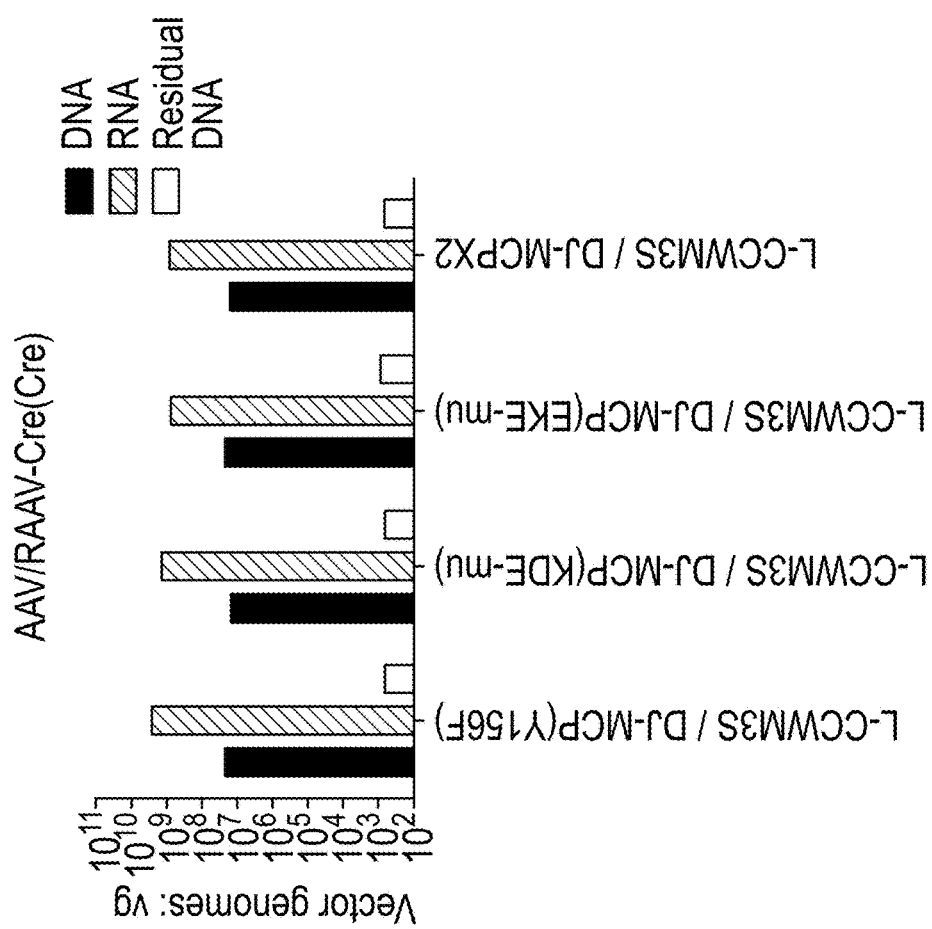
FIGS. 13A and 13B show results of reducing DNA packaging of AAV and RAAV.

Therefore, in addition to the removal of DNA packaging signals ITR as shown in the previous Examples, modifying, for example, mutating the functional proteins like Rep78/68 proteins participating in the DNA packaging process to weaken or eliminate their DNA-packaging-associated functions could serve as another strategy to reduce or inhibit the conventional DNA packaging of AAV particles (FIG. 13A).

Then, L-CCWM3S in Example 5 was used as a RAAV transgene plasmid to provide viral genomes in place of pssAAV-Cre-MS2X3. The DJ-MCP, which was trs-endonuclease positive, was used as a control against DJ-MCP (Y156F). Viral particles were produced, purified, and titrated as described in Example 3. Two pairs of primers were used here to titrate viral genomes, one pair for targeting WPRE sequence as above and one pair (see sequence tables below) for targeting the 5' terminus of the Cre coding sequence.

The results showed that the Y156F mutation in Rep78/68 protein not only reduced the undesired DNA packaging by about 10-fold, but also increased the desired RNA packaging by about 50%. The patterns of the packaging efficiency difference between the packaged DNA and RNA genomes were substantially the same for both pairs of primers (i.e., WPRE primer pairs and Cre primer pairs) used in Q-PCR (FIGS. 12A-12B).

Figure 13B:
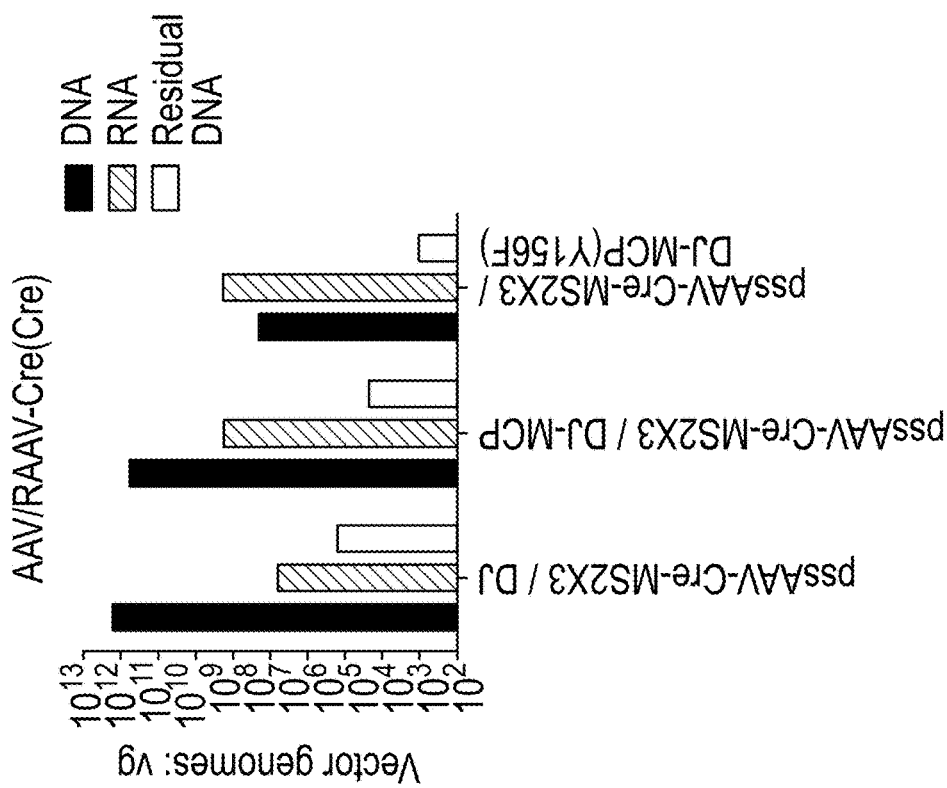

Two other trs-endonuclease mutants, DJ-MCP (KDE-mu) and DJ-MCP (EKE-mu), were also tested, and were demonstrated to have the same ability to reduce undesired DNA packaging as DJ-MCP (Y156F), but only DJ-MCP (Y156F) showed improved RNA packaging (FIG. 13B).

It was further demonstrated that fusing two copies of MCP to the N-terminus of Rep 78/68 proteins (MCPx2-Rep78 and MCPx2-Rep68) could also achieve the result of reducing undesired DNA packaging (FIG. 13B).

Figure 12D:
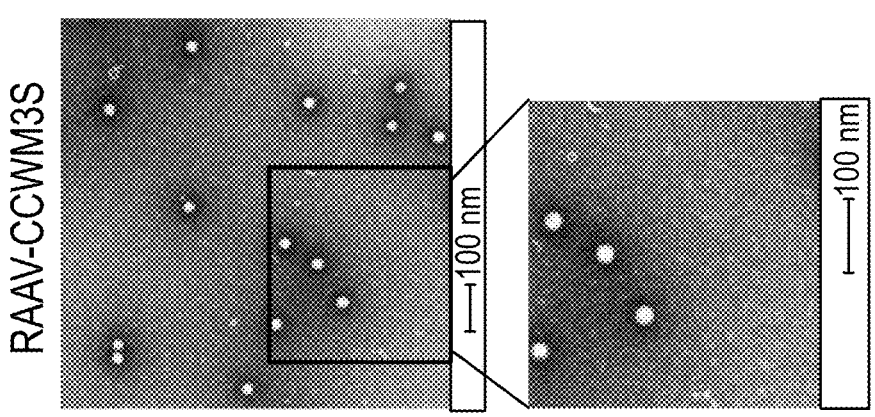
Figure 12C:
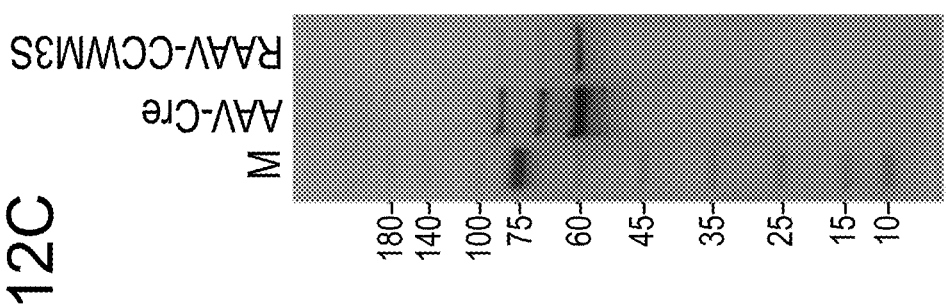

The compositions of the AAV and RAAV particles were analyzed by silver-stained SDS-PAGE, and the RAAV capsids were also composed of three VP proteins (VP1, VP2 and VP3) with a similar VP1/2/3 ratio to conventional AAV particles (FIG. 12C).

In order to analyze the morphology of the RAAV particles, 10 μL of the purified AAV and RAAV particles were placed on a 300 μm carbon-over-Pioloform-coated copper grid and incubated for 2 min. at room temperature. The excess of the sample was blotted with filter paper and immediately replaced by 10 μL of staining agent (3% phosphotungstic acid), which was allowed to settle for 2 min and then blotted again. Visualization of the samples was performed by using a Talos L120C transmission electron microscope. The RAAV particles were morphologically similar to the conventional AAV vectors, where full viral particles encapsidating genomes were viewed as 25-nm solid spheres, and empty viral particles without genomes encapsidated were 25-nm donut-like structures (FIG. 12D).

In conclusion, the mutation of functional proteins including Rep proteins participating in the DNA packaging process of AAV production to weaken or eliminate their DNA-packaging-associated functions in combination with the removal of DNA packaging signals, ITRs, is an optimized strategy to reduce or inhibit undesired DNA packaging of RAAV particles. The produced RAAV particles have similar compositions and morphology to the conventional AAV particles.

Example 7 RAAV Vectors Expressing Functional Proteins

This Example demonstrated that the subject RAAV vectors were infectious and can be used as gene delivery vectors.

Cre-loxP system, a highly sensitive system, was used for investigating the infectivity of the inventive RAAV vectors. Mouse embryonic fibroblast (MEF) cells isolated from homo-Ai9 (bearing loxP-tdTomato-reporter system) mice were incubated with the purified AAV (pssAAV-Cre/DJ) or RAAV (L-CCWM3S/DJ-MCP (Y156F)) vectors in Example 5 overnight, and Multiplicity of Infections (MOIs) (the number of virions added per cell during infection) were set, including 7 MOIs for conventional AAV vectors and 3 MOIs for RAAV vectors. The dominant genome titer quantified by detecting Cre coding sequence with the 5'-terminus Cre primers aforementioned was used as the infection titer. In other words, the DNA genome titer was used for the conventional AAV vectors, and the RNA genome titer was used for the RAAV vectors.

Specifically, Ai9-MEF cells were plated into 48-well plates in about $5 \times 10^4$ cells per well about 24 hrs before infection. AAV vectors or RAAV vectors were mixed completely with 0.5 mL of DMEM containing 2% FBS. The culture medium of the plated cells was removed, and then the cells were incubated with mixed AAV or RAAV vectors overnight at 37° C. The infected cells were collected at different time points and subjected to RNA and DNA analysis. A pair of primers targeting the 5'-terminus of Cre-coding sequence as aforementioned was used for detecting the specific Cre-coding DNA and mRNA derived from the vectors. Fluorescence photos were taken daily post infection (p.i), and the fluorescence-positive cells were quantified by flow cytometry 5 days p.i.

Figure 14C:
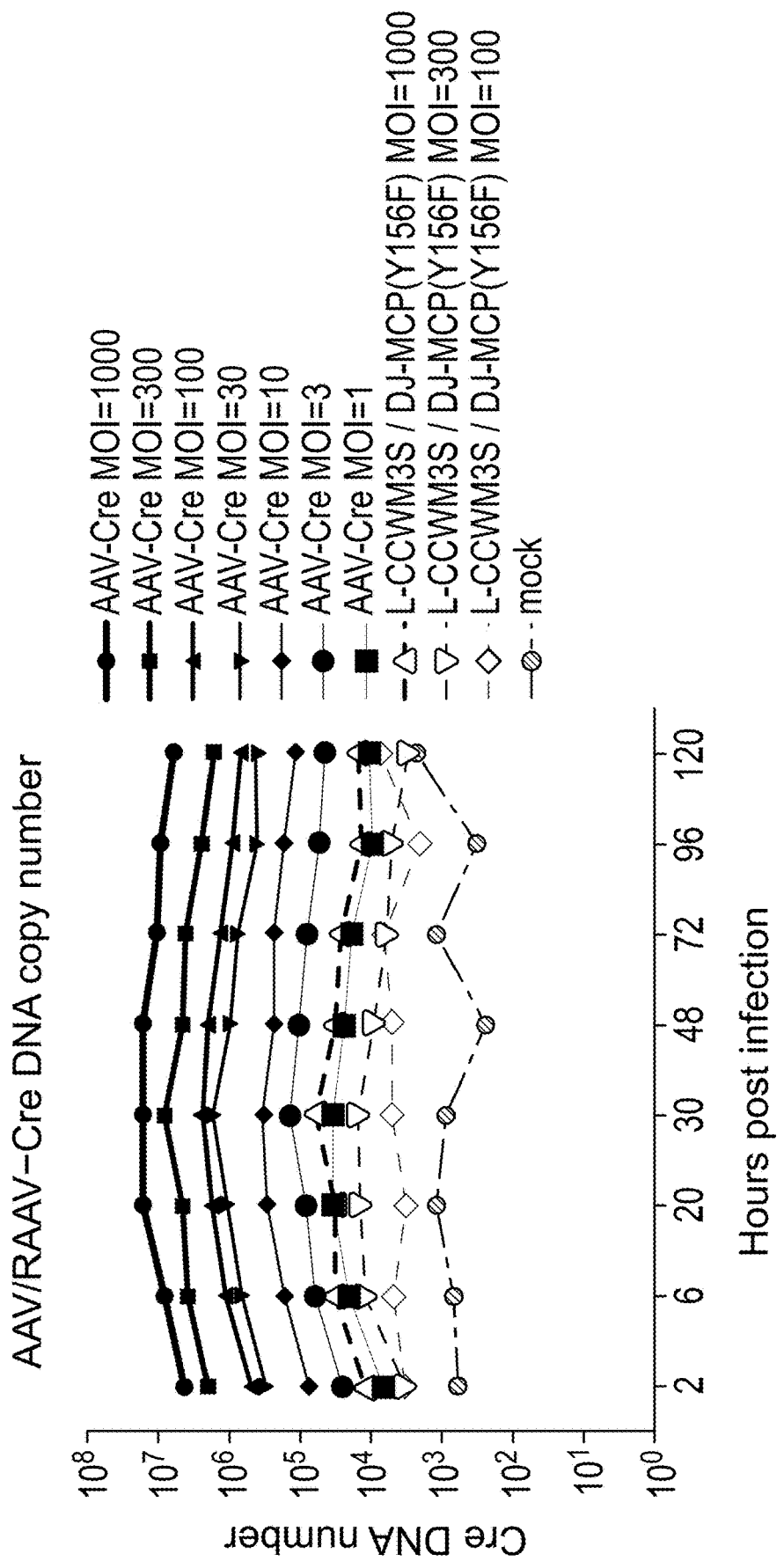
Figure 15B:
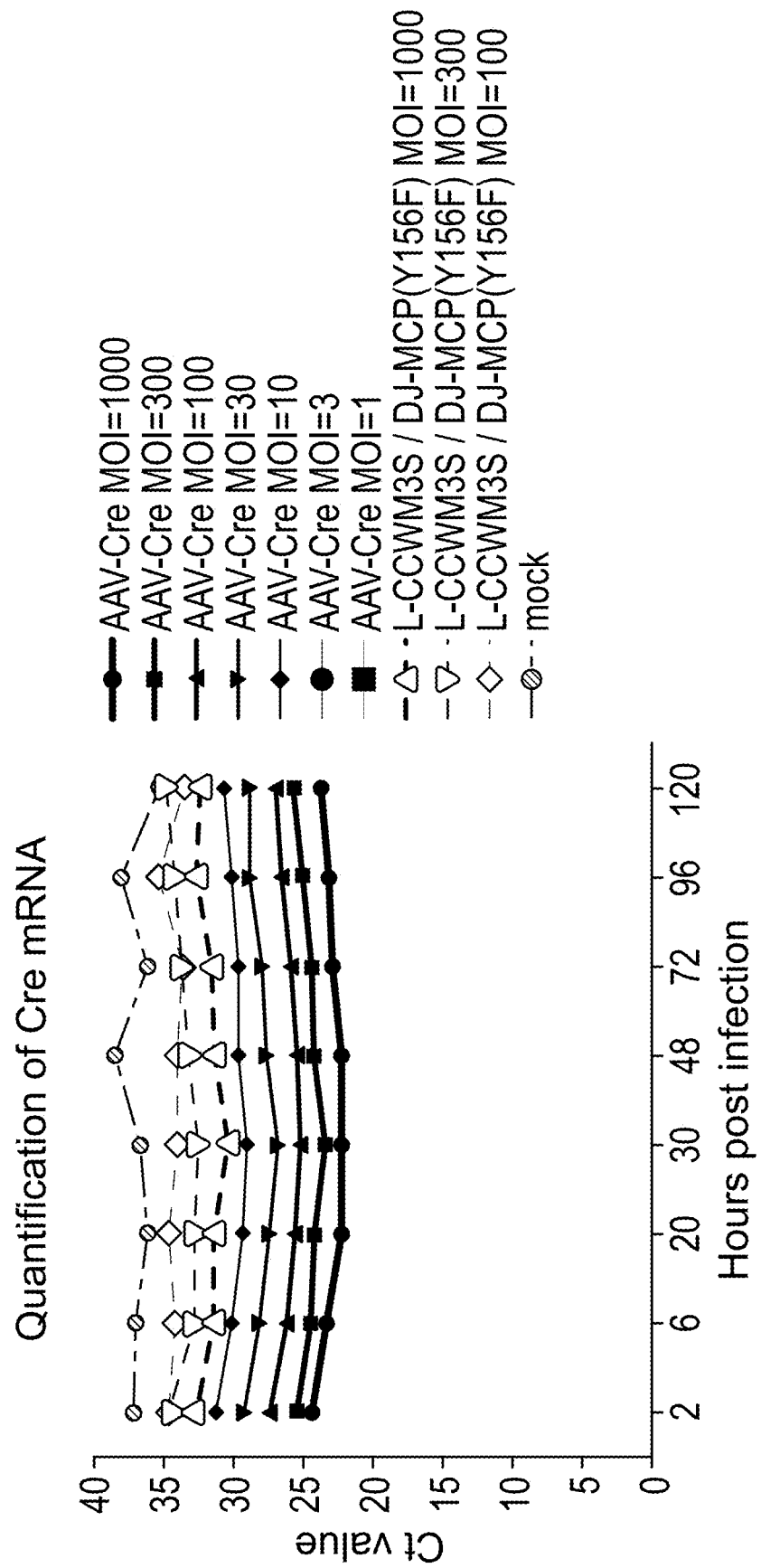
Figure 15C:
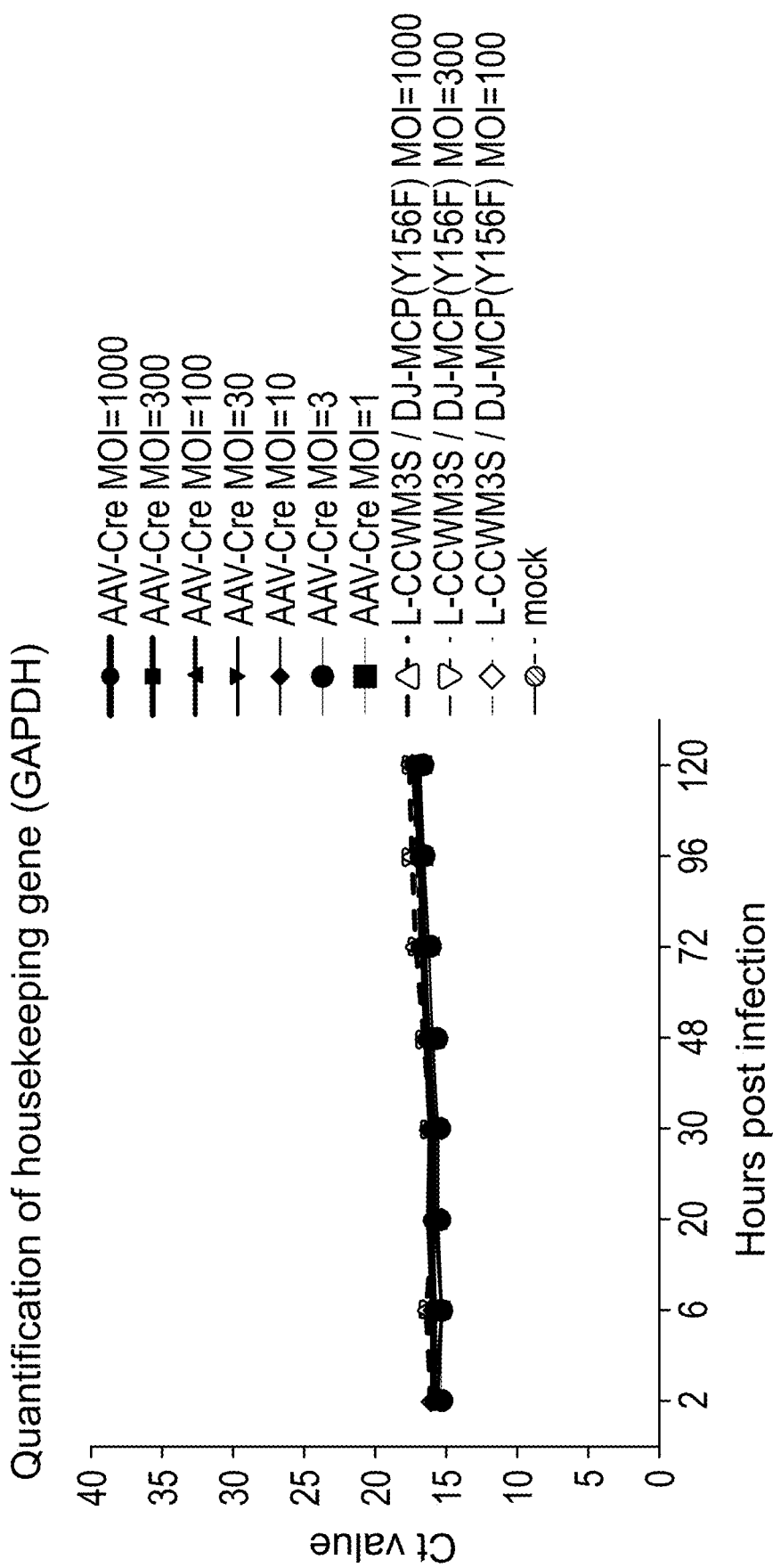

The mRNA analysis results showed that the specific mRNA was detected in the RAAV-infected cells as early as 2 hrs p.i, peaked at 6 hrs p.i, and then decreased. In the cells infected with the conventional AAV vectors, no apparent transcription was detected at 2 hrs p.i, but a rapid increase of transcribed mRNA was observed from 6 hrs to 20 hrs p.i, reaching a plateau at 30 hrs. In contrast to the results for the RAAV vectors, the mRNA level in the cells infected with the conventional AAV vectors did not decrease after reaching the plateau. The copy numbers of the Cre mRNAs were positively correlated with MOIs in all the samples (FIGS. 14A-14B and FIG. 15A). Meanwhile, mGAPDH mRNA was tested as a reference transcript (housekeeping gene), and as expected, there was no difference in mGAPDH mRNA levels among all the samples (FIG. 15C).

The DNA results were quite different from the mRNA results. Conventional AAV and RAAV vectors had substantially the same DNA copy number pattern, the majority of DNA genomes was detected in the infected cells as early as 2 hrs post infection, and then a slight increase followed from 2 hrs to 20 hrs p.i, which was very similar to the trend of the mRNA levels in the RAAV-infected cells. After that, the DNA level reached a plateau or descended slowly. The copy numbers of the Cre DNA were also positively correlated with MOIs in all the samples, but much lower numbers of the Cre DNA were detected in the RAAV-infected cells (the DNA copy number of RAAV-CCWM3S MOI=100 or 300 group was less than that of AAV-Cre MOI=1 group, and the DNA copy number of RAAV-CCWM3S MOI=1000 group was less than that of AAV-Cre MOI=3 group) (FIG. 14C and FIG. 15B). Similarly, the DNA level of another housekeeping gene 36B4 was quantified as a reference gene, and as expected, no obvious difference in the DNA levels was observed among all the samples (FIG. 15D).

Figure 14D:
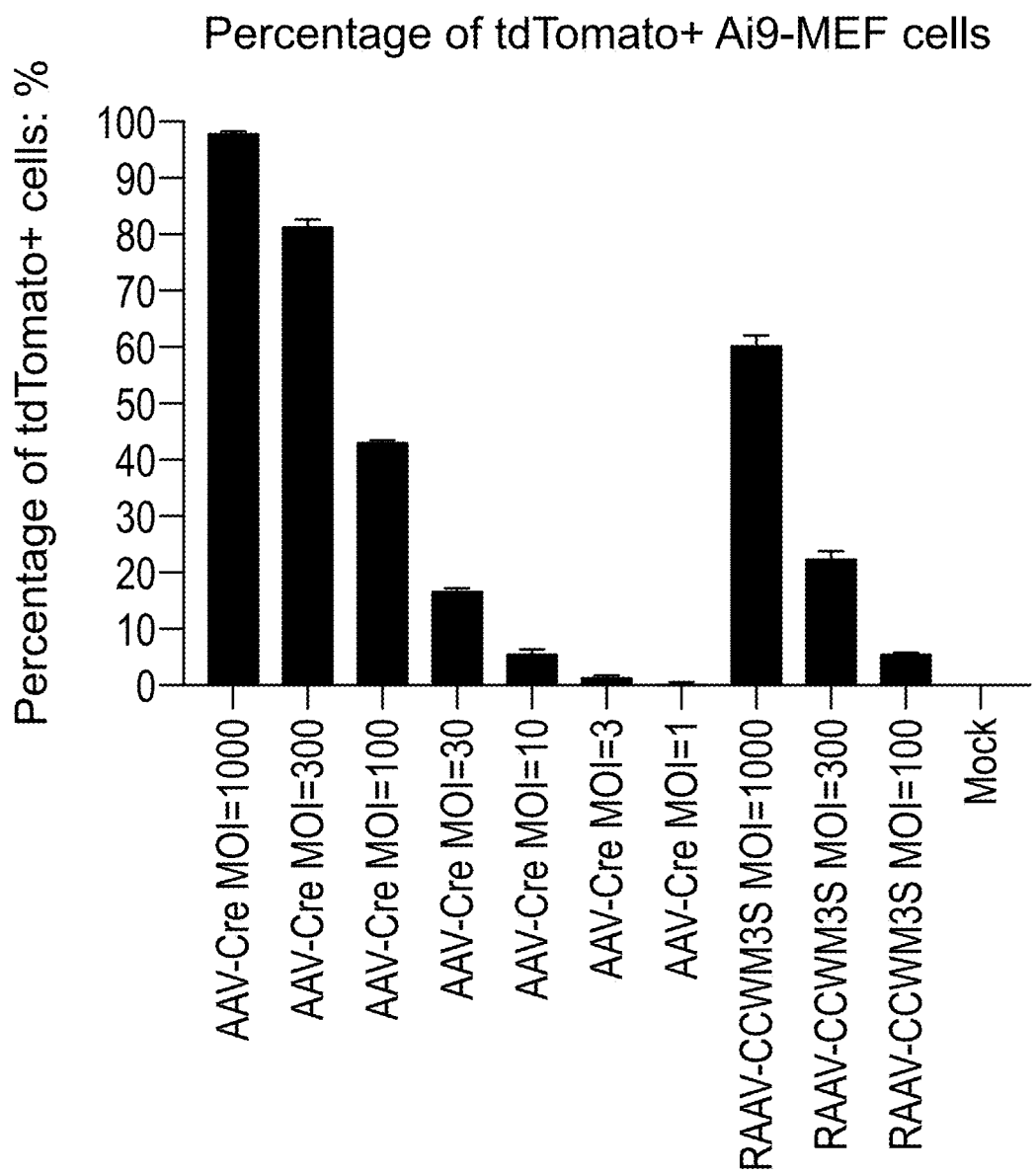
Figure 16:
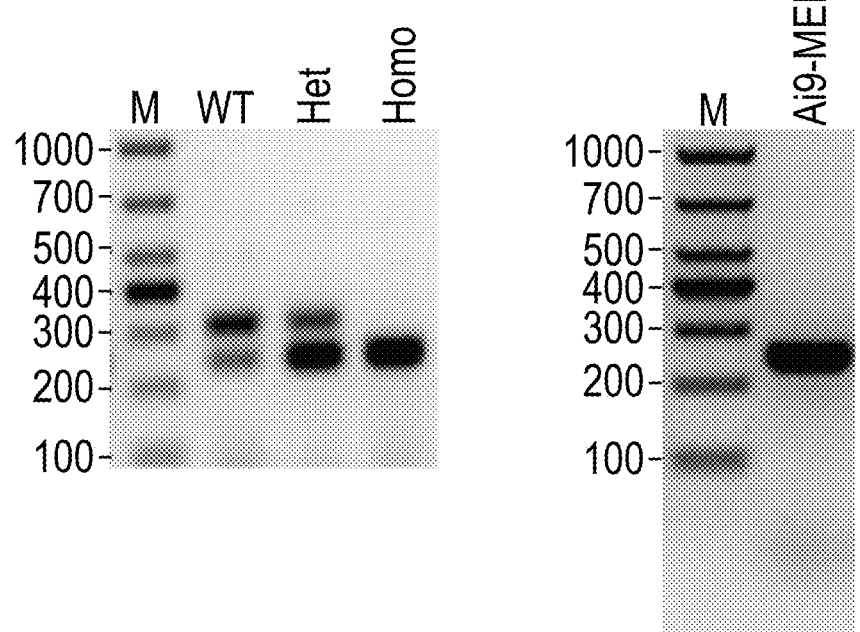
FIG. 16 shows genotype identification of Ai9-MEF cells.

Successful infection of AAV-Cre or RAAV-CCWM3S vectors would lead to the expression of functional Cre recombinase and rescue the tdTomato expression in Ai9-MEF cells, and thus the fluorescence photos of the infected cells were taken and analyzed to assess the infectivity of the viral vectors by counting cells emitting tdTomato red fluorescence. The results showed that the number of fluorescence-positive cells generated by RAAV-CCWM3S was comparable to that generated by AAV-Cre with a 10-fold lower MOI (FIG. 14D). The lower fluorescent intensity of tdTomato in the RAAV-infected cells was possibly due to the short lifetime of the Cre mRNAs delivered thereinto and the inability of the limited amount of the translated Cre recombinase to rescue both of the two copies of tdTomato expression cassettes in the homo-Ai9-MEF cells (FIG. 16).

By comparing the results of the DNA titer and cytometric data, it was indicated that the majority of the tdTomato red fluorescence signals in the RAAV-CCWM3S infected cells were generated by the Cre mRNA-harboring RAAV particles.

In conclusion, the inventive RAAV vector could deliver functional Cre mRNAs into cells and express functional Cre recombinase.

Example 8 In Vitro Transient Transfer of Functional Gene by RAAV Particles into Cells To determine the exact lifespan of the Cre protein produced via AAV-Cre or RAAV-CCWM3S delivery as in Example 7, Ai9-MEF cells were seeded 24 hrs before infection at a cell confluence of $5 \times 10^4$ cells per well, and then incubated with AAV-Cre (MOI=300) or RAAV-CCWM3S (MOI=10,000) vectors overnight as described above. After infection, cells were collected at several time points, and fluorescence photos were taken prior to the cell collection.

Figure 17A:
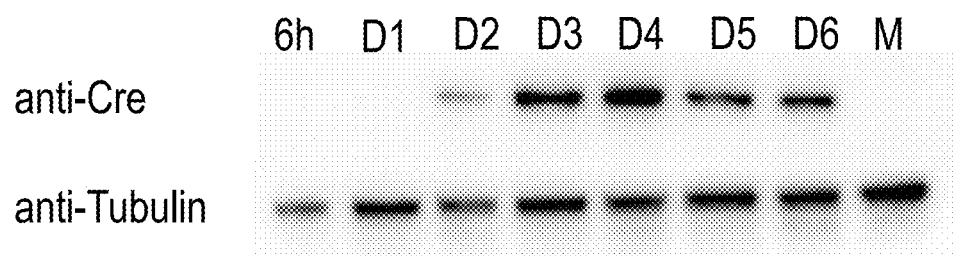
FIGS. 17A-17B show transient transfer of RAAV particles.
Figure 17B:
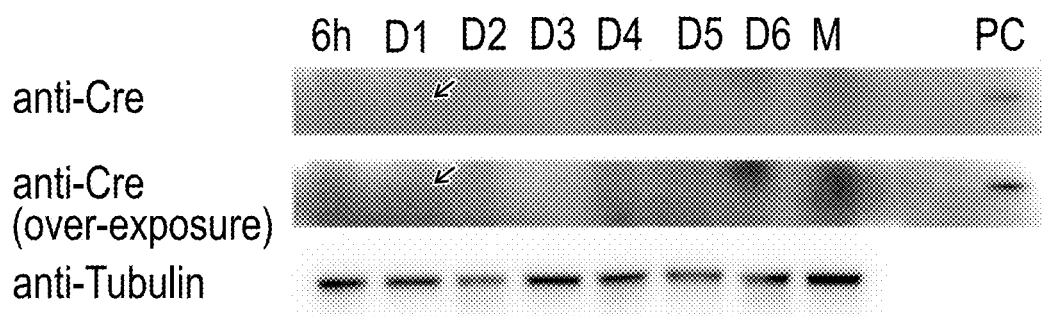

For AAV-Cre, Cre expression increased during the first 4 days, but then decreased. By contrast, a small amount of Cre was detected at as early as about 24 hrs after RAAV-CCWM3S transfer and disappeared after Day 2. This quick expression and degradation phenomenon may be due to the instant appearance and short lifetime of the delivered functional Cre mRNA (FIGS. 17A and 17B).

Example 9 In Vivo Transient Transfer of Functional Gene by RAAV Particles into Ai9-Mouse This example demonstrates that the RAAV particles can be used as a tool for in vivo gene delivery and to express the functional Cre recombinase transiently.

To investigate the infectivity of RAAV particles in vivo, Ai9-Mice (2.5-4 months old) were anesthetized and injected with 1 µL AAV-Cre (pssAAV-Cre/DJ) (high dose: 1E9 vg/mouse; low dose: 3E6 vg/mouse) or 1 µL RAAV-Cre (L-CCWM3S/DJ-MCP (Y156F)) (1E9 vg/mouse) into the right hippocampus according to the following coordinates: anteroposterior (A/P)=−1.7 mm, mediolateral (M/L)=−1.0 mm, dorsoventral (D/V)=−2.1 mm. Also, AAV capsid-DJ was used in this assay as a control.

Six weeks after AAV or RAAV injection, mice were anesthetized and transcardially perfused with PBS at room temperature at pH 7.4 and then with freshly prepared, ice-cold 4% paraformaldehyde (PFA) in phosphate buffers (PB). The brains were post-fixed in 4% PFA overnight. The fixed brains were embedded with OCT for frozen section after dehydration. Brains were sectioned in 20 µm thickness using a freezing microtome (Leica CM1950), and the sections were mounted to slides directly. The slides were baked at 60° C. for 1-2 hours followed by blocking with 5% BSA serum in PBS for 1 h. Subsequently, the slides were incubated with the primary antibody against Cre (10536; Cell Signaling Technology; 1:800 dilution) in 5% BSA in PBS (0.1% Triton-X) overnight at room temperature. After five washes with PBS, the slides were incubated in 1% BSA in PBS containing secondary antibody against the primary antibody and DAPI (D3571, Invitrogen). The secondary antibody used was Alexa Fluor 488 donkey anti-rabbit IgG (711-545-152, Jackson ImmunoResearch) (at 1:1000 dilution). Images were acquired with Nikon C2si+ Confocal Microscope.

The acquired images showing fluorescence from tdTomato expression system demonstrated that RAAV-Cre infected the cells in Ai9-mice hippocampus and rescued the expression of tdTomato. The number of the infected cells in the RAAV-Cre group was less than that of the AAV-Cre group at the same dose. However, the RAAV-Cre infection generated much more tdTomato positive cells relative to the low-dose group (30-fold lower dose) of AAV-Cre infection.

Very interestingly, the Cre expression was easily detected in both the high-dose and low-dose groups of AAV-Cre infection, but no significant Cre expression was detected in the RAAV-Cre infected cells despite of the detected tdTomato fluorescence proving the once existence of Cre.

Figure 21A:
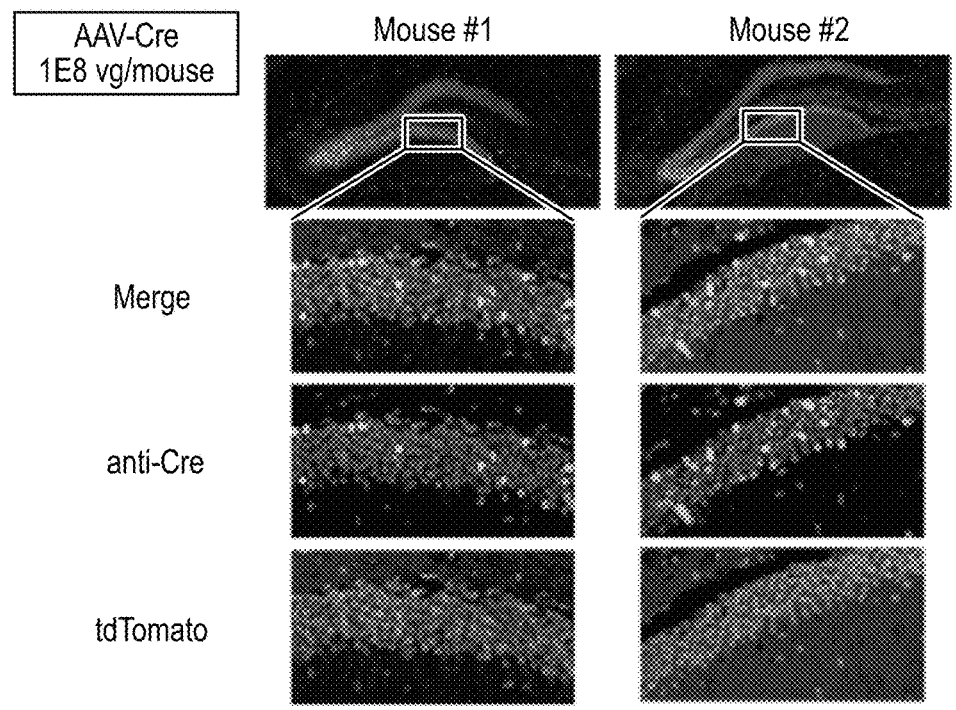
FIGS. 21A-21C show results of transient transfer of RAAV-Cre into the hippocampus of Ai9-Mice.
Figure 21B:
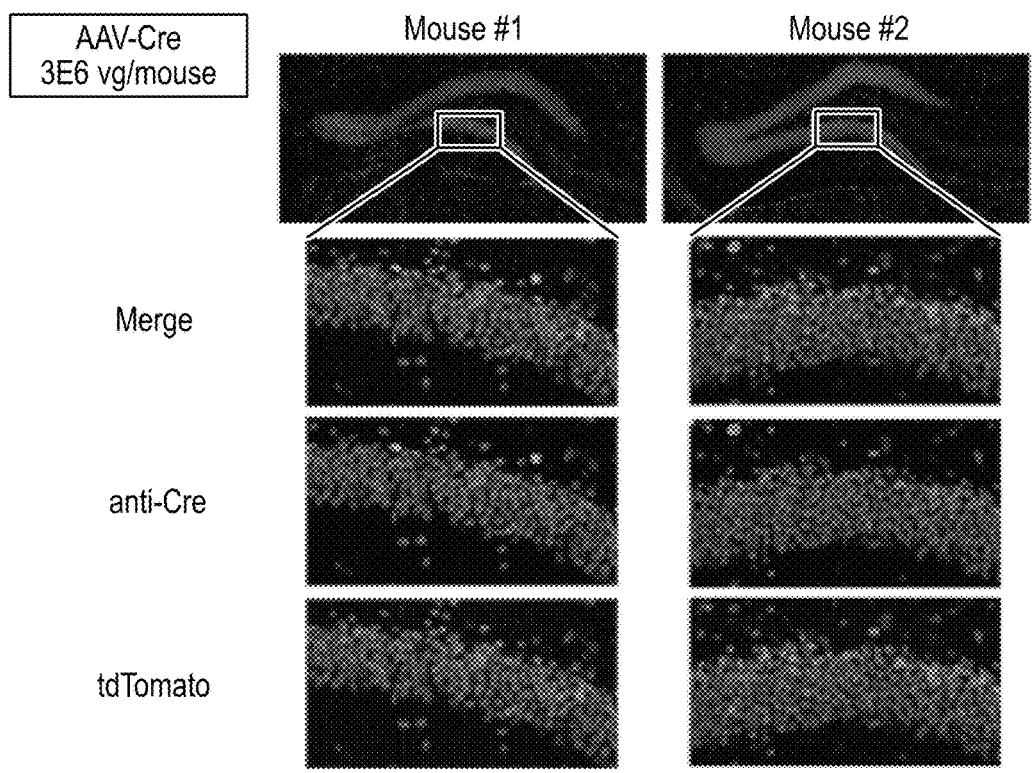
Figure 21C:
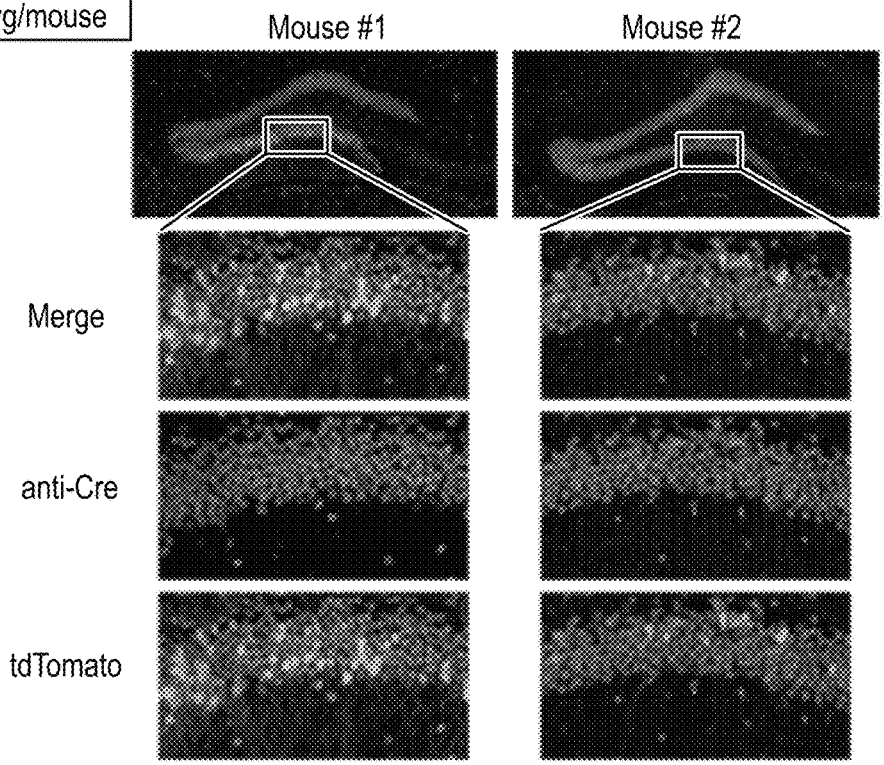
Figure 21D:
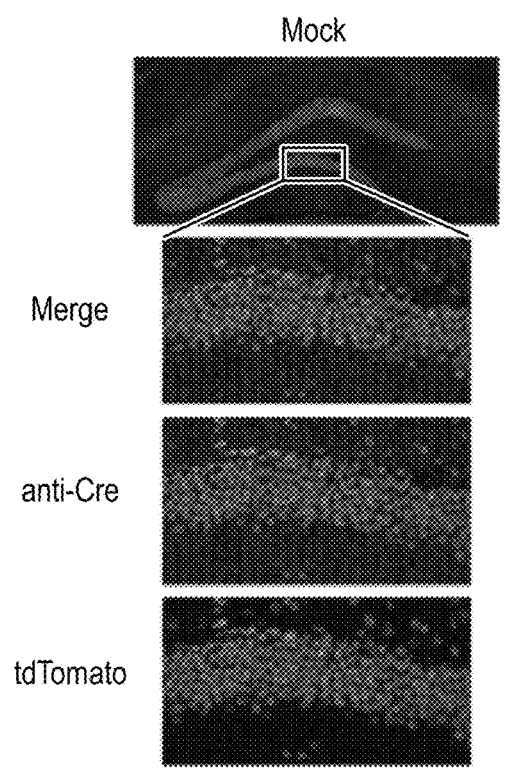
FIG. 21D shows the results in a control mouse. Red signal: tdTomato; Green signal: Cre; Blue signal: DAPI (nuclei stationing).

Overall, the RAAV-Cre had an inferior transduction efficiency compared to the conventional AAV-Cre as shown by the fluorescent photos (positive cell counts) for the two at the same high dose of 1E9 vg/mouse (FIG. 21A vs. FIG. 21C), since multiple mRNAs for protein translation can be transcribed from one successfully transduced AAV DNA genome. To further evaluate the Cre expression levels, the transduction efficiency of the AAV-Cre was normalized to that of the RAAV-Cre by reducing the high dose of AAV-Cre of 1E9 vg/mouse to a low dose of 3E6 vg/mouse (FIG. 21B), and the results showed that although the RAAV-Cre had a superior transduction efficiency to the low dose group of AAV-Cre as shown by the fluorescent photos (positive cell counts), no Cre expression was detected in the RAAV-Cre infected cells as compared with the AAV-Cre group, which indicated that the Cre expression in RAAV-Cre group was transient but functional.

Example 10 Additional RPS/RBP Pairs for RAAV System

In addition to the MS2/MCP pair used in Examples 3-8, two additional pairs of RNA aptamer/aptamer-binding proteins (or RNA packaging signal/RNA binding protein, "RPS/RBP" herein) were tested for RAAV packaging: (1) PP7 binding site/PP7 bacteriophage coat protein ("PP7/PCP," or "PCP" or "P" for short, or "P" in L-CCWP3S) and (2) Com binding site/phage COM protein ("com/COM," or "COM" for short, or "C" in L-CCWC3S). Unlike MS2/MCP and PP7/PCP that are natural viral packaging systems, com/COM is not a natural viral packaging system but known to be transcription regulators that play roles in the transcription initiation of the bacteriophage Mu mom gene.

Transgene plasmids harboring three copies of RPS (L-CCWP3S and L-CCWC3S) and their corresponding packaging plasmids [DJ-PCP (Y156F) with PP7 bacteriophage coat protein (PCP) fused to the N-terminus of Rep78-Y156F and Rep68-Y156F and DJ-COM (Y156F) with phage COM protein (COM) fused to the N-terminus of Rep78-Y156F and Rep68-Y156F] were constructed. Viral particles were produced, purified, and titrated as described in Example 3.

The results showed that similar to the MS2/MCP pair well demonstrated in various aspects in Examples 3-8, the two pairs of PP7/PCP and com/COM also led to the remarkable RNA packaging of RAAV particles (FIG. 18), thereby expanding the scope of various RAAV packaging system.

Example 11 Application of RAAV System to Various AAV Serotypes

To investigate the application of the inventive RAAV packaging system to various AAV serotypes in addition to AAV-DJ tested in Examples 3-9, two pairs of RPS/RBP (MS2/MCP and com/COM) were examined in AAV-DJ and another three different AAV serotypes (AAV5, AAV8 and AAV9). Viral particles were produced, purified, and titrated as described in Example 3.

Both RAAV-MS2/MCP and RAAV-com/COM system worked well in all the four serotypes, suggesting the general applicability of the RAAV packaging systems to different AAV serotypes (i.e., not limited to AAV-DJ). In the presence of the RBP, Cre RNA genomes containing the corresponding RPS were efficiently encapsidated into the respective RAAV particles. Though the yields of the RNA-packaged RAAV particles varied from serotype to serotype, all of the RAAV5, RAAV8 and RAAV9 particles had a higher productivity than RAAV-DJ (FIG. 19).

Example 12 AAP and MCP Fusion Protein Increased RAAV Yield

Generally, AAV encodes a unique assembly-activating protein (AAP) within their natural viral genomes that is essential for capsid assembly. Specifically, AAP was found to be essential for capsid protein stabilization and generation of functional AAV particles.

An AAP-MCP (with MCP fused to the C-terminus of AAP) or MCP-AAP (with MCP fused to the N-terminus of AAP) fusion protein expression cassette was inserted inversely into the backbone of the packaging plasmid DJ-MCP (Y156F) used in Examples 6-10, and the resulting constructs were named DJ-MCP (Y156F)-AM and DJ-MCP (Y156F)-MA, respectively. Such constructs then expressed both MCP-Rep78/68 (Y156F) fusion and AAP-MCP or MCP-AAP fusion, increasing the amount of RNA binding proteins (RBPs) assisting in RNA packaging compared with MCP-Rep78/68 fusion alone. Viral particles were produced, purified, and titrated as described in Example 3.

Figure 20B:
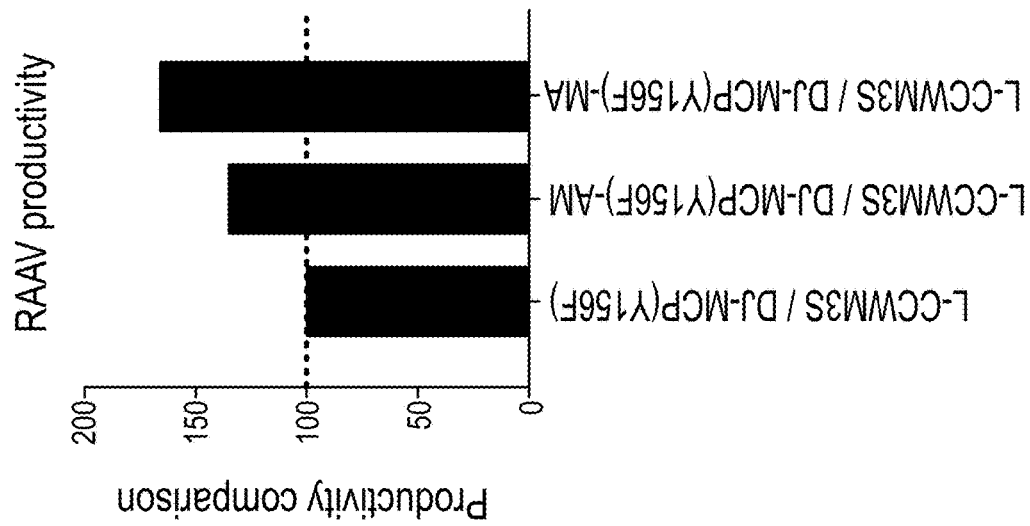
FIGS. 20A and 20B shows that additional AAP and MCP fusion proteins increased RAAV yield.
Figure 20A:
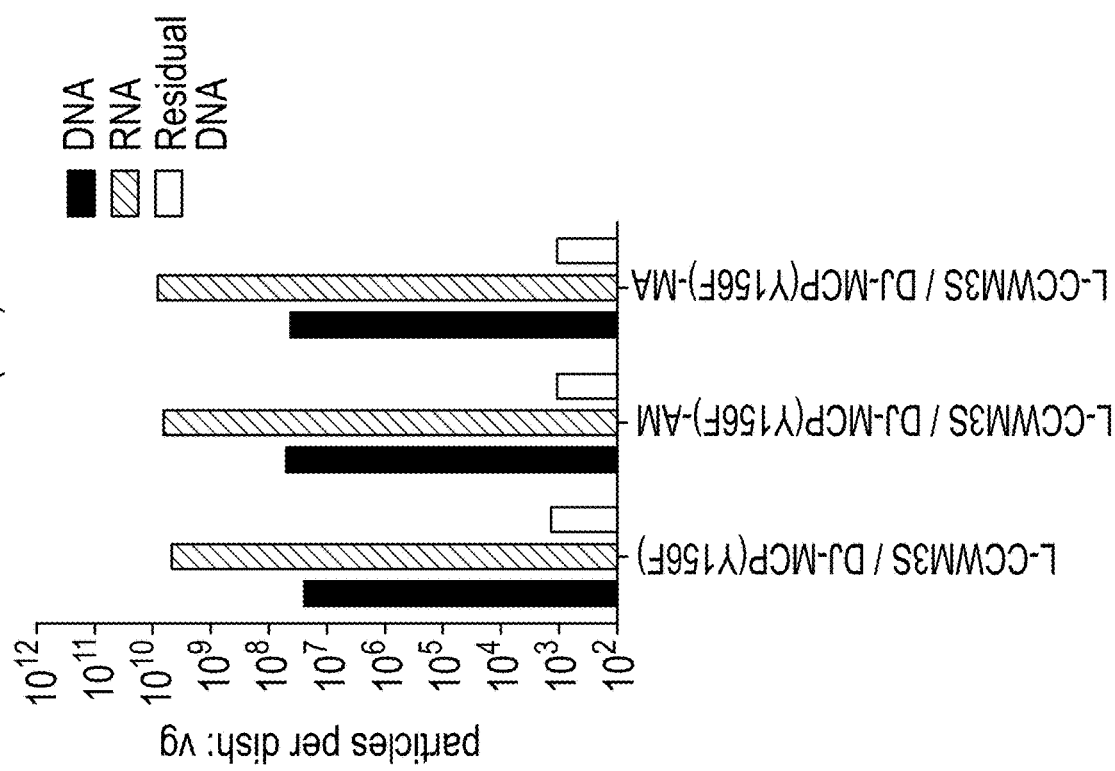

The results showed that the yields of RNA-packaged RAAV particles were increased by about 65% in DJ-MCP (Y156F)-MA and about 35% in DJ-MCP (Y156F)-AM compared with MCP-Rep78/68 fusion alone (FIGS. 20A and 20B), suggesting that RBPs could be additionally fused to or associated with any other proteins which play roles in the packaging or assembly of AAV particles in order to enhance the RNA packaging of RAAV particles.

Using AAP-MCP or MCP-AAP alone, without MCP-Rep78/68, are also within the scope of the invention.

Sequences

Certain sequences, including those referenced in the examples above, are provided herein below.

TABLE A

Nucleic Acid Sequence and Amino Acid Sequence of RBP

| RNA binding protein | Sequences |
|---|---|
| MCP nucleic acid sequence SEQ ID NO: 109 | GCTTCTAACTTTACTCAGTTCGTTCTCGTCGACAATGGCGGAACTGGCG ACGTGACTGTCGCCCCAAGCAACTTCGCTAACGGGGTCGCTGAATGGAT CAGCTCTAACTCGCGTTCACAGGCTTACAAAGTAACCTGTAGCGTTCGT CAGAGCTCTGCGCAGAATCGCAAATACACCATCAAAGTCGAGGTGCCTA AAGTGGCAACCCAGACTGTTGGTGGAGTAGAGCTTCCTGTAGCCGCATG GCGTTCGTACTTAAATATGGAACTAACCATTCCAATTTTCGCTACGAAT TCCGACTGCGAGCTTATTGTTAAGGCAATGCAAGGTCTCCTAAAAGATG GAAACCCGATTCCCTCAGCAATCGCAGCAAACTCCGGCATCTAC |
| MCP amino acid sequence SEQ ID NO: 110 | ASNFTQFVLVDNGGTGDVTVAPSNFANGVAEWISSNSRSQAYKVTCSVR QSSAQNRKYTIKVEVPKVATQTVGGVELPVAAWRSYLNMELTIPIFATN SDCELIVKAMQGLLKDGNPIPSAIAANSGIY |
| PCP nucleic acid sequence SEQ ID NO: 111 | TCCAAAACAATAGTCCTCTCCGTAGGGGAGGCAACACGGACTTTGACCG AAATCCAGTCAACCGCTGACCGACAAATCTTTGAAGAGAAAGTAGGGCC TCTTGTGGGCCGACTGCGCTTGACTGCAAGCTTGCGACAAAACGGCGCA AAGACTGCCTATAGGGTCAACCTTAAACTCGACCAAGCCGACGTGGTCG ATAGCGGTCTCCCTAAGGTTCGGTATACGCAGGTCTGGAGTCATGACGT AACAATCGTAGCAAACAGCACAGAAGCCTCCCGAAAAAGCCTCTACGAT CTGACGAAATCCTTGGTGGCTACGTCACAGGTGGAAGACCTCGTTGTCA ACCTTGTACCTCTGGGTCGA |

TABLE A-continued

Nucleic Acid Sequence and Amino Acid Sequence of RBP

| RNA binding protein | Sequences |
| --- | --- |
| PCP amino acid sequence SEQ ID NO: 112 | SKTIVLSVGEATRTLTEIQSTADRQIFEEKVGPLVGRLRLTASLRQNGA KTAYRVNLKLDQADVVDSGLPKVRYTQVWSHDVTIVANSTEASRKSLYD LTKSLVATSQVEDLVVNLVPLGR |
| COM nucleic acid sequence SEQ ID NO: 113 | ATGAAATCAATTCGCTGTAAAAACTGCAACAAACTGTTATTTAAGGCGG ATTCCTTTGATCACATTGAAATCAGGTGTCCGCGTTGCAAACGTCACAT CATAATGCTGAATGCCTGCGAGCATCCCACGGAGAAACATTGTGGGAAA AGAGAAAAATCACGCATTCTGACGAAACCGTGCGTTAT |
| COM amino acid sequence SEQ ID NO: 114 | MKSIRCKNCNKLLFKADSFDHIEIRCPRCKRHIIMLNACEHPTEKHCGK REKITHSDETVRY |

TABLE B

Nucleic Acid Sequences of RPS

| Packaging signal | Nucleic acid sequences |
| --- | --- |
| MS2 SEQ ID NO: 115 | ACATGAGGATCACCCATGT |
| MS2 X3 (MS2-linker-MS2-linker-MS2) SEQ ID NO: 116 | *ACATGAGGATCACCCATGT*CTGCAGGTCGACTCTAGAAA *ACATGAGGAT CACCCATGT*CTGCAGTATTCCCGGGTTCATTAGATCCTAAGGTACCTAA TTGCCTAGAAA *ACATGAGGATCACCCATGT* |
| PP7 SEQ ID NO: 117 | GGAGCAGACGATATGGCGTCGCTCC |
| PP7 X3 (PP7-linker-PP7-linker-PP7) SEQ ID NO: 118 | *GGAGCAGACGATATGGCGTCGCTCC* CTGCAGGTCGACTCTAGAAA *GGAG CAGACGATATGGCGTCGCTCC* CTGCAGTATTCCCGGGTTCATTAGATCC TAAGGTACCTAATTGCCTAGAAA *GGAGCAGACGATATGGCGTCGCTCC* |
| Com SEQ ID NO: 119 | GAATGCCTGCGAGCATCC |
| com X3 (com-linker-com-linker-com) SEQ ID NO: 120 | *GAATGCCTGCGAGCATCC* CTGCAGGTCGACTCTAGAAA *GAATGCCTGCG AGCATCC* CTGCAGTATTCCCGGGTTCATTAGATCCTAAGGTACCTAATT GCCTAGAAA *GAATGCCTGCGAGCATCC* |

* Sequence elements are matched based on formatting styles (e.g., bold and/or italic fonts, etc.)

TABLE C

Nucleic Acid Sequence and Amino Acid Sequence of Rep proteins

| Rep proteins | Sequences |
| --- | --- |
| Rep2 nucleic acid sequence SEQ ID NO: 121 | ATGCCGGGGTTTTACGAGATTGTGATTAAGGTCCCCAGCGACCTTGACG AGCATCTGCCCGGCATTTCTGACAGCTTTGTGAACTGGGTGGCCGAGAA GGAATGGGAGTTGCCGCCAGATTCTGACATGGATCTGAATCTGATTGAG CAGGCACCCCTGACCGTGGCCGAGAAGCTGCAGCGCGACTTTCTGACGG AATGGCGCCGTGTGAGTAAGGCCCCGGAGGCCCTTTTCTTTGTGCAATT TGAGAAGGGAGAGAGCTACTTCCACATGCACGTGCTCGTGGAAACCACC GGGGTGAAATCCATGGTTTTGGGACGTTTCCTGAGTCAGATTCGCGAAA AACTGATTCAGAGAATTTACCGCGGGATCGAGCCGACTTTGCCAAACTG GTTCGCGGTCACAAAGACCAGAAATGGCGCCGGAGGCGGGAACAAGGTG GTGGATGAGTGCTACATCCCCAATTACTTGCTCCCCAAAACCCAGCCTG AGCTCCAGTGGGCGTGGACTAATATGGAACAGTATTTAAGCGCCTGTTT GAATCTCACGGAGCGTAAACGGTTGGTGGCGCAGCATCTGACGCACGTG TCGCAGACGCAGGAGCAGAACAAAGAGAATCAGAATCCCAATTCTGATG CGCCGGTGATCAGATCAAAAACTTCAGCCAGGTACATGGAGCTGGTCGG GTGGCTCGTGGACAAGGGGATTACCTCGGAGAAGCAGTGGATCCAGGAG GACCAGGCCTCATACATCTCCTTCAATGCGGCCTCCAACTCGCGGTCCC AAATCAAGGCTGCCTTGGACAATGCGGGAAAGATTATGAGCCTGACTAA AACCGCCCCCGACTACCTGGTGGGCCAGCAGCCCGTGGAGGACATTTCC AGCAATCGGATTTATAAAATTTTGGAACTAAACGGGTACGATCCCCAAT ATGCGGCTTCCGTCTTTCTGGGATGGGCCACGAAAAAGTTCGGCAAGAG GAACACCATCTGGCTGTTTGGGCCTGCAACTACCGGGAAGACCAACATC |

TABLE C-continued

Nucleic Acid Sequence and Amino Acid Sequence of Rep proteins

| Rep proteins | Sequences |
| --- | --- |
| | GCGGAGGCCATAGCCCACACTGTGCCCTTCTACGGGTGCGTAAACTGGA<br>CCAATGAGAACTTTCCCTTCAACGACTGTGTCGACAAGATGGTGATCTG<br>GTGGGAGGAGGGGAAGATGACCGCCAAGGTCGTGGAGTCGGCCAAAGCC<br>ATTCTCGGAGGAAGCAAGGTGCGCGTGGACCAGAAATGCAAGTCCTCGG<br>CCCAGATAGACCCGACTCCCGTGATCGTCACCTCCAACACCAACATGTG<br>CGCCGTGATTGACGGGAACTCAACGACCTTCGAACACCAGCAGCCGTTG<br>CAAGACCGGATGTTCAAATTTGAACTCACCCGCCGTCTGGATCATGACT<br>TTGGGAAGGTCACCAAGCAGGAAGTCAAAGACTTTTTCCGGTGGGCAAA<br>GGATCACGTGGTTGAGGTGGAGCATGAATTCTACGTCAAAAAGGGTGGA<br>GCCAAGAAAAGACCCGCCCCCAGTGACGCAGATATAAGTGAGCCCAAAC<br>GGGTGCGCGAGTCAGTTGCGCAGCCATCGACGTCAGACGCGGAAGCTTC<br>GATCAACTACGCAGACAGGTACCAAAACAAATGTTCTCGTCACGTGGGC<br>ATGAATCTGATGCTGTTTCCCTGCAGACAATGCGAGAGAATGAATCAGA<br>ATTCAAATATCTGCTTCACTCACGGACAGAAAGACTGTTTAGAGTGCTT<br>TCCCGTGTCAGAATCTCAACCCGTTTCTGTCGTCAAAAAGGCGTATCAG<br>AAACTGTGCTACATTCATCATATCATGGGAAAGGTGCCAGACGCTTGCA<br>CTGCCTGCGATCTGGTCAATGTGGATTTGGATGACTGCATCTTTGAACA<br>ATAA |
| Rep2 amino acid sequence<br>SEQ ID NO: 122 | MPGFYEIVIKVPSDLDEHLPGISDSFVNWVAEKEWELPPDSDMDLNLIE<br>QAPLTVAEKLQRDFLTEWRRVSKAPEALFFVQFEKGESYFHMHVLVETT<br>GVKSMVLGRFLSQIREKLIQRIYRGIEPTLPNWFAVTKTRNGAGGGNKV<br>VDECYIPNYLLPKTQPELQWAWINMEQYLSACLNLTERKRLVAQHLTHV<br>SQTQEQNKENQNPNSDAPVIRSKTSARYMELVGWLVDKGITSEKQWIQE<br>DQASYISFNAASNSRSQIKAALDNAGKIMSLIKTAPDYLVGQQPVEDIS<br>SNRIYKILELNGYDPQYAASVELGWATKKFGKRNTIWLFGPATTGKTNI<br>AEAIAHTVPFYGCVNWTNENFPFNDCVDKMVIWWEEGKMTAKVVESAKA<br>ILGGSKVRVDQKCKSSAQIDPTPVIVTSNTNMCAVIDGNSTTFEHQQPL<br>QDRMFKFELTRRLDHDFGKVTKQEVKDFFRWAKDHVVEVEHEFYVKKGG<br>AKKRPAPSDADISEPKRVRESVAQPSTSDAEASINYADRYQNKCSRHVG<br>MNLMLFPCRQCERMNQNSNICFTHGQKDCLECFPVSESQPVSVVKKAYQ<br>KLCYIHHIMGKVPDACTACDLVNVDLDDCIFEQ |
| MCP-<br>Rep nucleic acid sequence (linker-MCP-linker-Rep)<br>SEQ ID NO: 123 | ATGCCCGGCAGCTCCGGCAGTAGC*GCTTCTAACTTTACTCAGTTCGTTC*<br>*TCGTCGACAATGGCGGAACTGGCGACGTGACTGTCGCCCCAAGCAACTT*<br>*CGCTAACGGGGTCGCTGAATGGATCAGCTCTAACTCGCGTTCACAGGCT*<br>*TACAAAGTAACCTGTAGCGTTCGTCAGAGCTCTGCGCAGAATCGCAAAT*<br>*ACACCATCAAAGTCGAGGTGCCTAAAGTGGCAACCCAGACTGTTGGTGG*<br>*AGTAGAGCTTCCTGTAGCCGCATGGCGTTCGTACTTAAATATGGAACTA*<br>*ACCATTCCAATTTTCGCTACGAATTCCGACTGCGAGCTTATTGTTAAGG*<br>*CAATGCAAGGTCTCCTAAAAGATGGAAACCCGATTCCCTCAGCAATCGC*<br>*AGCAAACTCCGGCATCTAC*GGCAGTAGTGGGTCCTCTGGGTTTTACGAG<br>ATTGTGATTAAGGTCCCCAGCGACCTTGACGAGCATCTGCCCGGCATTT<br>CTGACAGCTTTGTGAACTGGGTGGCCGAGAAGGAATGGGAGTTGCCGCC<br>AGATTCTGACATGGATCTGAATCTGATTGAGCAGGCACCCCTGACCGTG<br>GCCGAGAAGCTGCAGCGCGACTTTCTGACGGAATGGCGCCGTGTGAGTA<br>AGGCCCCGGAGGCCCTTTTCTTTGTGCAATTTGAGAAGGGAGAGAGCTA<br>CTTCCACATGCACGTGCTCGTGGAAACCACCGGGGTGAAATCCATGGTT<br>TTGGGACGTTTCCTGAGTCAGATTCGCGAAAAACTGATTCAGAGAATTT<br>ACCGCGGGATCGAGCCGACTTTGCCAAACTGGTTCGCGGTCACAAAGAC<br>CAGAAATGGCGCCGGAGGCGGGAACAAGGTGGTGGATGAGTGCTACATC<br>CCCAATTACTTGCTCCCCAAAACCCAGCCTGAGCTCCAGTGGGCGTGGA<br>CTAAATATGGAACAGTATTTAAGCGCCTGTTTGAATCTCACGGAGCGTAA<br>ACGGTTGGTGGCGCAGCATCTGACGCACGTGTCGCAGACGCAGGAGCAG<br>AACAAAGAGAATCAGAATCCCAATTCTGATGCGCCGGTGATCAGATCAA<br>AAACTTCAGCCAGGTACATGGAGCTGGTCGGGTGGCTCGTGGACAAGGG<br>GATTACCTCGGAGAAGCAGTGGATCCAGGAGGACCAGGCCTCATACATC<br>TCCTTCAATGCGGCCTCCAACTCGCGGTCCCAAATCAAGGCTGCCTTGG<br>ACAATGCGGGAAAGATTATGAGCCTGACTAAAACCGCCCCCGACTACCT<br>GGTGGGCCAGCAGCCCGTGGAGGACATTTCCAGCAATCGGATTTATAAA<br>ATTTTGGAACTAAACGGGTACGATCCCCAATATGCGGCTTCCGTCTTTC<br>TGGGATGGGCCACGAAAAAGTTCGGCAAGAGGAACACCATCTGGCTGTT<br>TGGGCCTGCAACTACCGGGAAGACCAACATCGCGGAGGCCATAGCCCAC<br>ACTGTGCCCTTCTACGGGTGCGTAAACTGGACCAATGAGAACTTTCCCT<br>TCAACGACTGTGTCGACAAGATGGTGATCTGGTGGGAGGAGGGGAAGAT<br>GACCGCCAAGGTCGTGGAGTCGGCCAAAGCCATTCTCGGAGGAAGCAAG<br>GTGCGCGTGGACCAGAAATGCAAGTCCTCGGCCCAGATAGACCCGACTC<br>CCGTGATCGTCACCTCCAACACCAACATGTGCGCCGTGATTGACGGGAA<br>CTCAACGACCTTCGAACACCAGCAGCCGTTGCAAGACCGGATGTTCAAA<br>TTTGAACTCACCCGCCGTCTGGATCATGACTTTGGGAAGGTCACCAAGC<br>AGGAAGTCAAAGACTTTTTCCGGTGGGCAAAGGATCACGTGGTTGAGGT<br>GGAGCATGAATTCTACGTCAAAAAGGGTGGAGCCAAGAAAAGACCCGCC<br>CCCAGTGACGCAGATATAAGTGAGCCCAAACGGGTGCGCGAGTCAGTTG<br>CGCAGCCATCGACGTCAGACGCGGAAGCTTCGATCAACTACGCAGACAG<br>GTACCAAAACAAATGTTCTCGTCACGTGGGCATGAATCTGATGCTGTTT<br>CCCTGCAGACAATGCGAGAGAATGAATCAGAATTCAAATATCTGCTTCA |

TABLE C-continued

Nucleic Acid Sequence and Amino Acid Sequence of Rep proteins

| Rep proteins | Sequences |
|---|---|
| | CTCACGGACAGAAAGACTGTTTAGAGTGCTTTCCCGTGTCAGAATCTCA<br>ACCCGTTTCTGTCGTCAAAAAGGCGTATCAGAAACTGTGCTACATTCAT<br>CATATCATGGGAAAGGTGCCAGACGCTTGCACTGCCTGCGATCTGGTCA<br>ATGTGGATTTGGATGACTGCATCTTTGAACAATAA |
| MCP-<br>Rep amino acid<br>sequence(linker-<br>MCP-linker-Rep)<br>SEQ ID NO: 124 | MPGSSGSS*ASNFTQFVLVDNGGTGDVTVAPSNFANGVAEWISSNSRSQA*<br>*YKVTCSVRQSSAQNRKYTIKVEVPKVATQTVGGVELPVAAWRSYLNMEL*<br>*TIPIFATNSDCELIVKAMQGLLKDGNPIPSAIAANSGIY*GSSGSSGFYE<br>IVIKVPSDLDEHLPGISDSFVNWVAEKEWELPPDSDMDLNLIEQAPLTV<br>AEKLQRDFLTEWRRVSKAPEALFFVQFEKGESYFHMHVLVETTGVKSMV<br>LGRFLSQIREKLIQRIYRGIEPTLPNWFAVTKTRNGAGGGNKVVDECYI<br>PNYLLPKTQPELQWAWTNMEQYLSACLNLTERKRLVAQHLTHVSQTQEQ<br>NKENQNPNSDAPVIRSKTSARYMELVGWLVDKGITSEKQWIQEDQASYI<br>SFNAASNSRSQIKAALDNAGKIMSLIKTAPDYLVGQQPVEDISSNRIYK<br>ILELNGYDPQYAASVELGWATKKFGKRNTIWLFGPATTGKINIAEAIAH<br>TVPFYGCVNWTNENFPFNDCVDKMVIWWEEGKMTAKVVESAKAILGGSK<br>VRVDQKCKSSAQIDPTPVIVTSNTNMCAVIDGNSTTFEHQQPLQDRMFK<br>FELTRRLDHDFGKVTKQEVKDFFRWAKDHVVEVEHEFYVKKGGAKKRPA<br>PSDADISEPKRVRESVAQPSTSDAEASINYADRYQNKCSRHVGMNLMLF<br>PCRQCERMNQNSNICFTHGQKDCLECFPVSESQPVSVVKKAYQKLCYIH<br>HIMGKVPDACTACDLVNVDLDDCIFEQ |
| MCP-Rep-Y156F<br>nucleic acid<br>sequence (linker-<br>MCP-linker-Rep)<br>SEQ ID NO: 125 | ATGCCCGGCAGCTCCGGCAGTAGC*GCTTCTAACTTTACTCAGTTCGTTC*<br>*TCGTCGACAATGGCGGAACTGGCGACGTGACTGTCGCCCCAAGCAACTT*<br>*CGCTAACGGGGTCGCTGAATGGATCAGCTCTAACTCGCGTTCACAGGCT*<br>*TACAAAGTAACCTGTAGCGTTCGTCAGAGCTCTGCGCAGAATCGCAAAT*<br>*ACACCATCAAAGTCGAGGTGCCTAAAGTGGCAACCCAGACTGTTGGTGG*<br>*AGTAGAGCTTCCTGTAGCCGCATGGCGTTCGTACTTAAATATGGAACTA*<br>*ACCATTCCAATTTTCGCTACGAATTCCGACTGCGAGCTTATTGTTAAGG*<br>*CAATGCAAGGTCTCCTAAAAGATGGAAACCCGATTCCCTCAGCAATCGC*<br>*AGCAAACTCCGGCATCTAC*GGCAGTAGTGGGTCCTCTGGGTTTTACGAG<br>ATTGTGATTAAGGTCCCCAGCGACCTTGACGAGCATCTGCCCGGCATTT<br>CTGACAGCTTTGTGAACTGGGTGGCCGAGAAGGAATGGGAGTTGCCGCC<br>AGATTCTGACATGGATCTGAATCTGATTGAGCAGGCACCCCTGACCGTG<br>GCCGAGAAGCTGCAGCGCGACTTTCTGACGGAATGGCGCCGTGTGAGTA<br>AGGCCCCGGAGGCCCTTTTCTTTGTGCAATTTGAGAAGGGAGAGAGCTA<br>CTTCCACATGCACGTGCTCGTGGAAACCACCGGGGTGAAATCCATGGTT<br>TTGGGACGTTTCCTGAGTCAGATTCGCGAAAAACTGATTCAGAGAATTT<br>ACCGCGGGATCGAGCCGACTTTGCCAAACTGGTTCGCGGTCACAAAGAC<br>CAGAAATGGCGCCGGAGGCGGGAACAAGGTGGTGGATGAGTGCTACATC<br>CCCAAT*TTC*TTGCTCCCCAAAACCCAGCCTGAGCTCCAGTGGGCGTGGA<br>CTAAATATGGAACAGTATTTAAGCGCCTGTTTGAATCTCACGGAGCGTAA<br>ACGGTTGGTGGCGCAGCATCTGACGCACGTGTCGCAGACGCAGGAGCAG<br>AACAAAGAGAATCAGAATCCCAATTCTGATGCGCCGGTGATCAGATCAA<br>AAACTTCAGCCAGGTACATGGAGCTGGTCGGGTGGCTCGTGGACAAGGG<br>GATTACCTCGGAGAAGCAGTGGATCCAGGAGGACCAGGCCTCATACATC<br>TCCTTCAATGCGGCCTCCAACTCGCGGTCCCAAATCAAGGCTGCCTTGG<br>ACAATGCGGGAAAGATTATGAGCCTGACTAAAACCGCCCCCGACTACCT<br>GGTGGGCCAGCAGCCCGTGGAGGACATTTCCAGCAATCGGATTTATAAA<br>ATTTTGGAACTAAACGGGTACGATCCCCAATATGCGGCTTCCGTCTTTC<br>TGGGATGGGCCACGAAAAAGTTCGGCAAGAGGAACACCATCTGGCTGTT<br>TGGGCCTGCAACTACCGGGAAGACCAACATCGCGGAGGCCATAGCCCAC<br>ACTGTGCCCTTCTACGGGTGCGTAAACTGGACCAATGAGAACTTTCCCT<br>TCAACGACTGTGTCGACAAGATGGTGATCTGGTGGGAGGAGGGGAAGAT<br>GACCGCCAAGGTCGTGGAGTCGGCCAAAGCCATTCTCGGAGGAAGCAAG<br>GTGCGCGTGGACCAGAAATGCAAGTCCTCGGCCCAGATAGACCCGACTC<br>CCGTGATCGTCACCTCCAACACCAACATGTGCGCCGTGATTGACGGGAA<br>CTCAACGACCTTCGAACACCAGCAGCCGTTGCAAGACCGGATGTTCAAA<br>TTTGAACTCACCCGCCGTCTGGATCATGACTTTGGGAAGGTCACCAAGC<br>AGGAAGTCAAAGACTTTTTCCGGTGGGCAAAGGATCACGTGGTTGAGGT<br>GGAGCATGAATTCTACGTCAAAAAGGGTGGAGCCAAGAAAAGACCCGCC<br>CCCAGTGACGCAGATATAAGTGAGCCCAAACGGGTGCGCGAGTCAGTTG<br>CGCAGCCATCGACGTCAGACGCGGAAGCTTGATCAACTACGCAGACAG<br>GTACCAAAACAAATGTTCTCGTCACGTGGGCATGAATCTGATGCTGTTT<br>CCCTGCAGACAATGCGAGAGAATGAATCAGAATTCAAATATCTGCTTCA<br>CTCACGGACAGAAAGACTGTTTAGAGTGCTTTCCCGTGTCAGAATCTCA<br>ACCCGTTTCTGTCGTCAAAAAGGCGTATCAGAAACTGTGCTACATTCAT<br>CATATCATGGGAAAGGTGCCAGACGCTTGCACTGCCTGCGATCTGGTCA<br>ATGTGGATTTGGATGACTGCATCTTTGAACAATAA |
| MCP-Rep-Y156F<br>amino acid<br>sequence (linker-<br>MCP-linker-Rep)<br>SEQ ID NO: 126 | MPGSSGSS*ASNFTQFVLVDNGGTGDVTVAPSNFANGVAEWISSNSRSQA*<br>*YKVTCSVRQSSAQNRKYTIKVEVPKVATQTVGGVELPVAAWRSYLNMEL*<br>*TIPIFATNSDCELIVKAMQGLLKDGNPIPSAIAANSGIY*GSSGSSGFYE<br>IVIKVPSDLDEHLPGISDSFVNWVAEKEWELPPDSDMDLNLIEQAPLTV<br>AEKLQRDFLTEWRRVSKAPEALFFVQFEKGESYFHMHVLVETTGVKSMV<br>LGRFLSQIREKLIQRIYRGIEPTLPNWFAVTKTRNGAGGGNKVVDECYI |

TABLE C-continued

Nucleic Acid Sequence and Amino Acid Sequence of Rep proteins

| Rep proteins | Sequences |
|---|---|
| | PNFLLPKTQPELQWAWTNMEQYLSACLNLTERKRLVAQHLTHVSQTQEQ<br>NKENQNPNSDAPVIRSKTSARYMELVGWLVDKGITSEKQWIQEDQASYI<br>SFNAASNSRSQIKAALDNAGKIMSLIKTAPDYLVGQQPVEDISSNRIYK<br>ILELNGYDPQYAASVELGWATKKFGKRNTIWLFGPATTGKTNIAEAIAH<br>TVPFYGCVNWTNENFPFNDCVDKMVIWWEEGKMTAKVVESAKAILGGSK<br>VRVDQKCKSSAQIDPTPVIVTSNTNMCAVIDGNSTTFEHQQPLQDRMFK<br>FELTRRLDHDFGKVTKQEVKDFFRWAKDHVVEVEHEFYVKKGGAKKRPA<br>PSDADISEPKRVRESVAQPSTDAEASINYADRYQNKCSRHVGMNLMLF<br>PCRQCERMNONSNICFTHGQKDCLECFPVSESQPVSVVKKAYQKLCYIH<br>HIMGKVPDACTACDLVNVDLDDCIFEQ |
| MCP-Rep-KDE-<br>mu nucleic acid<br>sequence (linker-<br>MCP-linker-Rep)<br>SEQ ID NO: 127 | ATGCCCGGCAGCTCCGGCAGTAGC*GCTTCTAACTTTACTCAGTTCGTTC*<br>*TCGTCGACAATGGCGGAACTGGCGACGTGACTGTCGCCCCAAGCAACTT*<br>*CGCTAACGGGGTCGCTGAATGGATCAGCTCTAACTCGCGTTCACAGGCT*<br>*TACAAAGTAACCTGTAGCGTTCGTCAGAGCTCTGCGCAGAATCGCAAAT*<br>*ACACCATCAAAGTCGAGGTGCCTAAAGTGGCAACCCAGACTGTTGGTGG*<br>*AGTAGAGCTTCCTGTAGCCGCATGGCGTTCGTACTTAAATATGGAACTA*<br>*ACCATTCCAATTTTCGCTACGAATTCCGACTGCGAGCTTATTGTTAAGG*<br>*CAATGCAAGGTCTCCTAAAAGATGGAAACCCGATTCCCTCAGCAATCGC*<br>*AGCAAACTCCGGCATCTAC*GGCAGTAGTGGGTCCTCTGGGTTTTACGAG<br>ATTGTGATTAAGGTCCCCAGCGACCTTGACGAGCATCTGCCCGGCATTT<br>CTGACAGCTTTGTGAACTGGGTGGCCGAGAAGGAATGGGAGTTGCCGCC<br>AGATTCTGACATGGATCTGAATCTGATTGAGCAGGCACCCCTGACCGTG<br>GCCGAGAAGCTGCAGCGCGACTTTCTGACGGAATGGCGCCGTGTGAGTA<br>AGGCCCCGGAGGCCCTTTTCTTTGTGCAATTTGAGAAGGGAGAGAGCTA<br>CTTCCACATGCACGTGCTCGTGGAAACCACCGGGGTGAAATCCATGGTT<br>TTGGGACGTTTCCTGAGTCAGATTCGCGAAAAACTGATTCAGAGAATTT<br>ACCGCGGGATCGAGCCGACTTTGCCAAACTGGTTCGCGGTCACAAAGAC<br>CAGAAATGGCGCCGGAGGCGGGAAC*GCG*GTGGTG*GCTGCG*TGCTACATC<br>CCCAATTACTTGCTCCCCAAAACCCAGCCTGAGCTCCAGTGGGCGTGGA<br>CTAATATGGAACAGTATTTAAGCGCCTGTTTGAATCTCACGGAGCGTAA<br>ACGGTTGGTGGCGCAGCATCTGACGCACGTGTCGCAGACGCAGGAGCAG<br>AACAAAGAGAATCAGAATCCCAATTCTGATGCGCCGGTGATCAGATCAA<br>AAACTTCAGCCAGGTACATGGAGCTGGTCGGGTGGCTCGTGGACAAGGG<br>GATTACCTCGGAGAAGCAGTGGATCCAGGAGGACCAGGCCTCATACATC<br>TCCTTCAATGCGGCCTCCAACTCGCGGTCCCAAATCAAGGCTGCCTTGG<br>ACAATGCGGGAAAGATTATGAGCCTGACTAAAACCGCCCCCGACTACCT<br>GGTGGGCCAGCAGCCCGTGGAGGACATTTCCAGCAATCGGATTTATAAA<br>ATTTTGGAACTAAACGGGTACGATCCCCAATATGCGGCTTCCGTCTTTC<br>TGGGATGGGCCACGAAAAAGTTCGGCAAGAGGAACACCATCTGGCTGTT<br>TGGGCCTGCAACTACCGGGAAGACCAACATCGCGGAGGCCATAGCCCAC<br>ACTGTGCCCTTCTACGGGTGCGTAAACTGGACCAATGAGAACTTTCCCT<br>TCAACGACTGTGTCGACAAGATGGTGATCTGGTGGGAGGAGGGGAAGAT<br>GACCGCCAAGGTCGTGGAGTCGGCCAAAGCCATTCTCGGAGGAAGCAAG<br>GTGCGCGTGGACCAGAAATGCAAGTCCTCGGCCCAGATAGACCCGACTC<br>CCGTGATCGTCACCTCCAACACCAACATGTGCGCCGTGATTGACGGGAA<br>CTCAACGACCTTCGAACACCAGCAGCCGTTGCAAGACCGGATGTTCAAA<br>TTTGAACTCACCCGCCGTCTGGATCATGACTTTGGGAAGGTCACCAAGC<br>AGGAAGTCAAAGACTTTTTCCGGTGGGCAAAGGATCACGTGGTTGAGGT<br>GGAGCATGAATTCTACGTCAAAAAGGGTGGAGCCAAGAAAAGACCCGCC<br>CCCAGTGACGCAGATATAAGTGAGCCCAAACGGGTGCGCGAGTCAGTTG<br>CGCAGCCATCGACGTCAGACGCGGAAGCTTCGATCAACTACGCAGACAG<br>GTACCAAAACAAATGTTCTCGTCACGTGGGCATGAATCTGATGCTGTTT<br>CCCTGCAGACAATGCGAGAGAATGAATCAGAATTCAAATATCTGCTTCA<br>CTCACGGACAGAAAGACTGTTTAGAGTGCTTTCCCGTGTCAGAATCTCA<br>ACCCGTTTCTGTCGTCAAAAAGGCGTATCAGAAACTGTGCTACATTCAT<br>CATATCATGGGAAAGGTGCCAGACGCTTGCACTGCCTGCGATCTGGTCA<br>ATGTGGATTTGGATGACTGCATCTTTGAACAATAA |
| MCP-Rep-KDE-<br>mu amino acid<br>sequence (linker-<br>MCP-linker-Rep)<br>SEQ ID NO: 128 | MPGSSGSS*ASNFTQFVLVDNGGTGDVTVAPSNFANGVAEWISSNSRSQA*<br>*YKVTCSVRQSSAQNRKYTIKVEVPKVATQTVGGVELPVAAWRSYLNMEL*<br>*TIPIFATNSDCELIVKAMQGLLKDGNPIPSAIAANSGIY*GSSGSSGFYE<br>IVIKVPSDLDEHLPGISDSFVNWVAEKEWELPPDSDMDLNLIEQAPLTV<br>AEKLQRDFLTEWRRVSKAPEALFFVQFEKGESYFHMHVLVETTGVKSMV<br>LGRFLSQIREKLIQRIYRGIEPTLPNWFAVTKIRNGAGGGNAVVAACYI<br>PNYLLPKTQPELQWAWTNMEQYLSACLNLTERKRLVAQHLTHVSQTQEQ<br>NKENQNPNSDAPVIRSKTSARYMELVGWLVDKGITSEKQWIQEDQASYI<br>SFNAASNSRSQIKAALDNAGKIMSLIKTAPDYLVGQQPVEDISSNRIYK<br>ILELNGYDPQYAASVFLGWATKKFGKRNTIWLFGPATTGKINIAEAIAH<br>TVPFYGCVNWTNENFPFNDCVDKMVIWWEEGKMTAKVVESAKAILGGSK<br>VRVDQKCKSSAQIDPTPVIVTSNTNMCAVIDGNSTTFEHQQPLQDRMFK<br>FELTRRLDHDFGKVTKQEVKDFFRWAKDHVVEVEHEFYVKKGGAKKRPA<br>PSDADISEPKRVRESVAQPSTDAEASINYADRYQNKCSRHVGMNLMLF<br>PCRQCERMNQNSNICFTHGQKDCLECFPVSESQPVSVVKKAYQKLCYIH<br>HIMGKVPDACTACDLVNVDLDDCIFEQ |

TABLE C-continued

Nucleic Acid Sequence and Amino Acid Sequence of Rep proteins

| Rep proteins | Sequences |
| --- | --- |
| MCP-Rep-EKE-mu nucleic acid sequence (linker-MCP-linker-Rep) SEQ ID NO: 129 | ATGCCCGGCAGCTCCGGCAGTAGC*GCTTCTAACTTTACTCAGTTCGTTC* *TCGTCGACAATGGCGGAACTGGCGACGTGACTGTCGCCCCAAGCAACTT* *CGCTAACGGGGTCGCTGAATGGATCAGCTCTAACTCGCGTTCACAGGCT* *TACAAAGTAACCTGTAGCGTTCGTCAGAGCTCTGCGCAGAATCGCAAAT* *ACACCATCAAAGTCGAGGTGCCTAAAGTGGCAACCCAGACTGTTGGTGG* *AGTAGAGCTTCCTGTAGCCGCATGGCGTTCGTACTTAAATATGGAACTA* *ACCATTCCAATTTTCGCTACGAATTCCGACTGCGAGCTTATTGTTAAGG* *CAATGCAAGGTCTCCTAAAAGATGGAAACCCGATTCCCTCAGCAATCGC* *AGCAAACTCCGGCATCTAC*GGCAGTAGTGGGTCCTCTGGGTTTTACGAG ATTGTGATTAAGGTCCCCAGCGACCTTGACGAGCATCTGCCCGGCATTT CTGACAGCTTTGTGAACTGGGTGGCCGAGAAGGAATGGGAGTTGCCGCC AGATTCTGACATGGATCTGAATCTGATTGAGCAGGCACCCCTGACCGTG GCCGAGAAGCTGCAGCGCGACTTTCTGACGGAATGGCGCCGTGTGAGTA AGGCCCCGGAGGCCCTTTTCTTTGTGCAATTT*GCGGCG*GGA*GCG*AGCTA CTTCCACATGCACGTGCTCGTGGAAACCACCGGGGTGAAATCCATGGTT TTGGGACGTTTCCTGAGTCAGATTCGCGAAAAACTGATTCAGAGAATTT ACCGCGGGATCGAGCCGACTTTGCCAAACTGGTTCGCGGTCACAAAGAC CAGAAATGGCGCCGGAGGCGGGAACAAGGTGGTGGATGAGTGCTACATC CCCAATTACTTGCTCCCCAAAACCCAGCCTGAGCTCCAGTGGGCGTGGA CTAATATGGAACAGTATTTAAGCGCCTGTTTGAATCTCACGGAGCGTAA ACGGTTGGTGGCGCAGCATCTGACGCACGTGTCGCAGACGCAGGAGCAG AACAAAGAGAATCAGAATCCCAATTCTGATGCGCCGGTGATCAGATCAA AAACTTCAGCCAGGTACATGGAGCTGGTCGGGTGGCTCGTGGACAAGGG GATTACCTCGGAGAAGCAGTGGATCCAGGAGGACCAGGCCTCATACATC TCCTTCAATGCGGCCTCCAACTCGCGGTCCCAAATCAAGGCTGCCTTGG ACAATGCGGGAAAGATTATGAGCCTGACTAAAACCGCCCCCGACTACCT GGTGGGCCAGCAGCCCGTGGAGGACATTTCCAGCAATCGGATTTATAAA ATTTTGGAACTAAACGGGTACGATCCCCAATATGCGGCTTCCGTCTTTC TGGGATGGGCCACGAAAAAGTTCGGCAAGAGGAACACCATCTGGCTGTT TGGGCCTGCAACTACCGGGAAGACCAACATCGCGGAGGCCATAGCCCAC ACTGTGCCCTTCTACGGGTGCGTAAACTGGACCAATGAGAACTTTCCCT TCAACGACTGTGTCGACAAGATGGTGATCTGGTGGGAGGAGGGGAAGAT GACCGCCAAGGTCGTGGAGTCGGCCAAAGCCATTCTCGGAGGAAGCAAG GTGCGCGTGGACCAGAAATGCAAGTCCTCGGCCCAGATAGACCCGACTC CCGTGATCGTCACCTCCAACACCAACATGTGCGCCGTGATTGACGGGAA CTCAACGACCTTCGAACACCAGCAGCCGTTGCAAGACCGGATGTTCAAA TTTGAACTCACCCGCCGTCTGGATCATGACTTTGGGAAGGTCACCAAGC AGGAAGTCAAAGACTTTTTCCGGTGGGCAAAGGATCACGTGGTTGAGGT GGAGCATGAATTCTACGTCAAAAAGGGTGGAGCCAAGAAAAGACCCGCC CCCAGTGACGCAGATATAAGTGAGCCCAAACGGGTGCGCGAGTCAGTTG CGCAGCCATCGACGTCAGACGCGGAAGCTTCGATCAACTACGCAGACAG GTACCAAAACAAATGTTCTCGTCACGTGGGCATGAATCTGATGCTGTTT CCCTGCAGACAATGCGAGAGAATGAATCAGAATTCAAATATCTGCTTCA CTCACGGACAGAAAGACTGTTTAGAGTGCTTTCCCGTGTCAGAATCTCA ACCCGTTTCTGTCGTCAAAAAGGCGTATCAGAAACTGTGCTACATTCAT CATATCATGGGAAAGGTGCCAGACGCTTGCACTGCCTGCGATCTGGTCA ATGTGGATTTGGATGACTGCATCTTTGAACAATAA |
| MCP-Rep-EKE-mu amino acid sequence (linker-MCP-linker-Rep) SEQ ID NO: 130 | MPGSSGSS*ASNFTQFVLVDNGGTGDVTVAPSNFANGVAEWISSNSRSQA* *YKVTCSVRQSSAQNRKYTIKVEVPKVATQTVGGVELPVAAWRSYLMEL* *TIPIFATNSDCELIVKAMQGLLKDGNPIPSAIAANSGIY*GSSGSSGFYE IVIKVPSDLDEHLPGISDSFVNWVAEKEWELPPDSDMDLNLIEQAPLTV AEKLQRDFLTEWRRVSKAPEALFFVQF*AAGA*SYFHMHVLVETTGVKSMV LGRFLSQIREKLIQRIYRGIEPTLPNWFAVTKTRNGAGGGNKVVDECYI PNYLLPKTQPELQWAWINMEQYLSACLNLTERKRLVAQHLTHVSQTQEQ NKENQNPNSDAPVIRSKTSARYMELVGWLVDKGITSEKQWIQEDQASYI SFNAASNSRSQIKAALDNAGKIMSLIKTAPDYLVGQQPVEDISSNRIYK ILELNGYDPQYAASVELGWATKKFGKRNTIWLFGPATTGKTNIAEAIAH TVPFYGCVNWTNENFPFNDCVDKMVIWWEEGKMTAKVVESAKAILGGSK VRVDQKCKSSAQIDPTPVIVTSNTNMCAVIDGNSTTFEHQQPLQDRMFK FELTRRLDHDFGKVTKQEVKDFFRWAKDHVVEVEHEFYVKKGGAKKRPA PSDADISEPKRVRESVAQPSTSDAEASINYADRYQNKCSRHVGMNLMLF PCRQCERMNQNSNICFTHGQKDCLECFPVSESQPVSVVKKAYQKLCYIH HIMGKVPDACTACDLVNVDLDDCIFEQ |
| 2XMCP-Rep nucleic acid sequence (linker-2XMCP-linker-Rep) SEQ ID NO: 131 | ATGCCCGGCAGCTCCGGCAGTAGC*GCTTCTAACTTTACTCAGTTCGTTC* *TCGTCGACAATGGCGGAACTGGCGACGTGACTGTCGCCCCAAGCAACTT* *CGCTAACGGGATCGCTGAATGGATCAGCTCTAACTCGCGTTCACAGGCT* *TACAAAGTAACCTGTAGCGTTCGTCAGAGCTCTGCGCAGAATCGCAAAT* *ACACCATCAAAGTCGAGGTGCCTAAAGGCGCCTGGCGTTCGTACTTAAA* *TATGGAACTAACCATTCCAATTTTCGCCACGAATTCCGACTGCGAGCTT* *ATTGTTAAGGCAATGCAAGGTCTCCTAAAAGATGGAAACCCGATTCCCT* *CAGCAATCGCAGCAAACTCCGGCATCTACGGTGGTGGAGGAGGAATGGC* *GTCCAATTTCACGCAGTTCGTCCTGGTTGACAACGGGGGGACTGGGGAC* *GTTACGGTCGCTCCGAGCAACTTTGCCAATGGTATTGCGGAGTGGATTT* *CTTCTAATTCACGGTCCCAAGCTTACAAAGTGACCTGTTCCGTGCGGCA* |

TABLE C-continued

Nucleic Acid Sequence and Amino Acid Sequence of Rep proteins

| Rep proteins | Sequences |
|---|---|
| | *AAGTTCTGCTCAGAATAGAAAGTACACTATAAAGGTCGAAGTCCCTAAG*<br>*GGGGCCTGGCGATCATATCTCAATATGGAGCTTACCATCCCAATATTTG*<br>*CCACTAATTCTGATTGTGAATTGATTGTCAAAGCAATGCAAGGACTCTT*<br>*GAAAGACGGAAACCCAATCCCCAGCGCAATCGCAGCCAACTCCGGTATA*<br>*TAC*GGCAGTAGTGGGTCCTCTGGGTTTTACGAGATTGTGATTAAGGTCC<br>CCAGCGACCTTGACGAGCATCTGCCCGGCATTTCTGACAGCTTTGTGAA<br>CTGGGTGGCCGAGAAGGAATGGGAGTTGCCGCCAGATTCTGACATGGAT<br>CTGAATCTGATTGAGCAGGCACCCCTGACCGTGGCCGAGAAGCTGCAGC<br>GCGACTTTCTGACGGAATGGCGCCGTGTGAGTAAGGCCCCGGAGGCCCT<br>TTTCTTTGTGCAATTTGAGAAGGGAGAGAGCTACTTCCACATGCACGTG<br>CTCGTGGAAACCACCGGGGTGAAATCCATGGTTTTGGGACGTTTCCTGA<br>GTCAGATTCGCGAAAAACTGATTCAGAGAATTTACCGCGGGATCGAGCC<br>GACTTTGCCAAACTGGTTCGCGGTCACAAAGACCAGAAATGGCGCCGGA<br>GGCGGGAACAAGGTGGTGGATGAGTGCTACATCCCCAATTACTTGCTCC<br>CCAAAACCCAGCCTGAGCTCCAGTGGGCGTGGACTAATATGGAACAGTA<br>TTTAAGCGCCTGTTTGAATCTCACGGAGCGTAAACGGTTGGTGGCGCAG<br>CATCTGACGCACGTGTCGCAGACGCAGGAGCAGAACAAAGAGAATCAGA<br>ATCCCAATTCTGATGCGCCGGTGATCAGATCAAAAACTTCAGCCAGGTA<br>CATGGAGCTGGTCGGGTGGCTCGTGGACAAGGGGATTACCTCGGAGAAG<br>CAGTGGATCCAGGAGGACCAGGCCTCATACATCTCCTTCAATGCGGCCT<br>CCAACTCGCGGTCCCAAATCAAGGCTGCCTTGGACAATGCGGGAAAGAT<br>TATGAGCCTGACTAAAACCGCCCCCGACTACCTGGTGGGCCAGCAGCCC<br>GTGGAGGACATTTCCAGCAATCGGATTTATAAAATTTTGGAACTAAACG<br>GGTACGATCCCCAATATGCGGCTTCCGTCTTTCTGGGATGGGCCACGAA<br>AAAGTTCGGCAAGAGGAACACCATCTGGCTGTTTGGGCCTGCAACTACC<br>GGGAAGACCAACATCGCGGAGGCCATAGCCCACACTGTGCCCTTCTACG<br>GGTGCGTAAACTGGACCAATGAGAACTTTCCCTTCAACGACTGTGTCGA<br>CAAGATGGTGATCTGGTGGGAGGAGGGGAAGATGACCGCCAAGGTCGTG<br>GAGTCGGCCAAAGCCATTCTCGGAGGAAGCAAGGTGCGCGTGGACCAGA<br>AATGCAAGTCCTCGGCCCAGATAGACCCGACTCCCGTGATCGTCACCTC<br>CAACACCAACATGTGCGCCGTGATTGACGGGAACTCAACGACCTTCGAA<br>CACCAGCAGCCGTTGCAAGACCGGATGTTCAAATTTGAACTCACCCGCC<br>GTCTGGATCATGACTTTGGGAAGGTCACCAAGCAGGAAGTCAAAGACTT<br>TTTCCGGTGGGCAAAGGATCACGTGGTTGAGGTGGAGCATGAATTCTAC<br>GTCAAAAAGGGTGGAGCCAAGAAAAGACCCGCCCCCAGTGACGCAGATA<br>TAAGTGAGCCCAAACGGGTGCGCGAGTCAGTTGCGCAGCCATCGACGTC<br>AGACGCGGAAGCTTCGATCAACTACGCAGACAGGTACCAAAACAAATGT<br>TCTCGTCACGTGGGCATGAATCTGATGCTGTTTCCCTGCAGACAATGCG<br>AGAGAATGAATCAGAATTCAAATATCTGCTTCACTCACGGACAGAAAGA<br>CTGTTTAGAGTGCTTTCCCGTGTCAGAATCTCAACCCGTTTCTGTCGTC<br>AAAAAGGCGTATCAGAAACTGTGCTACATTCATCATATCATGGGAAAGG<br>TGCCAGACGCTTGCACTGCCTGCGATCTGGTCAATGTGGATTTGGATGA<br>CTGCATCTTTGAACAATAA |
| 2XMCP-Rep<br>amino acid<br>sequence (linker-<br>2XMCP-linker-<br>Rep)<br>SEQ ID NO: 132 | MPGSSGSS*ASNFTQFVLVDNGGTGDVTVAPSNFANGIAEWISSNSRSQA*<br>*YKVTCSVRQSSAONRKYTIKVEVPKGAWRSYLNMELTIPIFATNSDCEL*<br>*IVKAMQGLLKDGNPIPSAIAANSGIYGGGGGMASNFTQFVLVDNGGTGD*<br>*VTVAPSNFANGIAEWISSNSRSQAYKVTCSVRQSSAONRKYTIKVEVPK*<br>*GAWRSYLNMELTIPIFATNSDCELIVKAMQGLLKDGNPIPSAIAANSGI*<br>*YGSSGSSG*FYEIVIKVPSDLDEHLPGISDSFVNWVAEKEWELPPDSDMD<br>LNLIEQAPLTVAEKLQRDFLTEWRRVSKAPEALFFVQFEKGESYFHMHV<br>LVETTGVKSMVLGRFLSQIREKLIQRIYRGIEPTLPNWFAVTKTRNGAG<br>GGNKVVDECYIPNYLLPKTQPELQWAWTNMEQYLSACLNLTERKRLVAQ<br>HLTHVSQTQEQNKENQNPNSDAPVIRSKTSARYMELVGWLVDKGITSEK<br>QWIQEDQASYISFNAASNSRSQIKAALDNAGKIMSLTKTAPDYLVGQQP<br>VEDISSNRIYKILELNGYDPQYAASVFLGWATKKFGKRNTIWLFGPATT<br>GKTNIAEAIAHTVPFYGCVNWTNENFPFNDCVDKMVIWWEEGKMTAKVV<br>ESAKAILGGSKVRVDQKCKSSAQIDPTPVIVTSNTNMCAVIDGNSTTFE<br>HQQPLQDRMFKFELTRRLDHDFGKVTKQEVKDFFRWAKDHVVEVEHEFY<br>VKKGGAKKRPAPSDADISEPKRVRESVAQPSTSDAEASINYADRYQNKC<br>SRHVGMNLMLFPCRQCERMNQNSNICFTHGQKDCLECFPVSESQPVSVV<br>KKAYQKLCYIHHIMGKVPDACTACDLVNVDLDDCIFEQ |
| PCP-Rep-Y156F<br>nucleic acid<br>sequence (linker-<br>PCP-linker-Rep)<br>SEQ ID NO: 133 | ATGCCCGGCAGCTCCGGCAGTAGC*TCCAAAACAATAGTCCTCTCCGTAG*<br>*GGGAGGCAACACGGACTTTGACCGAAATCCAGTCAACCGCTGACCGACA*<br>*AATCTTTGAAGAGAAAGTAGGGCCTCTTGTGGGCCGACTGCGCTTGACT*<br>*GCAAGCTTGCGACAAAACGGCGCAAAGACTGCCTATAGGGTCAACCTTA*<br>*AACTCGACCAAGCCGACGTGGTCGATAGCGGTCTCCCTAAGGTTCGGTA*<br>*TACGCAGGTCTGGAGTCATGACGTAACAATCGTAGCAAACAGCACAGAA*<br>*GCCTCCCGAAAAAGCCTCTACGATCTGACGAAATCCTTGGTGGCTACGT*<br>*CACAGGTGGAAGACCTCGTTGTCAACCTTGTACCTCTGGGTCGA*GGCAG<br>TAGTGGGTCCTCTGGGTTTTACGAGATTGTGATTAAGGTCCCCAGCGAC<br>CTTGACGAGCATCTGCCCGGCATTTCTGACAGCTTTGTGAACTGGGTGG<br>CCGAGAAGGAATGGGAGTTGCCGCCAGATTCTGACATGGATCTGAATCT<br>GATTGAGCAGGCACCCCTGACCGTGGCCGAGAAGCTGCAGCGCGACTTT<br>CTGACGGAATGGCGCCGTGTGAGTAAGGCCCCGGAGGCCCTTTTCTTTG |

TABLE C-continued

Nucleic Acid Sequence and Amino Acid Sequence of Rep proteins

| Rep proteins | Sequences |
|---|---|
| | TGCAATTTGAGAAGGGAGAGAGCTACTTCCACATGCACGTGCTCGTGGA<br>AACCACCGGGGTGAAATCCATGGTTTTGGGACGTTTCCTGAGTCAGATT<br>CGCGAAAAACTGATTCAGAGAATTTACCGCGGGATCGAGCCGACTTTGC<br>CAAACTGGTTCGCGGTCACAAAGACCAGAAATGGCGCCGGAGGCGGGAA<br>CAAGGTGGTGGATGAGTGCTACATCCCCAATTTCTTGCTCCCCAAAACC<br>CAGCCTGAGCTCCAGTGGGCGTGGACTAATATGGAACAGTATTTAAGCG<br>CCTGTTTGAATCTCACGGAGCGTAAACGGTTGGTGGCGCAGCATCTGAC<br>GCACGTGTCGCAGACGCAGGAGCAGAACAAAGAGAATCAGAATCCCAAT<br>TCTGATGCGCCGGTGATCAGATCAAAAACTTCAGCCAGGTACATGGAGC<br>TGGTCGGGTGGCTCGTGGACAAGGGGATTACCTCGGAGAAGCAGTGGAT<br>CCAGGAGGACCAGGCCTCATACATCTCCTTCAATGCGGCCTCCAACTCG<br>CGGTCCCAAATCAAGGCTGCCTTGGACAATGCGGGAAAGATTATGAGCC<br>TGACTAAAACCGCCCCCGACTACCTGGTGGGCCAGCAGCCCGTGGAGGA<br>CATTTCCAGCAATCGGATTTATAAAATTTTGGAACTAAACGGGTACGAT<br>CCCCAATATGCGGCTTCCGTCTTTCTGGGATGGGCCACGAAAAAGTTCG<br>GCAAGAGGAACACCATCTGGCTGTTTGGGCCTGCAACTACCGGGAAGAC<br>CAACATCGCGGAGGCCATAGCCCACACTGTGCCCTTCTACGGGTGCGTA<br>AACTGGACCAATGAGAACTTTCCCTTCAACGACTGTGTCGACAAGATGG<br>TGATCTGGTGGGAGGAGGGGAAGATGACCGCCAAGGTCGTGGAGTCGGC<br>CAAAGCCATTCTCGGAGGAAGCAAGGTGCGCGTGGACCAGAAATGCAAG<br>TCCTCGGCCCAGATAGACCCGACTCCCGTGATCGTCACCTCCAACACCA<br>ACATGTGCGCCGTGATTGACGGGAACTCAACGACCTTCGAACACCAGCA<br>GCCGTTGCAAGACCGGATGTTCAAATTTGAACTCACCCGCCGTCTGGAT<br>CATGACTTTGGGAAGGTCACCAAGCAGGAAGTCAAAGACTTTTTCCGGT<br>GGGCAAAGGATCACGTGGTTGAGGTGGAGCATGAATTCTACGTCAAAAA<br>GGGTGGAGCCAAGAAAAGACCCGCCCCCAGTGACGCAGATATAAGTGAG<br>CCCAAACGGGTGCGCGAGTCAGTTGCGCAGCCATCGACGTCAGACGCGG<br>AAGCTTCGATCAACTACGCAGACAGGTACCAAAACAAATGTTCTCGTCA<br>CGTGGGCATGAATCTGATGCTGTTTCCCTGCAGACAATGCGAGAGAATG<br>AATCAGAATTCAAATATCTGCTTCACTCACGGACAGAAAGACTGTTTAG<br>AGTGCTTTCCCGTGTCAGAATCTCAACCCGTTTCTGTCGTCAAAAAGGC<br>GTATCAGAAACTGTGCTACATTCATCATATCATGGGAAAGGTGCCAGAC<br>GCTTGCACTGCCTGCGATCTGGTCAATGTGGATTTGGATGACTGCATCT<br>TTGAACAATAA |
| PCP-Rep-Y156F<br>amino acid<br>sequence (linker-<br>PCP-linker-Rep)<br>SEQ ID NO: 134 | MPGSSGSS*SKTIVLSVGEATRTLTEIQSTADRQIFEEKVGPLVGRLRLT<br>ASLRQNGAKTAYRVNLKLDQADVVDSGLPKVRYTQVWSHDVTIVANSTE<br>ASRKSLYDLTKSLVATSQVEDLVVNLVPLGR*GSSGSSGFYEIVIKVPSD<br>LDEHLPGISDSFVNWVAEKEWELPPDSDMDLNLIEQAPLTVAEKLQRDE<br>LTEWRRVSKAPEALFFVQFEKGESYFHMHVLVETTGVKSMVLGRELSQI<br>REKLIQRIYRGIEPTLPNWFAVTKTRNGAGGGNKVVDECYIPN*F*LLPKT<br>QPELQWAWINMEQYLSACLNLTERKRLVAQHLTHVSQTQEQNKENQNPN<br>SDAPVIRSKTSARYMELVGWLVDKGITSEKQWIQEDQASYISENAASNS<br>RSQIKAALDNAGKIMSLIKTAPDYLVGQQPVEDISSNRIYKILELNGYD<br>PQYAASVFLGWATKKFGKRNTIWLFGPATTGKINIAEAIAHTVPFYGCV<br>NWTNENFPFNDCVDKMVIWWEEGKMTAKVVESAKAILGGSKVRVDQKCK<br>SSAQIDPTPVIVTSNTNMCAVIDGNSTTFEHQQPLQDRMEKFELTRRLD<br>HDFGKVTKQEVKDFFRWAKDHVVEVEHEFYVKKGGAKKRPAPSDADISE<br>PKRVRESVAQPSTSDAEASINYADRYQNKCSRHVGMNLMLFPCRQCERM<br>NQNSNICFTHGQKDCLECFPVSESQPVSVVKKAYQKLCYIHHIMGKVPD<br>ACTACDLVNVDLDDCIFEQ |
| COM-Rep-Y156F<br>nucleic acid<br>sequence (linker-<br>COM-linker-Rep)<br>SEQ ID NO: 135 | ATGCCCGGCAGCTCCGGCAGTAGC*ATGAAATCAATTCGCTGTAAAAACT<br>GCAACAAACTGTTATTTAAGGCGGATTCCTTTGATCACATTGAAATCAG<br>GTGTCCGCGTTGCAAACGTCACATCATAATGCTGAATGCCTGCGAGCAT<br>CCCACGGAGAAACATTGTGGGAAAAGAGAAAAAATCACGCATTCTGACG<br>AAACCGTGCGTTAT*GGCAGTAGTGGGTCCTCTGGGTTTTACGAGATTGT<br>GATTAAGGTCCCCAGCGACCTTGACGAGCATCTGCCCGGCATTTCTGAC<br>AGCTTTGTGAACTGGGTGGCCGAGAAGGAATGGGAGTTGCCGCCAGATT<br>CTGACATGGATCTGAATCTGATTGAGCAGGCACCCCTGACCGTGGCCGA<br>GAAGCTGCAGCGCGACTTTCTGACGGAATGGCGCCGTGTGAGTAAGGCC<br>CCGGAGGCCCTTTTCTTTGTGCAATTTGAGAAGGGAGAGAGCTACTTCC<br>ACATGCACGTGCTCGTGGAAACCACCGGGGTGAAATCCATGGTTTTGGG<br>ACGTTTCCTGAGTCAGATTCGCGAAAAACTGATTCAGAGAATTTACCGC<br>GGGATCGAGCCGACTTTGCCAAACTGGTTCGCGGTCACAAAGACCAGAA<br>ATGGCGCCGGAGGCGGGAACAAGGTGGTGGATGAGTGCTACATCCCCAA<br>T*TTC*TTGCTCCCCAAAACCCAGCCTGAGCTCCAGTGGGCGTGGACTAAT<br>ATGGAACAGTATTTAAGCGCCTGTTTGAATCTCACGGAGCGTAAACGGT<br>TGGTGGCGCAGCATCTGACGCACGTGTCGCAGACGCAGGAGCAGAACAA<br>AGAGAATCAGAATCCCAATTCTGATGCGCCGGTGATCAGATCAAAAACT<br>TCAGCCAGGTACATGGAGCTGGTCGGGTGGCTCGTGGACAAGGGGATTA<br>CCTCGGAGAAGCAGTGGATCCAGGAGGACCAGGCCTCATACATCTCCTT<br>CAATGCGGCCTCCAACTCGCGGTCCCAAATCAAGGCTGCCTTGGACAAT<br>GCGGGAAAGATTATGAGCCTGACTAAAACCGCCCCCGACTACCTGGTGG<br>GCCAGCAGCCCGTGGAGGACATTTCCAGCAATCGGATTTATAAAATTTT<br>GGAACTAAACGGGTACGATCCCCAATATGCGGCTTCCGTCTTTCTGGGA |

TABLE C-continued

Nucleic Acid Sequence and Amino Acid Sequence of Rep proteins

| Rep proteins | Sequences |
| --- | --- |
| | TGGGCCACGAAAAAGTTCGGCAAGAGGAACACCATCTGGCTGTTTGGGC<br>CTGCAACTACCGGGAAGACCAACATCGCGGAGGCCATAGCCCACACTGT<br>GCCCTTCTACGGGTGCGTAAACTGGACCAATGAGAACTTTCCCTTCAAC<br>GACTGTGTCGACAAGATGGTGATCTGGTGGGAGGAGGGGAAGATGACCG<br>CCAAGGTCGTGGAGTCGGCCAAAGCCATTCTCGGAGGAAGCAAGGTGCG<br>CGTGGACCAGAAATGCAAGTCCTCGGCCCAGATAGACCCGACTCCCGTG<br>ATCGTCACCTCCAACACCAACATGTGCGCCGTGATTGACGGGAACTCAA<br>CGACCTTCGAACACCAGCAGCCGTTGCAAGACCGGATGTTCAAATTTGA<br>ACTCACCCGCCGTCTGGATCATGACTTTGGGAAGGTCACCAAGCAGGAA<br>GTCAAAGACTTTTTCCGGTGGGCAAAGGATCACGTGGTTGAGGTGGAGC<br>ATGAATTCTACGTCAAAAAGGGTGGAGCCAAGAAAAGACCCGCCCCCAG<br>TGACGCAGATATAAGTGAGCCCAAACGGGTGCGCGAGTCAGTTGCGCAG<br>CCATCGACGTCAGACGCGGAAGCTTCGATCAACTACGCAGACAGGTACC<br>AAAACAAATGTTCTCGTCACGTGGGCATGAATCTGATGCTGTTTCCCTG<br>CAGACAATGCGAGAGAATGAATCAGAATTCAAATATCTGCTTCACTCAC<br>GGACAGAAAGACTGTTTAGAGTGCTTTCCCGTGTCAGAATCTCAACCCG<br>TTTCTGTCGTCAAAAAGGCGTATCAGAAACTGTGCTACATTCATCATAT<br>CATGGGAAAGGTGCCAGACGCTTGCACTGCCTGCGATCGGTCAATGTG<br>GATTTGGATGACTGCATCTTTGAACAATAA |
| COM-Rep-Y156F<br>amino acid<br>sequence (linker-<br>COM-linker-Rep)<br>SEQ ID NO: 136 | MPGSSGSS*MKSIRCKNCNKLLFKADSFDHIEIRCPRCKRHIIMLNACEH*<br>*PTEKHCGKREKITHSDETVRY*GSSGSSGFYEIVIKVPSDLDEHLPGISD<br>SFVNWVAEKEWELPPDSDMDLNLIEQAPLTVAEKLQRDFLTEWRRVSKA<br>PEALFFVQFEKGESYFHMHVLVETTGVKSMVLGRELSQIREKLIQRIYR<br>GIEPTLPNWFAVTKTRNGAGGGNKVVDECYIPN*F*LLPKTQPELQWAWTN<br>MEQYLSACLNLTERKRLVAQHLTHVSQTQEQNKENQNPNSDAPVIRSKT<br>SARYMELVGWLVDKGITSEKQWIQEDQASYISFNAASNSRSQIKAALDN<br>AGKIMSLIKTAPDYLVGQQPVEDISSNRIYKILELNGYDPQYAASVFLG<br>WATKKFGKRNTIWLFGPATTGKTNIAEAIAHTVPFYGCVNWTNENFPFN<br>DCVDKMVIWWEEGKMTAKVVESAKAILGGSKVRVDQKCKSSAQIDPTPV<br>IVTSNTNMCAVIDGNSTTFEHQQPLQDRMFKFELTRRLDHDFGKVTKQE<br>VKDFFRWAKDHVVEVEHEFYVKKGGAKKRPAPSDADISEPKRVRESVAQ<br>PSTSDAEASINYADRYQNKCSRHVGMNLMLFPCRQCERMNQNSNICFTH<br>GQKDCLECFPVSESQPVSVVKKAYQKLCYIHHIMGKVPDACTACDLVNV<br>DLDDCIFEQ |

* Sequence elements are matched based on formatting styles (e.g., double underline, bold, and/or italic fonts, etc.)

TABLE D

Nucleic Acid Sequence and Amino Acid Sequence of AAP and MCP fusion proteins

| AAP and MCP fusion proteins | Sequences |
| --- | --- |
| MCP-AAP(DJ)<br>nucleic acid<br>sequence (linker-<br>MCP-linker-<br>AAP) SEQ ID NO: 137 | ATG<u>GGCAGCTCCGGCAGTAGC</u>*GCTTCTAACTTTACTCAGTTCGTTCTCG*<br>*TCGACAATGGCGGAACTGGCGACGTGACTGTCGCCCCAAGCAACTTCGC*<br>*TAACGGGGTCGCTGAATGGATCAGCTCTAACTCGCGTTCACAGGCTTAC*<br>*AAAGTAACCTGTAGCGTTCGTCAGAGCTCTGCGCAGAATCGCAAATACA*<br>*CCATCAAAGTCGAGGTGCCTAAAGTGGCAACCCAGACTGTTGGTGGAGT*<br>*AGAGCTTCCTGTAGCCGCATGGCGTTCGTACTTAAATATGGAACTAACC*<br>*ATTCCAATTTTCGCTACGAATTCCGACTGCGAGCTTATTGTTAAGGCAA*<br>*TGCAAGGTCTCCTAAAAGATGGAAACCCGATTCCCTCAGCAATCGCAGC*<br>*AAACTCCGGCATCTAC*<u>GGCAGTAGTGGGTCCTCT</u>CTGGAGACGCAGACT<br>CAGTCCCAGACCCTCAACCAATCGGAGAACCTCCCGCAGCCCCCTCAGG<br>TGTGGGATCTCTTACAATGGCTGCAGGCGGTGGCGCACCAATGGCAGAC<br>AATAACGAGGGCGCCGACGGAGTGGGTAATTCCTCGGGAAATTGGCATT<br>GCGATTCCACATGGATGGGCGACAGAGTCATCACCACCAGCACCCGAAC<br>CTGGGCCCTGCCCACCTACAACAACCACCTCTACAAGCAAATCTCCAAC<br>AGCACATCTGGAGGATCTTCAAATGACAACGCCTACTTCGGCTACAGCA<br>CCCCCTGGGGGTATTTTGACTTTAACAGATTCCACTGCCACTTTTCACC<br>ACGTGACTGGCAGCGACTCATCAACAACAACTGGGGATTCCGGCCCAAG<br>AGACTCAGCTTCAAGCTCTTCAACATCCAGGTCAAGGAGGTCACGCAGA<br>ATGAAGGCACCAAGACCATCGCCAATAACCTCACCAGCACCATCCAGGT<br>GTTTACGGACTCGGAGTACCAGCTGCCGTACGTTCTCGGCTCTGCCCAC<br>CAGGGCTGCCTGCCTCCGTTCCCGGCGGACGTGTTCATGA |
| MCP-AAP(DJ)<br>amino acid<br>sequence (linker-<br>MCP-linker-<br>AAP) SEQ ID NO: 138 | <u>MGSSGSS</u>*ASNFTQFVLVDNGGTGDVTVAPSNFANGVAEWISSNSRSQAY*<br>*KVTCSVRQSSAQNRKYTIKVEVPKVATQTVGGVELPVAAWRSYLNMELT*<br>*IPIFATNSDCELIVKAMQGLLKDGNPIPSAIAANSGIY*<u>GSSGSS</u>LETQT<br>QSQTLNQSENLPQPPQVWDLLQWLQAVAHQWQTITRAPTEWVIPREIGI<br>AIPHGWATESSPPAPEPGPCPPTTTTSTSKSPTAHLEDLQMTTPTSATA |

TABLE D-continued

Nucleic Acid Sequence and Amino Acid Sequence of AAP and MCP fusion proteins

| AAP and MCP fusion proteins | Sequences |
|---|---|
| | PPGGILTLTDSTATFHHVTGSDSSTTTGDSGPRDSASSSSTSRSRRSRR MKAPRPSPITSPAPSRCLRTRSTSCRTFSALPTRAACLRSRRTCS |
| AAP-MCP(DJ) nucleic acid sequence (AAP-linker-MCP-linker) SEQ ID NO: 139 | ATGCTGGAGACGCAGACTCAGTCCCAGACCCTCAACCAATCGGAGAACC TCCCGCAGCCCCCTCAGGTGTGGGATCTCTTACAATGGCTGCAGGCGGT GGCGCACCAATGGCAGACAATAACGAGGGCGCCGACGGAGTGGGTAATT CCTCGGGAAATTGGCATTGCGATTCCACATGGATGGGCGACAGAGTCAT CACCACCAGCACCCGAACCTGGGCCCTGCCCACCTACAACAACCACCTC TACAAGCAAATCTCCAACAGCACATCTGGAGGATCTTCAAATGACAACG CCTACTTCGGCTACAGCACCCCCTGGGGGTATTTTGACTTTAACAGATT CCACTGCCACTTTTCACCACGTGACTGGCAGCGACTCATCAACAACAAC TGGGGATTCCGGCCCAAGAGACTCAGCTTCAAGCTCTTCAACATCCAGG TCAAGGAGGTCACGCAGAATGAAGGCACCAAGACCATCGCCAATAACCT CACCAGCACCATCCAGGTGTTTACGGACTCGGAGTACCAGCTGCCGTAC GTTCTCGGCTCTGCCCACCAGGGCTGCCTGCCTCCGTTCCCGGCGGACG TGTTCA<u>GGCAGCTCCGGCAGTAGG</u>*GCTTCTAACTTTACTCAGTTCGTTC TCGTCGACAATGGCGGAACTGGCGACGTGACTGTCGCCCCAAGCAACTT CGCTAACGGGGTCGCTGAATGGATCAGCTCTAACTCGCGTTCACAGGCT TACAAAGTAACCTGTAGCGTTCGTCAGAGCTCTGCGCAGAATCGCAAAT ACACCATCAAAGTCGAGGTGCCTAAAGTGGAACCCAGACTGTTGGTGG AGTAGAGCTTCCTGTAGCCGCATGGCGTTCGTACTTAAATATGGAACTA ACCATTCCAATTTTCGCTACGAATTCCGACTGCGAGCTTATTGTTAAGG CAATGCAAGGTCTCCTAAAAGATGGAAACCCGATTCCCTCAGCAATCGC AGCAAACTCCGGCATCTAC*<u>GGCAGTAGTGGGTCCTCTTGA</u> |
| AAP-MCP(DJ) amino acid sequence (AAP-linker-MCP-linker) SEQ ID NO: 140 | MLETQTQSQTLNQSENLPQPPQVWDLLQWLQAVAHQWQTITRAPTEWVI PREIGIAIPHGWATESSPPAPEPGPCPPTTTSTSKSPTAHLEDLQMTT PTSATAPPGGILTLTDSTATFHHVTGSDSSTTTGDSGPRDSASSSSTSR SRRSRRMKAPRPSPITSPAPSRCLRTRSTSCRTFSALPTRAACLRSRRT CS<u>GSSGSS</u>*ASNFTQFVLVDNGGTGDVTVAPSNFANGVAEWISSNSRSQA YKVTCSVRQSSAQNRKYTIKVEVPKVATQTVGGVELPVAAWRSYLNMEL TIPIFATNSDCELIVKAMQGLLKDGNPIPSAIAANSGIY*<u>GSSGSS</u> |

* Sequence elements are matched based on formatting styles (e.g., double underline, bold and/or italic fonts, etc.)

TABLE E

Primer sequences

| Primer | Sequences |
|---|---|
| WPRE-F SEQ ID NO: 141 | CCCGTATGGCTTTCATTTTCTCC |
| WPRE-R SEQ ID NO: 142 | GGCAATGCCCCAACCAGTG |
| Cre-F SEQ ID NO: 143 | CCAGTAGATGCCACTAGCGA |
| Cre-R SEQ ID NO: 144 | GCCTGGAGATACAGCAGGTA |
| CAG-F SEQ ID NO: 145 | CTTCTCCTCCGGGCTGTAAT |
| CAG-R SEQ ID NO: 146 | CTTTCACGCAGCCACAGAAA |

* F and R stand for forward and reverse primers, respectively.

TABLE F

Stuffer sequence

| Stuffer | Sequences |
|---|---|
| Stuffer nucleic acid sequence SEQ ID NO: 147 | ATATTTGGAGGGCAGCTTGATTTCGACTTCGGGAGGGAAGCTGCGCCAT GCGATGTTATCGGTGCGGTGAATGCAAAGAAGATAACCGCTTCCGACCA AATCAACCTTACTGGAATCGATGGTGTCTCCGGTGTGAAAGAACACCAA CAGGGGTGTTACCACTACCGCAGGAAAAGGAGGACGTGCCGCGAGACAG CGACGAAGTATCACCGACATAATCTGCGAAAACTGCAAATACCTTCCAA CGAAACGCCACCAGAAATAAACCCAAGCCAATCCCAAAAGAATCTGACGT AAAAACCTTCAACTACACGGCTCACCTGTGGGATATCCGGTGGCTAAGA CGTCGTGCGAGGAAAACAAGGCCATTGACCAAAATCGAAGTTACGAACA AGAAAGCGTCGAGCGAGCTTAACGTGCGCTAACTGCCGGTCAGAAGCTG CATGTGCTGGAAGTTCACGTGTGTGAGCACTGCTGCGCAGAACTGATGA GCGATCCGAATAGCTCGATGCACGAGGAAGAAGGCCGCCGCTAAACCAG CGCGAAGACGATGTAAAAACGATGAATGCCGGGAATGGTTTCACCCTGC |

TABLE F-continued

Stuffer sequence

| Stuffer | Sequences |
|---|---|
| | ATTCGCTAATCAGTGGTGGTGCTCTCCAGAGTGTGGAACCAAGATAGCA
CTCGAACGACGAAGTAAAGAACGCGAAAAAGCGGAAAAAGCAGCAGAGA
AGAAACGACGACGAGAGGAGCAGAAACAGAAAGATAAACTTAAGATTCG
AAAACTCGCCTTAAAGCCCCGCAGTTACTGGATTAAACAAGCCCAACAA
GCCGTAAACGCCTTCATCAGAGAAAGAGACCGCGACTTACCATGTATCT
CGTGCGGAACGCTCACGTCTGCTCAGTGGGATGCCGGACATTACCGGAC
AACTGCTGCGGCACCTCAACTCCGATTTAATGAACGCAATATTCACAAG
CAATGCGTGGTGTGCAACCAGCACAAAAGCGGAAATCTCGTTCCGTATC
GCGTCGAACTGATTAGCCGCATCGGGCAGGAAGCAGTAGACGAAATCGA
ATCAAACCATAACCGCCATCGCTGGACTATCGAAGAGTGCAAGGCGATC
AAGGCAGAGTACCAACAGAAACTCAAAGACCTGCGAAATAGCAGAAGTG
AGGCCGCGCCACGTTCTCAGTAAAAACCATTCCAGACATGCTCGTTGAA
GCATACGGAAATCAGACAGAAGTAGCACGCAGACTGAAATGTAGTCGCG
GTACGGTCAGAAAATACGTTGATGATAAAGACGGGAAAATGCACGCCAT
CGTCAACGACGTTCTCATGGTTCATCGCGGATGGAGTGAAAGAGGCCCG
CTATTACGAAAAAATTGATGGCAGCAAATACCGAAATATTTGGGTAGTT
GGCGATCTGCACGGATGCTACACGAACCTGATGAACAAACTGGATACGA
TTGGATTCGACAACAAAAAAGACCTGCTTATCTCGGTGGGCGATTTGGT
TGATCGTGGTGCAGAGAACGTTGAATGCCTGGAATTAATCACATTCCCC
TGGTTCAGAGCTGTACGTGGAAACCATGAGCAAATGATGATTGATGGCT
TATCAGAGCGTGGAAACGTTAATCACTGGCTGCTTAATGGCGGTGGCTG
GTTCTTTAATCTCGATTACGACAAAGAAATTCTGGCTAAAGCTCTTGCC
CATAAAGCAGATGAACTTCCGTTAATCATCGAACTGGTGAGCAAAGATA
AAAAATATGTTATCTGCCACGCCGATTATCCCTTTGACGAATACGAGTT
TGGAAAGCCAGTTGATCATCAGCAGGTAATCTGGAACCGCGAACGAATC
AGCAACTCACAAAACGGGATCGTGAAAGAAATCAAAGGCGCGGACACGT
TCATCTTTGGTCATACGCCAGCAGTGAAACCACTCAAGTTTGCCAACCA
AATGTATATCGATACCGGCGCAGTGTTCTGCGGAAACCTAACATTGATT
CAGGTACAGGGAGAAGGCGCGCCAGACTCGAAAGCGTAGCTAAATTTCA
TTCGCCAAAAAGCCCGATGATGAGCGACTCACCACGGGCCACGGCTTCT
GACTCTCTTTCCGGTACTGATGTGATGGCTGCTATGGGGATGGCGCAAT
CACAAGCCGGATTCGGTATGGCTGCATTCTGCGGTAAGCACGAACTCAG
CCAGAACGACAAACAAAAGGCTATCAACTATCTGATGCAATTTGCACAC
AAGGTATCGGGGAAATACCGTGGTGTGGCAAAGCTTGAAGGAAATACTA
AGGCAAAGGTACTGCAAGTGCTCGCAACATTCGCTTATGCGGATTATTG
CCGTAGTGCCGCGACGCCGGGGGCAAGATGCAGAGATTGCCATGGTACA
GGCCGTGCGGTTGATATTGCCAAAACAGAGCTGTGGGGGAGAGTTGTCG
AGAAAGAGTGCGGAAGATGCAAAGGCGTCGGCTATTCAAGGATGCCAGC
AAGCGCAGCATATCGCGCTGTGACGATGCTAATCCCAAACCTTACCCAA
CCCACCTGGTCACGCACTGTTAAGCCGCTGTATGACGCTCTGGTGGTGC
AATGCCACAAAGAAGAGTCAATCGCAGACAACATTTTGAATGCGGTCAC
ACGTTAGCAGCATGATTGCCACGGATGGCAACATATTAACGGCATGATA
TTGACTTATTGAATAAAATTGGGTAAATTTGACTCAACGATGGGTTAAT
TCGCTCGTTGTGGTAGTGAGGCCAAAAGAGGCGGCGCTTACTACCGATT
CCGCCTAGTTGGTCACTTCGACGTATCGTCTGGAACTCCAACCATCGCA
GGCAGAGAGGTCTGCAAAATGCAATCCCGAAACAGTTCGCAGGTAATAG
TTAGAGCCTGCATAACGGTTTCGGGATTTTTTATATCTGCACAACAGGT
AAGAGCATTGAGTCGATAATCGTGAAGAGTCGGCGAGCCTGGTTAGCCA
GTGCTCTTTCCGTTGTGCTGAATTAAGCGAATACCGGAAGCAGAACCGG
ATCACCAAATGCGTACAGGCGTCATCGCCGCCCAGCAACAGCACAACCC
AAACTGAGCCGTAGCCACTGTCTGTCCTAAATTCATTAGTAATAGTTAC
GCTGCGCCTTTTACACATGACCTTCGTGAAAGCGGGTGGCAGGAGGTC
GCGCTAACAACCTCCTGCCGTTTTGCCCGTGCATATCGGTCACGAACAA
ATCTGATTACTAAACACAGTAGCCTGGATTTGTTCTATCAGTAATCGAC
CTTATTCCTAATTAAATAGAGCAAATCCCCTT |

INCORPORATION BY REFERENCE

The entire disclosure of each of the patent documents, including patent application documents, scientific articles, governmental reports, websites, and other references referred to herein is incorporated by reference herein in its entirety for all purposes. In case of a conflict in terminology, the present specification controls. All sequence listings, or SEQ ID NOs. disclosed herein are incorporated herein in their entirety.

The following references, to the extent that they provide exemplary procedural or other details supplementary to those set forth herein, are specifically incorporated herein by reference.

Although illustrative embodiments of the present invention have been described herein, it should be understood that the invention is not limited to those described, and that various other changes or modifications may be made by one skilled in the art without departing from the scope or spirit of the invention.

The invention claimed is:

1. A ribonucleotide (RNA) sequence capable of being packaged into a DNA virus viral particle, wherein said RNA sequence comprises:
    (1) an RNA sequence of interest (RSI); and,
    (2) an RNA-packaging signal (RPS) capable of binding directly or indirectly to an RPS-interacting molecule that facilitates packaging of the RNA sequence into the DNA virus viral particle.

2. The RNA sequence of claim 1, wherein the RPS is located at or near the 5' end of the RSI, at or near the 3' end of the RSI, or internal to the RSI.

3. The RNA sequence of claim 1, comprising more than one RPS that are identical or different, and wherein two or more of said more than one RPS are
    (1) adjacent to each other, or are in tandem, via the same or different linkers; or
    (2) not adjacent to each other.

4. The RNA sequence of claim 1, wherein the DNA virus viral particle is an AAV viral particle, and wherein the RPS comprises a transcribed modified AAV inverted terminal repeat (ITR), wherein said transcribed modified AAV ITR:
    (a) comprises a transcribed functional Rep-Binding Element (RBE); and,
    (b) lacks either a transcribed terminal resolution site (TRS), or a transcribed reverse complement TRS (rc-TRS), or both.

5. The RNA sequence of claim 4, wherein the transcribed modified AAV ITR is modified from a transcribed wild-type flip or flop ITR.

6. The RNA sequence of claim 5, wherein said wild-type flop ITR has the nucleotide sequence of SEQ ID NO: 1.

7. The RNA sequence of claim 5, wherein the wild-type flip or flop ITR is from AAV1, AAV2, AAV3A, AAV3B, AAV4, AAV5, AAV6, AAV7, AAVrh74, AAV8, AAV9, AAV10, AAV11, AAV12, or AAV13.

8. The RNA sequence of claim 4, wherein the transcribed modified AAV ITR comprises the transcribed D region sequence, or wherein the transcribed modified AAV ITR lacks the transcribed D region sequence.

9. The RNA sequence of claim 8, wherein said transcribed modified AAV ITR has the nucleotide sequence of SEQ ID NO: 2.

10. The RNA sequence of claim 8, wherein said transcribed modified AAV ITR has the nucleotide sequence of SEQ ID NO: 3.

11. The RNA sequence of claim 4, further comprising a second transcribed modified AAV ITR having a second transcribed functional RBE sequence but lacking either a second transcribed terminal resolution site (TRS or a second transcribed reverse complement TRS (rcTRS) or both.

12. The RNA sequence of claim 11, wherein the second transcribed modified AAV ITR is within 5' end 1000 nucleotides, 800 nucleotides, 500 nucleotides, 250 nucleotides, or 150 nucleotides of the RNA sequence.

13. The RNA sequence of claim 11, wherein the second transcribed modified AAV ITR further comprises a second transcribed D region sequence.

14. The RNA sequence of claim 4, wherein said transcribed modified AAV ITR further comprises a transcribed functional RBE'.

15. The RNA sequence of claim 14, wherein the protein component of the viral packaging system for the DNA virus viral particle comprises Rep78 and/or Rep68 of adeno-associated virus 2 (AAV2), or an assembly-activating protein (AAP).

16. The RNA sequence of claim 4, wherein said transcribed modified AAV ITR further comprises a transcribed D region sequence.

17. The RNA sequence of claim 4, wherein the RPS-interacting molecule is Rep78, Rep68, Rep52, and/or Rep40.

18. The RNA sequence of claim 1, wherein the RPS comprises an MS2 sequence, an PP7 binding site, or a com binding site, and the RPS-interacting molecule comprises an RPS-interacting protein (RPSIP) capable of binding directly or indirectly to the RPS.

19. The RNA sequence of claim 18, wherein:
    (a) the RPS comprises the MS2 sequence, and the RPSIP comprises a bacteriophage MS2 coat protein (MCP);

(b) the RPS comprises the PP7 binding site, and the RPSIP comprises a PP7 bacteriophage coat protein (PCP); or, (c) The RPS comprises the com binding site, and the RPSIP comprises a phage COM protein (COM).

20. The RNA sequence of claim 18, wherein the RPSIP is associated directly or indirectly with a protein component of the viral packaging system for the DNA virus viral particle.

21. The RNA sequence of claim 1, which is a single-stranded RNA less than about 8,900 nucleotides in length, less than about 8,000 nucleotides in length, less than about 7,000 nucleotides in length, less than about 6,000 nucleotides in length, less than about 5,200 nucleotides in length, less than about 4,000 nucleotides in length, less than about 3,000 nucleotides in length, less than about 2,000 nucleotides in length, about 4,700-5,200 nucleotides in length, about 4,700-5,000 nucleotide in length, about 4,700-4,800 nucleotides in length, or about 4,700 nucleotides in length.

22. The RNA sequence of claim 1, wherein said RNA sequence of interest is an RNA coding sequence for a gene of interest (GOI), a protein-encoding RNA, a non-coding functional RNA, or a precursor thereof.

23. The RNA sequence of claim 22, wherein the gene of interest (GOI) encodes a protein, an enzyme, a structural protein, an mRNA, a non-coding RNA (ncRNA), an siRNA, a piRNA, a short hairpin RNA or shRNA, a microRNA (miRNA) or a precursor thereof, a ribosomal RNA (rRNA), an antisense sequence or oligonucleotide (ASO), an RNA component of a CRISPR-Cas system, an rRNA, a tRNA, a snoRNA, a snRNA, an exRNA, a scaRNA, a lncRNA, an X inactive specific transcript (Xist), or a HOX transcript antisense RNA (HOTAIR).

24. The RNA sequence of claim 22, wherein the protein-encoding RNA encodes a therapeutic protein, an antigen protein, or a gene-editing protein.

25. The RNA sequence of claim 24, wherein the gene-editing protein is a CRISPR/Cas effector enzyme, a ZFN protein, or a TALEN protein.

26. The RNA sequence of claim 22, wherein the non-coding functional RNA is a transfer RNA (tRNA), a ribosomal RNA (rRNA), a small interfering RNA (siRNA), a short hairpin RNA (shRNA), an antisense RNA, an antisense oligonucleotide, a micro RNA (miRNA), or an RNA component of a CRISPR-Cas system.

27. The RNA sequence of claim 26, wherein the CRISPR-Cas system comprises Cas9, Cas12, or Cas13.

28. The RNA sequence of claim 26, wherein the RNA component of the CRISPR-Cas system comprises a guide RNA (gRNA), a CRISPR RNA (crRNA), and/or a tracr RNA.

29. The RNA sequence of claim 23, wherein said protein is a fluorescent protein, a therapeutic protein, an antigen protein, or a gene-editing protein.

30. The RNA sequence of claim 23, wherein said enzyme is a Cre protein, or a CRISPR/Cas effector enzyme.

31. The RNA sequence of claim 23, wherein said RNA component of the CRISPR-Cas system includes a guide RNA (gRNA), a CRISPR RNA (crRNA), and/or a tracr RNA.

32. The RNA sequence of claim 1, wherein the DNA virus viral particle is an AAV viral particle or an oncolytic viral particle.

33. The RNA sequence of claim 32, wherein the AAV viral particle comprises a capsid from an AAV of the serotype AAV1, AAV2, AAV3A, AAV3B, AAV4, AAV5, AAV6, AAV7, AAVrh74, AAV8, AAV9, AAV10, AAV11, AAV12, AAV13, AAV-DJ, AAV PHP.eB, Anc80L65, Anc80L65AAP, or 7m8.

34. The RNA sequence of claim 1, further comprising:
(1) a transcribed transcription enhancer;
(2) a transcribed intron sequence or exon sequence;
(3) a 5' UTR sequence;
(4) a 3' UTR sequence;
(5) a polyA sequence, or a polyadenylation (polyA) signal sequence, and optionally a GU-rich region downstream of the polyA signal sequence;
(6) a posttranscriptional regulatory element or sequence; and/or,
(7) a transcription termination sequence.

35. The RNA sequence of claim 34, comprising, in 5' to 3' orientation, the RSI, an optional transcribed woodchuck hepatitis virus posttranscriptional regulatory element (WPRE) sequence, the RPS, and the polyA sequence or the polyA signal sequence.

36. The RNA sequence of claim 34, wherein the RNA sequence comprises an RPS located 3' to the posttranscriptional regulatory element or sequence, and 5' to the polyA sequence or the polyA signal sequence.

37. The RNA sequence of claim 1, wherein a DNA sequence encoding or corresponding to said RNA sequence, or a reverse complement of said DNA sequence, has reduced, diminished, or no capacity of being packaged into the DNA virus viral particle.

38. The RNA sequence of claim 37, wherein the DNA virus viral particle is an AAV viral particle and wherein said DNA sequence or the reverse complement thereof lacks a DNA packaging signal for AAV packaging.

39. The RNA sequence of claim 38, wherein said DNA packaging signal comprises a functional AAV ITR.

40. A polynucleotide comprising a cassette encoding the RNA sequence of claim 1.

41. The polynucleotide of claim 40, further comprising a promoter operably linked to and driving the transcription of the RNA sequence encoded by the cassette.

42. The RNA sequence of claim 40, wherein the polynucleotide is a DNA sequence.

43. The RNA sequence of claim 40, wherein the polynucleotide is a DNA plasmid comprising a stuffer sequence in the backbone of the DNA plasmid.

44. The RNA sequence of claim 40, wherein the polynucleotide is a DNA sequence comprising no functional DNA packaging signal.

45. An isolated host cell comprising the RNA sequence of claim 1.

\* \* \* \* \*

SEQUENCE LISTING

<160> NUMBER OF SEQ ID NOS: 148

<210> SEQ ID NO 1
<211> LENGTH: 145
<212> TYPE: DNA
<213> ORGANISM: Adeno-associated virus 2

<400> SEQUENCE: 1
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcct                                           145

<210> SEQ ID NO 2
<211> LENGTH: 113
<212> TYPE: DNA
<213> ORGANISM: Artificial Sequence
<220> FEATURE:
<223> OTHER INFORMATION: Synthetic polynucleotide

<400> SEQUENCE: 2
tccctctctg cgcgctcgct cgctcactga ggccgcccgg gcaaagcccg ggcgtcgggc      60
gacctttggt cgcccggcct cagtgagcga gcgagcgcgc agagagggag tgg            113

<210> SEQ ID NO 3
<211> LENGTH: 138
<212> TYPE: DNA
<213> ORGANISM: Artificial Sequence
<220> FEATURE:
<223> OTHER INFORMATION: Synthetic polynucleotide

<400> SEQUENCE: 3
tccctctctg cgcgctcgct cgctcactga ggccgcccgg gcaaagcccg ggcgtcgggc      60
gacctttggt cgcccggcct cagtgagcga gcgagcgcgc agagagggag tggactagct     120
ccatcactag gggttcct                                                   138

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
ctccatcact aggggttcct                                                  20

<210> SEQ ID NO 5
<211> LENGTH: 145
<212> TYPE: DNA
<213> ORGANISM: Adeno-associated virus 2

<400> SEQUENCE: 5
aggaacccct agtgatggag ttggccactc cctctctgcg cgctcgctcg ctcactgagg      60
ccgcccgggc aaagcccggg cgtcgggcga cctttggtcg cccggcctca gtgagcgagc     120
gagcgcgcag agagggagtg gccaa                                           145

<210> SEQ ID NO 6
<211> LENGTH: 736
<212> TYPE: PRT
<213> ORGANISM: Adeno-associated virus 1

<400> SEQUENCE: 6

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
                35                  40                  45

Gly Tyr Lys Tyr Leu Gly Pro Phe Asn Gly Leu Asp Lys Gly Glu Pro
            50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Gly Lys Lys Arg
            130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Thr Pro Ala Ala Val Gly Pro Thr Thr Met Ala Ser Gly Gly Gly
                195                 200                 205

Ala Pro Met Ala Asp Asn Asn Glu Gly Ala Asp Gly Val Gly Asn Ala
            210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
                340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415
```

Glu Glu Val Pro Phe His Ser Ser Tyr Ala His Ser Gln Ser Leu Asp
             420                 425                 430

Arg Leu Met Asn Pro Leu Ile Asp Gln Tyr Leu Tyr Tyr Leu Asn Arg
         435                 440                 445

Thr Gln Asn Gln Ser Gly Ser Ala Gln Asn Lys Asp Leu Leu Phe Ser
     450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                 485                 490                 495

Asn Asn Ser Asn Phe Thr Trp Thr Gly Ala Ser Lys Tyr Asn Leu Asn
             500                 505                 510

Gly Arg Glu Ser Ile Ile Asn Pro Gly Thr Ala Met Ala Ser His Lys
         515                 520                 525

Asp Asp Glu Asp Lys Phe Phe Pro Met Ser Gly Val Met Ile Phe Gly
     530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                 565                 570                 575

Phe Gly Thr Val Ala Val Asn Phe Gln Ser Ser Ser Thr Asp Pro Ala
             580                 585                 590

Thr Gly Asp Val His Ala Met Gly Ala Leu Pro Gly Met Val Trp Gln
         595                 600                 605

Asp Arg Asp Val Tyr Leu Gln Gly Pro Ile Trp Ala Lys Ile Pro His
     610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                 645                 650                 655

Asn Pro Pro Ala Glu Phe Ser Ala Thr Lys Phe Ala Ser Phe Ile Thr
             660                 665                 670

Gln Tyr Ser Thr Gly Gln Val Ser Val Glu Ile Glu Trp Glu Leu Gln
         675                 680                 685

Lys Glu Asn Ser Lys Arg Trp Asn Pro Glu Val Gln Tyr Thr Ser Asn
     690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                 725                 730                 735

<210> SEQ ID NO 7
<211> LENGTH: 735
<212> TYPE: PRT
<213> ORGANISM: Adeno-associated virus 2

<400> SEQUENCE: 7

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
             20                  25                  30

Lys Pro Ala Glu Arg His Lys Asp Asp Ser Arg Gly Leu Val Leu Pro
         35                  40                  45

Gly Tyr Lys Tyr Leu Gly Pro Phe Asn Gly Leu Asp Lys Gly Glu Pro
     50                  55                  60

```
Val Asn Glu Ala Asp Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480
```

-continued

```
Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
            610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 8
<211> LENGTH: 736
<212> TYPE: PRT
<213> ORGANISM: Adeno-associated virus 3

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125
```

```
Leu Gly Leu Val Glu Glu Ala Ala Lys Thr Ala Pro Gly Lys Lys Gly
    130                 135                 140

Ala Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Ala Pro Thr Ser Leu Gly Ser Asn Thr Met Ala Ser Gly Gly Gly
                195                 200                 205

Ala Pro Met Ala Asp Asn Asn Glu Gly Ala Asp Gly Val Gly Asn Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
                275                 280                 285

Cys His Phe Ser Pro Arg Asp Trp Gln Arg Leu Ile Asn Asn Asn Trp
290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
                370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Asn Arg Thr
                435                 440                 445

Gln Gly Thr Thr Ser Gly Thr Thr Asn Gln Ser Arg Leu Leu Phe Ser
                450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
                500                 505                 510

Gly Arg Asp Ser Leu Val Asn Pro Gly Pro Ala Met Ala Ser His Lys
                515                 520                 525

Asp Asp Glu Glu Lys Phe Phe Pro Met His Gly Asn Leu Ile Phe Gly
530                 535                 540
```

```
Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
            565                 570                 575

Tyr Gly Thr Val Ala Asn Asn Leu Gln Ser Ser Asn Thr Ala Pro Thr
                580                 585                 590

Thr Gly Thr Val Asn His Gln Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 9
<211> LENGTH: 736
<212> TYPE: PRT
<213> ORGANISM: Adeno-associated virus 3

<400> SEQUENCE: 9

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Glu Arg Leu Gln Glu Asp Thr Ser Phe Gly Gly Asn
            100                 105                 110

Leu Gly Arg Ala Val Phe Gln Ala Lys Lys Arg Ile Leu Glu Pro Leu
        115                 120                 125

Gly Leu Val Glu Glu Ala Ala Lys Thr Ala Pro Gly Lys Lys Arg Pro
    130                 135                 140

Val Asp Gln Ser Pro Gln Glu Pro Asp Ser Ser Ser Gly Val Gly Lys
145                 150                 155                 160

Ser Gly Lys Gln Pro Ala Arg Lys Arg Leu Asn Phe Gly Gln Thr Gly
                165                 170                 175

Asp Ser Glu Ser Val Pro Asp Pro Gln Pro Leu Gly Glu Pro Pro
            180                 185                 190
```

```
Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
        290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
        450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
        530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605
```

```
Asp Arg Asp Val Tyr Leu Gln Gly Pro Ile Trp Ala Lys Ile Pro His
610             615                 620

Thr Asp Gly His Phe His Pro Ser Pro Leu Met Gly Phe Gly Leu
625             630                 635                 640

Lys His Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 10
<211> LENGTH: 734
<212> TYPE: PRT
<213> ORGANISM: Adeno-associated virus 4

<400> SEQUENCE: 10

```
Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
                20                  25                  30

Ala Asn Gln Gln His Gln Asp Asn Ala Arg Gly Leu Val Leu Pro Gly
                35                  40                  45

Tyr Lys Tyr Leu Gly Pro Gly Asn Gly Leu Asp Lys Gly Glu Pro Val
50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
                100                 105                 110

Leu Gly Arg Ala Val Phe Gln Ala Lys Lys Arg Val Leu Glu Pro Leu
            115                 120                 125

Gly Leu Val Glu Gln Ala Gly Glu Thr Ala Pro Gly Lys Lys Arg Pro
130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Lys Leu Val Phe Glu Asp Glu Thr
                165                 170                 175

Gly Ala Gly Asp Gly Pro Pro Glu Gly Ser Thr Ser Gly Ala Met Ser
                180                 185                 190

Asp Asp Ser Glu Met Arg Ala Ala Ala Gly Gly Ala Ala Val Glu Gly
            195                 200                 205

Gly Gln Gly Ala Asp Gly Val Gly Asn Ala Ser Gly Asp Trp His Cys
            210                 215                 220

Asp Ser Thr Trp Ser Glu Gly His Val Thr Thr Thr Ser Thr Arg Thr
225                 230                 235                 240

Trp Val Leu Pro Thr Tyr Asn Asn His Leu Tyr Lys Arg Leu Gly Glu
                245                 250                 255
```

```
Ser Leu Gln Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
            275                 280                 285

Arg Leu Ile Asn Asn Asn Trp Gly Met Arg Pro Lys Ala Met Arg Val
290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
            355                 360                 365

Cys Gly Leu Val Thr Gly Asn Thr Ser Gln Gln Gln Thr Asp Arg Asn
370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
            435                 440                 445

Asn Ala Gly Thr Ala Thr Thr Asn Phe Thr Lys Leu Arg Pro Thr Asn
450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
            500                 505                 510

Arg Trp Ser Ala Leu Thr Pro Gly Pro Pro Met Ala Thr Ala Gly Pro
            515                 520                 525

Ala Asp Ser Lys Phe Ser Asn Ser Gln Leu Ile Phe Ala Gly Pro Lys
530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
            595                 600                 605

Asp Ile Tyr Tyr Gln Gly Pro Ile Trp Ala Lys Ile Pro His Thr Asp
610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
            660                 665                 670
```

```
Ser Thr Gly Gln Val Ser Val Gln Ile Asp Trp Glu Ile Gln Lys Glu
                675                 680                 685

Arg Ser Lys Arg Trp Asn Pro Glu Val Gln Phe Thr Ser Asn Tyr Gly
            690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                725                 730
```

<210> SEQ ID NO 11
<211> LENGTH: 724
<212> TYPE: PRT
<213> ORGANISM: Adeno-associated virus 5

<400> SEQUENCE: 11

```
Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
        290                 295                 300

Lys Ile Phe Asn Ile Gln Val Lys Glu Val Thr Val Gln Asp Ser Thr
305                 310                 315                 320
```

```
Thr Thr Ile Ala Asn Asn Leu Thr Ser Thr Val Gln Val Phe Thr Asp
            325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
            355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
            435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
            515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
            595                 600                 605

Ala Lys Ile Pro Glu Thr Gly Ala His Phe His Pro Ser Pro Ala Met
    610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
            675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu
```

-continued

```
<210> SEQ ID NO 12
<211> LENGTH: 736
<212> TYPE: PRT
<213> ORGANISM: Adeno-associated virus 6

<400> SEQUENCE: 12
```

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
370                 375                 380

-continued

```
Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Asp Val Pro Phe His Ser Ser Tyr Ala His Ser Gln Ser Leu Asp
        420                 425                 430

Arg Leu Met Asn Pro Leu Ile Asp Gln Tyr Leu Tyr Tyr Leu Asn Arg
    435                 440                 445

Thr Gln Asn Gln Ser Gly Ser Ala Gln Asn Lys Asp Leu Leu Phe Ser
450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
            565                 570                 575

Phe Gly Thr Val Ala Val Asn Leu Gln Ser Ser Ser Thr Asp Pro Ala
        580                 585                 590

Thr Gly Asp Val His Val Met Gly Ala Leu Pro Gly Met Val Trp Gln
    595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
            645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
            725                 730                 735

<210> SEQ ID NO 13
<211> LENGTH: 737
<212> TYPE: PRT
<213> ORGANISM: Adeno-associated virus 7

<400> SEQUENCE: 13

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30
```

-continued

```
Lys Ala Asn Gln Gln Lys Gln Asp Asn Gly Arg Gly Leu Val Leu Pro
         35                  40                  45

Gly Tyr Lys Tyr Leu Gly Pro Phe Asn Gly Leu Asp Lys Gly Glu Pro
     50                  55                  60

Val Asn Ala Ala Asp Ala Ala Leu Glu His Asp Lys Ala Tyr Asp
 65              70                  75                  80

Gln Gln Leu Lys Ala Gly Asp Asn Pro Tyr Leu Arg Tyr Asn His Ala
              85                  90                  95

Asp Ala Glu Phe Gln Glu Arg Leu Gln Glu Asp Thr Ser Phe Gly Gly
             100                 105                 110

Asn Leu Gly Arg Ala Val Phe Gln Ala Lys Lys Arg Val Leu Glu Pro
         115                 120                 125

Leu Gly Leu Val Glu Glu Gly Ala Lys Thr Ala Pro Ala Lys Lys Arg
         130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                 165                 170                 175

Thr Gly Asp Ser Glu Ser Val Pro Asp Pro Gln Pro Leu Gly Glu Pro
             180                 185                 190

Pro Ala Ala Pro Ser Ser Val Gly Ser Thr Val Ala Ala Gly Gly
             195                 200                 205

Gly Ala Pro Met Ala Asp Asn Asn Glu Gly Ala Asp Gly Val Gly Asn
210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                 245                 250                 255

Leu Tyr Lys Gln Ile Ser Ser Glu Thr Ala Gly Ser Thr Asn Asp Asn
             260                 265                 270

Thr Tyr Phe Gly Tyr Ser Thr Pro Trp Gly Tyr Phe Asp Phe Asn Arg
         275                 280                 285

Phe His Cys His Phe Ser Pro Arg Asp Trp Gln Arg Leu Ile Asn Asn
         290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                 325                 330                 335

Asn Leu Thr Ser Thr Ile Gln Val Phe Ser Asp Ser Glu Tyr Gln Leu
             340                 345                 350

Pro Tyr Val Leu Gly Ser Ala His Gln Gly Cys Leu Pro Pro Phe Pro
         355                 360                 365

Ala Asp Val Phe Met Ile Pro Gln Tyr Gly Tyr Leu Thr Leu Asn Asn
370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
             405                 410                 415

Phe Glu Asp Val Pro Phe His Ser Ser Tyr Ala His Ser Gln Ser Leu
             420                 425                 430

Asp Arg Leu Met Asn Pro Leu Ile Asp Gln Tyr Leu Tyr Tyr Leu Ala
         435                 440                 445
```

-continued

```
Arg Thr Gln Ser Asn Pro Gly Gly Thr Ala Gly Asn Arg Glu Leu Gln
            450                 455                 460
Phe Tyr Gln Gly Gly Pro Ser Thr Met Ala Glu Gln Ala Lys Asn Trp
465                 470                 475                 480
Leu Pro Gly Pro Cys Phe Arg Gln Gln Arg Val Ser Lys Thr Leu Asp
                485                 490                 495
Gln Asn Asn Asn Ser Asn Phe Ala Trp Thr Gly Ala Thr Lys Tyr His
            500                 505                 510
Leu Asn Gly Arg Asn Ser Leu Val Asn Pro Gly Val Ala Met Ala Thr
            515                 520                 525
His Lys Asp Asp Glu Asp Arg Phe Phe Pro Ser Ser Gly Val Leu Ile
530                 535                 540
Phe Gly Lys Thr Gly Ala Thr Asn Lys Thr Thr Leu Glu Asn Val Leu
545                 550                 555                 560
Met Thr Asn Glu Glu Glu Ile Arg Pro Thr Asn Pro Val Ala Thr Glu
                565                 570                 575
Glu Tyr Gly Ile Val Ser Ser Asn Leu Gln Ala Ala Asn Thr Ala Ala
            580                 585                 590
Gln Thr Gln Val Val Asn Asn Gln Gly Ala Leu Pro Gly Met Val Trp
            595                 600                 605
Gln Asn Arg Asp Val Tyr Leu Gln Gly Pro Ile Trp Ala Lys Ile Pro
610                 615                 620
His Thr Asp Gly Asn Phe His Pro Ser Pro Leu Met Gly Gly Phe Gly
625                 630                 635                 640
Leu Lys His Pro Pro Pro Gln Ile Leu Ile Lys Asn Thr Pro Val Pro
                645                 650                 655
Ala Asn Pro Pro Glu Val Phe Thr Pro Ala Lys Phe Ala Ser Phe Ile
            660                 665                 670
Thr Gln Tyr Ser Thr Gly Gln Val Ser Val Glu Ile Glu Trp Glu Leu
            675                 680                 685
Gln Lys Glu Asn Ser Lys Arg Trp Asn Pro Glu Ile Gln Tyr Thr Ser
690                 695                 700
Asn Phe Glu Lys Gln Thr Gly Val Asp Phe Ala Val Asp Ser Gln Gly
705                 710                 715                 720
Val Tyr Ser Glu Pro Arg Pro Ile Gly Thr Arg Tyr Leu Thr Arg Asn
                725                 730                 735
Leu
```

<210> SEQ ID NO 14
<211> LENGTH: 738
<212> TYPE: PRT
<213> ORGANISM: Adeno-associated virus 8

<400> SEQUENCE: 14

```
Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Lys Pro
                20                  25                  30
Lys Ala Asn Gln Gln Lys Gln Asp Asp Gly Arg Gly Leu Val Leu Pro
            35                  40                  45
Gly Tyr Lys Tyr Leu Gly Pro Phe Asn Gly Leu Asp Lys Gly Glu Pro
        50                  55                  60
Val Asn Ala Ala Asp Ala Ala Ala Leu Glu His Asp Lys Ala Tyr Asp
65                  70                  75                  80
```

```
Gln Gln Leu Gln Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
    130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Arg Lys Arg Leu Asn Phe Gly Gln
                165                 170                 175
Thr Gly Asp Ser Glu Ser Val Pro Asp Pro Gln Pro Leu Gly Glu Pro
            180                 185                 190
Pro Ala Ala Pro Ser Gly Val Gly Pro Asn Thr Met Ala Ala Gly Gly
        195                 200                 205
Gly Ala Pro Met Ala Asp Asn Asn Glu Gly Ala Asp Gly Val Gly Ser
    210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ala Thr Asn Asp
            260                 265                 270
Asn Thr Tyr Phe Gly Tyr Ser Thr Pro Trp Gly Tyr Phe Asp Phe Asn
        275                 280                 285
Arg Phe His Cys His Phe Ser Pro Arg Asp Trp Gln Arg Leu Ile Asn
    290                 295                 300
Asn Asn Trp Gly Phe Arg Pro Lys Arg Leu Ser Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
            340                 345                 350
Leu Pro Tyr Val Leu Gly Ser Ala His Gln Gly Cys Leu Pro Pro Phe
        355                 360                 365
Pro Ala Asp Val Phe Met Ile Pro Gln Tyr Gly Tyr Leu Thr Leu Asn
    370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Gln Phe Thr Tyr
                405                 410                 415
Thr Phe Glu Asp Val Pro Phe His Ser Ser Tyr Ala His Ser Gln Ser
            420                 425                 430
Leu Asp Arg Leu Met Asn Pro Leu Ile Asp Gln Tyr Leu Tyr Tyr Leu
        435                 440                 445
Ser Arg Thr Gln Thr Thr Gly Gly Thr Ala Asn Thr Gln Thr Leu Gly
    450                 455                 460
Phe Ser Gln Gly Gly Pro Asn Thr Met Ala Asn Ala Lys Asn Trp
465                 470                 475                 480
Leu Pro Gly Pro Cys Tyr Arg Gln Gln Arg Val Ser Thr Thr Gly
                485                 490                 495
Gln Asn Asn Asn Ser Asn Phe Ala Trp Thr Ala Gly Thr Lys Tyr His
```

```
                500             505             510
Leu Asn Gly Arg Asn Ser Leu Ala Asn Pro Gly Ile Ala Met Ala Thr
            515                 520             525

His Lys Asp Asp Glu Glu Arg Phe Phe Pro Ser Asn Gly Ile Leu Ile
        530                 535             540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
        565                 570             575

Glu Glu Tyr Gly Ile Val Ala Asp Asn Leu Gln Gln Gln Asn Thr Ala
            580                 585             590

Pro Gln Ile Gly Thr Val Asn Ser Gln Gly Ala Leu Pro Gly Met Val
        595                 600             605

Trp Gln Asn Arg Asp Val Tyr Leu Gln Gly Pro Ile Trp Ala Lys Ile
        610                 615             620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
            645                 650             655

Pro Ala Asp Pro Pro Thr Thr Phe Asn Gln Ser Lys Leu Asn Ser Phe
        660                 665             670

Ile Thr Gln Tyr Ser Thr Gly Gln Val Ser Val Glu Ile Glu Trp Glu
        675                 680             685

Leu Gln Lys Glu Asn Ser Lys Arg Trp Asn Pro Glu Ile Gln Tyr Thr
        690                 695             700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
            725                 730             735

Asn Leu

<210> SEQ ID NO 15
<211> LENGTH: 736
<212> TYPE: PRT
<213> ORGANISM: Adeno-associated virus 9

<400> SEQUENCE: 15

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
```

-continued

```
            130                 135                 140
Pro Val Glu Gln Ser Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
                195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
                290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
                370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560
```

-continued

```
Thr Asn Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
        580                 585                 590

Thr Gly Trp Val Gln Asn Gln Gly Ile Leu Pro Gly Met Val Trp Gln
    595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735
```

<210> SEQ ID NO 16
<211> LENGTH: 738
<212> TYPE: PRT
<213> ORGANISM: Adeno-associated virus 10

<400> SEQUENCE: 16

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Glu Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
```

```
            195                 200                 205
Gly Ala Pro Met Ala Asp Asn Asn Glu Gly Ala Asp Gly Val Gly Ser
210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ser Thr Asn Asp
                260                 265                 270
Asn Thr Tyr Phe Gly Tyr Ser Thr Pro Trp Gly Tyr Phe Asp Phe Asn
                275                 280                 285
Arg Phe His Cys His Phe Ser Pro Arg Asp Trp Gln Arg Leu Ile Asn
                290                 295                 300
Asn Asn Trp Gly Phe Arg Pro Lys Arg Leu Ser Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
                340                 345                 350
Leu Pro Tyr Val Leu Gly Ser Ala His Gln Gly Cys Leu Pro Pro Phe
                355                 360                 365
Pro Ala Asp Val Phe Met Ile Pro Gln Tyr Gly Tyr Leu Thr Leu Asn
370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
                405                 410                 415
Thr Phe Glu Asp Val Pro Phe His Ser Ser Tyr Ala His Ser Gln Ser
                420                 425                 430
Leu Asp Arg Leu Met Asn Pro Leu Ile Asp Gln Tyr Leu Tyr Tyr Leu
                435                 440                 445
Ser Arg Thr Gln Ser Thr Gly Gly Thr Gln Gly Thr Gln Gln Leu Leu
450                 455                 460
Phe Ser Gln Ala Gly Pro Ala Asn Met Ser Ala Gln Ala Lys Asn Trp
465                 470                 475                 480
Leu Pro Gly Pro Cys Tyr Arg Gln Gln Arg Val Ser Thr Thr Leu Ser
                485                 490                 495
Gln Asn Asn Asn Ser Asn Phe Ala Trp Thr Gly Ala Thr Lys Tyr His
                500                 505                 510
Leu Asn Gly Arg Asp Ser Leu Val Asn Pro Gly Val Ala Met Ala Thr
                515                 520                 525
His Lys Asp Asp Glu Glu Arg Phe Phe Pro Ser Ser Gly Val Leu Met
                530                 535                 540
Phe Gly Lys Gln Gly Ala Gly Arg Asp Asn Val Asp Tyr Ser Ser Val
545                 550                 555                 560
Met Leu Thr Ser Glu Glu Ile Lys Thr Thr Asn Pro Val Ala Thr
                565                 570                 575
Glu Gln Tyr Gly Val Val Ala Asp Asn Leu Gln Ala Asn Thr Gly
                580                 585                 590
Pro Ile Val Gly Asn Val Asn Ser Gln Gly Ala Leu Pro Gly Met Val
                595                 600                 605
Trp Gln Asn Arg Asp Val Tyr Leu Gln Gly Pro Ile Trp Ala Lys Ile
610                 615                 620
```

```
Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
            645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 17
<211> LENGTH: 733
<212> TYPE: PRT
<213> ORGANISM: Adeno-associated virus 11

<400> SEQUENCE: 17

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Leu Glu Ser Pro Gln Glu Pro Asp Ser Ser Ser Gly Ile Gly Lys
145                 150                 155                 160

Lys Gly Lys Gln Pro Ala Arg Lys Arg Leu Asn Phe Glu Glu Asp Thr
                165                 170                 175

Gly Ala Gly Asp Gly Pro Pro Glu Gly Ser Asp Thr Ser Ala Met Ser
            180                 185                 190

Ser Asp Ile Glu Met Arg Ala Ala Pro Gly Gly Asn Ala Val Asp Ala
        195                 200                 205

Gly Gln Gly Ser Asp Gly Val Gly Asn Ala Ser Gly Asp Trp His Cys
    210                 215                 220

Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
                245                 250                 255
```

```
Thr Ser Ser Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
            275                 280                 285

Arg Leu Ile Asn Asn Trp Gly Leu Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
            355                 360                 365

Cys Gly Ile Val Thr Gly Glu Asn Gln Asn Gln Thr Asp Arg Asn Ala
    370                 375                 380

Phe Tyr Cys Leu Glu Tyr Phe Pro Ser Gln Met Leu Arg Thr Gly Asn
385                 390                 395                 400

Asn Phe Glu Met Ala Tyr Asn Phe Glu Lys Val Pro Phe His Ser Met
                405                 410                 415

Tyr Ala His Ser Gln Ser Leu Asp Arg Leu Met Asn Pro Leu Leu Asp
                420                 425                 430

Gln Tyr Leu Trp His Leu Gln Ser Thr Thr Ser Gly Glu Thr Leu Asn
            435                 440                 445

Gln Gly Asn Ala Ala Thr Thr Phe Gly Lys Ile Arg Ser Gly Asp Phe
            450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Pro Met Ala Thr Ala Gly Pro Ser
            515                 520                 525

Asp Gly Asp Phe Ser Asn Ala Gln Leu Ile Phe Pro Gly Pro Ser Val
            530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
            595                 600                 605

Ile Tyr Tyr Gln Gly Pro Ile Trp Ala Lys Ile Pro His Ala Asp Gly
            610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
            660                 665                 670
```

```
Thr Gly Gln Val Ala Val Gln Ile Glu Trp Glu Ile Glu Lys Glu Arg
            675                 680                 685

Ser Lys Arg Trp Asn Pro Glu Val Gln Phe Thr Ser Asn Tyr Gly Asn
    690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730

<210> SEQ ID NO 18
<211> LENGTH: 742
<212> TYPE: PRT
<213> ORGANISM: Adeno-associated virus 12

<400> SEQUENCE: 18

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Gln Arg Leu Ala Thr Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Gly Val Lys Thr Ala Pro Gly Lys Lys Arg
    130                 135                 140

Pro Leu Glu Lys Thr Pro Asn Arg Pro Thr Asn Pro Asp Ser Gly Lys
145                 150                 155                 160

Ala Pro Ala Lys Lys Lys Gln Lys Asp Gly Glu Pro Ala Asp Ser Ala
                165                 170                 175

Arg Arg Thr Leu Asp Phe Glu Asp Ser Gly Ala Gly Asp Gly Pro Pro
            180                 185                 190

Glu Gly Ser Ser Ser Gly Glu Met Ser His Asp Ala Glu Met Arg Ala
        195                 200                 205

Ala Pro Gly Gly Asn Ala Val Glu Ala Gly Gln Gly Ala Asp Gly Val
    210                 215                 220

Gly Asn Ala Ser Gly Asp Trp His Cys Asp Ser Thr Trp Ser Glu Gly
225                 230                 235                 240

Arg Val Thr Thr Thr Ser Thr Arg Thr Trp Val Leu Pro Thr Tyr Asn
                245                 250                 255

Asn His Leu Tyr Leu Arg Ile Gly Thr Thr Ala Asn Ser Asn Thr Tyr
            260                 265                 270

Asn Gly Phe Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Leu Arg Pro Lys Ser Met Arg Val Lys Ile Phe Asn Ile Gln Val
305                 310                 315                 320
```

```
Lys Glu Val Thr Thr Ser Asn Gly Glu Thr Thr Val Ala Asn Asn Leu
                325                 330                 335

Thr Ser Thr Val Gln Ile Phe Ala Asp Ser Thr Tyr Glu Leu Pro Tyr
            340                 345                 350

Val Met Asp Ala Gly Gln Glu Gly Ser Phe Pro Pro Phe Pro Asn Asp
        355                 360                 365

Val Phe Met Val Pro Gln Tyr Gly Tyr Cys Gly Val Val Thr Gly Lys
    370                 375                 380

Asn Gln Asn Gln Thr Asp Arg Asn Ala Phe Tyr Cys Leu Glu Tyr Phe
385                 390                 395                 400

Pro Ser Gln Met Leu Arg Thr Gly Asn Asn Phe Glu Val Ser Tyr Gln
                405                 410                 415

Phe Glu Lys Val Pro Phe His Ser Met Tyr Ala His Ser Gln Ser Leu
            420                 425                 430

Asp Arg Met Met Asn Pro Leu Leu Asp Gln Tyr Leu Trp His Leu Gln
        435                 440                 445

Ser Thr Thr Thr Gly Asn Ser Leu Asn Gln Gly Thr Ala Thr Thr Thr
    450                 455                 460

Tyr Gly Lys Ile Thr Thr Gly Asp Phe Ala Tyr Tyr Arg Lys Asn Trp
465                 470                 475                 480

Leu Pro Gly Ala Cys Ile Lys Gln Gln Lys Phe Ser Lys Asn Ala Asn
                485                 490                 495

Gln Asn Tyr Lys Ile Pro Ala Ser Gly Gly Asp Ala Leu Leu Lys Tyr
            500                 505                 510

Asp Thr His Thr Thr Leu Asn Gly Arg Trp Ser Asn Met Ala Pro Gly
        515                 520                 525

Pro Pro Met Ala Thr Ala Gly Ala Gly Asp Ser Asp Phe Ser Asn Ser
    530                 535                 540

Gln Leu Ile Phe Ala Gly Pro Asn Pro Ser Gly Asn Thr Thr Thr Ser
545                 550                 555                 560

Ser Asn Asn Leu Leu Phe Thr Ser Glu Glu Glu Ile Ala Thr Thr Asn
                565                 570                 575

Pro Arg Asp Thr Asp Met Phe Gly Gln Ile Ala Asp Asn Asn Gln Asn
            580                 585                 590

Ala Thr Thr Ala Pro His Ile Ala Asn Leu Asp Ala Met Gly Ile Val
        595                 600                 605

Pro Gly Met Val Trp Gln Asn Arg Asp Ile Tyr Tyr Gln Gly Pro Ile
    610                 615                 620

Trp Ala Lys Val Pro His Thr Asp Gly His Phe His Pro Ser Pro Leu
625                 630                 635                 640

Met Gly Gly Phe Gly Leu Lys His Pro Pro Pro Gln Ile Phe Ile Lys
                645                 650                 655

Asn Thr Pro Val Pro Ala Asn Pro Asn Thr Thr Phe Ser Ala Ala Arg
            660                 665                 670

Ile Asn Ser Phe Leu Thr Gln Tyr Ser Thr Gly Gln Val Ala Val Gln
        675                 680                 685

Ile Asp Trp Glu Ile Gln Lys Glu His Ser Lys Arg Trp Asn Pro Glu
    690                 695                 700

Val Gln Phe Thr Ser Asn Tyr Gly Thr Gln Asn Ser Met Leu Trp Ala
705                 710                 715                 720

Pro Asp Asn Ala Gly Asn Tyr His Glu Leu Arg Ala Ile Gly Ser Arg
                725                 730                 735
```

```
Phe Leu Thr His His Leu
            740

<210> SEQ ID NO 19
<211> LENGTH: 733
<212> TYPE: PRT
<213> ORGANISM: Adeno-associated virus 13

<400> SEQUENCE: 19

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

Tyr Lys Tyr Leu Gly Pro Gly Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Glu Arg Leu Gln Glu Asp Thr Ser Phe Gly Gly Asn
            100                 105                 110

Leu Gly Arg Ala Val Phe Gln Ala Lys Lys Arg Ile Leu Glu Pro Leu
        115                 120                 125

Gly Leu Val Glu Glu Ala Ala Lys Thr Ala Pro Gly Lys Lys Arg Pro
    130                 135                 140

Val Glu Gln Ser Pro Ala Glu Pro Asp Ser Ser Ser Gly Ile Gly Lys
145                 150                 155                 160

Ser Gly Gln Gln Pro Ala Arg Lys Arg Leu Asn Phe Gly Gln Thr Gly
                165                 170                 175

Asp Thr Glu Ser Val Pro Asp Pro Gln Pro Leu Gly Gln Pro Pro Ala
            180                 185                 190

Ala Pro Ser Gly Val Gly Ser Thr Thr Met Ala Ser Gly Gly Gly Ala
        195                 200                 205

Pro Met Ala Asp Asn Asn Glu Gly Ala Asp Gly Val Gly Asn Ser Ser
    210                 215                 220

Gly Asn Trp His Cys Asp Ser Gln Trp Leu Gly Asp Arg Val Ile Thr
225                 230                 235                 240

Thr Ser Thr Arg Thr Trp Ala Leu Pro Thr Tyr Asn Asn His Leu Tyr
                245                 250                 255

Lys Gln Ile Ser Ser Gln Ser Gly Ala Thr Asn Asp Asn His Tyr Phe
            260                 265                 270

Gly Tyr Ser Thr Pro Trp Gly Tyr Phe Asp Phe Asn Arg Phe His Cys
        275                 280                 285

His Phe Ser Pro Arg Asp Trp Gln Arg Leu Ile Asn Asn Asn Trp Gly
    290                 295                 300

Phe Arg Pro Lys Arg Leu Asn Phe Lys Leu Phe Asn Ile Gln Val Lys
305                 310                 315                 320

Glu Val Thr Gln Asn Asp Gly Thr Thr Thr Ile Ala Asn Asn Leu Thr
                325                 330                 335

Ser Thr Val Gln Val Phe Thr Asp Ser Glu Tyr Gln Leu Pro Tyr Val
            340                 345                 350

Leu Gly Ser Ala His Gln Gly Cys Leu Pro Pro Phe Pro Ala Asp Val
        355                 360                 365
```

Phe Met Val Pro Gln Tyr Gly Tyr Leu Thr Leu Asn Gly Ser Gln
        370                 375                 380

Ala Val Gly Arg Ser Ser Phe Tyr Cys Leu Glu Tyr Phe Pro Ser Gln
385                 390                 395                 400

Met Leu Arg Thr Gly Asn Asn Phe Gln Phe Ser Tyr Thr Phe Glu Asp
                405                 410                 415

Val Pro Phe His Ser Ser Tyr Ala His Ser Gln Ser Leu Asp Arg Leu
            420                 425                 430

Met Asn Pro Leu Ile Asp Gln Tyr Leu Tyr Tyr Leu Asn Arg Thr Gln
                435                 440                 445

Thr Ala Ser Gly Thr Gln Gln Ser Arg Leu Leu Phe Ser Gln Ala Gly
        450                 455                 460

Pro Thr Ser Met Ser Leu Gln Ala Lys Asn Trp Leu Pro Gly Pro Cys
465                 470                 475                 480

Tyr Arg Gln Gln Arg Leu Ser Lys Gln Ala Asn Asp Asn Asn Asn Ser
                485                 490                 495

Asn Phe Pro Trp Thr Gly Ala Thr Lys Tyr His Leu Asn Gly Arg Asp
            500                 505                 510

Ser Leu Val Asn Pro Gly Pro Ala Met Ala Ser His Lys Asp Asp Lys
        515                 520                 525

Glu Lys Phe Phe Pro Met His Gly Thr Leu Ile Phe Gly Lys Glu Gly
530                 535                 540

Thr Asn Ala Asn Asn Ala Asp Leu Glu Asn Val Met Ile Thr Asp Glu
545                 550                 555                 560

Glu Glu Ile Arg Thr Thr Asn Pro Val Ala Thr Glu Gln Tyr Gly Thr
                565                 570                 575

Val Ser Asn Asn Leu Gln Asn Ser Asn Ala Gly Pro Thr Thr Gly Thr
            580                 585                 590

Val Asn His Gln Gly Ala Leu Pro Gly Met Val Trp Gln Asp Arg Asp
        595                 600                 605

Val Tyr Leu Gln Gly Pro Ile Trp Ala Lys Ile Pro His Thr Asp Gly
610                 615                 620

His Phe His Pro Ser Pro Leu Met Gly Gly Phe Gly Leu Lys His Pro
625                 630                 635                 640

Pro Pro Gln Ile Met Ile Lys Asn Thr Pro Val Pro Ala Asn Pro Pro
                645                 650                 655

Thr Asn Phe Ser Ala Ala Lys Phe Ala Ser Phe Ile Thr Gln Tyr Ser
            660                 665                 670

Thr Gly Gln Val Ser Val Glu Ile Glu Trp Glu Leu Gln Lys Glu Asn
        675                 680                 685

Ser Lys Arg Trp Asn Pro Glu Ile Gln Tyr Thr Ser Asn Tyr Asn Lys
690                 695                 700

Ser Val Asn Val Asp Phe Thr Val Asp Thr Asn Gly Val Tyr Ser Glu
705                 710                 715                 720

Pro Arg Pro Ile Gly Thr Arg Tyr Leu Thr Arg Asn Leu
                725                 730

<210> SEQ ID NO 20
<211> LENGTH: 737
<212> TYPE: PRT
<213> ORGANISM: Artificial Sequence
<220> FEATURE:
<223> OTHER INFORMATION: Synthetic polypeptide"

<400> SEQUENCE: 20

-continued

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25              30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65              70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Ile Gly Glu Pro Pro
                180                 185                 190

Ala Ala Pro Ser Gly Val Gly Ser Leu Thr Met Ala Ala Gly Gly Gly
            195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
    275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Ser Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
    355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Thr Tyr Thr
                405                 410                 415
```

```
Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Gln Thr Thr Gly Gly Thr Thr Asn Thr Gln Thr Leu Gly Phe
    450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Lys Thr Ser Ala Asp
                485                 490                 495

Asn Asn Asn Ser Glu Tyr Ser Trp Thr Gly Ala Thr Lys Tyr His Leu
            500                 505                 510

Asn Gly Arg Asp Ser Leu Val Asn Pro Gly Pro Ala Met Ala Ser His
        515                 520                 525

Lys Asp Asp Glu Glu Lys Phe Phe Pro Gln Ser Gly Val Leu Ile Phe
530                 535                 540

Gly Lys Gln Gly Ser Lys Thr Asn Val Asp Ile Glu Lys Val Met
545                 550                 555                 560

Ile Thr Asp Glu Glu Glu Ile Arg Thr Thr Asn Pro Val Ala Thr Glu
                565                 570                 575

Gln Tyr Gly Ser Val Ser Thr Asn Leu Gln Arg Gly Asn Arg Gln Ala
            580                 585                 590

Ala Thr Ala Asp Val Asn Thr Gln Gly Val Leu Pro Gly Met Val Trp
        595                 600                 605

Gln Asp Arg Asp Val Tyr Leu Gln Gly Pro Ile Trp Ala Lys Ile Pro
    610                 615                 620

His Thr Asp Gly His Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Asn Gln Ser Lys Leu Asn Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Tyr Tyr Lys Ser Thr Ser Val Asp Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 21
<211> LENGTH: 743
<212> TYPE: PRT
<213> ORGANISM: Artificial Sequence
<220> FEATURE:
<223> OTHER INFORMATION: Synthetic polypeptide"

<400> SEQUENCE: 21

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
```

-continued

```
                35                  40                  45
Gly Tyr Lys Tyr Leu Gly Pro Gly Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
        130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Ile Asn Gly Ser Gly Gln Asn Gln Gln Thr Leu Lys Phe Ser
450                 455                 460
```

```
Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Asp Gly Thr Leu Ala Val
            580                 585                 590

Pro Phe Lys Ala Gln Ala Gln Thr Gly Trp Val Gln Asn Gln Gly Ile
            595                 600                 605

Leu Pro Gly Met Val Trp Gln Asp Arg Asp Val Tyr Leu Gln Gly Pro
            610                 615                 620

Ile Trp Ala Lys Ile Pro His Thr Asp Gly Asn Phe His Pro Ser Pro
625                 630                 635                 640

Leu Met Gly Gly Phe Gly Met Lys His Pro Pro Gln Ile Leu Ile
                645                 650                 655

Lys Asn Thr Pro Val Pro Ala Asp Pro Pro Thr Ala Phe Asn Lys Asp
                660                 665                 670

Lys Leu Asn Ser Phe Ile Thr Gln Tyr Ser Thr Gly Gln Val Ser Val
                675                 680                 685

Glu Ile Glu Trp Glu Leu Gln Lys Glu Asn Ser Lys Arg Trp Asn Pro
690                 695                 700

Glu Ile Gln Tyr Thr Ser Asn Tyr Tyr Lys Ser Asn Asn Val Glu Phe
705                 710                 715                 720

Ala Val Asn Thr Glu Gly Val Tyr Ser Glu Pro Arg Pro Ile Gly Thr
                725                 730                 735

Arg Tyr Leu Thr Arg Asn Leu
            740
```

<210> SEQ ID NO 22
<211> LENGTH: 736
<212> TYPE: PRT
<213> ORGANISM: Artificial Sequence
<220> FEATURE:
<223> OTHER INFORMATION: Synthetic polypeptide"

<400> SEQUENCE: 22

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80
```

```
Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Lys Gly Gln Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Ala Ala Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Gly Ser Thr Asn Asp Asn Thr
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Lys Leu Asn Phe Lys Leu Phe Asn Ile Gln
305                 310                 315                 320

Val Lys Glu Val Thr Thr Asn Asp Gly Thr Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Thr Thr Ser Gly Thr Ala Gly Asn Arg Thr Leu Gln Phe Ser
    450                 455                 460

Gln Ala Gly Pro Ser Ser Met Ala Asn Gln Ala Lys Asn Trp Leu Pro
465                 470                 475                 480

Gly Pro Cys Tyr Arg Gln Gln Arg Val Ser Lys Thr Thr Asn Gln Asn
                485                 490                 495
```

Asn Asn Ser Asn Phe Ala Trp Thr Gly Ala Thr Lys Tyr His Leu Asn
            500                 505                 510

Gly Arg Asp Ser Leu Val Asn Pro Gly Pro Ala Met Ala Thr His Lys
        515                 520                 525

Asp Asp Glu Asp Lys Phe Phe Pro Met Ser Gly Val Leu Ile Phe Gly
    530                 535                 540

Lys Gln Gly Ala Gly Asn Ser Asn Val Asp Leu Asp Asn Val Met Ile
545                 550                 555                 560

Thr Asn Glu Glu Glu Ile Lys Thr Thr Asn Pro Val Ala Thr Glu Glu
                565                 570                 575

Tyr Gly Thr Val Ala Thr Asn Leu Gln Ser Ala Asn Thr Ala Pro Ala
            580                 585                 590

Thr Gly Thr Val Asn Ser Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Thr Asn Val Asp Phe Ala Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 23
<211> LENGTH: 736
<212> TYPE: PRT
<213> ORGANISM: Artificial Sequence
<220> FEATURE:
<223> OTHER INFORMATION: Synthetic polypeptide"

<400> SEQUENCE: 23

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

```
Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Gly Ile Gly
145                 150                 155                 160

Lys Lys Gly Gln Gln Pro Ala Arg Lys Arg Leu Asn Phe Gly Gln Thr
                    165                 170                 175

Gly Asp Ser Glu Ser Val Pro Asp Pro Gln Pro Leu Gly Glu Pro Pro
                180                 185                 190

Ala Ala Pro Ser Gly Val Gly Ser Asn Thr Met Ala Ala Gly Gly Gly
            195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Gly Ser Thr Asn Asp Asn Thr
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
    290                 295                 300

Trp Gly Phe Arg Pro Lys Lys Leu Asn Phe Lys Leu Phe Asn Ile Gln
305                 310                 315                 320

Val Lys Glu Val Thr Thr Asn Asp Gly Thr Thr Thr Ile Ala Asn Asn
                325                 330                 335

Leu Thr Ser Thr Val Gln Val Phe Thr Asp Ser Glu Tyr Gln Leu Pro
                340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Ser Tyr Thr Phe
                405                 410                 415

Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Ser Arg
            435                 440                 445

Thr Gln Thr Thr Ser Gly Thr Ala Gly Asn Arg Thr Leu Gln Phe Ser
    450                 455                 460

Gln Ala Gly Pro Ser Ser Met Ala Asn Gln Ala Lys Asn Trp Leu Pro
465                 470                 475                 480

Gly Pro Cys Tyr Arg Gln Gln Arg Val Ser Lys Thr Thr Asn Gln Asn
                485                 490                 495

Asn Asn Ser Asn Phe Ala Trp Thr Gly Ala Thr Lys Tyr His Leu Asn
                500                 505                 510

Gly Arg Asp Ser Leu Val Asn Pro Gly Pro Ala Met Ala Thr His Lys
            515                 520                 525

Asp Asp Glu Asp Lys Phe Phe Pro Met Ser Gly Val Leu Ile Phe Gly
    530                 535                 540

Lys Gln Gly Ala Gly Asn Ser Asn Val Asp Leu Asp Asn Val Met Ile
```

```
                545                 550                 555                 560
            Thr Asn Glu Glu Glu Ile Lys Thr Thr Asn Pro Val Ala Thr Glu Glu
                                565                 570                 575

Tyr Gly Thr Val Ala Thr Asn Leu Gln Ser Ala Asn Thr Ala Pro Ala
                            580                 585                 590

Thr Gly Thr Val Asn Ser Gln Gly Ala Leu Pro Gly Met Val Trp Gln
                        595                 600                 605

Asp Arg Asp Val Tyr Leu Gln Gly Pro Ile Trp Ala Lys Ile Pro His
                    610                 615                 620

Thr Asp Gly His Phe His Pro Ser Pro Leu Met Gly Phe Gly Leu
            625                 630                 635                 640

Lys His Pro Pro Gln Ile Leu Ile Lys Asn Thr Pro Val Pro Ala
                            645                 650                 655

Asn Pro Pro Thr Thr Phe Ser Pro Ala Lys Phe Ala Ser Phe Ile Thr
                        660                 665                 670

Gln Tyr Ser Thr Gly Gln Val Ser Val Glu Ile Glu Trp Glu Leu Gln
                    675                 680                 685

Lys Glu Asn Ser Lys Arg Trp Asn Pro Glu Ile Gln Tyr Thr Ser Asn
                690                 695                 700

Tyr Asn Lys Ser Thr Asn Val Asp Phe Ala Val Asp Thr Asn Gly Val
            705                 710                 715                 720

Tyr Ser Glu Pro Arg Pro Ile Gly Thr Arg Tyr Leu Thr Arg Asn Leu
                            725                 730                 735

<210> SEQ ID NO 24
<211> LENGTH: 745
<212> TYPE: PRT
<213> ORGANISM: Artificial Sequence
<220> FEATURE:
<223> OTHER INFORMATION: Synthetic polypeptide"

<400> SEQUENCE: 24

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
                20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
```

-continued

```
                180                 185                 190
Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Thr
225                 230                 235                 240

Thr Thr Ser Thr Arg Thr Trp Ala Leu Pro Thr Tyr Asn Asn His Leu
            245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
            325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Leu Ala Leu Gly Glu
            580                 585                 590

Thr Thr Arg Pro Ala Arg Gln Ala Ala Thr Ala Asp Val Asn Thr Gln
            595                 600                 605
```

```
Gly Val Leu Pro Gly Met Val Trp Gln Asp Arg Asp Val Tyr Leu Gln
    610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Gln Ile
                645                 650                 655

Leu Ile Lys Asn Thr Pro Val Pro Ala Asn Pro Ser Thr Thr Phe Ser
            660                 665                 670

Ala Ala Lys Phe Ala Ser Phe Ile Thr Gln Tyr Ser Thr Gly Gln Val
        675                 680                 685

Ser Val Glu Ile Glu Trp Glu Leu Gln Lys Glu Asn Ser Lys Arg Trp
    690                 695                 700

Asn Pro Glu Ile Gln Tyr Thr Ser Asn Tyr Asn Lys Ser Ile Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu Thr Arg Asn Leu
                740                 745

<210> SEQ ID NO 25
<211> LENGTH: 143
<212> TYPE: DNA
<213> ORGANISM: Adeno-associated virus 1

<400> SEQUENCE: 25
ttgcccactc cctctctgcg cgctcgctcg ctcggtgggg cctgcggacc aaaggtccgc     60
agacggcaga gctctgctct gccggcccca ccgagcgagc gagcgcgcag agagggagtg    120
ggcaactcca tcactagggg taa                                            143

<210> SEQ ID NO 26
<211> LENGTH: 143
<212> TYPE: DNA
<213> ORGANISM: Adeno-associated virus 1

<400> SEQUENCE: 26 ttaccccctag tgatggagtt gcccactccc tctctgcgcg ctcgctcgct cggtggggcc    60
tgcggaccaa aggtccgcag acggcagagc tctgctctgc cggccccacc gagcgagcga   120
gcgcgcagag agggagtggg caa                                            143

<210> SEQ ID NO 27
<211> LENGTH: 145
<212> TYPE: DNA
<213> ORGANISM: Adeno-associated virus 2

<400> SEQUENCE: 27
ttggccactc cctctctgcg cgctcgctcg ctcactgagg ccgggcgacc aaaggtcgcc     60
cgacgcccgg gctttgcccg gcggcctcag tgagcgagc gagcgcgcag agagggagtg    120
gccaactcca tcactagggg ttcct                                          145

<210> SEQ ID NO 28
<211> LENGTH: 145
<212> TYPE: DNA
<213> ORGANISM: Adeno-associated virus 2

<400> SEQUENCE: 28
aggaacccct agtgatggag ttggccactc cctctctgcg cgctcgctcg ctcactgagg     60
```

```
ccgggcgacc aaaggtcgcc cgacgcccgg gctttgcccg gcggcctca gtgagcgagc    120 gagcgcgcag agagggagtg gccaa                                         145

<210> SEQ ID NO 29
<211> LENGTH: 143
<212> TYPE: DNA
<213> ORGANISM: Adeno-associated virus 3

<400> SEQUENCE: 29
ttggccactc cctctatgcg cactcgctcg ctcggtgggg cctggcgacc aaaggtcgcc    60
agacggacgt gctttgcacg tccggcccca ccgagcgagc gagtgcgcat agagggagtg   120
gccaactcca tcactagagg tat                                          143

<210> SEQ ID NO 30
<211> LENGTH: 143
<212> TYPE: DNA
<213> ORGANISM: Adeno-associated virus 3

<400> SEQUENCE: 30
atacctctag tgatggagtt ggccactccc tctatgcgca ctcgctcgct cggtggggcc    60
tggcgaccaa aggtcgccag acggacgtgc tttgcacgtc cggccccacc gagcgagcga   120
gtgcgcatag agggagtggc caa                                          143

<210> SEQ ID NO 31
<211> LENGTH: 146
<212> TYPE: DNA
<213> ORGANISM: Adeno-associated virus 4

<400> SEQUENCE: 31
ttggccactc cctctatgcg cgctcgctca ctcactcggc cctggagacc aaaggtctcc    60
agactgccgg cctctggccg gcagggccga gtgagtgagc gagcgcgcat agagggagtg   120
gccaactcca tcatctaggt ttgccc                                       146

<210> SEQ ID NO 32
<211> LENGTH: 144
<212> TYPE: DNA
<213> ORGANISM: Adeno-associated virus 4

<400> SEQUENCE: 32
ggcaaaccag atgatggagt tggccacatt agctatgcgc gctcgctcac tcactcggcc    60
ctggagacca aaggtctcca gactgccggc ctctggccgg cagggccgag tgagtgagcg   120
agcgcgcata gagggagtgg ccaa                                         144

<210> SEQ ID NO 33
<211> LENGTH: 167
<212> TYPE: DNA
<213> ORGANISM: Adeno-associated virus 5

<400> SEQUENCE: 33
ctctcccccc tgtcgcgttc gctcgctcgc tggctcgttt ggggggtgg cagctcaaag    60 agctgccaga cgacgccct ctggccgtcg ccccccaaa cgagccagcg agcgagcgaa    120
cgcgacaggg gggagagtgc cacactctca agcaaggggg ttttgta              167

<210> SEQ ID NO 34
<211> LENGTH: 167
<212> TYPE: DNA
```

<213> ORGANISM: Adeno-associated virus 5

<400> SEQUENCE: 34

| tacaaaacct ccttgcttga gagtgtggca ctctcccccc tgtcgcgttc gctcgctcgc | 60 |
| tggctcgttt ggggggtgg cagctcaaag agctgccaga cgacggccct ctggccgtcg | 120 |
| ccccccaaa cgagccagcg agcgagcgaa cgcgacaggg gggagag | 167 |

<210> SEQ ID NO 35
<211> LENGTH: 145
<212> TYPE: DNA
<213> ORGANISM: Adeno-associated virus 6

<400> SEQUENCE: 35

| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcct | 145 |

<210> SEQ ID NO 36
<211> LENGTH: 143
<212> TYPE: DNA
<213> ORGANISM: Adeno-associated virus 6

<400> SEQUENCE: 36

| ataccctag tgatggagtt gcccactccc tctatgcgcg ctcgctcgct cggtggggcc | 60 |
| ggcagagcag agctctgccg tctgcggacc tttggtccgc aggccccacc gagcgagcga | 120 |
| gcgcgcatag agggagtggg caa | 143 |

<210> SEQ ID NO 37
<211> LENGTH: 145
<212> TYPE: DNA
<213> ORGANISM: Adeno-associated virus 7

<400> SEQUENCE: 37

| ttggccactc cctctatgcg cgctcgctcg ctcggtgggg cctgcggacc aaaggtccgc | 60 |
| agacggcaga gctctgctct gccggcccca ccgagcgagc gagcgcgcat agagggagtg | 120 |
| gccaactcca tcactagggg taccg | 145 |

<210> SEQ ID NO 38
<211> LENGTH: 145
<212> TYPE: DNA
<213> ORGANISM: Adeno-associated virus 7

<400> SEQUENCE: 38

| cggtacccct agtgatggag ttggccactc cctctatgcg cgctcgctcg ctcggtgggg | 60 |
| cctgcggacc aaaggtccgc agacggcaga gctctgctct gccggcccca ccgagcgagc | 120 |
| gagcgcgcat agagggagtg gccaa | 145 |

<210> SEQ ID NO 39
<211> LENGTH: 80
<212> TYPE: DNA
<213> ORGANISM: Artificial Sequence
<220> FEATURE:
<223> OTHER INFORMATION: Synthetic oligonucleotide

<400> SEQUENCE: 39

| gccacggcgg aactcatcgc cgcctgcctt gcccgctgct ggacaggggc tcggctgttg | 60 |
| ggcactgaca attccgtggt | 80 |

<210> SEQ ID NO 40
<211> LENGTH: 289
<212> TYPE: PRT
<213> ORGANISM: Artificial Sequence
<220> FEATURE:
<223> OTHER INFORMATION: Synthetic polypeptide"

<400> SEQUENCE: 40

Met Pro Leu Ile Phe Lys Ile Gly Tyr Asn Val Ile Pro Leu Gln Asp
1               5                   10                  15

Val Ile Leu Pro Thr Pro Ser Ser Lys Val Leu Lys Tyr Leu Ile Gln
            20                  25                  30

Ser Gly Lys Leu Ile Pro Ser Leu Lys Asp Leu Ile Thr Ser Arg Asp
        35                  40                  45

Lys Tyr Lys Pro Ile Phe Ile Ser His Leu Gly Phe Asn Gln Arg Arg
    50                  55                  60

Ile Phe Gln Thr Asn Gly Asn Leu Lys Thr Ile Thr Lys Gly Ser Arg
65                  70                  75                  80

Leu Ser Ser Ile Ile Ala Phe Ser Thr Gln Ala Asn Val Leu Ser Glu
                85                  90                  95

Val Ala Asp Glu Gly Ile Phe Glu Thr Val Tyr Gly Lys Phe His Ile
            100                 105                 110

Met Ile Glu Ser Ile Glu Ile Val Glu Val Lys Leu Lys Glu Glu
        115                 120                 125

Val Glu Lys His Met Asn Asp Asn Ile Arg Val Arg Phe Val Ser Pro
    130                 135                 140

Thr Leu Leu Ser Ser Lys Val Leu Leu Pro Pro Ser Leu Ser Glu Arg
145                 150                 155                 160

Tyr Lys Lys Ile His Ala Gly Tyr Ser Thr Leu Pro Ser Val Gly Leu
                165                 170                 175

Ile Val Ala Tyr Ala Tyr Asn Val Tyr Cys Asn Leu Ile Gly Lys Lys
            180                 185                 190

Glu Val Glu Val Arg Ala Phe Lys Phe Gly Ile Leu Ser Asn Ala Leu
        195                 200                 205

Ser Arg Ile Ile Gly Tyr Asp Leu His Pro Val Thr Val Ala Ile Gly
    210                 215                 220

Glu Asp Ser Lys Gly Asn Leu Arg Lys Ala Arg Gly Val Met Gly Trp
225                 230                 235                 240

Ile Glu Phe Asp Ile Pro Asp Glu Arg Leu Lys Arg Arg Ala Leu Asn
                245                 250                 255

Tyr Leu Leu Thr Ser Ser Tyr Leu Gly Ile Gly Arg Ser Arg Gly Ile
            260                 265                 270

Gly Phe Gly Glu Ile Arg Leu Glu Phe Arg Lys Ile Glu Glu Lys Glu
        275                 280                 285

Gly

<210> SEQ ID NO 41
<211> LENGTH: 218
<212> TYPE: PRT
<213> ORGANISM: Artificial Sequence
<220> FEATURE:
<223> OTHER INFORMATION: Synthetic polypeptide"

<400> SEQUENCE: 41

Met Asp Leu Glu Tyr Met His Ile Ser Tyr Pro Asn Ile Leu Leu Asn
1               5                   10                  15

Met Arg Asp Gly Ser Lys Leu Arg Gly Tyr Phe Ala Lys Lys Tyr Ile
            20                  25                  30

Asp Glu Glu Ile Val His Asn His Arg Asp Asn Ala Phe Val Tyr Lys
        35                  40                  45

Tyr Pro Gln Ile Gln Phe Lys Ile Ile Asp Arg Ser Pro Leu Ile Ile
    50                  55                  60

Gly Ile Gly Ser Leu Gly Ile Asn Phe Leu Glu Ser Lys Arg Ile Phe
65                  70                  75                  80

Phe Glu Lys Glu Leu Ile Ile Ser Asn Asp Thr Asn Asp Ile Thr Glu
                85                  90                  95

Val Asn Val His Lys Asp Met Asp His Phe Gly Thr Thr Asp Lys Ile
            100                 105                 110

Leu Lys Tyr Gln Phe Lys Thr Pro Trp Met Ala Leu Asn Ala Lys Asn
        115                 120                 125

Ser Glu Ile Tyr Lys Asn Ser Asp Glu Ile Asp Arg Glu Glu Phe Leu
130                 135                 140

Lys Arg Val Leu Ile Gly Asn Ile Leu Ser Met Ser Lys Ser Leu Gly
145                 150                 155                 160

Tyr Thr Ile Glu Glu Lys Leu Lys Val Lys Ile Asn Leu Lys Glu Val
                165                 170                 175

Pro Val Lys Phe Lys Asn Gln Asn Met Val Gly Phe Arg Gly Glu Phe
            180                 185                 190

Tyr Ile Asn Phe Asp Ile Pro Gln Tyr Leu Gly Ile Gly Arg Asn Val
        195                 200                 205

Ser Arg Gly Phe Gly Thr Val Val Lys Val
    210                 215

<210> SEQ ID NO 42
<211> LENGTH: 242
<212> TYPE: PRT
<213> ORGANISM: Artificial Sequence
<220> FEATURE:
<223> OTHER INFORMATION: Synthetic polypeptide"

<400> SEQUENCE: 42

Met Tyr Arg Ser Arg Asp Phe Tyr Val Arg Val Ser Gly Gln Arg Ala
1               5                   10                  15

Leu Phe Thr Asn Pro Ala Thr Lys Gly Gly Ser Glu Arg Ser Ser Tyr
            20                  25                  30

Ser Val Pro Thr Arg Gln Ala Leu Asn Gly Ile Val Asp Ala Ile Tyr
        35                  40                  45

Tyr Lys Pro Thr Phe Thr Asn Ile Val Thr Glu Val Lys Val Ile Asn
    50                  55                  60

Gln Ile Gln Thr Glu Leu Gln Gly Val Arg Ala Leu Leu His Asp Tyr
65                  70                  75                  80

Ser Ala Asp Leu Ser Tyr Val Ser Tyr Leu Ser Asp Val Val Tyr Leu
                85                  90                  95

Ile Lys Phe His Phe Val Trp Asn Glu Asp Arg Lys Asp Leu Asn Ser
            100                 105                 110

Asp Arg Leu Pro Ala Lys His Glu Ala Ile Met Glu Arg Ser Ile Arg
        115                 120                 125

Lys Gly Gly Arg Arg Asp Val Phe Leu Gly Thr Arg Glu Cys Leu Gly
    130                 135                 140

Leu Leu Asp Asp Ile Ser Gln Glu Glu Tyr Glu Thr Thr Val Ser Tyr
145                 150                 155                 160

```
Tyr Asn Gly Val Asn Ile Asp Leu Gly Ile Met Phe His Ser Phe Ala
                165                 170                 175

Tyr Pro Lys Asp Lys Lys Thr Pro Leu Lys Ser Tyr Phe Thr Lys Thr
            180                 185                 190

Val Met Lys Asn Gly Val Ile Thr Phe Lys Ala Gln Ser Glu Cys Asp
        195                 200                 205

Ile Val Asn Thr Leu Ser Ser Tyr Ala Phe Lys Ala Pro Glu Glu Ile
    210                 215                 220

Lys Ser Val Asn Asp Glu Cys Met Glu Tyr Asp Ala Met Glu Lys Gly
225                 230                 235                 240

Glu Asn

<210> SEQ ID NO 43
<211> LENGTH: 236
<212> TYPE: PRT
<213> ORGANISM: Artificial Sequence
<220> FEATURE:
<223> OTHER INFORMATION: Synthetic polypeptide"

<400> SEQUENCE: 43

Met Arg Asn Glu Val Gln Phe Glu Leu Phe Gly Asp Tyr Ala Leu Phe
1               5                   10                  15

Thr Asp Pro Leu Thr Lys Ile Gly Gly Glu Lys Leu Ser Tyr Ser Val
            20                  25                  30

Pro Tyr Gln Ala Leu Lys Gly Ile Ala Glu Ser Ile Tyr Trp Lys
        35                  40                  45

Pro Thr Ile Val Phe Val Ile Asp Glu Leu Arg Val Met Lys Pro Ile
    50                  55                  60

Gln Met Glu Ser Lys Gly Val Arg Pro Ile Glu Tyr Gly Gly Asn
65                  70                  75                  80

Thr Leu Ala His Tyr Thr Tyr Leu Lys Asp Val His Tyr Gln Val Lys
                85                  90                  95

Ala His Phe Glu Phe Asn Leu His Arg Pro Asp Leu Ala Phe Asp Arg
            100                 105                 110

Asn Glu Gly Lys His Tyr Ser Ile Leu Gln Arg Ser Leu Lys Ala Gly
        115                 120                 125

Gly Arg Arg Asp Ile Phe Leu Gly Ala Arg Glu Cys Gln Gly Tyr Val
130                 135                 140

Ala Pro Cys Glu Phe Gly Ser Gly Asp Gly Phe Tyr Asp Gly Gln Gly
145                 150                 155                 160

Lys Tyr His Leu Gly Thr Met Val His Gly Phe Asn Tyr Pro Asp Glu
                165                 170                 175

Thr Gly Gln His Gln Leu Asp Val Arg Leu Trp Ser Ala Val Met Glu
            180                 185                 190

Asn Gly Tyr Ile Gln Phe Pro Arg Pro Glu Asp Cys Pro Ile Val Arg
        195                 200                 205

Pro Val Lys Glu Met Glu Pro Lys Ile Phe Asn Pro Asp Asn Val Gln
    210                 215                 220

Ser Ala Glu Gln Leu Leu His Asp Leu Gly Gly Glu
225                 230                 235

<210> SEQ ID NO 44
<211> LENGTH: 260
<212> TYPE: PRT
<213> ORGANISM: Artificial Sequence
<220> FEATURE:
```

<223> OTHER INFORMATION: Synthetic polypeptide"

<400> SEQUENCE: 44

Met Pro Asn Asp Pro Tyr Ser Leu Tyr Ser Ile Val Ile Glu Leu Gly
1               5                   10                  15

Ala Ala Glu Lys Gly Phe Pro Thr Gly Ile Leu Gly Arg Ser Leu His
            20                  25                  30

Ser Gln Val Leu Gln Trp Phe Lys Gln Asp Asn Pro Phe Leu Ala Thr
        35                  40                  45

Glu Leu His Gln Ser Gln Ile Ser Pro Phe Ser Ile Ser Pro Leu Met
    50                  55                  60

Gly Lys Arg His Ala Lys Leu Thr Lys Ala Gly Asp Arg Leu Phe Phe
65                  70                  75                  80

Arg Ile Cys Leu Leu Arg Gly Asp Leu Leu Gln Pro Leu Leu Asn Gly
                85                  90                  95

Ile Glu Gln Thr Val Asn Gln Ser Val Cys Leu Asp Lys Phe Arg Phe
            100                 105                 110

Arg Leu Cys Gln Thr His Ile Leu Pro Gly Ser His Pro Leu Ala Gly
        115                 120                 125

Ala Ser His Tyr Ser Leu Ile Ser Gln Thr Pro Val Ser Ser Lys Ile
    130                 135                 140

Thr Leu Asp Phe Lys Ser Ser Thr Ser Phe Lys Val Asp Arg Lys Ile
145                 150                 155                 160

Ile Gln Val Phe Pro Leu Gly Glu His Val Phe Asn Ser Leu Leu Arg
                165                 170                 175

Arg Trp Asn Asn Phe Ala Pro Glu Asp Leu His Phe Ser Gln Val Asp
            180                 185                 190

Trp Ser Ile Pro Ile Ala Ala Phe Asp Val Lys Thr Ile Pro Ile His
        195                 200                 205

Leu Lys Lys Val Glu Ile Gly Ala Gln Gly Trp Val Thr Tyr Ile Phe
    210                 215                 220

Pro Asn Thr Glu Gln Ala Lys Ile Ala Ser Val Leu Ser Glu Phe Ala
225                 230                 235                 240

Phe Phe Ser Gly Val Gly Arg Lys Thr Thr Met Gly Met Gly Gln Val
                245                 250                 255

Gln Val Arg Ser
            260

<210> SEQ ID NO 45
<211> LENGTH: 199
<212> TYPE: PRT
<213> ORGANISM: Artificial Sequence
<220> FEATURE:
<223> OTHER INFORMATION: Synthetic polypeptide"

<400> SEQUENCE: 45

Met Tyr Leu Ser Lys Val Ile Ile Ala Arg Ala Trp Ser Arg Asp Leu
1               5                   10                  15

Tyr Gln Leu His Gln Gly Leu Trp His Leu Phe Pro Asn Arg Pro Asp
            20                  25                  30

Ala Ala Arg Asp Phe Leu Phe His Val Glu Lys Arg Asn Thr Pro Glu
        35                  40                  45

Gly Cys His Val Leu Leu Gln Ser Ala Gln Met Pro Val Ser Thr Ala
    50                  55                  60

Val Ala Thr Val Ile Lys Thr Lys Gln Val Glu Phe Gln Leu Gln Val
65                  70                  75                  80

-continued

```
Gly Val Pro Leu Tyr Phe Arg Leu Arg Ala Asn Pro Ile Lys Thr Ile
                85                  90                  95

Leu Asp Asn Gln Lys Arg Leu Asp Ser Lys Gly Asn Ile Lys Arg Cys
            100                 105                 110

Arg Val Pro Leu Ile Lys Glu Ala Glu Gln Ile Ala Trp Leu Gln Arg
        115                 120                 125

Lys Leu Gly Asn Ala Ala Arg Val Glu Asp Val His Pro Ile Ser Glu
    130                 135                 140

Arg Pro Gln Tyr Phe Ser Gly Asp Gly Lys Ser Gly Lys Ile Gln Thr
145                 150                 155                 160

Val Cys Phe Glu Gly Val Leu Thr Ile Asn Asp Ala Pro Ala Leu Ile
                165                 170                 175

Asp Leu Val Gln Gln Gly Ile Gly Pro Ala Lys Ser Met Gly Cys Gly
            180                 185                 190

Leu Leu Ser Leu Ala Pro Leu
            195
```

<210> SEQ ID NO 46
<211> LENGTH: 187
<212> TYPE: PRT
<213> ORGANISM: Artificial Sequence
<220> FEATURE:
<223> OTHER INFORMATION: Synthetic polypeptide"

<400> SEQUENCE: 46

```
Met Asp His Tyr Leu Asp Ile Arg Leu Arg Pro Asp Pro Glu Phe Pro
1               5                   10                  15

Pro Ala Gln Leu Met Ser Val Leu Phe Gly Lys Leu His Gln Ala Leu
            20                  25                  30

Val Ala Gln Gly Gly Asp Arg Ile Gly Val Ser Phe Pro Asp Leu Asp
        35                  40                  45

Glu Ser Arg Ser Arg Leu Gly Glu Arg Leu Arg Ile His Ala Ser Ala
    50                  55                  60

Asp Asp Leu Arg Ala Leu Leu Ala Arg Pro Trp Leu Glu Gly Leu Arg
65                  70                  75                  80

Asp His Leu Gln Phe Gly Glu Pro Ala Val Val Pro His Pro Thr Pro
                85                  90                  95

Tyr Arg Gln Val Ser Arg Val Gln Ala Lys Ser Asn Pro Glu Arg Leu
            100                 105                 110

Arg Arg Arg Leu Met Arg Arg His Asp Leu Ser Glu Glu Glu Ala Arg
        115                 120                 125

Lys Arg Ile Pro Asp Thr Val Ala Arg Ala Leu Asp Leu Pro Phe Val
    130                 135                 140

Thr Leu Arg Ser Gln Ser Thr Gly Gln His Phe Arg Leu Phe Ile Arg
145                 150                 155                 160

His Gly Pro Leu Gln Val Thr Ala Glu Glu Gly Gly Phe Thr Cys Tyr
                165                 170                 175

Gly Leu Ser Lys Gly Gly Phe Val Pro Trp Phe
            180                 185
```

<210> SEQ ID NO 47
<211> LENGTH: 314
<212> TYPE: PRT
<213> ORGANISM: Artificial Sequence
<220> FEATURE:
<223> OTHER INFORMATION: Synthetic polypeptide"

<400> SEQUENCE: 47

```
Met Ala Ala Arg Arg Gly Gly Ile Arg Arg Thr Asp Leu Leu Arg Arg
1               5                   10                  15

Ser Gly Gln Pro Arg Gly Arg His Arg Ala Ser Ala Ala Glu Ser Gly
            20                  25                  30

Leu Thr Trp Ile Ser Pro Thr Leu Ile Leu Val Gly Phe Ser His Arg
        35                  40                  45

Gly Asp Arg Arg Met Thr Glu His Leu Ser Arg Leu Thr Leu Thr Leu
    50                  55                  60

Glu Val Asp Ala Pro Leu Glu Arg Ala Arg Val Ala Thr Leu Gly Pro
65                  70                  75                  80

His Leu His Gly Val Leu Met Glu Ser Ile Pro Ala Asp Tyr Val Gln
                85                  90                  95

Thr Leu His Thr Val Pro Val Asn Pro Tyr Ser Gln Tyr Ala Leu Ala
            100                 105                 110

Arg Ser Thr Thr Ser Leu Glu Trp Lys Ile Ser Thr Leu Thr Asn Glu
        115                 120                 125

Ala Arg Gln Gln Ile Val Gly Pro Ile Asn Asp Ala Ala Phe Ala Gly
    130                 135                 140

Phe Arg Leu Arg Ala Ser Gly Ile Ala Thr Gln Val Thr Ser Arg Ser
145                 150                 155                 160

Leu Glu Gln Asn Pro Leu Ser Gln Phe Ala Arg Ile Phe Tyr Ala Arg
                165                 170                 175

Pro Glu Thr Arg Lys Phe Arg Val Glu Phe Leu Thr Pro Thr Ala Phe
            180                 185                 190

Lys Gln Ser Gly Glu Tyr Val Phe Trp Pro Asp Pro Arg Leu Val Phe
        195                 200                 205

Gln Ser Leu Ala Gln Lys Tyr Gly Ala Ile Val Asp Gly Glu Pro
    210                 215                 220

Asp Pro Gly Leu Ile Ala Glu Phe Gly Gln Ser Val Arg Leu Ser Ala
225                 230                 235                 240

Phe Arg Val Ala Ser Ala Pro Phe Ala Val Gly Ala Ala Arg Val Pro
                245                 250                 255

Gly Phe Thr Gly Ser Ala Thr Phe Thr Val Arg Gly Val Asp Thr Phe
            260                 265                 270

Ala Ser Tyr Ile Ala Ala Leu Leu Trp Phe Gly Glu Phe Ser Gly Cys
        275                 280                 285

Gly Ile Lys Ala Ser Met Gly Met Gly Ala Ile Arg Val Gln Pro Leu
    290                 295                 300

Ala Pro Arg Glu Lys Cys Val Pro Lys Pro
305                 310
```

<210> SEQ ID NO 48
<211> LENGTH: 264
<212> TYPE: PRT
<213> ORGANISM: Artificial Sequence
<220> FEATURE:
<223> OTHER INFORMATION: Synthetic polypeptide"

<400> SEQUENCE: 48

```
Met Arg Phe Leu Ile Arg Leu Val Pro Glu Asp Lys Asp Arg Ala Phe
1               5                   10                  15

Lys Val Pro Tyr Asn His Gln Tyr Tyr Leu Gln Gly Leu Ile Tyr Asn
            20                  25                  30

Ala Ile Lys Ser Ser Asn Pro Lys Leu Ala Thr Tyr Leu His Glu Val
```

```
            35                  40                  45
Lys Gly Pro Lys Leu Phe Thr Tyr Ser Leu Phe Met Ala Glu Lys Arg
 50                      55                  60

Glu His Pro Lys Gly Leu Pro Tyr Phe Leu Gly Tyr Lys Lys Gly Phe
 65                  70                  75                  80

Phe Tyr Phe Ser Thr Cys Val Pro Glu Ile Ala Glu Ala Leu Val Asn
                 85                  90                  95

Gly Leu Leu Met Asn Pro Glu Val Arg Leu Trp Asp Glu Arg Phe Tyr
             100                 105                 110

Leu His Glu Ile Lys Val Leu Arg Glu Pro Lys Lys Phe Asn Gly Ser
         115                 120                 125

Thr Phe Val Thr Leu Ser Pro Ile Ala Val Thr Val Val Arg Lys Gly
     130                 135                 140

Lys Ser Tyr Asp Val Pro Pro Met Glu Lys Phe Tyr Ser Ile Ile
145                 150                 155                 160

Lys Asp Asp Leu Gln Asp Lys Tyr Val Met Ala Tyr Gly Asp Lys Pro
                 165                 170                 175

Pro Ser Glu Phe Glu Met Glu Val Leu Ile Ala Lys Pro Lys Arg Phe
             180                 185                 190

Arg Ile Lys Pro Gly Ile Tyr Gln Thr Ala Trp His Leu Val Phe Arg
         195                 200                 205

Ala Tyr Gly Asn Asp Asp Leu Leu Lys Val Gly Tyr Glu Val Gly Phe
     210                 215                 220

Gly Glu Lys Asn Ser Leu Gly Phe Gly Met Val Lys Val Glu Gly Asn
225                 230                 235                 240

Lys Thr Thr Lys Glu Ala Glu Gln Glu Lys Ile Thr Phe Asn Ser
                 245                 250                 255

Arg Glu Glu Leu Lys Thr Gly Val
             260

<210> SEQ ID NO 49
<211> LENGTH: 236
<212> TYPE: PRT
<213> ORGANISM: Artificial Sequence
<220> FEATURE:
<223> OTHER INFORMATION: Synthetic polypeptide"

<400> SEQUENCE: 49

Met Phe Val Thr Gln Val Ile Phe Asn Ile Gly Glu Arg Thr Tyr Pro
 1               5                  10                  15

Asp Arg Ala Arg Ala Met Val Ala Glu Leu Met Asp Gly Val Gln Pro
                 20                  25                  30

Gly Leu Val Ala Thr Leu Met Asn Tyr Ile Pro Gly Thr Ser Thr Ser
             35                  40                  45

Arg Thr Glu Phe Pro Thr Val Gln Phe Gly Gly Ala Ser Asp Gly Phe
         50                  55                  60

Cys Leu Leu Gly Phe Gly Asp Gly Gly Ala Ile Val Arg Asp Ala
 65                  70                  75                  80

Val Pro Leu Ile His Ala Ala Leu Ala Arg Arg Met Pro Asp Arg Ile
                 85                  90                  95

Ile Gln Val Glu His Lys Glu His Ser Leu Ser Ala Glu Ala Arg Pro
             100                 105                 110

Tyr Val Leu Ser Tyr Thr Val Pro Arg Met Val Gln Lys Lys Gln
         115                 120                 125

Arg His Ala Glu Arg Leu Leu His Glu Ala Glu Gly Lys Ala His Leu
```

```
            130                 135                 140
Glu Gly Leu Phe Leu Arg Ser Leu Gln Arg Gln Ala Ala Val Gly
145                 150                 155                 160

Leu Pro Leu Pro Glu Asn Leu Glu Val Glu Phe Lys Gly Ala Val Gly
                165                 170                 175

Asp Phe Ala Ala Lys His Asn Pro Asn Ser Lys Val Ala Tyr Arg Gly
                180                 185                 190

Leu Arg Gly Ala Val Phe Asp Val Asn Ala Arg Leu Gly Gly Ile Trp
                195                 200                 205

Thr Ala Gly Phe Met Leu Ser Lys Gly Tyr Gly Gln Phe Asn Ala Thr
                210                 215                 220

His Gln Leu Ser Gly Ala Val Asn Ala Leu Ser Glu
225                 230                 235

<210> SEQ ID NO 50
<211> LENGTH: 259
<212> TYPE: PRT
<213> ORGANISM: Artificial Sequence
<220> FEATURE:
<223> OTHER INFORMATION: Synthetic polypeptide"

<400> SEQUENCE: 50

Met His Gln Thr Leu Ile Arg Ile Asn Trp Pro Lys Gly Phe Lys Cys
1               5                   10                  15

Pro Pro Ala Glu Phe Arg Glu Lys Leu Ala Lys Ser Glu Met Phe Pro
                20                  25                  30

Pro Glu Phe Phe His Tyr Gly Thr Glu Leu Ala Val Trp Asp Lys Gln
                35                  40                  45

Thr Ala Glu Val Glu Gly Lys Ile Lys Thr Val Ser Lys Glu Lys Ile
            50                  55                  60

Ile Lys Thr Phe Asp Lys Pro Ile Pro Leu Asn Gly Arg Ala Pro Val
65                  70                  75                  80

Arg Val Ile Gly Gly Gln Ala Trp Ala Gly Val Ile Ala Asp Pro Glu
                85                  90                  95

Met Glu Gly Met Leu Ile Pro His Leu Gly Ser Ile Leu Lys Val Ala
                100                 105                 110

Ser Ser Ala Ala Gly Cys Ala Val Lys Ile Glu Leu Glu Gln Arg Lys
            115                 120                 125

Phe Gly Ile Ser Tyr Thr Glu Tyr Pro Val Lys Tyr Asn Leu Arg Glu
            130                 135                 140

Leu Val Leu Lys Arg Arg Cys Glu Asp Ala Arg Ser Thr Asp Ile Glu
145                 150                 155                 160

Ser Leu Ile Ala Asp Arg Ile Trp Gly Gly Val Ser Gly Glu Ser Tyr
                165                 170                 175

Tyr Gly Ile Asp Gly Thr Cys Ala Lys Phe Gly Phe Glu Pro Pro Ser
                180                 185                 190

Arg Glu Gln Leu Glu Leu Arg Ile Phe Pro Met Lys Asn Ile Gly Leu
            195                 200                 205

His Met Lys Ser Ser Asp Gly Leu Ser Lys Glu Tyr Met Ser Leu Ile
            210                 215                 220

Asp Ala Glu Val Trp Met Asn Ala Lys Leu Glu Gly Val Trp Gln Val
225                 230                 235                 240

Gly Asn Leu Ile Ser Arg Gly Tyr Gly Arg Phe Ile Lys Ser Ile Gly
                245                 250                 255

Ala Gln Ser
```

<210> SEQ ID NO 51
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 51
gataatctct tatagaattg aaag                                    24

<210> SEQ ID NO 52
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 52
ctaaaagaat aacttgcaaa ataacaagca ttgaaac                      37

<210> SEQ ID NO 53
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 53
gtctcaccct tcatgggtga gtggattgaa at                           32

<210> SEQ ID NO 54
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 54
gtcgcactct tcatgggtgc gtggattgaa at                           32

<210> SEQ ID NO 55
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 55
gtttcagtcc cgtagtcggg atttagtggt tggaaag                      37

<210> SEQ ID NO 56
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 56
gagttccccg cgccagcggg gataaaccg                               29

<210> SEQ ID NO 57
<211> LENGTH: 28
<212> TYPE: DNA
<213> ORGANISM: Artificial Sequence
<220> FEATURE:

<223> OTHER INFORMATION: Synthetic oligonucleotide

<400> SEQUENCE: 57
gttcactgcc gtataggcag ctaagaaa                                              28

<210> SEQ ID NO 58
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 58
gtcgtcagac ccaaaacccc gagaggggac ggaaac                                     36

<210> SEQ ID NO 59
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 59
gttacaataa gactaaaata gaattgaaag                                            30

<210> SEQ ID NO 60
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 60
gtatttcccg cgtgcgcggg ggtgagcgg                                             29

<210> SEQ ID NO 61
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 61
tattggatac acccactcat tggtgggtgg ttagaac                                    37

<210> SEQ ID NO 62
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 62
gauaaucucu uauagaauug aaag                                                  24

<210> SEQ ID NO 63
<211> LENGTH: 37
<212> TYPE: RNA
<213> ORGANISM: Artificial Sequence
<220> FEATURE:
<223> OTHER INFORMATION: Synthetic oligonucleotide

<400> SEQUENCE: 63
cuaaaagaau aacuugcaaa auaacaagca uugaaac                                    37

```
<210> SEQ ID NO 64
<211> LENGTH: 32
<212> TYPE: RNA
<213> ORGANISM: Artificial Sequence
<220> FEATURE:
<223> OTHER INFORMATION: Synthetic oligonucleotide

<400> SEQUENCE: 64
gucucacccu ucauggguga guggauugaa au                                      32

<210> SEQ ID NO 65
<211> LENGTH: 32
<212> TYPE: RNA
<213> ORGANISM: Artificial Sequence
<220> FEATURE:
<223> OTHER INFORMATION: Synthetic oligonucleotide

<400> SEQUENCE: 65
gucgcacucu ucaugggugc guggauugaa au                                      32

<210> SEQ ID NO 66
<211> LENGTH: 37
<212> TYPE: RNA
<213> ORGANISM: Artificial Sequence
<220> FEATURE:
<223> OTHER INFORMATION: Synthetic oligonucleotide

<400> SEQUENCE: 66
guuucagucc cguagucggg auuuaguggu uggaaag                                 37

<210> SEQ ID NO 67
<211> LENGTH: 29
<212> TYPE: RNA
<213> ORGANISM: Artificial Sequence
<220> FEATURE:
<223> OTHER INFORMATION: Synthetic oligonucleotide

<400> SEQUENCE: 67
gaguuccccg cgccagcggg gauaaaccg                                          29

<210> SEQ ID NO 68
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 68
guucacugcc guauaggcag cuaagaaa                                           28

<210> SEQ ID NO 69
<211> LENGTH: 36
<212> TYPE: RNA
<213> ORGANISM: Artificial Sequence
<220> FEATURE:
<223> OTHER INFORMATION: Synthetic oligonucleotide

<400> SEQUENCE: 69
gucgucagac ccaaaacccc gagagggggac ggaaac                                 36

<210> SEQ ID NO 70
<211> LENGTH: 30
<212> TYPE: RNA
<213> ORGANISM: Artificial Sequence
<220> FEATURE:
<223> OTHER INFORMATION: Synthetic oligonucleotide
```

<400> SEQUENCE: 70
guuacaauaa gacuaaaaua gaauugaaag                                    30

<210> SEQ ID NO 71
<211> LENGTH: 29
<212> TYPE: RNA
<213> ORGANISM: Artificial Sequence
<220> FEATURE:
<223> OTHER INFORMATION: Synthetic oligonucleotide

<400> SEQUENCE: 71 guauucccg cgugcgcggg ggugagcgg                                      29

<210> SEQ ID NO 72
<211> LENGTH: 37
<212> TYPE: RNA
<213> ORGANISM: Artificial Sequence
<220> FEATURE:
<223> OTHER INFORMATION: Synthetic oligonucleotide

<400> SEQUENCE: 72
uauuggauac acccacucau ugguggugg uuagaac                             37

<210> SEQ ID NO 73
<211> LENGTH: 2133
<212> TYPE: DNA
<213> ORGANISM: Artificial Sequence
<220> FEATURE:
<223> OTHER INFORMATION: Synthetic polynucleotide

<400> SEQUENCE: 73
atgcccaaga agaagcggaa ggtgatgcct ctgatcttca agatcggcta taacgtgatc    60
cccctgcagg acgtgatcct gcccacccct tccagcaagg tgctgaagta cctgatccag   120
agcggcaagc tgatccccag cctgaaggac ctgatcacca gccgggacaa gtacaagcca   180
atcttcatct cccacctggg cttcaaccag cggaggattt tccagaccaa cggcaatctg   240
aaaaccatca ccaagggcag tagactgagc tccatcatcg ccttcagcac ccaggccaac   300
gtgctgtccg aggtggccga tgaagggatc ttcgaaaccg tgtacggaaa gttccacatc   360
atgatcgaaa gcatcgagat cgtggaggtg gaaaagctga aggaggaggt ggagaagcac   420
atgaacgaca catcagagt gagattcgtg tctcccacac tgctgagctc aaggtgctg    480 ctgccccca gcctgtccga agatacaag aagatccacg ccgggtacag caccctgccc    540
agcgtgggcc tgatcgtggc ctacgcctac aacgtgtact gcaatctgat cggcaagaag   600
gaagtggaag tgcgggcctt caagtttgga atcctgagca cgccctgtc cagaatcatc    660 ggctacgacc tgcaccctgt gaccgtggcc atcggcgagg acagcaaggg gaatctgaga   720
aaggctcggg gcgtgatggg ctggatcgag ttcgacatcc ccgacgaaag actgaagcgg   780
cgggccctga actatctgct gaccagcagc tacctgggca tcgggagatc tcggggcatc   840
ggcttcggcg agatccggct ggagttccgg aagattgaa gaaggagggg acccaagaag   900
aagcggaagg tgggtggagg cggaggttct ggggaggag gtagtggcgg tggtggttca   960
ggaggcggcg gaagccagct gcatttaccg caggttttag ctgacgctgt ctcacgcctg  1020
gtcataggta agtttggtga cctgaccgac aacttctcct cccctcacgc tcgcagaata  1080
ggtctggctg gagtcgtcat gacaacaggc acagatgtta agatgccaa ggtgatatgt   1140 gtttctacag gagcaaaatg tattaatggt gaatacctaa gtgatcgtgg ccttgcatta  1200
aatgactgcc atgcagaaat agtatctcgg agatccttgc tcagatttct ttatacacaa  1260

```
cttgagcttt acttaaataa cgaggatgat caaaaaagat ccatctttca gaaatcagag    1320 cgagggggt ttaggctgaa ggagaatata cagtttcatc tgtacatcag cacctctccc    1380
tgtggagatg ccagaatctt ctcaccacat gaggcaatcc tggaagaacc agcagataga   1440
cacccaaatc gtaaagcaag aggacagcta cggaccaaaa tagaggctgg tcaggggacg   1500
attccagtgc gcaacaatgc gagcatccaa acgtgggacg gggtgctgca aggggagcgg   1560
ctgctcacca tgtcctgcag tgacaagatt gcacgctgga acgtggtggg catccaggga   1620
tcactgctca gcattttcgt ggagcccatt tacttctcga gcatcatcct gggcagcctt   1680
taccacgggg accaccttc cagggccatg taccagcgga tctccaacat agaggacctg    1740
ccacctctct acaccctcaa caagccttg ctcacaggca tcagcaatgc agaagcacgg    1800
cagccaggga aggcccccat attcagtgtc aactggacgg taggcgactc cgctattgag   1860
gtcatcaacg ccacgactgg gaagggagag ctgggccgcg cgtcccgcct gtgtaagcac   1920
gcgttgtact gtcgctggat gcgtgtgcac ggcaaggttc cctccacttt actacgctcc   1980
aagattacca agcccaacgt gtaccatgag acaaagctgg cggcaaagga gtaccaggcc   2040
gccaaggcgc gtctgttcac agccttcatc aaggcgggc tgggggcctg ggtggagaag    2100
cccaccgagc aggaccagtt ctcactcacg taa                                2133
```

<210> SEQ ID NO 74
<211> LENGTH: 1920
<212> TYPE: DNA
<213> ORGANISM: Artificial Sequence
<220> FEATURE:
<223> OTHER INFORMATION: Synthetic polynucleotide

<400> SEQUENCE: 74

```
atgcccaaga agaagcggaa ggtgatggac ctggagtaca tgcacatctc ctaccctaac     60
atcctgctga acatgcggga cggcagcaag ctgcggggct acttcgccaa gaagtacatc    120
gacgaagaga ttgtgcacaa ccacagagac aacgcctttg tgtacaagta cccccagatc    180
cagtttaaga tcatcgatag aagccccctg atcatcggca ttggctctct gggcatcaat    240
ttcctggaga gcaagcggat cttcttcgag aaggaactga ttatcagcaa cgacaccaac    300
gacatcaccg aggtgaacgt gcacaaggac atggatcact tcggcacgac cgacaagatc    360
ctgaagtacc agttcaagac cccttggatg gcactgaacg ccaagaatag cgagatctac    420
aagaactctg acgagatcga ccgggaggag ttcctgaaga gagtgctgat tgggaatatc    480
ctgagcatgt ctaagagcct gggctatacc atcgaagaaa agctgaaggt gaagattaac    540
ctgaaggaag tgcccgtgaa gttcaagaac cagaacatgg tgggctttcg gggcgagttc    600
tacatcaact tcgacatccc tcagtatctg gcatcggcc ggaatgtgtc ccggggattc    660
ggcacagtgg tgaaggtgcc caagaagaag cggaaggtgg tggaggcgg aggttctggg    720 ggaggaggta gtggcggtgg tggttcagga ggcggcggaa gccagctgca tttaccgcag   780
gttttagctg acgctgtctc acgcctggtc ataggtaagt ttggtgacct gaccgacaac    840
ttctcctccc ctcacgctcg cagaataggt ctggctggag tcgtcatgac aacaggcaca    900
gatgttaaag atgccaaggt gatatgtgtt tctacaggag caaatgtat taatggtgaa    960 tacctaagtg atcgtggcct tgcattaaat gactgccatg cagaaatagt atctcggaga   1020
tccttgctca gatttcttta tacacaactt gagctttact aaataacga ggatgatcaa    1080 aaaagatcca tctttcagaa atcagagcga ggggggttta ggctgaagga gaatatacag   1140
```

```
tttcatctgt acatcagcac ctctccctgt ggagatgcca gaatcttctc accacatgag    1200
gcaatcctgg aagaaccagc agatagacac ccaaatcgta aagcaagagg acagctacgg    1260
accaaaatag aggctggtca ggggacgatt ccagtgcgca acaatgcgag catccaaacg    1320
tgggacgggg tgctgcaagg ggagcggctg ctcaccatgt cctgcagtga caagattgca    1380
cgctggaacg tggtgggcat ccagggatca ctgctcagca ttttcgtgga gcccatttac    1440
ttctcgagca tcatcctggg cagcctttac cacggggacc acctttccag gccatgtac    1500 cagcggatct ccaacataga ggacctgcca cctctctaca ccctcaacaa gcctttgctc    1560
acaggcatca gcaatgcaga agcacggcag ccagggaagg cccccatatt cagtgtcaac    1620
tggacggtag gcgactccgc tattgaggtc atcaacgcca cgactgggaa gggagagctg    1680
ggccgcgcgt cccgcctgtg taagcacgcg ttgtactgtc gctggatgcg tgtgcacggc    1740
aaggttccct cccacttact acgctccaag attaccaagc caacgtgta ccatgagaca    1800 aagctggcgg caaaggagta ccaggccgcc aaggcgcgtc tgttcacagc cttcatcaag    1860
gcggggctgg gggcctgggt ggagaagccc accgagcagg accagttctc actcacgtaa    1920

<210> SEQ ID NO 75
<211> LENGTH: 1974
<212> TYPE: DNA
<213> ORGANISM: Artificial Sequence
<220> FEATURE:
<223> OTHER INFORMATION: Synthetic polynucleotide

<400> SEQUENCE: 75
atgcccaaga agaagcggaa ggtgatgaga aatgaagtgc agttcgagct gttcggcgac     60
tacgccctgt tcaccgaccc cctgaccaag atcggcggcg aaaagctgag ctacagcgtg    120
cctacctacc aggccctgaa gggcatcgcc gagagcatct actggaagcc caccatcgtg    180
ttcgtgatcg acgaactgcg ggtcatgaag cccattcaga tggagtctaa gggcgtgagg    240
cccatcgagt acgcggcgg caacaccctg gcccactaca cctacctgaa ggatgtgcac    300
taccaggtga aggcccactt cgagttcaac ctgcaccggc ccgacctggc cttcgataga    360
aacgagggca gcactactc catcctgcag agaagcctga aggccggcgg cagaagagat    420
attttcctgg gcgcccggga gtgccagggc tacgtggccc cctgcgagtt cggcagcggc    480
gacggcttct acgacggcca gggcaagtac cacctgggaa ccatggtgca cggtttcaac    540 tacccccgacg aaaccggaca gcaccagctg gatgtgagac tgtggtctgc cgtcatggaa    600
aacggctaca tccagttccc ccgccctgag gactgcccca tcgtgcggcc tgtgaaggag    660
atggaaccca agatcttcaa ccccgacaac gtgcagtccg ccgaacagct gctgcacgac    720
ctgggcggcg aacccaagaa gaagcggaag gtggtggag gcggaggttc tgggggagga    780
ggtagtggcg gtggtggttc aggaggcggc ggaagccagc tgcatttacc gcaggtttta    840
gctgacgctg tctcacgcct ggtcataggt aagtttggtg acctgaccga caacttctcc    900 tccccctcacg ctcgcagaat aggtctggct ggagtcgtca tgacaacagg cacagatgtt    960
aaagatgcca aggtgatatg tgttttctaca ggagcaaaat gtattaatgg tgaataccta    1020
agtgatcgtg gccttgcatt aaatgactgc catgcagaaa tagtatctcg agatccttg    1080 ctcagatttc tttatacaca acttgagctt tacttaaata acgaggatga tcaaaaaga    1140 tccatctttc agaaatcaga gcgaggggg tttaggctga aggagaatat acagtttcat    1200
ctgtacatca gcacctctcc ctgtggagat gccagaatct tctcaccaca tgaggcaatc    1260
ctggaagaac cagcagatag acacccaaat cgtaaagcaa gaggacagct acggaccaaa    1320
```

```
atagaggctg gtcaggggac gattccagtg cgcaacaatg cgagcatcca aacgtgggac    1380
ggggtgctgc aagggagcg gctgctcacc atgtcctgca gtgacaagat tgcacgctgg    1440
aacgtggtgg gcatccaggg atcactgctc agcattttcg tggagcccat ttacttctcg    1500
agcatcatcc tgggcagcct ttaccacggg gaccacctttt ccaggccat gtaccagcgg    1560 atctccaaca tagaggacct gccacctctc tacaccctca acaagccttt gctcacaggc    1620
atcagcaatg cagaagcacg gcagccaggg aaggccccca tattcagtgt caactggacg    1680
gtaggcgact ccgctattga ggtcatcaac gccacgactg ggaagggaga gctgggccgc    1740
gcgtcccgcc tgtgtaagca cgcgttgtac tgtcgctgga tgcgtgtgca cggcaaggtt    1800
ccctcccact tactacgctc aagattacc aagcccaacg tgtaccatga gacaaagctg    1860
gcggcaaagg gtaccaggc cgccaaggcg cgtctgttca cagccttcat caaggcgggg    1920
ctgggggcct gggtggagaa gcccaccgag caggaccagt tctcactcac gtaa    1974

<210> SEQ ID NO 76
<211> LENGTH: 1992
<212> TYPE: DNA
<213> ORGANISM: Artificial Sequence
<220> FEATURE:
<223> OTHER INFORMATION: Synthetic polynucleotide

<400> SEQUENCE: 76
atgcccaaga agaagcggaa ggtgatgtac agaagccggg acttctacgt gagagtgtcc      60
ggccagcggg ccctgttcac caaccccgcc accaagggcg gctccgaacg gagctcctac     120
tccgtgccta cccggcaggc cctgaacggg attgtggacg ccatctacta caagcccacg     180
ttcaccaaca tcgtgaccga ggtgaaggtg attaaccaga tccagaccga actgcagggc     240
gtgcgggccc tgctgcatga ctacagcgcc gacctgagct acgtgtccta cctgagcgac     300
gtggtgtacc tgattaagtt tcatttcgtg tggaacgagg atagaaagga cctgaatagc     360
gaccggctgc agccaagca tgaggccatc atggagcggt ctatccggaa gggcggcaga     420
cgggacgtgt tcctgggcac cagagaatgc ctgggcctgc tggacgacat cagccaggaa     480
gaatacgaaa ccacagtgag ctattacaat ggggtgaaca tcgacctggg catcatgttc     540
cacagcttcg cttaccccaa ggacaagaaa acccccctga gtcctactt cacaaagacc     600 gtgatgaaga acgcgtgat caccttcaag gcccagtccg aatgcgatat tgtgaacacc     660
ctgagctcct acgccttcaa ggcccccgag gagatcaaga gcgtgaacga cgagtgcatg     720
gagtacgacg ccatggagaa gggcgaaaac cccaagaaga agcggaaggt gggtggaggc     780
ggaggttctg ggggaggagg tagtggcggt ggtggttcag gaggcggcgg aagccagctg     840
catttaccgc aggttttagc tgacgctgtc tcacgcctgg tcataggtaa gtttggtgac     900
ctgaccgaca acttctcctc ccctcacgct cgcagaatag gtctggctgg agtcgtcatg     960
acaacaggca cagatgttaa agatgccaag gtgatatgtg tttctacagg agcaaaatgt    1020
attaatggtg aatacctaag tgatcgtggc cttgcattaa atgactgcca tgcagaaata    1080
gtatctcgga gatccttgct cagatttctt tatacacaac ttgagcttta cttaaataac    1140
gaggatgatc aaaaaagatc catctttcag aaatcagagc gagggggtt taggctgaag    1200 gagaatatac agtttcatct gtacatcagc acctctccct gtggagatgc cagaatcttc    1260
tcaccacatg aggcaatcct ggaagaacca gcagatagac acccaaatcg taagcaaga    1320 ggacagctac ggaccaaaat agaggctggt caggggacga ttccagtgcg caacaatgcg    1380
```

| | |
|---|---|
| agcatccaaa cgtgggacgg ggtgctgcaa ggggagcggc tgctcaccat gtcctgcagt | 1440 |
| gacaagattg cacgctggaa cgtggtgggc atccagggat cactgctcag cattttcgtg | 1500 |
| gagcccattt acttctcgag catcatcctg ggcagccttt accacgggga ccacctttcc | 1560 |
| agggccatgt accagcggat ctccaacata gaggacctgc cacctctcta caccctcaac | 1620 |
| aagcctttgc tcacaggcat cagcaatgca gaagcacggc agccagggaa ggcccccata | 1680 |
| ttcagtgtca actggacggt aggcgactcc gctattgagg tcatcaacgc cacgactggg | 1740 |
| aagggagagc tgggccgcgc gtcccgcctg tgtaagcacg cgttgtactg tcgctggatg | 1800 |
| cgtgtgcacg gcaaggttcc ctcccactta ctacgctcca agattaccaa gcccaacgtg | 1860 |
| taccatgaga caaagctggc ggcaaaggag taccaggccg ccaaggcgcg tctgttcaca | 1920 |
| gccttcatca aggcggggct gggggcctgg gtggagaagc ccaccgagca ggaccagttc | 1980 |
| tcactcacgt aa | 1992 |

<210> SEQ ID NO 77
<211> LENGTH: 2046
<212> TYPE: DNA
<213> ORGANISM: Artificial Sequence
<220> FEATURE:
<223> OTHER INFORMATION: Synthetic polynucleotide

<400> SEQUENCE: 77

| | |
|---|---|
| atgcccaaga gaagcggaa ggtgatgccc aacgatccct acagcctgta ctccatcgtg | 60 |
| atcgaactgg gcgccgccga aaagggattc cccacaggca tcctgggcag aagcctgcat | 120 |
| agccaggtgc tgcagtggtt caagcaggat aaccccttcc tggccaccga gctgcaccag | 180 |
| agccagatct ccccettete catctctcca ctgatgggca gcggcacgc caagctgacc | 240 |
| aaggccggcg accggctgtt ctttcggatc tgcctgctga ggagagatct gctgcagccc | 300 |
| ctgctgaacg gcattgagca gaccgtgaac cagagcgtgt gcctggacaa gttccggttc | 360 |
| cggctgtgcc agacccacat cctgcccggc agccacccte tggctggcgc ctcccactat | 420 |
| agcctgatca gccagacccc agtgagctcc aagattaccc tggacttcaa gagttctacc | 480 |
| tccttcaagg tggaccggaa gatcatccaa gtgttccctc gggcgaaaca cgtgttcaac | 540 |
| agcctgctca gacgctggaa taacttcgcc cccgaggacc tgcacttctc tcaggtggac | 600 |
| tggagcatcc ccatcgccgc attcgacgtg aaaaccatcc ccatccacct gaagaaggtc | 660 |
| gagatcggcg cacagggctg ggtgacctac atcttcccca acacagaaca ggccaagatc | 720 |
| gcctccgtgc tgagcgaatt cgccttcttc agcggagtgg gacggaaaac caccatgggc | 780 |
| atgggccagg tgcaggtgcg gtcccccaag aagaagcgga aggtgggtgg aggcggaggt | 840 |
| tctggggggag gaggtagtgg cggtggtggt tcaggaggcg gcggaagcca gctgcattta | 900 |
| ccgcaggttt tagctgacgc tgtctcacgc ctggtcatag gtaagtttgg tgacctgacc | 960 |
| gacaacttct cctcccctca cgctcgcaga ataggtctgg ctggagtcgt catgacaaca | 1020 |
| ggcacagatg ttaaagatgc caaggtgata tgtgtttcta caggagcaaa atgtattaat | 1080 |
| ggtgaatacc taagtgatcg tggccttgca ttaaatgact gccatgcaga aatagtatct | 1140 |
| cggagatcct gctcagatt tctttataca caacttgagc tttacttaaa taacgaggat | 1200 |
| gatcaaaaaa gatccatctt tcagaaatca gagcgagggg ggtttaggct gaaggagaat | 1260 |
| atacagtttc atctgtacat cagcacctct ccctgtggag atgccagaat cttctcacca | 1320 |
| catgaggcaa tcctgaaaga accagcagat agacacccaa atcgtaaagc aagaggacag | 1380 |
| ctacggacca aaatagaggc tggtcagggg acgattccag tgcgcaacaa tgcgagcatc | 1440 |

```
caaacgtggg acggggtgct gcaaggggag cggctgctca ccatgtcctg cagtgacaag    1500
attgcacgct ggaacgtggt gggcatccag ggatcactgc tcagcatttt cgtggagccc    1560
atttacttct cgagcatcat cctgggcagc ctttaccacg ggaccacct ttccagggcc     1620 atgtaccagc ggatctccaa catagaggac ctgccacctc tctacaccct caacaagcct    1680
ttgctcacag gcatcagcaa tgcagaagca cggcagccag ggaaggcccc catattcagt    1740
gtcaactgga cggtaggcga ctccgctatt gaggtcatca acgccacgac tgggaaggga    1800
gagctgggcc gcgcgtcccg cctgtgtaag cacgcgttgt actgtcgctg gatgcgtgtg    1860
cacggcaagg ttccctccca cttactacgc tccaagatta ccaagcccaa cgtgtaccat    1920
gagacaaagc tggcggcaaa ggagtaccag gccgccaagg cgcgtctgtt cacagccttc    1980
atcaaggcgg ggctggggc ctgggtggag aagcccaccg agcaggacca gttctcactc     2040
acgtaa                                                                2046

<210> SEQ ID NO 78
<211> LENGTH: 1860
<212> TYPE: DNA
<213> ORGANISM: Artificial Sequence
<220> FEATURE:
<223> OTHER INFORMATION: Synthetic polynucleotide

<400> SEQUENCE: 78
atgcctaaga agaagcggaa ggtgtacctg agcaaggtga tcatcgccag agcctggagc      60
agagacctgt accagctgca ccagggcctg tggcacctgt tccccaaccg gcccgacgcc     120
gcccgggatt tcctgttcca cgtggagaag agaaacaccc cggaaggctg ccacgtgctg     180
ctgcagagcg cacagatgcc tgtgagcacc gccgtggcca ccgtgatcaa gaccaagcag     240
gtggagttcc agctgcaggt gggcgtgccc ctgtatttca ggctgcgggc gaatcccatc     300
aagaccatcc tggacaacca gaagcggctg gacagcaagg gcaacatcaa gaggtgcaga     360
gtgcctctga tcaaggaggc cgaacagatc gcctggctgc agcggaagct gggcaatgcc     420
gccagagtgg aggacgtgca ccccatcagc gagcggcccc agtacttctc cggcgacgga     480
aagagcggaa agatccagac cgtgtgcttc gagggcgtgc tgaccatcaa cgacgcaccc     540
gccctgatcg acctcgtgca gcaggggatc ggccctgcca gtccatgggc tgcggactg      600 ctgtccctgg cccccctgcc caagaagaag cggaaggtgg tggaggcgg aggttctggg      660 ggaggaggta gtggcggtgg tggttcagga ggcggcggaa gccagctgca tttaccgcag     720
gttttagctg acgctgtctc acgcctggtc ataggtaagt ttggtgacct gaccgacaac     780
ttctcctccc ctcacgctcg cagaataggt ctggctggag tcgtcatgac aacaggcaca     840
gatgttaaag atgccaaggt gatatgtgtt tctacaggga caaatgtat taatggtgaa     900 tacctaagtg atcgtggcct tgcattaaat gactgccatg cagaaatagt atctcggaga     960
tccttgctca gatttcttta tacacaactt gagctttact taaataacga ggatgatcaa    1020
aaaagatcca tctttcagaa atcagagcga ggggggttta ggctgaagga gaatatacag    1080
tttcatctgt acatcagcac ctctcccctgt ggagatgcca gaatcttctc accacatgag    1140
gcaatcctgg aagaaccagc agatagacac ccaaatcgta agcaagagg acagctacgg      1200 accaaaatag aggctggtca ggggacgatt ccagtgcgca caatgcgag catccaaacg      1260 tgggacgggg tgctgcaagg ggagcggctg ctcaccatgt cctgcagtga caagattgca    1320
cgctggaacg tggtgggcat ccagggatca ctgctcagca ttttcgtgga gcccatttac    1380
```

```
ttctcgagca tcatcctggg cagcctttac cacggggacc acctttccag ggccatgtac    1440
cagcggatct ccaacataga ggacctgcca cctctctaca ccctcaacaa gcctttgctc    1500
acaggcatca gcaatgcaga agcacggcag ccagggaagg cccccatatt cagtgtcaac    1560
tggacggtag cgcactccgc tattgaggtc atcaacgcca cgactgggaa gggagagctg    1620
ggccgcgcgt cccgcctgtg taagcacgcg ttgtactgtc gctggatgcg tgtgcacggc    1680
aaggttccct cccacttact acgctccaag attaccaagc caacgtgta ccatgagaca    1740 aagctggcgg caaaggagta ccaggccgcc aaggcgcgtc tgttcacagc cttcatcaag    1800
gcggggctgg gggcctgggt ggagaagccc accgagcagg accagttctc actcacgtaa    1860
```

<210> SEQ ID NO 79
<211> LENGTH: 1824
<212> TYPE: DNA
<213> ORGANISM: Artificial Sequence
<220> FEATURE:
<223> OTHER INFORMATION: Synthetic polynucleotide

<400> SEQUENCE: 79

```
atgcctaaga agaagagaaa ggtggaccac tacctggaca ttagactgcg ccctgaccca      60
gagttccctc ctgcccagct gatgtctgtg ctgtttggca agctgcacca ggccctggtg     120
gcccagggcg gtgacagaat cggagtgtct ttccctgatc tggacgaatc tagatctaga     180
ctgggagaga gactgagaat ccacgcgtct gccgacgacc tgagagctct gctggccaga     240
ccatggctgg aaggactgcg cgaccacctg cagttcggtg aacctgccgt ggtgcctcac     300
ccaactccat acagacaggt gagtagagtg caggcaaagt ctaatccaga gagactgaga     360
cgcagactga tgagaaggca tgacctgtcc gaagaagaag ccagaaagag aatcccagac     420
acagtggcca gagccctgga tctgcctttt gtgaccctga gaagccagtc taccggccag     480
cacttcagac tgtttattcg ccacggacca ctgcaggtga ccgccgaaga gggaggtttt     540
acctgctacg gactgagcaa ggagggtttc gtgccttggt tccccaagaa gaagcggaag     600
gtgggtggag gcggaggttc tggggaggga ggtagtggcg gtggtggttc aggaggcggc     660
ggaagccagc tgcatttacc gcaggtttta gctgacgctg tctcacgcct ggtcataggt     720
aagtttggtg acctgaccga caacttctcc tcccctcacg ctcgcagaat aggtctggct     780
ggagtcgtca tgacaacagg cacagatgtt aaagatgcca aggtgatatg tgttttctaca     840 ggagcaaaat gtattaatgg tgaataccta agtgatcgtg gccttgcatt aaatgactgc     900
catgcagaaa tagtatctcg gagatccttg ctcagatttc tttatacaca acttgagctt     960
tacttaaata cgaggatga tcaaaaaaga tccatctttc agaaatcaga gcgaggggggg    1020 tttaggctga aggagaatat acagtttcat ctgtacatca gcacctctcc ctgtggagat    1080
gccagaatct tctcaccaca tgaggcaatc ctggaagaac cagcagatag acacccaaat    1140
cgtaaagcaa gaggacagct acggaccaaa atagaggctg tcaggggac gattccagtg    1200 cgcaacaatg cgagcatcca aacgtgggac ggggtgctgc aaggggagcg gctgctcacc    1260
atgtcctgca gtgacaagat tgcacgctgg aacgtggtgg gcatccaggg atcactgctc    1320
agcattttcg tggagcccat ttacttctcg agcatcatcc tgggcagcct ttaccacggg    1380
gaccaccttt ccagggccat gtaccagcgg atctccaaca tagaggacct gccacctctc    1440
tacaccctca caagcctttt gctcacaggc atcagcaatg cagaagcacg gcagccaggg    1500 aaggcccca tattcagtgt caactggacg gtaggcgact ccgctattga ggtcatcaac    1560
gccacgactg ggaagggaga gctgggccgc gcgtcccgcc tgtgtaagca cgcgttgtac    1620
```

| | |
|---|---:|
| tgtcgctgga tgcgtgtgca cggcaaggtt ccctcccact tactacgctc caagattacc | 1680 |
| aagcccaacg tgtaccatga gacaaagctg gcggcaaagg agtaccaggc cgccaaggcg | 1740 |
| cgtctgttca cagccttcat caaggcgggg ctggggggcct gggtggagaa gcccaccgag | 1800 |
| caggaccagt tctcactcac gtaa | 1824 |

<210> SEQ ID NO 80
<211> LENGTH: 2208
<212> TYPE: DNA
<213> ORGANISM: Artificial Sequence
<220> FEATURE:
<223> OTHER INFORMATION: Synthetic polynucleotide

<400> SEQUENCE: 80

| | |
|---|---:|
| atgcccaaga agaagcggaa ggtgatggcc gccagaagag gcggaatccg gagaaccgac | 60 |
| ctgctgcgga ggtctggcca gcctcggggc agacaccggg cctccgccgc cgagagcggc | 120 |
| ctgacatgga tctcccctac cctgatcctg gtgggcttca gccacagggg cgataggaga | 180 |
| atgaccgagc acctgtccag actgaccctg accctggaag tggatgcccc cctggagaga | 240 |
| gcccgggtgg ccaccctggg ccccacctg catggcgtgc tgatggagtc tatccccgcc | 300 |
| gactacgtgc agacactgca cacagtgccg gtgaacccctt acagccagta cgctctggcc | 360 |
| cggagcacca ccagcctgga gtggaagatc tccaccctga caatgaggcc ccggcagcag | 420 |
| atcgtcggcc ccatcaacga cgccgccttc gccggcttcc ggctgcgggc cagcggcatc | 480 |
| gccacccagg tgacaagcag aagcctggag cagaaccccc tgtcccagtt tgccagaatc | 540 |
| ttctacgcca ggcccgaaac ccgcaagttc agagtggagt cctgaccccc accgccttc | 600 |
| aagcagagcg gcgagtacgt gttttggccc gatcccagac tggtgttcca gtccctggcc | 660 |
| cagaagtacg gcgccatcgt ggacggagaa gagcccgacc ccggcctgat cgccgagttt | 720 |
| ggccagtccg tgagactgag cgccttcaga gtggccagcg ccccttttgc cgtgggcgcc | 780 |
| gccagggtgc ccggattcac cggcagcgcc accttcaccg tgcggggagt ggacaccttc | 840 |
| gccagctaca tcgccgctct gctgtggttc ggcgagttca gcggatgcgg catcaaggcc | 900 |
| tccatgggaa tgggcgccat ccgggtgcag cctctggccc ccggagaa gtgcgtgccc | 960 |
| aagcccccca gaagaagcg gaaggtgggt ggaggcggag gttctggggg aggaggtagt | 1020 |
| ggcggtggtg gttcaggagg cggcggaagc cagctgcatt taccgcaggt tttagctgac | 1080 |
| gctgtctcac gcctggtcat aggtaagttt ggtgacctga ccgacaactt ctcctcccct | 1140 |
| cacgctcgca gaataggtct ggctggagtc gtcatgacaa caggcacaga tgttaaagat | 1200 |
| gccaaggtga tatgtgtttc tacaggagca aaatgtatta atggtgaata cctaagtgat | 1260 |
| cgtggccttg cattaaatga ctgccatgca gaaatagtat tcggagatc cttgctcaga | 1320 |
| tttcttttata cacaacttga gctttactta aataacgagg atgatcaaaa aagatccatc | 1380 |
| tttcagaaat cagagcgagg gggggtttagg ctgaaggaga atatacagtt tcatctgtac | 1440 |
| atcagcacct ctccctgtgg agatgccaga atcttctcac cacatgaggc aatcctggaa | 1500 |
| gaaccagcag atagacaccc aaatcgtaaa gcaagaggac agctacggac caaaatagag | 1560 |
| gctggtcagg ggacgattcc agtgcgcaac atgcgagca tccaaacgtg ggacggggtg | 1620 |
| ctgcaagggg agcggctgct caccatgtcc tgcagtgaca agattgcacg ctggaacgtg | 1680 |
| gtgggcatcc aggatcact gctcagcatt ttcgtggagc ccatttactt ctcgagcatc | 1740 |
| atcctgggca gccttttacca cggggaccac ctttccaggg ccatgtacca gcggatctcc | 1800 |

| aacatagagg acctgccacc tctctacacc ctcaacaagc ctttgctcac aggcatcagc | 1860 |
| aatgcagaag cacggcagcc agggaaggcc cccatattca gtgtcaactg gacggtaggc | 1920 |
| gactccgcta ttgaggtcat caacgccacg actgggaagg gagagctggg ccgcgcgtcc | 1980 |
| cgcctgtgta agcacgcgtt gtactgtcgc tggatgcgtg tgcacggcaa ggttccctcc | 2040 |
| cacttactac gctccaagat taccaagccc aacgtgtacc atgagacaaa gctggcggca | 2100 |
| aaggagtacc aggccgccaa ggcgcgtctg ttcacagcct tcatcaaggc ggggctgggg | 2160 |
| gcctgggtgg agaagcccac cgagcaggac cagttctcac tcacgtaa | 2208 |

<210> SEQ ID NO 81
<211> LENGTH: 2058
<212> TYPE: DNA
<213> ORGANISM: Artificial Sequence
<220> FEATURE:
<223> OTHER INFORMATION: Synthetic polynucleotide

<400> SEQUENCE: 81

| atgcccaaga agaagcggaa ggtgatgaga ttcctgatca gactggtgcc cgaggacaag | 60 |
| gacagagcct tcaaggtgcc ttacaaccac cagtactatc tgcagggcct gatctacaac | 120 |
| gccatcaagt cctccaaccc caagctggcc acctacctgc acgaggtgaa gggccccaag | 180 |
| ctgttcacct acagcctgtt catggccgaa aagcgggagc accctaaggg cctgccctac | 240 |
| tttctgggct acaagaaggg cttcttctac ttcagcacct gcgtgcccga gatcgccgag | 300 |
| gccctggtga acggcctgct gatgaatccc gaggtgcggc tgtgggacga gagattctac | 360 |
| ctgcacgaaa tcaaggtcct gcgggagccc aagaagttca acggcagcac cttcgtgacc | 420 |
| ctgagcccca tcgccgtgac cgtggtgaga aagggcaagt cctacgacgt gccccccatg | 480 |
| gaaaaggagt tctacagcat tatcaaggat gacctgcagg acaagtacgt gatggcctac | 540 |
| ggcgacaagc cccccagtga gttcgagatg gaagtgctga tcgccaagcc caagcggttc | 600 |
| cggatcaagc ccgcatcta tcagaccgcc tggcacctgg tgtttcgggc ctacggcaat | 660 |
| gacgacctgc tgaaggtggg ctacgaagtg ggattcgggg agaagaactc cctgggattc | 720 |
| ggaatggtca aggtggaggg caacaagacc accaaggaag ccgaagaaca ggagaagatc | 780 |
| accttcaact cccgggaaga gctgaaaaca ggcgtgccca gaagaagcg aaggtgggt | 840 |
| ggaggcggag gttctggggg aggaggtagt ggcggtggtg gttcaggagg cggcggaagc | 900 |
| cagctgcatt taccgcaggt tttagctgac gctgtctcac gcctggtcat aggtaagttt | 960 |
| ggtgacctga ccgacaactt ctcctcccct cacgctcgca gaataggtct ggctggagtc | 1020 |
| gtcatgacaa caggcacaga tgttaaagat gccaaggtga tatgtgtttc tacaggagca | 1080 |
| aaatgtatta atggtgaata cctaagtgat cgtggccttg cattaaatga ctgccatgca | 1140 |
| gaaatagtat ctcggagatc cttgctcaga tttctttata cacaacttga gctttactta | 1200 |
| aataacgagg atgatcaaaa agatccatc tttcagaaat cagagcgagg ggggtttagg | 1260 |
| ctgaaggaga atatacagtt tcatctgtac atcagcacct ctccctgtgg agatgccaga | 1320 |
| atcttctcac cacatgaggc aatcctggaa gaaccagcag atagacaccc aaatcgtaaa | 1380 |
| gcaagaggac agctacggac caaaatagag gctggtcagg ggacgattcc agtgcgcaac | 1440 |
| aatgcgagca tccaaacgtg gacgggtg ctgcaagggg agcggctgct caccatgtcc | 1500 |
| tgcagtgaca agattgcacg ctggaacgtg gtgggcatcc agggatcact gctcagcatt | 1560 |
| ttcgtgagc ccatttactt ctcgagcatc atcctgggca gcctttacca cggggaccac | 1620 |
| cttccaggg ccatgtacca gcggatctcc aacatagagg acctgccacc tctctacacc | 1680 |

```
ctcaacaagc ctttgctcac aggcatcagc aatgcagaag cacggcagcc agggaaggcc    1740
cccatattca gtgtcaactg gacggtaggc gactccgcta ttgaggtcat caacgccacg    1800
actgggaagg gagagctggg ccgcgcgtcc cgcctgtgta agcacgcgtt gtactgtcgc    1860
tggatgcgtg tgcacggcaa ggttccctcc cacttactac gctccaagat taccaagccc    1920
aacgtgtacc atgagacaaa gctggcggca aaggagtacc aggccgccaa ggcgcgtctg    1980
ttcacagcct tcatcaaggc ggggctgggg gcctgggtgg agaagcccac cgagcaggac    2040
cagttctcac tcacgtaa                                                  2058
```

<210> SEQ ID NO 82
<211> LENGTH: 1971
<212> TYPE: DNA
<213> ORGANISM: Artificial Sequence
<220> FEATURE:
<223> OTHER INFORMATION: Synthetic polynucleotide

<400> SEQUENCE: 82

```
atgcctaaga agaagcggaa ggtgttcgtg acccaggtga tcttcaacat cggcgaacgg      60
acgtaccccg acagggctcg ggctatggtg gccgagctga tggatggcgt ccagcctggc     120
ctggtggcca ccctgatgaa ctacatcccc ggcaccagca cgagccggac agagttcccc     180
accgtgcagt tcgcggcgc cagcgacggc ttttgcctgc tgggcttcgg cgacggcggc     240
ggcgccatcg tgagagatgc cgtgcccctg atccacgccg ccctggcaag gcggatgcct     300
gatcggatca tccaggtgga acacaaggag cacagcctgt ccgccgaggc ccggccctac     360
gtgctgagct acaccgtgcc tcggatggtg gtgcagaaga agcagcggca cgccgagaga     420
ctgctgcacg aagccgaggg aaaggctcac ctggagggcc tgttcctgcg agcctgcag     480 aggcaggccg ccgccgtggg cctgccctg cccgagaacc tggaggtgga gttcaaggga     540
gccgtgggcg acttcgccgc aaagcacaat ccaaatagca aggtggccta ccggggactg     600
agaggcgccg tgttcgatgt gaacgccaga ctgggcggca tctggaccgc cggattcatg     660
ctgagcaagg gctacggcca gtttaacgcc acccaccagc tgagcggcgc cgtgaacgct     720
ctgtccgaac caagaagaa gcggaaggtg ggtggaggcg gaggttctgg gggaggaggt     780
agtggcggtg gtggttcagg aggcggcgga agccagctgc atttaccgca ggttttagct     840
gacgctgtct cacgcctggt cataggtaag tttggtgacc tgaccgacaa cttctcctcc     900
cctcacgctc gcagaatagg tctggctgga gtcgtcatga caacaggcac agatgttaaa     960
gatgccaagt gatatgtgt ttctacagga gcaaaatgta ttaatggtga ataccctaagt    1020 gatcgtggcc ttgcattaaa tgactgccat gcagaaatag tatctcggag atccttgctc    1080 agatttctt atacacaact tgagctttac ttaaataacg aggatgatca aaaagatcc     1140 atctttcaga aatcagagcg agggggggttt aggctgaagg agaatataca gtttcatctg    1200
tacatcagca cctctccctg tggagatgcc agaatcttct caccacatga ggcaatcctg    1260
gaagaaccag cagatagaca cccaaatcgt aaagcaagag acagctacg gaccaaaata    1320 gaggctggtc aggggacgat tccagtgcgc aacaatgcga gcatccaaac gtgggacggg    1380
gtgctgcaag gggagcggct gctcaccatg tcctgcagtg acaagattgc acgctggaac    1440
gtggtgggca tccagggatc actgctcagc attttcgtgg agcccattta cttctcgagc    1500
atcatcctgg gcagccttta ccacgggac caccttccca gggccatgta ccagcggatc    1560
tccaacatag aggacctgcc acctctctac accctcaaca agcctttgct cacaggcatc    1620
```

| agcaatgcag aagcacggca gccagggaag gcccccatat tcagtgtcaa ctggacggta | 1680 |
| ggcgactccg ctattgaggt catcaacgcc acgactggga agggagagct gggccgcgcg | 1740 |
| tcccgcctgt gtaagcacgc gttgtactgt cgctggatgc gtgtgcacgg caaggttccc | 1800 |
| tcccacttac tacgctccaa gattaccaag cccaacgtgt accatgagac aaagctggcg | 1860 |
| gcaaaggagt accaggccgc caaggcgcgt ctgttcacag ccttcatcaa ggcggggctg | 1920 |
| ggggcctggg tggagaagcc caccgagcag gaccagttct cactcacgta a | 1971 |

```
<210> SEQ ID NO 83
<211> LENGTH: 2040
<212> TYPE: DNA
<213> ORGANISM: Artificial Sequence
<220> FEATURE:
<223> OTHER INFORMATION: Synthetic polynucleotide

<400> SEQUENCE: 83
```

| atgcccaaga agaagagaaa ggtgcaccag accctgatcc ggatcaactg gcccaaggga | 60 |
| ttcaagtgcc ccctgccga gttccggaa agctggcca gagcgagat gttcccccc | 120 |
| gagttcttcc actacggcac ggaactggcc gtgtgggaca gcagaccgc cgaggtggag | 180 |
| ggcaagatca agaccgtgtc caaggagaag atcatcaaga cctttgacaa gcccatcccc | 240 |
| ctgaatggcc gggcccccgt cagagtgatc ggcggccagg cctgggccgg cgtgatcgcc | 300 |
| gaccccgaga tggagggcat gctgatccca cacctgggga gcatcctgaa ggtggccagc | 360 |
| agcgcggccg gatgcgcagt gaagatcgaa ctggaacaga gaaagttcgg catcagctac | 420 |
| accgagtacc ccgtgaagta caacctgcgg gagctggtgc tgaagagaag atgcgaggac | 480 |
| gcccggtcta ccgatatcga gagcctgatt gccgatagaa tctgggcgg cgtgtccggc | 540 |
| gagagctact atggcatcga cggcacatgc gccaagtttg gcttcgaacc ccccagcaga | 600 |
| gagcagctgg agctgcggat cttccccatg aagaacatcg gactgcacat gaagtccagc | 660 |
| gacgactgt ccaaggagta catgagcctg attgacgccg aggtgtggat gaacgctaag | 720 |
| ctggaaggag tgtggcaggt gggcaacctg atcagcaggg gctacggccg gttcatcaag | 780 |
| tctatcggcg cccagtcccc caagaagaag cggaaggtgg tggaggcgg aggttctggg | 840 |
| ggaggaggta gtggcggtgg tggttcagga ggcggcggaa gccagctgca tttaccgcag | 900 |
| gttttagctg acgctgtctc acgcctggtc ataggtaagt ttggtgacct gaccgacaac | 960 |
| ttctcctccc ctcacgctcg cagaataggt ctggctggag tcgtcatgac aacaggcaca | 1020 |
| gatgttaaag atgccaaggt gatatgtgtt tctacaggag caaaatgtat taatggtgaa | 1080 |
| tacctaagtg atcgtggcct tgcattaaat gactgccatg cagaaatagt atctcggaga | 1140 |
| tccttgctca gatttctta tacacaactt gagctttact taaataacga ggatgatcaa | 1200 |
| aaaagatcca tctttcagaa atcagagcga gggggggttta ggctgaagga gaatatacag | 1260 |
| tttcatctgt acatcagcac ctctccctgt ggagatgcca gaatcttctc accacatgag | 1320 |
| gcaatcctgg aagaaccagc agatagacac ccaaatcgta aagcaagagg acagctacgg | 1380 |
| accaaaatag aggctggtca ggggacgatt ccagtgcgca acaatgcgag catccaaacg | 1440 |
| tgggacgggg tgctgcaagg ggagcggctg ctcaccatgt cctgcagtga caagattgca | 1500 |
| cgctggaacg tggtgggcat ccaggatca ctgctcagca ttttcgtgga gcccatttac | 1560 |
| ttctcgagca tcatcctggg cagcctttac cacggggacc accttccag ggccatgtac | 1620 |
| cagcggatct ccaacataga ggacctgcca cctctctaca ccctcaacaa gcctttgctc | 1680 |
| acaggcatca gcaatgcaga agcacggcag ccagggaagg cccccatatt cagtgtcaac | 1740 |

```
tggacggtag gcgactccgc tattgaggtc atcaacgcca cgactgggaa gggagagctg    1800
ggccgcgcgt cccgcctgtg taagcacgcg ttgtactgtc gctggatgcg tgtgcacggc    1860
aaggttccct cccacttact acgctccaag attaccaagc caacgtgta ccatgagaca     1920 aagctggcgg caaaggagta ccaggccgcc aaggcgcgtc tgttcacagc cttcatcaag    1980
gcggggctgg gggcctgggt ggagaagccc accgagcagg accagttctc actcacgtaa    2040

<210> SEQ ID NO 84
<211> LENGTH: 867
<212> TYPE: DNA
<213> ORGANISM: Artificial Sequence
<220> FEATURE:
<223> OTHER INFORMATION: Synthetic polynucleotide

<400> SEQUENCE: 84
atgcctctga tcttcaagat cggctataac gtgatccccc tgcaggacgt gatcctgccc      60
accccttcca gcaaggtgct gaagtacctg atccagagcg caagctgat ccccagcctg     120 aaggacctga tcaccagccg ggacaagtac aagccaatct tcatctccca cctgggcttc    180
aaccagcgga ggattttcca gaccaacggc aatctgaaaa ccatcaccaa gggcagtaga    240
ctgagctcca tcatcgccct cagcacccag gccaacgtgc tgtccgaggt ggccgatgaa    300
gggatcttcg aaaccgtgta cggaaagttc cacatcatga tcgaaagcat cgagatcgtg    360
gaggtggaaa agctgaagga ggaggtggag aagcacatga cgacaacat cagagtgaga     420 ttcgtgtctc ccacactgct gagctccaag gtgctgctgc cccccagcct gtccgaaaga    480
tacaagaaga tccacgccgg gtacagcacc ctgcccagcg tgggcctgat cgtggcctac    540
gcctacaacg tgtactgcaa tctgatcggc aagaaggaag tggaagtgcg ggccttcaag    600
tttggaatcc tgagcaacgc cctgtccaga atcatcggct acgacctgca ccctgtgacc    660
gtggccatcg gcgaggacag caaggggaat ctgagaaagg ctcggggcgt gatgggctgg    720
atcgagttcg acatccccga cgaaagactg aagcggcggg ccctgaacta tctgctgacc    780
agcagctacc tgggcatcgg gagatctcgg ggcatcggct tcggcgagat ccggctggag    840
ttccggaaga ttgaagagaa ggaggga                                         867

<210> SEQ ID NO 85
<211> LENGTH: 654
<212> TYPE: DNA
<213> ORGANISM: Artificial Sequence
<220> FEATURE:
<223> OTHER INFORMATION: Synthetic polynucleotide

<400> SEQUENCE: 85
atggacctgg agtacatgca catctcctac cctaacatcc tgctgaacat gcgggacggc      60
agcaagctgc ggggctactt cgccaagaag tacatcgacg aagagattgt gcacaaccac    120
agagacaacg cctttgtgta caagtacccc cagatccagt taagatcat cgatagaagc     180 cccctgatca tcggcattgg ctctctgggc atcaatttcc tggagagcaa gcggatcttc    240
ttcgagaagg aactgattat cagcaacgac accaacgaca tcaccgaggt gaacgtgcac    300
aaggacatga tcacttcgg cacgaccgac aagatcctga gtaccagtt caagaccccct     360 tggatggcac tgaacgccaa gaatagcgag atctacaaga actctgacga atcgaccgg     420 gaggagttcc tgaagagagt gctgattggg aatatcctga gcatgtctaa agcctgggc     480 tataccatcg aagaaaagct gaaggtgaag attaacctga aggaagtgcc cgtgaagttc    540
```

```
aagaaccaga acatggtggg ctttcggggc gagttctaca tcaacttcga catccctcag    600
tatctgggca tcggccggaa tgtgtcccgg ggattcggca cagtggtgaa ggtg          654
```

```
<210> SEQ ID NO 86
<211> LENGTH: 708
<212> TYPE: DNA
<213> ORGANISM: Artificial Sequence
<220> FEATURE:
<223> OTHER INFORMATION: Synthetic polynucleotide

<400> SEQUENCE: 86
atgagaaatg aagtgcagtt cgagctgttc ggcgactacg ccctgttcac cgacccctg     60 accaagatcg gcggcgaaaa gctgagctac agcgtgccta cctaccaggc cctgaagggc   120
atcgccgaga gcatctactg gaagcccacc atcgtgttcg tgatcgacga actgcgggtc   180
atgaagccca ttcagatgga gtctaagggc gtgaggccca tcgagtacgg cggcggcaac   240
accctggccc actacaccta cctgaaggat gtgcactacc aggtgaaggc ccacttcgag   300
ttcaacctgc accggcccga cctggccttc gatagaaacg agggcaagca ctactccatc   360
ctgcagagaa gcctgaaggc cggcggcaga agagatattt tcctgggcgc ccggggagtgc   420 cagggctacg tggcccccctg cgagttcggc agcggcgacg gcttctacga cggccagggc   480
aagtaccacc tgggaaccat ggtgcacggt ttcaactacc ccgacgaaac cggacagcac   540
cagctggatg tgagactgtg gtctgccgtc atggaaaacg gctacatcca gttccccgc     600 cctgaggact gccccatcgt gcggcctgtg aaggagatgg aacccaagat cttcaacccc   660
gacaacgtgc agtccgccga acagctgctg cacgacctgg gcggcgaa                708
```

```
<210> SEQ ID NO 87
<211> LENGTH: 726
<212> TYPE: DNA
<213> ORGANISM: Artificial Sequence
<220> FEATURE:
<223> OTHER INFORMATION: Synthetic polynucleotide

<400> SEQUENCE: 87
atgtacagaa gccgggactt ctacgtgaga gtgtccggcc agcgggccct gttcaccaac    60
cccgccacca agggcggctc cgaacggagc tcctactccg tgcctacccg gcaggccctg   120
aacgggattg tggacgccat ctactacaag cccacgttca ccaacatcgt gaccgaggtg   180
aaggtgatta accagatcca gaccgaactg cagggcgtgc gggccctgct gcatgactac   240
agcgccgacc tgagctacgt gtcctacctg agcgacgtgg tgtacctgat taagtttcat   300
ttcgtgtgga acgaggatag aaaggacctg aatagcgacc ggctgccagc caagcatgag   360
gccatcatgg agcggtctat ccggaagggc ggcagacggg acgtgttcct gggcaccaga   420
gaatgcctgg gcctgctgga cgacatcagc caggaagaat acgaaaccac agtgagctat   480
tacaatgggg tgaacatcga cctgggcatc atgttccaca gcttcgctta ccccaaggac   540
aagaaaaccc ccctgaagtc ctacttcaca aagaccgtga tgaagaacgg cgtgatcacc   600
ttcaaggccc agtccgaatg cgatattgtg aacacctga gctcctacgc cttcaaggcc    660
cccgaggaga tcaagagcgt gaacgacgag tgcatggagt acgacgccat ggagaagggc   720
gaaaac                                                              726
```

```
<210> SEQ ID NO 88
<211> LENGTH: 780
<212> TYPE: DNA
<213> ORGANISM: Artificial Sequence
```

```
<220> FEATURE:
<223> OTHER INFORMATION: Synthetic polynucleotide

<400> SEQUENCE: 88
atgcccaacg atccctacag cctgtactcc atcgtgatcg aactgggcgc cgccgaaaag      60
ggattcccca caggcatcct gggcagaagc ctgcatagcc aggtgctgca gtggttcaag     120
caggataacc ccttcctggc caccgagctg caccagagcc agatctcccc cttctccatc     180
tctccactga tgggcaagcg gcacgccaag ctgaccaagg ccggcgaccg gctgttcttt     240
cggatctgcc tgctgagagg agatctgctg cagcccctgc tgaacggcat tgagcagacc     300
gtgaaccaga gcgtgtgcct ggacaagttc cggttccggc tgtgccagac ccacatcctg     360
cccggcagcc accctctggc tggcgcctcc cactatagcc tgatcagcca gaccccagtg     420
agctccaaga ttaccctgga cttcaagagt tctacctcct tcaaggtgga ccggaagatc     480
atccaagtgt tccctctggg cgaacacgtg ttcaacagcc tgctcagacg ctggaataac     540 ttcgccccg aggacctgca cttctctcag gtggactgga gcatccccat cgccgcattc     600
gacgtgaaaa ccatccccat ccacctgaag aaggtcgaga tcggcgcaca gggctgggtg     660
acctacatct tccccaacac agaacaggcc aagatcgcct ccgtgctgag cgaattcgcc     720
ttcttcagcg gagtgggacg gaaaaccacc atgggcatgg ccaggtgca ggtgcggtcc      780

<210> SEQ ID NO 89
<211> LENGTH: 597
<212> TYPE: DNA
<213> ORGANISM: Artificial Sequence
<220> FEATURE:
<223> OTHER INFORMATION: Synthetic polynucleotide

<400> SEQUENCE: 89
atgtacctga gcaaggtgat catcgccaga gcctggagca gagacctgta ccagctgcac      60
cagggcctgt ggcacctgtt ccccaaccgg cccgacgccg cccgggattt cctgttccac     120
gtggagaaga gaaacacccc ggaaggctgc cacgtgctgc tgcagagcgc acagatgcct     180
gtgagcaccg ccgtggccac cgtgatcaag accaagcagg tggagttcca gctgcaggtg     240
ggcgtgcccc tgtatttcag gctgcgggcg aatcccatca agaccatcct ggacaaccag     300
aagcggctgg acagcaaggg caacatcaag aggtgcagag tgcctctgat caaggaggcc     360
gaacagatcg cctggctgca gcggaagctg ggcaatgccg ccagagtgga ggacgtgcac     420
cccatcagcg agcggcccca gtacttctcc ggcgacggaa agagcggaaa gatccagacc     480
gtgtgcttcg agggcgtgct gaccatcaac gacgcacccg ccctgatcga cctcgtgcag     540
caggggatcg gccctgccaa gtccatgggc tgcggactgc tgtccctggc ccccctg       597

<210> SEQ ID NO 90
<211> LENGTH: 561
<212> TYPE: DNA
<213> ORGANISM: Artificial Sequence
<220> FEATURE:
<223> OTHER INFORMATION: Synthetic polynucleotide

<400> SEQUENCE: 90
atggaccact acctggacat tagactgcgc cctgacccag agttccctcc tgcccagctg      60
atgtctgtgc tgtttggcaa gctgcaccag gccctggtgg cccagggcgg tgacagaatc     120
ggagtgtctt tccctgatct ggacgaatct agatctagac tggagagag actgagaatc     180 cacgcgtctg ccgacgacct gagagctctg ctggccagac catggctgga aggactgcgc     240
```

```
gaccacctgc agttcggtga acctgccgtg gtgcctcacc caactccata cagacaggtg   300
agtagagtgc aggcaaagtc taatccagag agactgagac gcagactgat gagaaggcat   360
gacctgtccg aagaagaagc cagaaagaga atcccagaca cagtggccag agccctggat   420
ctgccttttg tgaccctgag aagccagtct accggccagc acttcagact gtttattcgc   480
cacggaccac tgcaggtgac cgccgaagag ggaggtttta cctgctacgg actgagcaag   540
ggaggtttcg tgccttggtt c                                             561
```

```
<210> SEQ ID NO 91
<211> LENGTH: 942
<212> TYPE: DNA
<213> ORGANISM: Artificial Sequence
<220> FEATURE:
<223> OTHER INFORMATION: Synthetic polynucleotide

<400> SEQUENCE: 91
atggccgcca gaagaggcgg aatccggaga accgacctgc tgcggaggtc tggccagcct    60
cggggcagac accgggcctc cgccgccgag agcggcctga catggatctc ccctaccctg   120
atcctggtgg gcttcagcca cagggggcgat aggagaatga ccgagcacct gtccagactg   180
accctgaccc tggaagtgga tgcccccctg gagagagccc gggtggccac cctgggcccc   240
cacctgcatg gcgtgctgat ggagtctatc cccgccgact acgtgcagac actgcacaca   300
gtgccggtga acccttacag ccagtacgct ctggcccgga gcaccaccag cctggagtgg   360
aagatctcca ccctgacaaa tgaggcccgg cagcagatcg tcggccccat caacgacgcc   420
gccttcgccg gcttccggct gcgggccagc ggcatcgcca cccaggtgac aagcagaagc   480
ctggagcaga accccctgtc ccagtttgcc agaatcttct acgccaggcc cgaaacccgc   540
aagttcagag tggagttcct gaccccacc gccttcaagc agagcggcga gtacgtgttt   600
tggcccgatc ccagactggt gttccagtcc ctggcccaga gtacggcgc atcgtggac    660 ggagaagagc ccgaccccgg cctgatcgcc gagtttggcc agtccgtgag actgagcgcc   720
ttcagagtgg ccagcgcccc ttttgccgtg gcgccgcca gggtgcccgg attcaccggc   780
agcgccacct tcaccgtgcg gggagtggac accttcgcca gctacatcgc cgctctgctg   840
tggttcggcg agttcagcgg atgcggcatc aaggcctcca tgggaatggg cgccatccgg   900
gtgcagcctc tggcccccg ggagaagtgc gtgcccaagc cc                       942
```

```
<210> SEQ ID NO 92
<211> LENGTH: 792
<212> TYPE: DNA
<213> ORGANISM: Artificial Sequence
<220> FEATURE:
<223> OTHER INFORMATION: Synthetic polynucleotide

<400> SEQUENCE: 92
atgagattcc tgatcagact ggtgcccgag gacaaggaca gagccttcaa ggtgccttac    60
aaccaccagt actatctgca gggcctgatc tacaacgcca tcaagtcctc caaccccaag   120
ctggccacct acctgcacga ggtgaagggc cccaagctgt tcacctacag cctgttcatg   180
gccgaaaagc gggagcaccc taagggcctg cctactttc tgggctacaa gaagggcttc   240
ttctacttca gcacctgcgt gcccgagatc gccgaggccc tggtgaacgg cctgctgatg   300
aatcccgagg tgcggctgtg ggacgagaga ttctacctgc acgaaatcaa ggtcctgcgg   360
gagcccaaga agttcaacgg cagcaccttc gtgccctga gccccatcgc cgtgaccgtg   420
gtgagaaagg gcaagtccta cgacgtgccc cccatggaaa aggagttcta cagcattatc   480
```

```
aaggatgacc tgcaggacaa gtacgtgatg gcctacggcg acaagccccc cagtgagttc    540
gagatggaag tgctgatcgc caagcccaag cggttccgga tcaagcccgg catctatcag    600
accgcctggc acctggtgtt tcgggcctac ggcaatgacg acctgctgaa ggtgggctac    660
gaagtgggat tcggggagaa gaactccctg ggattcggaa tggtcaaggt ggagggcaac    720
aagaccacca aggaagccga agaacaggag aagatcacct tcaactcccg ggaagagctg    780
aaaacaggcg tg                                                       792

<210> SEQ ID NO 93
<211> LENGTH: 708
<212> TYPE: DNA
<213> ORGANISM: Artificial Sequence
<220> FEATURE:
<223> OTHER INFORMATION: Synthetic polynucleotide

<400> SEQUENCE: 93
atgttcgtga cccaggtgat cttcaacatc ggcgaacgga cgtacccccga cagggctcgg     60 gctatggtgg ccgagctgat ggatggcgtc cagcctggcc tggtggccac cctgatgaac    120
tacatccccg gcaccagcac gagccggaca gagttcccca ccgtgcagtt cggcggcgcc    180
agcgacggct tttgcctgct gggcttcggc gacgcggcg cgccatcgt gagagatgcc    240 gtgcccctga tccacgccgc cctggcaagg cggatgcctg atcggatcat ccaggtggaa    300
cacaaggagc acagcctgtc cgccgaggcc cggccctacg tgctgagcta caccgtgcct    360
cggatggtgg tgcagaagaa gcagcggcac gccgagagac tgctgcacga agccgaggga    420
aaggctcacc tggagggcct gttcctgcgg agcctgcaga ggcaggccgc cgccgtgggc    480
ctgcccctgc cgagaacct ggaggtggag ttcaagggag ccgtgggcga cttcgccgca    540
aagcacaatc caaatagcaa ggtggcctac cggggactga gaggcgccgt gttcgatgtg    600
aacgccagac tgggcggcat ctggaccgcc ggattcatgc tgagcaaggg ctacggccag    660
tttaacgcca cccaccagct gagcggcgcc gtgaacgctc tgtccgaa              708

<210> SEQ ID NO 94
<211> LENGTH: 777
<212> TYPE: DNA
<213> ORGANISM: Artificial Sequence
<220> FEATURE:
<223> OTHER INFORMATION: Synthetic polynucleotide

<400> SEQUENCE: 94
atgcaccaga ccctgatccg gatcaactgg cccaagggat tcaagtgccc ccctgccgag     60
ttccgggaaa agctggccaa gagcgagatg ttcccccccg agttcttcca ctacggcacg    120
gaactggccg tgtgggacaa gcagaccgcc gaggtggagg gcaagatcaa gaccgtgtcc    180
aaggagaaga tcatcaagac ctttgacaag cccatccccc tgaatggccg ggccccggtc    240
agagtgatcg gcggccaggc ctgggccggc gtgatcgccg accccgagat ggagggcatg    300
ctgatcccac acctggggag catcctgaag gtggccagca gcgcggccgg atgcgcagtg    360
aagatcgaac tggaacagag aaagttcggc atcagctaca ccgagtaccc cgtgaagtac    420
aacctgcggg agctggtgct gaagagaaga tgcgaggacc cccggtctac cgatatcgag    480
agcctgattg ccgatagaat ctggggcggc gtgtccggcg agagctacta tggcatcgac    540
ggcacatgcg ccaagtttgg cttcgaaccc ccagcagag agcagctgga gctgcggatc    600
ttccccatga agaacatcgg actgcacatg aagtccagca cggactgtc caaggagtac    660
```

```
atgagcctga ttgacgccga ggtgtggatg aacgctaagc tggaaggagt gtggcaggtg    720
ggcaacctga tcagcagggg ctacggccgg ttcatcaagt ctatcggcgc ccagtcc       777
```

<210> SEQ ID NO 95
<211> LENGTH: 6
<212> TYPE: PRT
<213> ORGANISM: Artificial Sequence
<220> FEATURE:
<223> OTHER INFORMATION: Synthetic peptide"
<220> FEATURE:
<221> NAME/KEY: SITE
<222> LOCATION: (1)..(6)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (3)..(3)
<223> OTHER INFORMATION: /replace="Phe"
<220> FEATURE:
<221> NAME/KEY: VARIANT
<222> LOCATION: (4)..(4)
<223> OTHER INFORMATION: /replace="Tyr"

<400> SEQUENCE: 95

Arg Asn Tyr Phe Ser His
1               5

<210> SEQ ID NO 96
<211> LENGTH: 6
<212> TYPE: PRT
<213> ORGANISM: Artificial Sequence
<220> FEATURE:
<223> OTHER INFORMATION: Synthetic peptide"

<400> SEQUENCE: 96

Arg Asn Tyr Phe Ser His
1               5

<210> SEQ ID NO 97
<211> LENGTH: 6
<212> TYPE: PRT
<213> ORGANISM: Artificial Sequence
<220> FEATURE:
<223> OTHER INFORMATION: Synthetic peptide"

<400> SEQUENCE: 97

Arg Asn Phe Tyr Ser His
1               5

<210> SEQ ID NO 98
<211> LENGTH: 6
<212> TYPE: PRT
<213> ORGANISM: Artificial Sequence
<220> FEATURE:
<223> OTHER INFORMATION: Synthetic peptide"
<220> FEATURE:
<221> NAME/KEY: SITE
<222> LOCATION: (1)..(6)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (3)..(3)
<223> OTHER INFORMATION: /replace="Lys"

<400> SEQUENCE: 98

Arg Asn Ala Ala Leu His
1               5

<210> SEQ ID NO 99
<211> LENGTH: 6
<212> TYPE: PRT
<213> ORGANISM: Artificial Sequence
<220> FEATURE:
<223> OTHER INFORMATION: Synthetic peptide"

<400> SEQUENCE: 99

Arg Ala Phe Phe His His
1               5

<210> SEQ ID NO 100
<211> LENGTH: 6
<212> TYPE: PRT
<213> ORGANISM: Artificial Sequence
<220> FEATURE:
<223> OTHER INFORMATION: Synthetic peptide"

<400> SEQUENCE: 100

Arg Arg Ala Phe Phe His
1               5

<210> SEQ ID NO 101
<211> LENGTH: 145
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(145)
<223> OTHER INFORMATION: /note="Variant nucleotides given in the
      sequence have no preference with respect to those in the
      annotations for variant positions"
<220> FEATURE:
<221> NAME/KEY: modified_base
<222> LOCATION: (70)..(70)
<223> OTHER INFORMATION: a, c, t, or g
<220> FEATURE:
<221> NAME/KEY: variation
<222> LOCATION: (145)..(145)
<223> OTHER INFORMATION: /replace=" "

<400> SEQUENCE: 101
ttggccactc cctcthtgcg cgctcgctcg ctcgctgggg cctggvgacc aaaggtcgcc      60
agacggccgn gctctgcccg gccggcccca gcgagcgagc gagcgcgcad agagggagtg     120
gccaactcca tcactagggg tdccb                                           145

<210> SEQ ID NO 102
<211> LENGTH: 144
<212> TYPE: DNA
<213> ORGANISM: Artificial Sequence
<220> FEATURE:
<223> OTHER INFORMATION: Synthetic polynucleotide
<220> FEATURE:
<221> NAME/KEY: variation
<222> LOCATION: (1)..(1)
<223> OTHER INFORMATION: /replace=" "
<220> FEATURE:
<221> NAME/KEY: misc_feature
<222> LOCATION: (1)..(144)
<223> OTHER INFORMATION: /note="Variant nucleotides given in the
      sequence have no preference with respect to those in the
      annotations for variant positions"
<220> FEATURE:
<221> NAME/KEY: modified_base
<222> LOCATION: (89)..(89)
<223> OTHER INFORMATION: a, c, t, or g

<400> SEQUENCE: 102

```
rdtaccccta gtgatggagt tggccactcc ctctatgcgc gctcgctcgc tcggtggggc      60
ctgcvgacca aaggtcbcca gacggcvgng ctctgchcgg ccggccccac cgagcgagcg     120
agcgcgcata gagggagtgg ccaa                                            144
```

<210> SEQ ID NO 103
<211> LENGTH: 22
<212> TYPE: DNA
<213> ORGANISM: Adeno-associated virus 2

<400> SEQUENCE: 103

```
ctgcgcgctc gctcgctcac tg                                               22
```

<210> SEQ ID NO 104
<211> LENGTH: 22
<212> TYPE: DNA
<213> ORGANISM: Adeno-associated virus 2

<400> SEQUENCE: 104

```
cagtgagcga gcgagcgcgc ag                                               22
```

<210> SEQ ID NO 105
<211> LENGTH: 4
<212> TYPE: PRT
<213> ORGANISM: Artificial Sequence
<220> FEATURE:
<223> OTHER INFORMATION: Synthetic: linker

<400> SEQUENCE: 105

Gly Ser Ser Ser
1

<210> SEQ ID NO 106
<211> LENGTH: 5
<212> TYPE: PRT
<213> ORGANISM: Artificial Sequence
<220> FEATURE:
<223> OTHER INFORMATION: Synthetic: linker

<400> SEQUENCE: 106

Gly Ser Ser Ser Ser
1               5

<210> SEQ ID NO 107
<211> LENGTH: 6
<212> TYPE: PRT
<213> ORGANISM: Artificial Sequence
<220> FEATURE:
<223> OTHER INFORMATION: Synthetic: linker

<400> SEQUENCE: 107

Gly Ser Ser Gly Ser Ser
1               5

<210> SEQ ID NO 108
<211> LENGTH: 9
<212> TYPE: RNA
<213> ORGANISM: Artificial Sequence
<220> FEATURE:
<223> OTHER INFORMATION: Synthetic: Kozak

<400> SEQUENCE: 108

```
ccrccaugg                                                               9
```

<210> SEQ ID NO 109
<211> LENGTH: 387
<212> TYPE: DNA
<213> ORGANISM: Artificial Sequence
<220> FEATURE:
<223> OTHER INFORMATION: Synthetic: MCP nucleic acid sequence

<400> SEQUENCE: 109

```
gcttctaact ttactcagtt cgttctcgtc gacaatggcg gaactggcga cgtgactgtc    60
gccccaagca acttcgctaa cggggtcgct gaatggatca gctctaactc gcgttcacag   120
gcttacaaag taacctgtag cgttcgtcag agctctgcgc agaatcgcaa atacaccatc   180
aaagtcgagg tgcctaaagt ggcaacccag actgttggtg gagtagagct tcctgtagcc   240
gcatggcgtt cgtacttaaa tatggaacta accattccaa ttttcgctac gaattccgac   300
tgcgagctta ttgttaaggc aatgcaaggt ctcctaaaag atggaaaccc gattccctca   360
gcaatcgcag caaactccgg catctac                                       387
```

<210> SEQ ID NO 110
<211> LENGTH: 129
<212> TYPE: PRT
<213> ORGANISM: Artificial Sequence
<220> FEATURE:
<223> OTHER INFORMATION: Synthetic: MCP amino acid sequence

<400> SEQUENCE: 110

```
Ala Ser Asn Phe Thr Gln Phe Val Leu Val Asp Asn Gly Gly Thr Gly
1               5                   10                  15
Asp Val Thr Val Ala Pro Ser Asn Phe Ala Asn Gly Val Ala Glu Trp
            20                  25                  30
Ile Ser Ser Asn Ser Arg Ser Gln Ala Tyr Lys Val Thr Cys Ser Val
        35                  40                  45
Arg Gln Ser Ser Ala Gln Asn Arg Lys Tyr Thr Ile Lys Val Glu Val
    50                  55                  60
Pro Lys Val Ala Thr Gln Thr Val Gly Gly Val Glu Leu Pro Val Ala
65                  70                  75                  80
Ala Trp Arg Ser Tyr Leu Asn Met Glu Leu Thr Ile Pro Ile Phe Ala
                85                  90                  95
Thr Asn Ser Asp Cys Glu Leu Ile Val Lys Ala Met Gln Gly Leu Leu
            100                 105                 110
Lys Asp Gly Asn Pro Ile Pro Ser Ala Ile Ala Ala Asn Ser Gly Ile
        115                 120                 125
Tyr
```

<210> SEQ ID NO 111
<211> LENGTH: 363
<212> TYPE: DNA
<213> ORGANISM: Artificial Sequence
<220> FEATURE:
<223> OTHER INFORMATION: Synthetic: PCP nucleic acid sequence

<400> SEQUENCE: 111

```
tccaaaacaa tagtcctctc cgtaggggag gcaacacgga ctttgaccga aatccagtca    60
accgctgacc gacaaatctt tgaagagaaa gtagggcctc ttgtgggccg actgcgcttg   120
actgcaagct tgcgacaaaa cggcgcaaag actgcctata gggtcaacct taaactcgac   180
caagccgacg tggtcgatag cggtctccct aaggttcggt atacgcaggt ctggagtcat   240
gacgtaacaa tcgtagcaaa cagcacagaa gcctcccgaa aaagcctcta cgatctgacg   300
```

```
aaatccttgg tggctacgtc acaggtggaa gacctcgttg tcaaccttgt acctctgggt    360
cga                                                                  363
```

<210> SEQ ID NO 112
<211> LENGTH: 121
<212> TYPE: PRT
<213> ORGANISM: Artificial Sequence
<220> FEATURE:
<223> OTHER INFORMATION: Synthetic: PCP amino acid sequence

<400> SEQUENCE: 112

```
Ser Lys Thr Ile Val Leu Ser Val Gly Glu Ala Thr Arg Thr Leu Thr
1               5                   10                  15

Glu Ile Gln Ser Thr Ala Asp Arg Gln Ile Phe Glu Glu Lys Val Gly
            20                  25                  30

Pro Leu Val Gly Arg Leu Arg Leu Thr Ala Ser Leu Arg Gln Asn Gly
        35                  40                  45

Ala Lys Thr Ala Tyr Arg Val Asn Leu Lys Leu Asp Gln Ala Asp Val
    50                  55                  60

Val Asp Ser Gly Leu Pro Lys Val Arg Tyr Thr Gln Val Trp Ser His
65                  70                  75                  80

Asp Val Thr Ile Val Ala Asn Ser Thr Glu Ala Ser Arg Lys Ser Leu
                85                  90                  95

Tyr Asp Leu Thr Lys Ser Leu Val Ala Thr Ser Gln Val Glu Asp Leu
            100                 105                 110

Val Val Asn Leu Val Pro Leu Gly Arg
        115                 120
```

<210> SEQ ID NO 113
<211> LENGTH: 186
<212> TYPE: DNA
<213> ORGANISM: Artificial Sequence
<220> FEATURE:
<223> OTHER INFORMATION: Synthetic: COM nucleic acid sequence

<400> SEQUENCE: 113

```
atgaaatcaa ttcgctgtaa aaactgcaac aaactgttat ttaaggcgga ttcctttgat    60
cacattgaaa tcaggtgtcc gcgttgcaaa cgtcacatca taatgctgaa tgcctgcgag   120
catcccacgg agaaacattg tgggaaaaga gaaaaaatca cgcattctga cgaaaccgtg   180
cgttat                                                              186
```

<210> SEQ ID NO 114
<211> LENGTH: 62
<212> TYPE: PRT
<213> ORGANISM: Artificial Sequence
<220> FEATURE:
<223> OTHER INFORMATION: Synthetic: COM amino acid sequence

<400> SEQUENCE: 114

```
Met Lys Ser Ile Arg Cys Lys Asn Cys Asn Lys Leu Leu Phe Lys Ala
1               5                   10                  15

Asp Ser Phe Asp His Ile Glu Ile Arg Cys Pro Arg Cys Lys Arg His
            20                  25                  30

Ile Ile Met Leu Asn Ala Cys Glu His Pro Thr Glu Lys His Cys Gly
        35                  40                  45

Lys Arg Glu Lys Ile Thr His Ser Asp Glu Thr Val Arg Tyr
    50                  55                  60
```

<210> SEQ ID NO 115
<211> LENGTH: 19
<212> TYPE: DNA
<213> ORGANISM: Artificial Sequence
<220> FEATURE:
<223> OTHER INFORMATION: Synthetic: MS2

<400> SEQUENCE: 115
acatgaggat cacccatgt                                                    19

<210> SEQ ID NO 116
<211> LENGTH: 128
<212> TYPE: DNA
<213> ORGANISM: Artificial Sequence
<220> FEATURE:
<223> OTHER INFORMATION: Synthetic: MS2 X3(MS2-linker-MS2-linker-MS2)

<400> SEQUENCE: 116
acatgaggat cacccatgtc tgcaggtcga ctctagaaaa catgaggatc acccatgtct       60
gcagtattcc cgggttcatt agatcctaag gtacctaatt gcctagaaaa catgaggatc      120
acccatgt                                                              128

<210> SEQ ID NO 117
<211> LENGTH: 25
<212> TYPE: DNA
<213> ORGANISM: Artificial Sequence
<220> FEATURE:
<223> OTHER INFORMATION: Synthetic: PP7

<400> SEQUENCE: 117
ggagcagacg atatggcgtc gctcc                                             25

<210> SEQ ID NO 118
<211> LENGTH: 146
<212> TYPE: DNA
<213> ORGANISM: Artificial Sequence
<220> FEATURE:
<223> OTHER INFORMATION: Synthetic: PP7 X3(PP7-linker-PP7-linker-PP7)

<400> SEQUENCE: 118
ggagcagacg atatggcgtc gctccctgca ggtcgactct agaaaggagc agacgatatg       60
gcgtcgctcc ctgcagtatt cccgggttca ttagatccta aggtacctaa ttgcctagaa      120
aggagcagac gatatggcgt cgctcc                                          146

<210> SEQ ID NO 119
<211> LENGTH: 18
<212> TYPE: DNA
<213> ORGANISM: Artificial Sequence
<220> FEATURE:
<223> OTHER INFORMATION: Synthetic: com

<400> SEQUENCE: 119
gaatgcctgc gagcatcc                                                     18

<210> SEQ ID NO 120
<211> LENGTH: 125
<212> TYPE: DNA
<213> ORGANISM: Artificial Sequence
<220> FEATURE:
<223> OTHER INFORMATION: Synthetic: com X3(com-linker-com-linker-com)

<400> SEQUENCE: 120
gaatgcctgc gagcatccct gcaggtcgac tctagaaaga atgcctgcga gcatccctgc       60

```
agtattcccg ggttcattag atcctaaggt acctaattgc ctagaaagaa tgcctgcgag    120
catcc                                                                125

<210> SEQ ID NO 121
<211> LENGTH: 1866
<212> TYPE: DNA
<213> ORGANISM: Artificial Sequence
<220> FEATURE:
<223> OTHER INFORMATION: Synthetic: Rep2 nucleic acid sequence

<400> SEQUENCE: 121
atgccggggt tttacgagat tgtgattaag gtccccagcg accttgacga gcatctgccc     60
ggcatttctg acagctttgt gaactgggtg gccgagaagg aatgggagtt gccgccagat    120
tctgacatgg atctgaatct gattgagcag gcaccctga ccgtggccga gaagctgcag     180
cgcgactttc tgacggaatg gcgccgtgtg agtaaggccc cggaggccct tttctttgtg    240
caatttgaga agggagagag ctacttccac atgcacgtgc tcgtggaaac caccggggtg    300
aaatccatgg tttttgggacg tttcctgagt cagattcgcg aaaaactgat tcagagaatt    360
taccgcggga tcgagccgac tttgccaaac tggttcgcgg tcacaaagac cagaaatggc    420
gccggaggcg ggaacaaggt ggtggatgag tgctacatcc ccaattactt gctccccaaa    480
acccagcctg agctccagtg ggcgtggact aatatggaac agtatttaag cgcctgtttg    540
aatctcacgg agcgtaaacg gttggtggcg cagcatctga cgcacgtgtc gcagacgcag    600
gagcagaaca aagagaatca gaatcccaat tctgatgcgc cggtgatcag atcaaaaact    660
tcagccaggt acatggagct ggtcgggtgg ctcgtggaca aggggattac ctcggagaag    720
cagtggatcc aggaggacca ggcctcatac atctccttca atgcggcctc caactcgcgg    780
tcccaaatca aggctgcctt ggacaatgcg ggaaagatta tgagcctgac taaaaccgcc    840
cccgactacc tggtgggcca gcagcccgtg gaggacattt ccagcaatcg gatttataaa    900 atttttggaac taaacgggta cgatccccaa tatgcggctt ccgtctttct gggatgggcc    960
acgaaaaagt tcggcaagag gaacaccatc tggctgtttg gcctgcaac taccgggaag   1020 accaacatcg cggaggccat agcccacact gtgcccttct acgggtgcgt aaactggacc   1080
aatgagaact ttcccttcaa cgactgtgtc gacaagatgg tgatctggtg gaggaggggg   1140
aagatgaccg ccaaggtcgt ggagtcggcc aaagccattc tcggaggaag caaggtcgcg   1200
gtggaccaga aatgcaagtc ctcggcccag atagacccga ctcccgtgat cgtcacctcc   1260
aacaccaaca tgtgcgccgt gattgacggg aactcaacga ccttcgaaca ccagcagccg   1320
ttgcaagacc ggatgttcaa atttgaactc accgccgtc tggatcatga ctttgggaag   1380
gtcaccaagc aggaagtcaa agacttttc cggtgggcaa aggatcacgt ggttgaggtg   1440
gagcatgaat tctacgtcaa aaagggtgga gccaagaaaa gacccgcccc cagtgacgca   1500
gatataagtg agcccaaacg ggtgcgcgag tcagttgcgc agccatcgac gtcagacgcg   1560
gaagcttcga tcaactacgc agacaggtac caaaacaaat gttctcgtca cgtgggcatg   1620
aatctgatgc tgtttccctg cagacaatgc gagagaatga atcagaattc aaatatctgc   1680
ttcactcacg gacagaaaga ctgtttagag tgctttcccg tgtcagaatc tcaacccgtt   1740
tctgtcgtca aaaaggcgta tcagaaactg tgctacattc atcatatcat gggaaaggtg   1800
ccagacgctt gcactgcctg cgatctggtc aatgtggatt tggatgactg catctttgaa   1860
caataa                                                              1866
```

<210> SEQ ID NO 122
<211> LENGTH: 621
<212> TYPE: PRT
<213> ORGANISM: Artificial Sequence
<220> FEATURE:
<223> OTHER INFORMATION: Synthetic: Rep2 amino acid sequence

<400> SEQUENCE: 122

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365
```

```
Cys Val Asp Lys Met Val Ile Trp Trp Glu Glu Gly Lys Met Thr Ala
    370                 375                 380
Lys Val Val Glu Ser Ala Lys Ala Ile Leu Gly Gly Ser Lys Val Arg
385                 390                 395                 400
Val Asp Gln Lys Cys Lys Ser Ser Ala Gln Ile Asp Pro Thr Pro Val
                405                 410                 415
Ile Val Thr Ser Asn Thr Asn Met Cys Ala Val Ile Asp Gly Asn Ser
            420                 425                 430
Thr Thr Phe Glu His Gln Gln Pro Leu Gln Asp Arg Met Phe Lys Phe
                435                 440                 445
Glu Leu Thr Arg Arg Leu Asp His Asp Phe Gly Lys Val Thr Lys Gln
450                 455                 460
Glu Val Lys Asp Phe Phe Arg Trp Ala Lys Asp His Val Val Glu Val
465                 470                 475                 480
Glu His Glu Phe Tyr Val Lys Gly Gly Ala Lys Lys Arg Pro Ala
                485                 490                 495
Pro Ser Asp Ala Asp Ile Ser Glu Pro Lys Arg Val Arg Glu Ser Val
                500                 505                 510
Ala Gln Pro Ser Thr Ser Asp Ala Glu Ala Ser Ile Asn Tyr Ala Asp
                515                 520                 525
Arg Tyr Gln Asn Lys Cys Ser Arg His Val Gly Met Asn Leu Met Leu
530                 535                 540
Phe Pro Cys Arg Gln Cys Glu Arg Met Asn Gln Asn Ser Asn Ile Cys
545                 550                 555                 560
Phe Thr His Gly Gln Lys Asp Cys Leu Glu Cys Phe Pro Val Ser Glu
                565                 570                 575
Ser Gln Pro Val Ser Val Val Lys Lys Ala Tyr Gln Lys Leu Cys Tyr
                580                 585                 590
Ile His His Ile Met Gly Lys Val Pro Asp Ala Cys Thr Ala Cys Asp
                595                 600                 605
Leu Val Asn Val Asp Leu Asp Asp Cys Ile Phe Glu Gln
        610                 615                 620

<210> SEQ ID NO 123
<211> LENGTH: 2289
<212> TYPE: DNA
<213> ORGANISM: Artificial Sequence
<220> FEATURE:
<223> OTHER INFORMATION: Synthetic: MCP-Rep nucleic acid sequence
      (linker-MCP-linker-Rep)

<400> SEQUENCE: 123
atgcccggca gctccggcag tagcgcttct aactttactc agttcgttct cgtcgacaat      60
ggcggaactg gcgacgtgac tgtcgcccca agcaacttcg ctaacggggt cgctgaatgg     120
atcagctcta actcgcgttc acaggcttac aaagtaacct gtagcgttcg tcagagctct     180
gcgcagaatc gcaaatacac catcaaagtc gaggtgccta agtggcaac ccagactgtt     240 ggtggagtag agcttcctgt agccgcatgg cgttcgtact taaatatgga actaaccatt     300
ccaattttcg ctacgaattc cgactgcgag cttattgtta aggcaatgca aggtctccta     360
aaagatggaa acccgattcc ctcagcaatc gcagcaaact ccggcatcta cggcagtagt     420
gggtcctctg gttttacga gattgtgatt aaggtcccca gcgaccttga cgagcatctg     480
cccggcattt ctgacagctt tgtgaactgg gtggccgaga aggaatggga gttgccgcca     540
gattctgaca tggatctgaa tctgattgag caggcacccc tgaccgtggc cgagaagctg     600
```

| | |
|---|---|
| cagcgcgact ttctgacgga atggcgccgt gtgagtaagg ccccggaggc ccttttcttt | 660 |
| gtgcaatttg agaagggaga gagctacttc cacatgcacg tgctcgtgga aaccaccggg | 720 |
| gtgaaatcca tggttttggg acgtttcctg agtcagattc gcgaaaaact gattcagaga | 780 |
| atttaccgcg ggatcgagcc gactttgcca aactggttcg cggtcacaaa gaccagaaat | 840 |
| ggcgccggag gcgggaacaa ggtggtggat gagtgctaca tccccaatta cttgctcccc | 900 |
| aaaacccagc ctgagctcca gtgggcgtgg actaatatgg aacagtattt aagcgcctgt | 960 |
| ttgaatctca cggagcgtaa acggttggtg gcgcagcatc tgacgcacgt gtcgcagacg | 1020 |
| caggagcaga acaaagagaa tcagaatccc aattctgatg cgccggtgat cagatcaaaa | 1080 |
| acttcagcca ggtacatgga gctggtcggg tggctcgtgg acaaggggat tacctcggag | 1140 |
| aagcagtgga tccaggagga ccaggcctca tacatctcct tcaatgcggc ctccaactcg | 1200 |
| cggtcccaaa tcaaggctgc cttggacaat gcgggaaaga ttatgagcct gactaaaacc | 1260 |
| gcccccgact acctggtggg ccagcagccc gtggaggaca tttccagcaa tcggatttat | 1320 |
| aaaattttgg aactaaacgg gtacgatccc caatatgcgg cttccgtctt tctgggatgg | 1380 |
| gccacgaaaa agttcggcaa gaggaacacc atctggctgt ttgggcctgc aactaccggg | 1440 |
| aagaccaaca tcgcggaggc catagcccac actgtgccct tctacgggtg cgtaaactgg | 1500 |
| accaatgaga ctttcccctt caacgactgt gtcgacaaga tggtgatctg gtgggaggag | 1560 |
| gggaagatga ccgccaaggt cgtggagtcg gccaaagcca ttctcggagg aagcaaggtg | 1620 |
| cgcgtggacc agaaatgcaa gtcctcggcc cagatagacc cgactcccgt gatcgtcacc | 1680 |
| tccaacacca acatgtgcgc cgtgattgac gggaactcaa cgaccttcga acaccagcag | 1740 |
| ccgttgcaag accggatgtt caaatttgaa ctcacccgcc gtctggatca tgactttggg | 1800 |
| aaggtcacca gcaggaagt caaagacttt ttccggtggg caaggatca cgtggttgag | 1860 |
| gtggagcatg aattctacgt caaaaagggt ggagccaaga aaagaccgc ccccagtgac | 1920 |
| gcagatataa gtgagcccaa acgggtgcgc gagtcagttg cgcagccatc gacgtcagac | 1980 |
| gcggaagctt cgatcaacta cgcagacagg taccaaaaca atgttctcg tcacgtgggc | 2040 |
| atgaatctga tgctgtttcc ctgcagacaa tgcgagagaa tgaatcagaa ttcaaatatc | 2100 |
| tgcttcactc acggacagaa agactgttta gagtgctttc ccgtgtcaga atctcaaccc | 2160 |
| gtttctgtcg tcaaaaaggc gtatcagaaa ctgtgctaca ttcatcatat catgggaaag | 2220 |
| gtgccagacg cttgcactgc ctgcgatctg gtcaatgtgg atttggatga ctgcatcttt | 2280 |
| gaacaataa | 2289 |

<210> SEQ ID NO 124
<211> LENGTH: 762
<212> TYPE: PRT
<213> ORGANISM: Artificial Sequence
<220> FEATURE:
<223> OTHER INFORMATION: Synthetic: MCP-Rep amino acid sequence(linker-MCP-linker-Rep)

<400> SEQUENCE: 124

Met Pro Gly Ser Ser Gly Ser Ser Ala Ser Asn Phe Thr Gln Phe Val
1               5                   10                  15

Leu Val Asp Asn Gly Gly Thr Gly Asp Val Thr Val Ala Pro Ser Asn
            20                  25                  30

Phe Ala Asn Gly Val Ala Glu Trp Ile Ser Ser Asn Ser Arg Ser Gln
        35                  40                  45

Ala Tyr Lys Val Thr Cys Ser Val Arg Gln Ser Ser Ala Gln Asn Arg

```
            50                  55                  60
Lys Tyr Thr Ile Lys Val Glu Val Pro Lys Val Ala Gln Thr Val
 65                  70                  75                  80

Gly Gly Val Glu Leu Pro Val Ala Ala Trp Arg Ser Tyr Leu Asn Met
                     85                  90                  95

Glu Leu Thr Ile Pro Ile Phe Ala Thr Asn Ser Asp Cys Glu Leu Ile
                    100                 105                 110

Val Lys Ala Met Gln Gly Leu Leu Lys Asp Gly Asn Pro Ile Pro Ser
                115                 120                 125

Ala Ile Ala Ala Asn Ser Gly Ile Tyr Gly Ser Ser Gly Ser Ser Gly
            130                 135                 140

Phe Tyr Glu Ile Val Ile Lys Val Pro Ser Asp Leu Asp Glu His Leu
145                 150                 155                 160

Pro Gly Ile Ser Asp Ser Phe Val Asn Trp Val Ala Glu Lys Glu Trp
                    165                 170                 175

Glu Leu Pro Pro Asp Ser Asp Met Asp Leu Asn Leu Ile Glu Gln Ala
                180                 185                 190

Pro Leu Thr Val Ala Glu Lys Leu Gln Arg Asp Phe Leu Thr Glu Trp
            195                 200                 205

Arg Arg Val Ser Lys Ala Pro Glu Ala Leu Phe Phe Val Gln Phe Glu
210                 215                 220

Lys Gly Glu Ser Tyr Phe His Met His Val Leu Val Glu Thr Thr Gly
225                 230                 235                 240

Val Lys Ser Met Val Leu Gly Arg Phe Leu Ser Gln Ile Arg Glu Lys
                245                 250                 255

Leu Ile Gln Arg Ile Tyr Arg Gly Ile Glu Pro Thr Leu Pro Asn Trp
            260                 265                 270

Phe Ala Val Thr Lys Thr Arg Asn Gly Ala Gly Gly Asn Lys Val
            275                 280                 285

Val Asp Glu Cys Tyr Ile Pro Asn Tyr Leu Leu Pro Lys Thr Gln Pro
290                 295                 300

Glu Leu Gln Trp Ala Trp Thr Asn Met Glu Gln Tyr Leu Ser Ala Cys
305                 310                 315                 320

Leu Asn Leu Thr Glu Arg Lys Arg Leu Val Ala Gln His Leu Thr His
                325                 330                 335

Val Ser Gln Thr Gln Glu Gln Asn Lys Glu Asn Gln Asn Pro Asn Ser
            340                 345                 350

Asp Ala Pro Val Ile Arg Ser Lys Thr Ser Ala Arg Tyr Met Glu Leu
            355                 360                 365

Val Gly Trp Leu Val Asp Lys Gly Ile Thr Ser Glu Lys Gln Trp Ile
370                 375                 380

Gln Glu Asp Gln Ala Ser Tyr Ile Ser Phe Ala Ala Ser Asn Ser
385                 390                 395                 400

Arg Ser Gln Ile Lys Ala Ala Leu Asp Asn Ala Gly Lys Ile Met Ser
                405                 410                 415

Leu Thr Lys Thr Ala Pro Asp Tyr Leu Val Gly Gln Pro Val Glu
                420                 425                 430

Asp Ile Ser Ser Asn Arg Ile Tyr Lys Ile Leu Glu Leu Asn Gly Tyr
            435                 440                 445

Asp Pro Gln Tyr Ala Ala Ser Val Phe Leu Gly Trp Ala Thr Lys Lys
            450                 455                 460

Phe Gly Lys Arg Asn Thr Ile Trp Leu Phe Gly Pro Ala Thr Thr Gly
465                 470                 475                 480
```

Lys Thr Asn Ile Ala Glu Ala Ile Ala His Thr Val Pro Phe Tyr Gly
                485                 490                 495

Cys Val Asn Trp Thr Asn Glu Asn Phe Pro Phe Asn Asp Cys Val Asp
                500                 505                 510

Lys Met Val Ile Trp Trp Glu Glu Gly Lys Met Thr Ala Lys Val Val
            515                 520                 525

Glu Ser Ala Lys Ala Ile Leu Gly Gly Ser Lys Val Arg Val Asp Gln
        530                 535                 540

Lys Cys Lys Ser Ser Ala Gln Ile Asp Pro Thr Pro Val Ile Val Thr
545                 550                 555                 560

Ser Asn Thr Asn Met Cys Ala Val Ile Asp Gly Asn Ser Thr Thr Phe
                565                 570                 575

Glu His Gln Gln Pro Leu Gln Asp Arg Met Phe Lys Phe Glu Leu Thr
            580                 585                 590

Arg Arg Leu Asp His Asp Phe Gly Lys Val Thr Lys Gln Glu Val Lys
        595                 600                 605

Asp Phe Phe Arg Trp Ala Lys Asp His Val Val Glu Val Glu His Glu
    610                 615                 620

Phe Tyr Val Lys Lys Gly Gly Ala Lys Lys Arg Pro Ala Pro Ser Asp
625                 630                 635                 640

Ala Asp Ile Ser Glu Pro Lys Arg Val Arg Glu Ser Val Ala Gln Pro
                645                 650                 655

Ser Thr Ser Asp Ala Glu Ala Ser Ile Asn Tyr Ala Asp Arg Tyr Gln
            660                 665                 670

Asn Lys Cys Ser Arg His Val Gly Met Asn Leu Met Leu Phe Pro Cys
        675                 680                 685

Arg Gln Cys Glu Arg Met Asn Gln Asn Ser Asn Ile Cys Phe Thr His
    690                 695                 700

Gly Gln Lys Asp Cys Leu Glu Cys Phe Pro Val Ser Glu Ser Gln Pro
705                 710                 715                 720

Val Ser Val Val Lys Lys Ala Tyr Gln Lys Leu Cys Tyr Ile His His
                725                 730                 735

Ile Met Gly Lys Val Pro Asp Ala Cys Thr Ala Cys Asp Leu Val Asn
            740                 745                 750

Val Asp Leu Asp Asp Cys Ile Phe Glu Gln
        755                 760

<210> SEQ ID NO 125
<211> LENGTH: 2289
<212> TYPE: DNA
<213> ORGANISM: Artificial Sequence
<220> FEATURE:
<223> OTHER INFORMATION: Synthetic: MCP-Rep-Y156F nucleic acid sequence
      (linker-MCP-linker-Rep)

<400> SEQUENCE: 125
atgcccggca gctccggcag tagcgcttct aactttactc agttcgttct cgtcgacaat      60
ggcggaactg gcgacgtgac tgtcgcccca agcaacttcg ctaacggggt cgctgaatgg     120
atcagctcta actcgcgttc acaggcttac aaagtaaccc tgtagcgttcg tcagagctct    180 gcgcagaatc gcaaatacac catcaaagtc gaggtgccta aagtggcaac ccagactgtt    240
ggtggagtag agcttcctgt agccgcatgg cgttcgtact taaatatgga actaaccatt    300
ccaattttcg ctacgaattc cgactgcgag cttattgtta aggcaatgca aggtctccta    360
aaagatggaa acccgattcc ctcagcaatc gcagcaaact ccggcatcta cggcagtagt    420

```
gggtcctctg ggttttacga gattgtgatt aaggtcccca gcgaccttga cgagcatctg    480
cccggcattt ctgacagctt tgtgaactgg gtggccgaga aggaatggga gttgccgcca    540
gattctgaca tggatctgaa tctgattgag caggcacccc tgaccgtggc cgagaagctg    600
cagcgcgact ttctgacgga atggcgccgt gtgagtaagg ccccggaggc ccttttcttt    660
gtgcaatttg agaagggaga gagctacttc cacatgcacg tgctcgtgga accaccggg    720 gtgaaatcca tggttttggg acgtttcctg agtcagattc gcgaaaaact gattcagaga    780
atttaccgcg ggatcgagcc gactttgcca aactggttcg cggtcacaaa gaccagaaat    840
ggcgccggag gcgggaacaa ggtggtggat gagtgctaca tccccaattt cttgctcccc    900
aaaacccagc ctgagctcca gtgggcgtgg actaatatgg aacagtattt aagcgcctgt    960
ttgaatctca cggagcgtaa acggttggtg gcgcagcatc tgacgcacgt gtcgcagacg   1020
caggagcaga acaaagagaa tcagaatccc aattctgatg cgccggtgat cagatcaaaa   1080
acttcagcca ggtacatgga gctggtcggg tggctcgtgg acaaggggat tacctcggag   1140
aagcagtgga tccaggagga ccaggcctca tacatctcct tcaatgcggc ctccaactcg   1200
cggtcccaaa tcaaggctgc cttggacaat gcgggaaaga ttatgagcct gactaaaacc   1260
gcccccgact acctggtggg ccagcagccc gtggaggaca tttccagcaa tcggatttat   1320
aaaattttgg aactaaacgg gtacgatccc aatatgcgg cttccgtctt tctgggatgg   1380
gccacgaaaa agttcggcaa gaggaacacc atctggctgt ttgggcctgc aactaccggg   1440
aagaccaaca tcgcggaggc catagcccac actgtgccct tctacgggtg cgtaaactgg   1500
accaatgaga actttcccctt caacgactgt gtcgacaaga tggtgatctg gtgggaggag   1560
gggaagatga ccgccaaggt cgtggagtcg gccaaagcca ttctcggagg aagcaaggtg   1620
cgcgtggacc agaaatgcaa gtcctcggcc cagatagacc cgactcccgt gatcgtcacc   1680
tccaacacca catgtgcgc cgtgattgac gggaactcaa cgaccttcga acaccagcag   1740
ccgttgcaag accggatgtt caaatttgaa ctcacccgcc gtctggatca tgactttggg   1800
aaggtcacca gcaggaagt caaagacttt ttccggtggg caaggatca cgtggttgag   1860 gtggagcatg aattctacgt caaaaagggt ggagccaaga aagacccgc ccccagtgac   1920 gcagatataa gtgagcccaa cgggtgcgc gagtcagttg cgcagccatc gacgtcagac   1980
gcggaagctt cgatcaacta cgcagacagg taccaaaaca aatgttctcg tcacgtgggc   2040
atgaatctga tgctgtttcc ctgcagacaa tgcgagagaa tgaatcagaa ttcaaatatc   2100
tgcttcactc acggacagaa agactgttta gagtgctttc ccgtgtcaga atctcaaccc   2160
gtttctgtcg tcaaaaaggc gtatcagaaa ctgtgctaca ttcatcatat catgggaaag   2220
gtgccagacg cttgcactgc ctgcgatctg gtcaatgtgg atttggatga ctgcatcttt   2280
gaacaataa                                                           2289

<210> SEQ ID NO 126
<211> LENGTH: 762
<212> TYPE: PRT
<213> ORGANISM: Artificial Sequence
<220> FEATURE:
<223> OTHER INFORMATION: Synthetic: MCP-Rep-Y156F amino acid sequence
      (linker-MCP-linker-Rep)

<400> SEQUENCE: 126

Met Pro Gly Ser Ser Gly Ser Ser Ala Ser Asn Phe Thr Gln Phe Val
1               5                   10                  15
```

-continued

```
Leu Val Asp Asn Gly Gly Thr Gly Asp Val Thr Val Ala Pro Ser Asn
             20                  25                  30

Phe Ala Asn Gly Val Ala Glu Trp Ile Ser Ser Asn Ser Arg Ser Gln
         35                  40                  45

Ala Tyr Lys Val Thr Cys Ser Val Arg Gln Ser Ser Ala Gln Asn Arg
     50                  55                  60

Lys Tyr Thr Ile Lys Val Glu Val Pro Lys Val Ala Thr Gln Thr Val
 65                  70                  75                  80

Gly Gly Val Glu Leu Pro Val Ala Ala Trp Arg Ser Tyr Leu Asn Met
                 85                  90                  95

Glu Leu Thr Ile Pro Ile Phe Ala Thr Asn Ser Asp Cys Glu Leu Ile
             100                 105                 110

Val Lys Ala Met Gln Gly Leu Leu Lys Asp Gly Asn Pro Ile Pro Ser
         115                 120                 125

Ala Ile Ala Ala Asn Ser Gly Ile Tyr Gly Ser Ser Gly Ser Ser Gly
     130                 135                 140

Phe Tyr Glu Ile Val Ile Lys Val Pro Ser Asp Leu Asp Glu His Leu
145                 150                 155                 160

Pro Gly Ile Ser Asp Ser Phe Val Asn Trp Val Ala Glu Lys Glu Trp
                 165                 170                 175

Glu Leu Pro Pro Asp Ser Asp Met Asp Leu Asn Leu Ile Glu Gln Ala
             180                 185                 190

Pro Leu Thr Val Ala Glu Lys Leu Gln Arg Asp Phe Leu Thr Glu Trp
         195                 200                 205

Arg Arg Val Ser Lys Ala Pro Glu Ala Leu Phe Phe Val Gln Phe Glu
     210                 215                 220

Lys Gly Glu Ser Tyr Phe His Met His Val Leu Val Glu Thr Thr Gly
225                 230                 235                 240

Val Lys Ser Met Val Leu Gly Arg Phe Leu Ser Gln Ile Arg Glu Lys
                 245                 250                 255

Leu Ile Gln Arg Ile Tyr Arg Gly Ile Glu Pro Thr Leu Pro Asn Trp
             260                 265                 270

Phe Ala Val Thr Lys Thr Arg Asn Gly Ala Gly Gly Asn Lys Val
         275                 280                 285

Val Asp Glu Cys Tyr Ile Pro Asn Phe Leu Leu Pro Lys Thr Gln Pro
     290                 295                 300

Glu Leu Gln Trp Ala Trp Thr Asn Met Glu Gln Tyr Leu Ser Ala Cys
305                 310                 315                 320

Leu Asn Leu Thr Glu Arg Lys Arg Leu Val Ala Gln His Leu Thr His
                 325                 330                 335

Val Ser Gln Thr Gln Glu Gln Asn Lys Glu Asn Gln Asn Pro Asn Ser
             340                 345                 350

Asp Ala Pro Val Ile Arg Ser Lys Thr Ser Ala Arg Tyr Met Glu Leu
         355                 360                 365

Val Gly Trp Leu Val Asp Lys Gly Ile Thr Ser Glu Lys Gln Trp Ile
     370                 375                 380

Gln Glu Asp Gln Ala Ser Tyr Ile Ser Phe Asn Ala Ala Ser Asn Ser
385                 390                 395                 400

Arg Ser Gln Ile Lys Ala Ala Leu Asp Asn Ala Gly Lys Ile Met Ser
                 405                 410                 415

Leu Thr Lys Thr Ala Pro Asp Tyr Leu Val Gly Gln Gln Pro Val Glu
             420                 425                 430

Asp Ile Ser Ser Asn Arg Ile Tyr Lys Ile Leu Glu Leu Asn Gly Tyr
```

```
            435                 440                 445
Asp Pro Gln Tyr Ala Ala Ser Val Phe Leu Gly Trp Ala Thr Lys Lys
    450                 455                 460

Phe Gly Lys Arg Asn Thr Ile Trp Leu Phe Gly Pro Ala Thr Thr Gly
465                 470                 475                 480

Lys Thr Asn Ile Ala Glu Ala Ile Ala His Thr Val Pro Phe Tyr Gly
                    485                 490                 495

Cys Val Asn Trp Thr Asn Glu Asn Phe Pro Phe Asn Asp Cys Val Asp
                500                 505                 510

Lys Met Val Ile Trp Trp Glu Glu Gly Lys Met Thr Ala Lys Val Val
            515                 520                 525

Glu Ser Ala Lys Ala Ile Leu Gly Gly Ser Lys Val Arg Val Asp Gln
        530                 535                 540

Lys Cys Lys Ser Ser Ala Gln Ile Asp Pro Thr Pro Val Ile Val Thr
545                 550                 555                 560

Ser Asn Thr Asn Met Cys Ala Val Ile Asp Gly Asn Ser Thr Thr Phe
                565                 570                 575

Glu His Gln Gln Pro Leu Gln Asp Arg Met Phe Lys Phe Glu Leu Thr
            580                 585                 590

Arg Arg Leu Asp His Asp Phe Gly Lys Val Thr Lys Gln Glu Val Lys
        595                 600                 605

Asp Phe Phe Arg Trp Ala Lys Asp His Val Val Glu Val Glu His Glu
610                 615                 620

Phe Tyr Val Lys Lys Gly Gly Ala Lys Lys Arg Pro Ala Pro Ser Asp
625                 630                 635                 640

Ala Asp Ile Ser Glu Pro Lys Arg Val Arg Glu Ser Val Ala Gln Pro
                645                 650                 655

Ser Thr Ser Asp Ala Glu Ala Ser Ile Asn Tyr Ala Asp Arg Tyr Gln
            660                 665                 670

Asn Lys Cys Ser Arg His Val Gly Met Asn Leu Met Leu Phe Pro Cys
        675                 680                 685

Arg Gln Cys Glu Arg Met Asn Gln Asn Ser Asn Ile Cys Phe Thr His
690                 695                 700

Gly Gln Lys Asp Cys Leu Glu Cys Phe Pro Val Ser Glu Ser Gln Pro
705                 710                 715                 720

Val Ser Val Val Lys Lys Ala Tyr Gln Lys Leu Cys Tyr Ile His His
                725                 730                 735

Ile Met Gly Lys Val Pro Asp Ala Cys Thr Ala Cys Asp Leu Val Asn
            740                 745                 750

Val Asp Leu Asp Asp Cys Ile Phe Glu Gln
        755                 760

<210> SEQ ID NO 127
<211> LENGTH: 2289
<212> TYPE: DNA
<213> ORGANISM: Artificial Sequence
<220> FEATURE:
<223> OTHER INFORMATION: Synthetic: MCP-Rep-KDE-mu nucleic acid
      sequence (linker-MCP-linker-Rep)

<400> SEQUENCE: 127
atgcccggca gctccggcag tagcgcttct aactttactc agttcgttct cgtcgacaat      60
ggcggaactg gcgacgtgac tgtcgcccca agcaacttcg ctaacggggt cgctgaatgg     120
atcagctcta actcgcgttc acaggcttac aaagtaacct gtagcgttcg tcagagctct     180
```

```
gcgcagaatc gcaaatacac catcaaagtc gaggtgccta aagtggcaac ccagactgtt    240
ggtggagtag agcttcctgt agccgcatgg cgttcgtact taaatatgga actaaccatt    300
ccaattttcg ctacgaattc cgactgcgag cttattgtta aggcaatgca aggtctccta    360
aaagatggaa acccgattcc ctcagcaatc gcagcaaact ccggcatcta cggcagtagt    420
gggtcctctg ggttttacga gattgtgatt aaggtcccca gcgaccttga cgagcatctg    480
cccggcattt ctgacagctt tgtgaactgg gtggccgaga aggaatggga gttgccgcca    540
gattctgaca tggatctgaa tctgattgag caggcacccc tgaccgtggc cgagaagctg    600
cagcgcgact ttctgacgga atggcgccgt gtgagtaagg ccccggaggc ccttttctt    660 gtgcaatttg agaagggaga gagctacttc cacatgcacg tgctcgtgga aaccaccggg    720
gtgaaatcca tggttttggg acgtttcctg agtcagattc gcgaaaaact gattcagaga    780
atttaccgcg ggatcgagcc gactttgcca aactggttcg cggtcacaaa gaccagaaat    840
ggcgccggag cgggaacgc ggtggtggct gcgtgctaca tccccaatta cttgctcccc    900
aaaacccagc ctgagctcca gtgggcgtgg actaatatgg aacagtattt aagcgcctgt    960
ttgaatctca cggagcgtaa acggttggtg gcgcagcatc tgacgcacgt gtcgcagacg   1020
caggagcaga acaaagagaa tcagaatccc aattctgatg cgccggtgat cagatcaaaa   1080
acttcagcca ggtacatgga gctggtcggg tggctcgtgg acaaggggat tacctcggag   1140
aagcagtgga tccaggagga ccaggcctca tacatctcct tcaatgcggc ctccaactcg   1200
cggtcccaaa tcaaggctgc cttggacaat gcgggaaaga ttatgagcct gactaaaacc   1260
gcccccgact acctggtggg ccagcagccc gtggaggaca tttccagcaa tcggatttat   1320
aaaattttgg aactaaacgg gtacgatccc caatatgcgg cttccgtctt tctgggatgg   1380
gccacgaaaa agttcggcaa gaggaacacc atcggctgt ttgggcctgc aactaccggg   1440
aagaccaaca tcgcggaggc catagcccac actgtgccct tctacgggtg cgtaaactgg   1500
accaatgaga actttccctt caacgactgt gtcgacaaga tggtgatctg gtgggaggag   1560
gggaagatga ccgccaaggt cgtggagtcg gccaaagcca ttctcggagg aagcaaggtg   1620
cgcgtggacc agaaatgcaa gtcctcggcc cagatagacc cgactcccgt gatcgtcacc   1680
tccaacacca acatgtgcgc cgtgattgac gggaactcaa cgaccttcga acaccagcag   1740
ccgttgcaag accggatgtt caaatttgaa ctcacccgcc gtctggatca tgactttggg   1800
aaggtcacca agcaggaagt caaagacttt ttccggtggg caaggatca cgtggttgag   1860 gtggagcatg aattctacgt caaaaagggt ggagccaaga aaagacccgc ccccagtgac   1920
gcagatataa gtgagcccaa acgggtgcgc gagtcagttg cgcagccatc gacgtcagac   1980
gcggaagctt cgatcaacta cgcagacagg taccaaaaca aatgttctcg tcacgtgggc   2040
atgaatctga tgctgtttcc ctgcagacaa tgcgagagaa tgaatcagaa ttcaaatatc   2100
tgcttcactc acggacagaa agactgttta gagtgctttc ccgtgtcaga atctcaaccc   2160
gtttctgtcg tcaaaaaggc gtatcagaaa ctgtgctaca ttcatcatat catgggaaag   2220
gtgccagacg cttgcactgc ctgcgatctg gtcaatgtgg atttggatga ctgcatcttt   2280
gaacaataa                                                          2289
```

<210> SEQ ID NO 128
<211> LENGTH: 762
<212> TYPE: PRT
<213> ORGANISM: Artificial Sequence
<220> FEATURE:
<223> OTHER INFORMATION: Synthetic: MCP-Rep-KDE-muamino acid sequence (linker-MCP-linker-Rep)

<400> SEQUENCE: 128

```
Met Pro Gly Ser Ser Gly Ser Ser Ala Ser Asn Phe Thr Gln Phe Val
1               5                   10                  15

Leu Val Asp Asn Gly Gly Thr Gly Asp Val Thr Val Ala Pro Ser Asn
                20                  25                  30

Phe Ala Asn Gly Val Ala Glu Trp Ile Ser Ser Asn Ser Arg Ser Gln
            35                  40                  45

Ala Tyr Lys Val Thr Cys Ser Val Arg Gln Ser Ser Ala Gln Asn Arg
        50                  55                  60

Lys Tyr Thr Ile Lys Val Glu Val Pro Lys Val Ala Thr Gln Thr Val
65                  70                  75                  80

Gly Gly Val Glu Leu Pro Val Ala Ala Trp Arg Ser Tyr Leu Asn Met
                85                  90                  95

Glu Leu Thr Ile Pro Ile Phe Ala Thr Asn Ser Asp Cys Glu Leu Ile
            100                 105                 110

Val Lys Ala Met Gln Gly Leu Leu Lys Asp Gly Asn Pro Ile Pro Ser
        115                 120                 125

Ala Ile Ala Ala Asn Ser Gly Ile Tyr Gly Ser Ser Gly Ser Ser Gly
    130                 135                 140

Phe Tyr Glu Ile Val Ile Lys Val Pro Ser Asp Leu Asp Glu His Leu
145                 150                 155                 160

Pro Gly Ile Ser Asp Ser Phe Val Asn Trp Val Ala Glu Lys Glu Trp
                165                 170                 175

Glu Leu Pro Pro Asp Ser Asp Met Asp Leu Asn Leu Ile Glu Gln Ala
            180                 185                 190

Pro Leu Thr Val Ala Glu Lys Leu Gln Arg Asp Phe Leu Thr Glu Trp
        195                 200                 205

Arg Arg Val Ser Lys Ala Pro Glu Ala Leu Phe Phe Val Gln Phe Glu
    210                 215                 220

Lys Gly Glu Ser Tyr Phe His Met His Val Leu Val Glu Thr Thr Gly
225                 230                 235                 240

Val Lys Ser Met Val Leu Gly Arg Phe Leu Ser Gln Ile Arg Glu Lys
                245                 250                 255

Leu Ile Gln Arg Ile Tyr Arg Gly Ile Glu Pro Thr Leu Pro Asn Trp
            260                 265                 270

Phe Ala Val Thr Lys Thr Arg Asn Gly Ala Gly Gly Gly Asn Ala Val
        275                 280                 285

Val Ala Ala Cys Tyr Ile Pro Asn Tyr Leu Leu Pro Lys Thr Gln Pro
    290                 295                 300

Glu Leu Gln Trp Ala Trp Thr Asn Met Glu Gln Tyr Leu Ser Ala Cys
305                 310                 315                 320

Leu Asn Leu Thr Glu Arg Lys Arg Leu Val Ala Gln His Leu Thr His
                325                 330                 335

Val Ser Gln Thr Gln Glu Gln Asn Lys Glu Asn Gln Asn Pro Asn Ser
            340                 345                 350

Asp Ala Pro Val Ile Arg Ser Lys Thr Ser Ala Arg Tyr Met Glu Leu
        355                 360                 365

Val Gly Trp Leu Val Asp Lys Gly Ile Thr Ser Glu Lys Gln Trp Ile
    370                 375                 380

Gln Glu Asp Gln Ala Ser Tyr Ile Ser Phe Asn Ala Ala Ser Asn Ser
385                 390                 395                 400
```

```
Arg Ser Gln Ile Lys Ala Ala Leu Asp Asn Ala Gly Lys Ile Met Ser
                405                 410                 415

Leu Thr Lys Thr Ala Pro Asp Tyr Leu Val Gly Gln Gln Pro Val Glu
            420                 425                 430

Asp Ile Ser Ser Asn Arg Ile Tyr Lys Ile Leu Glu Leu Asn Gly Tyr
        435                 440                 445

Asp Pro Gln Tyr Ala Ala Ser Val Phe Leu Gly Trp Ala Thr Lys Lys
    450                 455                 460

Phe Gly Lys Arg Asn Thr Ile Trp Leu Phe Gly Pro Ala Thr Thr Gly
465                 470                 475                 480

Lys Thr Asn Ile Ala Glu Ala Ile Ala His Thr Val Pro Phe Tyr Gly
                485                 490                 495

Cys Val Asn Trp Thr Asn Glu Asn Phe Pro Phe Asn Asp Cys Val Asp
            500                 505                 510

Lys Met Val Ile Trp Trp Glu Glu Gly Lys Met Thr Ala Lys Val Val
        515                 520                 525

Glu Ser Ala Lys Ala Ile Leu Gly Gly Ser Lys Val Arg Val Asp Gln
    530                 535                 540

Lys Cys Lys Ser Ser Ala Gln Ile Asp Pro Thr Pro Val Ile Val Thr
545                 550                 555                 560

Ser Asn Thr Asn Met Cys Ala Val Ile Asp Gly Asn Ser Thr Thr Phe
                565                 570                 575

Glu His Gln Gln Pro Leu Gln Asp Arg Met Phe Lys Phe Glu Leu Thr
            580                 585                 590

Arg Arg Leu Asp His Asp Phe Gly Lys Val Thr Lys Gln Glu Val Lys
        595                 600                 605

Asp Phe Phe Arg Trp Ala Lys Asp His Val Val Glu Val Glu His Glu
    610                 615                 620

Phe Tyr Val Lys Lys Gly Gly Ala Lys Lys Arg Pro Ala Pro Ser Asp
625                 630                 635                 640

Ala Asp Ile Ser Glu Pro Lys Arg Val Arg Glu Ser Val Ala Gln Pro
                645                 650                 655

Ser Thr Ser Asp Ala Glu Ala Ser Ile Asn Tyr Ala Asp Arg Tyr Gln
            660                 665                 670

Asn Lys Cys Ser Arg His Val Gly Met Asn Leu Met Leu Phe Pro Cys
        675                 680                 685

Arg Gln Cys Glu Arg Met Asn Gln Asn Ser Asn Ile Cys Phe Thr His
    690                 695                 700

Gly Gln Lys Asp Cys Leu Glu Cys Phe Pro Val Ser Glu Ser Gln Pro
705                 710                 715                 720

Val Ser Val Val Lys Lys Ala Tyr Gln Lys Leu Cys Tyr Ile His His
                725                 730                 735

Ile Met Gly Lys Val Pro Asp Ala Cys Thr Ala Cys Asp Leu Val Asn
            740                 745                 750

Val Asp Leu Asp Asp Cys Ile Phe Glu Gln
        755                 760

<210> SEQ ID NO 129
<211> LENGTH: 2289
<212> TYPE: DNA
<213> ORGANISM: Artificial Sequence
<220> FEATURE:
<223> OTHER INFORMATION: Synthetic: MCP-Rep-EKE-mu nucleic acid sequence
      (linker-MCP-linker-Rep)

<400> SEQUENCE: 129
```

-continued

```
atgcccggca gctccggcag tagcgcttct aactttactc agttcgttct cgtcgacaat    60
ggcggaactg gcgacgtgac tgtcgcccca agcaacttcg ctaacggggt cgctgaatgg   120
atcagctcta actcgcgttc acaggcttac aaagtaacct gtagcgttcg tcagagctct   180
gcgcagaatc gcaaatacac catcaaagtc gaggtgccta agtggcaac ccagactgtt    240
ggtggagtag agcttcctgt agccgcatgg cgttcgtact taaatatgga actaaccatt   300
ccaattttcg ctacgaattc cgactgcgag cttattgtta aggcaatgca aggtctccta   360
aaagatggaa acccgattcc ctcagcaatc gcagcaaact ccggcatcta cggcagtagt   420
gggtcctctg ggttttacga gattgtgatt aaggtcccca cgaccttga cgagcatctg    480
cccggcattt ctgacagctt tgtgaactgg gtggccgaga aggaatggga gttgccgcca   540
gattctgaca tggatctgaa tctgattgag caggcacccc tgaccgtggc cgagaagctg   600
cagcgcgact ttctgacgga atggcgccgt gtgagtaagg ccccggaggc ccttttcttt   660
gtgcaatttg cggcgggagc gagctacttc cacatgcacg tgctcgtgga aaccaccggg   720
gtgaaatcca tggttttggg acgtttcctg agtcagattc gcgaaaaact gattcagaga   780
atttaccgcg ggatcgagcc gactttgcca aactggttcg cggtcacaaa gaccagaaat   840
ggcgccggag gcgggaacaa ggtggtggat gagtgctaca tccccaatta cttgctcccc   900
aaaacccagc ctgagctcca gtgggcgtgg actaatatgg aacagtattt aagcgcctgt   960
ttgaatctca cggagcgtaa acggttggtg gcgcagcatc tgacgcacgt gtcgcagacg  1020
caggagcaga acaaagagaa tcagaatccc aattctgatg cgccggtgat cagatcaaaa  1080
acttcagcca ggtacatgga gctggtcggg tggctcgtgg acaaggggat tacctcggag  1140
aagcagtgga tccaggagga ccaggcctca tacatctcct tcaatgcggc ctccaactcg  1200
cggtcccaaa tcaaggctgc cttggacaat gcgggaaaga ttatgagcct gactaaaacc  1260
gcccccgact acctggtggg ccagcagccc gtggaggaca tttccagcaa tcggatttat  1320
aaaattttgg aactaaacgg gtacgatccc caatatgcgg cttccgtctt tctgggatgg  1380
gccacgaaaa agttcggcaa gaggaacacc atctggctgt ttgggcctgc aactaccggg  1440
aagaccaaca tcgcggaggc catagcccac actgtgccct tctacgggtg cgtaaactgg  1500
accaatgaga actttccctt caacgactgt gtcgacaaga tggtgatctg gtgggaggag  1560
gggaagatga ccgccaaggt cgtggagtcg gccaaagcca ttctcggagg aagcaaggtg  1620
cgcgtggacc agaaatgcaa gtcctcggcc cagatagacc cgactcccgt gatcgtcacc  1680
tccaacacca acatgtgcgc cgtgattgac gggaactcaa cgaccttcga acaccagcag  1740
ccgttgcaag accggatgtt caaatttgaa ctcacccgcc gtctggatca tgactttggg  1800
aaggtcacca agcaggaagt caaagacttt ttccggtggg caaggatca cgtggttgag  1860
gtggagcatg aattctacgt caaaaagggt ggagccaaga aaagaccgc ccccagtgac   1920
gcagatataa gtgagcccaa acgggtgcgc gagtcagttg cgcagccatc gacgtcagac  1980
gcggaagctt cgatcaacta cgcagacagg taccaaaaca aatgttctcg tcacgtgggc  2040
atgaatctga tgctgtttcc ctgcagacaa tgcgagagaa tgaatcagaa ttcaaatatc  2100
tgcttcactc acggacagaa agactgttta gagtgctttc ccgtgtcaga atctcaaccc  2160
gtttctgtcg tcaaaaaggc gtatcagaaa ctgtgctaca ttcatcatat catgggaaag  2220
gtgccagacg cttgcactgc ctgcgatctg gtcaatgtgg atttggatga ctgcatcttt  2280
gaacaataa                                                          2289
```

<210> SEQ ID NO 130
<211> LENGTH: 762
<212> TYPE: PRT
<213> ORGANISM: Artificial Sequence
<220> FEATURE:
<223> OTHER INFORMATION: Synthetic: MCP-Rep-EKE-muamino acid sequence (linker-MCP-linker-Rep)

<400> SEQUENCE: 130

```
Met Pro Gly Ser Ser Gly Ser Ser Ala Ser Asn Phe Thr Gln Phe Val
1               5                   10                  15

Leu Val Asp Asn Gly Gly Thr Gly Asp Val Thr Val Ala Pro Ser Asn
            20                  25                  30

Phe Ala Asn Gly Val Ala Glu Trp Ile Ser Ser Asn Ser Arg Ser Gln
        35                  40                  45

Ala Tyr Lys Val Thr Cys Ser Val Arg Gln Ser Ser Ala Gln Asn Arg
    50                  55                  60

Lys Tyr Thr Ile Lys Val Glu Val Pro Lys Val Ala Thr Gln Thr Val
65                  70                  75                  80

Gly Gly Val Glu Leu Pro Val Ala Ala Trp Arg Ser Tyr Leu Asn Met
                85                  90                  95

Glu Leu Thr Ile Pro Ile Phe Ala Thr Asn Ser Asp Cys Glu Leu Ile
            100                 105                 110

Val Lys Ala Met Gln Gly Leu Leu Lys Asp Gly Asn Pro Ile Pro Ser
        115                 120                 125

Ala Ile Ala Ala Asn Ser Gly Ile Tyr Gly Ser Ser Gly Ser Ser Gly
    130                 135                 140

Phe Tyr Glu Ile Val Ile Lys Val Pro Ser Asp Leu Asp Glu His Leu
145                 150                 155                 160

Pro Gly Ile Ser Asp Ser Phe Val Asn Trp Val Ala Glu Lys Glu Trp
                165                 170                 175

Glu Leu Pro Pro Asp Ser Asp Met Asp Leu Asn Leu Ile Glu Gln Ala
            180                 185                 190

Pro Leu Thr Val Ala Glu Lys Leu Gln Arg Asp Phe Leu Thr Glu Trp
        195                 200                 205

Arg Arg Val Ser Lys Ala Pro Glu Ala Leu Phe Phe Val Gln Phe Ala
    210                 215                 220

Ala Gly Ala Ser Tyr Phe His Met His Val Leu Val Glu Thr Thr Gly
225                 230                 235                 240

Val Lys Ser Met Val Leu Gly Arg Phe Leu Ser Gln Ile Arg Glu Lys
                245                 250                 255

Leu Ile Gln Arg Ile Tyr Arg Gly Ile Glu Pro Thr Leu Pro Asn Trp
            260                 265                 270

Phe Ala Val Thr Lys Thr Arg Asn Gly Ala Gly Gly Gly Asn Lys Val
        275                 280                 285

Val Asp Glu Cys Tyr Ile Pro Asn Tyr Leu Leu Pro Lys Thr Gln Pro
    290                 295                 300

Glu Leu Gln Trp Ala Trp Thr Asn Met Glu Gln Tyr Leu Ser Ala Cys
305                 310                 315                 320

Leu Asn Leu Thr Glu Arg Lys Arg Leu Val Ala Gln His Leu Thr His
                325                 330                 335

Val Ser Gln Thr Gln Glu Gln Asn Lys Glu Asn Gln Asn Pro Asn Ser
            340                 345                 350

Asp Ala Pro Val Ile Arg Ser Lys Thr Ser Ala Arg Tyr Met Glu Leu
        355                 360                 365
```

```
Val Gly Trp Leu Val Asp Lys Gly Ile Thr Ser Glu Lys Gln Trp Ile
    370                 375                 380

Gln Glu Asp Gln Ala Ser Tyr Ile Ser Phe Asn Ala Ala Ser Asn Ser
385                 390                 395                 400

Arg Ser Gln Ile Lys Ala Ala Leu Asp Asn Ala Gly Lys Ile Met Ser
                405                 410                 415

Leu Thr Lys Thr Ala Pro Asp Tyr Leu Val Gly Gln Pro Val Glu
            420                 425                 430

Asp Ile Ser Ser Asn Arg Ile Tyr Lys Ile Leu Glu Leu Asn Gly Tyr
        435                 440                 445

Asp Pro Gln Tyr Ala Ala Ser Val Phe Leu Gly Trp Ala Thr Lys Lys
    450                 455                 460

Phe Gly Lys Arg Asn Thr Ile Trp Leu Phe Gly Pro Ala Thr Gly
465                 470                 475                 480

Lys Thr Asn Ile Ala Glu Ala Ile Ala His Thr Val Pro Phe Tyr Gly
                485                 490                 495

Cys Val Asn Trp Thr Asn Glu Asn Phe Pro Phe Asn Asp Cys Val Asp
            500                 505                 510

Lys Met Val Ile Trp Trp Glu Glu Gly Lys Met Thr Ala Lys Val Val
        515                 520                 525

Glu Ser Ala Lys Ala Ile Leu Gly Gly Ser Lys Val Arg Val Asp Gln
    530                 535                 540

Lys Cys Lys Ser Ser Ala Gln Ile Asp Pro Thr Pro Val Ile Val Thr
545                 550                 555                 560

Ser Asn Thr Asn Met Cys Ala Val Ile Asp Gly Asn Ser Thr Thr Phe
                565                 570                 575

Glu His Gln Gln Pro Leu Gln Asp Arg Met Phe Lys Phe Glu Leu Thr
            580                 585                 590

Arg Arg Leu Asp His Asp Phe Gly Lys Val Thr Lys Gln Glu Val Lys
        595                 600                 605

Asp Phe Phe Arg Trp Ala Lys Asp His Val Val Glu Val Glu His Glu
    610                 615                 620

Phe Tyr Val Lys Lys Gly Gly Ala Lys Lys Arg Pro Ala Pro Ser Asp
625                 630                 635                 640

Ala Asp Ile Ser Glu Pro Lys Arg Val Arg Glu Ser Val Ala Gln Pro
                645                 650                 655

Ser Thr Ser Asp Ala Glu Ala Ser Ile Asn Tyr Ala Asp Arg Tyr Gln
            660                 665                 670

Asn Lys Cys Ser Arg His Val Gly Met Asn Leu Met Leu Phe Pro Cys
        675                 680                 685

Arg Gln Cys Glu Arg Met Asn Gln Asn Ser Asn Ile Cys Phe Thr His
    690                 695                 700

Gly Gln Lys Asp Cys Leu Glu Cys Phe Pro Val Ser Glu Ser Gln Pro
705                 710                 715                 720

Val Ser Val Val Lys Lys Ala Tyr Gln Lys Leu Cys Tyr Ile His His
                725                 730                 735

Ile Met Gly Lys Val Pro Asp Ala Cys Thr Ala Cys Asp Leu Val Asn
            740                 745                 750

Val Asp Leu Asp Asp Cys Ile Phe Glu Gln
        755                 760

<210> SEQ ID NO 131
<211> LENGTH: 2616
```

<212> TYPE: DNA
<213> ORGANISM: Artificial Sequence
<220> FEATURE:
<223> OTHER INFORMATION: Synthetic: 2XMCP-Rep nucleic acid sequence
(linker-2XMCP-linker-Rep)

<400> SEQUENCE: 131

```
atgcccggca gctccggcag tagcgcttct aactttactc agttcgttct cgtcgacaat      60
ggcggaactg cgacgtgac tgtcgcccca agcaacttcg ctaacgggat cgctgaatgg     120
atcagctcta actcgcgttc acaggcttac aaagtaacct gtagcgttcg tcagagctct    180
gcgcagaatc gcaaatacac catcaaagtc gaggtgccta aggcgcctg gcgttcgtac     240
ttaaatatgg aactaaccat tccaattttc gccacgaatt ccgactgcga gcttattgtt    300
aaggcaatgc aaggtctcct aaaagatgga acccgattc cctcagcaat cgcagcaaac     360
tccggcatct acggtggtgg aggaggaatg gcgtccaatt tcacgcagtt cgtcctggtt    420
gacaacgggg ggactgggga cgttacggtc gctccgagca ctttgccaa tggtattgcg     480
gagtggattt cttctaattc acggtcccaa gcttacaaag tgacctgttc cgtgcggcaa    540
agttctgctc agaatagaaa gtacactata aaggtcgaag tcctaagggg ggcctggcga   600
tcatatctca atatggagct taccatccca atatttgcca ctaattctga ttgtgaattg    660
attgtcaaag caatgcaagg actcttgaaa gacggaaacc caatcccag cgcaatcgca     720
gccaactccg gtatatacgg cagtagtggg tcctctgggt tttacgagat tgtgattaag    780
gtccccagcg accttgacga gcatctgccc ggcatttctg acagctttgt gaactgggtg    840
gccgagaagg aatgggagtt gccgccagat tctgacatgg atctgaatct gattgagcag    900
gcacccctga ccgtggccga gaagctgcag cgcgactttc tgacggaatg cgccgtgtg    960
agtaaggccc cggaggccct tttctttgtg caatttgaga agggagagag ctacttccac  1020
atgcacgtgc tcgtggaaac caccggggtg aaatccatgg ttttgggacg tttcctgagt   1080
cagattcgcg aaaaactgat tcagagaatt taccgcggga tcgagccgac tttgccaaac   1140
tggttcgcgg tcacaaagac cagaaatggc gccggaggcg ggaacaaggt ggtggatgag   1200
tgctacatcc ccaattactt gctccccaaa acccagcctg agctcagtg ggcgtggact   1260
aatatggaac agtatttaag cgcctgtttg aatctcacgg agcgtaaacg gttggtggcg   1320
cagcatctga cgcacgtgtc gcagacgcag gagcagaaca agagaatca gaatcccaat   1380
tctgatgcgc cggtgatcag atcaaaaact tcagccaggt acatggagct ggtcgggtgg   1440
ctcgtggaca aggggattac ctcggagaag cagtggatcc aggaggacca ggcctcatac   1500
atctccttca atgcggcctc caactcgcgg tcccaaatca aggctgcctt ggacaatgcg   1560
ggaaagatta tgagcctgac taaaaccgcc ccgactacc tggtgggcca gcagcccgtg   1620
gaggacattt ccagcaatcg gatttataaa attttggaac taaacgggta cgatccccaa   1680
tatgcggctt ccgtctttct gggatgggcc acgaaaaagt tcggcaagag gaacaccatc   1740
tggctgtttg ggcctgcaac taccgggaag accaacatcg cggaggccat agcccacact   1800
gtgcccttct acgggtgcgt aaactggacc aatgagaact ttcccttcaa cgactgtgtc   1860
gacaagatgg tgatctggtg ggaggagggg aagatgaccg ccaaggtcgt ggagtcggcc   1920
aaagccattc tcggaggaag caaggtgcgc gtggaccaga atgcaagtc ctcggcccag   1980
atagacccga ctcccgtgat cgtcacctcc aacaccaaca tgtgcgccgt gattgacggg   2040
aactcaacga ccttcgaaca ccagcagccg ttgcaagacc ggatgttcaa atttgaactc   2100
acccgccgtc tggatcatga ctttgggaag gtcaccaagc aggaagtcaa agacttttc   2160
```

-continued

```
cggtgggcaa aggatcacgt ggttgaggtg gagcatgaat tctacgtcaa aaagggtgga   2220
gccaagaaaa gacccgcccc cagtgacgca gatataagtg agcccaaacg ggtgcgcgag   2280
tcagttgcgc agccatcgac gtcagacgcg gaagcttcga tcaactacgc agacaggtac   2340
caaaacaaat gttctcgtca cgtgggcatg aatctgatgc tgtttccctg cagacaatgc   2400
gagagaatga atcagaattc aaatatctgc ttcactcacg gacagaaaga ctgtttagag   2460
tgctttcccg tgtcagaatc tcaacccgtt tctgtcgtca aaaaggcgta tcagaaactg   2520
tgctacattc atcatatcat gggaaaggtg ccagacgctt gcactgcctg cgatctggtc   2580
aatgtggatt tggatgactg catctttgaa caataa                             2616
```

<210> SEQ ID NO 132
<211> LENGTH: 871
<212> TYPE: PRT
<213> ORGANISM: Artificial Sequence
<220> FEATURE:
<223> OTHER INFORMATION: Synthetic: 2XMCP-Rep amino acid sequence (linker-2XMCP-linker-Rep)

<400> SEQUENCE: 132

```
Met Pro Gly Ser Ser Gly Ser Ser Ala Ser Asn Phe Thr Gln Phe Val
1               5                   10                  15

Leu Val Asp Asn Gly Gly Thr Gly Asp Val Thr Val Ala Pro Ser Asn
            20                  25                  30

Phe Ala Asn Gly Ile Ala Glu Trp Ile Ser Ser Asn Ser Arg Ser Gln
        35                  40                  45

Ala Tyr Lys Val Thr Cys Ser Val Arg Gln Ser Ser Ala Gln Asn Arg
    50                  55                  60

Lys Tyr Thr Ile Lys Val Glu Val Pro Lys Gly Ala Trp Arg Ser Tyr
65                  70                  75                  80

Leu Asn Met Glu Leu Thr Ile Pro Ile Phe Ala Thr Asn Ser Asp Cys
                85                  90                  95

Glu Leu Ile Val Lys Ala Met Gln Gly Leu Leu Lys Asp Gly Asn Pro
            100                 105                 110

Ile Pro Ser Ala Ile Ala Ala Asn Ser Gly Ile Tyr Gly Gly Gly Gly
        115                 120                 125

Gly Met Ala Ser Asn Phe Thr Gln Phe Val Leu Val Asp Asn Gly Gly
    130                 135                 140

Thr Gly Asp Val Thr Val Ala Pro Ser Asn Phe Ala Asn Gly Ile Ala
145                 150                 155                 160

Glu Trp Ile Ser Ser Asn Ser Arg Ser Gln Ala Tyr Lys Val Thr Cys
                165                 170                 175

Ser Val Arg Gln Ser Ser Ala Gln Asn Arg Lys Tyr Thr Ile Lys Val
            180                 185                 190

Glu Val Pro Lys Gly Ala Trp Arg Ser Tyr Leu Asn Met Glu Leu Thr
        195                 200                 205

Ile Pro Ile Phe Ala Thr Asn Ser Asp Cys Glu Leu Ile Val Lys Ala
    210                 215                 220

Met Gln Gly Leu Leu Lys Asp Gly Asn Pro Ile Pro Ser Ala Ile Ala
225                 230                 235                 240

Ala Asn Ser Gly Ile Tyr Gly Ser Ser Gly Ser Ser Gly Phe Tyr Glu
                245                 250                 255

Ile Val Ile Lys Val Pro Ser Asp Leu Asp Glu His Leu Pro Gly Ile
            260                 265                 270
```

```
Ser Asp Ser Phe Val Asn Trp Val Ala Glu Lys Glu Trp Glu Leu Pro
            275                 280                 285

Pro Asp Ser Asp Met Asp Leu Asn Leu Ile Glu Gln Ala Pro Leu Thr
290                 295                 300

Val Ala Glu Lys Leu Gln Arg Asp Phe Leu Thr Glu Trp Arg Arg Val
305                 310                 315                 320

Ser Lys Ala Pro Glu Ala Leu Phe Phe Val Gln Phe Glu Lys Gly Glu
                325                 330                 335

Ser Tyr Phe His Met His Val Leu Val Glu Thr Thr Gly Val Lys Ser
            340                 345                 350

Met Val Leu Gly Arg Phe Leu Ser Gln Ile Arg Glu Lys Leu Ile Gln
            355                 360                 365

Arg Ile Tyr Arg Gly Ile Glu Pro Thr Leu Pro Asn Trp Phe Ala Val
370                 375                 380

Thr Lys Thr Arg Asn Gly Ala Gly Gly Gly Asn Lys Val Val Asp Glu
385                 390                 395                 400

Cys Tyr Ile Pro Asn Tyr Leu Leu Pro Lys Thr Gln Pro Glu Leu Gln
                405                 410                 415

Trp Ala Trp Thr Asn Met Glu Gln Tyr Leu Ser Ala Cys Leu Asn Leu
            420                 425                 430

Thr Glu Arg Lys Arg Leu Val Ala Gln His Leu Thr His Val Ser Gln
            435                 440                 445

Thr Gln Glu Gln Asn Lys Glu Asn Gln Asn Pro Asn Ser Asp Ala Pro
            450                 455                 460

Val Ile Arg Ser Lys Thr Ser Ala Arg Tyr Met Glu Leu Val Gly Trp
465                 470                 475                 480

Leu Val Asp Lys Gly Ile Thr Ser Glu Lys Gln Trp Ile Gln Glu Asp
                485                 490                 495

Gln Ala Ser Tyr Ile Ser Phe Asn Ala Ala Ser Asn Ser Arg Ser Gln
            500                 505                 510

Ile Lys Ala Ala Leu Asp Asn Ala Gly Lys Ile Met Ser Leu Thr Lys
            515                 520                 525

Thr Ala Pro Asp Tyr Leu Val Gly Gln Gln Pro Val Glu Asp Ile Ser
            530                 535                 540

Ser Asn Arg Ile Tyr Lys Ile Leu Glu Leu Asn Gly Tyr Asp Pro Gln
545                 550                 555                 560

Tyr Ala Ala Ser Val Phe Leu Gly Trp Ala Thr Lys Lys Phe Gly Lys
                565                 570                 575

Arg Asn Thr Ile Trp Leu Phe Gly Pro Ala Thr Thr Gly Lys Thr Asn
            580                 585                 590

Ile Ala Glu Ala Ile Ala His Thr Val Pro Phe Tyr Gly Cys Val Asn
            595                 600                 605

Trp Thr Asn Glu Asn Phe Pro Phe Asn Asp Cys Val Asp Lys Met Val
            610                 615                 620

Ile Trp Trp Glu Glu Gly Lys Met Thr Ala Lys Val Val Glu Ser Ala
625                 630                 635                 640

Lys Ala Ile Leu Gly Gly Ser Lys Val Arg Val Asp Gln Lys Cys Lys
                645                 650                 655

Ser Ser Ala Gln Ile Asp Pro Thr Pro Val Ile Val Thr Ser Asn Thr
            660                 665                 670

Asn Met Cys Ala Val Ile Asp Gly Asn Ser Thr Thr Phe Glu His Gln
            675                 680                 685

Gln Pro Leu Gln Asp Arg Met Phe Lys Phe Glu Leu Thr Arg Arg Leu
```

```
                  690              695               700
Asp His Asp Phe Gly Lys Val Thr Lys Gln Glu Val Lys Asp Phe Phe
705                 710               715                 720

Arg Trp Ala Lys Asp His Val Val Glu Val Glu His Glu Phe Tyr Val
                725              730                735

Lys Lys Gly Gly Ala Lys Lys Arg Pro Ala Pro Ser Asp Ala Asp Ile
            740              745              750

Ser Glu Pro Lys Arg Val Arg Glu Ser Val Ala Gln Pro Ser Thr Ser
        755              760              765

Asp Ala Glu Ala Ser Ile Asn Tyr Ala Asp Arg Tyr Gln Asn Lys Cys
    770              775              780

Ser Arg His Val Gly Met Asn Leu Met Leu Phe Pro Cys Arg Gln Cys
785              790              795                  800

Glu Arg Met Asn Gln Asn Ser Asn Ile Cys Phe Thr His Gly Gln Lys
                805              810               815

Asp Cys Leu Glu Cys Phe Pro Val Ser Glu Ser Gln Pro Val Ser Val
            820              825              830

Val Lys Lys Ala Tyr Gln Lys Leu Cys Tyr Ile His His Ile Met Gly
        835              840              845

Lys Val Pro Asp Ala Cys Thr Ala Cys Asp Leu Val Asn Val Asp Leu
    850              855              860

Asp Asp Cys Ile Phe Glu Gln
865                 870

<210> SEQ ID NO 133
<211> LENGTH: 2265
<212> TYPE: DNA
<213> ORGANISM: Artificial Sequence
<220> FEATURE:
<223> OTHER INFORMATION: Synthetic: PCP-Rep-Y156F  nucleic acid sequence
      (linker-PCP-linker-Rep)

<400> SEQUENCE: 133
atgcccggca gctccggcag tagctccaaa acaatagtcc tctccgtagg ggaggcaaca      60
cggactttga ccgaaatcca gtcaaccgct gaccgacaaa tctttgaaga gaaagtaggg     120
cctcttgtgg gccgactgcg cttgactgca agcttgcgac aaaacggcgc aaagactgcc     180
tatagggtca accttaaact cgaccaagcc gacgtggtcg atagcggtct ccctaaggtt     240
cggtatacgc aggtctggag tcatgacgta acaatcgtag caaacagcac agaagcctcc     300
cgaaaaagcc tctacgatct gacgaaatcc ttggtggcta cgtcacaggt ggaagacctc     360
gttgtcaacc ttgtacctct gggtcgaggc agtagtgggt cctctgggtt ttacgagatt     420
gtgattaagg tccccagcga ccttgacgag catctgcccg gcatttctga cagctttgtg     480
aactgggtgg ccgagaagga atgggagttg ccgccagatt ctgacatgga tctgaatctg     540
attgagcagg cacccctgac cgtggccgag aagctgcagc gcgactttct gacggaatgg     600
cgccgtgtga gtaaggcccc ggaggccctt ttctttgtgc aatttgagaa gggagagagc     660
tacttccaca tgcacgtgct cgtggaaacc accggggtga atccatggt tttgggacgt     720 ttcctgagtc agattcgcga aaaactgatt cagagaattt accgcgggat cgagccgact     780
ttgccaaact ggttcgcggt cacaaagacc agaaatggcg ccggaggcgg gaacaaggtg     840
gtggatgagt gctacatccc caatttcttg ctccccaaaa cccagcctga gctccagtgg     900
gcgtggacta tatgggaaca gtatttaagc gcctgtttga atctcacgga gcgtaaacgg     960
ttggtggcgc agcatctgac gcacgtgtcg cagacgcagg agcagaacaa agagaatcag    1020
```

```
aatcccaatt ctgatgcgcc ggtgatcaga tcaaaaactt cagccaggta catggagctg    1080
gtcgggtggc tcgtggacaa ggggattacc tcggagaagc agtggatcca ggaggaccag    1140
gcctcataca tctccttcaa tgcggcctcc aactcgcggt cccaaatcaa ggctgccttg    1200
gacaatgcgg gaaagattat gagcctgact aaaaccgccc ccgactacct ggtgggccag    1260
cagcccgtgg aggacatttc cagcaatcgg atttataaaa ttttggaact aaacgggtac    1320 gatcccaat atgcggcttc cgtctttctg ggatgggcca cgaaaaagtt cggcaagagg    1380
aacaccatct ggctgtttgg gcctgcaact accgggaaga ccaacatcgc ggaggccata    1440
gcccacactg tgcccttcta cgggtgcgta actggacca atgagaactt tcccttcaac    1500
gactgtgtcg acaagatggt gatctggtgg gaggagggga agatgaccgc caaggtcgtg    1560
gagtcggcca agccattct cggaggaagc aaggtgcgcg tggaccagaa atgcaagtcc    1620
tcggcccaga tagacccgac tcccgtgatc gtcacctcca acaccaacat gtgcgccgtg    1680
attgacggga actcaacgac cttcgaacac cagcagccgt tgcaagaccg gatgttcaaa    1740
tttgaactca cccgccgtct ggatcatgac tttgggaagg tcaccaagca ggaagtcaaa    1800
gactttttcc ggtgggcaaa ggatcacgtg gttgaggtgg agcatgaatt ctacgtcaaa    1860
aagggtggag ccaagaaaag acccgccccc agtgacgcag atataagtga gcccaaacgg    1920
gtgcgcgagt cagttgcgca gccatcgacg tcagacgcgg aagcttcgat caactacgca    1980
gacaggtacc aaaacaaatg ttctcgtcac gtgggcatga atctgatgct gtttccctgc    2040
agacaatgcg agagaatgaa tcagaattca aatatctgct tcactcacgg acagaaagac    2100
tgtttagagt gctttcccgt gtcagaatct caacccgttt ctgtcgtcaa aaaggcgtat    2160
cagaaactgt gctacattca tcatatcatg ggaaaggtgc cagacgcttg cactgcctgc    2220
gatctggtca atgtggattt ggatgactgc atctttgaac aataa                    2265
```

<210> SEQ ID NO 134
<211> LENGTH: 754
<212> TYPE: PRT
<213> ORGANISM: Artificial Sequence
<220> FEATURE:
<223> OTHER INFORMATION: Synthetic: PCP-Rep-Y156F amino acid sequence
      (linker-PCP-linker-Rep)

<400> SEQUENCE: 134

Met Pro Gly Ser Ser Gly Ser Ser Ser Lys Thr Ile Val Leu Ser Val
1               5                   10                  15

Gly Glu Ala Thr Arg Thr Leu Thr Glu Ile Gln Ser Thr Ala Asp Arg
            20                  25                  30

Gln Ile Phe Glu Glu Lys Val Gly Pro Leu Val Gly Arg Leu Arg Leu
        35                  40                  45

Thr Ala Ser Leu Arg Gln Asn Gly Ala Lys Thr Ala Tyr Arg Val Asn
    50                  55                  60

Leu Lys Leu Asp Gln Ala Asp Val Val Asp Ser Gly Leu Pro Lys Val
65                  70                  75                  80

Arg Tyr Thr Gln Val Trp Ser His Asp Val Thr Ile Val Ala Asn Ser
                85                  90                  95

Thr Glu Ala Ser Arg Lys Ser Leu Tyr Asp Leu Thr Lys Ser Leu Val
            100                 105                 110

Ala Thr Ser Gln Val Glu Asp Leu Val Val Asn Leu Val Pro Leu Gly
        115                 120                 125

Arg Gly Ser Ser Gly Ser Ser Gly Phe Tyr Glu Ile Val Ile Lys Val

```
              130                 135                 140
Pro Ser Asp Leu Asp Glu His Leu Pro Gly Ile Ser Asp Ser Phe Val
145                 150                 155                 160

Asn Trp Val Ala Glu Lys Glu Trp Glu Leu Pro Asp Ser Asp Met
                165                 170                 175

Asp Leu Asn Leu Ile Glu Gln Ala Pro Leu Thr Val Ala Glu Lys Leu
            180                 185                 190

Gln Arg Asp Phe Leu Thr Glu Trp Arg Arg Val Ser Lys Ala Pro Glu
        195                 200                 205

Ala Leu Phe Phe Val Gln Phe Glu Lys Gly Glu Ser Tyr Phe His Met
210                 215                 220

His Val Leu Val Glu Thr Thr Gly Val Lys Ser Met Val Leu Gly Arg
225                 230                 235                 240

Phe Leu Ser Gln Ile Arg Glu Lys Leu Ile Gln Arg Ile Tyr Arg Gly
                245                 250                 255

Ile Glu Pro Thr Leu Pro Asn Trp Phe Ala Val Thr Lys Thr Arg Asn
            260                 265                 270

Gly Ala Gly Gly Asn Lys Val Val Asp Glu Cys Tyr Ile Pro Asn
        275                 280                 285

Phe Leu Leu Pro Lys Thr Gln Pro Glu Leu Gln Trp Ala Trp Thr Asn
290                 295                 300

Met Glu Gln Tyr Leu Ser Ala Cys Leu Asn Leu Thr Glu Arg Lys Arg
305                 310                 315                 320

Leu Val Ala Gln His Leu Thr His Val Ser Gln Thr Gln Glu Gln Asn
                325                 330                 335

Lys Glu Asn Gln Asn Pro Asn Ser Asp Ala Pro Val Ile Arg Ser Lys
            340                 345                 350

Thr Ser Ala Arg Tyr Met Glu Leu Val Gly Trp Leu Val Asp Lys Gly
        355                 360                 365

Ile Thr Ser Glu Lys Gln Trp Ile Gln Glu Asp Gln Ala Ser Tyr Ile
370                 375                 380

Ser Phe Asn Ala Ala Ser Asn Ser Arg Ser Gln Ile Lys Ala Ala Leu
385                 390                 395                 400

Asp Asn Ala Gly Lys Ile Met Ser Leu Thr Lys Thr Ala Pro Asp Tyr
                405                 410                 415

Leu Val Gly Gln Gln Pro Val Glu Asp Ile Ser Ser Asn Arg Ile Tyr
            420                 425                 430

Lys Ile Leu Glu Leu Asn Gly Tyr Asp Pro Gln Tyr Ala Ala Ser Val
        435                 440                 445

Phe Leu Gly Trp Ala Thr Lys Lys Phe Gly Lys Arg Asn Thr Ile Trp
450                 455                 460

Leu Phe Gly Pro Ala Thr Thr Gly Lys Thr Asn Ile Ala Glu Ala Ile
465                 470                 475                 480

Ala His Thr Val Pro Phe Tyr Gly Cys Val Asn Trp Thr Asn Glu Asn
                485                 490                 495

Phe Pro Phe Asn Asp Cys Val Asp Lys Met Val Ile Trp Trp Glu Glu
            500                 505                 510

Gly Lys Met Thr Ala Lys Val Val Glu Ser Ala Lys Ala Ile Leu Gly
        515                 520                 525

Gly Ser Lys Val Arg Val Asp Gln Lys Cys Lys Ser Ser Ala Gln Ile
530                 535                 540

Asp Pro Thr Pro Val Ile Val Thr Ser Asn Thr Asn Met Cys Ala Val
545                 550                 555                 560
```

Ile Asp Gly Asn Ser Thr Thr Phe Glu His Gln Gln Pro Leu Gln Asp
            565                 570                 575

Arg Met Phe Lys Phe Glu Leu Thr Arg Arg Leu Asp His Asp Phe Gly
            580                 585                 590

Lys Val Thr Lys Gln Glu Val Lys Asp Phe Phe Arg Trp Ala Lys Asp
            595                 600                 605

His Val Val Glu Val Glu His Glu Phe Tyr Val Lys Lys Gly Gly Ala
            610                 615                 620

Lys Lys Arg Pro Ala Pro Ser Asp Ala Asp Ile Ser Glu Pro Lys Arg
625                 630                 635                 640

Val Arg Glu Ser Val Ala Gln Pro Ser Thr Ser Asp Ala Glu Ala Ser
            645                 650                 655

Ile Asn Tyr Ala Asp Arg Tyr Gln Asn Lys Cys Ser Arg His Val Gly
            660                 665                 670

Met Asn Leu Met Leu Phe Pro Cys Arg Gln Cys Glu Arg Met Asn Gln
            675                 680                 685

Asn Ser Asn Ile Cys Phe Thr His Gly Gln Lys Asp Cys Leu Glu Cys
            690                 695                 700

Phe Pro Val Ser Glu Ser Gln Pro Val Ser Val Lys Lys Ala Tyr
705                 710                 715                 720

Gln Lys Leu Cys Tyr Ile His His Ile Met Gly Lys Val Pro Asp Ala
            725                 730                 735

Cys Thr Ala Cys Asp Leu Val Asn Val Asp Leu Asp Asp Cys Ile Phe
            740                 745                 750

Glu Gln

<210> SEQ ID NO 135
<211> LENGTH: 2088
<212> TYPE: DNA
<213> ORGANISM: Artificial Sequence
<220> FEATURE:
<223> OTHER INFORMATION: Synthetic: COM-Rep-Y156F  nucleic acid sequence
      (linker-COM-linker-Rep)

<400> SEQUENCE: 135
atgcccggca gctccggcag tagcatgaaa tcaattcgct gtaaaaactg caacaaactg      60
ttatttaagg cggattcctt tgatcacatt gaaatcaggt gtccgcgttg caaacgtcac     120
atcataatgc tgaatgcctg cgagcatccc acggagaaac attgtgggaa aagagaaaaa     180
atcacgcatt ctgacgaaac cgtgcgttat ggcagtagtg ggtcctctgg gttttacgag     240
attgtgatta aggtccccag cgaccttgac gagcatctgc ccggcatttc tgacagcttt     300
gtgaactggg tggccgagaa ggaatgggag ttgccgccag attctgacat ggatctgaat     360
ctgattgagc aggcacccct gaccgtggcc gagaagctgc agcgcgactt tctgacggaa     420
tggcgccgtg tgagtaaggc cccggaggcc cttttctttg tgcaatttga agggagag       480 agctacttcc acatgcacgt gctcgtgaaa accaccgggg tgaaatccat ggttttggga     540
cgtttcctga gtcagattcg cgaaaaactg attcagagaa tttaccgcgg gatcgagccg     600
actttgccaa actggttcgc ggtcacaaag accagaaatg cgccggaggc gggaacaag      660 gtggtggatg agtgctacat ccccaatttc ttgctcccca aacccagcc tgagctccag      720 tgggcgtgga ctaatatgga acagtattta agcgcctgtt tgaatctcac ggagcgtaaa     780
cggttggtgg cgcagcatct gacgcacgtg tcgcagacgc aggagcagaa caaagagaat     840
cagaatccca attctgatgc gccggtgatc agatcaaaaa cttcagccag gtacatggag     900

```
ctggtcgggt ggctcgtgga caagggatt acctcggaga agcagtggat ccaggaggac    960
caggcctcat acatctcctt caatgcggcc tccaactcgc ggtcccaaat caaggctgcc   1020
ttggacaatg cgggaaagat tatgagcctg actaaaaccg cccccgacta cctggtgggc   1080
cagcagcccg tggaggacat ttccagcaat cggatttata aaattttgga actaaacggg   1140
tacgatcccc aatatgcggc ttccgtcttt ctgggatggg ccacgaaaaa gttcggcaag   1200
aggaacacca tctggctgtt tgggcctgca actaccggga agaccaacat cgcggaggcc   1260
atagcccaca ctgtgccctt ctacgggtgc gtaaactgga ccaatgagaa ctttcccttc   1320
aacgactgtg tcgacaagat ggtgatctgg tgggaggagg ggaagatgac cgccaaggtc   1380
gtggagtcgg ccaaagccat tctcggagga agcaaggtgc gcgtggacca gaaatgcaag   1440
tcctcggccc agatagaccc gactcccgtg atcgtcacct ccaacaccaa catgtgcgcc   1500
gtgattgacg ggaactcaac gaccttcgaa caccagcagc cgttgcaaga ccggatgttc   1560
aaatttgaac tcacccgccg tctggatcat gactttggga aggtcaccaa gcaggaagtc   1620
aaagactttt tccggtgggc aaaggatcac gtggttgagg tggagcatga attctacgtc   1680
aaaaagggtg agccaagaa aagacccgcc cccagtgacg cagatataag tgagcccaaa   1740
cgggtgcgcg agtcagttgc gcagccatcg acgtcagacg cggaagcttc gatcaactac   1800
gcagacaggt accaaaacaa atgttctcgt cacgtgggca tgaatctgat gctgtttccc   1860
tgcagacaat gcgagagaat gaatcagaat tcaaatatct gcttcactca cggacagaaa   1920
gactgtttag agtgctttcc cgtgtcagaa tctcaacccg tttctgtcgt caaaaaggcg   1980
tatcagaaac tgtgctacat tcatcatatc atgggaaagg tgccagacgc ttgcactgcc   2040
tgcgatctgg tcaatgtgga tttggatgac tgcatctttg aacaataa                2088

<210> SEQ ID NO 136
<211> LENGTH: 695
<212> TYPE: PRT
<213> ORGANISM: Artificial Sequence
<220> FEATURE:
<223> OTHER INFORMATION: Synthetic: COM-Rep-Y156F amino acid sequence
      (linker-COM-linker-Rep)

<400> SEQUENCE: 136

Met Pro Gly Ser Ser Gly Ser Ser Met Lys Ser Ile Arg Cys Lys Asn
1               5                   10                  15

Cys Asn Lys Leu Leu Phe Lys Ala Asp Ser Phe Asp His Ile Glu Ile
            20                  25                  30

Arg Cys Pro Arg Cys Lys Arg His Ile Ile Met Leu Asn Ala Cys Glu
        35                  40                  45

His Pro Thr Glu Lys His Cys Gly Lys Arg Glu Lys Ile Thr His Ser
    50                  55                  60

Asp Glu Thr Val Arg Tyr Gly Ser Ser Gly Ser Gly Phe Tyr Glu
65                  70                  75                  80

Ile Val Ile Lys Val Pro Ser Asp Leu Asp Glu His Leu Pro Gly Ile
                85                  90                  95

Ser Asp Ser Phe Val Asn Trp Val Ala Glu Lys Glu Trp Glu Leu Pro
            100                 105                 110

Pro Asp Ser Asp Met Asp Leu Asn Leu Ile Glu Gln Ala Pro Leu Thr
        115                 120                 125

Val Ala Glu Lys Leu Gln Arg Asp Phe Leu Thr Glu Trp Arg Arg Val
    130                 135                 140
```

```
Ser Lys Ala Pro Glu Ala Leu Phe Phe Val Gln Phe Glu Lys Gly Glu
145                 150                 155                 160

Ser Tyr Phe His Met His Val Leu Val Glu Thr Thr Gly Val Lys Ser
            165                 170                 175

Met Val Leu Gly Arg Phe Leu Ser Gln Ile Arg Glu Lys Leu Ile Gln
        180                 185                 190

Arg Ile Tyr Arg Gly Ile Glu Pro Thr Leu Pro Asn Trp Phe Ala Val
    195                 200                 205

Thr Lys Thr Arg Asn Gly Ala Gly Gly Asn Lys Val Val Asp Glu
210                 215                 220

Cys Tyr Ile Pro Asn Phe Leu Leu Pro Lys Thr Gln Pro Glu Leu Gln
225                 230                 235                 240

Trp Ala Trp Thr Asn Met Glu Gln Tyr Leu Ser Ala Cys Leu Asn Leu
                245                 250                 255

Thr Glu Arg Lys Arg Leu Val Ala Gln His Leu Thr His Val Ser Gln
            260                 265                 270

Thr Gln Glu Gln Asn Lys Glu Asn Gln Asn Pro Asn Ser Asp Ala Pro
        275                 280                 285

Val Ile Arg Ser Lys Thr Ser Ala Arg Tyr Met Glu Leu Val Gly Trp
    290                 295                 300

Leu Val Asp Lys Gly Ile Thr Ser Glu Lys Gln Trp Ile Gln Glu Asp
305                 310                 315                 320

Gln Ala Ser Tyr Ile Ser Phe Asn Ala Ala Ser Asn Ser Arg Ser Gln
                325                 330                 335

Ile Lys Ala Ala Leu Asp Asn Ala Gly Lys Ile Met Ser Leu Thr Lys
            340                 345                 350

Thr Ala Pro Asp Tyr Leu Val Gly Gln Gln Pro Val Glu Asp Ile Ser
        355                 360                 365

Ser Asn Arg Ile Tyr Lys Ile Leu Glu Leu Asn Gly Tyr Asp Pro Gln
    370                 375                 380

Tyr Ala Ala Ser Val Phe Leu Gly Trp Ala Thr Lys Lys Phe Gly Lys
385                 390                 395                 400

Arg Asn Thr Ile Trp Leu Phe Gly Pro Ala Thr Thr Gly Lys Thr Asn
                405                 410                 415

Ile Ala Glu Ala Ile Ala His Thr Val Pro Phe Tyr Gly Cys Val Asn
            420                 425                 430

Trp Thr Asn Glu Asn Phe Pro Phe Asn Asp Cys Val Asp Lys Met Val
        435                 440                 445

Ile Trp Trp Glu Glu Gly Lys Met Thr Ala Lys Val Val Glu Ser Ala
    450                 455                 460

Lys Ala Ile Leu Gly Gly Ser Lys Val Arg Val Asp Gln Lys Cys Lys
465                 470                 475                 480

Ser Ser Ala Gln Ile Asp Pro Thr Pro Val Ile Val Thr Ser Asn Thr
                485                 490                 495

Asn Met Cys Ala Val Ile Asp Gly Asn Ser Thr Thr Phe Glu His Gln
            500                 505                 510

Gln Pro Leu Gln Asp Arg Met Phe Lys Phe Glu Leu Thr Arg Arg Leu
        515                 520                 525

Asp His Asp Phe Gly Lys Val Thr Lys Gln Glu Val Lys Asp Phe Phe
    530                 535                 540

Arg Trp Ala Lys Asp His Val Val Glu Val Glu His Glu Phe Tyr Val
545                 550                 555                 560

Lys Lys Gly Gly Ala Lys Lys Arg Pro Ala Pro Ser Asp Ala Asp Ile
```

565                 570                 575
Ser Glu Pro Lys Arg Val Arg Glu Ser Val Ala Gln Pro Ser Thr Ser
            580                 585                 590

Asp Ala Glu Ala Ser Ile Asn Tyr Ala Asp Arg Tyr Gln Asn Lys Cys
        595                 600                 605

Ser Arg His Val Gly Met Asn Leu Met Leu Phe Pro Cys Arg Gln Cys
    610                 615                 620

Glu Arg Met Asn Gln Asn Ser Asn Ile Cys Phe Thr His Gly Gln Lys
625                 630                 635                 640

Asp Cys Leu Glu Cys Phe Pro Val Ser Glu Ser Gln Pro Val Ser Val
                645                 650                 655

Val Lys Lys Ala Tyr Gln Lys Leu Cys Tyr Ile His His Ile Met Gly
            660                 665                 670

Lys Val Pro Asp Ala Cys Thr Ala Cys Asp Leu Val Asn Val Asp Leu
        675                 680                 685

Asp Asp Cys Ile Phe Glu Gln
    690                 695

<210> SEQ ID NO 137
<211> LENGTH: 1020
<212> TYPE: DNA
<213> ORGANISM: Artificial Sequence
<220> FEATURE:
<223> OTHER INFORMATION: Synthetic: MCP-AAP(DJ)  nucleic acid sequence
      (linker-MCP-linker-AAP)

<400> SEQUENCE: 137
atgggcagct ccggcagtag cgcttctaac tttactcagt tcgttctcgt cgacaatggc        60
ggaactggcg acgtgactgt cgccccaagc aacttcgcta cggggtcgc tgaatggatc       120 agctctaact cgcgttcaca ggcttacaaa gtaacctgta gcgttcgtca gagctctgcg       180
cagaatcgca aatacaccat caaagtcgag gtgcctaaag tggcaaccca gactgttggt       240
ggagtagagc ttcctgtagc cgcatggcgt tcgtacttaa atatggaact aaccattcca       300
attttcgcta cgaattccga ctgcgagctt attgttaagg caatgcaagg tctcctaaaa       360
gatgaaaacc cgattccctc agcaatcgca gcaaactccg gcatctacgg cagtagtggg       420
tcctctctgg agacgcagac tcagtcccag accctcaacc aatcggagaa cctcccgcag       480
ccccctcagg tgtgggatct cttacaatgg ctgcaggcgg tggcgcacca atggcagaca       540
ataacgaggg cgccgacgga gtgggtaatt cctcgggaaa ttggcattgc gattccacat       600
ggatgggcga cagagtcatc accaccagca cccgaacctg ggccctgccc acctacaaca       660
accacctcta caagcaaatc tccaacagca catctggagg atcttcaaat gacaacgcct       720
acttcggcta cagcaccccc tgggggtatt ttgactttaa cagattccac tgccactttt       780
caccacgtga ctggcagcga ctcatcaaca caactgggg attccggccc aagagactca       840
gcttcaagct cttcaacatc caggtcaagg aggtcacgca gaatgaaggc accaagacca       900
tcgccaataa cctcaccagc accatccagg tgtttacgga ctcggagtac cagctgccgt       960
acgttctcgg ctctgcccac cagggctgcc tgcctccgtt cccggcggac gtgttcatga      1020

<210> SEQ ID NO 138
<211> LENGTH: 339
<212> TYPE: PRT
<213> ORGANISM: Artificial Sequence
<220> FEATURE:
<223> OTHER INFORMATION: Synthetic: MCP-AAP(DJ) amino acid sequence
      (linker-MCP-linker-AAP)

<400> SEQUENCE: 138

```
Met Gly Ser Ser Gly Ser Ser Ala Ser Asn Phe Thr Gln Phe Val Leu
1               5                   10                  15

Val Asp Asn Gly Gly Thr Gly Asp Val Thr Val Ala Pro Ser Asn Phe
            20                  25                  30

Ala Asn Gly Val Ala Glu Trp Ile Ser Ser Asn Ser Arg Ser Gln Ala
        35                  40                  45

Tyr Lys Val Thr Cys Ser Val Arg Gln Ser Ser Ala Gln Asn Arg Lys
50                  55                  60

Tyr Thr Ile Lys Val Glu Val Pro Lys Val Ala Thr Gln Thr Val Gly
65                  70                  75                  80

Gly Val Glu Leu Pro Val Ala Ala Trp Arg Ser Tyr Leu Asn Met Glu
                85                  90                  95

Leu Thr Ile Pro Ile Phe Ala Thr Asn Ser Asp Cys Glu Leu Ile Val
            100                 105                 110

Lys Ala Met Gln Gly Leu Leu Lys Asp Gly Asn Pro Ile Pro Ser Ala
        115                 120                 125

Ile Ala Ala Asn Ser Gly Ile Tyr Gly Ser Ser Gly Ser Ser Leu Glu
130                 135                 140

Thr Gln Thr Gln Ser Gln Thr Leu Asn Gln Ser Glu Asn Leu Pro Gln
145                 150                 155                 160

Pro Pro Gln Val Trp Asp Leu Leu Gln Trp Leu Gln Ala Val Ala His
                165                 170                 175

Gln Trp Gln Thr Ile Thr Arg Ala Pro Thr Glu Trp Val Ile Pro Arg
            180                 185                 190

Glu Ile Gly Ile Ala Ile Pro His Gly Trp Ala Thr Glu Ser Ser Pro
        195                 200                 205

Pro Ala Pro Glu Pro Gly Pro Cys Pro Pro Thr Thr Thr Ser Thr
210                 215                 220

Ser Lys Ser Pro Thr Ala His Leu Glu Asp Leu Gln Met Thr Thr Pro
225                 230                 235                 240

Thr Ser Ala Thr Ala Pro Pro Gly Gly Ile Leu Thr Leu Thr Asp Ser
                245                 250                 255

Thr Ala Thr Phe His His Val Thr Gly Ser Asp Ser Ser Thr Thr Thr
            260                 265                 270

Gly Asp Ser Gly Pro Arg Asp Ser Ala Ser Ser Ser Thr Ser Arg
        275                 280                 285

Ser Arg Arg Ser Arg Arg Met Lys Ala Pro Arg Pro Ser Pro Ile Thr
290                 295                 300

Ser Pro Ala Pro Ser Arg Cys Leu Arg Thr Arg Ser Thr Ser Cys Arg
305                 310                 315                 320

Thr Phe Ser Ala Leu Pro Thr Arg Ala Ala Cys Leu Arg Ser Arg Arg
                325                 330                 335

Thr Cys Ser
```

<210> SEQ ID NO 139
<211> LENGTH: 1020
<212> TYPE: DNA
<213> ORGANISM: Artificial Sequence
<220> FEATURE:
<223> OTHER INFORMATION: Synthetic: AAP-MCP(DJ) nucleic acid sequence (AAP-linker-MCP-linker)

<400> SEQUENCE: 139

-continued

```
atgctggaga cgcagactca gtcccagacc ctcaaccaat cggagaacct cccgcagccc    60
cctcaggtgt gggatctctt acaatggctg caggcggtgg cgcaccaatg cagacaata   120
acgagggcgc cgacggagtg ggtaattcct cgggaaattg gcattgcgat tccacatgga   180
tgggcgacag agtcatcacc accagcaccc gaacctgggc cctgccacc tacaacaacc    240
acctctacaa gcaaatctcc aacagcacat ctggaggatc ttcaaatgac aacgcctact   300
tcggctacag cacccctgg gggtattttg actttaacag attccactgc cacttttcac    360
cacgtgactg gcagcgactc atcaacaaca actggggatt ccgcccaag agactcagct    420
tcaagctctt caacatccag gtcaaggagg tcacgcagaa tgaaggcacc aagaccatcg   480
ccaataacct caccagcacc atccaggtgt ttacggactc ggagtaccag ctgccgtacg   540
ttctcggctc tgcccaccag ggctgcctgc ctccgttccc ggcggacgtg ttcaggcagc   600
tccggcagta gcgcttctaa ctttactcag ttcgttctcg tcgacaatgg cggaactggc   660
gacgtgactg tcgccccaag caacttcgct aacgggtcg ctgaatggat cagctctaac    720
tcgcgttcac aggcttacaa agtaacctgt agcgttcgtc agagctctgc gcagaatcgc   780
aaatacacca tcaaagtcga ggtgcctaaa gtggcaaccc agactgttgg tggagtagag   840
cttcctgtag ccgcatggcg ttcgtactta aatatggaac taaccattcc aattttcgct   900
acgaattccg actgcgagct tattgttaag gcaatgcaag gtctcctaaa agatggaaac   960
ccgattccct cagcaatcgc agcaaactcc ggcatctacg gcagtagtgg gtcctcttga  1020
```

<210> SEQ ID NO 140
<211> LENGTH: 339
<212> TYPE: PRT
<213> ORGANISM: Artificial Sequence
<220> FEATURE:
<223> OTHER INFORMATION: Synthetic: AAP-MCP(DJ) amino acid sequence
      (AAP-linker-MCP-linker)

<400> SEQUENCE: 140

Met Leu Glu Thr Gln Thr Gln Ser Gln Thr Leu Asn Gln Ser Glu Asn
1               5                   10                  15

Leu Pro Gln Pro Pro Gln Val Trp Asp Leu Leu Gln Trp Leu Gln Ala
            20                  25                  30

Val Ala His Gln Trp Gln Thr Ile Thr Arg Ala Pro Thr Glu Trp Val
        35                  40                  45

Ile Pro Arg Glu Ile Gly Ile Ala Ile Pro His Gly Trp Ala Thr Glu
    50                  55                  60

Ser Ser Pro Pro Ala Pro Glu Pro Gly Pro Cys Pro Pro Thr Thr Thr
65                  70                  75                  80

Thr Ser Thr Ser Lys Ser Pro Thr Ala His Leu Glu Asp Leu Gln Met
                85                  90                  95

Thr Thr Pro Thr Ser Ala Thr Ala Pro Pro Gly Gly Ile Leu Thr Leu
            100                 105                 110

Thr Asp Ser Thr Ala Thr Phe His His Val Thr Gly Ser Asp Ser Ser
        115                 120                 125

Thr Thr Thr Gly Asp Ser Gly Pro Arg Asp Ser Ala Ser Ser Ser Ser
    130                 135                 140

Thr Ser Arg Ser Arg Arg Ser Arg Arg Met Lys Ala Pro Arg Pro Ser
145                 150                 155                 160

Pro Ile Thr Ser Pro Ala Pro Ser Arg Cys Leu Arg Thr Arg Ser Thr
                165                 170                 175

Ser Cys Arg Thr Phe Ser Ala Leu Pro Thr Arg Ala Ala Cys Leu Arg

```
            180                 185                 190
Ser Arg Arg Thr Cys Ser Gly Ser Gly Ser Ser Ala Ser Asn Phe
            195                 200                 205

Thr Gln Phe Val Leu Val Asp Asn Gly Gly Thr Gly Asp Val Thr Val
            210                 215                 220

Ala Pro Ser Asn Phe Ala Asn Gly Val Ala Glu Trp Ile Ser Ser Asn
225                 230                 235                 240

Ser Arg Ser Gln Ala Tyr Lys Val Thr Cys Ser Val Arg Gln Ser Ser
                245                 250                 255

Ala Gln Asn Arg Lys Tyr Thr Ile Lys Val Glu Val Pro Lys Val Ala
                260                 265                 270

Thr Gln Thr Val Gly Gly Val Glu Leu Pro Val Ala Ala Trp Arg Ser
            275                 280                 285

Tyr Leu Asn Met Glu Leu Thr Ile Pro Ile Phe Ala Thr Asn Ser Asp
            290                 295                 300

Cys Glu Leu Ile Val Lys Ala Met Gln Gly Leu Leu Lys Asp Gly Asn
305                 310                 315                 320

Pro Ile Pro Ser Ala Ile Ala Ala Asn Ser Gly Ile Tyr Gly Ser Ser
                325                 330                 335

Gly Ser Ser

<210> SEQ ID NO 141
<211> LENGTH: 23
<212> TYPE: DNA
<213> ORGANISM: Artificial Sequence
<220> FEATURE:
<223> OTHER INFORMATION: Synthetic: WPRE-F

<400> SEQUENCE: 141
cccgtatggc tttcattttc tcc                                          23

<210> SEQ ID NO 142
<211> LENGTH: 19
<212> TYPE: DNA
<213> ORGANISM: Artificial Sequence
<220> FEATURE:
<223> OTHER INFORMATION: Synthetic: WPRE-R

<400> SEQUENCE: 142
ggcaatgccc caaccagtg                                               19

<210> SEQ ID NO 143
<211> LENGTH: 20
<212> TYPE: DNA
<213> ORGANISM: Artificial Sequence
<220> FEATURE:
<223> OTHER INFORMATION: Synthetic: Cre-F

<400> SEQUENCE: 143
ccagtagatg ccactagcga                                              20

<210> SEQ ID NO 144
<211> LENGTH: 20
<212> TYPE: DNA
<213> ORGANISM: Artificial Sequence
<220> FEATURE:
<223> OTHER INFORMATION: Synthetic: Cre-R

<400> SEQUENCE: 144
gcctggagat acagcaggta                                              20
```

<210> SEQ ID NO 145
<211> LENGTH: 20
<212> TYPE: DNA
<213> ORGANISM: Artificial Sequence
<220> FEATURE:
<223> OTHER INFORMATION: Synthetic: CAG-F

<400> SEQUENCE: 145
cttctcctcc gggctgtaat                                              20

<210> SEQ ID NO 146
<211> LENGTH: 20
<212> TYPE: DNA
<213> ORGANISM: Artificial Sequence
<220> FEATURE:
<223> OTHER INFORMATION: Synthetic: CAG-R

<400> SEQUENCE: 146
ctttcacgca gccacagaaa                                              20

<210> SEQ ID NO 147
<211> LENGTH: 3266
<212> TYPE: DNA
<213> ORGANISM: Artificial Sequence
<220> FEATURE:
<223> OTHER INFORMATION: Synthetic: Stuffer nucleic acid sequence

<400> SEQUENCE: 147
atatttggag ggcagcttga tttcgacttc gggagggaag ctgcgccatg cgatgttatc    60
ggtgcggtga atgcaaagaa gataaccgct tccgaccaaa tcaaccttac tggaatcgat   120
ggtgtctccg gtgtgaaaga acaccaacag gggtgttacc actaccgcag gaaaaggagg   180
acgtgccgcg agacagcgac gaagtatcac cgacataatc tgcgaaaact gcaaataccc   240
tccaacgaaa cgcaccagaa ataaacccaa gccaatccca aaagaatctg acgtaaaaac   300
cttcaactac acggctcacc tgtgggatat ccggtggcta gacgtcgtg cgaggaaaac    360
aaggccattg accaaaatcg aagttacgaa caagaaagcg tcgagcgagc tttaacgtgc   420
gctaactgcg gtcagaagct gcatgtgctg gaagttcacg tgtgtgagca ctgctgcgca   480
gaactgatga gcgatccgaa tagctcgatg cacgaggaag aaggccgccg ctaaaccagc   540
gcgaagacga tgtaaaaacg atgaatgccg ggaatggttt caccctgcat cgctaatca    600
gtggtggtgc tctccagagt gtggaaccaa gatagcactc gaacgacgaa gtaaagaacg   660
cgaaaaagcg gaaaaagcag cagagaagaa acgacgacga gaggagcaga acagaaaga    720
taaacttaag attcgaaaac tcgccttaaa gccccgcagt tactggatta aacaagccca   780
acaagccgta aacgccttca tcagagaaag agaccgcgac ttaccatgta tctcgtgcgg   840
aacgctcacg tctgctcagt gggatgccgg acattaccgg acaactgctg cggcacctca   900
actccgattt aatgaacgca atattcacaa gcaatgcgtg gtgtgcaacc agcacaaaag   960
cggaaatctc gttccgtatc gcgtcgaact gattagccgc atcgggcagg aagcagtaga  1020
cgaaatcgaa tcaaaccata accgccatcg ctggactatc gaagagtgca aggcgatcaa  1080
ggcagagtac caacgaaac tcaaagacct gcgaaatagc agaagtgagg ccgcgccacg   1140
ttctcagtaa aaaccattcc agacatgctc gttgaagcat acggaaatca gacagaagta  1200
gcacgcagac tgaaatgtag tcgcggtacg tcagaaaat acgttgatga taaagacggg   1260
aaaatgcacg ccatcgtcaa cgacgttctc atggttcatc gcggatggag tgaaagaggc  1320
ccgctattac gaaaaaattg atggcagcaa ataccgaaat atttgggtag ttggcgatct  1380

```
gcacggatgc tacacgaacc tgatgaacaa actggatacg attggattcg acaacaaaaa    1440
agacctgctt atctcggtgg gcgatttggt tgatcgtggt gcagagaacg ttgaatgcct    1500
ggaattaatc acattcccct ggttcagagc tgtacgtgga aaccatgagc aaatgatgat    1560
tgatggctta tcagagcgtg gaaacgttaa tcactggctg cttaatggcg gtggctggtt    1620
ctttaatctc gattacgaca aagaaattct ggctaaagct cttgcccata aagcagatga    1680
acttccgtta atcatcgaac tggtgagcaa agataaaaaa tatgttatct gccacgccga    1740
ttatcccttt gacgaatacg agtttggaaa gccagttgat catcagcagg taatctggaa    1800
ccgcgaacga atcagcaact cacaaaacgg gatcgtgaaa gaaatcaaag cgcggacac    1860 gttcatctttt ggtcatacgc cagcagtgaa accactcaag tttgccaacc aaatgtatat    1920
cgataccggc gcagtgttct gcggaaacct aacattgatt caggtacagg agaaggcgc    1980 gccagactcg aaagcgtagc taaatttcat tcgccaaaaa gcccgatgat gagcgactca    2040
ccacgggcca cggcttctga ctctctttcc ggtactgatg tgatggctgc tatggggatg    2100
gcgcaatcac aagccggatt cggtatggct gcattctgcg gtaagcacga actcagccag    2160
aacgacaaac aaaaggctat caactatctg atgcaatttg cacacaaggt atcggggaaa    2220
taccgtggtg tggcaaagct tgaaggaaat actaaggcaa aggtactgca agtgctcgca    2280
acattcgctt atgcggatta ttgccgtagt gccgcgacgc cggggcaag atgcagagat    2340 tgccatggta caggccgtgc ggttgatatt gccaaaacag agctgtgggg gagagttgtc    2400
gagaaagagt gcggaagatg caaaggcgtc ggctattcaa ggatgccagc aagcgcagca    2460
tatcgcgctg tgacgatgct aatcccaaac cttacccaac ccacctggtc acgcactgtt    2520
aagccgctgt atgacgctct ggtggtgcaa tgccacaaag aagagtcaat cgcagacaac    2580
attttgaatg cggtcacacg ttagcagcat gattgccacg gatggcaaca tattaacggc    2640
atgatattga cttattgaat aaaatttggt aaatttgact caacgatggg ttaattcgct    2700
cgttgtggta gtgaggccaa aagaggcggc gcttactacc gattccgcct agttggtcac    2760
ttcgacgtat cgtctggaac tccaaccatc gcaggcagag aggtctgcaa aatgcaatcc    2820
cgaaacagtt cgcaggtaat agttagagcc tgcataacgg tttcgggatt tttatatct    2880 gcacaacagg taagagcatt gagtcgataa tcgtgaagag tcggcgagcc tggttagcca    2940
gtgctctttc cgttgtgctg aattaagcga ataccggaag cagaaccgga tcaccaaatg    3000
cgtacaggcg tcatcgccgc ccagcaacag cacaacccaa actgagccgt agccactgtc    3060
tgtcctaaat tcattagtaa tagttacgct gcggcctttt acacatgacc ttcgtgaaag    3120
cgggtggcag gaggtcgcgc taacaacctc ctgccgtttt gcccgtgcat atcggtcacg    3180
aacaaatctg attactaaac acagtagcct ggatttgttc tatcagtaat cgaccttatt    3240
cctaattaaa tagagcaaat cccctt                                        3266
```

<210> SEQ ID NO 148
<211> LENGTH: 120
<212> TYPE: PRT
<213> ORGANISM: Artificial Sequence
<220> FEATURE:
<223> OTHER INFORMATION: Synthetic: linker
<220> FEATURE:
<221> NAME/KEY: VARIANT
<222> LOCATION: (1)..(120)
<223> OTHER INFORMATION: For every "GSSSSS" at least one "S" is present and others may be present or absent; "GSSSSS" or a variation thereof is present at least once, but all other instances may be present or absent

```
<400> SEQUENCE: 148

Gly Ser Ser Ser Ser Gly Ser Ser Ser Ser Gly Ser Ser Ser
1               5                   10                  15

Ser Ser Gly Ser Ser Ser Ser Gly Ser Ser Ser Ser Gly Ser
            20                  25                  30

Ser Ser Ser Ser Gly Ser Ser Ser Ser Gly Ser Ser Ser Ser
        35                  40                  45

Gly Ser Ser Ser Ser Gly Ser Ser Ser Ser Gly Ser Ser Ser
    50                  55                  60

Ser Ser Gly Ser Ser Ser Ser Gly Ser Ser Ser Ser Gly Ser
65                  70                  75              80

Ser Ser Ser Ser Gly Ser Ser Ser Ser Gly Ser Ser Ser Ser
                85                  90                  95

Gly Ser Ser Ser Ser Ser Gly Ser Ser Ser Ser Gly Ser Ser Ser
                100                 105                 110

Ser Ser Gly Ser Ser Ser Ser Ser
            115                 120
```